US011472847B2

(12) United States Patent
Fox et al.

(10) Patent No.: US 11,472,847 B2
(45) Date of Patent: Oct. 18, 2022

(54) GENETICALLY ENCODED SYSTEM FOR CONSTRUCTING AND DETECTING BIOLOGICALLY ACTIVE AGENTS

(71) Applicant: The Regents of the University of Colorado, Denver, CO (US)

(72) Inventors: Jerome Fox, Boulder, CO (US); Ankur Sarkar, Boulder, CO (US); Akarawin Hongdusit, Boulder, CO (US); Edward Kim, Oakland, CA (US)

(73) Assignee: The Regents of the University of Colorado, Denver, CO (US)

( * ) Notice: Subject to any disclaimer, the term of this patent is extended or adjusted under 35 U.S.C. 154(b) by 0 days.

(21) Appl. No.: 17/141,321

(22) Filed: Jan. 5, 2021

(65) Prior Publication Data
US 2021/0206813 A1   Jul. 8, 2021

Related U.S. Application Data

(63) Continuation of application No. PCT/US2019/040896, filed on Jul. 8, 2019.

(60) Provisional application No. 62/694,838, filed on Jul. 6, 2018.

(51) Int. Cl.
| C12N 9/16 | (2006.01) |
| C07K 14/005 | (2006.01) |
| C07K 14/47 | (2006.01) |
| C12N 1/20 | (2006.01) |

(52) U.S. Cl.
CPC ............ *C07K 14/005* (2013.01); *C07K 14/47* (2013.01); *C12N 1/20* (2013.01); *C07K 2319/80* (2013.01); *C12Y 205/01001* (2013.01); *C12Y 205/0101* (2013.01); *C12Y 207/01036* (2013.01); *C12Y 207/04002* (2013.01); *C12Y 301/01048* (2013.01); *C12Y 401/01033* (2013.01); *C12Y 402/03017* (2013.01); *C12Y 402/03018* (2013.01); *C12Y 402/03024* (2013.01); *C12Y 402/03056* (2013.01); *C12Y 503/03002* (2013.01)

(58) Field of Classification Search
CPC ........... C12N 9/1205; C12N 9/16; C12N 1/20
See application file for complete search history.

(56) References Cited

U.S. PATENT DOCUMENTS

| 6,200,759 | B1 | 3/2001 | Dove et al. |
| 6,303,319 | B1* | 10/2001 | Rickles ............. G01N 33/5011 435/7.1 |
| 6,428,951 | B1 | 8/2002 | Michnick et al. |
| 7,927,794 | B2 | 4/2011 | Keasling et al. |
| 8,586,725 | B2 | 11/2013 | Cummins et al. |
| 8,716,460 | B2 | 5/2014 | Alfano et al. |
| 8,859,232 | B2 | 10/2014 | Hahn et al. |
| 10,385,332 | B2 | 8/2019 | Hill et al. |
| 11,020,429 | B2 | 6/2021 | Thompson |
| 2002/0120947 | A1 | 8/2002 | Roch et al. |
| 2002/0164587 | A1 | 11/2002 | Camonis et al. |
| 2003/0170855 | A1 | 9/2003 | Zhang et al. |
| 2003/0203471 | A1 | 10/2003 | Althoff et al. |
| 2005/0040550 | A1 | 2/2005 | Short et al. |
| 2005/0227357 | A1 | 10/2005 | Bohlmann et al. |
| 2006/0292155 | A1 | 12/2006 | Golz et al. |
| 2011/0046018 | A1 | 2/2011 | Chen et al. |
| 2014/0315214 | A1 | 10/2014 | Taipale et al. |
| 2018/0057545 | A9 | 3/2018 | Liu et al. |
| 2018/0111929 | A1* | 4/2018 | Ibrahim ................. A61P 15/08 |
| 2018/0230449 | A1 | 8/2018 | Niesert et al. |
| 2020/0181598 | A1 | 6/2020 | Bode et al. |
| 2020/0347428 | A1 | 11/2020 | Bode et al. |

FOREIGN PATENT DOCUMENTS

| CN | 103160570 A | 6/2013 |
| EP | 2116263 A1 | 11/2009 |
| WO | WO-2004003550 A2 | 1/2004 |
| WO | WO-2004048549 A2 | 6/2004 |
| WO | WO-2008115420 A2 | 9/2008 |
| WO | WO-201 1002977 A2 | 1/2011 |
| WO | WO-201 1133493 A2 | 10/2011 |
| WO | WO-201 2111772 A1 | 8/2012 |

(Continued)

OTHER PUBLICATIONS

PCT/US2019/040896—Written Opinion. (dated 2019).*
Ajikumar et al., Isoprenoid pathway optimization forTaxol precursor overproduction in *Escherichia coli.* Science 330: 70-74 (2010).
Alonso et al., Protein tyrosine phosphatases in the human genome. Cell 117: 699-711 (2004).
Anderie et al., Characterization of the C-terminal ER membrane anchor of PTPIB. Exp. Cell Res. 313: 3189-3197 (2007).
Aramini et al., The RAS-Binding Domain of Human BRAF Protein Serine/Threonine Kinase Exhibits Allosteric Conformational Changes upon Binding HRAS. Structure 23: 1382-1393 (2015).
Arregiu et al., Protein tyrosine phosphatase PTPIB in cell adhesion and migration. Cell Adh. Migr. 7: 418-423 (2013).

(Continued)

*Primary Examiner* — Tekchand Saidha
(74) *Attorney, Agent, or Firm* — Wilson Sonsini Goodrich & Rosati

(57) ABSTRACT

This invention relates to the field of genetic engineering. Specifically, the invention relates to the construction of operons to produce biologically active agents. For example, operons may be constructed to produce agents that control the function of biochemical pathway proteins (e.g., protein phosphatases, kinases and/or proteases). Such agents may include inhibitors and modulators that may be used in studying or controlling phosphatase function associated with abnormalities in a phosphatase pathway or expression level. Fusion proteins, such as light activated protein phosphatases, may be genetically encoded and expressed as photoswitchable phosphatases. Systems are provided for use in controlling phosphatase function within living cells or in identifying small molecule inhibitors/activator/modulator molecules of protein phosphatases associated with cell signaling.

20 Claims, 52 Drawing Sheets

Specification includes a Sequence Listing.

(56) References Cited

FOREIGN PATENT DOCUMENTS

| WO | WO-2013016693 A2 | 1/2013 |
|---|---|---|
| WO | WO-2014022434 A1 | 2/2014 |
| WO | WO-2015040197 A1 | 3/2015 |
| WO | WO-2015189428 A1 | 12/2015 |
| WO | WO-2018096150 A1 | 5/2018 |
| WO | WO-2019032628 A1 | 2/2019 |
| WO | WO-2019232025 A2 | 12/2019 |
| WO | WO-2020010364 A1 | 1/2020 |
| WO | WO-2021142207 A1 | 7/2021 |

OTHER PUBLICATIONS

Atanasov et al., Discovery and resupply of pharmacologically active plant-derived natural products: A review. Biotechnol. Adv. 33: 1582-1614 (2015).
Auffinger et al., Halogen bonds in biological molecules. Proc. Natl. Acad. Sci. U.S. A. 101: 16789-16794 (2004).
Auldridge et al., Bacterial phytochromes: more than meets the light. Crit. Rev. Biochem. Mol. Biol. 46: 67-88 (2011).
Badran et al., Continuous evolution of Bacillus thuringiensis toxins overcomes insect resistance. Nature 533: 58-63 (2016).
Barr et al., Large-Scale Structural Analysis of the Classical Human Protein Tyrosine Phosphatome. Cell 136: 352-363 (2009).
Bence et al., Neuronal PTPIB regulates body weight, adiposity and leptin action. Nat. Med. 12: 917-24 (2006).
Brown et al., Halogenase Engineering for the Generation of New Natural Product Analogues. ChemBioChem 16: 2129-2135 (2015).
Butler et al., Key mutations alter the cytochrome P450 BM3 conformational landscape and remove inherent substrate bias. J. Biol. Chem. 288: 25387-25399 (2013).
Carter et al., Enthalpy-entropy compensation in biomolecular halogen bonds measured in DNA junctions. Biochemistry 52: 4891-4903 (2013).
Carter-Franklin et al., Vanadium haloperoxidase-catalyzed bromination and cyclization of terpenes. J. Am. Chem. Soc. 125: 3688-3689 (2003).
Chang et al., Production of isoprenoid pharmaceuticals by engineered microbes. Nat. Chem. Biol. 2: 674-681 (2006).
Chen et al., Allosteric inhibition of SHP2 phosphatase inhibits cancers driven by receptor tyrosine kinases. Nature 535: 148-52 (2016).
Choy et al., Conformational Rigidity and Protein Dynamics at Distinct Timescales Regulate PTPIB Activity and Allostery. Mol. Cell 65: 644-658 (2017).
Christianson, Structural biology and chemistry of the terpenoid cyclases. Chem. Rev. 106: 3412-3442 (2006).
Cortesio et al., Calpain 2 and PTPIB function in a novel pathway with Src to regulate invadopodia dynamics and breast cancer cell invasion. J. Cell Biol. 180: 957-971 (2008).
Cosentino et al., Engineering of a light-gated potassium channel. Science. 348: 707-710 (2015).
Cragg et al., Natural products: A continuing source of novel drug leads. Biochim. Biophys. Acta—Gen. Subj. 1830: 3670-3695 (2013).
Criswell et al., A single residue change leads to a hydroxylated product from the class II diterpene cyclization catalyzed by abietadiene synthase. Org. Lett. 14: 5828-5831 (2012).
Cui et al., A map of human cancer signaling. Mol. Syst. Biol. 3: 152 (2007).
Dagliyan et al., Engineering extrinsic disorder to control protein activity in living cells. Science. 354: 1441-1444 (2016).
Danial et al., Cell Death: Critical Control Points. Cell 116: 205-219 (2004).
Dietrich et al., A novel semi-biosynthetic route for artemisinin production using engineered substrate-promiscuous P450BM3. ACS Chem. Biol. 4: 261-267 (2009).
Dietrich et al., High-Throughput Metabolic Engineering: Advances in Small-Molecule Screening and Selection. Annu. Rev. Biochem. 79: 563-590 (2010).
Dube et al., Genetic ablation of protein tyrosine phosphatase IB accelerates lymphomagenesis of p53-null mice through the regulation of B-cell development. Cancer Res. 65: 10088-10095 (2005).
Dye, Flow cytometric analysis of CFP-YFP FRET as a marker for in vivo protein-protein interaction. Clin. Appl. Immunol. Rev. 5: 307-324 (2005).
Eden et al., Membrane contacts between endosomes and ER provide sites for PTPIB-epidermal growth factor receptor interaction. Nat. Cell Biol. 12: 267-72 (2010).
Esvelt et al., A system for the continuous directed evolution of biomolecules. Nature 472: 499-503 (2011).
Faeder et al., Rule-based modeling of biochemical systems with BioNetGen. Methods Mol. Biol. 500: 113-167 (2009).
Fan et al., Optical control of biological processes by light-switchable proteins. Wiley Interdiscip Rev Dev Biol 4(5):545-554 (2015).
Fan et al., Protein-tyrosine phosphatase IB antagonized signaling by insulin-like growth factor-1 receptor and kinase BRK/PTK6 in ovarian cancer cells. J. Biol. Chem. 288: 24923-34 (2013).
Fasan, Tuning P450 enzymes as oxidation catalysts. ACS Catal. 2: 647-666 (2012).
Fehr et al., In vivo imaging of the dynamics of glucose uptake in the cytosol of COS-7 cells by fluorescent nanosensors. J. Biol. Chem. 278: 19127-19133 (2003).
Feigner et al., Lipofection: a highly efficient, lipid-mediated DNA-transfection procedure. Proc. Natl. Acad. Sci. U. S. A. 84: 7413-7417 (1987).
Feiler et al., Directed Evolution of Mycobacterium tuberculosis (3-Lactamase Reveals Gatekeeper Residue That Regulates Antibiotic Resistance and Catalytic Efficiency. PLoS One 8, (2013).
Fox et al., Interactions between Hofmeister anions and the binding pocket of a protein. J. Am. Chem. Soc. 137: 3859-3866 (2015).
Fox et al., Water-Restructuring Mutations Can Reverse the Thermodynamic Signature of Ligand Binding to Human Carbonic Anhydrase. Angew. Chemie Int. Ed. 56: 3833-3837 (2017).
Fujimori et al., What's new in enzymatic halogenations. Curr. Opin. Chem. Biol. 11: 553-560 (2007).
Galanie et al., Complete biosynthesis of opioids in yeast. Science (80-.). 349: 1095-1100 (2015).
Gautier et al., How to control proteins with light in living systems. Nat. Chem. Biol. 10: 533-41 (2014).
George et al., Isoprenoid Drugs, Biofuels, and Chemicals-Artemisinin, Farnesene, and Beyond. Adv Biochem Eng Biotechnol 148: 355-389 (2014).
Gershenzon et al., The function of terpene natural products in the natural world. Nat. Chem. Biol. 3:408-414 (2007).
Gil-Parrado et al., Ionomycin-activated calpain triggers apoptosis. A probable role for Bcl-2 family members. J. Biol. Chem. 277: 27217-27226 (2002).
Govindarajan et al., Estimating the total number of protein folds. Proteins 35: 408-414 (1999).
Gruet et al., One-step generation of error-prone PCR libraries using Gateway® technology. Microb. Cell Fact. 11: 14(2012).
Haj et al., Imaging sites of receptor dephosphorylation by PTPIB on the surface of the endoplasmic reticulum. Science 295: 1708-1711 (2002).
Haj et al., Regulation of signaling at regions of cell-cell contact by endoplasmic reticulumbound protein-tyrosine phosphatase IB. PLoS One 7, (2012).
Halavaty et al., N- and C-terminal flanking regions modulate light-induced signal transduction in the LOV2 domain of the blue light sensor phototropin I from Avena sativa. Biochemistry 46: 14001-14009 (2007).
Hamberger et al., Evolution of diterpene metabolism: Sitka spruce CYP720B4 catalyzes multiple oxidations in resin acid biosynthesis of conifer defense against insects. Plant Physiol. 157: 1677-1695 (2011).
He et al., Protein tyrosine phosphatases as potential therapeutic targets. Acta Pharmacol. Sin. 35: 1227-1246 (2014).
Huang et al., Sesquiterpenes produced by truncated taxadiene synthase. Tetrahedron Lett. 41: 9701-9704 (2000).
Hubbard et al., Protein tyrosine kinase structure and function. Annu. Rev. Biochem. 69: 373-398 (2000).

(56) References Cited

OTHER PUBLICATIONS

Hughes et al., Principles of early drug discovery. Br. J. Pharmacol. 162: 1239-1249 (2011).
Ito et al., PTK6 inhibition suppresses metastases of triple-negative breast cancer via SNAIL-dependent E-cadherin regulation. Cancer Res. 76: 4406-4417 (2016).
Jia et al., Extreme promiscuity of a bacterial and a plant diterpene synthase enables combinatorial biosynthesis. Metab. Eng. 37: 24-34 (2016).
Johnson et al., Protein tyrosine phosphatase IB inhibitors for diabetes. Nat. Rev. Drug Discov. 1:696-709 (2002).
Jung et al., Cytochrome P450: Taming a wild type enzyme. Curr. Opin. Biotechnol. 22: 809-817 (2011).
Kaberniuk et al., A bacterial phytochrome-based optogenetic system controllable with near-infrared light. Nat. Methods 13: 1-15 (2016).
Kampranis et al., Rational conversion of substrate and product specificity in a Salvia monoterpene synthase: structural insights into the evolution of terpene synthase function. Plant Cell 19: 1994-2005 (2007).
Karunarathne et al., Subcellular optogenetics—controlling signaling and single-cell behavior. J Cell Sci 128(1):15-25 (2015).
Kennedy et al., Signal-Processing Machines at the Postsynaptic Density. Science. 290: 750-754 (2000).
Kennedy, Managing the drug discovery/development interface. Drug Discov. Today 2: 436-444 (1997).
Klebe et al., Applying thermodynamic profiling in lead finding and optimization. Nat. Rev. Drug Discov. 14:95-110 (2015).
Koh et al., Current trends in modern pharmaceutical analysis for drug discovery. Drug Discov. Today 8: 889-897 (2003).
Konc et al., ProBiS-CHARMMing: Web Interface for Prediction and Optimization of Ligands in Protein Binding Sites. J. Chem. Inf. Model. 55: 2308-2314 (2015).
Koren et al., Inhibition of the protein tyrosine phosphatase PTPIB: potential therapy for obesity, insulin resistance and type-2 diabetes mellitus. Best Pract. Res. Clin. Endocrinol. Metab. 21:621-640 (2007).
Krauss et al., LOVely enzymes—Towards engineering light-controllable biocatalysts. Microb. Biotechnol. 3:15-23 (2010).
Krimmer et al., Methyl, ethyl, propyl, butyl: Futile but not for water, as the correlation of structure and thermodynamic signature shows in a congeneric series of thermolysin inhibitors. ChemMedChem 9: 833-846 (2014).
Krishnan et al., Anxious moments for the protein tyrosine phosphatase PTPIB. Trends Neurosci. 38: 462-465 (2015).
Krishnan et al., Targeting the disordered C terminus of PTPIB with an allosteric inhibitor. Nat. Chem. Biol. 10: 558-566 (2014).
Lauchli et al., High-throughput screening for terpene-synthase-cyclization activity and directed evolution of a terpene synthase. Angew. Chemie—Int. Ed. 52: 5571-5574 (2013).
Lee et al., Phosphorylation of the AMPA receptor GluRI subunit is required for synaptic plasticity and retention of spatial memory. Cell 112: 631-643 (2003).
Lee et al., Surface sites for engineering allosteric control in proteins. Science 322: 438-442 (2008).
Lessard et al., PTPIB is an androgen receptor-regulated phosphatase that promotes the progression of prostate cancer. Cancer Res. 7 2: 1529-1537 (2012).
Lessard et al., The two faces of PTPIB in cancer. Biochim. Biophys. Acta—Proteins Proteomics 1804: 613-619 (2010).
Lewis et al., Combinatorial alanine substitution enables rapid optimization of cytochrome P450BM3 for selective hydroxylation of large substrates. ChemBioChem 11: 2502-2505.
Li et al., Reprogramming the chemodiversity of terpenoid cyclization by remolding the active site contour of epi-isozizaene synthase. Biochemistry 53: 1155-1168 (2014).
Liu et al., PTPIB promotes cell proliferation and metastasis through activating src and ERKI/2 innon-small cell lung cancer. Cancer Lett. 359: 218-225 (2015).

Lu et al., Co-expression of P450 BM3 and glucose dehydrogenase by recombinant *Escherichia coli* and its application in an NADPH-dependent indigo production system. J. Ind. Microbial. Biotechnol. 34: 247-253 (2007).
Lukyanov et al., Photoactivatable fluorescent proteins. Nat. Rev. Mol. Cell Biol. 6: 885-890 (2005).
Martin et al., Engineering a mevalonate pathway in *Escherichia coli* for production of terpenoids. Nat. Biotechnol. 21: 796-802 (2003).
Matulka et al., PTPIB is an effector of activin signaling and regulates neural specification of embryonic stem cells. Cell Stem Cell 13: 706-719 (2013).
Morrone et al., Increasing diterpene yield with a modular metabolic engineering system in *E. coli*: Comparison of MEV and MEP isoprenoid precursor pathway engineering. Appl. Microbial. Biotechnol. 85: 1893-1906 (2010).
Murphy et al., A flexible and accurate treatment of explicit water molecules in ligand-receptor docking. J. Med. Chem. acs.jmedchem. 6b00131 (2016).
Olsson et al., The Thermodynamics of Protein-Ligand Interaction and Salvation: Insights for Ligand Design. J. Mol. Biol. 384: 1002-1017 (2008).
O'Maille et al., Quantitative exploration of the catalytic landscape separating divergent plant sesquiterpene synthases. Nat. Chem. Biol. 4: 617-623 (2008).
Ouyang et al., Determination of hierarchical relationship of Src and Rae at subcellular locations with FRET biosensors. Proc Natl Acad Sci U S A 105: 14353-14358 (2008).
Packer et al., Methods for the directed evolution of proteins. Nat. Rev. Genet. 16: 379-394 (2015).
Pelander et al., In silico methods for predicting metabolism and mass fragmentation applied to quetiapine in liquid chromatography/time-of-flight mass spectrometry urine drug screening. Rapid Commun. Mass Spectrom. 23: 506-514 2009.
Peter et al., Mechanism of signal transduction of the LOV2-Ja photosensor from Avena sativa. Nat. Commun. 1: 122 (2010).
Peters et al., Abietadiene synthase catalysis: mutational analysis of a prenyl diphosphate ionization-initiated cyclization and rearrangement. Proc. Natl. Acad. Sci. U. S.A. 99: 580-584 (2002).
Pike et al., Protein tyrosine phosphatase IB is a regulator of the interleukin-10-induced transcriptional program in macrophages. Sci. Signal. 7: ra43 (2014).
Piserchio et al., Expression and purification of Src-family kinases for solution NMR studies. Methods Mol. Biol. 831: 111-131 (2012).
Qin et al., Chronic Stress Induces Anxiety via an Amygdalar Intracellular Cascade that Impairs Endocannabinoid Signaling. Neuron 85: 1319-1331 (2015).
Traves et al., Pivotal role of protein tyrosine phosphatase IB (PTPIB) in the macrophage response to proinflammatory and anti-inflammatory challenge. Cell Death Dis. 5: e1125 (2014).
Repina et al., At Light Speed: Advances in Optogenetic Systems for Regulating Cell Signaling and Behavior. Annu Rev Chem Biomol Eng 8:13-39 (2017).
Rhee et al., Protein tyrosine phosphatases in lymphocyte activation and autoimmunity. Nat. Immunol. 13: 439-447 (2012).
Rodriguez et al., The Growing and Glowing Toolbox of Fluorescent and Photoactive Proteins. Trends Biochem. Sci. 42: 111-129 (2017).
Romsicki et al., Protein Tyrosine Phosphatase-IE Dephosphorylation of the Insulin Receptor Occurs in a Perinuclear Endosome Compartment in Human Embryonic Kidney 293 Cells. J. Biol. Chem. 279: 12868-12875 (2004).
Rowland et al., ER contact sites define the position and timing of endosome fission. Cell 159: 1027-1041 (2014).
Ruttkies et al., MetFrag relaunched: Incorporating strategies beyond in silica fragmentation. J. Cheminform. 8, (2016).
Sato et al.: Fluorescent indicators for imaging protein phosphorylation in single living cells. Cell Biol. vol. 2:325-328 http:doi.org/10.1016/B978-012164730-8/50114-3 (2006).
Seifert et al., Rational design of a minimal and highly enriched CYP102AI mutant library with improved regio-, stereo- and chemoselectivity. ChemBioChem 10: 853-861 (2009).
Shepherd et al., A Structure-Guided Switch in the Regioselectivity of a Tryptophan Halogenase. ChemBioChem 17: 821-824 (2016).

(56) References Cited

OTHER PUBLICATIONS

Snyder et al., Is it the shape of the cavity, or the shape of the water in the cavity? Eur. Phys. J. Spec. Top. 223: 853-891 (2014).
Soysal et al., PTP1B expression is an independent positive prognostic factor in human breast cancer. Breast Cancer Res. Treat. 137: 637-644 (2013).
Steele et al., Sesquiterpene Synthases from Grand Fir (*Abies grandis*). J. Biol. Chem. 273: 2078-2089 (1998).
Strickland et al., Rationally improving LOV domain-based photoswitches. Nat. Methods 7: 623-6 (2010).
Sun et al., Crystal structure of PTP1B complexed with a potent and selective bidentate inhibitor. J. Biol. Chem. 278: 12406-12414 (2003).
Tachibana et al., Novel prenyltransferase gene encoding farnesylgeranyl diphosphate synthase from a hyperthermophilic archaeon, Aeropyrum pernix. Molecular evolution with alteration in product specificity. Eur. J. Biochem. 267: 321-328 (2000).
Tiganis et al., Epidermal growth factor receptor and the adaptor protein p52Shc are specific substrates of T-cell protein tyrosine phosphatase. Mol. Cell. Biol. 18: 1622-1634 (1998).
Ting et al., Genetically encoded fluorescent reporters of protein tyrosine kinase activities in living cells. Proc. Natl. Acad. Sci. U. S. A. 98: 15003-15008 (2001).
Tonks et al., A Brake Becomes an Accelerator: PTP1B-A New Therapeutic Target for Breast Cancer. Cancer Cell 11: 214-216 (2007).
Tzeng et al., Protein activity regulation by conformational entropy. Nature 488: 236-240 (2012).
Van Stokkum et al., The primary photophysics of the Avena sativa phototropin 1 LOV2 domain observed with time-resolved emission spectroscopy. Photochem. Photobiol. 87: 534-541 (2011).
Vereb et al., Flow cytometric FRET analysis of protein interaction. Methods Mol. Biol. 699: 371-92 (2011).
Volinksy et al., Complexity of receptor tyrosine kinase signal processing. Cold Spring Harb. Perspect. Biol. 5, (2013).
Weaver, Invadopodia: Specialized cell structures for cancer invasion. Clin. Exp. Metastasis 23: 97-105 (2006).
Welsch et al., Privileged scaffolds for library design and drug discovery. Curr. Opin. Chem. Biol. 14: 347-361 (2010).
Whitesides et al., Designing ligands to bind proteins. Q. Rev. Biophys. 38(4): 385-395 (2005).
Wiesmann et al., Allosteric inhibition of protein tyrosine phosphatase 1B. Nat. Struct. Mol. Biol. 11: 730-737 (2004).
Wilderman et al., A single residue switch converts abietadiene synthase into a pimaradiene specific cyclase. J. Am. Chem. Soc. 129: 15736-15737 (2007).
Wray et al., Inhibition of glycogen synthase kinase-3 alleviates Tcf3 repression of the pluripotency network and increases embryonic stem cell resistance to differentiation. Nat. Cell Biol. 13: 838-845 (2011).
Wu et al., A genetically encoded photoactivatable Rac1 controls the motility of living cells. Nature 461: 104-108 (2009).
Wu et al., FDA-approved small-molecule kinase inhibitors. Trends Pharmacol. Sci. 36: 422-439 (2015).
Wu et al., Protein tyrosine phosphatase PTP1B is involved in neuroendocrine differentiation of prostate cancer. Prostate 66: 1124-1135 (2006).
Yao et al., Estimation of the available free energy in a LOV2-Jα photoswitch. Nat. Chem. Biol. 4: 491-497 (2008).
Yoshikuni et al., Designed divergent evolution of enzyme function. Nature 440: 1078-1082 (2006).
Zayner et al., The amino-terminal helix modulates light-activated conformational changes in AsLOV2. J. Mol. Biol. 419: 61-74 (2012).
Zegzouti et al., ADP-Glo: A Bioluminescent and Homogeneous ADP Monitoring Assay for Kinases. Assay Drug Dev. Technol. 7: 560-572 (2009).
Zhang et al., Biosensors and their applications in microbial metabolic engineering. Trends Microbial. 19: 323-329 (2011).
Zhang et al., Genetic reduction of striatal-enriched tyrosine phosphatase (STEP) reverses cognitive and cellular deficits in an Alzheimer's disease mouse model. Proc. Natl. Acad. Sci. 107: 19014-19019 (2010).
Zhang et al., P450 fingerprinting method for rapid discovery of terpene hydroxylating P450 catalysts with diversified regioselectivity. J. Am. Chem. Soc. 133: 3242-3245 (2011).
Zhang et al., PTP1B as a drug target: recent developments in PTP1B inhibitor discovery. Drug Discov. Today 12: 373-381 (2007).
Zhou et al., Optical control of cell signaling by single-chain photoswitchable kinases. Science. 355: 836-842 (2017).
Zhu et al., PTP1B contributes to the oncogenic properties of colon cancer cells through Src activation. Cancer Res. 67: 10129-10137 (2007).
PCT/US2019/040896 International Search Report and Written Opinion dated Nov. 8, 2019.
Abraham, M. J. et al. Gromacs: High performance molecular simulations through multi-level parallelism from laptops to supercomputers. SoftwareX 1, 19-25 (2015).
Abu Bakar et al., Nonstructural proteins of alphavirus—potential targets for drug development. Viruses 10, 71 (2018).
Adams et al., Potent and selective inhibitors of the proteasome: dipeptidyl boronic acids. Bioorganic & medicinal chemistry letters 8, 333-338 (1998).
Aerts et al., Are public-private partnerships the solution to tackle neglected tropical diseases? A systematic review of the literature. Health Policy 121, 745-754 (2017).
Afonine, P. V et al. Towards automated crystallographic structure refinement with phenix.refine. Acta Crystallogr. D. Biol. Crystallogr. 68, 352-67 (2012).
Akutsu et al., Molecular basis for ubiquitin and ISG15 cross-reactivity in viral ovarian tumor domains. Proceedings of the National Academy of Sciences 108, 2228-2233 (2011).
Aleshin et al., Activity, specificity, and probe design for the smallpox virus protease K7L. Journal of Biological Chemistry 287, 39470-39479 (2012).
Aleshin et al., Structural evidence for regulation and specificity of flaviviral proteases and evolution of the Flaviviridae fold. Protein science 16, 795-806 (2007).
Amamuddy, O. S. et al. Integrated computational approaches and tools for allosteric drug discovery. Int. J. Mol. Sci. 21, 847 (2020).
Antosch, J., Schaefers, F. & Guider, T. A. M. Heterologous Reconstitution of Ikarugamycin Biosynthesis in *E. coli*. Angew. Chemie Int. Ed. 53, 3011-3014 (2014).
Atanasov et al., Natural products in drug discovery: Advances and opportunities. Nature Reviews Drug Discovery 20, 200-216 (2021).
Atta et al., Molecular cloning and characterization of (+)-epi-α-bisabolol synthase, catalyzing the first step in the biosynthesis of the natural sweetener, hernandulcin, in Lippia dulcis. Archives of Biochemistry and Biophysics 527, 37-44 (2012).
Banno, R. et al. PTP1B and SHP2 in POMC neurons reciprocally regulate energy balance in mice. J. Clin. Invest. 120, 720-734 (2010).
Benkert, P., Biasini, M. & Schwede, T. Toward the estimation of the absolute quality of individual protein structure models. Bioinformatics (2011). doi:10.1093/bioinformatics/btq662.
Bentires-Alj, M. & Neel, B. G. Protein-tyrosine phosphatase 1B is required for HER2/Neu-induced breast cancer. Cancer Res. (2007). doi:10.1158/0008-5472.CAN-06-4610.
Bergmann et al., The refined crystal structure of the 3C gene product from hepatitis A virus: specific proteinase activity and RNA recognition. Journal of Virology 71, 2436-2448 (1997).
Bernhardt, R. Cytochromes P450 as versatile biocatalysts. Journal of biotechnology 124, 128-145 (2006).
Bohlmann, J et al., Terpenoid-based defenses in conifers: cDNA cloning, characterization, and functional expression of wound-inducible (E)-bisabolene synthase from grand fir (*Abies grandis*) [sesquiterpene synthasejuvenile hormone analogueplant defense gene(E)-4-(1,5-dimethyl-1,4-hexadienyl)-1-methylcyclohexenetodomatuic acid]. 95, (1998).
Boras et al., Preclinical characterization of an intravenous coronavirus 3CL protease inhibitor for the potential treatment of COVID19. Nature Communications 12, 6055 (2021).

(56) References Cited

OTHER PUBLICATIONS

Boulware, K. T. & Daugherty, P. S. Protease specificity determination by using cellular libraries of peptide substrates (CLiPS). Proceedings of the National Academy of Sciences 103, 7583-7588 (2006).
Bozhüyük, K. A. J. et al., Modification and de novo design of non-ribosomal peptide synthetases using specific assembly points within condensation domains. Nature Chemistry 11, 653-661 (2019).
Bullock, B. N. et al., Assessing helical protein interfaces for inhibitor design. Journal of the American Chemical Society 133, 14220-14223 (2011).
Burnham, K. P. & Anderson, D. R. Model Selection and Multimodel Inference: a Practical Information-theoretic Approach, 2nd edn. Springer-Verlag, New York. New York Springer 60, (2002).
Bussi, G., Donadio, D. & Parrinello, M. Canonical sampling through velocity rescaling. J. Chem. Phys. 126, 014101 (2007).
Calla, B. et al., Cytochrome P450 diversification and hostplant utilization patterns in specialist and generalist moths: Birth, death and adaptation. Molecular ecology 26, 6021-6035 (2017).
Camuesco, D. et al., The intestinal anti-inflammatory effect of quercitrin is associated with an inhibition in iNOS expression. British journal of pharmacology 143, 908-918 (2004).
Carlson, J. C. et al., Negative selection and stringency modulation in phage-assisted continuous evolution. Nat. Chem. Biol. 10, 216-222 (2014).
Chandramouli et al., Serotype-specific structural differences in the protease-cofactor complexes of the dengue virus family. Journal of virology 84, 3059-3067 (2010).
Chang, M. C. Y. et al., Engineering *Escherichia coli* for production of functionalized terpenoids using plant P450s. Nature Chemical Biology 3, 274-277 (2007).
Chatzivasileiou, A. O. et al., Two-step pathway for isoprenoid synthesis. Proceedings of the National Academy of Sciences of the United States of America 116, 506-511 (2019).
Chaudhury, S. & Gray, J. J. Identification of Structural Mechanisms of HIV-1 Protease Specificity Using Computational Peptide Docking: Implications for Drug Resistance. Structure 17, 1636-1648 (2009).
Cheesman, M. J. et al., Soluble and membrane-bound *Drosophila melanogaster* CYP6G1 expressed in *Escherichia coli*: purification, activity, and binding properties toward multiple pesticides. Insect biochemistry and molecular biology 43, 455-465 (2013).
Chen et al., Mechanisms of activation and inhibition of Zika virus NS2B-NS3 protease. Cell research 26, 1260-1263 (2016).
Chen, M. J., Dixon, J. E. & Manning, G. Genomics and evolution of protein phosphatases. Sci. Signal. 10, 1-17 (2017).
Chen, M. S. & White, M. C. A predictably selective aliphatic C-H oxidation reaction for complex molecule synthesis. Science 318, 783-787 (2007).
Chen, X. et al. Statistical experimental design guided optimization of a one-pot biphasic multienzyme total synthesis of amorpha-4,11-diene. PLoS One 8, e79650 (2013).
Chen, Y. et al., Emerging coronaviruses: Genome structure, replication, and pathogenesis. Journal of Medical Virology 92, 418-423 (2020).
Cheng, Y. et al., Kidney disease is associated with in-hospital death of patients with COVID-19. Kidney International (2020). doi:10.1016/j.kint.2020.03.005.
Cho, I. et al., Site-selective enzymatic C-H amidation for synthesis of diverse lactams. Science 364, 575-578 (2019). Retraction (2020).
Choi, E. et al. Mitotic regulators and the SHP2-MAPK pathway promote IR endocytosis and feedback regulation of insulin signaling. Nat. Commun. 10, (2019).
Choi, J.-M. & Pappu, R. V. Improvements to the ABSINTH Force Field for Proteins Based on Experimentally Derived Amino Acid Specific Backbone Conformational Statistics. J. Chem. Theory Comput. 15, 1367-1382 (2019).
Choi, O. et al. Biosynthesis of plant-specific phenylpropanoids by construction of an artificial biosynthetic pathway in *Escherichia coli*. J. Ind. Microbiol. Biotechnol. (2011). doi:10.1007/s10295-011-0954-3.
Culp, E. J. et al., Evolution-guided discovery of antibiotics that inhibit peptidoglycan remodelling. Nature 578, 582-587 (2020).
Cutler, D. M. & Summers, L. H. The COVID-19 pandemic and the $16 trillion virus. Jama 324, 1495-1496 (2020).
D'Arcy, A. et al., Purification and crystallization of dengue and West Nile virus NS2B-NS3 complexes. Acta crystallographica. Section F, Structural biology and crystallization communications 62, 157-162 (2006).
Darden, T., York, D. & Pedersen, L. Particle mesh Ewald: An N·log(N) method for Ewald sums in large systems. J. Chem. Phys. 98, 10089 (1993).
Davis, A. M., Plowright, A. T. & Valeur, E. Directing evolution: The next revolution in drug discovery? Nature Reviews Drug Discovery 16, 681-698 (2017).
Davis, et al. Design, construction and characterization of a set of insulated bacterial promoters. Nucleic Acids Res. Feb. 2011;39(3):1131-41.
De Sousa, L. et al., Flavonoids as noncompetitive inhibitors of Dengue virus NS2B-NS3 protease: Inhibition kinetics and docking studies. Bioorganic & Medicinal Chemistry 23, 466-470 (2015).
Dias et al., A Historical overview of natural products in drug discovery. Metabolites 33, 1582-1614 (2012).
Dong et al.: An interactive web-based dashboard to track COVID-19 in real time. Lancet Infect Dis 20(5):533-534 (2020).
Douangamath, A. et al., Crystallographic and electrophilic fragment screening of the SARS-CoV-2 main protease. Nature Communications 11, 5047 (2020).
Douzery, E. J. P. et al., The timing of eukaryotic evolution: Does a relaxed molecular clock reconcile proteins and fossils? Proc. Natl. Acad. Sci. U. S. A. 101, 15386-15391 (2004).
Dove, S. L. & Hochschild, A. Conversion of the ω subunit of *Escherichia coli* RNA polymerase into a transcriptional activator or an activation target. Genes and Development 12, 745-754 (1998).
Dove, S. L. et al., Activation of prokaryotic transcription through arbitrary protein-protein contacts. Nature 386, 627-630 (1997).
Dubois, M. J. et al. The SHP-1 protein tyrosine phosphatase negatively modulates glucose homeostasis. Nat. Med. 12, 549-556 (2006).
Eche, S. & Gordon, M. L. Recombinant expression of HIV-1 protease using soluble fusion tags in *Escherichia coli*: A vital tool for functional characterization of HIV-1 protease. Virus Research 295, 198289 (2021).
Edgar, S. et al. Mechanistic Insights into Taxadiene Epoxidation by Taxadiene-5α-Hydroxylase. ACS Chem. Biol. 11, 460-469 (2016).
Emanuel, E. J. et al., Fair Allocation of Scarce Medical Resources in the Time of Covid-19. New England Journal of Medicine (2020). doi:10.1056/nejmsb2005114.
Emsley et al. Coot: model-building tools for molecular graphics. Acta crystallographica Section D, Biological crystallography 60:2126-2132 (2004).
EP Application No. 19831095.5 European Search Report dated Mar. 7, 2022.
Erbel et al., Structural basis for the activation of flaviviral NS3 proteases from dengue and West Nile virus. Nature structural & molecular biology 13, 372-373 (2006).
FDA Food and Drug Administration. Coronavirus (COVID-19) Drugs, at https://www.fda.gov/drugs/emergency-preparedness-drugs/coronavirus-covid-19-drugs (2022).
FDA Food and Drug Administration. Emergency Use Authorization. https://www.fda.gov/emergency-preparedness-and-response/mcm-legal-regulatory-and-policy-framework/emergency-use-authorization#coviddrugs (2022).
Ferguson, F. M. & Gray, N. S. Kinase inhibitors: The road ahead. Nature Reviews Drug Discovery 17, 353-376 (2018).
Ferreira, L. G. et al., Molecular docking and structure-based drug design strategies. Molecules 20, 13384-13421 (2015).
Fox, J. M. et al., The Molecular Origin of Enthalpy/Entropy Compensation in Biomolecular Recognition. Annu. Rev. Biophys. 47, (2018).

(56) References Cited

OTHER PUBLICATIONS

Fürstenberg-Hägg, J. et al., Plant defense against insect herbivores. International Journal of Molecular Sciences 14, 10242-10297 (2013).
Fujisawa, M. et al., Cloning and characterization of a novel gene that encodes (S)-β-bisabolene synthase from ginger, Zingiber officinale. Planta 232, 121-130 (2010).
Gallagher, T. COVID19 therapeutics: Expanding the antiviral arsenal. EBioMedicine 66, (2021).
Gao, Y. et al., Structure of the RNA-dependent RNA polymerase from COVID-19 virus. Science eabb7498 (2020). doi:10.1126/science.abb7498.
Gavory, G. et al., Discovery and characterization of highly potent and selective allosteric USP7 inhibitors. Nature Chemical Biology 14, 118-125 (2018).
Gibbs, A. C. et al., Inhibitor bound dengue NS2B-NS3pro reveals multiple dynamic binding modes. Biochemistry 57, 1591-1602 (2018).
Goldberg and Lee., Proteasome inhibitors: valuable new tools for cell biologists. Trends in cell biology 8, 397-403 (1998).
Goldstein, B. J., Bittner-Kowalczyk, A., White, M. F. & Harbeck, M. Tyrosine dephosphorylation and deactivation of insulin receptor substrate-1 by protein-tyrosine phosphatase 1B. Possible facilitation by the formation of a ternary complex with the GRB2 adaptor protein. J. Biol. Chem. 275, 4283-4289 (2000).
Gorbalenya, A. E. et al. Coronaviridae Study Group of the International Committee on Taxonomy of Viruses. The species Severe acute respiratory syndrome-related coronavirus: classifying 2019-nCoV and naming it SARS-CoV-2. Nature Microbiology 5, 536-544 (2020).
Gordon et al. A SARS-CoV-2-Human Protein-Protein Interaction Map Reveals Drug Targets and Potential Drug-Repurposing. Nature. 583:459-468 (2020) bioRxiv Available at https://doi.org/10.1101/2020.03.22.002386.
Grangeasse, C., Nessler, S. & Mijakovic, I. Bacterial tyrosine kinases: Evolution, biological function and structural insights. Philos. Trans. R. Soc. B Biol. Sci. 367, 2640-2655 (2012).
Gu et al., COVID-19: gastrointestinal manifestations and potential fecal-oral transmission. Gastroenterology, 158(6) (2020).
Guex, N., Peitsch, M. C. & Schwede, T. Automated comparative protein structure modeling with Swiss-Model and Swiss-PdbViewer: A historical perspective. Electrophoresis (2009). doi:10.1002/elps.200900140.
Gunst, J. D. et al., Efficacy of the TMPRSS2 inhibitor camostat mesilate in patients hospitalized with Covid-19-a double-blind randomized controlled trial. EClinicalMedicine 35, 100849 (2021).
Guo et al., Discovery of Reactive Microbiota-Derived Metabolites that Inhibit Host Proteases. Cell. Jan. 26, 2017;168(3):517-526.e18. doi:10.1016/j.cell.2016.12.021. Epub Jan. 19, 2017.
Hammamy et al., Development and Characterization of New Peptidomimetic Inhibitors of the West Nile Virus NS2B-NS3 Protease. ChemMedChem 8, 231-241 (2013).
Hartenfeller, M. & Schneider, G. De Novo Drug Design, in Chemoinformatics and Computational Chemical Biology (ed. Bajorath, J.) 299-323 (Humana Press, 2011). doi: 10.1007/978-1-60761-839-3_12.
Harvey, A. L. et al., The re-emergence of natural products for drug discovery in the genomics era. Nature reviews drug discovery 14, 111-129 (2015).
Harvey, A. L. Natural products in drug discovery. Drug Discovery Today 13, 894-901 (2008).
Henrich, C. J. & Beutler, J. A. Matching the power of high throughput screening to the chemical diversity of natural products. Nat. Prod. Rep. 30, 1284-1298 (2013).
Hert, J., Irwin, J. J., Laggner, C., Keiser, M. J. & Shoichet, B. K. Quantifying biogenic bias in screening libraries. Nat. Chem. Biol. 5, pp. 479-483 (2009).
Hess, B., Bekker, H., Berendsen, H. J. C. & Fraaije, J. G. E. M. Lincs: A linear constraint solver for molecular simulations. J. Comput. Chem. 18, 1463-1472 (1997).

Hjortness, M. K. et al. Abietane-Type Diterpenoids Inhibit Protein Tyrosine Phosphatases by Stabilizing an Inactive Enzyme Conformation. Biochemistry 57, 5886-5896 (2018).
Hjortness, M. K. et al. Evolutionarily Conserved Allosteric Communication in Protein Tyrosine Phosphatases. Biochemistry 57, 6443-6451 (2018).
Ho et al., Critical assessment of the important residues involved in the dimerization and catalysis of MERS coronavirus main protease. PLoS One 10, e0144865 (2015).
Hoffman et al., SARS-CoV-2 cell entry depends on ACE2 and TMPRSS2 and is blocked by a clinically proven protease inhibitor. Cell Press, 181, 271-280 (2020).
Hu, X. et al., Kinetic, mutational, and structural studies of the Venezuelan equine encephalitis virus nonstructural protein 2 cysteine protease. Biochemistry 55, 3007-3019 (2016).
Huang, J. et al. CHARMM36m: An improved force field for folded and intrinsically disordered proteins. Nat. Methods 14, 71-73 (2016).
Huang, L. & Chen, C. Understanding HIV-1 protease autoprocessing for novel therapeutic development. Future medicinal chemistry 5, 1215-1229 (2013).
Hubert, J. et al., Dereplication strategies in natural product research: How many tools and methodologies behind the same concept? Phytochemistry Reviews 16, 55-95 (2017).
Jantan, I., Ahmad, W. & Bukhari, S. N. A. Plant-derived immunomodulators: an insight on their preclinical evaluation and clinical trials. Frontiers in plant science 6, 655 (2015).
Jendresen, C. B. et al., Highly active and specific tyrosine ammonia-lyases from diverse origins enable enhanced production of aromatic compounds in bacteria and Saccharomyces cerevisiae. Applied and environmental microbiology 81, 4458-4476 (2015).
Jensen, P. R. et al., Challenges and triumphs to genomics-based natural product discovery. Journal of Industrial Microbiology and Biotechnology 41, 203-209 (2014).
Jensen, P. R. Natural Products and the Gene Cluster Revolution. Trends in Microbiology 24, 968-977 (2016).
Jewell, D. A. et al., Hepatitis A virus 3C proteinase substrate specificity. Biochemistry 31, 7862-7869 (1992).
Jia, M., et al., Combinatorial biosynthesis and the basis for substrate promiscuity in class I diterpene synthases. Metabolic engineering 55, 44-58 (2019).
Jiang, C. S., Liang, L. F. & Guo, Y. W. Natural products possessing protein tyrosine phosphatase 1B (PTP1B) inhibitory activity found in the last decades. Acta Pharmacologica Sinica 33, 1217-1245 (2012). doi:10.1038/aps.2012.90.
Jin et al., Structure of Mpro from SARS-CoV-2 and discovery of its inhibitors. Nature 582, 289-293 (2020).
Johnston, C. W., Badran, A. H. & Collins, J. J. Continuous bioactivity-dependent evolution of an antibiotic biosynthetic pathway. Nat. Commun. 11, 4202 (2020).
Joosten, R. P., Long, F., Murshudov, G. N. & Perrakis, A. The PDB_REDO server for macromolecular structure model optimization. IUCrJ 1, 213-220 (2014).
Kachroo, A. H. et al. Systematic humanization of yeast genes reveals conserved functions and genetic modularity. Science (80-.). 348, 921-925 (2015).
Kaneko, T. et al. Superbinder SH2 domains act as antagonists of cell signaling. Sci. Signal. 5, (2012).
Keedy, D. A. et al. An expanded allosteric network in PTP1B by multitemperature crystallography, fragment screening, and covalent tethering. Elife 7, doi: 10.7554/eLife.36307 (2018).
Khaerunnisa et al., Potential Inhibitor of COVID-19 Main Protease (M pro) from Several Medicinal Plant Compounds by Molecular Docking Study. Preprints (2020). doi: 10.20944/preprints202003.0226.v1.
Khrimian, A. et al., Absolute Configurations of Stink Bug- And Plant-Produced Sesquipiperitols via Synthesis of All Stereoisomers. Journal of Natural Products 83, 2281-2286 (2020).
Kitaoka, N. et al., Optimization of recombinant expression enables discovery of novel cytochrome P450 activity in rice diterpenoid biosynthesis. Applied Microbiology and Biotechnology 99, 7549-7558 (2015).

(56) References Cited

OTHER PUBLICATIONS

Koehn, F. E. & Carter, G. T. The evolving role of natural products in drug discovery. Nature reviews Drug discovery 4, 206-220 (2005).
Kondo et al., Yellow fever virus NS2B/NS3 protease: hydrolytic properties and substrate specificity. Biochemical and biophysical research communications 407, 640-644 (2011).
Krishnan, N. et al. PTP1B inhibition suggests a therapeutic strategy for Rett syndrome. J. Clin. Invest. (2015). doi:10.1172/JCI80323.
Lancaster, J. et al., An IDS-Type Sesquiterpene Synthase Produces the Pheromone Precursor (Z)-α-Bisabolene in Nezara viridula. Journal of Chemical Ecology 45, 187-197 (2019).
Lange, B. M. & Srividya, N. Enzymology of monoterpene functionalization in glandular trichomes. Journal of Experimental Botany 70, 1095-1108 (2019).
Lee et al., Identification of novel small molecule inhibitors against NS2B/NS3 serine protease from Zika virus. Antiviral research 139, 49-58 (2017).
Lee et al. Proteasome inhibitors: valuable new tools for cell biologists. Trends Cell Biol 8(10):397-403 (1998).
Lei et al., Crystal structure of the papain-like protease of MERS coronavirus reveals unusual, potentially druggable active-site features. Antiviral research 109, 72-82 (2014).
Lei et al., Crystal structure of Zika virus NS2B-NS3 protease in complex with a boronate inhibitor. Science 353, 503-505 (2016).
Li et al., Therapeutic options for the 2019 novel coronavirus (2019-nCoV). Nature Reviews, 19 149-150 (2020).
Li, H. et al. Crystal Structure and Substrate Specificity of PTPN12. Cell Rep. (2016). doi:10.1016/j.celrep.2016.04.016.
Li, J. et al., Production of plant-specific flavones baicalein and scutellarein in an engineered E. coli from available phenylalanine and tyrosine. Metabolic Engineering 52, 124-133 (2019).
Li, J. W. H. & Vederas, J. C. Drug discovery and natural products: End of era or an endless frontier? Biomeditsinskaya Khimiya 57, 148-160 (2011).
Li, Y. et al., Complete biosynthesis of noscapine and halogenated alkaloids in yeast. Proceedings of the National Academy of Sciences of the United States of America 115, E3922-E3931 (2018).
Lim, H. S. et al., (−)-α-Bisabolol Production in Engineered Escherichia coli Expressing a Novel (−)-α-Bisabolol Synthase from the Globe Artichoke Cynara cardunculus var. Scolymus. Journal of Agricultural and Food Chemistry 69, 8492-8503 (2021).
Lim, Y. et al., Human Coronaviruses: A Review of Virus-Host Interactions. Diseases 4, 26 (2016).
Lindner et al., The papain-like protease from the severe acute respiratory syndrome coronavirus is a deubiquitinating enzyme. Journal of virology 79, 15199-15208 (2005).
Ling, T. et al., Cytostatic and cytotoxic natural products against cancer cell models. Molecules 24, 2012 (2019).
Loehr et al., Yellow fever virus NS3 protease: peptide-inhibition studies. Journal of general virology 88, 2223-2227 (2007).
Luo et al., Crystal structure of the NS3 protease-helicase from dengue virus. Journal of virology 82, 173-183 (2008).
Luo et al., Flexibility between the protease and helicase domains of the dengue virus NS3 protein conferred by the linker region and its functional implications. Journal of biological chemistry 285, 18817-18827 (2010).
Luo, X. et al., Complete biosynthesis of cannabinoids and their unnatural analogues in yeast. Nature 567, 123-126 (2019). Correction (2020).
Lv et al. HIV protease inhibitors: a review of molecular selectivity and toxicity. Hiv Aids (Auckl). Apr. 8, 2015;7:95-104. doi: 10.2147/HIV.S79956. eCollection 2015.
Mackerell, A. D. et al. All-atom empirical potential for molecular modeling and dynamics studies of proteins. J. Phys. Chem. B 102, 3586-3616 (1998).
Mafu et al., Probing the promiscuity of ent -kaurene oxidases via combinatorial biosynthesis. Proceedings of the National Academy of Sciences 113, 2526-2531 (2016).

Maier, M. E. Design and synthesis of analogues of natural products. Organic and Biomolecular Chemistry 13, 5302-5343 (2015).
Malcolm, B. A. et al., Expression and characterization of recombinant hepatitis A virus 3C proteinase. Biochemistry 31, 3358-3363 (1992).
Manguso et al. In vivo CRISPR screening identifies Ptpn2 as a cancer immunotherapy target. Nature 547:413-418 (2017).
Mao, L. et al., Neurologic Manifestations of Hospitalized Patients With Coronavirus Disease 2019 in Wuhan, China. JAMA Neurol. Jun. 1, 2020;77(6):683-690. doi: 10.1001/jamaneurol.2020.1127.
Martins, A. et al., Marketed marine natural products in the pharmaceutical and cosmeceutical industries: Tips for success. Marine drugs 12, 1066-1101 (2014).
McAndrew, R. P. et al., Structure of a three-domain sesquiterpene synthase: A prospective target for advanced biofuels production. Structure 19, 1876-1884 (2011).
McKibbin, W. J. & Fernando, R. The Global Macroeconomic Impacts of COVID-19: Seven Scenarios. SSRN Electronic Journal (2020). doi:10.2139/ssrn.3547729.
Medema et al. antiSMASH: rapid identification, annotation and analysis of secondary metabolite biosynthesis gene clusters in bacterial and fungal genome sequences. Nucleic Acids Res. Jul. 2011;39(Web Server issue):W339-46.
Mehla, J. et al., A comparison of two-hybrid approaches for detecting protein-protein interactions. Methods in enzymology 586, 333-358 (2017).
Mellott, D. M. et al., A Clinical-Stage Cysteine Protease Inhibitor blocks SARS-CoV-2 Infection of Human and Monkey Cells. ACS Chemical Biology 16, 642-650 (2021).
Mendoza, E. J. et al., Two Detailed Plaque Assay Protocols for the Quantification of Infectious SARS-CoV-2. Current protocols in microbiology 57, ecpmc105 (2020).
Menon, B. R. K. et al., RadH: A Versatile Halogenase for Integration into Synthetic Pathways. Angewandte Chemie 129, 12003-12007 (2017).
Merck. Merck and Ridgeback Biotherapeutics Provide Update on Results from MOVe-OUT Study of Molnupiravir, an Investigational Oral Antiviral Medicine, in At Risk Adults With Mild-to-Moderate COVID-19, at https://www.merck.com/news/merck-and-ridgeback-biotherapeutics-provide-update-on-results-from-move-out-study-of-molnupiravir-an-investigational-oral-antiviral-medicine-in-at-risk-adults-with-mild-to-moderate-covid-19/ (2021).
Merck. Merck and Ridgeback's Investigational Oral Antiviral Molnupiravir Reduced the Risk of Hospitalization or Death by Approximately 50 Percent Compared to Placebo for Patients with Mild or Moderate COVID-19 in Positive Interim Analysis of Phase 3 Study, at https://www.merck.com/news/merck-and-ridgebacks-investigational-oral-antiviral-molnupiravir-reduced-the-risk-of-hospitalization-or-death-by-approximately-50-percent-compared-to-placebo-for-patients-with-mild-or-moderat/ (2021).
Mobley, D. L. & Gilson, M. K. Predicting Binding Free Energies: Frontiers and Benchmarks. Annu. Rev. Biophys. 46, 531-558 (2017).
Montalibet, J. & Kennedy, B. P. Using yeast to screen for inhibitors of protein tyrosine phosphatase 1B. Biochem. Pharmacol. 68, 1807-1814 (2004).
Montalibet, J. et al. Residues distant from the active site influence protein-tyrosine phosphatase 1B inhibitor binding. J. Biol. Chem. 281, 5258-5266 (2006).
Muangphrom, P. et al., Identification and characterization of a novel sesquiterpene synthase, 4-amorphen-11-ol synthase, from artemisia maritima. Plant Biotechnology 35, 113-121 (2018).
Muangphrom, P. et al. Functional analysis of amorpha-4,11-diene synthase (ADS) homologs from non-artemisinin-producing artemisia species: The discovery of novel koidzumiol and (+)-a-Bisabolol synthases. Plant and Cell Physiology 57, 1678-1688 (2016).
Muzzarelli et al., Structural and antiviral studies of the human norovirus GII.4 protease. Biochemistry 58, 900-907 (2019).
Nakamura et al., A norovirus protease structure provides insights into active and substrate binding site integrity. Journal of virology 79, 13685-13693 (2005).

(56) References Cited

OTHER PUBLICATIONS

Nalam, M. N. L. et al., Evaluating the substrate-envelope hypothesis: structural analysis of novel HIV-1 protease inhibitors designed to be robust against drug resistance. Journal of virology 84, 5368-78 (2010).

Namchuk, M. N. Early Returns on Small Molecule Therapeutics for SARS-CoV-2. ACS Infectious Diseases 7, 1298-1302 (2021).

Narwal, M. et al., Crystal structure of chikungunya virus nsP2 cysteine protease reveals a putative flexible loop blocking its active site. International journal of biological macromolecules 116, 451-462 (2018).

Needle et al., Structures of the Middle East respiratory syndrome coronavirus 3C-like protease reveal insights into substrate specificity. Acta Crystallographica Section D: Biological Crystallography 71, 1102-1111 (2015).

Newman, D. J. & Cragg, G. M., Natural Products as Sources of New Drugs from 1981 to 2014. Journal of Natural Products 79, 629-661 (2016).

Next Generation Sequencing: Amplicon-EZ. at https://www.genewiz.com/en/Public/Services/Next-Generation-Sequencing/Amplicon-Sequencing-Services/Amplicon-EZ (2022).

NIAID National Institute of Allergy and Infectious Diseases. Emerging Infectious Diseases/Pathogens, at https://www.niaid.nih.gov/research/emerging-infectious-diseases-pathogens (2018).

Nitsche, C. et al., Peptide-boronic acid inhibitors of flaviviral proteases: medicinal chemistry and structural biology. Journal of medicinal chemistry 60, 511-516 (2017).

Nitsche C., Proteases from dengue, West Nile and Zika viruses as drug targets. Biophysical reviews 11, 157-165 (2019).

Noble et al., Ligand-bound structures of the dengue virus protease reveal the active conformation. Journal of virology 86, 438-446 (2012).

Noske, G. D. et al., Structural characterization and polymorphism analysis of the NS2B-NS3 protease from the 2017 Brazilian circulating strain of Yellow Fever virus. Biochimica et Biophysica Acta (BBA)-General Subjects 1864, 129521 (2020).

O'Brien, K. P., Remm, M. & Sonnhammer, E. L. L. Inparanoid: A comprehensive database of eukaryotic orthologs. Nucleic Acids Res. 33, D476-D480 (2005).

Oleinikovas, V., Saladino, G., Cossins, B. P. & Gervasio, F. L. Understanding Cryptic Pocket Formation in Protein Targets by Enhanced Sampling Simulations. J. Am. Chem. Soc. 138, 14257-14263 (2016).

Otto, H.-H. & Schirmeister, T., Cysteine proteases and their inhibitors. Chemical reviews 97, 133-172 (1997).

Paddon, C. J. & Keasling, J. D. Semi-synthetic artemisinin: a model for the use of synthetic biology in pharmaceutical development. Nat. Rev. Microbiol. 12, 355-367 (2014).

Palazón-Riquelme, P. et al., USP7 and USP47 deubiquitinases regulate NLRP3 inflammasome activation. EMBO reports 19, (2018).

Paling, N. R. D. & Welham, M. J. Role of the protein tyrosine phosphatase SHP-1 (Src homology phosphatase-1) in the regulation of interleukin-3-induced survival, proliferation and signalling. Biochem. J. 368, 885-894 (2002).

Pallesen, J. et al., Immunogenicity and structures of a rationally designed prefusion MERS-CoV spike antigen. Proceedings of the National Academy of Sciences 114, E7348-E7357 (2017).

Park, H. et al., Whole-cell biocatalysis using cytochrome P450 monooxygenases for biotransformation of sustainable bioresources (fatty acids, fatty alkanes, and aromatic amino acids). Biotechnology advances 40, 107504 (2020).

Parrinello, M. Polymorphic transitions in single crystals: A new molecular dynamics method. J. Appl. Phys. 52, 7182 (1981).

Pastorino, B. A. M. et al., Expression and biochemical characterization of nsP2 cysteine protease of Chikungunya virus. Virus research 131, 293-298 (2008).

Pastorino, B. et al. Improvement of the purification of Saint Louis encephalitis virus NS2B-NS3 recombinant protease expressed in *Escherichia coli*. Journal of Chromatography B 868, 58-63 (2008).

Pathan, H. & Williams, J. Basic opioid pharmacology: an update. British journal of pain 6, 11-16 (2012).

Paul, M. K. & Mukhopadhyay, A. K. Tyrosine kinase—Role and significance in Cancer. Int. J. Med. Sci. 1, 101-115 (2004).

Paul, S. M. et al., How to improve RD productivity: The pharmaceutical industry's grand challenge. Nature Reviews Drug Discovery 9, 203-214 (2010).

PCT/US2021/012621 International Search Report and Written Opinion dated Apr. 6, 2021.

Peralta-Yahya, P. P. et al. Identification and microbial production of a terpene-based advanced biofuel. Nat. Commun. (2011). doi:10.1038/ncomms1494.

Peters, R. J. et al., Abietadiene synthase from grand fir (*Abies grandis*): Characterization and mechanism of action of the "pseudomature" recombinant enzyme. Biochemistry 39, 15592-15602 (2000).

Pfeifer, B. A. et al., Biosynthesis of Yersiniabactin, a Complex Polyketide-Nonribosomal Peptide, Using *Escherichia coli* as a Heterologous Host. Applied and Environmental Microbiology (2003). doi:10.1128/AEM.69.11.6698-6702.2003.

Pfizer. Pfizer Seeks Emergency Use Authorization For Novel COVID-19 Oral Antiviral Candidate, at https://www.pfizer.com/news/press-release/press-release-detail/pfizer-seeks-emergency-use-authorization-novel-covid-19 (2021).

PHE Public Health Emergency. Pause in the Distribution of Bamlanivimab/Etesevimab. at https://www.phe.gov/emergency/events/COVID19/investigation-MCM/Bamlanivimab-etesevimab/Pages/bamlanivimab-etesevimab-distribution-pause.aspx(2021).

Phoo, W. W. et al., Structures of Zika virus NS2B-NS3 protease in complex with peptidomimetic inhibitors. Antiviral research 160, 17-24 (2018).

Porter, J. R. et al., Cooperative Changes in Solvent Exposure Identify Cryptic Pockets, Switches, and Allosteric Coupling. Biophysical Journal 116, 818-830 (2019).

Price, M. N., Dehal, P. S. & Arkin, A. P. FastTree 2—Approximately maximum-likelihood trees for large alignments. PLoS One 5, e9490 (2010).

Rani, K. G. A. et al., Drug development post COVID-19 pandemic: toward a better system to meet current and future global health challenges. Expert Opinion on Drug Discovery 16, 365-371 (2021).

Ratia et al., Severe acute respiratory syndrome coronavirus papain-like protease: structure of a viral deubiquitinating enzyme. Proceedings of the National Academy of Sciences 103, 5717-5722 (2006).

Rinkel, J. & Dickschat, J. S. Stereochemical investigations on the biosynthesis of achiral (Z)-γ-bisabolene in Cryptosporangium arvum. Beilstein Journal of Organic Chemistry 15, 789-794 (2019).

Rizzuti, B. et al., Sub-Micromolar Inhibition of SARS-CoV-2 3CLpro by Natural Compounds. Pharmaceuticals (Basel, Switzerland) 14, (2021).

Robin, G. et al., Structure of West Nile virus NS3 protease: ligand stabilization of the catalytic conformation. Journal of molecular biology 385, 1568-1577 (2009).

Robinson, D. et al., Differential Water Thermodynamics Determine PI3K-Beta/Delta Selectivity for Solvent-Exposed Ligand Modifications. Journal of Chemical Information and Modeling acs.jcim.5b00641 (2016). doi:10.1021/acs.jcim.5b00641.

Rodrigues, T., Reker, D., Schneider, P. & Schneider, G. Counting on natural products for drug design. Nature chemistry 8, 531-541 (2016).

Rouge et al., Molecular Understanding of USP7 Substrate Recognition and C-Terminal Activation. Structure 24, 1335-1345 (2016).

Russo, A. T. et al., The crystal structure of the Venezuelan equine encephalitis alphavirus nsP2 protease. Structure 14, 1449-1458 (2006).

Rut, W. et al., Profiling of flaviviral NS2B-NS3 protease specificity provides a structural basis for the development of selective chemical tools that differentiate Dengue from Zika and West Nile viruses. Antiviral Research 175, 104731 (2020).

Rutledge et al. Discovery of microbial natural products by activation of silent biosynthetic gene clusters. Nat Rev Microbiol. Aug. 2015;13(8):509-23.

Salis, H. M. The ribosome binding site calculator. Methods in Enzymology 498, 19-42 (2011).

(56) References Cited

OTHER PUBLICATIONS

Sangster, J. J. et al., New trends and future opportunities in the enzymatic formation of C—C, C—N, and C—O bonds. ChemBioChem (2021).
Sarkar, A. et al., Microbially Guided Discovery and Biosynthesis of Biologically Active Natural Products. ACS Synthetic Biology 10, 1505-1519 (2021).
Sarrade-Loucheur, A. et al., Synthetic derivatives of (+)-epi-α-bisabolol are formed by mammalian cytochromes P450 expressed in a yeast reconstituted pathway. ACS synthetic biology 9, 368-380 (2020).
Sato, M., Ozawa, T., Inukai, K., Asano, T. & Umezawa, Y. Fluorescent indicators for imaging protein phosphorylation in single living cells. Nat Biotechnol 20, 287-294 (2002).
Scott, L. M., Lawrence, H. R., Sebti, S. M., Lawrence, N. J. & Wu, J. Targeting protein tyrosine phosphatases for anticancer drug discovery. Curr. Pharm. Des. 16, 1843-62 (2010).
Shang, L. et al., Biochemical characterization of recombinant enterovirus 71 3C protease with fluorogenic model peptide substrates and development of a biochemical assay. Antimicrobial agents and chemotherapy 59, 1827-1836 (2015).
Shchelkunov, S. N. et al., Analysis of the monkeypoxvirus genome. Virology 297, 172-194 (2002).
Shi, J. et al., Discovery and biosynthesis of guanipiperazine from a NRPS-like pathway. Chem. Sci. 12,2925-2930 (2021).
Shimada, T. et al. Selectivity of Polycyclic Inhibitors for Human Cytochrome P450s 1A1, 1A2, and 1B1. Chem. Res. Toxicol. 11, 1048-1056 (1998).
Shin et al., Papain-like protease regulates SARS-CoV-2 viral spread and innate immunity. Nature 587, 657-662 (2020).
Smanski et al., Synthetic biology to access and expand nature's chemical diversity. Nat Rev Microbiol. Mar. 2016;14(3):135-49. doi: 10.1038/nrmicro.2015.24.
Stanford et al. Targeting Tyrosine Phosphatases: Time to End the Stigma. Trends Pharmacol Sci 38(6):524-540 (2017).
Su et al., Anti-SARS-CoV-2 activities in vitro of Shuanghuanglian preparations and bioactive ingredients. Acta Pharmacologica Sinica 41, 1167-1177 (2020).
Su, H. et al., Identification of pyrogallol as a warhead in design of covalent inhibitors for the SARS-CoV-2 3CL protease. Nature Communications 12, 3623 (2021).
Sun, H. et al., Activity based fingerprinting of proteases using FRET peptides. Biopolymers—Peptide Science Section 88, 141-149 (2007).
Sycz G. et al., LOV Histidine Kinase Modulates the General Stress Response System and Affects the virB Operon Expression in *Brucella abortus*. PLoS One. May 19, 2015;10(5):e0124058.
Tan, J. et al., 3C protease of enterovirus 68: structure-based design of Michael acceptor inhibitors and their broad-spectrum antiviral effects against picornaviruses. Journal of virology 87, 4339-4351 (2013).
Tautz, L., Pellecchia, M. & Mustelin, T. Targeting the PTPome in human disease. Expert Opin. Ther. Targets 10, 157-77 (2006).
Tholl, D. Biosynthesis and biological functions of terpenoids in plants. Biotechnology of isoprenoids 63-106 (2015).
Tian J. and Quan J. Circular Polymerase Extension Cloning of Complex Gene Libraries and Pathways. PLoS One 4, e6441 (2009).
Tonks, N. K. Protein tyrosine phosphatases—From housekeeping enzymes to master regulators of signal transduction. FEBS Journal 280, 346-378 (2013).
Tonks, N. K. Protein tyrosine phosphatases: from genes, to function, to disease. Nat. Rev. Mol. Cell Biol. 7, 833-846 (2006).
Traylor, M. J. et al., Recombinant expression and characterization of Lucilia cuprina CYP6G3: Activity and binding properties toward multiple pesticides. Insect Biochemistry and Molecular Biology 90, 14-22 (2017).
Trouiller et al., Drug development for neglected diseases: a deficient market and a publichealth policy failure. The Lancet 359, 2188-2194 (2002).
Urlacher, V. B. & Girhard, M. Cytochrome P450 monooxygenases in biotechnology and synthetic biology. Trends in biotechnology 37, 882-897 (2019).
Ursu, O. et al., Understanding drug-likeness. Wiley Interdisciplinary Reviews: Computational Molecular Science 1, 760-781 (2011).
Vajda, S. et al., Cryptic binding sites on proteins: definition, detection, and druggability. Current Opinion in Chemical Biology 44, 1-8 (2018).
Vallurupalli, P., Bouvignies, G. & Kay, L. E. Studying 'invisible' excited protein states in slow exchange with a major state conformation. J. Am. Chem. Soc. 134, 8148-8161 (2012).
Van Vliet, C. et al. Selective regulation of tumor necrosis factor-induced Erk signaling by Src family kinases and the T cell protein tyrosine phosphatase. Nat. Immunol. 6, 253-260 (2005).
Vanommeslaeghe, K. et al. CHARMM general force field: A force field for drug-like molecules compatible with the CHARMM all-atom additive biological force fields. J. Comput. Chem. 31, 671-690 (2010).
Varone, A., Spano, D. & Corda, D. Shp1 in Solid Cancers and Their Therapy. Frontiers in Oncology 10, 935 (2020).
Varshavsky, A. N-degron and C-degron pathways of protein degradation. Proceedings of the National Academy of Sciences 116, 358-366 (2019).
Veening JW, Hamoen LW, Kuipers OP. Phosphatases modulate the bistable sporulation gene expression pattern in Bacillus subtilis. Mol Microbiol. Jun. 2005;56(6):1481-94.
Vidal, V. et al., Library-based discovery and characterization of daphnane diterpenes as potent and selective HIV inhibitors in Daphne gnidium. Journal of natural products 75, 414-419 (2012). Epub 2011.
Villamagna, A. H. et al., The Need for Antiviral Drugs for Pandemic Coronaviruses From a Global Health Perspective. Frontiers in Medicine 7, (2020).
Viskovska et al., GII. 4 norovirus protease shows pH-sensitive proteolysis with a unique Arg-His pairing in the catalytic site. Journal of virology 93, e01479-18 (2019).
Vistoli, G. et al., Assessing drug-likeness-what are we missing? Drug discovery today 13, 285-294 (2008).
Vitalis, A. & Pappu, R. V. Absinth: A new continuum solvation model for simulations of polypeptides in aqueous solutions. J. Comput. Chem. 30, 673-699 (2009).
Vitalis, A. & Pappu, R. V. Methods for Monte Carlo simulations of biomacromolecules. Annu Rep Comput Chem. Jan. 1, 2009;5:49-76.
Wang, S., Zhang, S., Xiao, A., Rasmussen, M., Skidmore, C. & Zhan, J. Metabolic engineering of *Escherichia coli* for the biosynthesis of various phenylpropanoid derivatives. Metabolic Engineering 29, 153-159 (2015).
Wang, Y. et al., Metabolic engineering of flavonoids in plants and microorganisms. Applied Microbiology and Biotechnology 91, 949-956 (2011).
Wang, Y. et al., Structure of the Enterovirus 71 3C Protease in Complex with NK-1.8k and Indications for the Development of Antienterovirus Protease Inhibitor. Antimicrobial agents and chemotherapy 61, e00298-17 (2017).
Waterhouse, A. et al. SWISS-MODEL: Homology modelling of protein structures and complexes. Nucleic Acids Res. (2018). doi:10.1093/nar/gky427.
Weaver, B. A. How Taxol/paclitaxel kills cancer cells. Molecular biology of the cell 25, 2677-2681 (2014).
Weinert, T. et al., Fast native-SAD phasing for routine macromolecular structure determination. Nature methods 12, 131-133 (2015).
WHO World Health Organization. Coronavirus disease 2019 (COVID-19): Situation Report—87. (2020).
WHO World Health Organization. Prioritizing diseases for research and development in emergency contexts, at https://www.who.int/activities/prioritizing-diseases-for-research-and-development-in-emergency-contexts (2022).
Williams, D. C. et al. Heterologous expression and characterization of a 'pseudomature' form of taxadiene synthase involved in paclitaxel (Taxol) biosynthesis and evaluation of a potential intermediate and inhibitors of the multistep diterpene cyclization reaction. Arch. Biochem. Biophys. (2000). doi:10.1006/abbi.2000.1865.

(56) References Cited

OTHER PUBLICATIONS

Winter, G. Xia2: An expert system for macromolecular crystallography data reduction. J. Appl. Crystallogr. 43, 186-190 (2010).
Wrapp et al., Cryo-EM structure of the 2019-nCoV spike in the prefusion conformation. Science 367(6483):1260-1263 (2020).
Xue et al., Production of Authentic SARS-CoV Mpro with Enhanced Activity: Application as a Novel Tag-cleavage Endopeptidase for Protein Overproduction. Journal of Molecular Biology 366, 965-975 (2007).
Yan, Y. et al., Resistance-gene-directed discovery of a natural-product herbicide with a new mode of action. Nature 559, 415-418 (2018). doi:10.1038/s41586-018-0319-4.
Yang, C. F. et al. Targeting protein tyrosine phosphatase PTP-PEST (PTPN12) for therapeutic intervention in acute myocardial infarction. Cardiovasc. Res. 116, 1032-1046 (2020).
Yang et al., The crystal structures of severe acute respiratory syndrome virus main protease and its complex with an inhibitor. Proceedings of the National Academy of Sciences 100, 13190-13195 (2003).
Yang, S. M., Shim, G. Y., Kim, B. G. & Ahn, J. H. Biological synthesis of coumarins in *Escherichia coli*. Microbial Cell Factories 14, (2015).
Yao et al., Discovery, X-ray crystallography and antiviral activity of allosteric inhibitors of flavivirus NS2B-NS3 protease. Journal of the American Chemical Society 141, 6832-6836 (2019).
Yesudhas, D. et al., COVID-19 outbreak: history, mechanism, transmission, structural studies and therapeutics. Infection 49, 199-213 (2021).
Yildiz et al., Allosteric inhibition of the NS2B-NS3 protease from dengue virus. ACS chemical biology 8, 2744-2752 (2013).
Yu, G., Smith, D. K., Zhu, H., Guan, Y. & Lam, T. T. Y. ggtree: an r package for visualization and annotation of phylogenetic trees with their covariates and other associated data. Methods Ecol. Evol. 8, 28-36 (2017).
Yu, W., He, X., Vanommeslaeghe, K. & MacKerell, A. D. Extension of the CHARMM general force field to sulfonyl-containing compounds and its utility in biomolecular simulations. J. Comput. Chem. 33, 2451-2468 (2012).
Zabolotny, J. M. et al. Protein-tyrosine phosphatase 1B expression is induced by inflammation in vivo. J. Biol. Chem. 283, 14230-14241 (2008).
Zhabinskii, V. N. et al., Steroid plant hormones: Effects outside plant kingdom. Steroids 97, 87-97 (2015).
Zhang, C., Chen, X., Stephanopoulos, G. & Too, H. P. Efflux transporter engineering markedly improves AD production in *Escherichia coli*. Biotechnol. Bioeng. (2016). doi:10.1002/bit.25943.
Zhang C. et al., Multidimensional heuristic process for high-yield production of astaxanthin and fragrance molecules in *Escherichia coli*. Nat Commun. May 11, 2018;9(1):1858.
Zhang et al., Crystal structure of SARS-CoV-2 main protease provides a basis for design of improved a-ketoamide inhibitors. Science, 368: 409-412 (2020).
Zhang, H., Wang, Y., Wu, J., Skalina, K. & Pfeifer, B. A. Complete biosynthesis of erythromycin A and designed analogs using *E. coli* as a heterologous host. Chem. Biol. 17, 1232-1240 (2010).
Zhang, R. K. et al. Enzymatic assembly of carbon-carbon bonds via iron-catalysed sp 3 C—H functionalization. Nature (2019). doi:10.1038/S41586-018-0808-5.
Zhang, S. & Zhang, Z. Y. PTP1B as a drug target: recent developments in PTP1B inhibitor discovery. Drug Discov. Today 12, 373-381 (2007).
Zhang, Z. et al., Crystal structure of unlinked NS2B-NS3 protease from Zika virus. Science 354, 1597-1600 (2016).
Zhao et al., Norovirus Protease Structure and Antivirals Development. Viruses 13, 2069 (2021).
Zhou et al.: A pneumonia outbreak associated with a new coronavirus of probable bat origin. Nature. 579:270-273 (2020).

\* cited by examiner

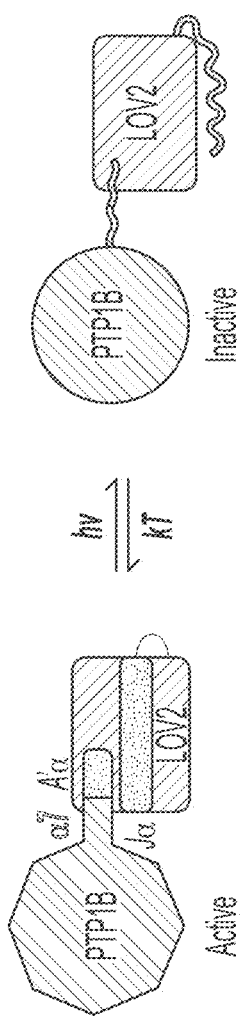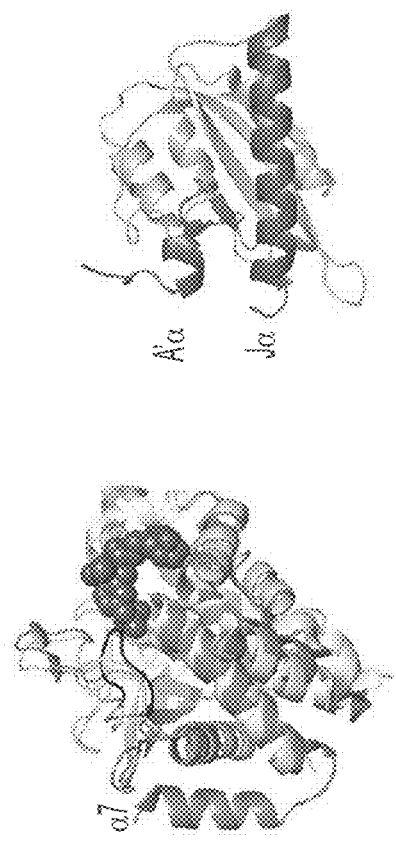
Fig. 1A
Fig. 1B

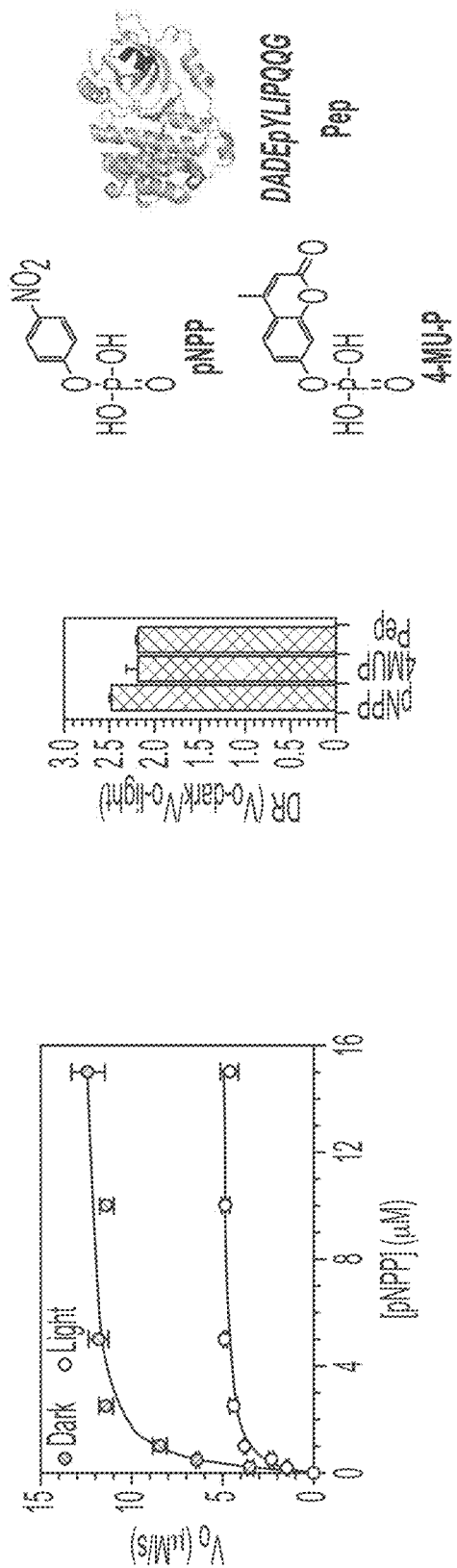
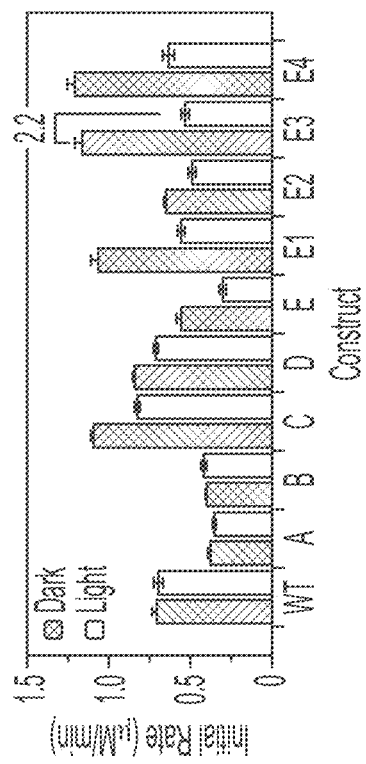
Fig. 1D  Fig. 1E  Fig. 1F  Fig. 1G

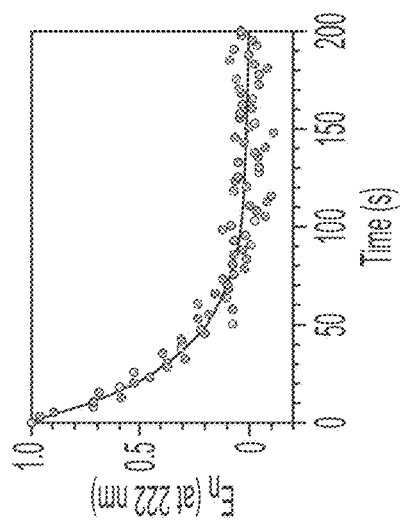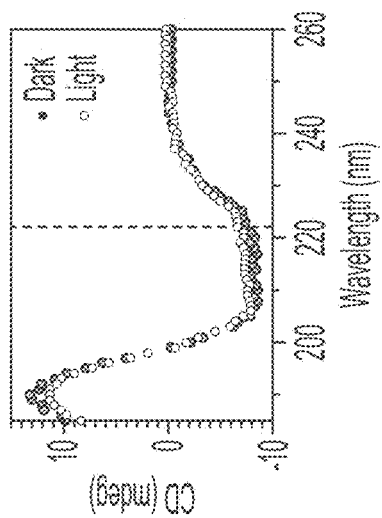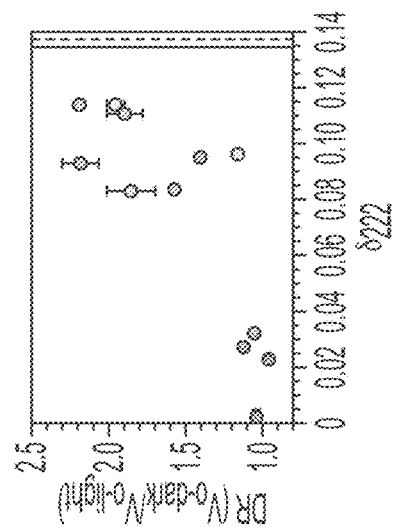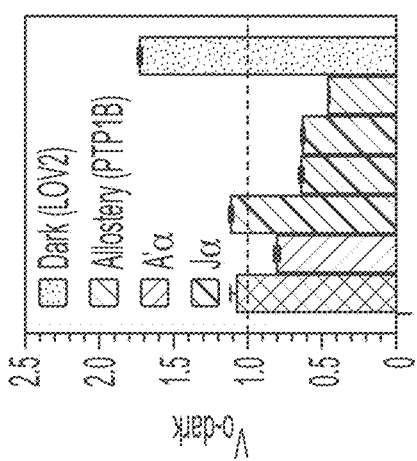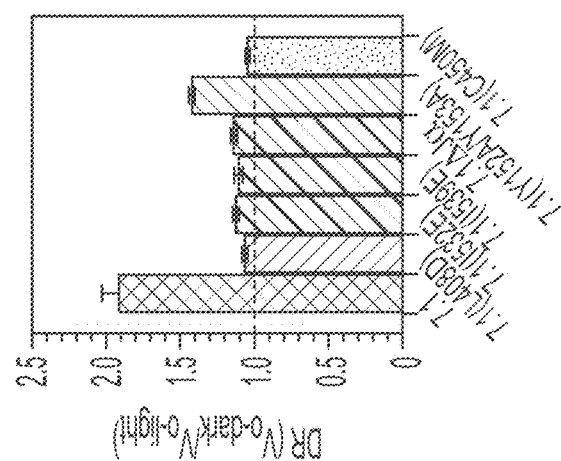

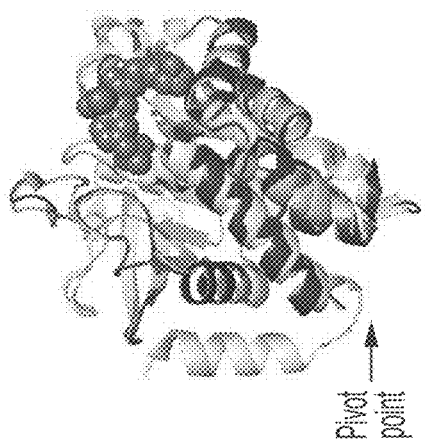
Fig. 2H
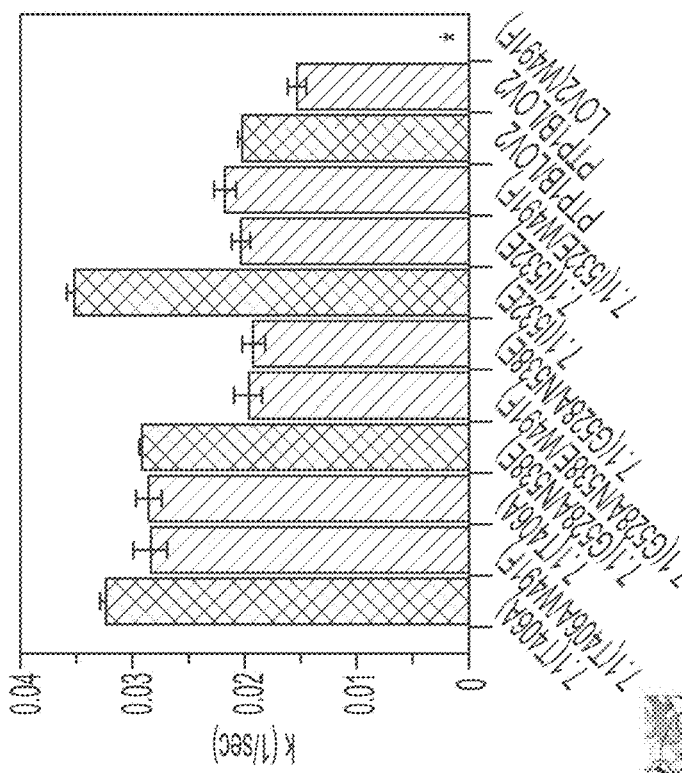
Fig. 2G
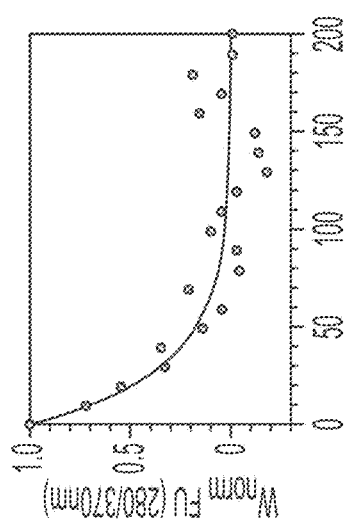
Fig. 2F
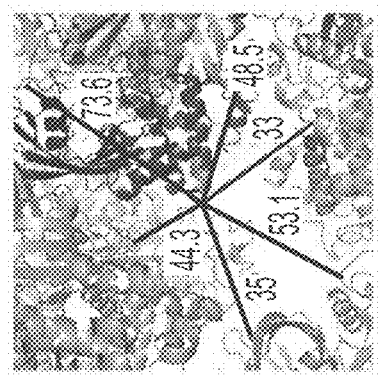
Fig. 2J
Fig. 2I

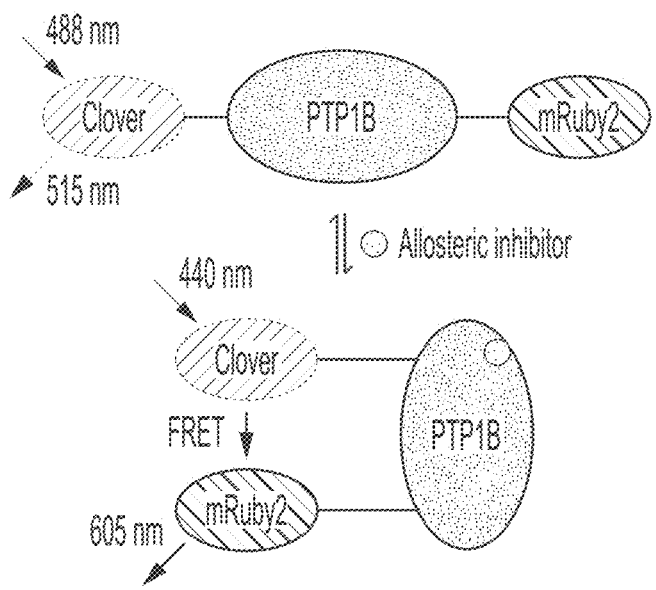
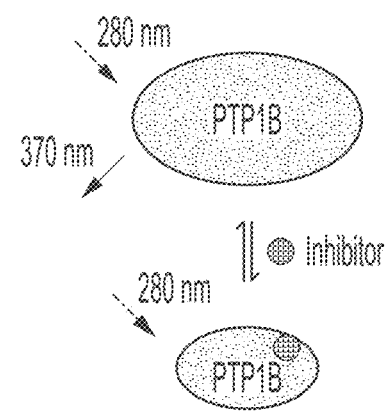
Fig. 21C        Fig. 21D
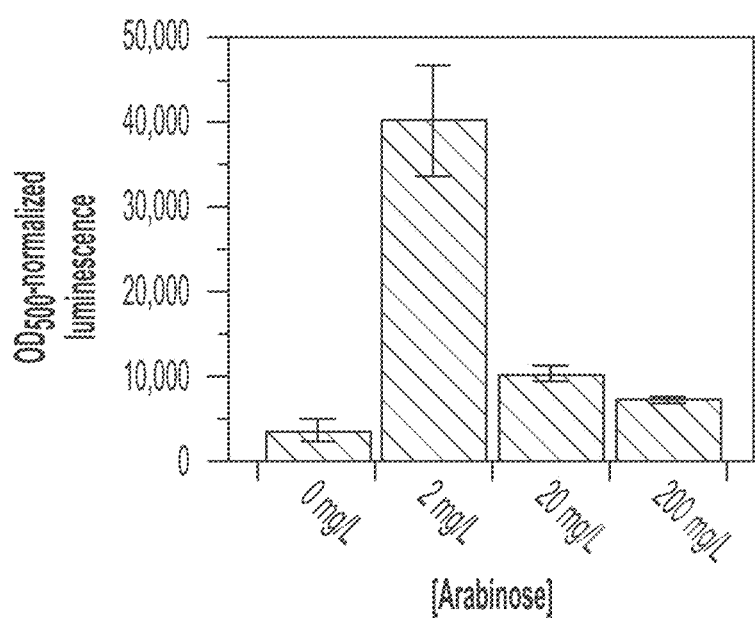
Fig. 21E

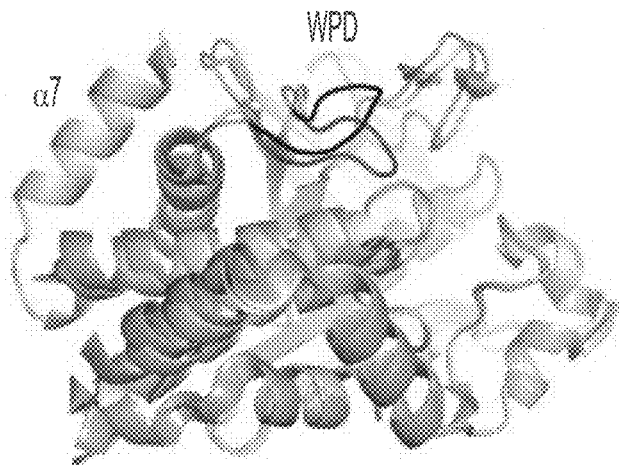
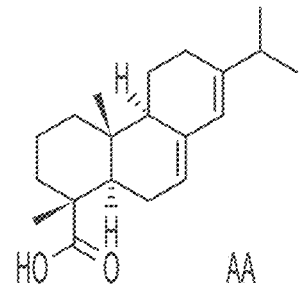
Fig. 22B
Fig. 22A
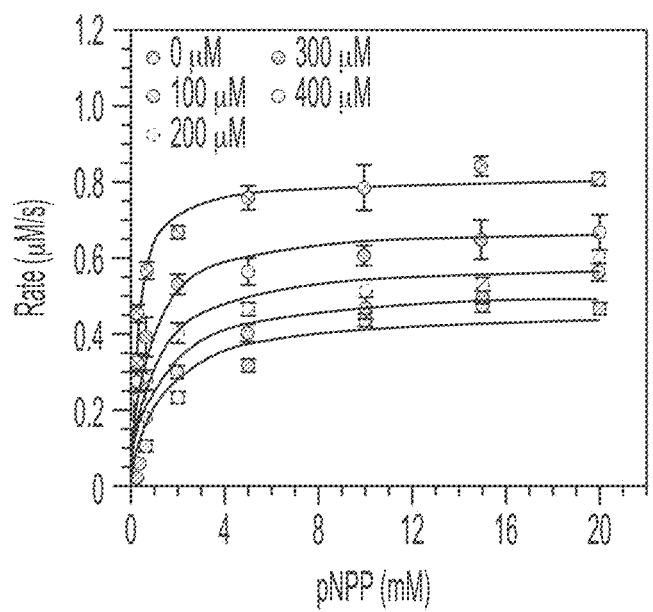
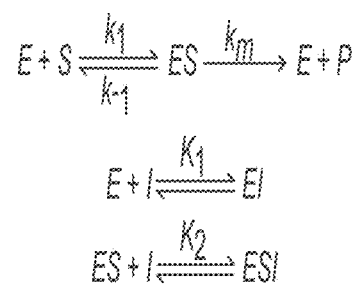
Fig. 22D
Fig. 22C

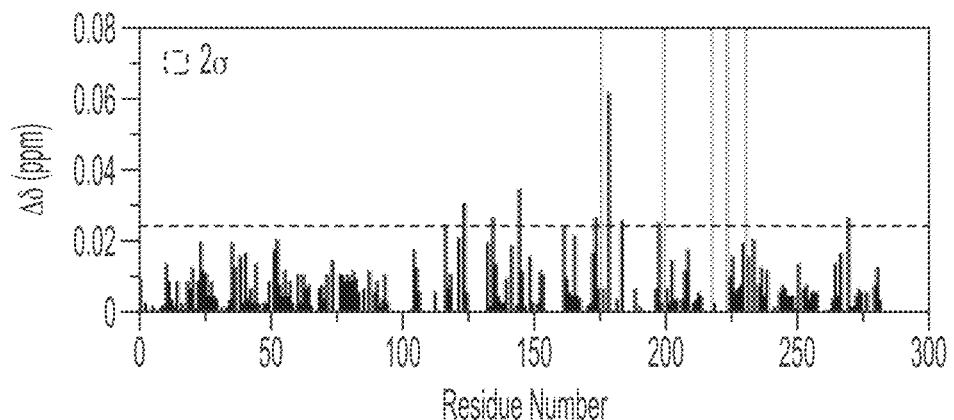
Fig. 23A
 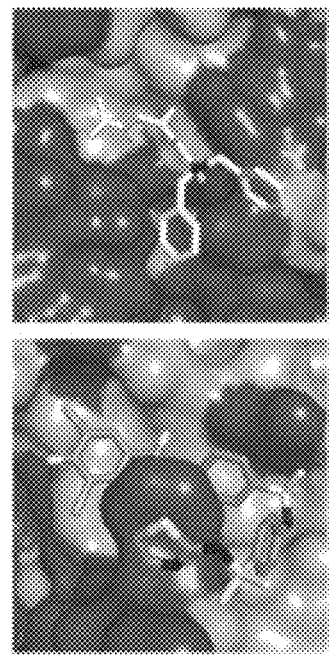
Fig. 23B          Fig. 23C

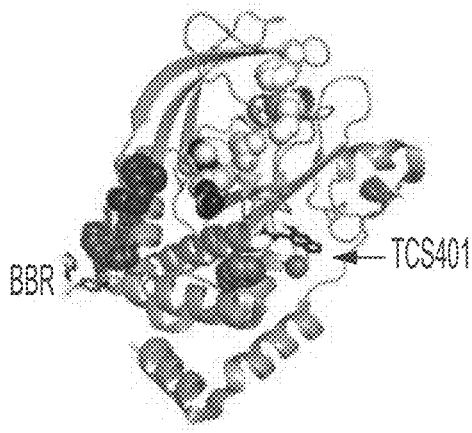
Fig. 24A
| Site | Mutation | Site | Mutation |
|---|---|---|---|
| Active | F182Y | Site 2 | A122F |
| Active | G259S | Site 2 | F135Y |
| Site 1 | R112A | Allosteric | A189S |
| Site 1 | V113T | Allosteric | F196Y |
| Site 1 | H175A | Allosteric | F280Y |
| Site 2 | C92A | L11 | YAYA |
| Site 2 | A122S | | |
Fig. 24B
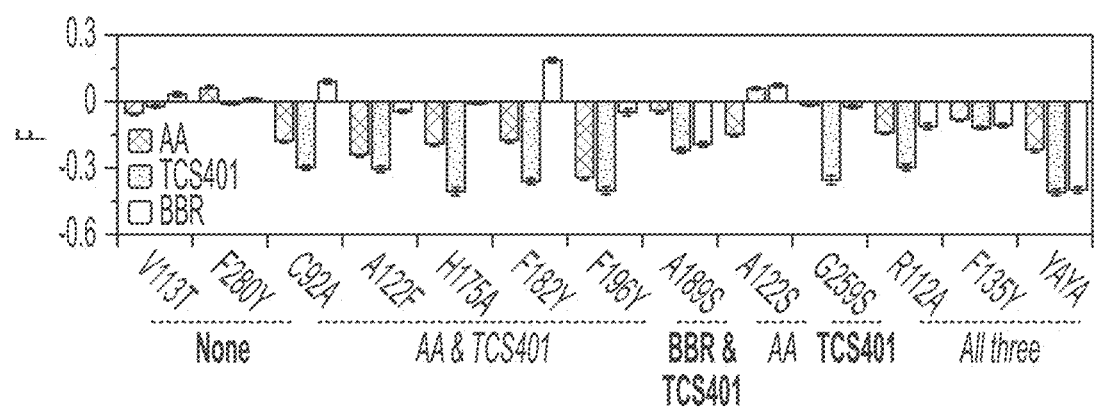
Fig. 24C

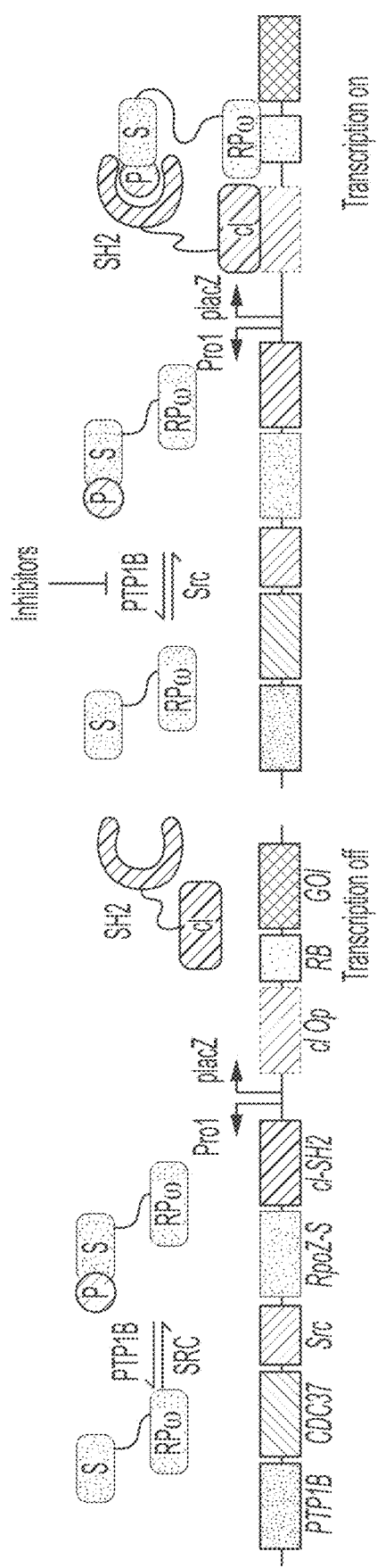
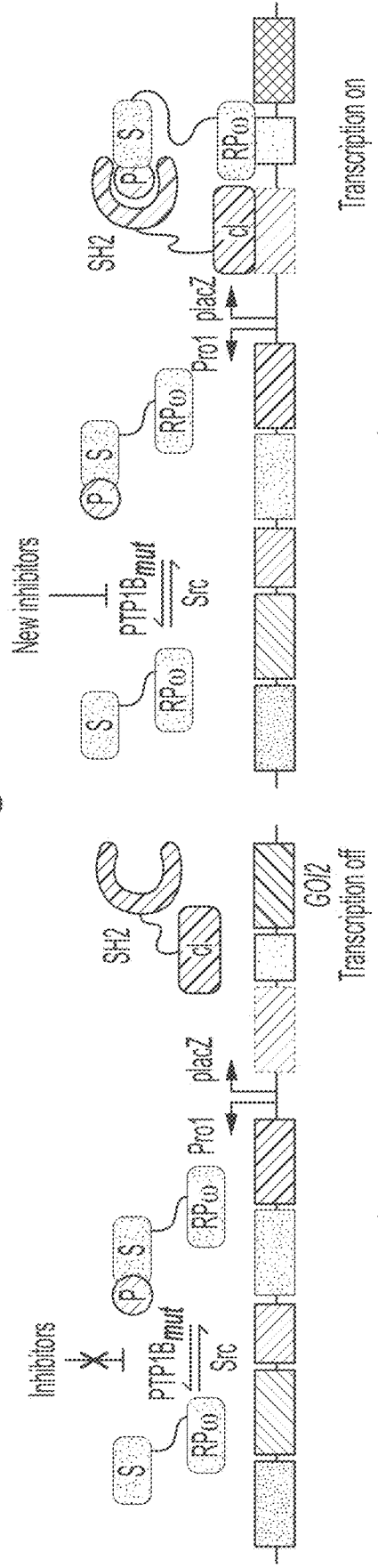
Fig. 40A
Fig. 40B
Fig. 40C

| PTPN6 | Resolution (Å) | Align w/ 3A5J (Å) | Align w/ 2F71 (Å) |
|---|---|---|---|
| 3A5J | 1.7 | - | 0.409 |
| 2F71 | 1.55 | 0.409 | - |
| 4HJP | 1.4 | 0.746 | 0.922 |
| 4HJQ | 1.8 | 0.76 | 0.776 |
| 4GRY | 1.7 | 0.761 | 0.922 |
| 4GRZ | 1.37 | 0.841 | 0.81 |
| 4GS0 | 1.8 | 0.842 | 0.892 |
| 3PS5 | 3.1 | 0.874 | 0.894 |
| 2B3O | 2.8 | 0.931 | 0.943 |
|  | Maximum | 0.931 | 0.943 |

```
EMBOSS_001  PTP1B   1   MEMEKEFEQID--KSGSWAAIYQDIRHEASDFPCRV-AKLPKNKNRNRYR   47
                        :|:.|:.|..|  |:|.|.........:|.:....|:.:.|:||.:|||:
EMBOSS_001  PTPN6   1   LELNKKQESEDTAKAGFWEEFESLQKQEVKNLHQRLEGQRPENKGKNRYK   50

EMBOSS_001          48  DVSPFDHSRIKLHQED------NDYINASLIK------MEEAQRSYILTQGP   87
                        :..||||||:.|...|      :||||:.||      .:|...:||.:||.
EMBOSS_001          51  NILPFDHSRVILQGRDSNIPGSDYINANYIKNQLLGPDENAKTYIASQGC   100

EMBOSS_001          88  LPNTCGHFWEMVWEQKSRGVVMLNRVMEKGSLKCAQYWPQKEEKEMI--F   135
                        |..|...||:|.|::.||.:||...:|||..||..||..|||.....  :
EMBOSS_001          101 LEATVNDFWQMAWQENSRVIVMTTREVEKGRNKCVPYWPEVGMQRAYGPY  150

EMBOSS_001          136 EDINLKLTLISEDIKSYYTVRQLELENLTTQE-TREILHPHYTTWPDFGV   184
                        :||    ..|...:|.:|.|:..|...: .|||.|:|.||:|||.||
EMBOSS_001          151 SVTN-----CGEHDTTEYKLRTLQVSPLDNGDLIREIWHQYLSWPDHGV   195

EMBOSS_001          185 PESPASFLNFLFKVRESGSLSPEHGPVVVHCSAGIGRSGTFCLADTCLLL   234
                        |..|.:||.:|::...|.:|||::|||||||:||||:|||:..|...::
EMBOSS_001          196 PSEPGGVLSFLDQINQRQESLPHAGPIIVHCSAGIGRTGTIIVIDMLMEN  245

EMBOSS_001          235 MDKRKDPSSVDIKKVLLEMRKFRMGLIQTADQLRFSYLAVIEGAKFIMGD  284
                        :....:||:|.:..:|.||.|:|:|:|||.|.:|:|:|:  :|||
EMBOSS_001          246 ISTKGLDCDIDIQKTIQMVRAQRSGMVQTEAQYKFIYVAI---AQFI---  289

EMBOSS_001          285 SSVQDQWKELSHED   298
                        .:..:.:|..
EMBOSS_001          290 ETTKKKLEVLQSQK  303
```

Fig. 44C

| Property | Value |
|---|---|
| Length | 314 |
| Identity | 107/314 (34.1%) |
| Similarity | 168/314 (53.5%) |
| Gaps | 27/314 (8.6%) |
| Score | 473.0 |
| Matrix | EBLOSUM62 |
| Gap Penalty | 10.0 |
| Extend Penalty | 0.5 |

Fig. 44D

GENETICALLY ENCODED SYSTEM FOR CONSTRUCTING AND DETECTING BIOLOGICALLY ACTIVE AGENTS

RELATED APPLICATIONS

This application is a continuation of international application PCT/US2019/040896, filed Jul. 8, 2019, which claims the benefit under 35 U.S.C. § 119(e) of U.S. provisional application Ser. No. 62/694,838, filed Jul. 6, 2018, the disclosures of which are incorporated by reference herein in their entireties.

STATEMENT OF GOVERNMENT SUPPORT

This invention was made with government support under grant numbers 1750244 and 1804897 awarded by the National Science Foundation. The government has certain rights in the invention.

FIELD OF THE INVENTION

This invention relates to the field of genetic engineering. Specifically, the invention relates to the construction of operons to produce biologically active agents. For example, operons may be constructed to produce agents that control the function of biochemical pathway proteins (e.g., protein phosphatases, kinases and/or proteases). Such agents may include inhibitors and modulators that may be used in studying or controlling phosphatase function associated with abnormalities in a phosphatase pathway or expression level. Fusion proteins, such as light activated protein phosphatases, may be genetically encoded and expressed as photoswitchable phosphatases. Systems are provided for use in controlling phosphatase function within living cells or in identifying small molecule inhibitors/activator/modulator molecules of protein phosphatases associated with cell signaling.

BACKGROUND

Protein phosphorylation is involved with cell signaling as in part it controls the location and timing of cellular differentiation, movement, proliferation, and death[1-4]; its misregulation is implicated in cancer, diabetes, obesity, and Alzheimer's disease, among other disorders[5-9]. Optical tools to exert spatiotemporal control over the activity of phosphorylation-regulating enzymes in living cells could elucidate the mechanisms by which cells transmit, filter, and integrate chemical signals[10,11], reveal links between seemingly disparate physiological processes (e.g., memory[12] and metabolism[13]), and facilitate the identification of new targets for phosphorylation-modulating therapeutics (a class of pharmaceuticals[14]). Therefore, there is a need for developing tools to control, reduce, or enhance the activity of phosphorylation-regulating enzymes in living cells.

SUMMARY OF THE INVENTION

This invention relates to the field of genetic engineering. Specifically, the invention relates to the construction of operons to produce biologically active agents. For example, operons may be constructed to produce agents that control the function of biochemical pathway proteins (e.g., protein phosphatases, kinases and/or proteases). Such agents may include inhibitors and modulators that may be used in studying or controlling phosphatase function associated with abnormalities in a phosphatase pathway or expression level. Fusion proteins, such as light activated protein phosphatases, may be genetically encoded and expressed as photoswitchable phosphatases. Systems are provided for use in controlling phosphatase function within living cells or in identifying small molecule inhibitors/activator/modulator molecules of protein phosphatases associated with cell signaling.

In one embodiment, the present invention contemplates a genetic operon comprising: a) providing; i) a first gene encoding a first fusion protein, the first fusion protein comprising a substrate recognition domain and either a DNA-binding domain or an anchoring unit for RNA polymerase; ii) a second gene encoding a second fusion protein, the second fusion protein comprising an enzyme substrate domain and either an anchoring unit for RNA polymerase or a DNA binding domain; iii) a first DNA sequence comprising a binding site for said DNA-binding domain; iv) a second DNA sequence comprising a binding site, proximal to the first, for said anchoring unit and for said RNA polymerase; v) a third gene encoding a first enzyme, wherein said first enzyme is capable of modifying said substrate domain, thereby changing the affinity of said substrate recognition domain; vi) a fourth gene encoding a second enzyme, wherein said second enzyme is capable of unmodifying said substrate domain; vii) a reporter gene encoding at least one capable of having a detectable output when said RNA polymerase and said anchoring unit binds to said second DNA sequence binding site after association of the two fusion proteins. In one embodiment, said substrate domain is a peptide substrate of a protein kinase. In one embodiment, said substrate domain is a peptide substrate of a protein tyrosine kinase. In one embodiment, said substrate domain is a peptide substrate of Src kinase (a protein tyrosine kinase). In one embodiment, said substrate recognition domain is capable of binding to said substrate domain in its phosphorylated state. In one embodiment, said substrate recognition domain is capable of binding to said substrate domain in its unphosphorylated state. In one embodiment, said DNA-binding domain is the 434 cI repressor and said DNA binding site is the binding sequence for that repressor. In one embodiment, said anchoring unit is the omega subunit of RNA polymerase and said second DNA binding site is the binding site for RNA polymerase. In one embodiment, said substrate domain is a peptide substrate of a protein kinase. In one embodiment, said operon further comprises a system of proteins. In one embodiment, said first enzyme is a protein phosphatase. In one embodiment, said first enzyme is a protein tyrosine phosphatase. In one embodiment, said first enzyme is protein tyrosine phosphatase 1B. In one embodiment, said second enzyme is a protein kinase. In one embodiment, said second enzyme is a protein tyrosine kinase. In one embodiment, said second enzyme is Src kinase. In one embodiment, said reporter protein yields a detectable output. In one embodiment, said reporter protein that yields a detectable output is a LuxAB bioreporters (e.g., output is a luminescence). In one embodiment, said reporter protein that yields a detectable output is a fluorescent protein. In one embodiment, said reporter protein that yields a detectable output is mClover. In one embodiment, said reporter protein that yields a detectable output confers antibiotic resistance. In one embodiment, said antibiotic resistance is to spectinomycin. In one embodiment, said operon further comprises a gene encoding a decoy protein fusion comprising: (i) a second enzyme substrate domain that is different from the first enzyme substrate domain and (ii) a protein that that does not bind specifically to DNA and/or to RNA polymerase, and a fifth gene encoding a third enzyme, wherein said third enzyme is capable of being active on the decoy substrate domain. In one embodiment, both said first enzyme substrate domain (of the base system) and said second enzyme substrate domain (of the decoy) are substrates of a protein kinases. In one embodiment, both said first enzyme substrate domain (of the base system) and said second enzyme substrate domain (of the decoy) are substrates of a protein tyrosine kinase. In one embodiment, both said first enzyme substrate domain (of the base system) and said second enzyme substrate domain (of the decoy) are substrates of Src kinase. In one embodiment, both said first enzyme substrate domain (of the base system) and said second substrate domain (of the decoy) are substrates of a protein phosphatase. In one embodiment, both said first enzyme substrate domain (of the base system) and said second substrate domain (of the decoy) are substrates of a protein tyrosine phosphatase. In one embodiment, both said first enzyme substrate domain (of the base system) and said second substrate domain (of the decoy) are substrates of protein tyrosine phosphatase 1B. In one embodiment, said first enzyme is a light modulated enzyme. In one embodiment, said first enzyme is a protein-LOV2 chimera. In one embodiment, said first enzyme is a PTP1B-LOV2 chimera. In one embodiment, said proteins that yield a detectable output include a protein that generates a toxic product in the presence of a non-essential substrate. In one embodiment, said additional protein is SacB, which converts sucrose to a nonstructural polysaccharide that is toxic in *E. coli*. In one embodiment, said operon further comprises an expression vector and a bacterial cell.

In one embodiment, the present invention contemplates a system for detecting inhibitors of an enzyme, comprising: a) providing; i) an operon comprising a gene encoding an enzyme; ii) a bacterium cell; iii) a small molecule test compound; and b) contacting said bacterium with said operon such that said contacted bacterium is capable of producing a detectable output; c) growing said contacted bacterium in the presence of said test compound under conditions allowing said detectable output; and d) assessing the influence of the test compound on said detectable output. In one embodiment, said enzyme is a protein phosphatase. In one embodiment, said enzyme is a protein tyrosine phosphatase. In one embodiment, said enzyme, is protein tyrosine phosphatase 1B.

In one embodiment, the present invention contemplates a method for evolving inhibitors of an enzyme, comprising: a) providing: i) an operon comprising a gene encoding an enzyme; ii) a library of bacteria cells, wherein each said bacteria cells has at least one mutated metabolic pathway; b) growing said library of bacteria cells; and c) screening said library of bacterial cells for a detectable output. In one embodiment, said operon further comprises an expression vector.

In one embodiment, the present invention contemplates a method for detecting selective inhibitors of a first enzyme over a second enzyme, comprising: a) providing; i) a system as described above comprising a library of bacterial cells; and ii) a small molecule test compound; b) growing said library of bacterial cells in the presence of the test compound; and c) assessing an influence of the test compound on a detectable output. In one embodiment, the system further provides an operon comprising a gene encoding a decoy fusion protein, said decoy fusion protein comprising; (i) a second enzyme substrate domain that is different from the first enzyme substrate domain and (ii) a protein that does not bind specifically to DNA and/or RNA polymerase. In one embodiment, said operon further comprises an expression vector.

In one embodiment, the present invention contemplates a method for evolving selective inhibitors of a first enzyme over a second enzyme, comprising; a) providing; a system as described herein comprising a library of bacterial cells having mutated metabolic pathways; b) growing said bacterial cell library; and b) screening the bacterial cell library for a detectable output. In one embodiment, the method further provides an operon comprising a gene encoding a decoy fusion protein, the decoy fusion protein comprising; (i) a second enzyme substrate domain that is different from the first enzyme substrate domain and (ii) a protein that that does not bind specifically to DNA and/or RNA polymerase. In one embodiment, said operon further comprises an expression vector.

In one embodiment, the present invention contemplates a method for evolving photoswitchable enzymes, comprising; a) providing; i) a system as described herein comprising a bacterial cell library having mutated photoswitchable enzymes; b) growing the bacterial cell library under at least two different light conditions; and c) comparing differences in detectable output for each cell between each of said two different light conditions. In one embodiment, said operon further comprises an expression vector.

In one embodiment, the present invention contemplates a method for evolving photoswitchable enzymes, comprising: a) providing; i) a system as described herein comprising a library of bacterial cells have mutated photoswitchable enzymes; b) growing the library of bacterial cells under a first light source in which activity is desired; c) subsequently growing the library of bacterial cells from step b) in the presence of: (i) a non-essential substrate; and (ii) a second light source in which activity is not desired; d) subsequently screening survivors of step c) for a mutant bacterial cell; and e) examining the mutant bacterial cell for activity under the first light source and the second light source. In one embodiment, the method further comprises an operon comprising a gene encoding a decoy fusion protein, the decoy fusion protein comprising; (i) a second enzyme substrate domain that is different from the first enzyme substrate domain; and (ii) a protein that that does not bind specifically to DNA and/or RNA polymerase. In one embodiment, said operon further comprises an expression vector.

In one embodiment, the present invention contemplates a method for evolving selective mutants of an enzyme, comprising: a) providing; a system as described above comprising a library of bacterial cells having a mutant enzyme; b) growing the library of bacterial cells; and c) comparing a detectable output between the cells to identify the mutant enzyme. In one embodiment, the method further comprises an operon comprising a gene encoding a decoy fusion protein, the decoy fusion protein comprising; (i) a second enzyme substrate domain that is different from the first enzyme substrate domain; and (ii) a protein that that does not bind specifically to DNA and/or RNA polymerase. In one embodiment, said operon further comprises an expression vector.

In one embodiment, the present invention contemplates a method for evolving substrate domains selective for an enzyme, comprising: a) providing; a method as described above comprising a library of bacterial cells comprising substrate domains fused to DNA binding domains; b) growing the library of bacterial cells in the presence of an inducer for a first enzyme and a non-essential substrate; c) subsequently growing the library of bacterial cells from step b) in the presence of an inducer for a second enzyme; and d) subsequently screening for survivor bacterial cells, thereby identifying substrates that bind to the first enzyme but not to the second enzyme. In one embodiment, said system comprises a reporter protein that yields a detectable output. In one embodiment, the reporter protein generates a toxic product in the presence of a non-essential substrate. In one embodiment, the system further comprises an operon comprising a gene selected from the group consisting of a first inducible promoter for a first enzyme and a second inducible promoter for a second enzyme, wherein the second enzyme has a similar activity to the first enzyme.

In one embodiment, the present invention contemplates a method of using a microbial biosensor comprising an operon, wherein said operon comprises; a) providing a reporter gene and a sensor fusion protein gene; and b) expressing said sensor fusion protein with a post-translational modification and the reporter gene. In one embodiment, said expressed sensor fusion protein has a protein tyrosine phosphatase substrate domain and is capable of binding to said DNA binding sequences in the presence of at least one expressible sensor fusion protein as a recognition domain (SH2) for said protein tyrosine phosphatase substrate domain attached to a phosphate molecule. In one embodiment, said operon further comprises gene segments encoding: i) a first expressible sensor fusion protein as a protein tyrosine phosphatase substrate domain capable of attaching to said phosphate molecule, said first expressible sensor fusion protein is in an operable combination with a DNA-binding protein; and ii) a second expressible sensor fusion protein as a recognition domain (SH2) for said protein tyrosine phosphatase substrate domain when attached to a phosphate molecule, said second expressible sensor fusion protein is in operable combination with a subunit of an RNA polymerase; and iii) individual expressible fragments including, but not limited to, a Src kinase protein; a protein tyrosine phosphatase 1B (PTP1B) and conjugated to said transcriptionally active binding sequences capable of binding to said DNA-binding protein of sensor fusion protein and said subunit of an RNA polymerase in operable combination with said reporter gene.

In one embodiment, the present invention contemplates a method of using a microbial biosensor comprising; a) providing; i) an operon, wherein said operon comprises a reporter gene and a sensor fusion protein gene; ii) a living bacterium; and iii) a test small molecule inhibitor of said protein tyrosine phosphatase enzyme; b) expressing said sensor fusion protein with a post-translational modification and a reporter gene; c) contacting said bacterium with said test small molecule; and d) determining whether said test small molecule is an inhibitor for said protein phosphatase enzyme by expression of said reporter gene. In one embodiment, said expressed sensor fusion protein has a protein tyrosine phosphatase substrate domain that is capable of binding to a DNA binding sequence in the presence of at least one expressible sensor fusion protein as a recognition domain (SH2) for said protein tyrosine phosphatase substrate domain attached to a phosphate molecule. In one embodiment, said expressed sensor fusion protein has a protein tyrosine phosphatase 1B substrate domain that is capable of binding to said DNA binding sequences in the presence of at least one expressible sensor fusion protein as a recognition domain (SH2) for said protein tyrosine phosphatase substrate domain attached to a phosphate molecule. In one embodiment, said operon further comprises gene segments encoding: i) said first expressible sensor fusion protein as said protein tyrosine phosphatase substrate domain capable of attaching to said phosphate molecule that is in operable combination with a DNA-binding; and ii) said second expressible sensor fusion protein as a recognition domain (SH2) for said protein tyrosine phosphatase substrate domain when attached to a phosphate molecule that is in operable combination with a subunit of an RNA polymerase; and iii) individual expressible fragments including but not limited to, a Src kinase protein; a protein tyrosine phosphatase 1B (PTP1B) and conjugated to said transcriptionally active binding sequences capable of binding to said DNA-binding protein of sensor fusion protein and said subunit of an RNA polymerase in operable combination with said reporter gene. In one embodiment, said biosensor further comprises an operon component for expressing a second gene. In one embodiment, said biosensor further comprises an operon component for expressing a second PTP that is different from the first PTP for identifying a said inhibitor selective for one of the TPT enzymes. In one embodiment, said test small molecule inhibitor includes, but is not limited to, abietane-type diterpenes, abietic acid (AA), dihydroabietic acid and structural variants thereof.

In one embodiment, the present invention contemplates a method of using a microbial biosensor, comprising: a) providing; i) an operon, wherein said operon comprises a reporter gene and a sensor fusion protein gene; ii) a living bacterium; and iii) a test small molecule inhibitor of said protein tyrosine phosphatase enzyme; b) expressing said sensor fusion protein with a post-translational modification and the reporter gene; c) expressing said expressible sensor fusion proteins in said bacterium; d) contacting said bacterium with said test small molecule; and e) determining whether said test small molecule is an inhibitor for said protein phosphatase enzyme by expression of said reporter gene. In one embodiment, said expressed sensor fusion protein has a protein tyrosine phosphatase substrate domain and is capable of binding to said DNA binding sequences in the presence of at least one expressible sensor fusion protein as a recognition domain (SH2) for said protein tyrosine phosphatase substrate domain attached to a phosphate molecule. In one embodiment, the expressed sensor fusion protein has a protein tyrosine phosphatase 1B substrate domain and capable of binding to said DNA binding sequences in the presence of at least one expressible sensor fusion protein as a recognition domain (SH2) for said protein tyrosine phosphatase substrate domain attached to a phosphate molecule, and an individual expressible fragment for a photoswitchable protein tyrosine phosphatase 1B. In one embodiment, said operon comprises gene segments encoding: i) said first expressible sensor fusion protein as said protein tyrosine phosphatase substrate domain that is capable of attaching to said phosphate molecule in operable combination with a DNA-binding protein; ii) said second said expressible sensor fusion protein as a recognition domain (SH2) for said protein tyrosine phosphatase substrate domain when attached to a phosphate molecule that is in operable combination with a subunit of an RNA polymerase; and iii) individual expressible fragments including, but not limited to, a Src kinase protein; a protein tyrosine phosphatase 1B (PTP1B) and conjugated to said transcriptionally active binding sequences capable of binding to said DNA-binding protein of sensor fusion protein and said subunit of an RNA polymerase in operable combination with said reporter gene.

In one embodiment, the present invention contemplates a method for providing variants of chemical structures for use as a potential therapeutic, comprising: a) providing; i) an *E. coli* bacterium comprising a metabolic terpenoid chemical structure-producing pathway providing an altered chemical structure, wherein said metabolic pathway comprises a synthetic enzyme, wherein said *E. coli* further comprises a microbial biosensor operon for detecting PTP inhibition; and ii) a mutated synthetic enzyme of system of enzymes; a) introducing said mutated synthetic enzyme of system of enzymes; c) expressing said mutated synthetic enzyme under conditions wherein said mutated synthetic enzyme or system of enzymes alters/alter the chemical structure of said terpenoid chemical structure; and d) determining whether said altered chemical structure is an inhibitor for said PTP as a test inhibitor for use as a potential therapeutic. In one embodiment, said metabolic pathway comprises synthetic enzymes including, but not limited to, terpene synthases, cytochrome P450s, halogenases, methyl transferases, or terpenoid-functionalizing enzymes. In one embodiment, said terpenoid includes, but is not limited to, labdane-related diterpenoids. In one embodiment, said terpenoid includes but is not limited to, abietane-type diterpenoids. In one embodiment, said terpenoid is abietic acid.

In one embodiment, the present invention contemplates a fusion protein DNA construct, comprising a protein phosphatase gene and a protein light switch gene conjugated within said phosphatase gene, wherein said protein phosphatase gene encodes a protein with a C-terminal domain and said protein light switch gene encodes a protein with an N-terminal alpha helical region such that said C-terminal domain is conjugated to said N-terminal alpha helical region. In one embodiment, said construct further comprises an expression vector and a living cell. In one embodiment, said protein phosphatase is a protein tyrosine phosphatase. In one embodiment, said protein phosphatase is protein tyrosine phosphatase 1B (PTP1B). In one embodiment, said C-terminal domain encodes an α7 helix of PTP1B. In one embodiment, said construct encodes $PTP1B_{PS}$-A. In one embodiment, said construct encodes $PTP1B_{PS}$-B. In one embodiment, said protein phosphatase is T-Cell protein tyrosine phosphatases (TC-PTP). In one embodiment, said protein light switch is a light-oxygen-voltage (LOV) domain. In one embodiment, said protein light switch is the LOV2 domain of phototropin 1 form *Avena sativa*. In one embodiment, said LOV2 domain comprises an A'a helix of LOV2. In one embodiment, said LOV2 has at least one mutation resulting in an amino acid mutation. It is not meant to limit such mutations. In fact, a mutation may include but is not limited to a nucleotide substitution, the addition of a nucleotide, and the deletion of a nucleotide from said gene. In one embodiment, said mutation is a substitution of a nucleotide. In one embodiment, said A'a helix of LOV2 has a T406A mutation. In one embodiment, said protein light switch is a phytochrome protein. In one embodiment, said phytochrome protein is a bacterial phytochrome protein. In one embodiment, said bacterial phytochrome protein is a bacterial phytochrome protein 1 (BphP1) from *Rhodopseudomonas palustris*. In one embodiment, said protein light switch is a light-oxygen-voltage (LOV) domain with an artificial chromophore. In one embodiment, said protein light switch is a phytochrome protein with an artificial chromophore.

In one embodiment, the present invention contemplates a fusion protein, comprising a protein phosphatase and a protein light switch conjugated within said phosphatase, wherein said protein phosphatase has a C-terminal domain and said protein light switch has a N-terminal alpha helical region such that said C-terminal domain is conjugated to said N-terminal alpha helical region. In one embodiment, said fusion protein further comprises an expression vector and a living cell. In one embodiment, said protein phosphatase is a protein tyrosine phosphatase. In one embodiment, said protein phosphatase is protein tyrosine phosphatase 1B (PTP1B). In one embodiment, said C-terminal domain encodes an α7 helix. In one embodiment, said fusion protein is $PTP1B_{PS}$-A. In one embodiment, said fusion protein is $PTP1B_{PS}$-B. In one embodiment, said protein phosphatase is T-Cell protein tyrosine phosphatases (TC-PTP). In one embodiment, said protein light switch is a light-oxygen-voltage (LOV) domain. In one embodiment, said protein light switch is the LOV2 domain of phototropin 1 form *Avena sativa*. In one embodiment, said LOV2 domain comprises an A'a helix of LOV2. In one embodiment, said A'a helix of LOV2 has a T406A mutation. In one embodiment, said protein light switch is a light-oxygen-voltage (LOV) domain with an artificial chromophore. In one embodiment, said protein light switch is a phytochrome protein with an artificial chromophore. In one embodiment, said protein light switch is a phytochrome protein. In one embodiment, said phytochrome protein is a bacterial phytochrome protein. In one embodiment, said bacterial phytochrome protein is a bacterial phytochrome protein 1 (BphP1) from *Rhodopseudomonas palustris*. In one embodiment, said protein light switch is a light-oxygen-voltage (LOV) domain with an artificial chromophore. In one embodiment, said protein light switch is a phytochrome protein with an artificial chromophore.

In one embodiment, the present invention contemplates a method of using a fusion protein, comprising; a) providing; i) a fusion protein; ii) a protein phosphatase, and iii) a living cell; and b) introducing said fusion protein in said a living cell such that illumination of said light switch alters a feature in said living cell. In one embodiment, said feature includes but is not limited to controlling cell movement, morphology, controlling cell signaling and having a modulatory effect. In one embodiment, said modulatory effect includes but is not limited to inactivation, activation, reversible inactivation and reversible activation. In one embodiment, said modulatory effect is dose dependent. In one embodiment, said illumination is light within the range of 450-500 nm. In one embodiment, said illumination is light within the range of 600-800 nm. In one embodiment, said protein light switch undergoes light-induced conformational change and said protein phosphatase has allosterically modulated catalytic activity that is altered by said conformational change. In one embodiment, said altering is enhanced or reduced. In one embodiment, said protein light switch is a light-oxygen-voltage (LOV) domain with an artificial chromophore. In one embodiment, said protein light switch is a phytochrome protein with an artificial chromophore. In one embodiment, said living cell has an activity. In one embodiment, said living cell is in vivo. In one embodiment, said method further comprises a step of controlling said cellular activity in vivo.

In one embodiment, the present invention contemplates a method for detecting a small molecule modulator of a protein phosphatase, comprising: a) providing; i) a fusion protein comprising a protein phosphatase and protein light switch; ii) a visual readout for phosphatase activity; iii) an optical source, wherein said source is capable of emitting light radiation; iv) a living cell; and v) a small molecule test compound; b) expressing said fusion protein in said living cell; c) contacting said living cell with said small molecule test compound; d) illuminating said fusion protein within said cell with said optical source; e) measuring a visual readout for a change in phosphatase activity for identifying said small molecule test compound as a modulator of said activity of said phosphatase; and f) using said modulatory small molecule test compound for treating a patient exhibiting at least one symptom of a disease associated with said phosphatase. In one embodiment, said method further comprises identifying said small molecule test compound as an inhibitor of the activity of said phosphatase. In one embodiment, said method further comprises identifying said small molecule test compound as an activator of the activity of said phosphatase. In one embodiment, said disease includes but is not limited to diabetes, obesity, cancer, anxiety, autoimmunity, or neurodegenerative diseases. In one embodiment, said protein light switch is a light-oxygen-voltage (LOV) domain with an artificial chromophore. In one embodiment, said protein light switch is a phytochrome protein with an artificial chromophore. In one embodiment, said method further provides a fluorescence-based biosensor, and comprises a step of introducing said fluorescence-based biosensor into said cell. In one embodiment, said method further comprises a step of controlling said cellular activity in vivo. In one embodiment, said visual readout for phosphatase activity is selected from the group consisting of a fluorescence-based biosensor; changes in cell morphology; and changes in cell motility.

In one embodiment, the present invention contemplates a photoswitchable protein tyrosine phosphatase enzyme construct comprising an N-terminal alpha helix of a protein light switch conjugated to a C-terminal allosteric domain region. In one embodiment, said protein tyrosine phosphatase enzyme is protein tyrosine phosphatase 1B (PTP1B). In one embodiment, said protein light switch is a LOV2 domain of phototropin 1 derived from *Avena sativa* (wild oats). In one embodiment, said enzyme construct further comprises an expression vector. In one embodiment, the present invention contemplates a biosensor for enzyme activity, comprising; a) a substrate domain as described above; b) a substrate recognition domain; c) a first fluorescent protein; and d) a second fluorescent protein.

In one embodiment, the invention provides a genetically encoded system for detecting small molecules that modulate enzyme activity, comprising, a. a first region in operable combination comprising: i. a first promoter; ii. a first gene encoding a first fusion protein comprising a substrate recognition domain linked to a DNA-binding protein; iii. a second gene encoding a second fusion protein comprising a substrate domain linked to a protein capable of recruiting RNA polymerase to DNA; iv. a second promoter; v. a third gene for a protein kinase; vi. a fourth gene for a molecular chaperone; vii. a fifth gene for a protein phosphatase; b. a second region in operable combination comprising: i. a first DNA sequence encoding an operator for said DNA-binding protein; ii. a second DNA sequence encoding a binding site for RNA polymerase; and iii. one or more genes of interest (GOI). In one embodiment, said first promoter is ProI. In one embodiment, said substrate recognition domain is a substrate homology 2 (SH2) domain from *H. sapiens*. In one embodiment, said DNA-binding protein is the 434 phage cI repressor. In one embodiment, said substrate domain is a peptide substrate of both said kinase and said phosphatase. In one embodiment, said second promoter is ProD. In one embodiment, said protein capable of recruiting RNA polymerase to DNA is the omega subunit of RNA polymerase (i.e., RpoZ or $RP_\omega$). In one embodiment, said protein kinase is Src kinase from *H. sapiens*. In one embodiment, said molecular chaperone is CDCl37 (i.e., the Hsp90 co-chaperone) from *H. sapiens*. In one embodiment, said protein phosphatase is protein tyrosine phosphatase 1B (PTP1B) from *H. sapiens*. In one embodiment, said operator is the operator for 434 phage cI repressor. In one embodiment, said binding site for RNA polymerase is the −35 to −10 region of the lacZ promoter. In one embodiment, said gene of interest is SpecR, a gene that confers resistance to spectinomycin. In one embodiment, said genes of interest are LuxA and LuxB, two genes that yield a luminescent output. In one embodiment, said gene of interest is a gene that confers resistance to an antibiotic. In one embodiment, said protein phosphatase is PTPN6 from *H. sapiens*. In one embodiment, said protein phosphatase is a protein tyrosine phosphatase (PTP). In one embodiment, said protein phosphatase is the catalytic domain of a PTP. In one embodiment, an alignment of the X-ray crystal structures of (i) the catalytic domain of said protein phosphatase and (ii) the catalytic domain of PTP1B yields a root-mean-square deviation (RMSD) of less than or equal to 0.95 Å (as defined by a function similar to the PyMol function align). In one embodiment, said catalytic domain of said protein phosphatase has at least 34.1% sequence identity with the catalytic domain of PTP1B. In one embodiment, said catalytic domain of said phosphatase has at least 53.5% sequence similarity with the catalytic domain of PTP1B. In one embodiment, said protein kinase is a protein tyrosine kinase (PTK). In one embodiment, said protein kinase is the catalytic domain of a PTK. In one embodiment, said first promoter is a constitutive promoter. In one embodiment, said second promoter is a constitutive promoter. In one embodiment, said first promoter is an inducible promoter. In one embodiment, said second promoter is an inducible promoter. In one embodiment, said binding site for RNA polymerase comprises part of a third promoter. In one embodiment, said first region lacks a gene for a molecular chaperone. In one embodiment, said first fusion protein consists of a substrate recognition domain linked a protein capable of recruiting RNA polymerase to DNA, and said second fusion protein consists of a substrate domain linked to a DNA-binding protein. In one embodiment, said first region further contains a third fusion protein (i.e., a "decoy") comprising a second substrate domain, which is distinct from the first substrate domain, linked to a protein that is incapable of recruiting RNA polymerase to DNA. In one embodiment, said substrate domain of said third fusion protein is a peptide substrate of both said kinase and said phosphatase. In one embodiment, said substrate domain of said third fusion protein is a peptide substrate of said kinase but is a poor substrate of said phosphatase. In one embodiment, said first region further contains a sixth gene for a second protein phosphatase, which is distinct from the first protein phosphatase and which acts on said substrate domain of said third fusion protein.

In one embodiment, the invention provides a method for using both (i) a genetically encoded system for detecting small molecules that modulate enzyme activity and (ii) a genetically encoded pathway for terpenoid biosynthesis to identify and/or build terpenoids that modulate enzyme activity, comprising, a. providing, i. a genetically encoded system for detecting small molecules that modulate enzyme activity, comprising, 1. a first region in operable combination comprising: a. a first promoter; b. a first gene encoding a first fusion protein comprising a substrate recognition domain linked to a DNA-binding protein; c. a second gene encoding a second fusion protein comprising a substrate domain linked to a protein capable of recruiting RNA polymerase to DNA; d. a second promoter; e. a third gene for a protein kinase; f. a fourth gene for a molecular chaperone; g. a fifth gene for a protein phosphatase; 2. a second region in operable combination comprising: a. a first DNA sequence encoding an operator for said DNA-binding protein; b. a second DNA sequence encoding a binding site for RNA polymerase; c. one or more genes of interest (GOI); ii. a genetically encoded pathway for terpenoid biosynthesis comprising: 1. a pathway that generates linear isoprenoid precursors; 2. a gene for a terpene synthase (TS); 3. a plurality of E. coli bacteria; b. transforming said bacteria with both (i) said genetically encoded system for detecting small molecules and (ii) said genetically encoded pathway for terpenoid biosynthesis, and allowing said transformed bacteria to replicate; c. observing the expression of a gene of interest through a measurable output. In one embodiment, said pathway that generates linear isoprenoid precursors generates farnesyl pyrophosphate (FPP). In one embodiment, said pathway that generates linear isoprenoid precursors is all or part of the mevalonate-dependent isoprenoid pathway of S. cerevisiae. In one embodiment, said pathway that generates linear isoprenoid precursors is carried by the plasmid pMBIS. In one embodiment, said gene of interest is SpecR, a gene that confers resistance to spectinomycin. In one embodiment, said TS gene is carried on a separate plasmid (pTS) from the rest of the terpenoid pathway. In one embodiment, said TS gene encodes for amorphadiene synthase (ADS) from Artemisia annua. In one embodiment, said TS gene encodes for γ-humulene synthase (GHS) from Abies grandis. In one embodiment, said TS gene encodes for abietadiene synthase (ABS) from Abies grandis, and this gene is carried in operable combination with a gene for geranylgeranyl diphosphate synthase (GPPS). In one embodiment, said TS gene encodes for taxadiene synthase (TXS) from Taxus brevifolia, and this gene is carried in operable combination with a gene for GGPPS. In one embodiment, the method further comprises, d. extracting terpenoids that enable the highest measurable output (e.g., growth at the highest concentration of spectinomycin); e. identifying said terpenoids; f. purifying said terpenoids. In one embodiment, the method further comprises, providing, g. a mammalian cell culture, h. treating said cell cultures with purified terpenoids, i. measuring a biochemical effect that results from changes in the activity of a protein phosphatase or protein kinase. In one embodiment, the method further comprises, j. providing, a purified enzyme target, k. measuring the modulatory effect of purified terpenoids on the enzyme target, l. quantifying that modulatory effect (e.g., by calculating an $IC_{50}$). In one embodiment, said TS gene has at least one mutation. In one embodiment, said TS gene is in operable combination with a gene for an enzyme that functionalizes terpenoids. In one embodiment, said TS gene is in operable combination with a gene for a cytochrome P450. In one embodiment, said TS gene is in operable combination with a gene for cytochrome P450 BM3 from Bacillus megaterium. In one embodiment, said TS gene is in operable combination with a gene for a halogenase. In one embodiment, said TS gene is in operable combination with a gene for 6-halogenase (SttH) from Streptomyces toxytricini. In one embodiment, said TS gene is in operable combination with a gene for vanadium haloperoxidase (VHPO) from Acaryochloris marina. In one embodiment, said mammalian cell is a HepG2, Hela, Hek393t, MCF-7, and/or Cho-hIR cell. In one embodiment, said cells are BT474, SKBR3, or MCF-7 and MDA-MB-231 cells. In one embodiment, said biochemical effect is insulin receptor phosphorylation, which can be measured by a western blot or enzyme-linked immunosorbent assay (ELISA). In one embodiment, said cells are triple negative (TN) cell lines. In one embodiment, said cells are TN cells from the American Type Culture Collection (ATCC). In one embodiment, said cells are TN cells from ATCC TCP-1002.

In one embodiment, said biochemical effect is cellular migration. In one embodiment, said biochemical effect is cellular viability. In one embodiment, said biochemical effect is cellular proliferation. In one embodiment, said protein phosphatase is PTP1B from H. sapiens. In one embodiment, said protein kinase is Src kinase from H. sapiens. In one embodiment, said gene of interest confers resistance to an antibiotic. In one embodiment, said gene of interest is SacB, a gene that confers sensitivity to sucrose. In one embodiment, said gene of interest confers conditional toxicity (i.e., toxicity in the presence of an exogenously added molecule). In one embodiment, said genes of interest are SpecR and SacB. In one embodiment, said protein phosphatase is the wild-type enzyme. In one embodiment, said protein phosphatase has at least one mutation. In one embodiment, said protein phosphatase has at least one mutation that reduces its sensitivity to a small molecule that modulates the activity of the wild-type protein phosphatase. In one embodiment, said protein kinase is the wild-type enzyme. In one embodiment, said protein kinase has at least one mutation. In one embodiment, said protein kinase has at least one mutation that reduces its sensitivity to a small molecule that modulates the activity of the wild-type protein kinase. In one embodiment, said at least one of said terpenoids inhibit a protein phosphatase. In one embodiment, said at least one of said terpenoids inhibit a PTP. In one embodiment, said least one of said terpenoids inhibit PTP1B. In one embodiment, said at least one of said terpenoids activate a protein phosphatase. In one embodiment, said least one of said terpenoids activates a PTP. In one embodiment, said at least one of aid terpenoids activate protein tyrosine phosphatase non-receptor type 12 (PTPN12). In one embodiment, said at least one of said terpenoids inhibit a protein kinase. In one embodiment, said at least one of said terpenoids inhibit a PTK. In one embodiment, said at least one of said terpenoid inhibit Src kinase. In one embodiment, said at least one of said terpenoids activate a protein kinase. In one embodiment, said at least one of said terpenoids activate a PTK. In one embodiment, said genetically encoded system for detecting small molecules further contains both (i) a third fusion protein comprising a second substrate domain, which is distinct from the first substrate domain, linked to a protein that is incapable of recruiting RNA polymerase to DNA and (ii) a sixth gene for a second protein phosphatase, which is distinct from the first protein phosphatase. In one embodiment, said genetically encoded system for detecting small molecules further contains both (i) a third fusion protein comprising a second substrate domain, which is distinct from the first substrate domain, linked to a protein that is incapable of recruiting RNA polymerase to DNA and (ii) a sixth gene for a second protein kinase, which is distinct from the first protein kinase. In one embodiment, said genetically encoded pathway for terpenoid biosynthesis comprises, instead, a library of pathways that differ in the identity of the TS gene such that upon transformation, the majority of cells contain a distinct TS gene (i.e., a gene that differs by at least one mutation). In one embodiment, said genetically encoded pathway for terpenoid biosynthesis comprises, instead, a library of pathways that differ in the identity of a gene that functionalizes terpenoids (e.g., a cytochrome P450 or halogenase), in operable combination with the SI gene, such that upon transformation, the majority of cells contain a distinct gene that functionalizes terpenoids (i.e., a gene that differs by at least one mutation). In one embodiment, said genetically encoded pathway for terpenoid biosynthesis comprises, instead, a library of pathways in which the TS gene has been replaced by a component of a eukaryotic complementary DNA (cDNA) library such that upon transformation, the majority of cells contain a distinct gene in place of the TS gene. In one embodiment, said genetically encoded pathway for terpenoid biosynthesis comprises, instead, a library of pathways in which the TS gene accompanied by a component of a eukaryotic complementary DNA (cDNA) library such that upon transformation, the majority of cells contain a distinct gene in operable combination with the TS gene (e.g., a gene that may encode for a terpenoid-functionalizing enzyme). In one embodiment, said genetically encoded system for detecting small molecules comprises, instead, a library of such systems that differ in the identity of the protein phosphatase gene such that upon transformation, the majority of cells contain a distinct protein phosphatase gene (i.e., a gene that differs by at least one mutation). In one embodiment, said genetically encoded pathway for terpenoid biosynthesis generates a terpenoid that modulates the activity of the wild-type form of said protein phosphatase, thereby enabling the growth study to isolate a mutant of said protein phosphatase that is less sensitive to the modulatory effect of the small molecule. In one embodiment, said genetically encoded system for detecting small molecules comprises, instead, a library of such systems that differ in the identity of the protein kinase gene, such that upon transformation, the majority of cells contain a separate protein kinase gene (i.e., a gene that differs by at least one mutation). In one embodiment, said genetically encoded pathway for terpenoid biosynthesis generates a terpenoid that modulates the activity of the wild-type form of said protein kinase, thereby enabling the growth study to isolate a mutant of said protein kinase that is less sensitive to the modulatory effect of the small molecule. In one embodiment, said at least one of said terpenoids modulates the activity of the wild-type form of said protein phosphatase, but not a mutated form of said protein phosphatase. In one embodiment, said at least one of said terpenoids modulates the activity of the said first protein phosphatase, but not the activity of said second protein phosphatase. In one embodiment, said at least one of said terpenoids modulates the activity of the wild-type form of said protein kinase, but not a mutated form of said protein kinase. In one embodiment, said at least one of said terpenoids modulates the activity of said first protein kinase, but not the activity of said second protein kinase.

In one embodiment, the invention provides an inhibitor detection operon comprising, A: a first region in operable combination under control of a first promoter including: i. a first DNA sequence encoding a first fusion protein comprising a substrate recognition homology 2 domain (SH2) and a repressor; ii. a second DNA sequence encoding a second fusion protein comprising a phosphate molecule binding domain of a substrate recognition domain, said substrate recognition domain and an omega subunit of RNA polymerase (RpoZ or $RP_\omega$); iii. a third DNA sequence encoding a Cell Division Cycle 37 protein (CDCl37); iv. a protein phosphatase; and B: a second region in operable combination under control of a second promoter comprising: i. an operator comprising a repressor binding domain said repressor, ii. a ribosome binding site (RB); and iii. a gene of interest (GOI). In one embodiment, said SH2 domain is a substrate recognition domain of said protein phosphatase. In one embodiment, said repressor is a 434 phage cI repressor. In one embodiment, said substrate recognition domain binds said protein phosphatase. In one embodiment, said decoy substrate domain is a Src kinase gene. In one embodiment, said operator is a 434cI operator. In one embodiment, said gene of interest encodes an antibiotic protein. In one embodiment, said protein phosphatase is a protein tyrosine phosphatase. In one embodiment, said first promoter is constitutive promoter. In one embodiment, said second promoter is an inducible promoter.

In one embodiment, the invention provides a method of using an inhibitor detection operon, comprising, a. providing, i. a detection operon, comprising A: a first region in operable combination under control of a first promoter including: 1. a first DNA sequence encoding a first fusion protein comprising a protein phosphatase enzyme's substrate recognition homology 2 domain (SH2) and a repressor binding domain; 2. a second DNA sequence encoding a second fusion protein comprising a phosphate molecule binding domain of a protein phosphatase enzyme's substrate recognition domain, said protein phosphatase enzyme's substrate recognition domain and an omega subunit of RNA polymerase (RpoZ or RP.); 4. a third DNA sequence encoding a Cell Division Cycle 37 (CDCl37) protein; 5. a protein phosphatase enzyme; and B: a second region in operable combination under control of a second promoter comprising: 6. an operator comprising a repressor binding domain biding said repressor, 7. a ribosome binding site (RB); and 8. a gene of interest (GOI); and ii. a mevalonate pathway operon having a missing gene, such that said pathway operon does not contain at least one gene in said pathway for producing said terpenoid compound, under control of a third promoter comprising a second gene of interest for producing a terpenoid compound, iii. a fourth DNA sequence under control of a fourth promoter comprising said missing gene from said mevalonate pathway operon and a third gene of interest; and iv. a plurality of E. coli bacteria, and b. transfecting said E. coli bacteria with said first operon for expressing said first gene of interest; c. transfecting said E. coli bacteria with said mevalonate pathway operon for expressing said first and said second gene of interest; d. transfecting said E. coli bacteria with said fourth DNA sequence for expressing said first and said second and said third gene of interest; e. growing said cells wherein said inhibitor terpenoid compounds for protein phosphatase enzymes are produced by said cells. In one embodiment, said method further comprising step e. isolating said protein phosphatase inhibitor molecules and providing a mammalian cell culture for step f. treating said cell cultures for reducing activity of said protein phosphatase enzyme. In one embodiment, said method further providing an inducer compound for inducing said inducible promoter and a step of contacting said baceria with said compound. In one embodiment, said method wherein reducing activity of said protein phosphatase enzyme reduces growth of said mammalian cells. In one embodiment, said protein phosphatase enzyme is human PTP1B. In one embodiment, said protein phosphatase enzyme is wild-type. In one embodiment, said protein phosphatase enzyme has at least one mutation. In one embodiment, said missing enzyme is a terpene synthase enzyme. In one embodiment, said terpene synthase enzyme is selected from the group consisting of amorphadiene synthase (ADS) and γ-humulene synthase (GHS). In one embodiment, said fourth DNA sequence further comprises a geranylgeranyl diphosphate synthase (GPPS) and said missing enzyme is selected from the group consisting of abietadiene synthase (ABS) and taxadiene synthase (TXS). In one embodiment, said terpene synthase enzyme is wild-type. In one embodiment, said terpene synthase enzyme has at least one mutation. In one embodiment, said terpenoid compounds are structural variants of terpenoid compounds. In one embodiment, said genes of interest are antibiotic genes. In one embodiment, said genes of interest are each different antibiotic genes.

In one embodiment, said genetically encoded detection operon system, comprising; Part A: a first region of DNA in operable combination comprising: a region of DNA encoding a first promoter; a first gene encoding a first fusion protein comprising a substrate recognition domain linked to a DNA-binding protein; a second gene encoding a second fusion protein comprising a substrate domain linked to a protein capable of recruiting RNA polymerase to DNA; a region of DNA encoding a second promoter; a third gene for a protein kinase; a fourth gene for a molecular chaperone; a fifth gene for a protein phosphatase; Part B: a second region of DNA in operable combination under control of a second promoter comprising: a first DNA sequence encoding an operator for said DNA-binding protein; a second DNA sequence encoding a binding site for RNA polymerase; and at least one gene of interest (GOI). In one embodiment, said substrate recognition domain is a substrate homology 2 (SH2) domain. In one embodiment, said DNA-binding protein is the 434 phage cI repressor. In one embodiment, said substrate domain is a peptide substrate of both said kinase and said phosphatase In one embodiment, said protein capable of recruiting RNA polymerase to DNA is the omega subunit of RNA polymerase ($RP_\omega$). In one embodiment, said gene for a kinase is a Src kinase gene. In one embodiment, said molecular chaperone is CDC137. In one embodiment, said molecular chaperone is the Hsp90 co-chaperone) from *H. sapiens*. In one embodiment, said operator is a 434 phage cI operator. In one embodiment, said gene of interest is a gene for antibiotic resistance. In one embodiment, said gene for antibiotic resistance produces an enzyme that allow the bacteria to degrade an antibiotic protein. In one embodiment, said protein phosphatase enzyme is protein tyrosine phosphatase 1B. In one embodiment, said first and second promoters of part A are constitutive promoters. In one embodiment, said second promoter of Part B is an inducible promoter.

In one embodiment, the invention provides a method of using a genetically encoded detection operon system, comprising, a. providing, i. an inhibitor detection operon, comprising Part A: a first region of DNA in operable combination comprising: 1. a region of DNA encoding a first promoter; 2. a first gene encoding a first fusion protein comprising a substrate recognition domain linked to a DNA-binding protein; 3. a second gene encoding a second fusion protein comprising a substrate domain linked to a protein capable of recruiting RNA polymerase to DNA; 4. a region of DNA encoding a second promoter; 5. a third gene for a protein kinase; 6. a fourth gene for a molecular chaperone; 7. a fifth gene for a protein phosphatase; Part B: a second region of DNA in operable combination under control of a second promoter comprising: 8. a first DNA sequence encoding an operator for said DNA-binding protein; 9. a second DNA sequence encoding a binding site for RNA polymerase; and 10. at least one gene of interest (GOI). ii. a mevalonate-terpene pathway operon not containing a terpene synthase gene, under control of a fourth promoter comprising a second gene of interest for producing a terpenoid compound, iii. a fourth DNA sequence under control of a fifth promoter comprising said terpene synthase gene and a third gene of interest; and iv. a plurality of bacteria, and b. transfecting said bacteria with said inhibitor detection operon for expressing said first gene of interest; c. transfecting said bacteria with said mevalonate pathway operon for expressing said second gene of interest; d. transfecting said bacteria with said fourth DNA sequence for expressing said third gene of interest; e. growing said bacteria cells expressing said three genes of interest wherein said inhibitor terpenoid compounds are produced by said bacteria cells inhibiting said protein phosphatase enzyme. In one embodiment, said method further comprising step e. isolating said protein phosphatase inhibitor molecules and providing a mammalian cell culture for step f. treating said cell cultures for reducing activity of said protein phosphatase enzyme. In one embodiment, said method wherein reducing activity of said protein phosphatase enzyme reduces growth of said mammalian cells. In one embodiment, said protein phosphatase enzyme is human PTP1B. In one embodiment, said protein phosphatase enzyme is wild-type. In one embodiment, said protein phosphatase enzyme has at least one mutation. In one embodiment, said mevalonate pathway operon comprises genes for expressing mevalonate kinase (ERG12), phosphomevalonate kinase (ERGS), mevalonate pyrophosphate decarboxylatse (MVD1), Isopentenyl pyrophosphate isomerase (IDI gene), and Farnesyl pyrophosphate (FPP) synthase (ispA). In one embodiment, said missing enzyme is a terpene synthase enzyme. In one embodiment, said terpene synthase enzyme is selected from the group consisting of amorphadiene synthase (ADS) and γ-humulene synthase (GHS). In one embodiment, said fourth DNA sequence further comprises a geranylgeranyl diphosphate synthase (GPPS) and said terpene synthase is selected from the group consisting of abietadiene synthase (ABS) and taxadiene synthase (TXS). In one embodiment, said terpene synthase enzyme is wild-type. In one embodiment, said terpene synthase enzyme has at least one mutation. In one embodiment, said terpenoid compounds are structural variants of terpenoid compounds. In one embodiment, said genes of interest are antibiotic genes. In one embodiment, said genes of interest are each different antibiotic genes. In one embodiment, said method further provides an inducer compound for inducing said inducible promoter and a step of contacting said baceria with said compound.

In one embodiment, the invention provides a method for using both (i) a genetically encoded system for detecting small molecules that modulate enzyme activity and (ii) a genetically encoded pathway for polyketide biosynthesis to identify and/or build polyketides that modulate enzyme activity, comprising, providing, A genetically encoded system for detecting small molecules that modulate enzyme activity, comprising, a first region in operable combination comprising: a first promoter; a first gene encoding a first fusion protein comprising a substrate recognition domain linked to a DNA-binding protein; a second gene encoding a second fusion protein comprising a substrate domain linked to a protein capable of recruiting RNA polymerase to DNA; a second promoter; a third gene for a protein kinase; a fourth gene for a molecular chaperone; a fifth gene for a protein phosphatase; a second region in operable combination comprising: a first DNA sequence encoding an operator for said DNA-binding protein; a second DNA sequence encoding a binding site for RNA polymerase; one or more genes of interest (GOI); a genetically encoded pathway for polyketide biosynthesis comprising; a gene for a polyketide synthase; a plurality of *E. coli* bacteria. In one embodiment, said polyketide synthase is 6-deoxyerythronolide B synthase (DEBS). In one embodiment, said polyketide synthase (PKS) is a modular combination of different PKS components.

In one embodiment, the invention provides a method for using both (i) a genetically encoded system for detecting small molecules that modulate enzyme activity and (ii) a genetically encoded pathway for polyketide biosynthesis to identify and/or build alkaloids that modulate enzyme activity, comprising, a. providing, a genetically encoded system for detecting small molecules that modulate enzyme activity, comprising, a first region in operable combination comprising: a first promoter; a first gene encoding a first fusion protein comprising a substrate recognition domain linked to a DNA-binding protein; a second gene encoding a second fusion protein comprising a substrate domain linked to a protein capable of recruiting RNA polymerase to DNA; a second promoter; a third gene for a protein kinase; a fourth gene for a molecular chaperone; a fifth gene for a protein phosphatase; a second region in operable combination comprising: a first DNA sequence encoding an operator for said DNA-binding protein; a second DNA sequence encoding a binding site for RNA polymerase; one or more genes of interest (GOI); a genetically encoded pathway for polyketide biosynthesis comprising, a pathway for alkaloid biosynthesis. a plurality of E. coli bacteria. In one embodiment, said pathway for alkaloid biosynthesis described herein.

In one embodiment, the invention provides an engineered bacreria cell line comprising expression plasmid 1, plasmid 2, plasmid 3 and plasmid 4.

In one embodiment, the invention provides a phosphatase inhibitor molecule produced by a bacterium expressing a plasmid 1 in contact with an inducer molecule for inducing a promoter expressing a terpenoid synthesis pathway operon in plasmid 2 and a terpene synthase enzyme in plasmid 3, wherien said plasmid 2 and plasmid 3 are coexpressed in said bacteria with plasmid 1. In one embodiment, said paslmid 2 and said plasmid 3 are under control of an inducible promoter. In one embodiment, said bacterium is contacted by an inducible molecule for inducing said promoter.

In one embodiment, the invention provides a bacteria strain producing a phosphatase inhibitor molecule. In one embodiment, said inhibitor is a terpenoid molecule.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1A-G illustrates embodiments and shows exemplary results of developing a photoswitchable phosphatase, e.g. $PTP1B_{PS}$.

FIG. 1A illustrates one embodiment of a design of $PTP1B_{PS}$: Light-induced unwinding of the A'α helix of LOV2 destabilizes the α7 helix of PTP1B and, thus, inhibits catalysis. FIG. 1B illustrates one embodiment of Elaboration: In the competitively inhibited structure of PTP1B (orange), the α7 helix (SEQ ID NO: 1) is stable, and the WPD loop (black) adopts a closed, catalytically competent conformation. In the apo structure (yellow), the α7 helix is disordered, and the WPD loop (blue) adopts an open, inactive conformation. We attached the C-terminal α7 helix of PTP1B to the N-terminal A'α helix of LOV2 (SEQ ID NO: 2) at homologous crossover points (1-7) to create a chimera for which the photoresponsive of LOV2 destabilizes the α7 helix. FIG. 1C shows exemplary results of optimization of one embodiment: Construct 7 exhibited the largest dynamic range of the crossover variants; 7.1 had an improved activity over 7, while 7.1(T406A) had an improved dynamic range over 7.1. FIG. 1D shows an exemplary analysis of the activity of $PTP1B_{PS}$ on pNPP indicates that light affects $k_{cat}$, but not $K_m$. FIG. 1E shows the dynamic range of $PTP1B_{PS}$ is similar for substrates of different sizes. FIG. 1F shows exemplary illustrations of two small molecules: p-nitrophenyl-phosphate (or pNPP), and 4-methylumbelliferyl phosphate (or 4MU) and a peptide domain from EGFR. FIG. 1G shows exemplary activity of PTP1B-LOV2 chimeras that differ in (A-D) crossover location and (E-E4) linker composition in the presence and absence of 455 nm light. Substrate: 4-methylumbelliferyl phosphate.

FIG. 2A-J shows exemplary biophysical characterizations of $PTP1B_{PS}$.

FIG. 2A shows exemplary mutations that (i) prevent the formation of the cysteine adduct in LOV2 (C450M), (ii) destabilize the A'α and Jα helices if LOV2 (I532E, I539E, and ΔJα), or (iii) disrupt the allosteric network of PTP1B (Y152A/Y153A) reduced the photosensitivity of 7.1 and, with the exception of I532E and C450M, lowered its specific activity. FIG. 2B shows exemplary exposure of $PTP1B_{PS}$ to 455 nm light reduces its α-helical content ($CD_{222\ nm}$). FIG. 2C shows exemplary optical modulation of α-helical content (i.e., $\delta_{222} = CD_{222\text{-}dark} - CD_{222\text{-}light}$) is necessary, but not sufficient for optical modulation of catalytic activity. The dashed line denotes $\delta_{222}$ for an equimolar solution of $PTP1B_{WT}$ and $LOV2_{WT}$. FIG. 2D shows exemplary fluorescence of six tryptophan residues in the catalytic domain of PTP1B which enables optical monitoring of its conformational state. FIG. 2E-F shows exemplary thermal recovery of (FIG. 2E) α-helical content and (FIG. 2F) tryptophan fluorescence of $PTP1B_{PS}$. FIG. 2G shows exemplary kinetic constants for thermal resetting are larger for α-helical content than for tryptophan fluorescence, suggesting that LOV2 resets more quickly than the PTP1B domain. This discrepancy is smallest for the most photosensitive variant: 7.1 (T406A). FIG. 2H shows exemplary alignments of the crystal structures of $PTP1B_{PS}$ (blue) and apo $PTP1B_{WT}$ (orange) indicate that LOV2 does not distort the structure of the catalytic domain. The LOV2 domain of $PTP1B_{PS}$ could not be resolved; a flexible loop at the beginning of the α7 helix likely causes LOV2 to adopt variable orientations in the crystal lattice. The α6 and α7 helices of an inhibited structure of PTP1B (yellow) are shown for reference. FIG. 2I shows an exemplary gap in the crystal structure of $PTP1B_{PS}$ that can accommodate LOV2. FIG. 2J shows where exemplary crystals of a PTP1B-LOV2 fusion are green and turn clear when illuminated with 455 nm light; LOV2 is, thus, unequivocally present. Error bars for A, C, and G denote standard error (n>3). Note: $PTP1B_{PS}$ corresponds to construct 7.1(T406A) from FIG. 1.

FIG. 3A shows one embodiment of a sensor for PTP1B activity. This sensor consists of a kinase substrate domain, a short flexible linker, and a phosphorylation recognition domain, sandwiched between two fluorescent proteins (e.g., a cyan fluorescent protein and a yellow fluorescent protein). When the sensor is in its unphosphorylated state, Förster resonance energy transfer (FRET) between the two fluorophores causes a decrease in CFP fluorescence and an increase in YFP fluorescence; when the sensor is in its phosphorylated state, the absence of FRET causes the opposite effect. FIG. 3B shows an exemplary increase in the ratio of donor fluorescence (CFP) to acceptor fluorescence (YPet) evidences the presence of Src kinase (i.e., a tyrosine kinase). When either (i) EDTA, which chelates a metal cofactor of Src, or (ii) PTP1B, which dephosphorylates the substrate domain, are additionally added, this increase does not occur.

FIG. 3C shows one embodiment as another variety of the FRET sensor for A; this one uses mClover3 and mRuby3. The excitation and emission wavelengths of these proteins make them compatible with LOV2-based imaging experiments. FIG. 3D shows an exemplary repeat of the experiment from B with the sensor from C.

FIG. 4A-C shows embodiments of three constructs are expressed in Cos-7 cells: (FIG. 4A) GFP-PTP1B$_{PS}$, (FIG. 4B) GFP-PTP1B$_{PS}$-A, and (FIG. 4C) GFP-PTP1B$_{PS}$-B. Here, GFP-PTP1B$_{PS}$ is a fusion of green fluorescent protein (GFP) and the N-terminus of 7.1(T406A) from FIG. 1B-C (without the histidine tag); GFP-PTP1B$_{PS}$-A is a fusion of GFP-PTP1B$_{PS}$ and the C-terminal domain of full-length PTP1B; and GFP-PTP1B$_{PS}$-B is fusion of GFP-PTP1B$_{PS}$ and the C-terminal endoplasmic reticulum (ER) anchor of full-length PTP1B (see below). GFP-PTP1B$_{PS}$ localizes to the cytosol and nucleus, while GFP-PTP1B$_{PS}$-A and GFP-PTP1B$_{PS}$-B localize to the ER. FIG. 4D-H shows exemplary results of cell-based studies of PTP1B$_{PS}$. We transformed Cos-7 cells with a plasmid containing (i) the FRET sensor from FIGS. 3C-3D and (ii) PTP1B$_{PS}$ or PTP1B$_{PS}$/C450M (a light-insensitive mutant). In this experiment, we illuminated individual cells with 447 nm light and immediately imaged them with 561 nm light. Light-modulated changes in FRET ratio (as defined in FIG. 3) allowed us to detect light-modulated changes in PTP1B activity. FIG. 4D-E shows an exemplary Cos-7 cell transformed with PTP1B$_{PS}$ at two time points: (FIG. 4D) immediately after excitation with 447 nm light and (FIG. 4E) after 1 min. A slight increase in FRET ratio (dark green to lighter green) evidences photoactivation of PTP1B. (F-G). A Cos-7 cell transformed with PTP1B$_{PS}$ (C450M) at two time points: (FIG. 4F) immediately after excitation with 447 nm light and (G) after 1 min. The absence of a detectable change in FRET-ratio indicates that the change observed in D-E results from light-induced changes in PTP1B activity. FIG. 4H shows an exemplary average fractional change in FRET ratio observed in the nucleus (nuc) and cytosol (cyt) after 1 min and 2.67 min. The change is higher for PTP1B$_{PS}$ than for PTP1B$_{PS}$(C450M), the light-insensitive mutant. Error bars indicate standard error.

FIG. 5A shows an exemplary use of a phosphatase, i.e. drug target (upper left depiction of PTP1B) for identifying a synthetic enzyme (lower right depiction) where the enzyme is then used for providing an inhibitor or modulatory molecule for the phosphatase, thus showing a general framework for using enzymes to build inhibitors of chosen protein targets. FIG. 5B shows an exemplary analysis of structural relationships between binding pockets. A matrix compares individual properties (e.g., volume) between binding pocket 1 and all other binding pockets (2 to n) capable of functionalizing (e.g., P450) or binding to (e.g., PTP1B) ligands synthesized within pocket 1. FIG. 5C shows an exemplary comparison of the ability of binding pockets in a biosynthetic pathway to bind to intermediates.

FIG. 7A shows embodiments of two binding partners of PTP1B: LMO4 and Stat3. FIG. 7B shows an exemplary binding isotherm based on binding-induced changes in the tryptophan fluorescence of PTP1B (the ligand is TCS 401, a competitive inhibitor).

FIG. 8B illustrates an exemplary structure of PTK6. Both STEP and PTK6 possess a C-terminal alpha-helix that is compatible with actuation by the N-terminal helix of LOV2 (i.e., an photomodulatory architecture similar to that depicted in FIG. 1).

FIG. 10A shows an exemplary illustration where in its active state (here the far-red state), PTP1B dephosphorylates the substrate domain, prevents substrate-SH2 association, and, thus, prevents transcription. FIG. 10B shows an exemplary illustration where in its inactive state (here, the red state), the phosphorylated substrate domain binds SH2, permitting transcription of a gene for antibiotic resistance.

FIG. 11A illustrates where we will compare the growth of colonies on replicate plates exposed to red and infrared light and select colonies that exhibit differential growth. FIG. 11B illustrates where we will further characterize the photosensitivity of top hits in liquid culture.

FIG. 14A illustrates Abietic acid. FIG. 14B demonstrates inhibition of PTP1B by abietic acid at concentrations (dark to light) of 0-400 uM. Analysis of different fits suggests noncompetitive or mixed-type inhibition. FIG. 14C illustrates Abietic acid (green) docked in the allosteric site of PTP1B. We have since shown that abietic acid binds to the active site of PTP1B. Inset highlights active site in black. FIG. 14D shows an exemplary X-ray crystal structure of a known allosteric inhibitor (blue).

FIG. 15B shows exemplary Abietadiene titers generated by E. coli DH5a transformed with the plasmids from A (with no P450). FIG. 15C-D shows exemplary GC-MS analysis of products of FIG. 15C) abietadiene-producing strain and FIG. 15D abietic-acid-producing strain: (1) abietadiene, (2) levopimaradiene, and (3) abietic acid (ion counts in 10,000 for C and 1,000 for FIG. 15D). Note: *E. coli* DH5a avoids protein overexpression is commonly used in metabolic engineering*[4].

FIG. 16A illustrates clockwise from abietic acid (1), neoabietic acid (2), levopimaric acid (3), dihydroabietic acid (4). FIG. 16B shows exemplary initial rates in PTP1B on 10 mM of p-NP phosphate in the presence of 200 uM inhibitor. No inhibitor (C). Error bars=standard error (n>5).

FIG. 17A N-HSQC spectra of PTP1B (red) and PTP1B bound to abietic acid (blue). Inset: Crystal structure of PTP1B. FIG. 17B-C shows exemplary Tryptophan (W) fluorescence of PTP1B in the presence of FIG. 17B culture extract of control ($ABS_X$), abietadiene-producing (ABS), and abietic-acid producing (ABS/BM3) strains and (FIG. 17C) various concentrations of abietic acid and 25 uM of known allosteric inhibitor (BBR). Error bars represent standard error (n>5).

FIG. 19D-E shows exemplary residues targeted for mutagenesis in FIG. 19D P450 BM3 and FIG. 19E SttH.

FIG. 21A-E illustrates an exemplary high-throughput screens for PTP1B inhibitors.

FIG. 21A Growth-coupled (i.e., selection; strategy 1). FIG. 21B) FRET sensor for PTP1B activity (strategy 2). FIG. 21C) FRET sensor and FIG. 21D) tryptophan fluorescence for changes in PTP1B conformation (strategies 3 and 4). FIG. 21E. Results for an operon similar to that shown in FIG. 21A, where Amp is replaced with Lux. Error bars=SD (n≥3).

FIG. 22A-D illustrates exemplary inhibition of PTP1B. Error bars in FIG. 22C denote SE (n≥3 independent reactions).

FIG. 22A shows exemplary alignments of the backbone of PTP1B in competitively inhibited (yellow and orange, PDB entry 2F71) and allosterically inhibited (gray and black, PDB entry 1T4J) poses. The binding of substrates and competitive inhibitors to the active site causes the WPD loop to adopt a closed (orange) conformation that stabilizes the C-terminal alpha7 helix through an allosteric network; this helix is unresolvable in allosterically inhibited, noncompetitively inhibited, and uninhibited structures, which exhibit WPD-open conformations (black). FIG. 22B shows an exemplary illustration of a chemical structure of abietic acid (AA). FIG. 22C shows exemplary initial rates of PTP1B-catalyzed hydrolysis of pNPP in the presence of increasing concentrations of AA. Lines show a fit to a model for mixed inhibition. FIG. 22D an exemplary illustration of this model, where the inhibitor (I) binds to the enzyme (E) and enzyme-substrate complex (ES) with different affinities.

FIG. 23A-C illustrates an exemplary NMR analysis of PTP1B-AA association.

FIG. 23A shows exemplary weighted differences in chemical shifts ($\Delta\square$) between 1H-15 N-HSQC spectra collected in the absence and presence of AA (PTP1B:AA of 10:1). The dashed red line delineates the threshold for values of $\Delta\square$ larger than two standard deviations (a) above the mean; gray bars mark residues for which chemical shifts broadened beyond recognition. FIG. 23B illustrates an exemplary crystal structure of PTP1B (PDB entry 3A5J, gray) highlights the locations of assigned residues (blue); inhibitors in the allosteric site (PDB entry 1T4J, green) and active site (PDB entry 3EB1, yellow) are overlaid for reference. Residues with significant CSPs (i.e., $\Delta\square>\Delta\square$ mean+2σ) are distributed across the protein (red) and, with the exception of two residues in the WPD loop, outside of known binding sites. FIG. 23C illustrates an exemplary detail of the active site (upper panel) and known allosteric site (lower panel) with inhibitors from (FIG. 23B) overlaid.

FIG. 24A-C illustrates an exemplary mutational analysis of the AA binding site.

FIG. 24A illustrates an exemplary crystal structure of PTP1B (gray, PDB entry 3A5J) shows the location of mutations introduced at five sites: the active site (red), the allosteric site (green), site 1 (orange), site 2 (yellow), and the L11 loop (blue). The bound configurations of BBR (allosteric site, PDB entry 1T4J) and TCS401 (active site, PDB entry 1C83) are overlaid for reference. FIG. 24B illustrates exemplary disruptive mutations introduced at each site. Mutations were designed to alter the size and/or polarity of targeted residues. The mutation denoted "YAYA" (Y152A/Y153A), which was identified in a previous study, attenuates allosteric communication between the C-terminus and the WPD loop. FIG. 24C illustrates exemplary fractional change in inhibition (F in Eq. 1) caused by the mutations from (B). Five mutations distributed across the protein reduced inhibition by AA and TCS401, but had negligible effect on inhibition by BBR. The similar effects of most mutations on AA and TCS401 suggest that both inhibitors bind to the active site. Error bars denote SE (propagated from n≥9 independent measurements of each V in Eq. 1).

FIG. 25A-B illustrates exemplary results of molecular dynamics simulations: backbone traces of PTP1B in (A) AA-free and FIG. 25B illustrates exemplary amino acid (AA)-bound states. The thickness of traces indicates the amplitude and direction of local motions (Methods). The binding of AA increases the flexibility of the WPD, E, and L10 loops. The WPD and L10 loops contain residues with significant CSPs (red), suggesting consistency between the results of MD and NMR analyses. FIG. 25C illustrates an exemplary representative bound conformation if AA (green). Upon binding to the active site, AA (i) forms a hydrogen bond with R221 that weakens a bond between R221 and E115 and (ii) prevents the formation of a hydrogen bond (red) between W179 and R221 that forms when the WPD loop closes. Both effects enhance the conformational dynamics of the WPD loop. FIG. 25D shows exemplary results of docking calculations are consistent with mixed-type inhibition: the binding of AA prevents the WPD loop from closing and disrupts, but does not preclude, the binding of pNPP (blue spheres).

FIG. 26A) Structural analogues of abietic acid (AA): continentalic acid (CA), isopimaric acid (IA), dehydroabietic acid (DeAA), and dihydroabietic acid (DiAA). FIG. 26B) Differences in degree of saturation yield pronounced differences in potency (i.e., IC 50), but not selectivity. Error bars represent 95% confidence intervals. FIG. 26C) shows binding of three of the analogues depicted in FIG. 26A).

FIG. 27A illustrates an exemplary Histogram of kinetically characterized mutations. All mutations proximal (<4 A) to five or more network residues were "influential" (i.e., they altered $k_{cat}$ or $K_M$ by >50% or had a detectable influence on inhibition); non-consequential mutations, by contrast, had fewer neighboring network residues. FIG. 27B illustrates an exemplary crystal structure of PTP IB (gray, PDB entry 3A5J) highlights the locations of influential mutations on network residues; colors indicate whether they were introduced in biophysical studies or found in diseases. FIG. 27C illustrates an exemplary two cumulative distribution functions describe numbers of network residues proximal to (i) mutations identified in diseases and (ii) a random selection of sites. The two distributions are indistinguishable from one another (P<0.05), suggesting that disease-associated mutations do not occur preferentially near the allosteric network.

FIG. 28A shows embodiments of Operon A. An example of the operon. S, tyrosine substrate; P, phosphate group; cI, the 434 phage cI repressor; RpoZ and $RP_\omega$, the omega subunit of RNA polymerase; cI OP, the binding sequence for the 434 phage cI repressor; and RB, the binding site for RNA polymerase (RNAP). Phosphorylation of the tyrosine substrate (by c-Src kinase) causes binding of the substrate-RP. fusion to the SH2-cI fusion; this binding event, in turn, localizes the RNA polymerase to RB, triggering transcription of the GOI. PTP1B dephosphorylates the substrate domain, preventing the association of substrate-RP. fusion and the SH2-cI, thereby, halting transcription of the GOI. Inactivation of PTP1B, in turn, re-enables transcription of the GOI. FIG. 28B illustrates one embodiment of a proposed medium-throughput screen for membrane-permeable inhibitors: A strain of the E. coli is transformed with the operon and grown in the presence of small molecules; small-molecule inhibitors of PTP1B modulate transcription of the GOI (e.g., a gene for luminescence, fluorescence, or antibiotic resistance) in a dose-dependent manner. The bar graph shows a predicted trend in data. FIG. 28C shows embodiments of Operon B. An operon that enables screens for selective inhibitors. This operon comprises operon A with (i) a second substrate-protein fusion (red), a "decoy", that can bind to the SH2-cI fusion but not specifically to DNA or RNA polymerase, and (ii) a second PTP (e.g., TC-PTP) that is active on the substrate domain of the decoy. Because complexes between the decoy and SH2-cI do not trigger transcription, the decoy inhibits transcription by competing with cI-substrate for binding sites. Accordingly, molecules that inhibit PTP1B, but not TC-PTP (which dephosphorylates the decoy)—that is, selective inhibitors—cause the greatest transcriptional activation. Molecules that inhibit both enzymes, by contrast, cause less activation. FIG. 28D shows embodiments of Operon C. This operon enables screens for photoswitchable enzymes. This operon comprises a version of operon A in which PTP1B has been replaced with a photoswitchable version of PTP1B. In this case, transcription of the GOI is different (e.g., higher or lower) under different sources of light. In the example shown, light inhibits the activity of a PTP1B-LOV2 chimera and, thus, enhances transcription of the GOI.

FIG. 29A shows one embodiment of Operon A in which the GOI is a bacterial luciferase (LuxAB). PTP1B inhibits luminescence (i.e., reduces transcription of the GOI), while a catalytically inactive version of PTP1B (a mimic for an inhibited version of PTP1B) enhances luminescence. FIG. 29B shows one embodiment of Operon A in which the GOI is a gene for spectinomycin resistance (SpecR). PTP1B inhibits growth on spectinomycin, while a catalytically inactive version of PTP1B (a mimic for an inhibited version of PTP1B) enhances growth. The MidT substrate is used herein.

FIG. 30A shows one embodiment of operon from A in which the GOI is a bacterial luciferase (LuxAB), the PTP1B is missing, and the substrate is a peptide from Kras, midT, ShcA, or EGFR. Although all substrates can be phosphorylated by Src kinase, only two substrates bind to the SH2 domain tightly enough to enable significant luminescence over background (0% arabinose). FIG. 30B shows one embodiment of operon from A (here, contained on a single plasmid) in which the GOI is a bacterial luciferase (LuxAB) and PTP1B is missing. The Y/F mutation on the substrate domain (blue) prevents it from being phosphorylated. The RBS sites toggle expression of the Src kinase.

FIG. 31A illustrates an exemplary conceptualization of a screen for microbially synthesizable inhibitors of PTP1B. When transformed with one embodiment of Operon A (or operon B), a cell capable of synthesizing PTP1B-inhibiting metabolites will produce a different GOI output than a cell that does not produce such metabolites. Because abietane-type diterpenoids can both (i) inhibit PTP1B and (ii) be synthesized in E. coli, we believe that a strain of E. coli that contains both Operon A and a pathway for building abietane-type diterpenoids could be "evolved" to build inhibitors of PTP1B. Here, the GOI could be a gene for luminescence or fluorescence (low throughput) or antibiotic resistance (high throughput). FIG. 31B illustrates an exemplary conceptualization of a screen for photoswitchable enzymes. Consider a fusion of PTP1B to LOV2 or BphP1 (here, the highlighted helices show N-terminal connection points on these two proteins). For this example, illumination of the PTP1B-LOV2 with 455 nm light reduces its activity; illumination of the PTP1B-BphP1 fusion with 650 nm light reduces its activity, while illumination of the PTP1B-BphP1 fusion with 750 nm light enhances its activity. When transformed with operon C (which would contain one of these fusions), a cell will produce a different GOI output under different illumination conditions. FIG. 31C illustrates an exemplary conceptualization of a screen for selective mutants of enzymes. When transformed with a version of operon B where (i) PTP1B is also active on the decoy and (ii) the second PTP (TC-PTP in our example) is missing, a cell containing a mutant of PTP1B will most effectively transcribe the GOI when PTP1B is only active on the decoy substrate. FIG. 31D illustrates an exemplary conceptualization of a screen for selective substrates. When transformed with a version of operon B where (i) the decoy is missing, (ii) the first enzyme (PTP1B in our example) is under an inducible promoter, (iii) a second PTP (TC-PTP in our example) is under a second inducible promoter, and (iv) the GOI includes a gene for antibiotic resistance and a gene that produces a toxic product in the presence of a non-essential substrate, a cell containing a mutated substrate domain will grow under both condition 1 (inducer of PTP1B and non-essential substrate) and condition 2 (inducer of TC-PTP), when it binds to PTP1B, but not to TC-PTP.

FIG. 32A refers to an exemplary results of a statistical coupling analysis. The orange and blue clusters represent two groups of interconnected residues, termed "sectors", that exhibit strong intragroup correlations in nonrandom distributions of amino acids. The allosteric site (green inhibitor, PDB entry 1T4J), WPD loop (purple spheres), and active site (red inhibitor, 3EB1) are highlighted for reference. FIG. 32B refers to an exemplary analysis of crosstalk between pockets of PTP1B modeled with MD simulations. Pockets are represented as spheres, colored according to their persistency along the MD trajectory; the size of each sphere indicates its average volume in MD simulations. Links have thicknesses proportional to the frequency of inter-pocket merging and splitting events (i.e., communication). Two independent sets of interconnected pockets map closely to the sectors identified in SCA and, thus, suggest that these two sectors represent distinct domains of an evolutionarily conserved allosteric network. In the PTP1B-LOV2 fusions of FIG. 1, LOV2 modulates the activity of PTP1B by tapping into the allosteric network defined by sector A. Identification of sector A with a statistical coupling analysis of the PTP family thus indicates that the architecture for photocontrol described in FIG. 1 is broadly applicable to all protein tyrosine phosphatases.

FIG. 33A illustrates an embodiment of a bacterial two-hybrid system that detects phosphorylation-dependent protein-protein interactions. Components include (i) a substrate domain fused to the omega subunit of RNA polymerase (yellow), (ii) an SH2 domain fused to the 434 phage cI repressor (light blue), (iii) an operator for 434cI (dark green), (iv) a binding site for RNA polymerase (purple), (v) Src kinase, and (vi) PTP1B. Src-catalyzed phosphorylation of the substrate domain enables a substrate-SH2 interaction that activates transcription of a gene of interest (GOI, black). PTP1B-catalyzed dephosphorylation of the substrate domain prevents that interaction; inhibition of PTP1B re-enables it. FIG. 33B refers to an embodiment of the two-hybrid system from FIG. 33A that (i) lacks PTP1B and (ii) contains luxAB as the GOI. We used an inducible plasmid to increase expression of specific components; overexpression of Src enhanced luminescence. FIG. 33C refers to an embodiment of the two-hybrid system from FIG. 33A that (i) lacks both PTP1B and Src and (ii) includes a "superbinder" SH2 domain (SH2*, i.e., an SH2 domain with mutations that enhance its affinity for phosphopeptides), a variable substrate domain, and LuxAB as the GOI. We used an inducible plasmid to increase expression of Src; luminescence increased most prominently for p130cas and MidT, suggesting that Src acts on both substrate domains. FIG. 33D refers to an embodiment of a two-hybrid system from FIG. 33C with one of two substrates: p130cas or MidT. We used a second plasmid to overexpress either (i) Src and PTP1B or (ii) Src and an inactive variant of PTP1B (C215S). The difference in luminescence between systems containing PTP1B or PTP1B (C215S) was greatest for MidT, suggesting that PTP1B acts on this substrate. Right: An optimized version of the two-hybrid system (with bb030 as the RBS for PTP1B) appears for reference. FIG. 33E displays the results of an exemplary growth-coupled assay performed using an optimized B2H including SH2*, a midT substrate, optimized promoters and ribosome binding sites (bb034 for PTP1B), and SpecR as the GOI. This system is illustrated at the top of the figure. Exemplary growth results demonstrate that inactivation of PTP1B enables strain of E. coli harboring this system to survive at high concentrations of spectinomycin (>250 μg/ml).

FIG. 36A depicts a plasmid-borne pathway for terpenoid biosynthesis: (i) pMBIS, which harbors the mevalonate-dependent isoprenoid pathway of S. cerevisiae, converts mevalonate to isopentyl pyrophosphate (IPP) and farnesyl pyrophosphate (FPP). (ii) pTS, which encodes a terpene synthase (TS) and, when necessary, a geranylgeranyl diphosphate synthase (GPPS), converts IPP and FPP to sesquiterpenes and/or diterpenes.

FIG. 36B depicts exemplary terpene synthases: amorphadiene synthase (ADS) from Artemisia annua, γ-humulene synthase (GHS) from Abies grandis, abietadiene synthase (ABS) from Abies grandis, and taxadiene synthase (TXS) from Taxus brevifolia.

FIG. 36C shows the results of an exemplary growth-coupled assay of strain of E. coli that contains both (i) an embodiment of the optimized bacterial two-hybrid (B2H) system (i.e., the B2H system from FIG. 33E) and (ii) an embodiment of a pathway for terpenoid biosynthesis (i.e., the pathway from FIG. 35A).

FIG. 37A depicts the results of our analysis of the inhibitory effect of DMSO containing (i) no inhibitor and (ii) extracted compounds from the culture broth of the ADS-containing strain. FIG. 37B depicts the results of our analysis of the inhibitory effect of DMSO containing (i) extracted compounds from the culture broth of the GHS-containing strain (gHUM) or (ii) extracted compounds from the culture broth of the strain including the L450Y mutant of GHS. FIG. 37C depicts the results of our analysis of the inhibitory effect of DMSO containing (i) no inhibitor, (ii) extracted compounds from the culture broth of the ABS-containing strain, (iii) extracted compounds from the culture broth of the TXS-containing strain, and (iv) extracted compounds from the culture broth of the train strain containing a catalytically inactive variant of ABS.

FIG. 40A-E depicts exemplary embodiments of genetically encoded systems that link the activity of an enzyme to the expression of a gene of interest, and the application of those embodiments to (i) the prediction of resistance mutations, (ii) the construction of inhibitors that combat resistance mutations, and (ii) the evolution of inhibitors of kinases.

FIG. 40A depicts an exemplary first step in examining potential resistance mutations. By evolving a metabolic pathway to produce molecules that inhibit a known drug target (e.g., PTP1B); these molecules will permit expression of a gene of interest (GOI) that confers survival in the presence of a selection pressure (e.g., the presence of spectinomycin, an antibiotic). FIG. 40B depicts an exemplary second step in examining potential resistance mutations. In a second strain of *E. coli*, we will replace the original gene of interest with a second (GOI2) that confers conditional toxicity (e.g., SacB, which converts sucrose to levan, a toxic product); we will evolve the drug target to become resistant to the endogenous inhibitors, while still retaining its activity. This mutant will prevent expression of the toxic gene. FIG. 40C depicts an exemplary third step in combating resistance mutations. In a third strain of *E. coli*, we will evolve a metabolic pathway that produces molecules that inhibit the mutated drug target. In this way, we will both predict—and, through our second evolved pathway, address—mutations that might cause resistance to terpenoid-based drugs. FIG. 40D depicts an exemplary genetically encoded system that detects inhibitors of an Src kinase. In brief, Src activity enables expression of a toxic gene (GOI2); inhibition of Src, in turn, would confer survival. FIG. 40E demonstrates one embodiment of a roof of principle for the B2H system describe in FIG. 40B. The system shown here includes two GOIs: SpecR and SacB. Expression of the GOIs confers survival in the presence of spectinomycin; expression of the GOIs causes toxicity in the presence of sucrose. The images depict the results of a growth-coupled assay performed on a strain of *E. coli* in the presence of various concentrations of sucrose. The strain harboring an active form of PTP1B (WT) grows better at high sucrose concentrations that the strain harboring an inactive form of PTP1B (C215S).

FIG. 41A depicts an exemplary structural analysis used to identify targets for mutagenesis in the active sites of terpene synthases. It shows an alignment of the class I active site of ABS (gray, PDB entry 3s9v) and TXS (blue, PDB entry 3p5r) with the locations of sites targeted for site-saturation mutagenesis (SSM) highlighted on ABS (red). A substrate analogue (yellow) of TXS appears for reference.

FIG. 44A-D provides exemplary structural and sequence-based evidence that supports the extension the B2H system to other protein tyrosine phosphatases (PTPs).

FIG. 44A provides an exemplary structural alignment PTP1B and PTPN6, two PTPs that are compatible with the B2H system (see FIGS. 1e and 7 of Update A for evidence of compatibility). We used the align function of PyMol to align each structure of PTPN6 with either (i) the ligand-free (3A5J) or (ii) ligand-bound (2F71) structure of the catalytic domain of PTP1B. The align function carries out a sequence alignment followed by a structural superposition and, thus, effectively aligns the catalytic domains of both proteins. FIG. 44B provides an exemplary structural comparison of PTP1B and PTPN6; the root-mean-square deviations (RMSD) of aligned structures of PTP1B and PTPN6 range from 0.75 to 0.94 Å. FIG. 44C proves an exemplary sequence alignment of the catalytic domains of PTP1B and PTPN6 (EMBOSS Needle[1]) (SEQ ID NOS: 3 and 4, respectively). FIG. 44D provides an exemplary sequence comparison of the catalytic domains of PTP1B and TPPN6. The sequences share 34.1% sequence identity and 53.5% sequence similarity. In summary, the results of this figure indicate that our B2H system can be readily extended to PTPs that possess catalytic domains that are (i) structurally similar to the catalytic domain of PTP1B (here, we define structural similarity as two structures that when aligned, have with an RMSD of ≤0.94 Å RMSD with the framework similar to the one used by the align function of PyMol) and/or (ii) sequence similar to the catalytic domain of PTP1B (here, we define sequence similarity as ≥34% sequence identity or ≥53.5% sequence similarity as defined by the EMBOSS Needle algorithm).

DEFINITIONS

Figure 1C:
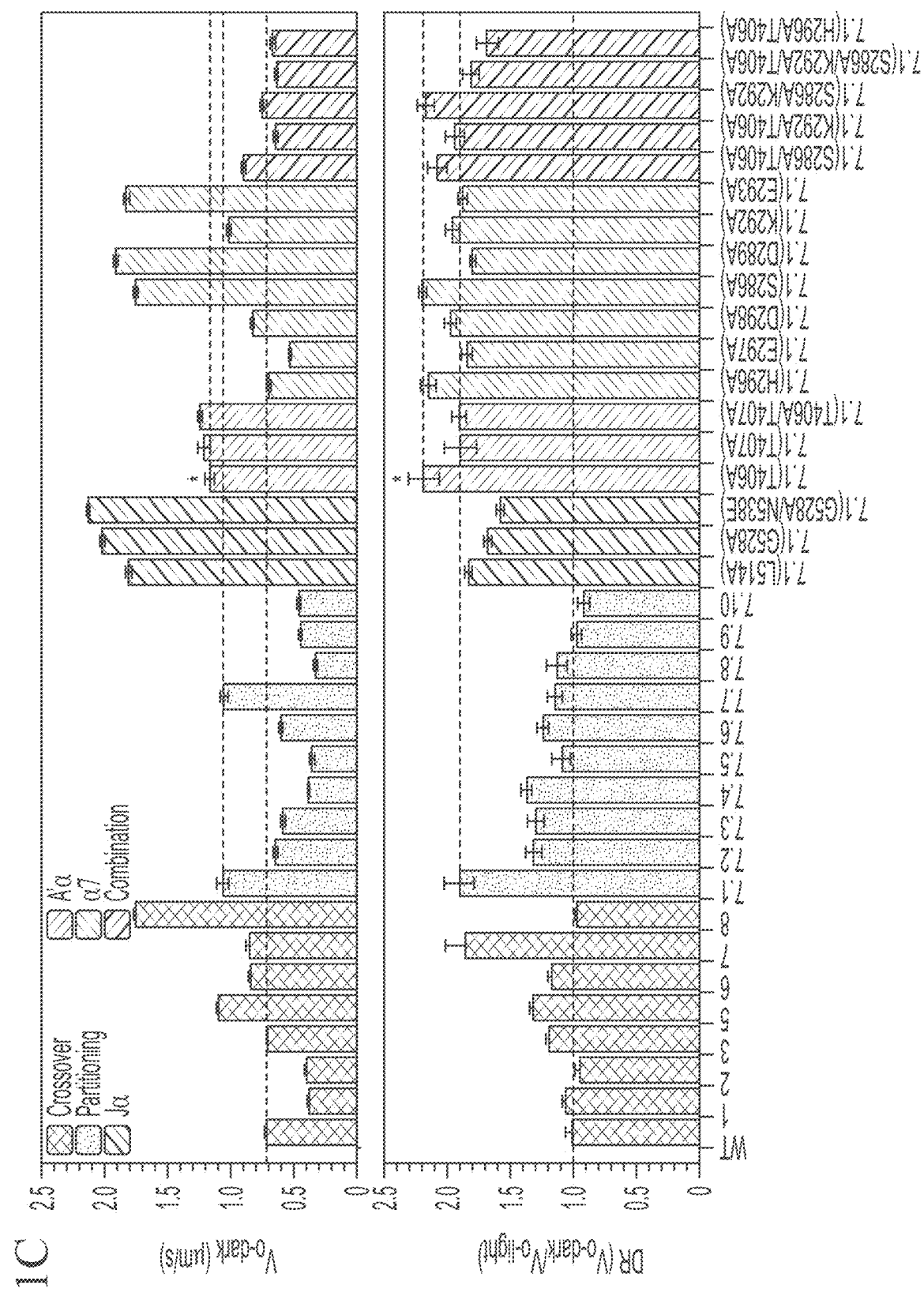

As used herein, the use of the term "operon" may refer to a cluster of genes under the control of a single promoter (as in a classical definition of an operon) and may also refer to a genetically encoded system comprising multiple operons (e.g., the bacterial two-hybrid system).

As used herein, "phosphorylation-regulating enzymes" refer to proteins that regulate phosphorylation.

As used herein, "phosphorylation" refers to a biochemical process that involves the addition of phosphate to an organic compound.

As used herein, "optogenetic actuator" refers to a genetically encodable protein that undergoes light-induced changes in conformation.

As used herein, "dynamic range" refers to the ratio of activity in dark and light state (i.e., the initial rate in the dark/the initial rate in the presence of 455 nm light).

As used herein, "operon" refers to a unit made up of multiple genes that regulate other genes responsible for protein synthesis, As used herein, "operably linked" refers to one or more genes (i.e. DNA sequences) suitably positioned and oriented in a DNA molecule for transcription to be initiated from the same promoter. DNA sequences that are operably linked to a promoter means that expression of the DNA sequence(s) is under transcriptional initiation regulation of the promoter.

As used herein, "construct" refers to an engineered molecule, e.g. ligated pieces of DNA as a DNA construct; a RNA construct as one contiguous sequence resulting from the expression of a DNA construct.

As used herein, "fusion" refers to an expressed product of an engineered construct i.e. a combination of several ligated sequences as one molecule or a single gene that encodes for a protein-protein fusion originally encoded by two genes.

As used herein, "expression vector" or "expression construct" refers to an operon, plasmid or virus designed for DNA expression of a construct in host cells, typically containing a promoter sequence operable within the host cell.

As used herein, "promoter" refers to a region of DNA that initiates transcription of a particular DNA sequence. Promoters are located near the transcription start sites of, towards the 5' region of the sense strand. Promoters may be constitutive promoters, such as cytomegalovirus (CMV) promoters in mammalian cells, or inducible promoters, such as tetracycline-inducible promoters in mammalian cells.

As used herein, "transformation" refers to a foreign nucleic acid sequence or plasmid delivery into a prokaryotic host cell, for example, an expression plasmid (e.g. a plasmid expression construct) inserted into or taken up by a host cell.

As used herein, "transfection" refers to the insertion of a nucleic acid sequence into a eukaryotic cell.

Transformation and transfection may be transient, such that the nucleic acid sequence or plasmid introduced into the host cell is not permanently incorporated into the cellular genome. A stable transformation and transfection refers to a host cell retaining the foreign nucleic acid sequence or plasmid for multip generations regardless of whether the nucleic acid or plasmid was integrated into the genome of the host cell.

As used herein, "host" in reference to a cell refers to a cell intended for receiving a nucelic acid sequence or plasmid or already harboring a a nucelic acid sequence or plasmid, eg. a bacterium.

As used herein, "conjugate" refers to a covalently attachment of at least two compounds, for example, a photosensing element attached to a phosphatase protein.

As used herein, "decoy" in reference to a protein construct that cannot bind to DNA and/or RNA polymerase.

DETAILED DESCRIPTION OF INVENTION

This invention relates to the field of genetic engineering. Specifically, the invention relates to the construction of operons to produce biologically active agents. For example, operons may be constructed to produce agents that control the function of biochemical pathway proteins (e.g., protein phosphatases, kinases and/or proteases). Such agents may include inhibitors and modulators that may be used in studying or controlling phosphatase function associated with abnormalities in a phosphatase pathway or expression level. Fusion proteins, such as light activated protein phosphatases, may be genetically encoded and expressed as photoswitchable phosphatases. Systems are provided for use in controlling phosphatase function within living cells or in identifying small molecule inhibitors/activator/modulator molecules of protein phosphatases associated with cell signaling.

The invention also relates to the assembly of genetically encoded systems (e.g., one or more operons) for detecting and/or constructing biologically active agents. For example, systems may be assembled in order to accomplish one or more goals, e.g. (i) to detect and/or synthesize small molecules that affect the activity of regulatory enzymes (e.g., protein phosphatases, kinases, and/or proteases); (ii) to detect and/or evolve regulatory enzymes modulated by light (e.g., light-responsive protein phosphatases, kinases, or proteases), etc. Small molecule modulators may include inhibitors of phosphatases known to be associated with human diseases or implicated with causing or perpetuating human diseases; activators of phosphatases implicated or known to be associated in human diseases (e.g., diabetes, obesity, and cancer); such small molecules may serve as chemical probes in studies of cell signaling; as structural starting points (i.e., leads); etc., for the development of pharmaceutical compounds for use in treating a human disease. Light-sensitive enzymes may include protein tyrosine phosphatases fused to optogenetic actuators (e.g., a LOV domain if phototropin 1). Such fusions could serve as tools for exerting spatiotemporal control over protein tyrosine phosphorylation in living cells Further, microbial operons are provided that are designed for use in identifying either small molecule inhibitors, activators, or modulator molecules, photoswitchable enzymes, or biological components, including intracellularly expressed molecules, including, for examples, operons having components for use in whole cell microbial screening assay systems. Inhibitors/modulator molecules discovered using compositions, systems and methods described herein are contemplated for use in treating diseases such as diabetes, type II diabetes, obesity, cancer, and Alzheimer's disease, among other disorders associated with protein phosphatase enzymes.

In one embodiment, the present invention relates to a Protein tyrosine phosphatase 1B (PTP1B). PTP1B represents a valuable starting point for this study for four reasons: (i) It is implicated in diabetes[5], obesity[6], cancer[30], anxiety[31], inflammation[32], the immune response, and neural specification in embryonic stem cells[33], (ii) The mechanisms underlying its subcellular localization are well understood (a short C-terminal anchor connects it to the ER; proteolysis of this anchor releases it to the cytosol)[29,34]. (iii) It can be expressed, purified, and assayed with ease[35], (iv) It is a member of a class of structurally similar enzymes (PTPs) that could facilitate the rapid extension of architectures for making it photoswitchable. PTP1B represents both an experimentally tractable model system for testing strategies for optical control, and an enzyme for which optical modulation is contemplated to permit detailed analyses of a wide range of diseases and physiological processes.

Figure 10A:
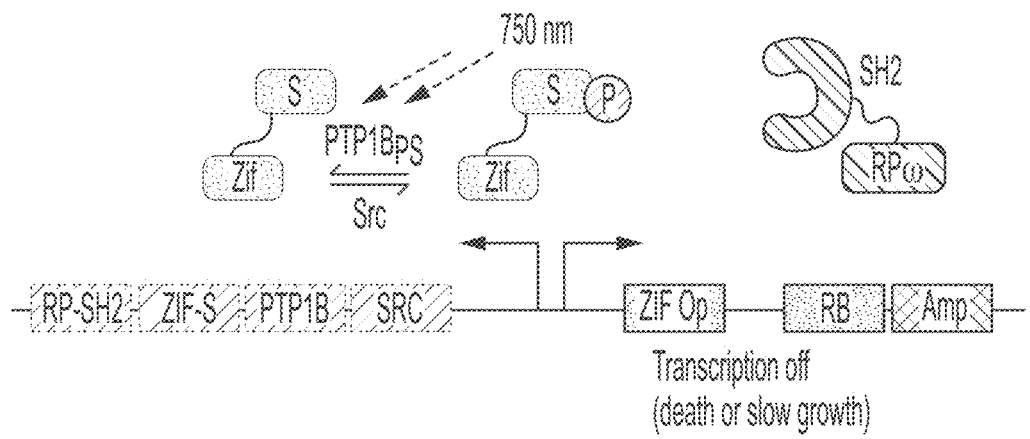
FIG. 10A-B illustrates an exemplary operon for screening photoswitchable variants of PTP1B.
Figure 10B:
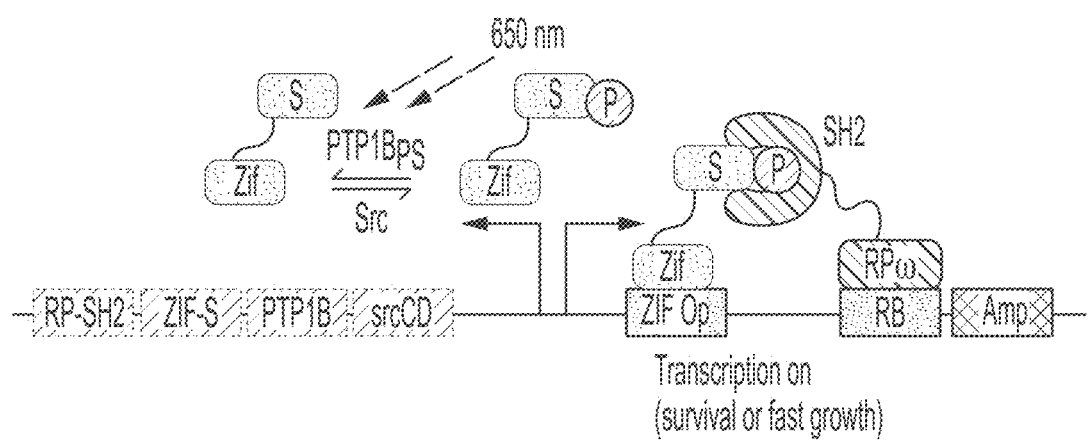
Figure 11A:
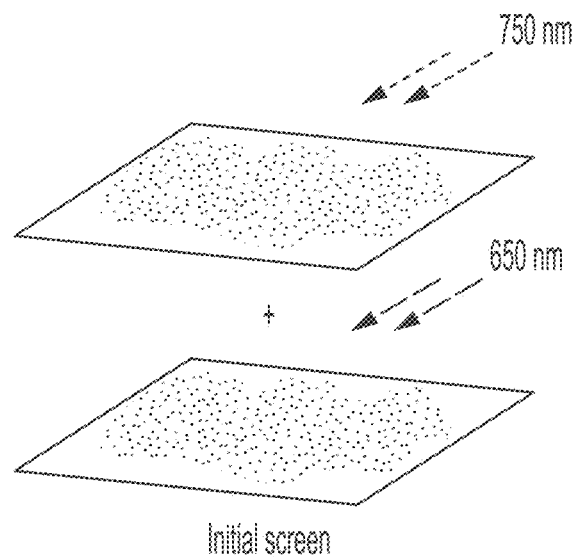
FIG. 11A-B illustrates an exemplary strategy for evolution of photoswitchable proteins.

Specifically related to exemplary Figures: FIGS. 1, 2, 3, 4, 8, 9, 12, and 13 describe optogenetic and imaging technologies (i.e., light-sensitive enzymes and genetically encodable biosensors) that could be evolved, improved, or optimized with the operon; FIGS. 10 and 11 describe strategies for using the operon to evolve, improve, or optimize light-sensitive enzymes; FIGS. 5, 6, 14, 15, 16, 17, 18, 19, 20, 28, 29, 30, and 31 support both (i) the development of an operon for detecting and/or evolving small molecules that inhibit known drug targets and (ii) the subsequent characterization of those molecules; FIGS. 22, 23, 24, 25, 26, 27, and 32 provide examples of kinetic and biophysical characterizations of a microbially synthesizable molecule that inhibits PTP1B.

I. Protein Tyrosine Phosphatases (PTPs) and Protein Tyrosine Kinases (PTKs) in Relation to Disease.

Protein tyrosine phosphatases (PTPs) and protein tyrosine kinases (PTKs) are two classes of enzymes contributing to anomalous signaling events in a wide range of diseases (e.g., diabetes, cancer, atherosclerosis, and Alzheimer's disease, among others) and understanding disease progression[14,36]. Further, they are involved with regulating memory, fear, appetite, energy expenditure, and metabolism, thus use of such phosphorylation regulating enzymes may reveal links between seemingly disparate physiological processes[14,22,13].

Embodiments for using light as photoswitchable constructs for controlling PTPs and PTKs is described herein. Accordingly, examples of photoswitchable constructs of PTPs and PTKs developed as described herein, should be broadly useful to biomedical researchers interested in understanding how healthy and diseased cells process chemical signals in addition to use for identifying specific alleles of PTPs and/or PTKs (i.e. gene sequences or proteins)—or other enzymes that they regulate—linked to specific diseases, such as diabetes, etc., including subtypes of diseases, i.e. early onset, late onset, etc., and specific types of cancer, and for screening and testing molecules, including small molecules, for treating diseases associated with these alleles.

Although other references describe photocontrol of proteins, including using LOV2 conjugates, these references do not mention using phosphatases. Fan, et al., "Optical Control Of Biological Processes By Light-Switchable Proteins." Wiley Interdiscip Rev Dev Biol. 4(5): 545-554. 2015. This reference describes blue light-oxygen-voltage-sensing (LOV) domains including the LOV2 C-terminal α-helix, termed Jα, from *Avena sativa* phototropin. Linkage to the LOV domain can cage a protein of interest (POI), while light-induced conformational change in the LOV domain results in its uncaging. As one example, peptide kinase inhibitors can be caged by fusion to the C-terminus of LOV2. Exposure to light results in uncaging of the inhibitors for light modulating protein kinase activities in cells. WO2011133493. "Allosteric regulation of kinase activity." Published Oct. 27, 2011. This reference describes fusion proteins comprising a kinase, including as examples, a tyrosine kinase (Src), a serine/threonine kinase (p38), and a ligand binding domain, e.g. a light-regulated LOV domain (where illumination is considered "ligand binding), inserted in the N-terminal and/or C-terminal end or near the catalytic domain to produce allosteric regulation using a light-dependent kinase. Further, a LOV domain includes a LOV2 domain and/or Ja domain from *A. sativa* phototropin I. WO2012111772 (A1) In Japanese with an English abstract. This reference abstract describes a polypeptide for the optical control of calcium signaling comprising an amino acid sequence including: a LOV2 domain composed of SEQ ID NO: 1 or an amino acid sequence having at least 80% sequence identity with SEQ ID NO: 1. The construct has a LOV2 domain followed by a LOV2-Jalpha optical switch at the N terminus of the construct. U.S. Pat. No. 8,859,232. "Genetically encoded photomanipulation of protein and peptide activity." Issued Oct. 14, 2014. This reference describes fusion proteins comprising protein light switches and methods of photomanipulating the activity of the fusion proteins to study protein function and analyze subcellular activity, as well as diagnostic and therapeutic methods. More specifically, a fusion protein comprising a protein of interest fused to a protein light switch comprising a light, oxygen or voltage (LOV2) domain of *Avena sativa* (oat) phototropin 1, wherein illumination of the fusion protein activates or inactivates the protein of interest. The protein of interest is a functional domain of a human protein. As an example, a LOV2-Jα sequence of phototropin1 (404-547) was fused to the N-terminus of RacI so that the LOV domain in its closed conformation would reversibly block the binding of effectors to RacI.

A. Protein Tyrosine Phosphatases (PTPs).

Protein tyrosine phosphatases (PTPs) are a class of regulatory enzymes that exhibit aberrant activities in a wide range of diseases. A detailed mapping of allosteric communication in these enzymes could, thus, reveal the structural basis of physiologically relevant—and, perhaps, therapeutically informative—perturbations (i.e., mutations, post-translational modifications, or binding events) that influence their catalytic states. This study combines detailed biophysical studies of protein tyrosine phosphatase IB (PTP IB) with large-scale bioinformatic analyses to examine allosteric communication in PTPs. Results of X-ray crystallography, molecular dynamics simulations, and sequence-based statistical analyses indicate that PTP IB possesses a broadly distributed allosteric network that is evolutionarily conserved across the PTP family, and findings from kinetic studies show that this network is functionally intact in sequence-diverse PTPs. The allosteric network resolved in this study reveals new sites for targeting allosteric inhibitors of PTPs and helps explain the functional influence of a diverse set of disease-associated mutations.

In one embodiment, a tyrosine phosphatase and photosensitive protein as described herein may be attached to a drug for use in medical treatments. In contrast to EP2116263, "Reversibly light-switchable drug-conjugates." Published Nov. 11, 2009 which does not mention tyrosine phosphatase, and which describes photoswitchable conjugates of protein phosphatase calcineurin attached to a photoisomerizable group B and also attached to a drug for use in medical treatments (neither of these groups are genetically encodable). As one example in EP2116263, tumor growth is suppressed by inhibition of the protein phosphatase calcineurin. A photoisomerizable group B, for near UV (e.g. 370 nm) or near IR (e.g. 740 nm) induced activity, does not include a light responsive plant protein phototropin 1 LOV2 N-terminal alpha helix.

Receptor PTPs are contemplated for conjugation to light sensing proteins, as described herein. In contrast, Karunarathne, et al., "Subcellular optogenetics—controlling signaling and single-cell behavior." J Cell Sci. 128(1):15-25, 2015, describes photosensitive domains, such as bacteria light-oxygen-voltage-sensing (LOV and LOV2) domains including a C-terminal helical Jα region, tagged to receptor tyrosine kinases (RTKs), there were no specific examples, there was no mention of a tyrosine phosphatase nor a plant phototropin 1 LOV2 N-terminal alpha helix. Optical activation of an inositol 5-phosphatase was shown, but inositol 5-phosphatase is not a protein phosphatase.

B. Enzymatic Phosphorylation of Tyrosine Residues.

Enzymatic phosphorylation of tyrosine residues has a role in cellular function and is anomalously regulated in an enormous range of diseases (e.g., diabetes, cancer, autoimmune disorders, and Noonan syndrome. It is controlled by the concerted action of two classes of structurally flexible—and dynamically regulatable—enzymes: protein tyrosine kinases (PTKs), which catalyze the ATP-dependent phosphorylation of tyrosine residues, and protein tyrosine phosphatases (PTPs), which catalyze the hydrolytic dephosphorylation of phosphotyrosines (5, 6). A detailed understanding of the mechanisms by which these enzymes respond to activity-modulating structural perturbations (i.e., mutations, post-translational modifications, or binding events) can, thus, illuminate their contributions to various diseases and facilitate the design of new PTK- or PTP-targeted therapeutics.

Over the last several decades, many biophysical studies have dissected the catalytic mechanisms and regulatory functions of PTKs (7, 8), which are common targets of pharmaceuticals.(9) Detailed analyses of PTPs, by contrast, have lagged behind.(10) These enzymes represent an underdeveloped source of biomedical insight and therapeutic potential (no inhibitors of PTPs have cleared clinical trials); they are, thus, the focus of this study.

PTPs uses two loops to dephosphorylate tyrosine residues. The eight-residue P-loop binds phosphate moieties through a positively charged arginine, which enables nucleophilic attack by a nearby cysteine, and the ten-residue WPD loop contains a general acid catalyst—an aspartate—that protonates the tyrosine leaving group and hydrolyzes the phosphoenzyme intermediate—11-13) During catalysis, the P-loop remains fixed, while the WPD loop moves ~10A between open and closed states; nuclear magnetic resonance (NMR) analyses suggest this movement controls the rate of catalysis.(14)

Recent analyses of protein tyrosine phosphatase IB (PTP IB) a drug target for the treatment of diabetes, obesity, and breast cancer, indicate that motions of its WPD loop are regulated by an allosteric network that extends to its C-terminus (FIG. 1B) (15, 16). This network is susceptible to modulation by both (i) inhibitors that displace its C-terminal α7 helix (17, 18) and (ii) mutations that disrupt communication between the a(alpha)7 helix and the WPD loop (15); the specific collection of residues that enable allosteric communication in PTP1B and other PTPs has yet to be fully resolved.

Protein tyrosine phosphatase 1B (PTP1B). PTP1B represents a valuable tool for use in identifying potential therapeutics for at least four reasons: (i) It is implicated in diabetes[5], obesity[6], cancer[30], anxiety[31], inflammation[32], the immune response, and neural specification in embryonic stem cells[33], (ii) The mechanisms underlying its subcellular localization are well understood (a short C-terminal anchor connects it to the ER; proteolysis of this anchor releases it to the cytosol)[29,34]. (iii) It can be expressed, purified, and assayed with ease[35], (iv) It is a member of a class of structurally similar enzymes (PTPs) that could facilitate the rapid extension of architectures for making it photoswitchable. PTP1B, thus, represents both an experimentally tractable model system for testing strategies for optical control, and an enzyme for which optical modulation will permit detailed analyses of a wide range of diseases and physiological processes.

Spatial regulation and intracellular signaling. PTP1B demonstrates, by example, the value of photoswitchable enzymes for studying spatial regulation in intracellular signaling. It is hypothesized to inactivate receptor tyrosine kinases through (i) contacts between endosomes and the ER[37,38], (ii) contacts between the plasma membrane and extended regions of the ER[39], and (iii) direct protein-protein interactions enabled by its partial proteolysis and release into the cytosol[34]. The role of different mechanisms (or locations) of PTP1B-substrate interaction in determining the outcomes of those interactions is poorly understood. Evidence suggesting a relationship between the location of PTP1B and its role in signaling has arisen in studies of tumorigenesis. Inhibition of PTP1B can suppress tumor growth and metastasis in breast[30,40], lung[3,41], colorectal[9], and prostate cancers,[42,43] while its upregulation has similar effects in lymphoma[3,44]. Recent evidence suggest that the former effect may result from inhibition of cytosolic PTP1B[45]; the cause of the latter is unclear. At present, there are no tools to investigate the differential influence of spatially distinct subpopulations of PTP1B on tumor-associated signaling events within the same cell. Photoswitchable variants of PTP1B represent such a tool.

Network biology. Signaling networks are often represented as nodes (proteins) connected by lines (interactions)[46]. Such maps capture the connectivity of biochemical relay systems, but obscure spatial context—the ability of a single interaction to occur in multiple locations and, perhaps, to stimulate multiple signaling outcomes. This study develops a set of tools that will enable detailed studies of the role of spatial context in guiding the propagation of signals through biochemical networks; such an examination contributes to understanding the role of PTP1B in cell signaling (and processes associated with tumorigenesis), and generally relevant to the study of any enzyme that exists in spatially distinct subpopulations within the cell.

II. Optogenetic Actuators.

Optogenetic actuators (genetically encodable proteins that undergo light-induced changes in conformation) provide a convenient means of placing biochemical events under optical control. Alone, or when fused to other proteins, they have enabled optical manipulation of biomolecular transport, binding, and catalysis with millisecond and submicron resolution in living cells. Our approach addresses two major deficiencies in existing technologies: Observational interference and illuminating half the story. Existing strategies to control the activity of enzymes with light interfere with native patterns of protein production, localization, and interaction (often by design) and, thus, make direct interrogation and/or control of those patterns—which determine how biochemical signals are processed—difficult. There are several methods to control protein kinases with light, but no analogous methods for controlling protein phosphatases. As signaling networks are regulated by the concerted action of both classes of enzyme, comprehensive control and/or detailed dissections of those networks require methods for controlling both.

Embodiments described herein comprise (i) an approach for controlling the activity of proteins with light without disrupting their wild-type activities and (ii) a demonstration of this approach on a protein of particular importance: protein tyrosine phosphatase 1B (PTP1B), a regulator of cell signaling and a validated drug target for the treatment of diabetes, obesity, and cancer. There are no known photoswitchable protein tyrosine phosphatases. The PTP1B-LOV2 construct reported in this filing is the first. (ii) The N-terminal alpha helix of LOV2 is ignored in most studies (even reviews of optical switches) and has not been used as an exclusive connection point for optical modulation of enzymes.

We have developed a photoswitchable version of PTP1B by fusing the C-terminal allosteric domain of this enzyme to the N-terminal alpha helix of a protein light switch (i.e., the LOV2 domain of phototropin 1 from *Avena sativa*). We present evidence that this general architecture—which is unique in the placement of LOV2 away from the active site of PTP1B (minimally disruptive)—can be extended to other PTPs and, perhaps, PTKs. For example, we used a statistical coupling analysis to show that the allosteric network exploited in our PTP1B design is preserved across the PTP family.

Alone, or when fused to other proteins, optogenetic actuators have enabled optical manipulation of biomolecular transport, binding, and catalysis with millisecond and submicron resolution[15,16]. At least three deficiencies limit their use in detailed studies of signaling networks: Observational interference. Existing strategies to control the activity of enzymes with light interfere with native patterns of protein production, localization, and interaction[16,17] (often by design) and, thus, make direct interrogation of those patterns—which determine how biochemical signals are processed[10] difficult. Illuminating half the story. There are several methods to control protein kinases with light[18,19], but no analogous methods for controlling protein phosphatases. As signaling networks are regulated by the concerted action of both classes of enzyme, detailed dissections of those networks require methods for controlling both. A limited palette of actuators. Optogenetic actuators that enable subcellular control of enzyme activity require the use of blue or green light[15]. These wavelengths exhibit significant phototoxicity[20], suffer from short biological penetration depths[21], and, as a result of their spectral similarity, limit actuation to individual signaling events, rather than multiple events simultaneously.

A. Photoswitchable Constructs: Advantages Over Other Exemplary Technologies.

As described herein, a photoswitch describes a protein-protein architecture (e.g., a PTP1B-LOV2 fusion) that is optically active in its monomeric form. A reference, WO2013016693. "Near-infrared light-activated proteins." Publication Date Jan. 31, 2013, relies on homodimerization. In contrast, optical control as described herein is over a larger range of proteins, including both those that require homodimerization and those that do not, unlike in WO2013016693. Further, this reference describes types of photosensory modules including blue light-sensitive flavoproteins found in plants; photoreceptors of blue-light using flavin adenine dinucleotide (BLUF); Light, Oxygen, or Voltage sensing (LOV) types, which includes plant and bacterial photoreceptors; and plant/microbe phytochromes, sensitive to light, i.e. light-induced helix rotation in the red-to-NIR region. More specifically described with examples are bacteriophytochrome (Bph)-based photoactivated fusion proteins, using light-responsive alpha helixes from *Rhodobacter sphaeroides* (BphG) fused to proteins such as protein phosphatases, protein kinases, membrane receptors, etc. *E. coli*, are modified so as to exhibit the level of photoactivity of these expressed fusion proteins, i.e. in the presence or absence of red-to-NIR light. Although blue color changes in *E. coli* expressing fusion proteins are described in response to light, these blue bacteria are the result of using far-red/NIR-light for photoactivating a fusion protein that in turn activates lacZ expression in the presence of Xgal, not a photoresponse to exposure to blue light. However, there is no specific mention of a tyrosine phosphatase or a plant phototropin 1 LOV2 N-terminal alpha helix. In fact, reviews on optogenetics tend to depict LOV2 as having one terminal helix: The C-terminal Jalpha helix. While there are studies/patents indicating that simple insertion of the LOV2 domain enables photocontrol they rely on the underlying assumption that the Jalpha helix is unwinding to produce the controlling effect, not the A alpha helix as described herein.

B. A "Cage-Free" Approach to Control Protein Tyrosine Phosphatases and Protein Tyrosine Kinases with Light.

Current strategies for using light to control the activity of enzymes (as opposed to their concentration or location) rely on cage-based systems: a light-responsive protein, when fused to an enzyme of interest, controls access to its active site[16,47]. Unfortunately, such architectures can alter the affinity of enzymes for binding partners and change their susceptibility to activity modulating modifications (e.g., phosphorylation)[16,18]. These effects complicate the use of optogenetics to study signaling. This study will develop a "cage-free", allostery-based approach for optical control that minimizes interference between enzymes and their substrates (and other binding partners). This approach will help preserve native patterns of protein localization, interaction, and post-translational modification and, thus, facilitate studies of the influence of those patterns on intracellular signaling.

2. A genetically encoded photoswitchable phosphatase. There are no genetically encodable photoswitchable phosphatases; the chimeras developed in this proposal will be the first. Photoswitchable variants of PTP1B will enable detailed studies of a wide range of interesting PTP1B-regulated processes (e.g., insulin, endocannabinoid, and epidermal growth factor signaling[49,51], and cell adhesion and migration[52]). Photoswitchable phosphatases, in general, will provide a useful class of tools for studying cell biology (particularly in concert with photoswitchable kinases, which could enable complementation experiments).

Hypothesis: The catalytic domains of PTPs and PTKs possess C-terminal a-helices that are distal to their active sites, yet capable of modulating their catalytic activities (for at least a subset of enzymes—the generality of this function is not known)[23,24]. We hypothesize that the fusion of this helix to the N-terminal α-helix of the light-oxygen voltage 2 (LOV2) domain of phototropin 1 from *Avena sativa*—a photosensory domain with terminal helices that unwind in response to blue light[25,26]—will yield enzyme-LOV2 chimeras that exhibit light-dependent catalytic activities, yet retain their native substrate specificities and binding affinities.

Experimental approach: We will attach the C-terminal α-helix of PTP1B to the N-terminal α-helix of LOV2 at homologous crossover points, and we will assess the influence of photoactivation on the catalytic activity of the resulting chimeras. This effort will involve the use of (i) kinetic assays and binding studies to characterize the substrate specificities and binding affinities of photoswitchable constructs and (ii) crystallographic and spectroscopic analyses to examine the structural basis of photocontrol. Informed by these studies, we will extend our approach to striatal-enriched protein tyrosine phosphatase (STEP) and protein tyrosine kinase 6 (PTK6), enzymes implicated in Alzheimer's disease and triple-negative breast cancer, respectively.

We will combine sophisticated biophysical studies, synthetic biology, and fluorescence microscopy to (i) develop protein architectures that enable optical control of protein tyrosine phosphatases (PTPs) and protein tyrosine kinases (PTKs) without interfering with their wild-type activities or binding specificities, (ii) evolve PTPs and PTKs modulated by red light, and (iii) develop an imaging methodology to study spatially localized signaling events in living cells.

We will begin our study with PTP1B, a validated drug target for the treatment of diabetes, obesity, and breast cancer, and an enzyme for which optogenetic tools will be particularly useful to address current gaps in knowledge (e.g., the role of spatially distinct subpopulations of PTP1B in promoting or suppressing the growth of tumors[22]). Using it as a model, we will establish the generality of our methods by extending them to other PTPs and PTKs.

C. A Photoswitchable Variant of PTP1B.

Figure 6:
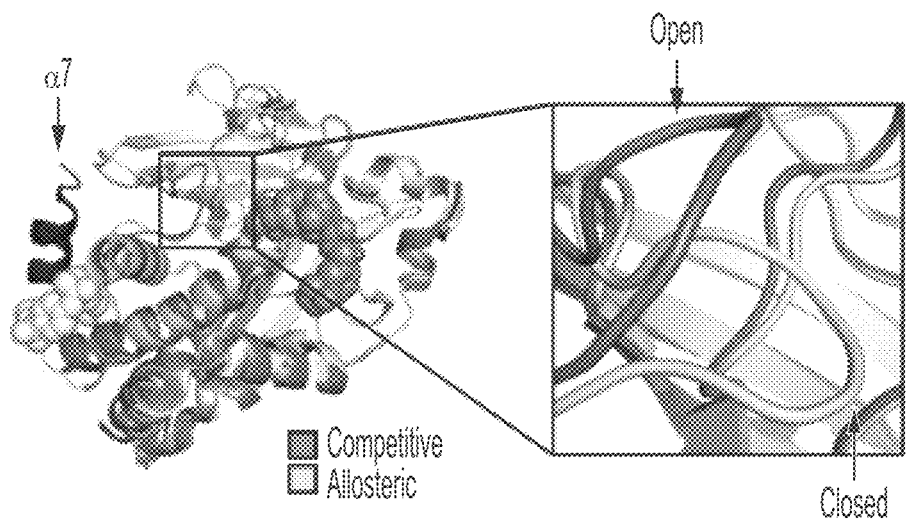
FIG. 6 illustrates PTP1B showing an overlay of allosterically inhibited (green) and competitively inhibited (orange) structures of PTP1B (PDB entries 1t4j and 2f71, respectively) show activity-modulating conformational changes: Unwinding of the α7 helix of LOV2 (blue) causes its catalytically essential WPD loop (right) to adopt an open, catalytically compromised conformation. Competitive (red) and allosteric (yellow) inhibitors highlight the active site and allosteric site, respectively.

Our first objective seeks to use LOV2, a protein with terminal helices that unwind in response to blue light, to control the activity of PTP1B, an enzyme for which unwinding of the C-terminal α-helix disrupts activity by distorting its catalytically essential WPD loop (FIG. 1AB, FIG. 6). To assess the feasibility of this goal, we constructed five PTP1B-LOV2 chimeras (joined at homologous crossover points): three chimeras showed light-dependent catalytic activity on 4-methylumbelliferyl phosphate (4M) (FIG. 1G). A subsequent mutational analysis of one chimera indicated that mutations in the α-helix that links PTP1B to LOV2 can improve catalytic activity and dynamic range (DR, the ratio of dark/light activities; FIG. 1G). Our ability to build—and begin optimizing—a photoswitchable PTP1B-LOV2 chimera by screening a small number of constructs suggests that rational design will allow us to build a chimera sufficient for intracellular signaling studies. We note: Our most photoswitchable chimera has a DR of 2.2; previous imaging studies suggest that a DR of 3-10 is sufficient to control intracellular signaling[2,18,19].

More specifically, FIG. 1C demonstrates some of differences over other types of optical control. The y-axis of the top plot indicates the activity of each construct in the dark (i.e., the initial rate of PTP1B-catalyzed hydrolysis of p-nitrophenyl phosphate); the y-axis of the bottom plot indicates the ratio of activity in dark and light state (i.e., the initial rate in the dark/the initial rate in the presence of 455 nm light), i.e. dynamic range.

Black bars show the activity and dynamic range for a set of eight initial constructs that differ in the crossover point (see the bottom of FIG. 1B). Some of these constructs are photoswitchable, and some are not. Version 7 shows the greatest photoswitchability—the dynamic range is approximately 1.8.

More specifically, colors are associated with different types of constructs. Black: different crossover point (see FIG. 1B for crossover points); Gray: different partitioning of the linker (see, Linker section below); Light blue: the Jalpha helix—this is at the C-terminus of the LOV2 domain; Dark blue: the A'alpha helix—this is at the N-terminus of the LOV2 domain and, thus, on the region that links it to PTP1B; Yellow: the alpha7 helix of PTP1B—this is at the C-terminus of PTP1B and, thus, on the region that links PTP1B to LOV2; Orange: combination: a combination of sites from the previous colors, see below for additional information.

These results were surprising, in part, because a recent review on optogenetics shows that that photocontrol of activity requires the Jα helix of LOV2, where Jα is a C-terminal helix which resides in a folded state against the LOV domain core, to be attached to a protein of interest, see Repina, N. A., Rosenbloom, A., Mukherjee, A., Schaffer, D. V. & Kane, R. S. At Light Speed: Advances in Optogenetic Systems for Regulating Cell Signaling and Behavior. *Annu. Rev. Chem. Biomol. Eng.* 8, 13-39 (2017). Photoactivation with blue light converts the noncovalent interaction between the LOV core and its bound flavin chromophore, FMN, into a covalent one through a conserved cysteine residue. The accompanying light-induced conformational change displaces the Jα helix away from the protein core, leading to uncaging of a fused effector domain (e.g., the kinase domain of phot1). Jα helix reverts to its dark-state caged conformation within minutes owing to spontaneous decay of the protein-cofactor bond.

Several limitations of the native AsLOV2 domain have motivated efforts to engineer improved variants. First, when fused to foreign protein domains, spontaneous undocking of the Jα helix can lead to a relatively high dark-state activity, resulting in a low dynamic range upon AsLOV2 uncaging (26). For example, the light-inducible DNA-binding system LovTAP has only a fivefold change in DNA affinity between the dark and illuminated states (27). To address this issue, Strickland et al. (26) used rational design to introduce four mutations into AsLOV2 that stabilized the docking of Jα to the LOV core. This increased the dynamic range of LovTAP from 5-fold to 70-fold, an approach that can be applied to other LOV domain optogenetic systems to reduce dark-state activity. AsLOV2 fusions are also particularly sensitive to linker lengths and the size and structure of attached domains (28, 29), and as a result, each new fusion protein switch requires optimization to achieve low dark-state and high light-state activity in mammalian cells.

In contrast to the Jα helix-protein chimers, as shown herein, the A'α helix not the Jα helix is attached to the protein of interest to form photoswitchable constructs, e.g. PTPB1.

Exemplary Linkers.

Gray bars of FIG. 1C show the activity and dynamic range of mutants of version 7 in which the linker has been re-partitioned. In other words, version 7 has the following linker region: LSHEDLATTL (SEQ ID NO: 5), where the underlined region "LSHED" (SEQ ID NO: 6) corresponds to the C-terminus of PTP1B, and the region "LATTL" (SEQ ID NO: 7) corresponds to the N-terminus of LOV2. Version 7.1 has sequence LSHEDATTL (SEQ ID NO: 8); version 7.2 has sequence LSHEDTTL (SEQ ID NO: 9), and so on. Here, we find that version 7.1 has the same dynamic range as version 7, but a higher activity. We, thus, used version 7.1 for further optimization.

Exemplary Mutations.

Light blue bars show the activity and dynamic range of mutants of version 7.1 in which the Jα helix contains helix-stabilizing mutations. Curiously, these improve the activity of 7.1, but do not improve its dynamic range.

Dark blue bars show the activity and dynamic range for mutants of version 7.1 in which the A'α helix contains helix-stabilizing mutations. One of these mutations (T406A) improves dynamic range; we used this version for further studies.

Yellow bars show the activity and dynamic range of mutants of version 7.1 in which the α7 of PTP1B has helix-stabilizing mutations; the orange bars show the activity and dynamic range for mutants of version 7.1 in which the multiple mutations are combined. Neither of the constructs associated with yellow and orange bars show improved characteristics of 7.1 (T406A).

A minimally disruptive approach. Two kinetic studies indicate that our architecture for photocontrol does not interfere with the native substrate specificity or binding behavior of PTP1B: (i) An analysis of the activity of chimera E3 (from FIG. 1D) on p-nitrophenyl phosphate (pN) indicates that light affects $k_{cat}$, but not $K_m$ (FIGS. 2K and L). (ii) An analysis of activities on three substrates of different sizes (4M, pN, and a peptide) shows that DR is the same for all three (FIG. 2L-K). The results of both studies are consistent with our hypothesized mechanism of photocontrol: LOV2-induced unwinding of the C-terminal α-helix of PTP1B disrupts the movement of its catalytically essential WPD loop, which controls the rate of catalysis, but has little influence on substrate binding affinity.

Biophysical studies. Photoswitchable chimeras express at titers (~100 mg/L) sufficient to carry out detailed biophysical analyses. We performed a preliminary set of these analyses on chimera E3. (i) We use circular dichroism (CD) to examine the influence of photoactivation on its secondary structure; spectral measurements indicate that photoactivation reduces α-helical content (222 nm; FIG. 2B). (ii) We used the amplitude at 222 nm to measure a post-activation recovery time for α-helical content: $T_r$~30 s (FIG. 2E). This value is similar to the recovery times of previously developed LOV2-based photoswitchable constructs, (iii) We used tryptophan fluorescence to measure a post-activation recovery time of tryptophan residues: $T_r$~50 s (FIG. 2F). Tryptophan fluorescence is a rough metric for the conformation of PTP1B (which has seven tryptophan residues, compared to one in LOV2); this slower recovery time, thus, suggests that PTP1B takes longer than LOV2 to refold, (iv) We identified a set of crystallization conditions (those previously used to crystallize PTP1B$_{WT}$) to grow crystals of E3 (FIG. 2F). (V) We collected a two-dimensional $^1$H-$^{15}$N HSQC spectrum of PTP1B$_{WT}$, and assigned ~65% of non-proline peaks. These NMR experiments, which are recent, have yet to include PTP1B-LOV2 chimeras; but the ease with which we carried them out (a single try) suggests that similar analyses of chimeras will be straightforward. The experimental tractability of PTP1B-LOV2 chimeras will enable a comprehensive biophysical analysis of variants with different photophysical properties.

Example 1. To develop a "cage-free" approach to control protein tyrosine phosphatases and kinases with light. This section develops an approach for placing enzymes under optical control without disrupting their native interactions. We will demonstrate this approach with PTP1B and, then, extend it to STEP and PTK6. We will know that we are successful when we have a PTP1B-LOV2 chimera that exhibits a three- to ten-fold change in activity between light and dark states, and when we have identified structure-based design rules that facilitate fine-tuning of the photophysical properties of photoswitchable variants of PTP1B, STEP, and PTK6.

D. Development of a Photoswitchable Variant of PTP1B.

The efforts in this section assume—and with crystallographic, kinetic, and binding studies, attempt to confirm—that optogenetic actuation systems located far from active sites are less likely to disrupt wild-type behaviors that actuation systems located nearby. Kinetic studies of preliminary PTP1B-LOV2 chimeras (i.e., chimeras in which the C-terminal helix of PTP1B is connected to the N-terminal helix of the LOV2 domain of phototropin 1 from A vena sativa) support this hypothesis: light inhibits their activity by affecting $k_{cat}$, not $K_m$, and they show wild-type kinetics on 4-methylumbelliferyl phosphate (4M), a model substrate (FIG. 1G and FIG. 2K). Photomodulation of $k_{cat}$, but not $K_m$ suggests that LOV2 exploits an allosteric network to distort the WPD loop (FIG. 6).

Our initial constructs, which represent the first reported examples photoswitchable protein phosphatases, will facilitate a systematic study of the functional advantages of different chimera architectures. We are particularly interested in understanding how (i) the length of the linker that connects PTP1B and LOV2 and (ii) the stability of the terminal helices of LOV2 affect catalytic activity and dynamic range. We will study these relationships by combing spectroscopic analyses with kinetic studies. Spectroscopic analyses will show how different PTP1B-LOV2 chimeras rearrange under illumination (e.g., we will use CD and fluorescence spectroscopy to measure photomodulation of α-helical content and tryptophan fluorescence), and kinetic studies will reveal the influence of those rearrangements on catalytic activity and dynamic range.

The results of our biophysical analyses will facilitate the optimization of our chimera for in vitro cell studies. We will target a chimera—hereafter, referred to as PTP1B$_{PS}$—with the following properties: a dynamic range (DR) of 3-10, a recovery time of $T_r$~15-60 s, and wild-type activity (in its activated state). Previous optogenetic studies suggest that these attributes enable optical control of cell signaling[2,18,19]. We note: Biophysical studies of PTP1B indicate that the removal of its C-terminal α-helix can reduce its activity by a factor of four[57]; accordingly, we believe that LOV2 can modulate the activity of PTP1B by at least fourfold (of course, LOV2 may trigger structural distortions more pronounced than those of a simple truncation).

E. Characterization of PTP1B-Substrate and PTP1B-Protein Interactions.

We will assess the influence of LOV2 on the substrate specificity of PTP1B by using kinetic analyses. Specifically, we will compare the activities of PTP1B$_{WT}$ and PTP1B$_{PS}$ on three substrates: (i) p-nitrophenyl phosphate, a general substrate for tyrosine phosphatases, (ii) ETGTEEpYMKMDLG (SEQ ID NO: 10), a substrate of PTPs closely related to PTP1B, and (iii) RRLIEDAEpYAARG (SEQ ID NO: 11), a substrate specific to PTP1B. A comparison of values of $k_{cat}$ and $K_m$ on these substrates (FIG. 2K shows an example kinetic study) will reveal differences in the catalytic activities and specificities of PTP1B$_{WT}$ and PTP1B$_{PS}$. These studies will also allow us to assess the substrate-dependence of photoswitchability (i.e., DR). Photomodulation is often assumed to be independent of substrate; there is, however, no biochemical basis for this assumption (particularly in cage-based systems, where substrates may bind with different affinities and, thus, have different abilities to compete with the caging protein). We will test it.

Figure 7A:
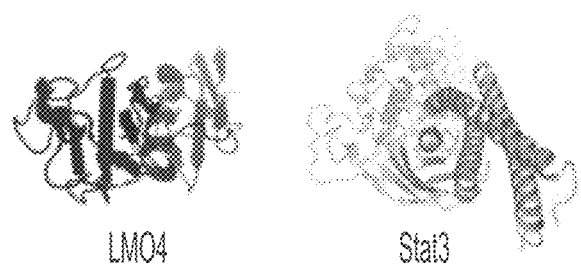
FIG. 7A-B shows and exemplary analysis of binding affinity.
Figure 7B:
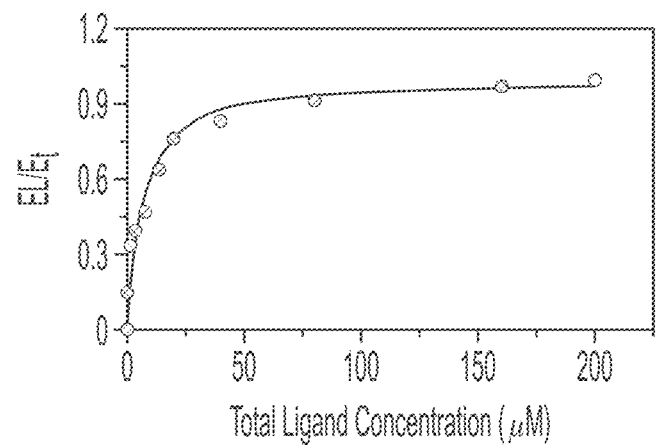

We will assess the ability of PTP1B$_{PS}$ to engage in the same protein-protein interactions as PTP1B$_{WT}$ by measuring the affinity of both enzymes for two native binding partners of PTP1B$_{WT}$: LMO4 and Stat3. Binding isotherms based on changes in tryptophan fluorescence of PTP1B will facilitate this study (FIG. 7).

Our biochemical comparison of PTP1B$_{WT}$ and PTP1B$_{PS}$ may seem tedious, but we believe that this analysis is necessary to establish the relevance of future optogenetic observations to wild-type processes.

Biostructural characterization. We will investigate the structural basis of photocontrol in PTP1B$_{PS}$ by using X-ray crystallography and NMR spectroscopy. X-ray crystal structures will show how LOV2 affects the structure of PTP1B (and vice versa); NMR spectroscopy will show how LOV2 modulates catalytic activity. For crystallographic studies, we will crystallize PTP1B$_{PS}$ in its dark state (we will use the C450S mutation, which prevents formation of the cysteine adduct[2,26]) by screening crystallization conditions previously used for LOV2, PTP1B, and LOV2-protein chimeras (all of which have crystal structures[2,35,58]); preliminary results suggest that those used to grow crystals of PTP1B$_{WT}$ also yield crystals of PTP1B-LOV2 chimeras (FIG. 2J). For NMR studies, we will use heteronuclear single quantum coherence (HSQC) spectroscopy and transverse relaxation-optimized spectroscopy (TROSY) to monitor changes in the conformation and backboned dynamics of PTP1B$_{PS}$ before and after illumination. (We note: Backbone $^1$H, $^{13}$C, and $^{15}$N chemical shifts have been assigned for PTP1B and LOV2[59,60]).

G. Exemplary Imaging Methodology to Study Subcellular Signaling Events in Living Cells.

This section uses PTP1B$_{PS}$ (a PTP1B-LOV2 chimera) to develop an approach for using confocal microscopy to probe—and study—subcellular signaling events. We will know that this objective is successful when we can inactivate a within subcellular regions, monitor the effect of that inactivation with an FRET-based sensor, and isolate the contributions of different subpopulations of PTP1B (e.g., ER-bound and cytosolic) to sensor phosphorylation.

Hypothesis. The subcellular localization of PTPs and PTKs is controlled by domains proximal to their catalytic cores[23,24]. We hypothesize that the attachment of these domains to photoswitchable chimeras will give them wild-type localization patterns, and enable the use of confocal microscopy to study the contribution of spatially distinct subpopulations of PTPs and PTKs to cell signaling. Experimental approach: Within the cell, PTP1B exists in two spatially distinct subpopulations: attached to the cytosolic face of the endoplasmic reticulum, and free in the cytosol—a result of proteolysis of its short (~80 residue) C-terminal ER anchor[29]. We will (i) attach the ER anchor of wild-type PTP1B (PTP1B$_{WT}$) to our PTP1B-LOV2 chimera, (ii) compare the subcellular localization of the resulting chimera with that of PTP1B$_{WT}$, (iii) use confocal microscopy—in conjunction with a FRET-based sensor for phosphatase activity—to control and monitor PTP1B activity within the cell, and (iv) develop a reaction-diffusion model to assess the contributions of spatially distinct subpopulations of PTP1B to changes in sensor phosphorylation over time and space. This work will yield a general approach for studying spatially localized signaling events in living cells.

Localization of PTP1B$_{PS}$.

To examine the localization of PTP1B$_{PS}$ in living cells, we will express three variants in COS-7 cells: (i) PTP1B$_{PS\_C}$45os, (ii) PTP1B$_{PS\_}$c45os attached to a short segment (~20 amino acids[29]) of the C-terminal ER anchor of PTP1B$_{WT}$ that contains only the transmembrane domain (but not the proteolysis site), and (iii) PTP1B$_{PS}$-c45os attached to the full C-terminal ER anchor of PTP1B$_{WT}$ (~80 amino acids[29]). We hypothesize that these constructs will have (i) cytosolic, (ii) ER-bound, and (iii) both cytosolic and ER-bound (i.e., wild-type) localization patterns, respectively. Using confocal microscopy, we will test this hypothesis by using the fluorescence of LOV2 to locate each chimera[70]. (In these studies, we will locate the ER with fluorescently-labeled SEC61B, an ER-associated transport complex[71]. The C450S mutation, which locks LOV2 in its fluorescent state, will prevent photoactivation during imaging).

COS-7 cells, fibroblast-like cells derived from the kidney tissue of the African green monkey, are particularly compatible with the aforementioned analysis for three reasons: (i) They are large and flat and, thus, facilitate imaging of spatially segregated subcellular regions[72], (ii) They are compatible with commercially available transfection reagents[73], (iii) Methods for inducing endocytosis[71] and calpain expression[74], two processes that influence the subcellular activity and localization of PTP1B, are well developed for these cells.

Figure 12A:
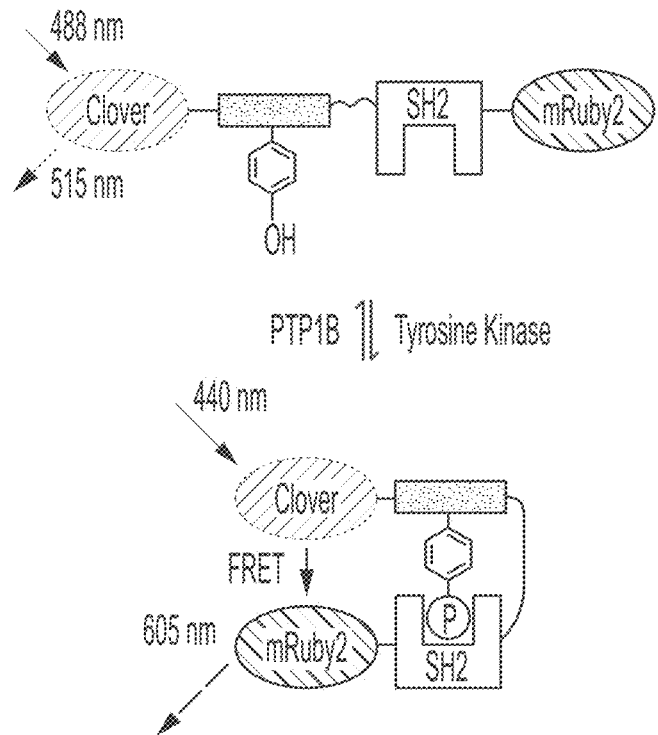
FIG. 12A-B illustrates an exemplary FRET-based sensor developed for measuring intracellular phosphatase or kinase activity. Binding of the substrate and SH2 domain either (FIG. 12A) enhance or (FIG. 12B) reduce FRET, depending on architecture.
Figure 12B:
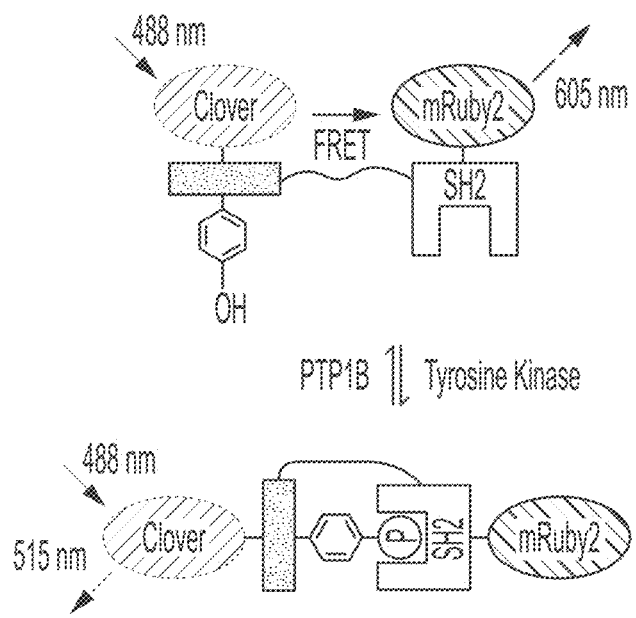

Control of PTP1B$_{PS}$ in living cells. We will examine the activity of PTP1B within subcellular regions by pairing confocal microscopy with a FRET-based sensor for protein phosphorylation (developed by the Umezawa group[54]; FIG. 12). This sensor will consist of a kinase substrate domain, a short flexible linker, and a phosphorylation recognition domain—all sandwiched between two fluorescent proteins (Clover, a green fluorescent protein, and mRuby2, a red fluorescent protein). Phosphorylation of the substrate domain will cause it to bind to the recognition domain, modulating (i.e., enhancing or reducing) FRET between the two fluorescent proteins. Our preliminary sensor, which uses substrate and SH2 domains compatible with PTP1B and src[23,55], exhibits a 20% change in FRET in response to phosphorylation. We will attempt to optimize our sensor further by screening different substrate domains, SH2 domains, and linker lengths. Ouyang et al. built a FRET sensor for Src kinase activity that exhibits a ~120% change in FRET when phosphorylated[55]; we will use the architecture of this sensor—or, perhaps the sensor itself—to inform our designs.

Figure 13:
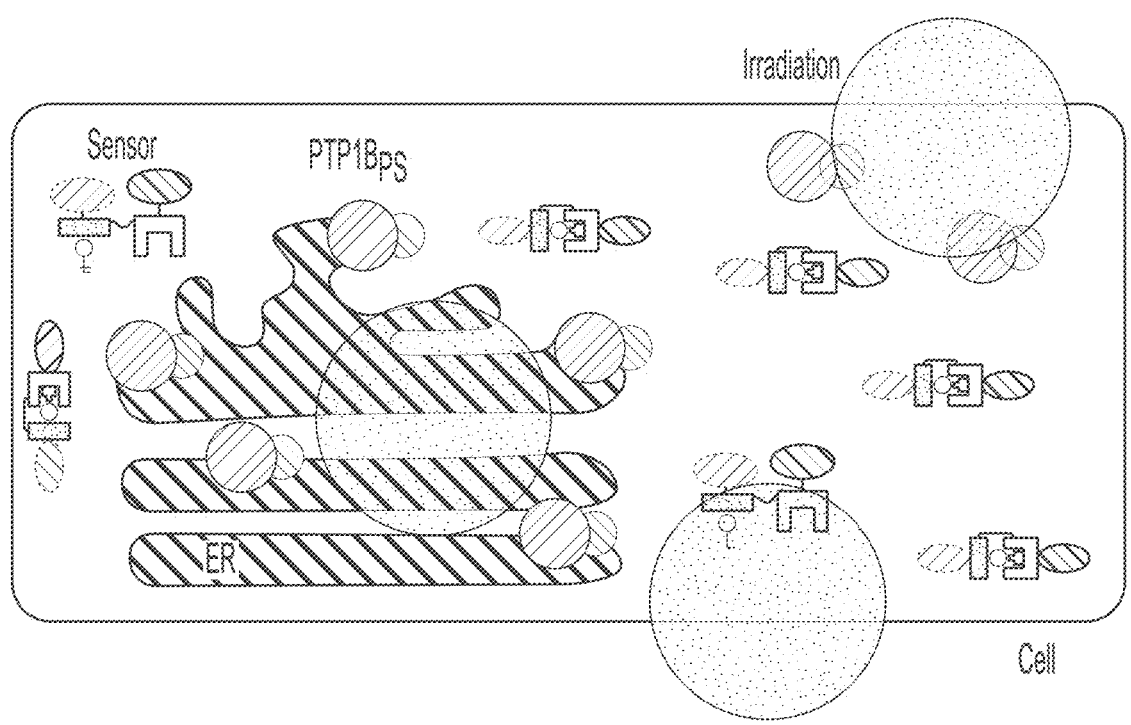
FIG. 13 shows a cartoon of imaging experiments. We will inactivate PTP1B PS within subcellular regions (1-10 µm) containing different amounts of plasma membrane, ER, and cytosol, and we will use fluorescence lifetime imaging to examine the phosphorylation state of our FRET-based sensor (from FIG. 12) throughout the cell.
Figure 14A:
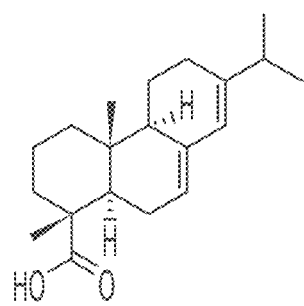
FIG. 14A-D illustrates an exemplary starting point for lead drug design and discovery.
Figure 14B:
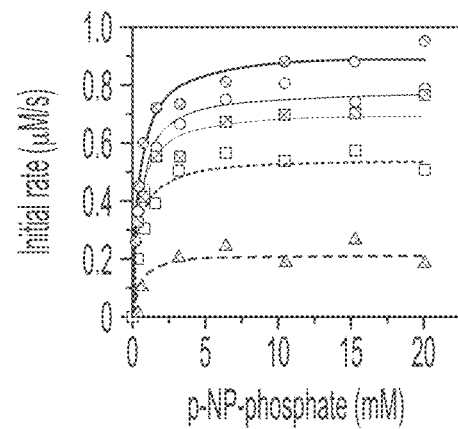
Figure 14C:
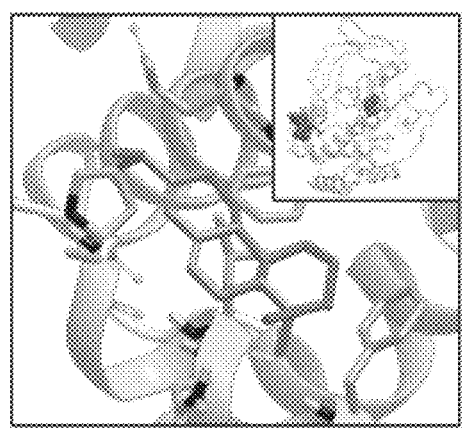
Figure 14D:
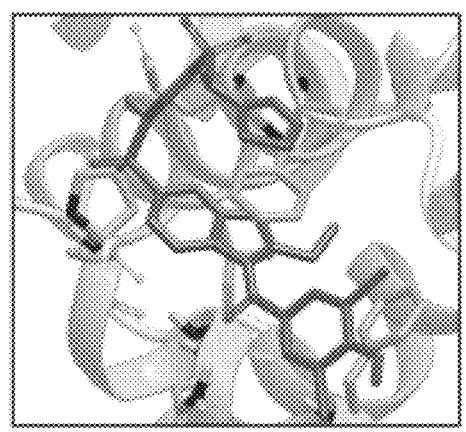
Figure 15A:
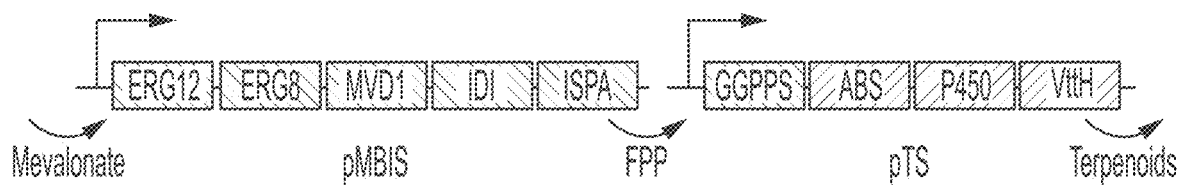
FIG. 15A-D illustrates an exemplary FIG. 15A Pathway for the synthesis of terpenoids (mevalonate can be synthesized through pMevT or added to the media).
Figure 15B:
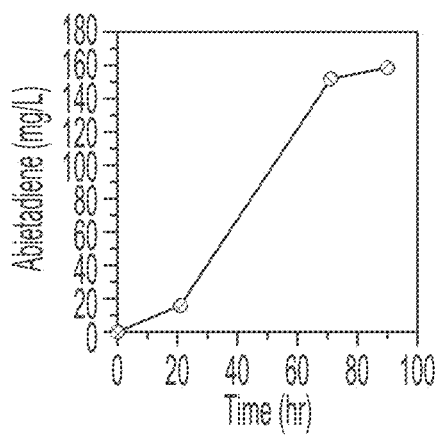
Figure 15C:
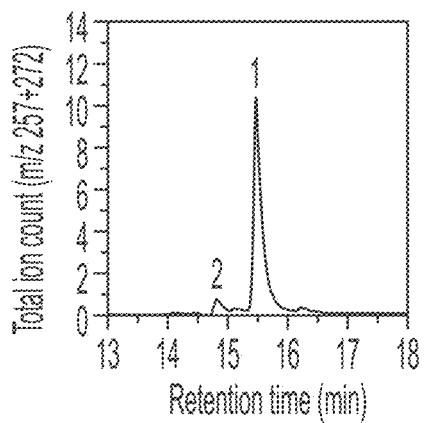
Figure 15D:
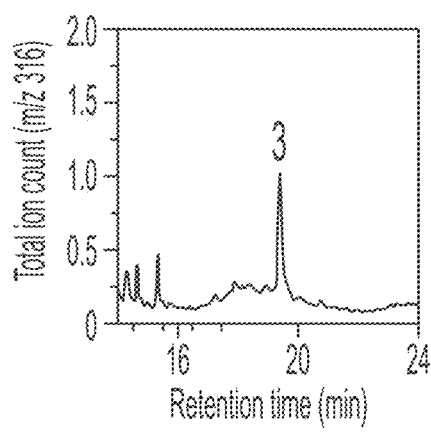
Figure 16A:
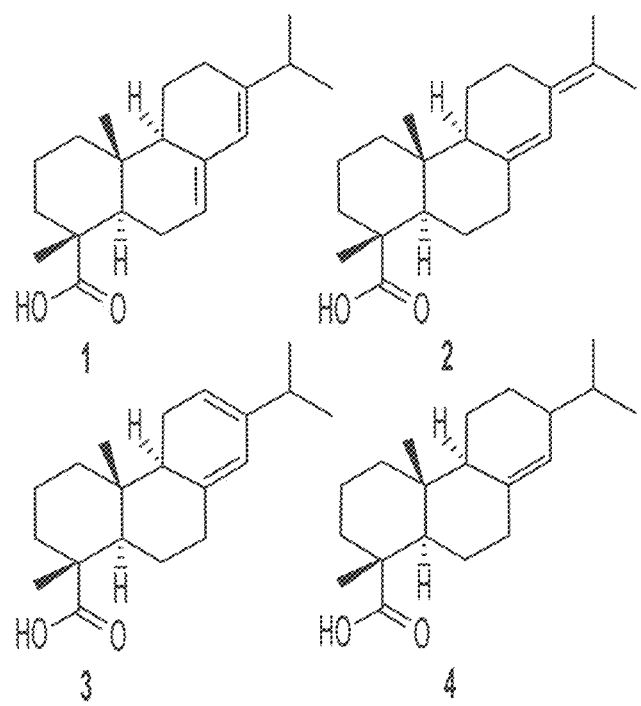
FIG. 16A-B illustrates exemplary terpenoids showing differences in stereochemistry, shape, size, and chemical functionality.
Figure 16B:
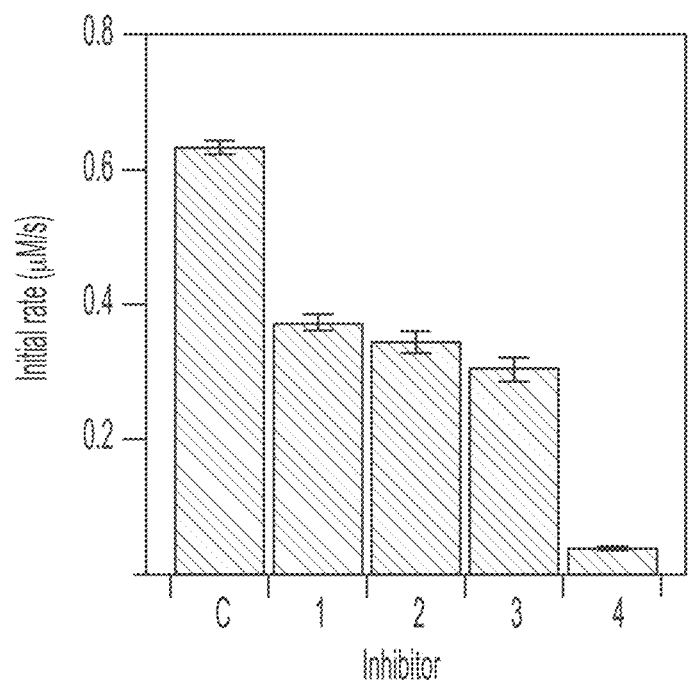

In our imaging experiments, we will use a 455-nm laser to inactivate PTP1B within subcellular regions (1-10 urn circles) and fluorescence lifetime imaging microscopy (FLIM) to monitor changes in sensor phosphorylation that result from that inactivation (FIG. 13). For these experiments, we will use siRNA to deplete PTP1B$_{WT}$ and SEC61B to label the ER. The output will be a series of images in which the intensity of a pixel is proportional to the fluorescence lifetime of Clover (and, thus, the extent of sensor phosphorylation).

With this study, we are particularly interested in examining relationships between (i) the location of PTPIBps activation/inactivation, (ii) the size of the region of activation/inactivation, and (iii) the location and timing of changes in the phosphorylation state of the sensor. We will investigate these relationships by using a reaction-diffusion model. Equation 1 provides a simple example of a governing equation:

$$\frac{\partial S_P(r,t)}{\partial t} = D_S \nabla^2 S_P + k_{cat}^K [KS] - k_{cat}^P [PS_P] - k_{on}^K [P][S_P] \quad \text{(Eq. 1)}$$

for the phosphorylated sensor ($S_P$). Here, $D_s$ is the diffusion coefficient for the sensor; KS is the concentration of tyrosine kinase bound to unphosphorylated sensor; $PS_p$ is the concentration of PTP1B bound to phosphorylated sensor; P and $S_p$ are the concentrations of free PTP1B and free phosphorylated sensor, respectively; $k^{\wedge}_{at}$ and $k^{\wedge}_{at}$ are the catalytic constants for the tyrosine kinase and PTP1B, respectively; and k %$_n$ is the kinetic constant for sensor-PTP1B association. The kinase and phosphatase are assumed to bind only weakly with their products (an assumption that can be easily re-examined later). We may also supplement this model with tools such as BioNetGen, a web-based platform for generating biochemical reaction networks from user-specified rules for the mechanisms and locations of biomolecular interactions[75]; such a tool, which can accommodate cellular heterogeneity (e.g., organelles and other compartments), will help to support and expand our kinetic model.

We hypothesize that a version of our kinetic model in which the phosphatase diffuses freely will more accurately capture the phosphorylation state of the sensor (at a specified time and position from the irradiation region) in the presence of cytosolic PTP1B$_{PS}$. By contrast, a version of the model in which phosphatase does not diffuse freely will more accurately capture the behavior of sensors in the presence of ER-bound PTP1B$_{PS}$. Regression of either model against imaging data will enable estimation of the extent to which cytosolic and ER-bound PTP1B contribute to changes in sensor phosphorylation over time and space.

Image analysis. The ER exists as a vesicular network that is spread throughout the cell; inactivation of subcellular regions that are entirely ER or entirely cytosol is difficult. To enable analysis of spatially distinct subpopulations of PTP1B, we must, thus, estimate the amount of ER in different regions of irradiation. The discrepancy in length scales of ER heterogeneity (~20-100 pm) and irradiation (~1-10 pm) will permit such an estimation. We will work with two metrics: (i) the total fluorescence of labeled ER, and (ii) the anisotropy of labeled ER. Both metrics, by facilitating estimates of the populations of cytosolic and ER-bound PTP1B in an illuminated region, will help us to assess the contributions of those populations to changes in sensor phosphorylation.

Spatial Regulation and Intracellular Signaling.

PTP1B demonstrates, by example, the value of photoswitchable enzymes for studying spatial regulation in intracellular signaling. It is hypothesized to inactivate receptor tyrosine kinases through (i) contacts between endosomes and the ER[37,38], (ii) contacts between the plasma membrane and extended regions of the ER[39], and (iii) direct protein-protein interactions enabled by its partial proteolysis and release into the cytosol[34]. The role of different mechanisms (or locations) of PTP1B-substrate interaction in determining the outcomes of those interactions is poorly understood. Evidence suggesting a relationship between the location of PTP1B and its role in signaling has arisen in studies of tumorigenesis. Inhibition of PTP1B can suppress tumor growth and metastasis in breast[30,40], lung[3,41], colorectal[9], and prostate cancers,[42,43] while its upregulation has similar effects in lymphoma[3,44]. Recent evidence suggests that the former effect may result from inhibition of cytosolic PTP1B[45]; the cause of the latter is unclear. At present, there are no tools to investigate the differential influence of spatially distinct subpopulations of PTP1B on tumor-associated signaling events within the same cell. Photoswitchable variants of PTP1B represent such a tool.

Network biology. Signaling networks are often represented as nodes (proteins) connected by lines (interactions)[46]. Such maps capture the connectivity of biochemical relay systems, but obscure spatial context—the ability of a single interaction to occur in multiple locations and, perhaps, to stimulate multiple signaling outcomes. This study develops a set of tools that will enable detailed studies of the role of spatial context in guiding the propagation of signals through biochemical networks; e.g. understanding the role of PTP1B in cell signaling (and processes associated with tumorigenesis), and generally relevant to the study of any enzyme that exists in spatially distinct subpopulations within the cells.

Generalization of Approach to Protein Tyrosine Phosphatases and Kinases.

Two observations suggest that our architecture for photocontrol (i.e., attachment of the N-terminus of LOV2 to the C-terminal α-helix of an enzyme) is broadly applicable to PTPs and PTKs. (i) Structural alignments show that all PTPs possess, or, with a few mutations, can possess—the same allosteric communication network as PTP1B (FIG. 8A)[23]. (ii) PTKs contain a C-terminal α-helix that is distal to their active sites, yet capable of modulating their catalytic activities (FIG. 8B)[61].

Figure 8A:
FIG. 8A-B illustrates exemplary structural alignment of PTP1B (light blue) and STEP (orange), FIG. 8A, which have only 31% sequence identity, shows remarkable structural similarity.

We will assess the generalizability of our approach by building photoswitchable variants of striatal-enriched protein tyrosine phosphatase (STEP) and protein tyrosine kinase 6 (PTK6; FIG. 8A). STEP is a neuron-specific phosphatase that is overactive in several neurological disorders, prominently Alzheimer's disease, schizophrenia, and drug addiction[62,63]. PTK6, which may function orthogonally to PTP1B in some signaling pathways, is expressed in approximately 70% of triple-negative breast cancers and promotes metastasis[50,64]. Photoswitchable variants of STEP and PTK6, both of which exist in multiple spatially distinct subpopulations within cells[50,62], will enable detailed studies of their intracellular signaling roles, which remain poorly characterized.

For STEP and PTK6, we will develop—and measure the substrate specificities of—photoswitchable chimeras by using several kinetic assays. For STEP, we will use assays analogous to those employed with PTP1B. For PTK6, we will use the ADP-Glo kit developed by Promega, Inc.[65]. This assay, which is compatible with any peptide substrate, converts ADP produced by PTK-catalyzed peptide phosphorylation to a luminescent signal. For both enzymes, we will collect crystal structures of optimal chimeras.

Exemplary photoswitch construct sequences for use in expressing in mammalian cells or within an operon for microbial cells. In some embodiments, the sequences may be optimized for microbial expression.

```
PPTP1B-LOV2, version 7.1(T406A): DNA sequence SEQ ID NO: 12:
ATGGAGATGGAAAAGGAGTTCGAGCAGATCGACAAGTCCGGGAGCTGGGCGGCC

ATTTACCAGGATATCCGACATGAAGCCAGTGACTTCCCATGTAGAGTGGCCAAGCT

TCCTAAGAACAAAAACCGAAATAGGTACAGAGACGTCAGTCCCTTTGACCATAGTC

GGATTAAACTACATCAAGAAGATAATGACTATATCAACGCTAGTTTGATAAAAATGG

AAGAAGCCCAAAGGAGTTACATTCTTACCCAGGGCCCTTTGCCTAACACATGCGGT

CACTTTTGGGAGATGGTGTGGGAGCAGAAAAGCAGGGGTGTCGTCATGCTCAACA

GAGTGATGGAGAAAGGTTCGTTAAAATGCGCACAATACTGGCCACAAAAAGAAGAA

AAAGAGATGATCTTTGAAGACACAAATTTGAAATTAACATTGATCTCTGAAGATATC

AAGTCATATTATACAGTGCGACAGCTAGAATTGGAAAACCTTACAACCCAAGAAAC

TCGAGAGATCTTACATTTCCACTATACCACATGGCCTGACTTTGGAGTCCCTGAAT

CACCAGCCTCATTCTTGAACTTTCTTTTCAAAGTCCGAGAGTCAGGGTCACTCAGC

CCGGAGCACGGGCCCGTTGTGGTGCACTGCAGTGCAGGCATCGGCAGGTCTGGA
```

-continued

```
ACCTTCTGTCTGGCTGATACCTGCCTCTTGCTGATGGACAAGAGGAAAGACCCTTC

TTCCGTTGATATCAAGAAAGTGCTGTTAGAAATGAGGAAGTTTCGGATGGGGCTGA

TCCAGACAGCCGACCAGCTGCGCTTCTCCTACCTGGCTGTGATCGAAGGTGCCAA

ATTCATCATGGGGGACTCTTCCGTGCAGGATCAGTGGAAGGAGCTTTCCCACGAG

GACGCTGCTACACTTGAACGTATTGAGAAGAACTTTGTCATTACTGACCCAAGGTT

GCCAGATAATCCCATTATATTCGCGTCCGATAGTTTCTTGCAGTTGACAGAATATAG

CCGTGAAGAAATTTTGGGAAGAAACTGCAGGTTTCTACAAGGTCCTGAAACTGATC

GCGCGACAGTGAGAAAAATTAGAGATGCCATAGATAACCAAACAGAGGTCACTGTT

CAGCTGATTAATTATACAAAGAGTGGTAAAAAGTTCTGGAACCTCTTTCACTTGCAG

CCTATGCGAGATCAGAAGGGAGATGTCCAGTACTTTATTGGGGTTCAGTTGGATG

GAACTGAGCATGTCCGAGATGCTGCCGAGAGAGAGGGAGTCATGCTGATTAAGAA

AACTGCAGAAAATATTGATGAGGCGGCAAAAGAACTTCTCGAGCACCACCACCAC

CACCACTGA
```

Protein sequence: SEQ ID NO: 13:
MEMEKEFEQIDKSGSWAAIYQDIRHEASDFPCRVAKLPKNKNRNRYRDVSPFDHSRIKL

HQEDNDYINASLIKMEEAQRSYILTQGPLPNTCGHFWEMVWEQKSRGVVMLNRVMEK

GSLKCAQYWPQKEEKEMIFEDTNLKLTLISEDIKSYYTVRQLELENLTTQETREILHFHY

TTWPDFGVPESPASFLNFLFKVRESGSLSPEHGPVVVHCSAGIGRSGTFCLADTCLLLMD

KRKDPSSVDIKKVLLEMRKFRMGLIQTADQLRFSYLAVIEGAKFIMGDSSVQDQWKELS

HEDAATLERIEKNFVITDPRLPDNPIIFASDSFLQLTEYSREEILGRNCRFLQGPETDRATV

RKIRDAIDNQTEVTVQLINYTKSGKKFWNLFHLQPMRDQKGDVQYFIGVQLDGTEHVR

DAAEREGVMLIKKTAENIDEAAKELLEHHHHHH

PTP1B-LOV2, version 7.1(S286A): DNA sequence: SEQ ID NO: 14:
```
ATGGAGATGGAAAAGGAGTTCGAGCAGATCGACAAGTCCGGGAGCTGGGCGGCCAT

TTACCAGGATATCCGACATGAAGCCAGTGACTTCCCATGTAGAGTGGCCAAGCTTCC

TAAGAACAAAAACCGAAATAGGTACAGAGACGTCAGTCCCTTTGACCATAGTCGGA

TTAAACTACATCAAGAAGATAATGACTATATCAACGCTAGTTTGATAAAAATGGAA

GAAGCCCAAAGGAGTTACATTCTTACCCAGGGCCCTTTGCCTAACACATGCGGTCAC

TTTTGGGAGATGGTGTGGGAGCAGAAAAGCAGGGGTGTCGTCATGCTCAACAGAGT

GATGGAGAAAGGTTCGTTAAAATGCGCACAATACTGGCCACAAAAAGAAGAAAAA

GAGATGATCTTTGAAGACACAAATTTGAAATTAACATTGATCTCTGAAGATATCAAG

TCATATTATACAGTGCGACAGCTAGAATTGGAAAACCTTACAACCCAAGAAACTCG

AGAGATCTTACATTTCCACTATACCACATGGCCTGACTTTGGAGTCCCTGAATCACC

AGCCTCATTCTTGAACTTTCTTTTCAAAGTCCGAGAGTCAGGGTCACTCAGCCCGGA

GCACGGGCCCGTTGTGGTGCACTGCAGTGCAGGCATCGGCAGGTCTGGAACCTTCTG

TCTGGCTGATACCTGCCTCTTGCTGATGGACAAGAGGAAAGACCCTTCTTCCGTTGA

TATCAAGAAAGTGCTGTTAGAAATGAGGAAGTTTCGGATGGGGCTGATCCAGACAG

CCGACCAGCTGCGCTTCTCCTACCTGGCTGTGATCGAAGGTGCCAAATTCATCATGG

GGGACTCTGCCGTGCAGGATCAGTGGAAGGAGCTTTCCCACGAGGACGCTACTACA

CTTGAACGTATTGAGAAGAACTTTGTCATTACTGACCCAAGGTTGCCAGATAATCCC

ATTATATTCGCGTCCGATAGTTTCTTGCAGTTGACAGAATATAGCCGTGAAGAAATT

-continued

TTGGGAAGAAACTGCAGGTTTCTACAAGGTCCTGAAACTGATCGCGCGACAGTGAG

AAAAATTAGAGATGCCATAGATAACCAAACAGAGGTCACTGTTCAGCTGATTAATT

ATACAAAGAGTGGTAAAAAGTTCTGGAACCTCTTTCACTTGCAGCCTATGCGAGATC

AGAAGGGAGATGTCCAGTACTTTATTGGGGTTCAGTTGGATGGAACTGAGCATGTCC

GAGATGCTGCCGAGAGAGGGAGTCATGCTGATTAAGAAAACTGCAGAAAATATT

GATGAGGCGGCAAAAGAACTTCTCGAGCACCACCACCACCACCACTGA

Protein sequence: SEQ ID NO: 15:
MEMEKEFEQIDKSGSWAAIYQDIRHEASDFPCRVAKLPKNKNRNRYRDVSPFDHSRIKL

HQEDNDYINASLIKMEEAQRSYILTQGPLPNTCGHFWEMVWEQKSRGVVMLNRVMEK

GSLKCAQYWPQKEEKEMIFEDTNLKLTLISEDIKSYYTVRQLELENLTTQETREILHFHY

TTWPDFGVPESPASFLNFLFKVRESGSLSPEHGPVVVHCSAGIGRSGTFCLADTCLLLMD

KRKDPSSVDIKKVLLEMRKFRMGLIQTADQLRFSYLAVIEGAKFIMGDSAVQDQWKELS

HEDATTLERIEKNFVITDPRLPDNPIIFASDSFLQLTEYSREEILGRNCRFLQGPETDRATV

RKIRDAIDNQTEVTVQLINYTKSGKKFWNLFHLQPMRDQKGDVQYFIGVQLDGTEHVR

DAAEREGVMLIKKTAENIDEAAKELLEHHHHHH

TCPTP-LOV2, best version:
DNA sequence: SEQ ID NO: 16:
ATGCCCACCACCATCGAGCGGGAGTTCGAAGAGTTGGATACTCAGCGTCGCTGGCA

GCCGCTGTACTTGGAAATTCGAAATGAGTCCCATGACTATCCTCATAGAGTGGCCAA

GTTTCCAGAAAACAGAAATCGAAACAGATACAGAGATGTAAGCCCATATGATCACA

GTCGTGTTAAACTGCAAATGCTGAGAATGATTATATTAATGCCAGTTTAGTTGACA

TAGAAGAGGCACAAAGGAGTTACATCTTAACACAGGGTCCACTTCCTAACACATGC

TGCCATTTCTGGCTTATGGTTTGGCAGCAGAAGACCAAAGCAGTTGTCATGCTGAAC

CGC<u>GTGATGGAGAAAGGTTCGTT</u>AAAATGTGCACAGTACTGGCCAACAGATGACCA

AGAGATGCTGTTTAAAGAAACAGGATTCAGTGTGAAGCTCTTGTCAGAAGATGTGA

AGTCGTATTATACAGTACATCTACTACAATTAGAAAATATCAATAGTGGTGAAACCA

GAACAATATCTCACTTTCATTATACTACCTGGCCAGATTTTGGAGTCCCTGAATCACC

AGCTTCATTTCTCAATTTCTTGTTTAAAGTGAGAGAATCTGGCTCCTTGAACCCTGAC

CATGGGCCTGCGGTGATCCACTGTAGTGCAGGCATTGGGCGCTCTGGCACCTTCTCT

CTGGTAGACACTTGTCTTTTGCTGATGGACAAGAGGAAAGACCCTTCTTCCGTTG

ATATCAAGAAAGTGCTGTTAGAAATGAGGAAGTTTCGGATGGGGCTGATCCAG

ACAGCCGACCAGCTGCGCTTCTCCTACCTGGCTGTGATCGAAGGTGCCAAATT

CATCATGGGGGACTCTTCCGTGCAGGATCAGTGGAAGGAGCTTTCCCACGAGG

ACGCTGCTACACTTGAACGTATTGAGAAGAACTTTGTCATTACTGACCCAAGGTTGC

CAGATAATCCCATTATATTCGCGTCCGATAGTTTCTTGCAGTTGACAGAATATAGCC

GTGAAGAAATTTTGGGAAGAAACTGCAGGTTTCTACAAGGTCCTGAAACTGATCGC

GCGACAGTGAGAAAAATTAGAGATGCCATAGATAACCAAACAGAGGTCACTGTTCA

GCTGATTAATTATACAAAGAGTGGTAAAAAGTTCTGGAACCTCTTTCACTTGCAGCC

TATGCGAGATCAGAAGGGAGATGTCCAGTACTTTATTGGGGTTCAGTTGGATGGAAC

TGAGCATGTCCGAGATGCTGCCGAGAGAGGGAGTCATGCTGATTAAGAAAACTG

CAGAAAATATTGATGAGGCGGCAAAAGAACTTCTCGAGCACCACCACCACCACCA

CTGA

-continued

The underlined letters indicate sequence from PTP1B. Protein sequence: SEQ ID NO: 17:
MPTTIEREFEELDTQRRWQPLYLEIRNESHDYPHRVAKFPENRNRNRYRDVSPYDHSRV KLQNAENDYINASLVDIEEAQRSYILTQGPLPNTCCHFWLMVWQQKTKAVVMLNR<u>VM</u>

<u>EKGSLK</u>CAQYWPTDDQEMLFKETGFSVKLLSEDVKSYYTVHLLQLENINSGETRTISHF

HYTTWPDFGVPESPASFLNFLFKVRESGSLNPDHGPAVIHCSAGIGRSGTFSLVDTCLLL

MDKRKDPSSVDIKKVLLEMRKFRMGLIQTADQLRFSYL<u>AVIEGAKFIMGDSSVQDQWK</u>

<u>ELSHED</u>AATLERIEKNFVITDPRLPDNPIIFASDSFLQLTEYSREEILGRNCRFLQGPETDR

ATVRKIRDAIDNQTEVTVQLINYTKSGKKFWNLFHLQPMRDQKGDVQYFIGVQLDGTE

HVRDAAEREGVMLIKKTAENIDEAAKELLEHHHHHH

TCPTP-LOV2 V2: DNA sequence: SEQ ID NO: 18:
ATGCCCACCACCATCGAGCGGGAGTTCGAAGAGTTGGATACTCAGCGTCGCTGGCA

GCCGCTGTACTTGGAAATTCGAAATGAGTCCCATGACTATCCTCATAGAGTGGCCAA

GTTTCCAGAAAACAGAAATCGAAACAGATACAGAGATGTAAGCCCATATGATCACA

GTCGTGTTAAACTGCAAATGCTGAGAATGATTATATTAATGCCAGTTTAGTTGACA

TAGAAGAGGCACAAAGGAGTTACATCTTAACACAGGGTCCACTTCCTAACACATGC

TGCCATTTCTGGCTTATGGTTTGGCAGCAGAAGACCAAAGCAGTTGTCATGCTGAAC

CGCATTGTGGAGAAAGAATCGGTTAAATGTGCACAGTACTGGCCAACAGATGACCA

AGAGATGCTGTTTAAAGAAACAGGATTCAGTGTGAAGCTCTTGTCAGAAGATGTGA

AGTCGTATTATACAGTACATCTACTACAATTAGAAAATATCAATAGTGGTGAAACCA

GAACAATATCTCACTTTCATTATACTACCTGGCCAGATTTTGGAGTCCCTGAATCACC

AGCTTCATTTCTCAATTTCTTGTTTAAAGTGAGAGAATCTGGCTCCTTGAACCCTGAC

CATGGGCCTGCGGTGATCCACTGTAGTGCAGGCATTGGGCGCTCTGGCACCTTCTCT

CTGGTAGACACTTGTCTT<u>TTGCTGATGGACAAGAGGAAAGACCCTTCTTCCGTTGAT</u>

<u>ATCAAGAAAGTGCTGTTAGAAATGAGGAAGTTTCGGATGGGGCTGATCCAGACAGC</u>

<u>CGACCAGCTGCGCTTCTCCTACCTGGCTGTGATCGAAGGTGCCAAATTCATCATGGG</u>

<u>GGACTCTTCCGTGCAGGATCAGTGGAAGGAGCTTTCCCACGAGGAC</u>GCTGCTACACT

TGAACGTATTGAGAAGAACTTTGTCATTACTGACCCAAGGTTGCCAGATAATCCCAT

TATATTCGCGTCCGATAGTTTCTTGCAGTTGACAGAATATAGCCGTGAAGAAATTTT

GGGAAGAAACTGCAGGTTTCTACAAGGTCCTGAAACTGATCGCGCGACAGTGAGAA

AAATTAGAGATGCCATAGATAACCAAACAGAGGTCACTGTTCAGCTGATTAATTATA

CAAAGAGTGGTAAAAAGTTCTGGAACCTCTTTCACTTGCAGCCTATGCGAGATCAGA

AGGGAGATGTCCAGTACTTTATTGGGGTTCAGTTGGATGGAACTGAGCATGTCCGAG

ATGCTGCCGAGAGAGAGGGAGTCATGCTGATTAAGAAAACTGCAGAAAATATTGAT

GAGGCGGCAAAAGAACTTCTCGAGCACCACCACCACCACCACTGA

Protein sequence: SEQ ID NO: 19:
MPTTIEREFEELDTQRRWQPLYLEIRNESHDYPHRVAKFPENRNRNRYRDVSPYDHSRV

KLQNAENDYINASLVDIEEAQRSYILTQGPLPNTCCHFWLMVWQQKTKAVVMLNRIVE

KESVKCAQYWPTDDQEMLFKETGFSVKLLSEDVKSYYTVHLLQLENINSGETRTISHFH

YTTWPDFGVPESPASFLNFLFKVRESGSLNPDHGPAVIHCSAGIGRSGTFSLVDTCLLLM

DKRKDPSSVDIKKVLLEMRKFRMGLIQTADQLRFSYL<u>AVIEGAKFIMGDSSVQDQWKEL</u>

<u>SHED</u>AATLERIEKNFVITDPRLPDNPIIFASDSFLQLTEYSREEILGRNCRFLQGPETDRAT

VRKIRDAIDNQTEVTVQLINYTKSGKKFWNLFHLQPMRDQKGDVQYFIGVQLDGTEHV

RDAAEREGVMLIKKTAENIDEAAKELLEHHHHHH

Figure 21A:
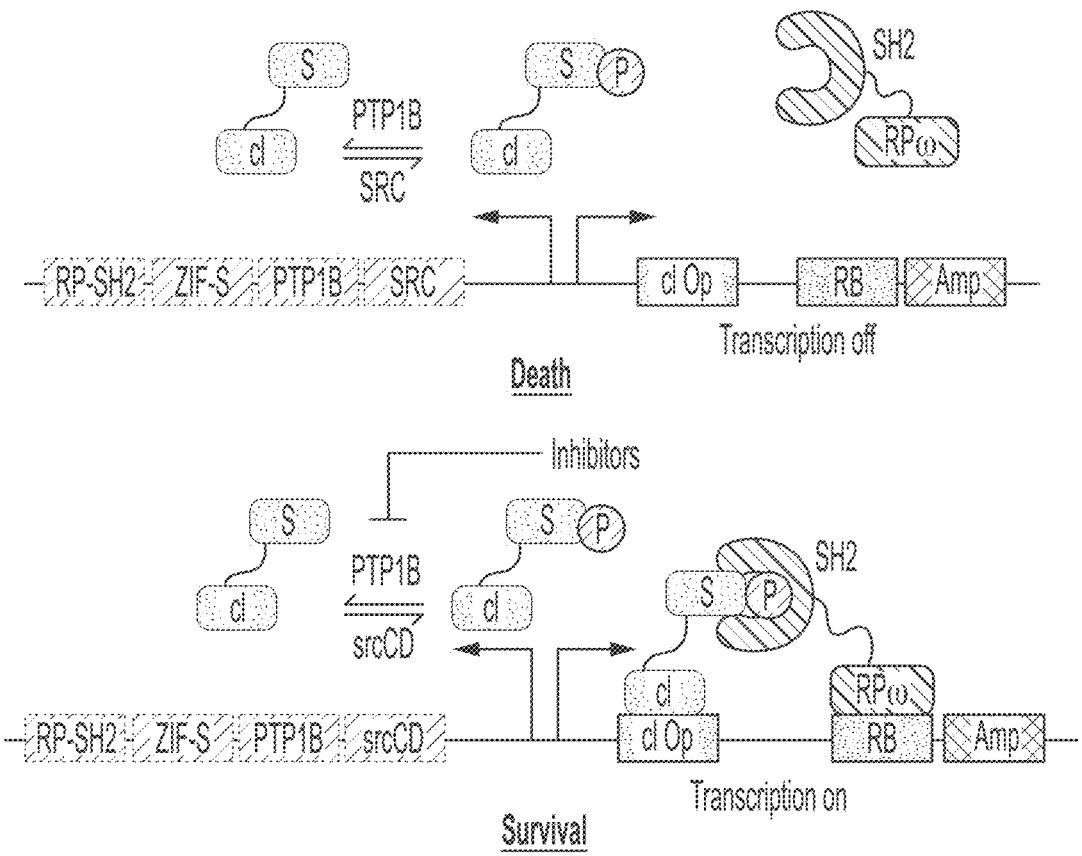
Figure 21B:
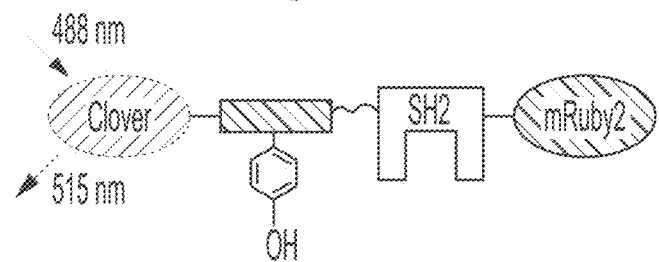
Figure 21B:
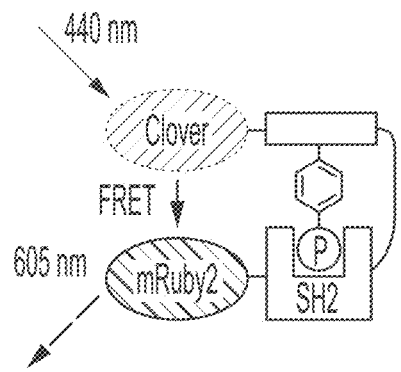
Figure 25A:
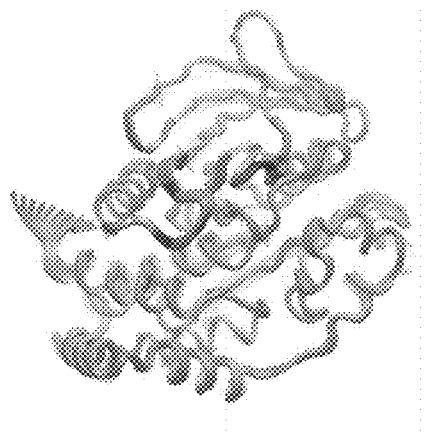
FIG. 25A-D illustrates exemplary computational analysis of AA binding.
Figure 25B:
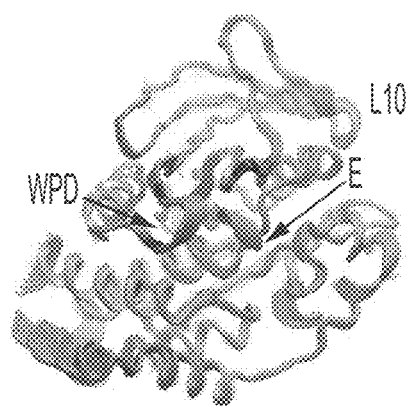
Figure 25C:
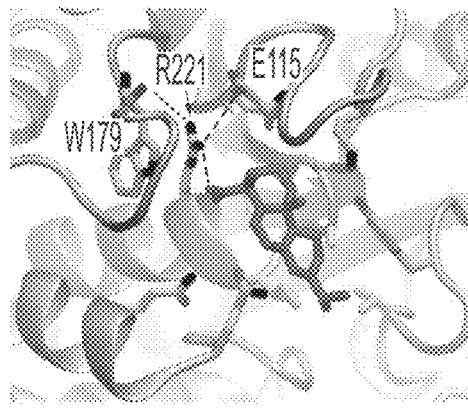
Figure 25D:
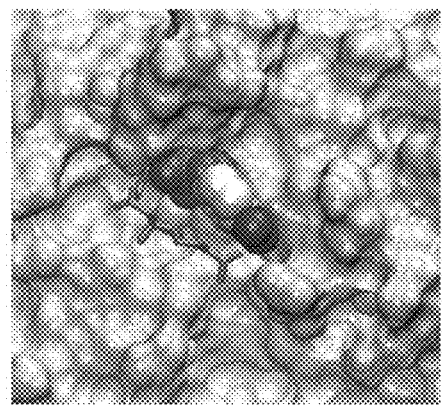
Figure 26B:
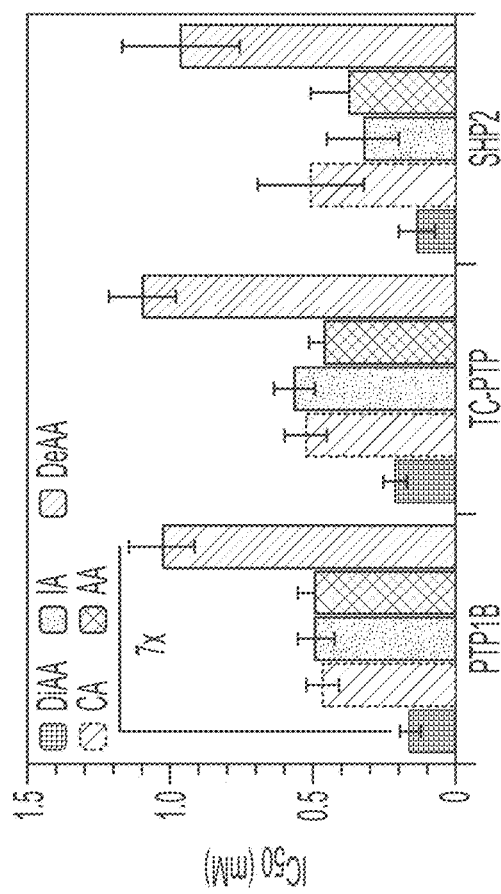
FIG. 26A-C illustrates exemplary terpenoids showing differences in stereochemistry, shape, size, and chemical functionality.
Figure 26B:
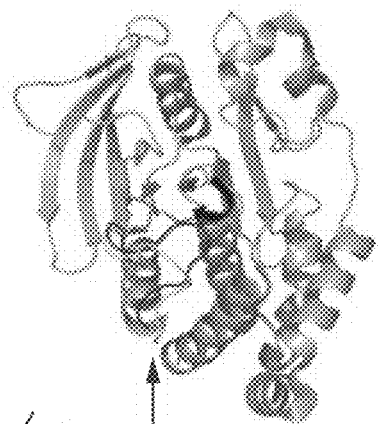
Figure 26A:
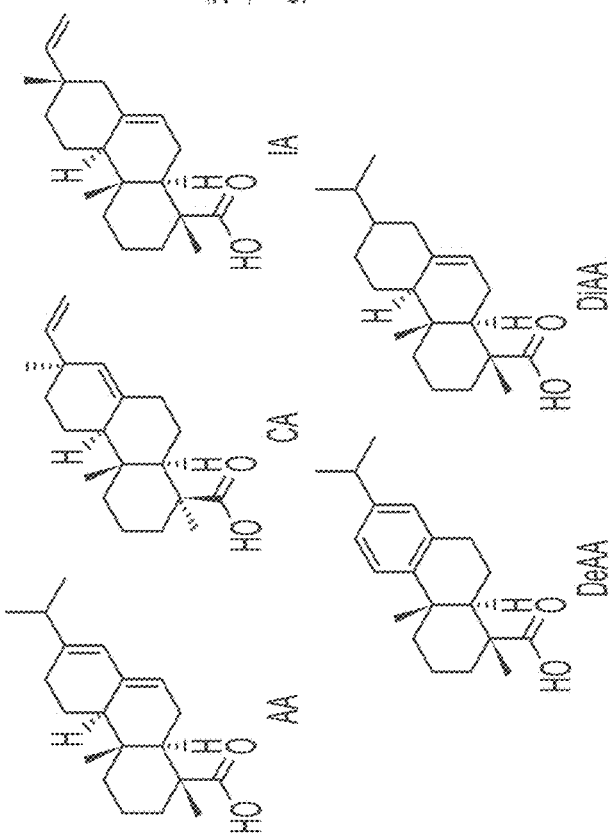
Figure 26C:
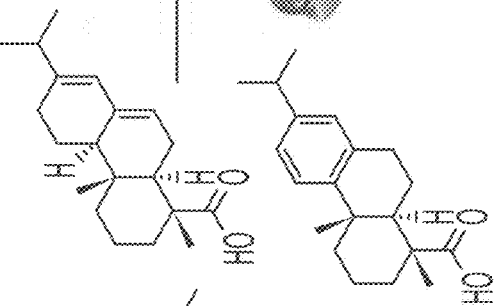
Figure 26C:
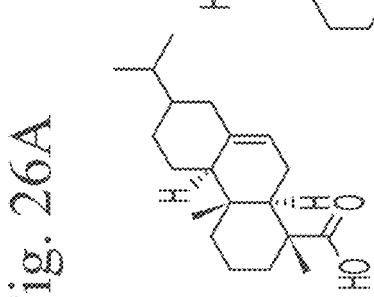
Figures 27A, 27B, 27C:
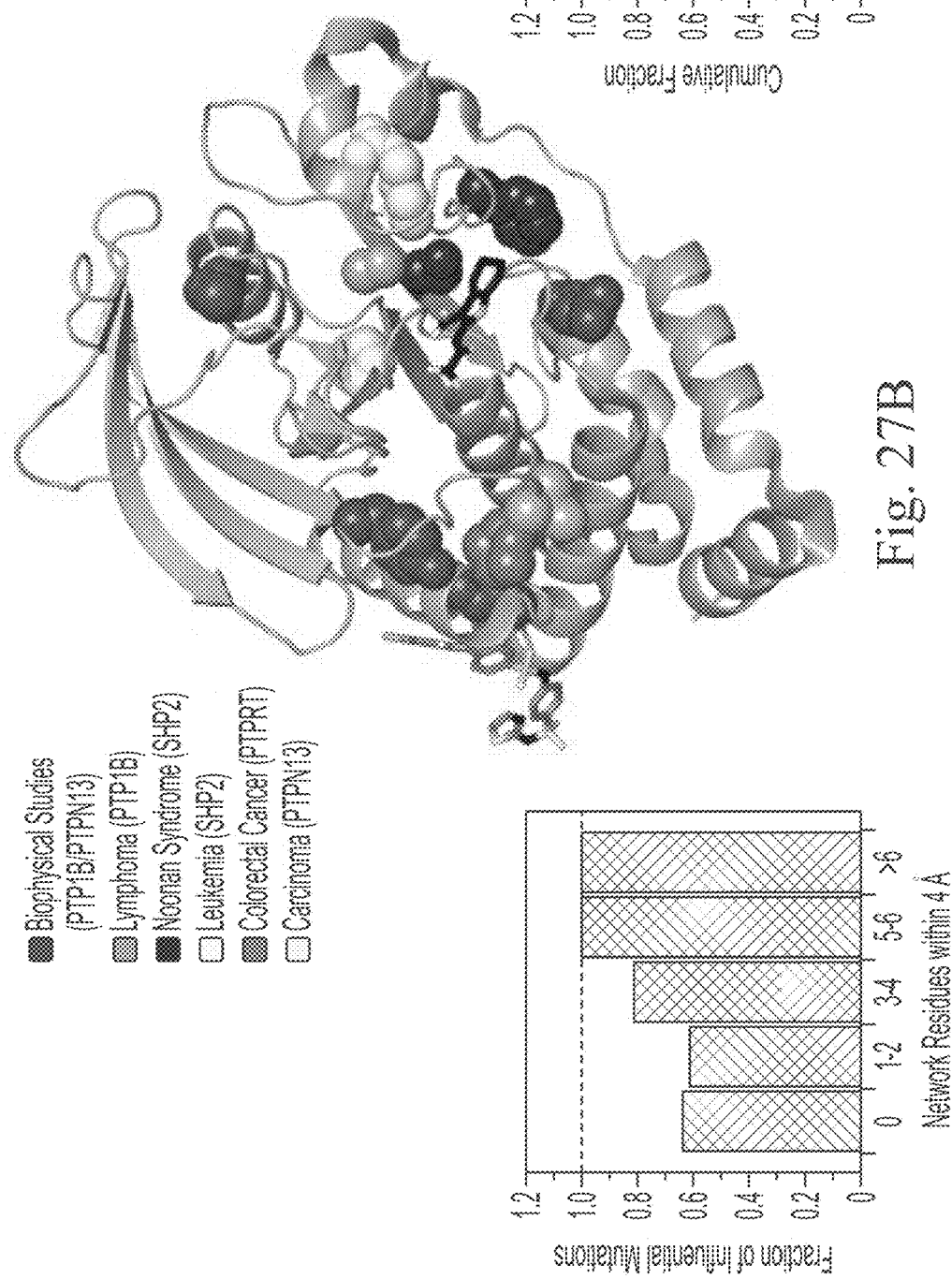
FIG. 27A-C Analysis of pathologically relevant mutations.
Figure 28A:
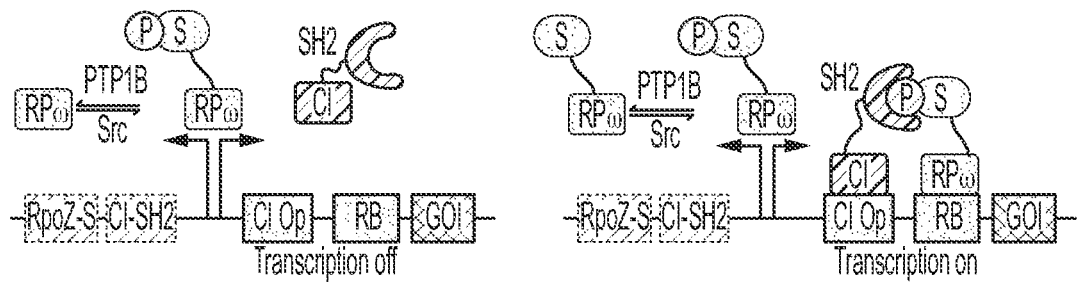
FIG. 28A-D illustrates and shows exemplary data using a Genetic operon linking PTP activity to the output of a gene of interest (GOI).
Figure 28B:
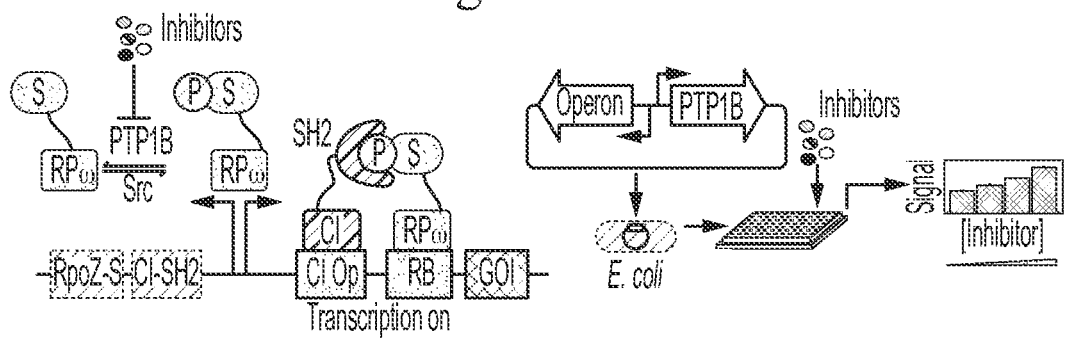
Figures 28C, 28D:
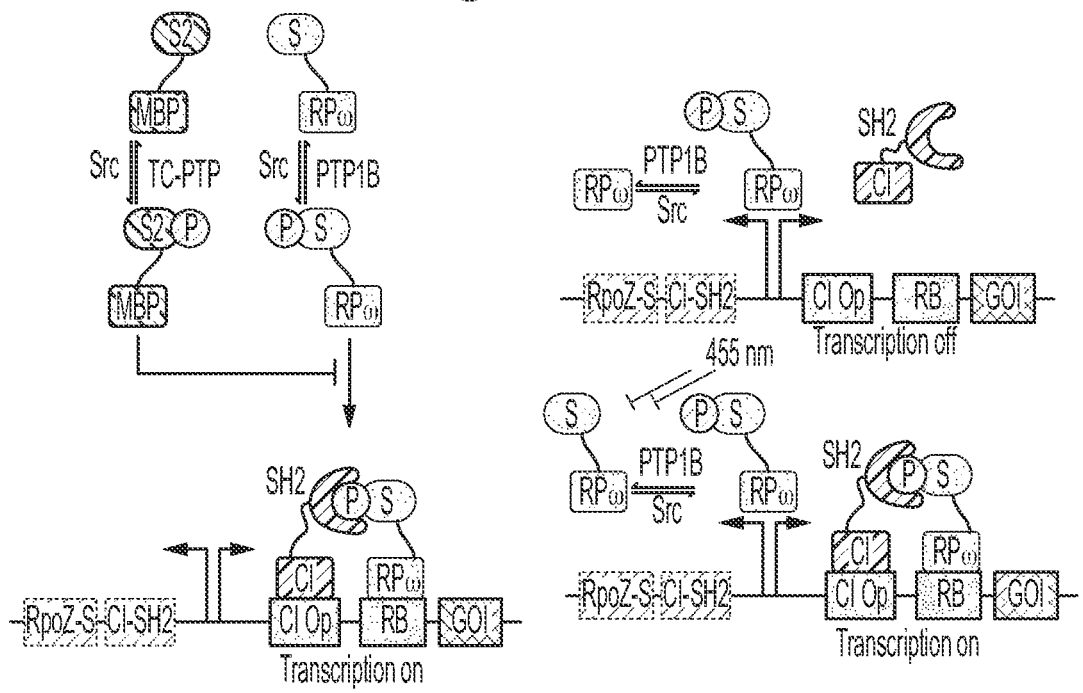
Figure 29A:
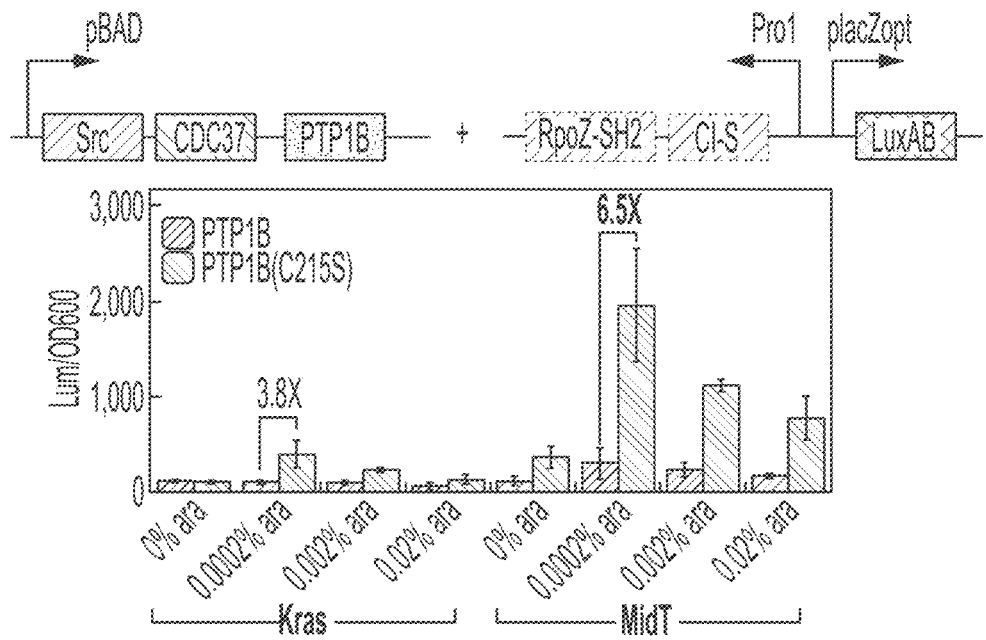
FIG. 29A-B shows exemplary Preliminary results showing phosphorylation-dependent expression of a GOI.
Figure 29B:
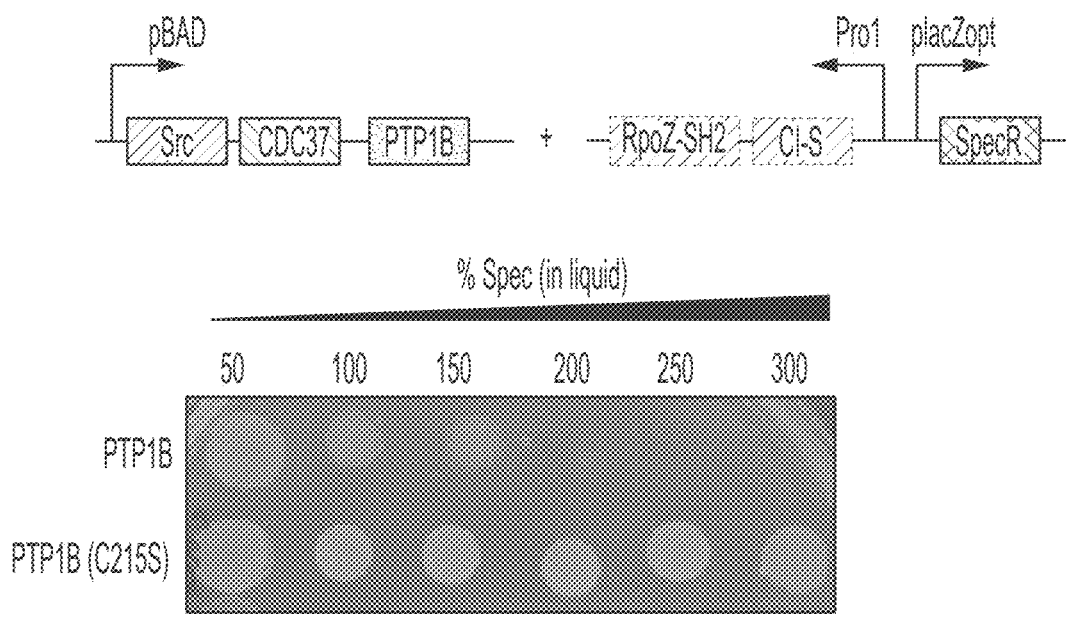
Figure 30A:
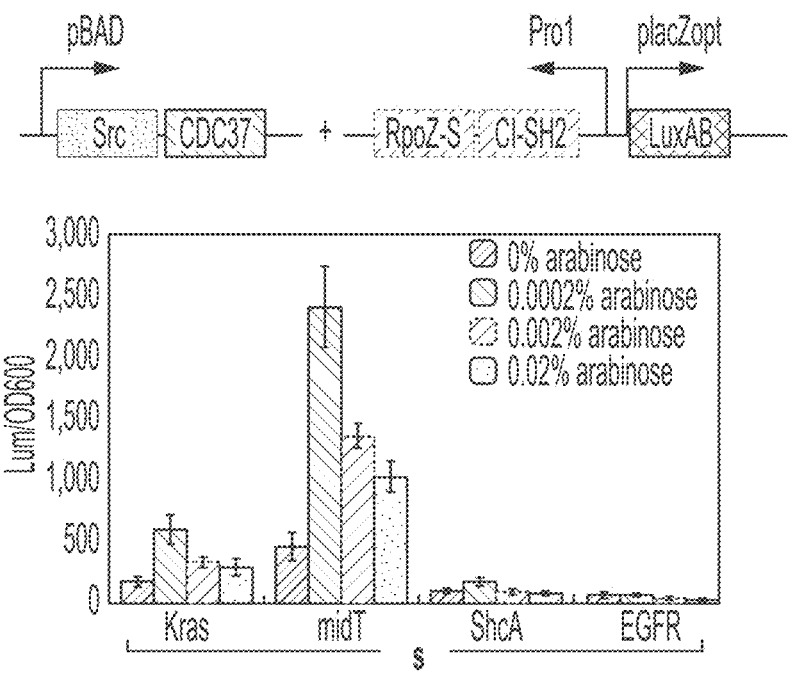
FIG. 30A-B illustrates Optimization of operon.
Figure 30B:
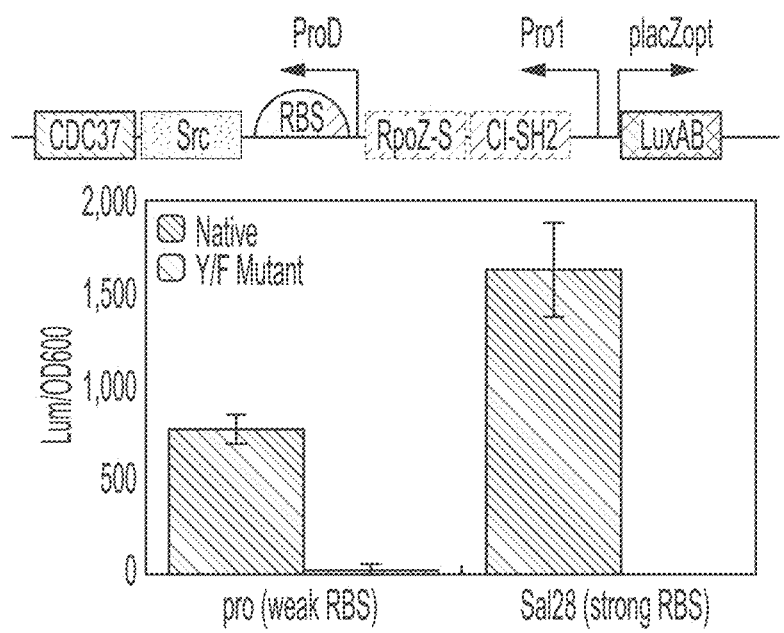
Figure 31A:
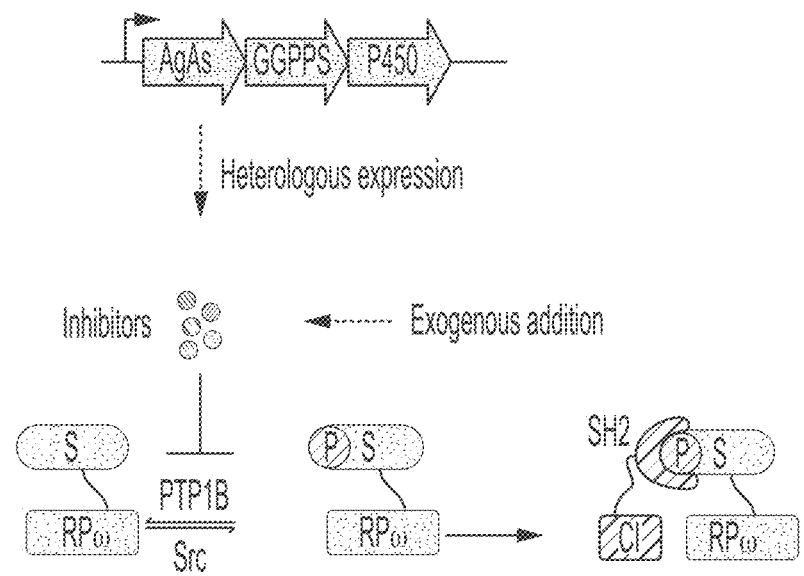
FIG. 31A-D illustrates Applications of operons.
Figure 31B:
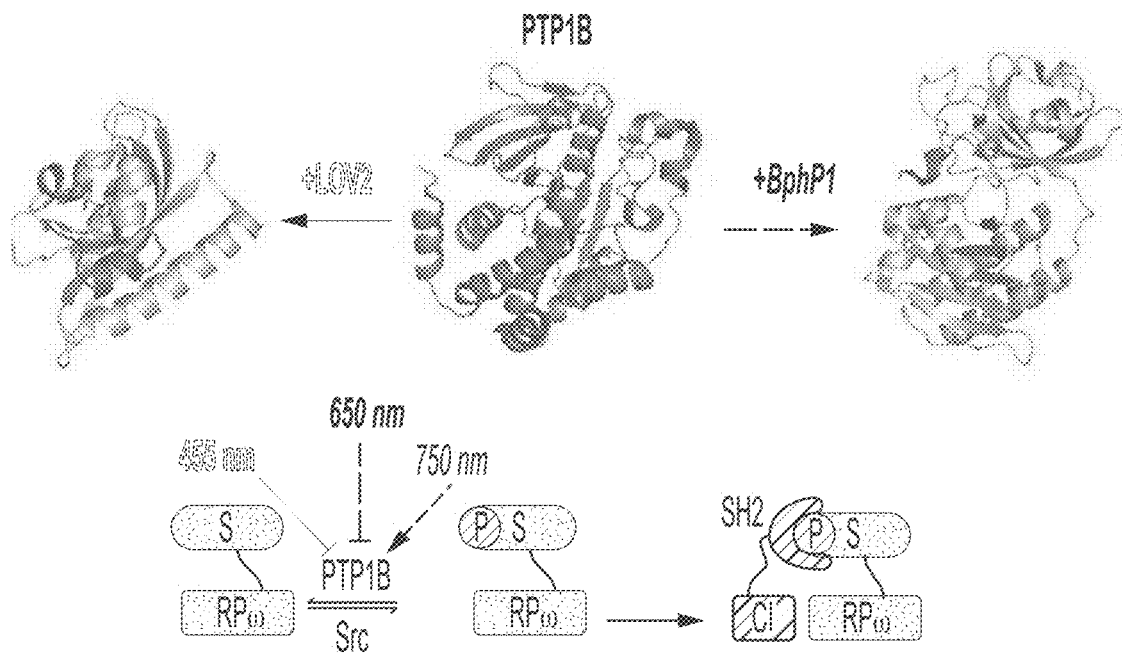
Figure 31C:
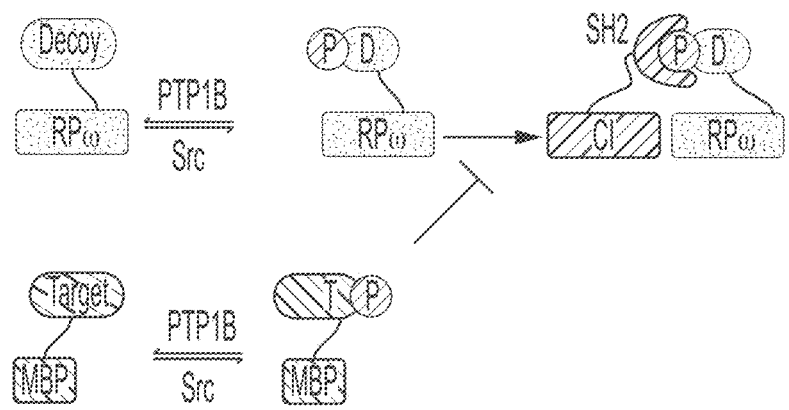
Figure 31D:
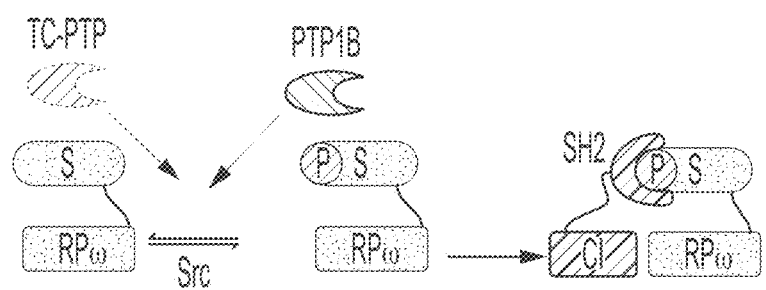
Figure 32A:
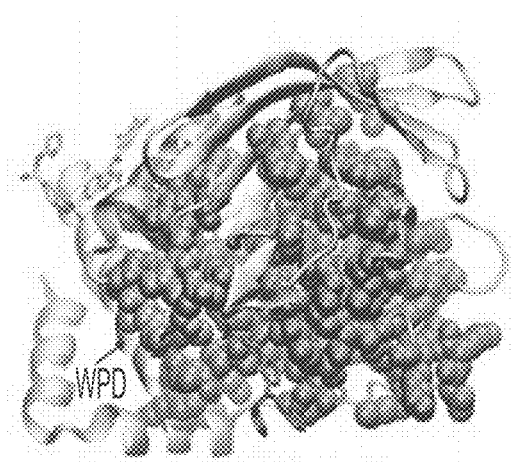
FIG. 32A-B presents exemplary evidence of an evolutionarily conserved allosteric network.
Figure 32B:
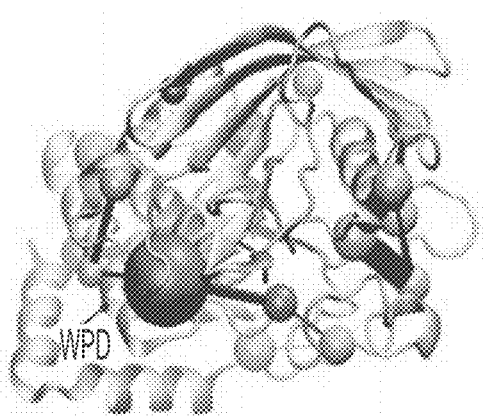

FRET sensors. Forster resonance energy transfer (FRET) is contemplated for use to monitor the activity of PTP1B in living cells. Sensor exhibits a 20% reduction in FRET signal when treated with Src kinase (FIG. 21B). Previous imaging studies indicate that a 20% change in FRET is sufficient to monitor intracellular kinase activity[54-56]. To enhance spatial resolution in imaging studies, we will attempt to optimize our sensor further (and use it to measure the activity of PTP1B in vitro).

Exemplary FRET sensors: underlined <u>mClover3</u>-SH2-Linker-Bold Substrate—underlined and Bold <u>mRuby3</u>.

mClover3-mRuby3: DNA sequence: SEQ ID NO: 20:
ATGCATCATCATCATCATCAT<u>GTGAGCAAGGGCGAGGAGCTGTTCACCGGGGTGG</u>

<u>TGCCCATCCTGGTCGAGCTGGACGGCGACGTAAACGGCCACAAGTTCAGCGTCCGC</u>

<u>GGCGAGGGCGAGGGCGATGCCACCAACGGCAAGCTGACCCTGAAGTTCATCTGCAC</u>

<u>CACCGGCAAGCTGCCCGTGCCCTGGCCCACCCTCGTGACCACCTTCGGCTACGGCGT</u>

<u>GGCCTGCTTCAGCCGCTACCCCGACCACATGAAGCAGCACGACTTCTTCAAGTCCGC</u>

<u>CATGCCCGAAGGCTACGTCCAGGAGCGCACCATCTCTTTCAAGGACGACGGTACCT</u>

<u>ACAAGACCCGCGCCGAGGTGAAGTTCGAGGGCGACACCCTGGTGAACCGCATCGAG</u>

<u>CTGAAGGGCATCGACTTCAAGGAGGACGGCAACATCCTGGGGCACAAGCTGGAGTA</u>

<u>CAACTTCAACAGCCACTACGTCTATATCACGGCCGACAAGCAGAAGAACTGCATCA</u>

<u>AGGCTAACTTCAAGATCCGCCACAACGTTGAGGACGGCAGCGTGCAGCTCGCCGAC</u>

<u>CACTACCAGCAGAACACCCCCATCGGCGACGGCCCCGTGCTGCTGCCCGACAACCA</u>

<u>CTACCTGAGCCATCAGTCCAAGCTGAGCAAGGACCCCAACGAGAAGCGCGATCACA</u>

<u>TGGTCCTGCTGGAGTTCGTGACCGCCGCCGGGATTACACATGGCATGGACGAGCTGT</u>

<u>ACAAGTGGTATTTTGGGAAGATCACTCGTCGGGAGTCCGAGCGGCTGCTGCTCAACC</u>

<u>CCGAAAACCCCCGGGGAACCTTCTTGGTCCGGGAGAGCGAGACGACAAAAGGTGCC</u>

<u>TATTGCCTCTCCGTTTCTGACTTTGACAACGCCAAGGGGCTCAATGTGAAGCACTAC</u>

<u>AAGATCCGCAAGCTGGACAGCGGCGGCTTCTACATCACCTCACGCACACAGTTCAG</u>

<u>CAGCCTGCAGCAGCTGGTGGCCTACTACTCCAAACATGCTGATGGCTTGTGCCACCG</u>

<u>CCTGACTAACGTCTGTGGGTCTACATCTGGATCTGGGAAGCCGGGTTCTGGTGAGGG</u>

<u>TTCT</u>TGGATGGAGGACTATGACTACGTCCACCTACAGGGGGAGCTC<u>GTGTCTAA</u>

<u>GGGCGAAGAGCTGATCAAGGAAAATATGCGTATGAAGGTGGTCATGGAAGGTT</u>

<u>CGGTCAACGGCCACCAATTCAAATGCACAGGTGAAGGAGAAGGCAGACCGTAC</u>

<u>GAGGGAACTCAAACCATGAGGATCAAAGTCATCGAGGGAGGACCCCTGCCATT</u>

<u>TGCCTTTGACATTCTTGCCACGTCGTTCATGTATGGCAGCCGTACTTTTATCAA</u>

<u>GTACCCGGCCGACATCCCTGATTTCTTTAAACAGTCCTTTCCTGAGGGTTTTAC</u>

<u>TTGGGAAAGAGTTACGAGATACGAAGATGGTGGAGTCGTCACCGTCACGCAGG</u>

<u>ACACCAGCCTTGAGGATGGCGAGCTCGTCTACAACGTCAAGGTCAGAGGGGTA</u>

<u>AACTTTCCCTCCAATGGTCCCGTGATGCAGAAGAAGACCAAGGGTTGGGAGCC</u>

<u>TAATACAGAGATGATGTATCCAGCAGATGGTGGTCTGAGAGGATACACTGACA</u>

<u>TCGCACTGAAAGTTGATGGTGGTGGCCATCTGCACTGCAACTTCGTGACAACTT</u>

<u>ACAGGTCAAAAAAGACCGTCGGGAACATCAAGATGCCCGGTGTCCATGCCGTT</u>

<u>GATCACCGCCTGGAAAGGATCGAGGAGAGTGACAATGAAACCTACGTAGTGCA</u>

ACGCGAAGTGGCAGTTGCCAAATACAGCAACCTTGGTGGTGGCATGGACGAGC

TGTACAAGTAA

Protein sequence: SEQ ID NO: 21:
MHHHHHHVSKGEELFTGVVPILVELDGDVNGHKFSVRGEGEGDATNGKLTLKFICTTG

KLPVPWPTLVTTFGYGVACFSRYPDHMKQHDFFKSAMPEGYVQERTISFKDDGTYKTR

AEVKFEGDTLVNRIELKGIDFKEDGNILGHKLEYNFNSHYVYITADKQKNCIKANFKIRH

NVEDGSVQLADHYQQNTPIGDGPVLLPDNHYLSHQSKLSKDPNEKRDHMVLLEFVTAA

GITHGMDELYKWYFGKITRRESERLLLNPENPRGTFLVRESETTKGAYCLSVSDFDNAK

GLNVKHYKIRKLDSGGFYITSRTQFSSLQQLVAYYSKHADGLCHRLTNVCGSTSGSGKP

GSGEGSWMEDYDYVHLQGELVSKGEELIKENMRMKVVMEGSVNGHQFKCTGEGE

GRPYEGTQTMRIKVIEGGPLPFAFDILATSFMYGSRTFIKYPADIPDFFKQSFPEGFT

WERVTRYEDGGVVTVTQDTSLEDGELVYNVKVRGVNFPSNGPVMQKKTKGWEP

NTEMMYPADGGLRGYTDIALKVDGGGHLHCNFVTTYRSKKTVGNIKMPGVHAVD

HRLERIEESDNETYVVQREVAVAKYSNLGGGMDELYK

Exemplary Mammalian expression vector(s) for expressing a photoswitch construct in a mammalian cell.
For insertion into a mammalian expression vector, e.g. lentiviral vector, pAcGFP1-C1 (Clontech); PTP1B-LOV2 (above), a promoter, e.g. CMV: GCAAATGGGCGGTAGGCGTGTACGGTGGGAGGTC-TATATAAGCAGAGCTGGTTTAG TGAACCGTCA-GATC (SEQ ID NO: 22); a RBS, e.g. Kozak consensus translation initiation site: GCCACCATG; an Intergenic spacer (e.g. P2A: DNA sequence: GGCAGCGGCGCCAC-CAACTTCTCCCTGCTGAAGCAGGCCGGCGACGTG-GAGGAGAA CCCCGGCCCC (SEQ ID NO: 23); a protein sequence: GSGATNFSLLKQAGDVEENPGP (SEQ ID NO: 24), etc.
An exemplary FRET Sensor included: a Promoter: Same as above; a RBS: Same as above, etc.

Exemplary FRET sensors are contemplated to avoid overlap between the excitation/emission wavelengths of LOV2 (455/495, we note that LOV2 is only weakly fluorescent[70]) and our FRET pair (505/515 for Clover and 560/605 for mRuby2), while we still expect to see some crosstalk during imaging, previous three-color imaging studies[71] suggest that it will not interfere with our ability to carry out the experiments described in this section.

Contemplative Embodiments Include but at not Limited to Invadopodia Formation and EGFR Regulation.

A photoswitchable variant of PTP1B is contemplated to determine if cytosolic PTP1B, released from the ER by proteolysis, is exclusively responsible for regulating the formation of invadopodia, or if ER-bound PTP1B can function similarly. Cancer cell invasion and metastasis is facilitated by the formation of invadopodia, actin-rich protrusions that enable matrix degradation[45].

Both PTP1B and PTK6 regulate epidermal growth factor receptor (EGFR), a regulator of cell proliferation and migration that exhibits aberrant activity in numerous cancers and inflammatory diseases[51,76]. We will use a variant of PTP1B stimulated by red light and a variant of PTK6 stimulated by blue light (or vice versa) to carry out a combinatorial analysis of the cooperative contribution of PTP1B and PTK6 to EGFR regulation within different regions of the cell.

REFERENCES FOR SECTIONS I, II, AND V ARE LISTED BELOW AND HEREIN INCORPORATED BY REFERENCE

1. Wray, J., Kalkan, T., Gomez-Lopez, S., Eckardt, D., Cook, A., Kemler, R. & Smith, A. Inhibition of glycogen synthase kinase-3 alleviates Tcf3 repression of the pluripotency network and increases embryonic stem cell resistance to differentiation. Nat. Cell Biol. 13, 838-45 (2011).
2. Wu, Y. I., Frey, D., Lungu, O. I., Jaehrig, A., Schlichting, I., Kuhlman, B. & Hahn, K. M. A genetically encoded photoactivatable Rac controls the motility of living cells. Nature 461, 104-108 (2009).
3. Liu, H., Wu, Y., Zhu, S., Liang, W., Wang, Z., Wang, Y., Lv, T., Yao, Y., Yuan, D. & Song, Y. PTP1B promotes cell proliferation and metastasis through activating src and ERK1/2 in non-small cell lung cancer. Cancer Lett. 359, 218-225 (2015).
4. Danial, N. N. & Korsmeyer, S. J. Cell Death: Critical Control Points. Cell 116, 205-219 (2004).
5. Johnson, T. O., Ermolieff, J. & Jirousek, M. R. Protein tyrosine phosphatase 1B inhibitors for diabetes. Nat. Rev. Drug Discov. 1, 696-709 (2002).
6. Koren, S. & Fantus, I. G. Inhibition of the protein tyrosine phosphatase PTP1B: potential therapy for obesity, insulin resistance and type-2 diabetes mellitus. Best Pract. Res. Clin. Endocrinol. Metab. 21, 621-640 (2007).
7. Pike, K. a, Hutchins, A. P., Vinette, V., Theberge, J.-F., Sabbagh, L., Tremblay, M. L. & Miranda-Saavedra, D. Protein tyrosine phosphatase 1B is a regulator of the interleukin-10-induced transcriptional program in macrophages. Sci. Signal. 7, ra43 (2014).
8. Rhee, I. & Veillette, a. Protein tyrosine phosphatases in lymphocyte activation and autoimmunity. Nat. Immunol. 13, 439-447 (2012).
9. Zhu, S., Bjorge, J. D. & Fujita, D. J. PTP1B contributes to the oncogenic properties of colon cancer cells through Src activation. Cancer Res. 67, 10129-10137 (2007).
10. Volinsky, N. & Kholodenko, B. N. Complexity of receptor tyrosine kinase signal processing. Cold Spring Harb. Perspect. Biol. 5, (2013).

11. Kennedy, M. B. Signal-Processing Machines at the Postsynaptic Density. Science. 290, 750-754 (2000).
12. Lee, H. K., Takamiya, K., Han, J. S., Man, H., Kim, C. H., Rumbaugh, G., Yu, S., Ding, L., He, C, Petralia, R. S., Wenthold, R. J., Gallagher, M. & Huganir, R. L. Phosphorylation of the AMPA receptor GluR1 subunit is required for synaptic plasticity and retention of spatial memory. Cell 112, 631-643 (2003).
13. Bence, K. K., Delibegovic, M., Xue, B., Gorgun, C. Z., Hotamisligil, G. S., Neel, B. G. & Kahn, B. B. Neuronal PTP1B regulates body weight, adiposity and leptin action. Nat. Med. 12, 917-24 (2006).
14. Wu, P., Nielsen, T. E. & Clausen, M. H. FDA-approved small-molecule kinase inhibitors. Trends Pharmacol. Sci. 36, 422-439 (2015).
15. Repina, N. A., Rosenbloom, A., Mukherjee, A., Schaffer, D. V. & Kane, R. S. At Light Speed: Advances in Optogenetic Systems for Regulating Cell Signaling and Behavior. Annu. Rev. Chem. Biomol. Eng. 8, 13-39 (2017).
16. Gautier, A., Gauron, C, Volovitch, M., Bensimon, D., Jullien, L. & Vriz, S. How to control proteins with light in living systems. Nat. Chem. Biol. 10, 533-41 (2014).
17. Krauss, U., Lee, J., Benkovic, S. J. & Jaeger, K. E. LOVely enzymes—Towards engineering light-controllable biocatalysts. Microb. Biotechnol. 3, 15-23 (2010).
18. Dagliyan, O., Tarnawski, M., Chu, P.-H., Shirvanyants, D., Schlichting, I., Dokholyan, N. V. & Hahn, K. M. Engineering extrinsic disorder to control protein activity in living cells. Science. 354, 1441-1444 (2016).
19. Zhou, X. X., Fan, L. Z., Li, P., Shen, K. & Lin, M. Z. Optical control of cell signaling by single-chain photoswitchable kinases. Science. 355, 836-842 (2017).
20. Lukyanov, K. a, Chudakov, D. M., Lukyanov, S. & Verkhusha, V. V. Photoactivatable fluorescent proteins. Nat. Rev. Mol. Cell Biol. 6, 885-890 (2005).
21. Rodriguez, E. A., Campbell, R. E., Lin, J. Y., Lin, M. Z., Miyawaki, A., Palmer, A. E., Shu, X., Zhang, J. & Tsien, R. Y. The Growing and Glowing Toolbox of Fluorescent and Photoactive Proteins. Trends Biochem. Sci. 42, 111-129 (2017).
22. Lessard, L., Stuible, M. & Tremblay, M. L. The two faces of PTP1B in cancer. Biochim. Biophys. Acta-Proteins Proteomics 1804, 613-619 (2010).
23. Barr, A. J., Ugochukwu, E., Lee, W. H., King, O. N. F., Filippakopoulos, P., Alfano, I., Savitsky, P., Burgess-Brown, N. A., Mtiller, S. & Knapp, S. Large-Scale Structural Analysis of the Classical Human Protein Tyrosine Phosphatome. Cell 136, 352-363 (2009).
24. Hubbard, S. R. & Till, J. H. Protein tyrosine kinase structure and function. Annu. Rev. Biochem. 69, 373-398 (2000).
25. Zayner, J. P., Antoniou, C. & Sosnick, T. R. The amino-terminal helix modulates light-activated conformational changes in AsLOV2. J. Mol. Biol. 419, 61-74 (2012).
26. Peter, E., Dick, B. & Baeurle, S. A. Mechanism of signal transduction of the LOV2-Ja photosensor from *Avena sativa*. Nat. Commun. 1, 122 (2010).
27. Kaberniuk, A. A., Shemetov, A. A. & Verkhusha, V. V. A bacterial phytochrome-based optogenetic system controllable with near-infrared light. Nat. Methods 13, 1-15 (2016).
28. Auldridge, M. E. & Forest, K. T. Bacterial phytochromes: more than meets the light. Crit. Rev. Biochem. Mol. Biol. 46, 67-88 (2011).
29. Anderie, I., Schulz, I. & Schmid, A. Characterization of the C-terminal ER membrane anchor of PTP1B. Exp. Cell Res. 313, 3189-3197 (2007).
30. Tonks, N. K. & Muthuswamy, S. K. A Brake Becomes an Accelerator: PTP1B-A New Therapeutic Target for Breast Cancer. Cancer Cell 11, 214-216 (2007).
31. Krishnan, N. & Tonks, N. K. Anxious moments for the protein tyrosine phosphatase PTP1B. Trends Neurosci. 38, 462-465 (2015).
32. T raves, P. G., Pardo, V., Pimentel-Santillana, M., Gonzalez-Rodrfguez, A., Mojena, M., Rico, D., Montenegro, Y., Cales, C, Martfn-Sanz, P., Valverde, a M. & Bosca, L. Pivotal role of protein tyrosine phosphatase 1B (PTP1B) in the macrophage response to proinflammatory and anti-inflammatory challenge. Cell Death Dis. 5, e1125 (2014).
33. Matulka, K., Lin, H. H., Hrfbkova, H., Uwanogho, D., Dvorak, P. & Sun, Y. M. PTP1B is an effector of activin signaling and regulates neural specification of embryonic stem cells. Cell Stem Cell 13, 706-719 (2013).
34. Cortesio, C. L., Chan, K. T., Perrin, B. J., Burton, N. O., Zhang, S., Zhang, Z. Y. & Huttenlocher, A. Calpain 2 and PTP1B function in a novel pathway with Src to regulate invadopodia dynamics and breast cancer cell invasion. J. Cell Biol. 180, 957-971 (2008).
35. Wiesmann, C, Barr, K. J., Kung, J., Zhu, J., Erlanson, D. A., Shen, W., Fahr, B. J., Zhong, M., Taylor, L., Randal, M., McDowell, R. S. & Hansen, S. K. Allosteric inhibition of protein tyrosine phosphatase 1B. Nat. Struct. Mol. Biol. 11, 730-737 (2004).
36. Alonso, A., Sasin, J., Bottini, N., Friedberg, I., Friedberg, I., Osterman, A., Godzik, A., Hunter, T., Dixon, J. & Mustelin, T. Protein tyrosine phosphatases in the human genome. Cell 117, 699-711 (2004).
37. Haj, F. G., Verveer, P. J., Squire, A., Neel, B. G. & Bastiaens, P. I. H. Imaging sites of receptor dephosphorylation by PTP1B on the surface of the endoplasmic reticulum. Science 295, 1708-1711 (2002).
38. Romsicki, Y., Reece, M., Gauthier, J. Y., Asante-Appiah, E. & Kennedy, B. P. Protein Tyrosine Phosphatase-1B Dephosphorylation of the Insulin Receptor Occurs in a Perinuclear Endosome Compartment in Human Embryonic Kidney 293 Cells. J. Biol. Chem. 279, 12868-12875 (2004).
39. Haj, F. G., Sabet, O., Kinkhabwala, A., Wimmer-Kleikamp, S., Roukos, V., Han, H. M., Grabenbauer, M., Bierbaum, M., Antony, C, Neel, B. G. & Bastiaens, P. I. Regulation of signaling at regions of cell-cell contact by endoplasmic reticulum-bound protein-tyrosine phosphatase 1B. PLoS One 7, (2012).
40. Soysal, S., Obermann, E. C, Gao, F., Oertli, D., Gillanders, W. E., Viehl, C. T. & Muenst, S. PTP1B expression is an independent positive prognostic factor in human breast cancer. Breast Cancer Res. Treat. 137, 637-644 (2013).
41. Zhang, S. & Zhang, Z. Y. PTP1B as a drug target: recent developments in PTP1B inhibitor discovery. Drug Discov. Today 12, 373-381 (2007).
42. Wu, C, Zhang, L, Bourne, P. A., Reeder, J. E., Di Sant & apos; Agnese, P. A., Yao, J. L, Na, Y. & Huang, J. Protein tyrosine phosphatase PTP1B is involved in neuroendocrine differentiation of prostate cancer. Prostate 66, 1124-1135 (2006).
43. Lessard, L, DP, L, Deblois, G., Begin, L, Hardy, S., Mes-Masson, A., Saad, F., Trotman, L, Giguere, V. & Tremblay, M. PTP1B is an androgen receptor-regulated phosphatase that promotes the progression of prostate cancer. Cancer Res. 7 2, 1529-1537 (2012).

44. Dube, N., Bourdeau, A., Heinonen, K. M., Cheng, A., Loy, A. L. & Tremblay, M. L. Genetic ablation of protein tyrosine phosphatase 1B accelerates lymphomagenesis of p53-null mice through the regulation of B-cell development. Cancer Res. 65, 10088-10095 (2005).

45. Weaver, A. M. Invadopodia: Specialized cell structures for cancer invasion. Clin. Exp. Metastasis 23, 97-105 (2006).

46. Cui, Q., Ma, Y., Jaramillo, M., Bari, H., Awan, A., Yang, S., Zhang, S., Liu, L., Lu, M., O'Connor-McCourt, M., Purisima, E. O. & Wang, E. A map of human cancer signaling. Mol. Syst. Biol. 3, 152 (2007).

47. Repina, N. A., Rosenbloom, A., Mukherjee, A., Schaffer, D. V. & Kane, R. S. At Light Speed: Advances in Optogenetic Systems for Regulating Cell Signaling and Behavior. Annu. Rev. Chem. Biomol. Eng. 8, 13-39 (2017).

48. Lee, J., Natarajan, M., Nashine, V. C, Socolich, M., Vo, T., Russ, W. P., Benkovic, S. J. & Ranganathan, R. Surface sites for engineering allosteric control in proteins. Science 322, 438-442 (2008).

49. Qin, Z., Zhou, X., Pandey, N. R., Vecchiarelli, H. A., Stewart, C. A., Zhang, X., Lagace, D. C, Brunei, J. M., Beique, J. C, Stewart, A. F. R., Hill, M. N. & Chen, H. H. Chronic Stress Induces Anxiety via an Amygdalar Intracellular Cascade that Impairs Endocannabinoid Signaling. Neuron 85, 1319-1331 (2015).

50. Fan, G., Lin, G., Lucito, R. & Tonks, N. K. Protein-tyrosine phosphatase 1B antagonized signaling by insulin-like growth factor-1 receptor and kinase BRK/PTK6 in ovarian cancer cells. J. Biol. Chem. 288, 24923-34 (2013).

51. Eden, E. R., White, I. J., Tsapara, A. & Futter, C. E. Membrane contacts between endosomes and ER provide sites for PTP1B-epidermal growth factor receptor interaction. Nat. Cell Biol. 12, 267-72 (2010).

52. Arregui, C. O., Gonzalez, A., Burdisso, J. E. & Gonzalez Wusener, A. E. Protein tyrosine phosphatase PTP1B in cell adhesion and migration. Cell Adh. Migr. 7, 418-423 (2013).

53. Badran, A. H., Guzov, V. M., Huai, Q., Kemp, M. M., Vishwanath, P., Kain, W., Nance, A. M., Evdokimov, A., Moshiri, F., Turner, K. H., Wang, P., Malvar, T. & Liu, D. R. Continuous evolution of *Bacillus thuringiensis* toxins overcomes insect resistance. Nature 533, 58-63 (2016).

54. Sato, M. & Umezawa, Y. in Cell Biol. Four-Volume Set 2, 325-328 (2006).

55. Ouyang, M., Sun, J., Chien, S. & Wang, Y. Determination of hierarchical relationship of Src and Rac at subcellular locations with FRET biosensors. Proc Natl Acad Sci USA 105, 14353-14358 (2008).
56. Ting, a Y., Kain, K. H., Klemke, R. L. & Tsien, R. Y. Genetically encoded fluorescent reporters of protein tyrosine kinase activities in living cells. Proc. Natl. Acad. Sci. U.S.A 98, 15003-15008 (2001).
57. Wiesmann, C, Barr, K. J., Kung, J., Zhu, J., Erlanson, D. A., Shen, W., Fahr, B. J., Zhong, M., Taylor, L, Randal, M., McDowell, R. S. & Hansen, S. K. Allosteric inhibition of protein tyrosine phosphatase 1B. Nat. Struct. Mol. Biol. 11, 730-737 (2004).
58. Halavaty, A. S. & Moffat, K. N- and C-terminal flanking regions modulate light-induced signal transduction in the LOV2 domain of the blue light sensor phototropin 1 from *Avena sativa*. Biochemistry 46, 14001-14009 (2007).
59. Yao, X., Rosen, M. K. & Gardner, K. H. Estimation of the available free energy in a LOV2-Ja photoswitch. Nat. Chem. Biol. 4, 491-497 (2008).
60. Choy, M. S., Li, Y., Machado, L. E. S. F., Kunze, M. B. A., Connors, C. R., Wei, X., Lindorff-Larson, K., Page, R. & Peti, W. Conformational Rigidity and Protein Dynamics at Distinct Timescales Regulate PTP1B Activity and Allostery. Mol. Cell 65, 644-658 (2017).
61. Hubbard, S. R. & Till, J. H. Protein tyrosine kinase structure and function. Annu. Rev. Biochem. 69, 373-398 (2000).
62. Zhang, Y., Kurup, P., Xu, J., Carty, N., Fernandez, S. M., Nygaard, H. B., Pittenger, C, Greengard, P., Strittmatter, S. M., Nairn, A. C. & Lombroso, P. J. Genetic reduction of striatal-enriched tyrosine phosphatase (STEP) reverses cognitive and cellular deficits in an Alzheimer's disease mouse model. Proc. Natl. Acad. Sci. 107, 19014-19019 (2010).
63. He, R., Yu, Z., Zhang, R. & Zhang, Z. Protein tyrosine phosphatases as potential therapeutic targets. Acta Pharmacol. Sin. 35, 1227-1246 (2014).
64. Ito, K., Park, S. H., Nayak, A., Byerly, J. H. & Irie, H. Y. PTK6 inhibition suppresses metastases of triple-negative breast cancer via SNAIL-dependent E-cadherin regulation. Cancer Res. 76, 4406-4417 (2016).
65. Zegzouti, H., Zdanovskaia, M., Hsiao, K. & Goueli, S. A. ADP-Glo: A Bioluminescent and Homogeneous ADP Monitoring Assay for Kinases. Assay Drug Dev. Technol. 7, 560-572 (2009).
66. Strickland, D., Yao, X., Gawlak, G., Rosen, M. K., Gardner, K. H. & Sosnick, T. R. Rationally improving LOV domain-based photoswitches. Nat. Methods 7, 623-6 (2010).
67. Cosentino, C, Alberio, L., Gazzarrini, S., Aquila, M., Romano, E., Cermenati, S., Zuccolini, P., Petersen, J., Beltrame, M., Van Etten, J. L., Christie, J. M., Thiel, G. & Moroni, A. Engineering of a light-gated potassium channel. Science. 348, 707-710 (2015).
68. Krishnan, N., Koveal, D., Miller, D. H., Xue, B., Akshinthala, S. D., Kragelj, J., Jensen, M. R., Gauss, C.-M., Page, R., Blackledge, M., Muthuswamy, S. K., Peti, W. & Tonks, N. K. Targeting the disordered C terminus of PTP1B with an allosteric inhibitor. Nat. Chem. Biol. 10, 558-566 (2014).
69. Piserchio, A., Cowburn, D. & Ghose, R. Expression and purification of Src-family kinases for solution NMR studies. Methods Mol. Biol. 831, 111-131 (2012).
70. Van Stokkum, I. H. M., Gauden, M., Crosson, S., Van Grondelle, R., Moffat, K. & Kennis, J. T. M. The primary photophysics of the *Avena sativa* phototropin 1 LOV2 domain observed with time-resolved emission spectroscopy. Photochem. Photobiol. 87, 534-541 (2011).
71. Rowland, A. A., Chitwood, P. J., Phillips, M. J. & Voeltz, G. K. ER contact sites define the position and timing of endosome fission. Cell 159, 1027-1041 (2014).
72. Fehr, M., Lalonde, S., Lager, I., Wolff, M. W. & Frommer, W. B. In vivo imaging of the dynamics of glucose uptake in the cytosol of COS-7 cells by fluorescent nanosensors. J. Biol. Chem. 278, 19127-19133 (2003).
73. Feigner, P. L., Gadek, T. R., Holm, M., Roman, R., Chan, H. W., Wenz, M., Northrop, J. P., Ringold, G. M. & Danielsen, M. Lipofection: a highly efficient, lipid-mediated DNA-transfection procedure. Proc. Natl. Acad. Sci. U.S.A 84, 7413-7 (1987).
74. Gil-Parrado, S., Fernandez-Montalvan, A., Assfalg-Machleidt, I., Popp, O., Bestvater, F., Holloschi, A., Knoch, T. A., Auerswald, E. A., Welsh, K., Reed, J. C, Fritz, H., Fuentes-Prior, P., Spiess, E., Salvesen, G. S. & Machleidt, W. Ionomycin-activated calpain triggers apoptosis. A probable role for Bcl-2 family members. J. Biol. Chem. 277, 27217-27226 (2002).
75. Faeder, J. R., Blinov, M. L. & Hlavacek, W. S. Rule-based modeling of biochemical systems with BioNetGen. Methods Mol. Biol. 500, 113-167 (2009).
76. Tiganis, T., Bennett, A. M., Ravichandran, K. S. & Tonks, N. K. Epidermal growth factor receptor and the adaptor protein p52Shc are specific substrates of T-cell protein tyrosine phosphatase. Mol. Cell. Biol. 18, 1622-34 (1998).

III. Genetically Encoded System for Constructing and Detecting Biologically Active Agents: Microbial Inhibitor Screening Systems.

Several types of operons were developed as described herein, each for a specific purpose, including but not limited to testing small molecules for their ability to inhibit, activate, or otherwise modulate a chosen PTP and/or PTK; operons for testing intracellularly provided small molecules for inhibiting, activating, or modulating effects on a chosen PTP and/or PTK; and evolving one or more proteins or small molecules of interest. More specifically, genetic operons were contemplated for insertion, using transfection and breeding techniques well known in the art, for providing microbial cells wherein the activity of an enzyme of interest (e.g., protein tyrosine phosphatase 1B, a drug target for the treatment of diabetes, obesity, and cancer) is linked to (i) cellular luminescence, (ii) cellular fluorescence, or (iii) cellular growth. In some embodiments, such operons are modified for use in detecting and/or evolving biologically active metabolites. When modified and/or induced to build various metabolites, the cell will be used for detection of metabolites that inhibit/activate a protein of interest (e.g., PTP1B).

These operons allow operon-containing microbial cells to be used to carry out the following tasks: Detecting biologically active molecules and non-native biologically active metabolites. When grown in the presence of biologically active molecules as a small molecule that is both (i) cell permeable and (ii) capable of inhibiting a protein of interest (e.g., PTP1B), the cell will enable detection of that molecule. That is, it will exhibit a concentration-dependent response in luminescence, fluorescence, or growth. Many non-native biologically active metabolites have useful pharmaceutical properties. Examples include paclitaxel and artemisinin, plant-derived terpenoids that are used to treat cancer and malaria, respectively. When the metabolic pathways responsible for making such natural metabolites are installed into microbial cells that also contain our operon, those cells will enable detection of interesting metabolite-based biological activities (e.g., the ability to inhibit PTP1B).

Genetic operons that, when installed into microbial cells, link the activity of an enzyme of interest (e.g., protein tyrosine phosphatase 1B, a drug target for the treatment of diabetes, obesity, and cancer) to (i) cellular luminescence, (ii) cellular fluorescence, or (iii) cellular growth.

Detect and/or evolve biologically active metabolites. When modified and/or induced to build various metabolites, the cell will enable detection of metabolites that inhibit/activate a protein of interest (e.g., PTP1B).

These operons allow operon-containing microbial cells to be used to carry out the following tasks: Detecting biologically active molecules and non-native biologically active metabolites. When grown in the presence of a biologically active molecules as a small molecule that is both (i) cell permeable and (ii) capable of inhibiting a protein of interest (e.g., PTP1B), the cell will enable detection of that molecule. That is, it will exhibit a concentration-dependent response in luminescence, fluorescence, or growth. Many non-native biologically active metabolites have useful pharmaceutical properties. Examples include paclitaxel and artemisinin, plant-derived terpenoids that are used to treat cancer and malaria, respectively. When the metabolic pathways responsible for making such natural metabolites are installed into microbial cells that also contain our operon, those cells will enable detection of metabolite-based biological activities (e.g., the ability to inhibit PTP1B).

In some embodiments, methods of evolving molecules may be modified from Moses, et al., "Bioengineering of plant (tri)terpenoids: from metabolic engineering of plants to synthetic biology in vivo and in vitro." New Phytologist, Volume 200, Issue 1, where this reference describes synthesis of artemisinic acid, the precursor of the antimalarial drug artemisinin, as diterpenoids expressed in *E. coli*. Further, enzyme engineering or directed evolution of terpenoid biosynthetic enzymes, e.g. engineer enzymes to accept unnatural substrates and to catalyze regions and stereospecific reactions with an efficiency comparable with that of the natural enzymes is described, along with discussions on enhancing the production of terpenoids in *Escherichia coli*. In some embodiments, methods of evolving molecules may be modified from Badran, et al., "Continuous evolution of *Bacillus thuringiensis* toxins overcomes insect resistance". Nature, Vol 533:58, 2016, where this reference describes a phage-assisted continuous evolution selection that rapidly evolves high-affinity protein—protein interactions, and applied this system to evolve variants of the Bt toxin Cry1Ac that bind a cadherin-like receptor from the insect pest *Trichoplusia ni* (TnCAD) that is not natively bound by wild-type Cry1Ac.

A. Protein Evolving Systems and Evolving Biologically Active Metabolites.

In some embodiments, methods of evolving molecules may be used to construct drug leads that can be readily synthesized in microbial hosts. It addresses a longstanding challenge—the development of low-cost pharmaceuticals—by using a sophisticated set of biophysical tools and analytical methodologies to narrow the molecular search space in lead discovery, and by explicitly considering the biosynthetic accessibility of therapeutic molecules. The approach, which departs from contemporary efforts to use microbial systems for the synthesis of clinically approved drugs and their precursors, is unique in its focus on using biology for the systematic construction of new molecules. It will accelerate the rate—and lower the cost—of pharmaceutical development.

The development of a drug requires optimization of many of its pharmacological properties—affinity, absorption, distribution, metabolism, excretion, toxicology, pharmacokinetics, and pharmacodynamics[1]. The first of these properties—protein-ligand binding affinity—generally determines whether the others are worth measuring or enhancing, and, thus, represents a property of drug leads[2]. Despite advances in computational chemistry and structural biology, the rational design of ligands that bind tightly to proteins—ligands, henceforth, referred to collectively as inhibitors—remains exceptionally difficult[3]; as a result, the development of drugs often begins with screens of large libraries of molecules[4]. An inhibitor, once discovered, must be synthesized in quantities sufficient for subsequent analysis, optimization, formulation, and clinical evaluation.

The difficulties associated with developing protein inhibitors are particularly problematic for natural products. These molecules, which account for over 50% of clinically approved drugs, tend to have favorable pharmacological properties (e.g., membrane permeability)[5]. Unfortunately, their low natural titers—which hamper the extraction of testable quantities from natural sources—and their chemical complexity—which complicates chemical synthesis—make the preparation of quantities sufficient for post-screen analyses time-consuming and expensive[6].

In some embodiments, enzymes are contemplated for use to construct terpenoid inhibitors that can be synthesized in *Escherichia coli*; such an approach takes advantage of the chemical diversity (and generally favorable pharmacological properties) of natural products without the constraints of their natural scarcity. In some embodiments, detailed biophysical study of the molecular-level origin and thermodynamic basis of affinity and activity in protein-terpenoid interactions are included for the rapid construction of high-affinity inhibitors. In some embodiments, development of selective inhibitors of protein tyrosine phosphatase 1B (PTP1B), a target for the treatment of diabetes, obesity, and cancer is contemplated in part for using enzymes to evolve readily synthesizable drug leads.

Structurally Varied Terpenoids with Different Affinities for the Allosteric Binding Pocket of Protein Tyrosine Phosphatase 1B (PTP1B).

Hypothesis. Results indicate that abietic acid, a monocarboxylated variant of abietadiene, is an allosteric inhibitor of PTP1B. Derivatives or structural analogs of abietadiene that differ in stereochemistry, shape, size, and/or chemical functionality (including carboxylation position) are likely to have different affinities for the allosteric binding pocket of PTP1B.

In some embodiments, (i) mutants of abietadiene synthase, cytochrome P450s, and halogenases are contemplated for use to make structural variants of abietadiene, (ii) GC/MS to identify those variants, (iii) preparative HPLC and flash chromatography to isolate them, and (iii) isothermal titration calorimetry to determine their free energies, enthalpies, and entropies of binding. In some embodiments, a set of structurally varied inhibitors with (i) affinities that differ by 100-fold and/or (ii) enthalpies and entropies of binding that suggest alternative binding geometries is contemplated.

To Examine the Molecular Basis and Thermodynamic Origin of Affinity and Activity in Enzyme-Terpenoid Interactions.

Hypothesis. Enzymes that bind, functionalize, and/or synthesize terpenoids possess large nonpolar binding pockets. We hypothesize that both (i) the affinity of an enzyme for terpenoids and (ii) the activity of an enzyme ON terpenoids is determined by the general shape and hydration structure of its binding pocket, not the position of specific protein-terpenoid contacts.

In some embodiments, a sophisticated set of biophysical tools (isothermal titration calorimetry, X-ray crystallography, molecular dynamics (MD) simulations, and NMR spectroscopy) are contemplated for use to (i) determine how protein-ligand contacts, rearrangements of water, and conformational constraints contribute to differences in affinity between terpenoid inhibitors and to (ii) develop a set of empirical relationships that predict how mutations in terpene synthases and terpene-functionalizing enzymes influence general attributes (e.g., shape) of their products.

To Evolve High-Affinity Terpenoid Inhibitors of PTP1B.

Hypothesis. Mutants from secondary metabolism (e.g., terpene synthases, cytochrome P450s, and halogenases) are highly promiscuous; a single mutation in or near their active sites can dramatically alter their product profiles. Mutagenesis of a small number (i.e., 2-4) of such enzymes, selected for their ability to synthesize and/or functionalize diterpenoids, will enable the development of inhibitors of PTP1B with sub-micromolar affinities.

In some embodiments, high-affinity inhibitors of PTP1B by pairing (i) high-throughput methods for detecting inhibitors with (ii) site-saturation and random mutagenesis is contemplated. For (i) we will develop four alternative fluorescence or growth-coupled assays to screen libraries of mutated pathways (and their respective products). For (ii) we use biostructural analyses and sequence alignments to identify residues likely to yield enzymes with favorable product profiles.

To Identify Structure-Activity Relationships that Enable the Evolution of Terpenoid Inhibitors of Arbitrary Protein Targets.

Hypothesis. Proteins that interact with similar classes of molecules (through binding or catalysis) have structurally similar binding pockets. Methods for evaluating these structural similarities—and their implications for enzyme activity—may enable the identification of enzymes capable of synthesizing inhibitors of ANY specified protein.

In some embodiments, a biophysical framework for using the crystal structure of a protein as a starting point to identify enzymes capable of synthesizing inhibitors of that protein is contemplated. We will examine (and formalize) structural relationships between (i) the active sites of enzymes used to synthesize allosteric inhibitors of PTP1B and (ii) the allosteric binding pocket of PTP1B, and we will validate these relationships by using them to identify—and, then, test—new enzymes capable of synthesizing inhibitors of PTP1B and (separately) undecaprenyl diphosphate synthase, a target for the treatment of antibiotic-resistant bacterial infections.

Diabetes, Obesity, and Cancer.

Protein tyrosine phosphatase 1B (PTP1B) contributes to insulin resistance in type 2 diabetes[7], leptin resistance in obesity[8], and tumor growth in breast, colorectal, and lung cancers[9,11]. To date, the development of selective, tight-binding inhibitors of PTP1B (i.e., treatments for diabetes, obesity, and cancer) has been hindered by the structure of its active site, where polar residues limit tight binding to charged, membrane-impermeable molecules, and where structural similarities to the active sites of other protein tyrosine phosphatases (PTPs) lead to off-target interactions[12,14]. In this proposal, we will construct selective inhibitors of PTP1B that bind to its C-terminal allosteric site, a largely nonpolar region that is not conserved across phosphatases[15]. Previous screens of large molecular libraries have identified several ligands that bind to this site, but have yet to yield clinically approved drugs[16,13]. The identification of new molecular alternatives—a feat tackled in this proposal—remains a goal in efforts to develop selective PTP1B-inhibiting therapeutics.

Development of pharmaceuticals. The development of enzyme inhibitors—or leads-represents an expensive part of drug development; for each successful drug, lead identification and optimization takes an average of 3 years and $250M to complete (~20-30% of the total time and cost to bring a drug to market)[17]. By narrowing the molecular search space in lead discovery, by enabling rapid construction of structurally-varied leads (often referred to as "back-ups"[18]), and by facilitating scale-up of molecular synthesis, the technology developed in this proposal could accelerate the rate—and lower the cost—of pharmaceutical development.

Molecular recognition. The hydrophobic effect—the free energetically favorable association of nonpolar species in aqueous solution—is, on average, responsible for ~75% of the free energy of protein-ligand association[19]. Unfortunately, hydrophobic interactions between ligands and proteins—which differ dramatically in rigidity, topography, chemical functionality, and hydration structure—remain difficult to predict[20]. This study uses detailed biophysical analyses and explicit-water calculations to examine the thermodynamic basis of hydrophobic interactions between terpenoids and protein binding pockets. It will develop a model system and corresponding conceptual framework—for studying the hydrophobic effect in the context of structurally varied protein-ligand complexes, for accounting for that effect in the design of biosynthetic pathways, and for exploiting it in the construction of new drug leads.

Biosynthesis of New Natural Products.

Synthetic biology offers a promising route to the discovery and production of natural products. When the metabolic machinery of one organism is installed into a genetically tractable production host (e.g., *S. cerevisiae* or *E. coli*), it enables the synthesis of complex compounds at high titers (relative to the native host). This approach has enabled the efficient production of pharmaceutically relevant metabolites from unculturable or low-yielding organisms[21,22], but, unfortunately, requires large investments of time and resources in pathway discovery and optimization; its use, as a result, is generally limited to the low-throughput characterization of newly discovered gene clusters or to the production of known, pharmaceutically relevant molecules (e.g., paclitaxel, artemisinin, or opioids)[22,24].

In some embodiments, a strategy for using synthetic biology to build new molecular function is contemplated. It begins with a pathologically relevant protein target and engineers pathway enzymes to produce molecules that selectively inhibit that target. This approach will yield molecules that can be produced in microbial hosts without extensive pathway optimization (it relies on enzymes that are expressible by default); it will, thus, expand the use of synthetic biology to the production of leads and backups. It is not a replacement for conventional approaches to the synthesis of complex natural products, but rather, a complementary strategy for constructing new compounds that will enhance the efficiency with which pharmaceuticals are developed.

In the presence of mutated metabolic pathways (e.g., version of a plant-based terpenoid-producing pathway in which the terpene synthase has been mutated), our operon will enable screens of large numbers of metabolites for their ability to inhibit our protein of interest (e.g., PTP1B). Such a platform could be used to evolve metabolites with specific biological activities.

Detect and/or evolve highly selective molecules. We have developed an idea for a version of our operon to detect molecules that inhibit one protein over a highly similar protein. Screens for molecular selectivity are, at present, remain very difficult.

Advantages of methods and systems described herein, over some other systems for detecting small molecule inhibitors includes but is not limited to enabling the detection of molecules that modulate or change the catalytic activity of an enzyme. Moreover, some embodiments of the systems described herein allow for the detection of test molecules that change the activity of an enzyme by binding anywhere on its surface. As one example, detection of an inhibitor is contemplated that inactivates PTP1B by binding to its C-terminal allosteric site; this binding event, which distorts catalytically essential motions of the WPD loop, would not necessarily prevent enzyme-substrate association. U.S. Pat. No. 6,428,951, herein incorporated by reference in its entirety, in contrast, enables the detection of molecules that prevent enzyme-substrate binding by competing for substrate binding sites (i.e., the active site). As another example, detection of molecules that activate an enzyme of interest is contemplated as an embodiment. U.S. Pat. No. 6,428,951, herein incorporated by reference in its entirety, in contrast, has methods that merely detect molecules that prevent enzymes from binding to their substrates, or that otherwise change the affinity of enzymes for their substrates. As another example, detection of molecules that do not require an enzyme and substrate to interact with any particular affinity, orientation, or half-life is contemplated as an embodiment. U.S. Pat. No. 6,428,951, herein incorporated by reference in its entirety, in contrast, requires an enzyme and substrate to bind one another with an affinity and orientation that enable assembly of a split reporter. As a result, it may require modifications to the enzyme; in contrast, the inventors use a "substrate trapping" mutant of PTP1B to improve its affinity for a substrate domain.

As another example, some embodiments enables the detection of inhibitors of wild-type enzymes. Tu S., U.S. Pat. No. 6,428,951, herein incorporated by reference in its entirety, in contrast, requires enzymes to be fused to one-half of a split reporter.

Further, the following two publications are examples of methods that for detecting molecules that merely disrupt the binding of an enzyme to a substrate. This characteristic, among others, is in contrast to U.S. Pat. No. 6,428,951. "Protein fragment complementation assays for the detection of biological or drug interactions." Pub. Date: Jan. 31, 2008, herein incorporated by reference in its entirety, which describes a high throughput bacteria based protein-fragment complementation assays (PCAs) wherein when two protein fragments derived from the enzyme dihydrofolate reductase (DHFR), coexpressed as fusion molecules in *Escherichia coli*, that interact in the absence of an inhibitor, then concentration dependent colony growth was observed. This reference states that PCA can be adapted to detecting interactions of proteins small molecules and provide examples, including complementary fragment fusions and a bait-fused fragment. In fact, protein tyrosine phosphatase PTP1B was provided in an example for detecting enzyme substrate interactions and an example of survival assay for detecting protein substrate interactions using aminoglycoside kinase (AK), an example of antibiotic resistance marker used for dominant selection of an *E. coli*,-based PCA. Further, a PCA is described as being applied to identify small molecule inhibitors of enzymes; natural products or small molecules from compound libraries of potential therapeutic value; may be used as survival assay for library screening; for detecting endogenous DHFR inhibitors, e.g. rapamycin; and for protein-drug interactions. Expression of PCA complementary fragments and fused cDNA libraries/target genes can be assembled on single plasmids as individual operons under the control of separate inducible or constitutive promoters with interceding region sequences, e.g. derived from a mel operon, or have polycistronic expression. The PCA can be adapted to detecting interactions of proteins with small molecules. In this conception, two proteins are fused to PCA complementary fragments, but the two proteins do not interact with each other. The interaction must be triggered by a third entity, which can be any molecule that will simultaneously bind to the two proteins or induce an interaction between the two proteins by causing a conformational change in one or both of the partners. Moreover, exemplary applications of the PCA Strategy in bacteria to protein engineering/evolution to generate peptides or proteins with novel binding properties that may have therapeutic value using phage display technology. One example of evolution produced novel zipper sequences; other examples of evolutions were described to produce endogenous toxins.

WO2004048549. Dep-1 Receptor Protein Tyrosine Phosphatase Interacting Proteins And Related Methods. Published Jun. 10, 2004, herein incorporated by reference in its entirety; describes screening assays for inhibitors that alter the interaction between a PTP and a tyrosine phosphorylated protein that is a substrate of the PTP, e.g. dephosphorylation by Density Enhanced Phosphatase-1 (DEP-1) of a DEP-1 substrate. DEP-1 polypeptides can be expressed in bacteria cells, including E. coli, under the control of appropriate promoters, e.g. E. coli arabinose operon ($P_{BAD}$ or $P_{ARA}$). This reference is similarly limited in focus as U.S. Pat. No. 6,428,951, herein incorporated by reference in its entirety; it enables the detection of molecules that disrupt the binding of a substrate to an enzyme, rather than the detection of molecules that modulate (i.e., enhance or reduce) the activity of an enzyme.

Advantages of methods and systems described herein, over some other systems for detecting small molecule inhibitors includes but is not limited to enabling the evolution of metabolites that change the catalytic activity of an enzyme. The technology described in Badran, et al., "Continuous evolution of *Bacillus thuringiensis* toxins overcomes insect resistance". Nature, Vol 533:58, 2016, herein incorporated by reference in its entirety; and the platform of continuous evolution in general, has been used to evolve proteins with different affinities for other proteins/peptide substrates. It has not, however, been used to evolve enzymes that produce small molecules (i.e., metabolites) that alter the activities of enzymes or the strength of protein-protein interactions.

Another advantage of methods and systems described herein, over some other systems for detecting small molecule inhibitors includes the discovery of metabolites with targeted biological activities but unknown structures (e.g., the ability to inhibit protein tyrosine phosphatase 1B). There are many inventions relevant to the production of terpenoids in *E. coli* or *S. cerevisiae* (e.g., Moses, et al., "Bioengineering of plant (tri)terpenoids: from metabolic engineering of plants to synthetic biology in vivo and in vitro." New Phytologist, Volume 200, Issue 1, where this reference describes synthesis of artemisinic acid, the precursor of the antimalarial drug artemisinin, as diterpenoids expressed in *E. coli*. Further, enzyme engineering or directed evolution of terpenoid biosynthetic enzymes, e.g. engineer enzymes to accept unnatural substrates and to catalyze regions and stereospecific reactions with an efficiency comparable with that of the natural enzymes is described, along with discussions on enhancing the production of terpenoids in *Escherichia coli*.); in many cases, the metabolic pathways responsible for making these terpenoids are mutated to improve production levels. However, the use of biosensors (i.e., constructs that report on the concentrations of various metabolites) has focused on the detection of specific intermediates (e.g., farnesyl pyrophosphate, a precursor to terpenoids) not for combining (i) mutagenesis of a metabolic pathway and (ii) a biosensor for specific biological activity (e.g., the ability to inhibit PTP1B) for the discovery of new biologically active molecules (which may possess unknown structures).

High-Throughput Metabolic Engineering.

Microbial pathways are most efficiently optimized with high-throughput screens. Unfortunately, at present, such screens are sparse, and those available rely on signals (e.g., absorbance or fluorescence, association with a product-specific transcription factor, or growth permitted by an essential metabolite) that are difficult to extend to broad classes of molecules (e.g., those without distinct optical or metabolic properties)[27]. The proposed work develops high-throughput screens for terpenoids with a targeted activity—the ability to inhibit PTP1B—rather than a targeted structure; these activity-focused screens could be broadly useful for building (i.e., evolving) new biologically active small molecules.

Identification of new inhibitors: a starting point. We recently discovered that abietic acid, the primary component of resin acid, is an allosteric inhibitor of PTP1B (FIG. 22). We will use abietadiene, the immediate precursor of this molecule, as a starting point for the design of inhibitors. Abietadiene has several attributes that make it particularly compatible with our approach: (i) It can be synthesized in *E. coli* at titers (200 mg/L) that permit purification, NMR analysis, and calorimetric studies[28], (ii) Mutants of its associated terpene synthase—abietadiene synthase—yield a range of hydrocarbon scaffolds that differ in stereochemistry, shape, and size (and that still enable analysis and purification)[29-31], (iii) It—and similar molecules—can be functionalized by cytochrome P450s and halogenases[32-34].

Metabolic engineering. We have engineered a strain of *E. coli* to produce abietadiene at titers (>150 mg/L) sufficient to permit the analytical methods (i.e., GC/MS, ITC, and NMR). Our biosynthetic pathway has two requisite operons: MBIS, which converts (RJ-mevalonate to farnesyl pyrophosphate (FPP), and TS, which converts farnesyl pyrophosphate to abietadiene. One optional operon—MevT, which converts acetyl-CoA to (RJ-mevalonate—is necessary when mevalonate is not included in the media[35]. The plasmids pMevT and pMBIS were developed by the Keasling Laboratory[36]. The plasmid pTS, which contains abietadiene synthase (ABS) from *Abies grandis*, was developed as in Morrone[28] with a gene for geranylgeranyl diphosphate synthase from Ajikumar[37].

Improved inhibitors. We assessed the ability of minor structural perturbations of abietadiene derivatives to yield improved inhibitors by comparing four structurally related (and commercially available) molecules (FIG. 16): abietic, neoabietic, levopimaric, and dihydroabietic acid. Surprisingly, dihydroabietic acid was ten times more inhibitory than abietic acid (K, ~25 uM vs. 250 uM). Our ability to find an improved inhibitor in this small screen suggests that the kinds of structural variations explored in this study—and the sizes of molecular libraries generated—are likely yield improved inhibitors.

Functionalization of abietadiene. We assessed the ability of mutants of cytochrome $P450_{b}m3$ to functionalize abietadiene-like molecules by installing five readily available mutants (G3, KSA-4, 9-1 OA, 139-3, and J, which were engineered for activity on amorphadiene[38] and steroids[39]) into our heterologous pathway; three mutants yielded hydroxylated and/or carboxylated products, generating up to 0.3 mg/L of abietic acid (FIG. 17). The abietadiene-functionalizing activity of mutants originally engineered for other targets suggests that we will be able to develop mutants of P450$_b$m3 with even higher activities on abietadiene-like molecules.

Figure 17A:
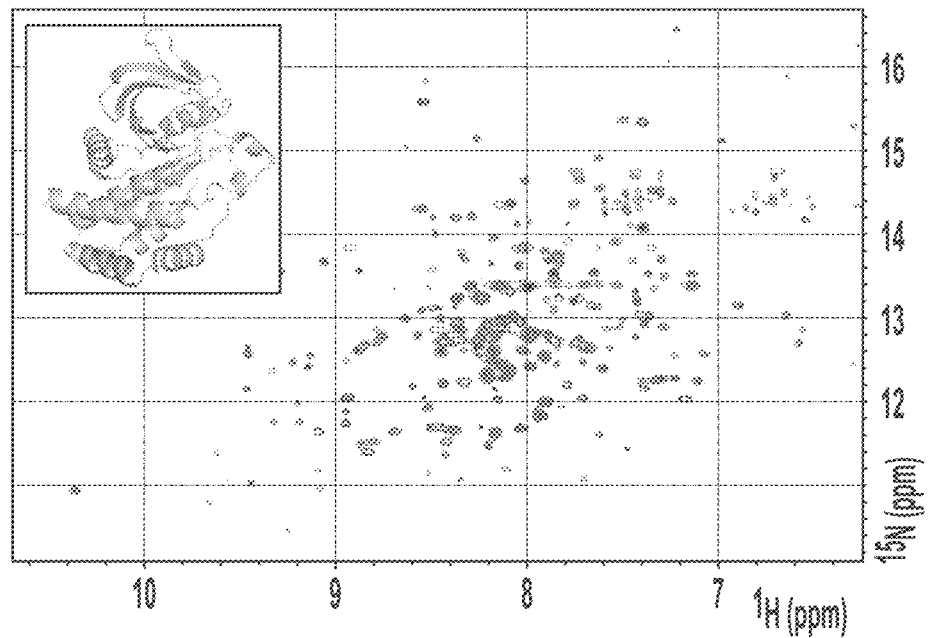
FIG. 17A-C shows results from exemplary studies.

Biostructural analyses. We have crystallized PTP1B in our lab, collected X-ray diffraction data in collaboration with Peter Zwart at Lawrence Berkeley National Lab (LBNL), and solved its crystal structure (FIG. 17A inset). We have also co-crystallized PTP1B with abietic acid; we will analyze these crystals in late July (first available beam time).

Recently, we expressed N[15]-labeled PTP1B and used it to collect two-dimensional $^1$H-$^{15}$N HSQC spectra in collaboration with Haribabu Arthanari at Harvard Medical School (FIG. 17A main). The spectra include PTP1B bound (separately) to abietic acid and known inhibitors; at present, we are processing the data. Preliminary results (X-ray and NMR) suggest that biostructural studies of PTP1B bound to different inhibitors will be straightforward.

Figure 17B:
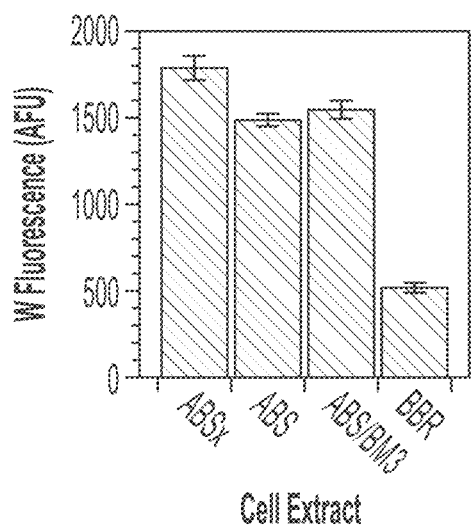
Figure 17C:
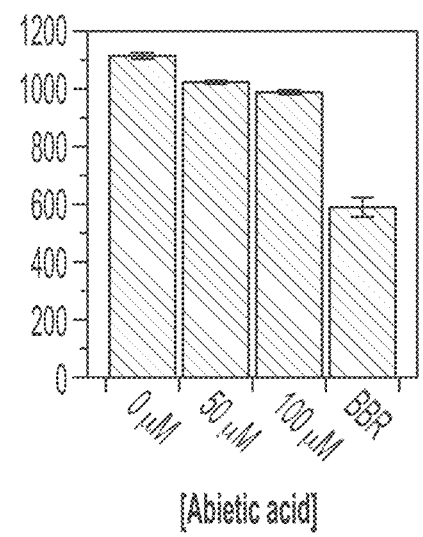
Figure 18A:
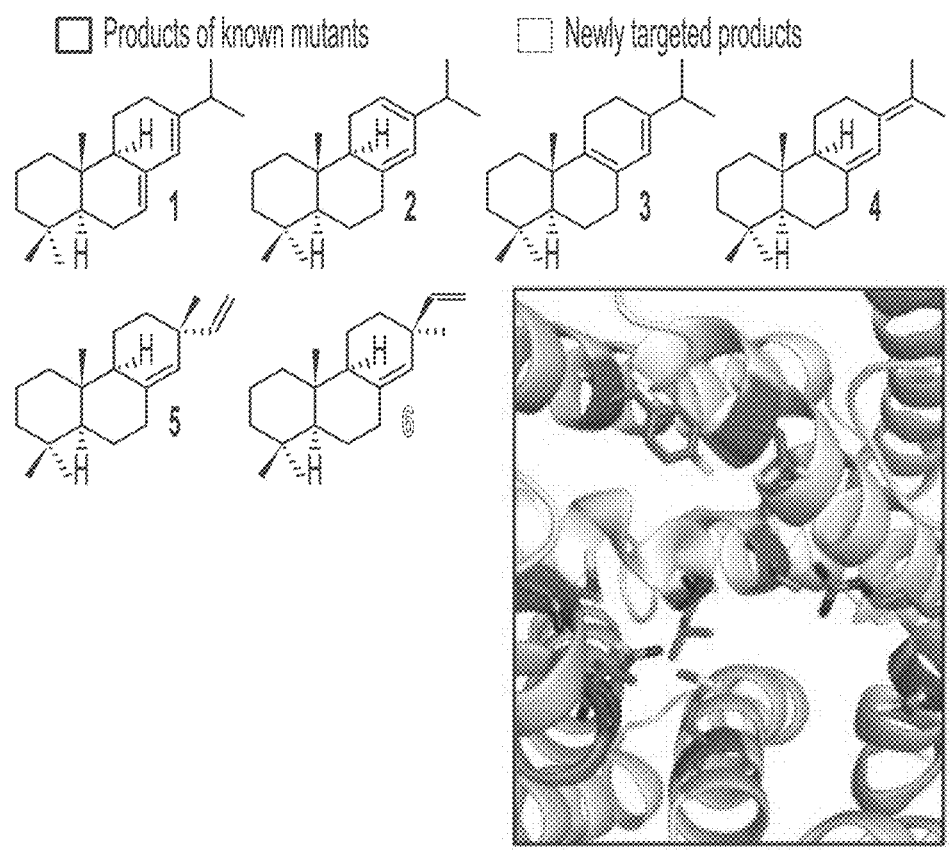
FIG. 18A-B illustrates exemplary terpenoids that differ in FIG. 18A stereochemistry and FIG. 18B shape. Inset: residues targeted for mutagenesis in class I site of ABS.
Figure 18B:
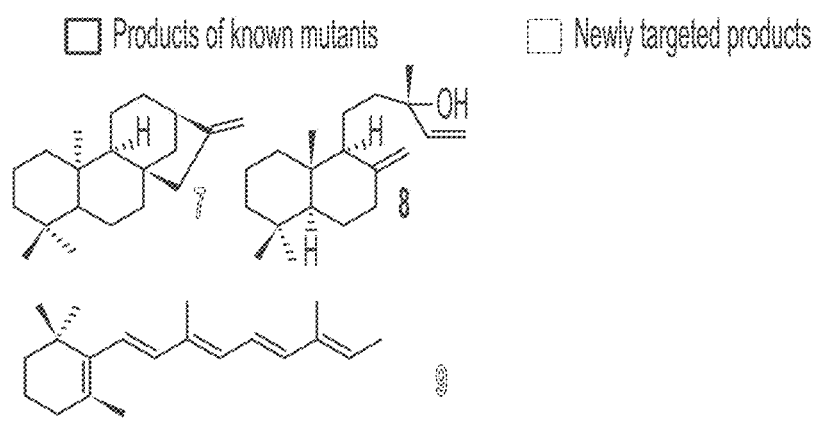

High-throughput screens. Upon binding to inhibitors (both competitive and allosteric), PTP1B exhibits changes in conformation that quench its tryptophan fluorescence (the basis of one of our four high-throughput screens). FIG. 17B indicates that such quenching can be used to distinguish between inhibitory extract (i.e., a hexane overlay) from an abietadiene-producing strain of E. coli and non-inhibitory extract from a control strain (i.e., one with a catalytically inactive ABS). FIG. 17C indicates that such changes can also be used to detect 50 uM (15 mg/L) of abietic acid. Our ability to detect (i) abietadiene in culture extract and (ii) abietic acid at low concentrations (i.e., tenfold lower than our titers of abietadiene) suggests that we will be able to detect improved inhibitors of PTP1B, even if they are accompanied by reductions in titer.

Providing structurally varied terpenoids with different affinities for the allosteric binding pocket. This section describes developing a set of inhibitors with incremental differences in affinity that result from systematic differences in structure. The goal (metric for success): a minimum of ~15 structurally varied inhibitors with (i) affinities for PTP1B that differ by 100-fold and/or (ii) enthalpies and entropies of binding that suggest alternative binding geometries.

Research plan. In the sections that follow, we use enzymes to build selective terpenoid inhibitors of PTP1B. This enzyme is the initial focus of our work because it is a therapeutic target for diabetes, obesity, and cancer, and it can be expressed, crystallized, and assayed with ease[15]. It, thus, serves as a pharmaceutically relevant model system with which to develop a general approach for the enzymatic construction of drug leads.

Hypothesis for structural changes. In this section, we use promiscuous enzymes to construct terpenoids that differ in stereochemistry, shape, size, and chemical functionality. We believe that these modifications will affect the affinity of ligands for PTP1B by altering (i) their ability to engage in van der Waals interactions with nonpolar residues (e.g., F280, L192, and F196) in the allosteric binding pocket, (ii) their ability to engage in direct or water-mediated hydrogen bonds with proximal polar residues (e.g., N193, E200, and E276), (iii) their ability to engage in halogen bonds with either set of residues, (iv) their influence on molecular conformational constraints, and, (v) their ability to reorganize water during binding. This hypothesis (which is supported, in part, by FIG. 16) motivates the synthetic strategy described herein.

Figure 8B:
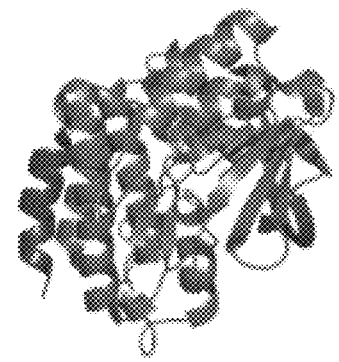
Figure 9A:
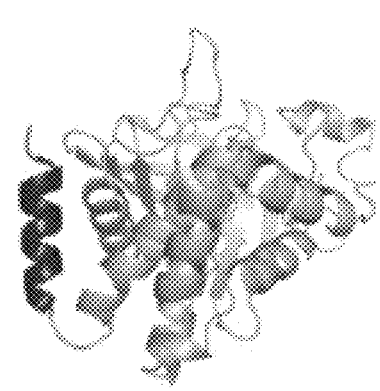
FIG. 9A-B illustrates an exemplary framework for building an enzyme modulated by red light. We will attach the C-terminal α-helix of PTP1B to the N-terminal α-helix of BphP1.
Figure 9B:

Stereochemistry, shape, and size. We will begin by using mutants of ABS to generate diterpenoids that differ in stereochemistry and shape FIG. 18A). ABS uses two active sites to catalyze sequential class II (protonation-dependent) and class I (ionization-dependent) cyclization of geranylgeranyl pyrophosphate (GGPP, $C_{20}$) into abietadiene[29]. Previous studies indicate that amino acid substitutions in its active sites can alter the stereochemistry or shape of its products[29,31]. We will use mutations (new and previously identified) that affect the position of deprotonation, intramolecular protein transfer, or carbocation stability (FIG. 8B). After installing these mutants into E. coli, we will use GC/MS to search for new products (fragmentation tools such as MetFrag[40] or ACD/MS Fragmenter[41] will facilitate identification of novel compounds).

We will generate terpenoids that differ in size by using mutations that increase/decrease the volume of the active sites of ABS. Previous attempts to change the substrate specificities of terpene synthases[42,43] suggest that such mutations could enable enhanced activity on farnesyl pyrophosphate (FPP, $C_{15}$) and farnesylgeranyl pyrophosphate (FGPP, $C_{25}$). To synthesize FGPP, we will incorporate an FGPP synthase previously expressed in E. coli[44].

We will isolate a subset of new terpenoids with particularly high titers by using flash chromatography and HPLC (a task for which feasibility has been established in several studies[28,31,45]), and we will use ITC to measure the free energy ($\Delta G°_{bind}$), enthalpy ($\Delta H°_{bind}$), and entropy ($-T\Delta S°_{bind}$) of binding to PTP1B. Differences in $\Delta G°_{bind}$ between ligands will reveal how structural changes affect the strength of binding; differences in $\Delta H°_{bind}$ and $-T\Delta S°_{bind}$ will reveal their influence on binding geometry[46,47].

Figure 19A:
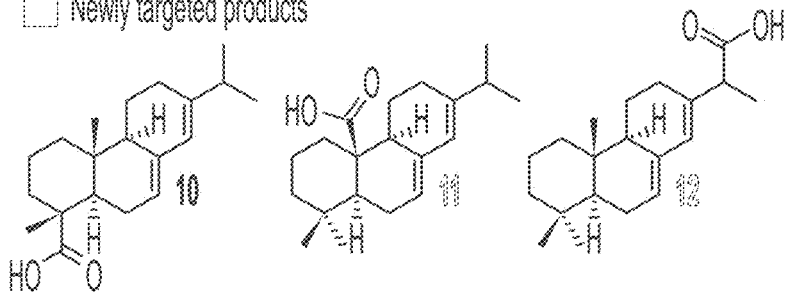
FIG. 19A-E illustrates exemplary terpenoids FIG. 19A carboxylated, FIG. 19B hydroxylated, FIG. 19C and halogenated diterpenoids.
Figure 19B:
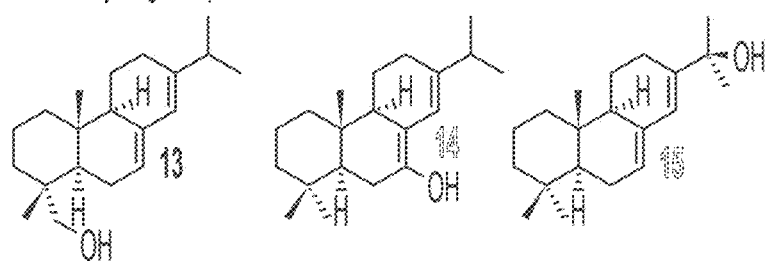
Figure 19C:
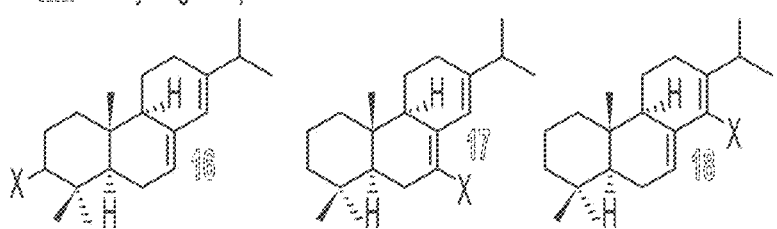
Figure 19D:
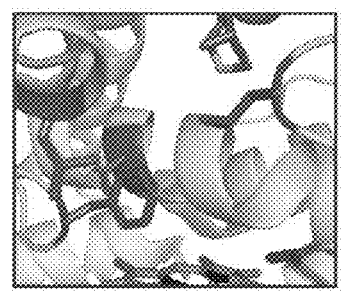

Hydroxylation and halogenation. For each of the three ligands selected in 6.1.2, we will use mutants of cytochrome P450 BM3 (P450$_b$m3) from Bacillus megaterium and/or CYP720B4 (P450$_{72}$o) from Picea sitchensis to construct five variants with hydroxyl or carboxyl groups at different positions (FIGS. 19A and 19B). P450$_b$m3 can hydroxylate a wide range of substrates, including terpenoids[48]; P450$_{72}$o can carboxylate over 20 diterpenoids, including abietadiene[49]. Both enzymes can be expressed in E. coli[44].

We will work with several sets of mutations: For P450$_{bm}$3, we will use (i) three (V78A, F87A, and A328L) that permit the stereoselective hydroxylation of sesquiterpenes and diterpenes[50], (ii) five (L75A, M177A, L181A, and L437A) that enable hydroxylation of alkaloids and steroids[51], and (iii) two (F87V and A82F) that permit carboxylation of heteroaromatics (FIG. 18D)[52]. For P450$_{72}$o, we will examine ~10 similar mutations likely to alter the position of oxidation. We will, again, screen each mutant in E. coli, isolate interesting products, and use ITC to analyze them.

Figure 19E:
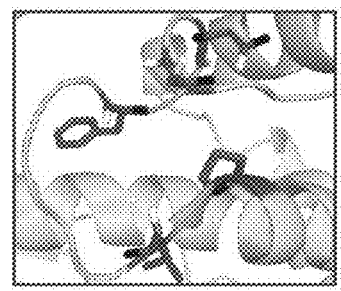
Figure 20:
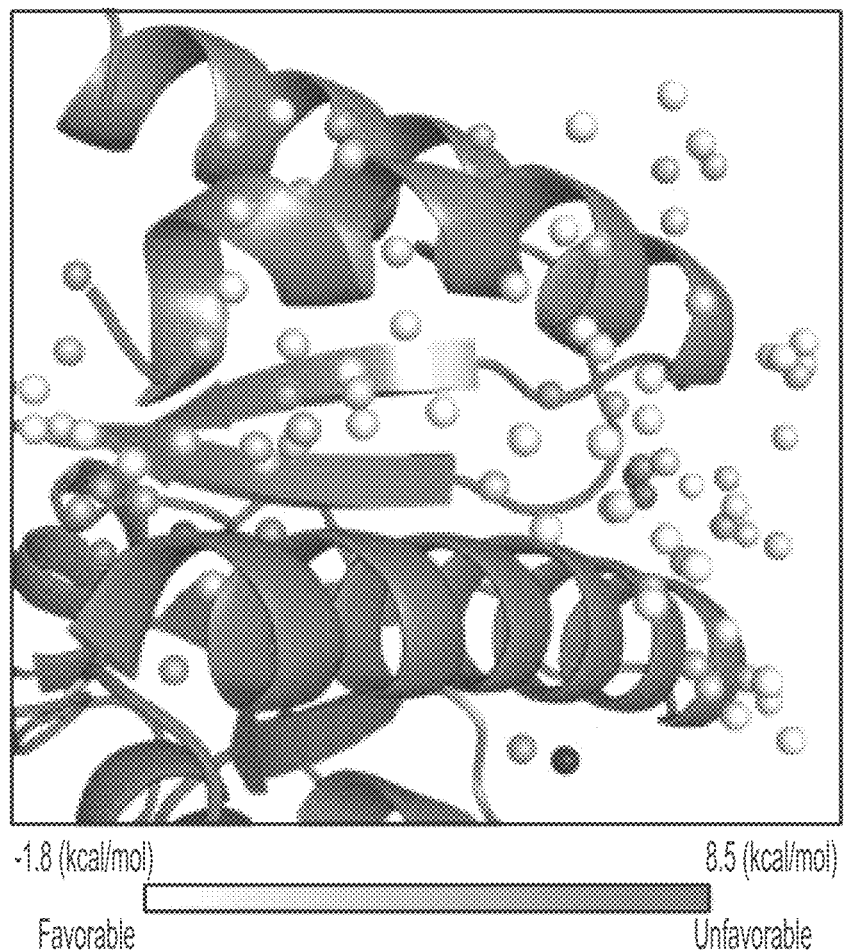
FIG. 20 illustrates an exemplary WaterMap analysis of UPPS. Colors of water molecules correspond to free energies, relative to bulk water.

For each of two high-affinity oxygenated ligands, we will construct six variants with bromide or iodide at different positions (FIG. 18C). These two halogens can engage in halogen bonds with oxygen, nitrogen, or sulfur acceptors in proteins[53], and can bind small nonpolar declivities on their surfaces[54]. The energetic contribution associated with both interactions tends to increase from Br to I[54,55] and, thus, lends itself to systematic analysis (i.e., a physical organic approach). To generate halogenated ligands, we will use mutants of tryptophan 6-halogenase (SttH) from Streptomyces toxytricini and vanadium haloperoxidase (VHPO) from Acaryochloris marina. These enzymes can introduce halogens (chloride, bromide, or iodide) into sp$^2$-hybridized carbons of alkaloids or terpenoids (before or after cyclization)[56,57]. For each enzyme, we will examine several mutations known to change regioselectivity (e.g., L460F, P461E, and P452T for SttH[56]) and 5-10 mutations likely to change the orientation of bound FIG. 19 Examples: (FIG. 19A) carboxylated, (B) hydroxylated, ligands (FIG. 19E). We will, again, screen (FIG. 19C) and halogenated diterpenoids. (FIG. 19D-E) Residues each mutant in *E. coli* and use ITC to targeted for mutagenesis in (FIG. 19D) P450$_{bm}$3 and (FIG. 19E) SttH.

IV. Evolving High-Affinity Terpenoid Inhibitors of PTP1B.

This section develops four high-throughput screens for rapidly evaluating the strength of PTP1B inhibitors, and it uses those methods, in conjunction with site-saturation and random mutagenesis, to evolve new inhibitors. The goal: a set of evolved inhibitors with particularly high affinities ($K_D$^1 uM) and/or unpredictable structures (i.e., structures inconsistent with rational design).

Biological selection. A selection method (i.e., a growth-coupled screen) in which the survival of *E. coli* is linked to inhibitor potency will enable rapid screening of extremely large libraries of molecules ($10^{10}$)[66]. In this section, we develop such a method.

PTP1B catalyzes the dephosphorylation—and inactivation—of several cell surface receptors. We will use the tyrosine-containing regions of these receptors to build an operon that links inhibition of PTP1B to cell growth. This operon will require six components (FIG. 21A): (i) a substrate domain (the tyrosine-containing region of a receptor) tethered to a DNA-binding protein, (ii) a substrate recognition domain (a protein that binds the tyrosine-containing region after its phosphorylation) tethered to the co subunit of an RNA polymerase, (iii) a tyrosine kinase, (iv) PTP1B, (v) a gene for antibiotic resistance, and (vi) an operator for that gene. With this system, inhibitors of PTP1B will enable binding of the substrate and substrate recognition domains, recruitment of RNA polymerase to the DNA, and transcription of the gene for antibiotic resistance. Previous groups have used similar operons to evolve protein-protein binding partners; here, we take the additional steps of (i) using a protein-protein interaction mediated by enzymes (PTP1B and a kinase) and of (ii) screening that interaction in the presence of potential inhibitors of one of those enzymes.

We will develop our operon by starting with a luminescence-based system, and we will add an antibiotic resistance gene as a final step. In our preliminary work with a system optimized by Liu et al.[67], we obtained a tenfold difference in Lux-based luminescence between a strain expressing two binding partners and a strain expressing one (FIG. 21E; arabinose induces expression of the second partner). We now plan to introduce—and test—different substrate domains, recognition domains, and kinases (eGFR and Src).

A FRET sensor for PTP1B activity. A high-throughput screen in which inhibition of PTP1B is linked to cell fluorescence will enable rapid screening via fluorescence-activated cell sorting (FACS). This technique tends to produce more false positives than selection and limits libraries to sizes of $10^7$-$10^8$, but it requires fewer heterologous genes[27,66].

For this strategy, we will make use of FRET (Forster resonance energy transfer) sensors commonly used to monitor kinase and phosphatase activity in mammalian cells[68,69]. These sensors consist of a kinase substrate domain, a short flexible linker, and a phosphorylation recognition domain—all sandwiched between two fluorescent proteins. Phosphorylation of the substrate domain causes it to bind to the recognition domain, inducing FRET between the two fluorescent proteins. In a PTP1B-compatible sensor, inhibitors of PTP1B will increase FRET (FIG. 21B). We have begun to develop such a sensor by trying different combinations of substrate domains, recognition domains, and kinases. (Note: FACS enables FRET-based screens[70,71]).

A FRET sensor for changes in the conformation of PTP1B. A FACS-based screen in which changes in cell fluorescence result from binding-induced changes in the conformation of PTP1B would be less generalizable than strategies 2 and 3 (which could be used for any kinase or phosphatase), but would require only one heterologous gene.

For this strategy, we will make use of a FRET experiment carried out by the Tonks Group[13]. These researchers sought to show that the binding of trodusquemine to PTP1B caused the protein to become more compact. To do so, they attached members of a FRET pair to each terminus of the PTP1B (FIG. 21C); upon protein-ligand association, an increase in FRET signal indicated that its termini approached one another. We hypothesize that this construct could be used as a sensor for identifying other molecules that bind to the allosteric site of PTP1B. We will begin by testing it with a variety of known inhibitors (a step the Tonks group did not take).

Binding-induced changes in the tryptophan fluorescence of PTP1B. A screen in which inhibition of PTP1B is linked to changes in tryptophan fluorescence (FIG. 21D) will enable rapid screening of moderately sized libraries ($10^3$-$10^4$)[27] in microtiter plates. Our use of binding-induced changes in tryptophan fluorescence is described in 5.6. In future work, we plan to extend this approach to other protein tyrosine phosphatases, many of which are allosteric and possess many tryptophans (e.g., SHP-2, a target for Noonan syndrome[72])

Mutagenesis. To use our high-throughput screens to evolve inhibitors of PTP1B, we will build libraries of mutated terpenoid pathways by using (i) site-saturation mutagenesis (SSM; we will target binary combinations of sites) and (ii) error-prone PCR (ep-PCR).

For SSM, we will identify "plastic" residues likely to accommodate useful mutations by developing functions similar to Eq. 1. This function scores residues based on their ability to accommodate mutations that influence the volume and hydration structure of an active site; S is a metric for the propensity of a residue to permit mutations, $cr^2$ is the variance in volume of $$s = 4 + RTW \tag{EQ 1}$$

similarly positioned residues in the active sites of other enzymes, $A^{\char`\^}_w$ is the variance in hydrophilicity of those residues, and $N_V$ and $N_{HW}$ are normalization factors. In our preliminary analysis of ABS, we successfully used Eq. 1 (and structure/sequence information from Taxadiene, y-humulene, 5-selenine, and epi-isozizaene synthases) to identify residues for which mutations are known to yield new products (e.g., H348 of ABS)[31]. We note: Previous attempts to identify plastic residues have scanned each site near the bound substrate[73]; our approach will be unique in its inclusion of biophysical considerations from (i) our study of optimal ligand attributes (6.2.1) and (ii) our study of the types of mutations that bring them about (6.2.2). For library construction, we will explore mutating our pathway (i) enzyme-by enzyme (e.g., ABS, then P450$_b$m3, and then VttH) or (ii) at random. The second approach could give us access to structures that might be difficult to find with conventional approaches to lead design.

To identify structure-activity relationships that enable the evolution of terpenoid inhibitors of arbitrary protein targets. This section develops a biophysical framework for using a crystal structure of a protein to identify enzymes capable of making inhibitors of that protein. The goal: the use of that framework to identify—and, then, test—enzymes capable of synthesizing new inhibitors of PTP1B and (separately) undecaprenyl diphosphate synthase (UPPS), a target for antibiotic-resistant bacterial infections.

Relationships between binding pockets. We will begin by determining how similarities in specific properties of binding pockets (e.g., volume, polarity, and shape) enable enzymes to synthesize, functionalize, and/or bind similar molecules. This effort will involve comparisons of the allosteric binding pocket of PTP1B with the binding pockets (i.e., active sites) of enzymes involved in inhibitor synthesis. For these comparisons, we will construct two matrices: matrix A in which each element (ay) represents the similarity of a specific property between binding pockets i and j ($0<a_{ij}<1$, where 1 is highly similar) and matrix B in which each element (by) describes the ability of binding pockets i and j to bind similar molecules ($0<b_{ij}<1$, where 1 represents identical binding specificities). The rank of the matrix formed by the product of these two matrices (AB) will suggest the number of independent variables (i.e., active site attributes) necessary to determine the functional compatibility of enzymes in a metabolic pathway; the eigenvalue will suggest the relative importance of the property under study (described by matrix A).

We will construct matrix A with PyMol- and MD-based analyses of protein crystal structures. We will construct matrix B by examining the binding of functionalized terpenoids and their precursors to each enzyme involved in terpenoid synthesis. Binding affinities for some of these ligand/protein combinations will be measured with ITC; most will be estimated with docking calculations (OEDocking[78]).

The result of this section will be an equation similar to Eq. 2, where J is a metric for an active site's ability to synthesize $$J = w_v V + w_p P + W_i L + w_w W \quad \text{(Eq. 2)}$$

terpenoids that bind a particular binding pocket; V, P, L, and W represent specific properties of that active site (volume, polarity, longest diameter, and shortest diameter); and w's represent weighting factors. The final number of variables—and their respective weights—will be determined through the above analysis. In parameterizing the equation, we plan to examine different metrics for properties of binding pockets (e.g. shape) and to explore/develop different matrix manipulations.

Validation and Extension.

The identification of promising active site motifs for inhibitor synthesis will require a search of available protein structural data. We will perform such a search by using PROBIS (probis.nih.gov[79]), an alignment-based platform that uses a specified binding site to find similar binding sites on other proteins in the Protein Data Bank. PROBIS can identify similarly shaped binding pockets, even when the protein folds that surround those pockets are different (i.e., it detects similar constellations of amino acids).

To begin, we will use a PROBIS-based search to identify enzymes with active sites that have some level of structural similarity (we will explore different thresholds) to either (i) the allosteric binding site of PTP1B or (ii) the active sites of enzymes capable of synthesizing inhibitors of PTP1B. Using Eq. 2, we will select enzymes with the most favorable active sites and test them with our platform for inhibitor development).

We will assess the generalizability of our approach by attempting to construct inhibitors of UPPS, a protein known to bind terpenoids and polycyclic molecules[80]. Structure-based searches will use two starting points: (i) UPPS and (ii) mutants of ABS, P450$_b$m3, or similar enzymes that our biophysical analyses suggest might yield UPPS inhibitors. We will, again, select a subset of enzymes to test with our platform.

REFERENCES FOR SECTIONS III-IV

1. Koh, H.-L., Yau, W.-P., Ong, P.-S. & Hegde, A. Current trends in modern pharmaceutical analysis for drug discovery. Drug Discov. Today 8, 889-897 (2003).
2. Whitesides, G. M. & Krishnamurthy, V. M. Designing ligands to bind proteins. Q. Rev. Biophys. 38, 385-395 (2005).
3. Olsson, T. S. G., Williams, M. a., Pitt, W. R. & Ladbury, J. E. The Thermodynamics of Protein-Ligand Interaction and Solvation: Insights for Ligand Design. J. Mol. Biol. 384, 1002-1017 (2008).
4. Welsch, M. E., Snyder, S. A. & Stockwell, B. R. Privileged scaffolds for library design and drug discovery. Curr. Opin. Chem. Biol. 14, 347-361 (2010).
5. Gershenzon, J. & Dudareva, N. The function of terpene natural products in the natural world. Nat. Chem. Biol. 3, 408-414 (2007).
6. Chang, M. C. Y. & Keasling, J. D. Production of isoprenoid pharmaceuticals by engineered microbes. Nat. Chem. Biol. 2, 674-681 (2006).
7. Johnson, T. O., Ermolieff, J. & Jirousek, M. R. Protein tyrosine phosphatase 1B inhibitors for diabetes. Nat. Rev. Drug Discov. 1, 696-709 (2002).
8. Koren, S. & Fantus, I. G. Inhibition of the protein tyrosine phosphatase PTP1B: potential therapy for obesity, insulin resistance and type-2 diabetes mellitus. Best Pract. Res. Clin. Endocrinol. Metab. 21, 621-640 (2007).
9. Soysal, S., Obermann, E. C, Gao, F., Oertli, D., Gillanders, W. E., Viehl, C. T. & Muenst, S. PTP1B expression is an independent positive prognostic factor in human breast cancer. Breast Cancer Res. Treat. 137, 637-644 (2013).
10. Tonks, N. K. & Muthuswamy, S. K. A Brake Becomes an Accelerator: PTP1B—A New Therapeutic Target for Breast Cancer. Cancer Cell 11, 214-216 (2007).
11. Lessard, L, Stuible, M. & Tremblay, M. L. The two faces of PTP1B in cancer. Biochim. Biophys. Acta-Proteins Proteomics 1804, 613-619 (2010).
12. Zhang, S. & Zhang, Z. Y. PTP1B as a drug target: recent developments in PTP1B inhibitor discovery. Drug Discov. Today 12, 373-381 (2007).
13. Krishnan, N., Koveal, D., Miller, D. H., Xue, B., Akshinthala, S. D., Kragelj, J., Jensen, M. R., Gauss, C.-M., Page, R., Blackledge, M., Muthuswamy, S. K., Peti, W. & Tonks, N. K. Targeting the disordered C terminus of PTP1B with an allosteric inhibitor. Nat. Chem. Biol. 10, 558-566 (2014).
14. Sun, J. P., Fedorov, A. A., Lee, S. Y., Guo, X. L, Shen, K., Lawrence, D. S., Almo, S. C. & Zhang, Z. Y. Crystal structure of PTP1B complexed with a potent and selective bidentate inhibitor. J. Biol. Chem. 278, 12406-12414 (2003).
15. Wiesmann, C, Barr, K. J., Kung, J., Zhu, J., Erlanson, D. A., Shen, W., Fahr, B. J., Zhong, M., Taylor, L., Randal, M., McDowell, R. S. & Hansen, S. K. Allosteric inhibition of protein tyrosine phosphatase 1B. Nat. Struct. Mol. Biol. 11, 730-737 (2004).
16. Krishnan, N. & Tonks, N. K. Anxious moments for the protein tyrosine phosphatase PTP1B. Trends Neurosci. 38, 462-465 (2015).

17. Hughes, J. P., Rees, S. S., Kalindjian, S. B. & Philpott, K. L. Principles of early drug discovery. Br. J. Pharmacol. 162, 1239-1249 (2011).
18. Kennedy, T. Managing the drug discovery/development interface. Drug Discov. Today 2, 436-444 (1997).
19. Snyder, P. W., Lockett, M. R., Moustakas, D. T. & Whitesides, G. M. Is it the shape of the cavity, or the shape of the water in the cavity? Eur. Phys. J. Spec. Top. 223, 853-891 (2014).
20. Klebe, G. Applying thermodynamic profiling in lead finding and optimization. Nat. Rev. Drug Discov. 14, 95-110 (2015).
21. Chang, M. C. Y. & Keasling, J. D. Production of isoprenoid pharmaceuticals by engineered microbes. Nat. Chem. Biol. 2, 674-681 (2006).
22. George, K. W., Alonso-Gutierrez, J., Keasling, J. D. & Lee, T. S. Isoprenoid Drugs, Biofuels, and Chemicals-Artemisinin, Farnesene, and Beyond. Adv Biochem Eng Biotechnol 148, 355-389 (2014).
23. Cragg, G. M. & Newman, D. J. Natural products: A continuing source of novel drug leads. Biochim. Biophys. Acta-Gen. Subj. 1830, 3670-3695 (2013).
24. Galanie, S., Thodey, K., Trenchard, I. J., Filsinger Interrante, M. & Smolke, C. D. Complete biosynthesis of opioids in yeast. Science (80-.). 349, 1095-1100 (2015).
25. Govindarajan, S., Recabarren, R. & Goldstein, R. a. Estimating the total number of protein folds. Proteins 35, 408-414 (1999).
26. Atanasov, A. G., Waltenberger, B., Pferschy-Wenzig, E. M., Linder, T., Wawrosch, C, Uhrin, P., Temml, V., Wang, L., Schwaiger, S., Heiss, E. H., Rollinger, J. M., Schuster, D., Breuss, J. M., Bochkov, V., Mihovilovic, M. D., Kopp, B., Bauer, R., Dirsch, V. M. & Stuppner, H. Discovery and resupply of pharmacologically active plant-derived natural products: A review. Biotechnol. Adv. 33, 1582-1614 (2015).
27. Lauchli, R., Rabe, K. S., Kalbarczyk, K. Z., Tata, A., Heel, T., Kitto, R. Z. & Arnold, F. H. High-throughput screening for terpene-synthase-cyclization activity and directed evolution of a terpene synthase. Angew. Chemie—Int. Ed. 52, 5571-5574 (2013).
28. Morrone, D., Lowry, L., Determan, M. K., Hershey, D. M., Xu, M. & Peters, R. J. Increasing diterpene yield with a modular metabolic engineering system in E. coli: Comparison of MEV and MEP isoprenoid precursor pathway engineering. Appl. Microbiol. Biotechnol. 85, 1893-1906 (2010).
29. Peters, R. J. & Croteau, R. B. Abietadiene synthase catalysis: mutational analysis of a prenyl diphosphate ionization-initiated cyclization and rearrangement. Proc. Natl. Acad. Sci. U.S.A. 99, 580-584 (2002).
30. Wilderman, P. R. & Peters, R. J. A single residue switch converts abietadiene synthase into a pimaradiene specific cyclase. J. Am. Chem. Soc. 129, 15736-15737 (2007).
31. Criswell, J., Potter, K., Shephard, F., Beale, M. H. & Peters, R. J. A single residue change leads to a hydroxylated product from the class II diterpene cyclization catalyzed by abietadiene synthase. Org. Lett. 14, 5828-5831 (2012).
32. Fasan, R. Tuning P450 enzymes as oxidation catalysts. ACS Catal. 2, 647-666 (2012).
33. Hamberger, B. B., Ohnishi, T., Hamberger, B. B., Seguin, A. & Bohlmann, J. Evolution of diterpene metabolism: Sitka spruce CYP720B4 catalyzes multiple oxidations in resin acid biosynthesis of conifer defense against insects. Plant Physiol. 157, 1677-95 (2011).
34. Fujimori, D. G. & Walsh, C. T. What's new in enzymatic halogenations. Curr. Opin. Chem. Biol. 11, 553-560 (2007).
35. Martin, V. J. J., Pitera, D. J., Withers, S. T., Newman, J. D. & Keasling, J. D. Engineering a mevalonate pathway in Escherichia coli for production of terpenoids. Nat. Biotechnol. 21, 796-802 (2003).
36. Zhang, F. & Keasling, J. Biosensors and their applications in microbial metabolic engineering. Trends Microbiol. 19, 323-329 (2011).
37. Ajikumar, P. K., Xiao, W.-H., Tyo, K. E. J., Wang, Y., Simeon, F., Leonard, E., Mucha, O., Phon, T. H., Pfeifer, B. & Stephanopoulos, G. Isoprenoid pathway optimization for Taxol precursor overproduction in Escherichia coli. Science 330, 70-74 (2010).
38. Dietrich, J. A., Yoshikuni, Y., Fisher, K. J., Woolard, F. X., Ockey, D., McPhee, D. J., Renninger, N. S., Chang, M. C. Y., Baker, D. & Keasling, J. D. A novel semi-biosynthetic route for artemisinin production using engineered substrate-promiscuous P450BM3. ACS Chem. Biol. 4, 261-267 (2009).
39. Zhang, K., El Damaty, S. & Fasan, R. P450 fingerprinting method for rapid discovery of terpene hydroxylating P450 catalysts with diversified regioselectivity. J. Am. Chem. Soc. 133, 3242-3245 (2011).
40. Ruttkies, C, Schymanski, E. L, Wolf, S., Hollender, J. & Neumann, S. MetFrag relaunched: Incorporating strategies beyond in silico fragmentation. J. Cheminform. 8, (2016).
41. Pelander, A., Tyrkko, E. & Ojanpera, I. In silico methods for predicting metabolism and mass fragmentation applied to quetiapine in liquid chromatography/time-of-flight mass spectrometry urine drug screening. Rapid Commun. Mass Spectrom. 23, 506-514 2009.
42. Kampranis, S. C, Ioannidis, D., Purvis, A., Mahrez, W., Ninga, E., Katerelos, N. A., Anssour, S., Dunwell, J. M., Degenhardt, J., Makris, A. M., Goodenough, P. W. & Johnson, C. B. Rational conversion of substrate and product specificity in a Salvia monoterpene synthase: structural insights into the evolution of terpene synthase function. Plant Cell 19, 1994-2005 (2007).
43. Huang, Q., Williams, H. J., Roessner, C. A. & Scott, A. I. Sesquiterpenes produced by truncated taxadiene synthase. Tetrahedron Lett. 41, 9701-9704 (2000).
44. Tachibana, A., Yano, Y., Otani, S., Nomura, N., Sako, Y. & Taniguchi, M. Novel prenyltransferase gene encoding farnesylgeranyl diphosphate synthase from a hyperthermophilic archaeon, Aeropyrum pernix. Molecular evolution with alteration in product specificity. Eur. J. Biochem. 267, 321-328 (2000).
45. Jia, M., Potter, K. C. & Peters, R. J. Extreme promiscuity of a bacterial and a plant diterpene synthase enables combinatorial biosynthesis. Metab. Eng. 37, 24-34 (2016).
46. Fox, J. M., Kang, K. K., Sastry, M., Sherman, W., Sankaran, B., Zwart, P. H. & Whitesides, G. M. Water-Restructuring Mutations Can Reverse the Thermodynamic Signature of Ligand Binding to Human Carbonic Anhydrase. Angew. Chemie Int. Ed. 56, 3833-3837 (2017).
47. Krimmer, S. G., Betz, M., Heine, A. & Klebe, G. Methyl, ethyl, propyl, butyl: Futile but not for water, as the correlation of structure and thermodynamic signature shows in a congeneric series of thermolysin inhibitors. ChemMedChem 9, 833-846 (2014).

48. Jung, S. T., Lauchli, R. & Arnold, F. H. Cytochrome P450: Taming a wild type enzyme. Curr. Opin. Biotechnol. 22, 809-817 (2011).
49. Hamberger, B. B., Ohnishi, T., Hamberger, B. B., Seguin, A. & Bohlmann, J. Evolution of diterpene metabolism: Sitka spruce CYP720B4 catalyzes multiple oxidations in resin acid biosynthesis of conifer defense against insects. Plant Physiol. 157, 1677-95 (2011).
50. Seifert, A., Vomund, S., Grohmann, K., Kriening, S., Urlacher, V. B., Laschat, S. & Pleiss, J. Rational design of a minimal and highly enriched CYP102A1 mutant library with improved regio-, stereo- and chemoselectivity. ChemBioChem 10, 853-861 (2009).
51. Lewis, J. C, Mantovani, S. M., Fu, Y., Snow, C. D., Komor, R. S., Wong, C. H. & Arnold, F. H. Combinatorial alanine substitution enables rapid optimization of cytochrome P450BM3 for selective hydroxylation of large substrates. ChemBioChem 11, 2502-2505
52. Butler, C. F., Peet, C, Mason, A. E., Voice, M. W., Leys, D. & Munro, A. W. Key mutations alter the cytochrome P450 BM3 conformational landscape and remove inherent substrate bias. J. Biol. Chem. 288, 25387-25399 (2013).
53. Auffinger, P., Hays, F. a, Westhof, E. & Ho, P. S. Halogen bonds in biological molecules. Proc. Natl. Acad. Sci. U.S.A 101, 16789-16794 (2004).
54. Fox, J., Kang, K., Sherman, W., Heroux, A., Sastry, G., Baghbanzadeh, M., Lockett, M. & Whitesides, G. Interactions between Hofmeister anions and the binding pocket of a protein. J. Am. Chem. Soc. 137, 3859-3866 (2015).
55. Carter, M., Voth, A. R., Scholfield, M. R., Rummel, B., Sowers, L. C. & Ho, P. S. Enthalpy-entropy compensation in biomolecular halogen bonds measured in DNA junctions. Biochemistry 52, 4891-4903 (2013).
56. Shepherd, S. A., Menon, B. R. K., Fisk, H., Struck, A.-W., Levey, C, Leyes, D. & Micklefield, J. A Structure-Guided Switch in the Regioselectivity of a Tryptophan Halogenase. ChemBioChem 17, 821-824 (2016).
57. Carter-Franklin, J. N., Parrish, J. D., Tschirret-Guth, R. A., Little, R. D. & Butler, A. Vanadium haloperoxidase-catalyzed bromination and cyclization of terpenes. J. Am. Chem. Soc. 125, 3688-3689 (2003).
58. Li, R., Chou, W. K. W., Himmelberger, J. A., Litwin, K. M., Harris, G. G., Cane, D. E. & Christianson, D. W. Reprogramming the chemodiversity of terpenoid cyclization by remolding the active site contour of epi-isozizaene synthase. Biochemistry 53, 1155-1168 (2014).
59. Brown, S. & O'Connor, S. E. Halogenase Engineering for the Generation of New Natural Product Analogues. ChemBioChem 16, 2129-2135 (2015).
60. Steele, C. L., Crock, J., Bohlmann, J. & Croteau, R. Sesquiterpene Synthases from Grand Fir (*Abies grandis*). J. Biol. Chem. 273, 2078-2089 (1998).
61. Lu, Y. & Mei, L. Co-expression of P450 BM3 and glucose dehydrogenase by recombinant *Escherichia coli* and its application in an NADPH-dependent indigo production system. J. Ind. Microbiol. Biotechnol. 34, 247-253 (2007).
62. Tzeng, S.-R. & Kalodimos, C. G. Protein activity regulation by conformational entropy. Nature 488, 236-240 (2012).
63. Aramini, J. M., Vorobiev, S. M., Tuberty, L. M., Janjua, H., Campbell, E. T., Seetharaman, J., Su, M., Huang, Y. J., Acton, T. B., Xiao, R., Tong, L. & Montelione, G. T. The RAS-Binding Domain of Human BRAF Protein Serine/Threonine Kinase Exhibits Allosteric Conformational Changes upon Binding HRAS. Structure 23, 1382-1393 (2015).
64. Christianson, D. W. Structural biology and chemistry of the terpenoid cyclases. Chem. Rev. 106, 3412-3442 (2006).
65. O'Maille, P. E., Malone, A., Delias, N., Andes Hess, B., Smentek, L., Sheehan, I., Greenhagen, B. T., Chappell, J., Manning, G. & Noel, J. P. Quantitative exploration of the catalytic landscape separating divergent plant sesquiterpene synthases. Nat. Chem. Biol. 4, 617-623 (2008).
66. Packer, M. S. & Liu, D. R. Methods for the directed evolution of proteins. Nat. Rev. Genet. 16, 379-394 (2015).
67. Badran, A. H., Guzov, V. M., Huai, Q., Kemp, M. M., Vishwanath, P., Kain, W., Nance, A. M., Evdokimov, A., Moshiri, F., Turner, K. H., Wang, P., Malvar, T. & Liu, D. R. Continuous evolution of *Bacillus thuringiensis* toxins overcomes insect resistance. Nature 533, 58-63 (2016).
68. Ting, a Y., Kain, K. H., Klemke, R. L. & Tsien, R. Y. Genetically encoded fluorescent reporters of protein tyrosine kinase activities in living cells. Proc. Natl. Acad. Sci. U.S.A 98, 15003-15008 (2001).
69. Sato, M. & Umezawa, Y. in Cell Biol. Four-Volume Set 2, 325-328 (2006).
70. Dye, B. T. Flow cytometric analysis of CFP-YFP FRET as a marker for in vivo protein-protein interaction. Clin. Appl. Immunol. Rev. 5, 307-324 (2005).
71. Vereb, G., Nagy, P. & Szollosi, J. Flow cytometric FRET analysis of protein interaction. Methods Mol. Biol. 699, 371-92 (2011).
72. Chen, Y.-N. P., LaMarche, M. J., Chan, H. M., Fekkes, P., Garcia-Fortanet, J., Acker, M. G., Antonakos, B., Chen, C. H.-T., Chen, Z., Cooke, V. G., Dobson, J. R., Deng, Z., Fei, F., Firestone, B., Fodor, M., Fridrich, C, Gao, H., Grunenfelder, D., Hao, H.-X., Jacob, J., Ho, S., Hsiao, K., Kang, Z. B., Karki, R., Kato, M., Larrow, J., La Bonte, L. R., Lenoir, F., Liu, G., Liu, S., Majumdar, D., Meyer, M. J., Palermo, M., Perez, L., Pu, M., Price, E., Quinn, C, Shakya, S., Shultz, M. D., Slisz, J., Venkatesan, K., Wang, P., Warmuth, M., Williams, S., Yang, G., Yuan, J., Zhang, J.-H., Zhu, P., Ramsey, T., Keen, N. J., Sellers, W. R., Stams, T. & Fortin, P. D. Allosteric inhibition of SHP2 phosphatase inhibits cancers driven by receptor tyrosine kinases. Nature 535, 148-52 (2016).
73. Yoshikuni, Y., Ferrin, T. E. & Keasling, J. D. Designed divergent evolution of enzyme function. Nature 440, 1078-1082 (2006).
74. Gruet, A., Longhi, S. & Bignon, C. One-step generation of error-prone PCR libraries using Gateway® technology. Microb. Cell Fact. 11, 14 (2012).
75. Dietrich, J. A., McKee, A. E. & Keasling, J. D. High-Throughput Metabolic Engineering: Advances in Small-Molecule Screening and Selection. Annu. Rev. Biochem. 79, 563-590 (2010).
76. Esvelt, K. M., Carlson, J. C. & Liu, D. R. A system for the continuous directed evolution of biomolecules. Nature 472, 499-503 (2011).
77. Feiler, C, Fisher, A. C, Boock, J. T., Marrichi, M. J., Wright, L., Schmidpeter, P. A. M., Blankenfeldt, W., Pavelka, M. & DeLisa, M. P. Directed Evolution of *Mycobacterium tuberculosis* (3-Lactamase Reveals Gatekeeper Residue That Regulates Antibiotic Resistance and Catalytic Efficiency. PLoS One 8, (2013).
78. Murphy, R. B., Repasky, M. P., Greenwood, J. R., Tubert-Brohman, I., Jerome, S., Annabhimoju, R., Boyles, N. A., Schmitz, C. D., Abel, R., Farid, R. &

Friesner, R. A. WScore: A flexible and accurate treatment of explicit water molecules in ligand-receptor docking. J. Med. Chem. acs.jmedchem.6b00131 (2016). doi:10.1021/acs.jmedchem.6b00131
79. Konc, J., Miller, B. T., Stular, T., Lesnik, S., Woodcock, H. L., Brooks, B. R. & Janezic, D. ProBiS-CHARMMing: Web Interface for Prediction and Optimization of Ligands in Protein Binding Sites. J. Chem. Inf. Model. 55, 2308-2314 (2015).
80. Guo, R.-T., Cao, R., Liang, P.-H., Ko, T.-P., Chang, T.-H., Hudock, M. P., Jeng, W.-Y., Chen, C. K.-M., Zhang, Y., Song, Y., Kuo, C.-J., Yin, F., Oldfield, E. & Wang, A. H.-J. Bisphosphonates target multiple sites in both cis- and trans-prenyltransferases. Proc. Natl. Acad. Sci. U.S.A 104, 10022-10027 (2007).
81. Teng, K. H. & Liang, P. H. Structures, mechanisms and inhibitors of undecaprenyl diphosphate synthase: A cis-prenyltransferase for bacterial peptidoglycan biosynthesis. Bioorg. Chem. 43, 51-57 (2012).
82. Zhu, W., Zhang, Y., Sinko, W., Hensler, M. E., Olson, J., Molohon, K. J., Lindert, S., Cao, R., Li, K., Wang, K., Wang, Y., Liu, Y.-L, Sankovsky, A., de Oliveira, C. A. F., Mitchell, D. a, Nizet, V., McCammon, J. A. & Oldfield, E. Antibacterial drug leads targeting isoprenoid biosynthesis. Proc. Natl. Acad. Sci. U.S.A 110, 123-8 (2013).
83. Leonard, E., Ajikumar, P. K., Thayer, K., Xiao, W.-H., Mo, J. D., Tidor, B., Stephanopoulos,
G. & Prather, K. L. J. Combining metabolic and protein engineering of a terpenoid biosynthetic pathway for overproduction and selectivity control. Proc. Natl. Acad. Sci. U.S.A. 107, 13654-13659 (2010).
84. Ro, D.-K., Paradise, E. M., Ouellet, M., Fisher, K. J., Newman, K. L., Ndungu, J. M., Ho, K. A., Eachus, R. A., Ham, T. S., Kirby, J., Chang, M. C. Y., Withers, S. T., Shiba, Y., Sarpong, R. & Keasling, J. D. Production of the antimalarial drug precursor artemisinic acid in engineered yeast. Nature 440, 940-943 (2006).

V. Specific Embodiments of Bacterial Systems for Identifying Small Molecules that Modulate the Activity of Enzymes.

As described herein, a strain of *Escherichia coli* was developed comprising both (i) a genetically encoded system (i.e., a "bacterial two-hybrid" or B2H system) that links cell survival to the modulation inhibition of a pathologically relevant enzyme from *Homo sapiens* (i.e., a drug target) and (ii) a pathway for metabolite biosynthesis. The genetically encoded system described herein contains more genetic elements than would traditionally constitute a single operon (e.g. it has more than one promoter), but it is sometimes referred to as an operon.

More specifically, as described herein, host organisms, e.g. *Escherichia (E.) coli*, were transformed with up to four plasmids, including a first plasmid (plasmid 1) an expression plasmid comprising a genetically encoded system that links the inhibition of a target enzyme to cell survival, wherein the target enzyme may be chosen for the purpose of identifying molecules that inhibit a specific target enzyme; a second plasmid (plasmid 2) an expression plasmid comprising an operon for expressing at least some of the genes necessary to synthesize products of a metabolic pathway, e.g. a meva-lonate-dependent pathway for terpenoid biosynthesis derived from *Saccharomyces cerevisiae* for providing ter-penoid product compounds; a third plasmid (plasmid 3) an expression plasmid comprising at least one additional gene, not present in plasmid (plasmid 2), e.g. a terpene synthase, such as ADS, GHS, ABS, or TXS, for providing desired products, e.g. terpenoid products, such that when the host bacterial expresses plasmids 1 and 2, desired products are not produced until the host bacterial expresses plasmid 3 for completing the pathway for desired compounds; and a fourth plasmid (plasmid 4) comprising additional genetic components specific to the strain of *E. coli*, e.g., the F-plasmid of S1030 (Addgene 105063).

Examples of plasmid 1 embodiments are shown in FIG. 33A, 33B, 33D, 33E, FIG. 34, FIG. 35, FIG. 40A, 40B, 40C, 40D, etc.

In some embodiments, a strain of *E. coli* used as a host for transformation possesses the ΔrpoZ mutation, which enable the system encoded by plasmid 1 to control the expression of a gene for antibiotic resistance.

In some embodiments, plasmids 2 and/or 3 constitute a pathway for terpenoid biosynthesis. In some embodiments, plasmids 2 and/or 3 constitute a pathway for alkaloid biosynthesis. In some embodiments, plasmids 2 and/or 3 constitute a pathway for polyketide biosynthesis.

In some embodiments, plasmid 3 further comprises a GGPPS gene in combination with either ABS or TXS. Examples of GGPPS genes provide substrates for terpene synthase genes, i.e. ABS, or TXS. In some embodiments, terpene synthase genes are wild-type genes. In some preferred embodiments, terpene synthase genes contain mutations for producing variants of terpenoid products, as described and shown herein. In some embodiments, plasmid 3 further comprises a gene for terpenoid functionalizing enzymes, e.g., cytochromes P450.

In some preferred embodiments, plasmid 1 is under control of constitutive promoters. Thus, in some preferred embodiments, at least some of the genes that are part of the operon in plasmid 1 are constituitvely expressed. In some preferred embodiments, at least some of the genes that are part of the operon in plasmid 1 are expressed when contacted with an inducible compound, i.e. under control of an inducible promoter, such as a lacZ promoter turned on when in contact with X-gal.

In some preferred embodiments, plasmids 2 and 3 are under control of inducible promoters. Thus, in some preferred embodiments, at least some of, and in some cases the entire set of genes contained in a metobolic pathway operon in plasmid 2 are expressed when contacted with an inducible compound. In some preferred embodiments, some genes expressed in plasmid 3 are under inducible control.

In some preferred embodiments, plasmid 4 is under the control of constitutive promoters. Thus, in some embodiments, at least one gene in plasmid 4 is under control of a constiuitive promoter. In some embodiments, at least one gene in plasmid 4 is under control of an inducible promoter.

In some preferred embodiments, a host bacterium undergoes at least 2 rounds of transformation, e.g. first to transform plasmids 1 and 2 simultaneously into a strain that already harbors plasmid 4 (e.g., a S1030 strain which already comprises this accessory plasmid), followed by transformation with plasmid 3. In some preferred embodiments, a host bacterium undergoes at least 3 rounds of transformation, e.g. first to transfect plasmid 1, then transfect plasmid 2, followed by transfection of plasmid 3.

In some preferred embodiments, each plasmid has an antibiotic resistance gene (or other type of selective gene) for identifying successfully transformed bacteria for that plasmid, i.e. antibiotic resistance genes may be different for each plasmid. Thus, when an antibiotic resistance gene is expressed, instead of a bacteria stopped from normal replication when in contact with the antibiotic, a bacteria has ressitance so is able to replicate at normal or near normal rates.

Thus, as described herein, laboratory stains of *E. coli* were engineered to comprise up to three types of expression plasmids by first transfecting with plasmid 1, then selecting for transformants (growing colonies) on/in antibiotic containing media wherein nontransformants do not grow, then transfecting transformants with plasmid 2 and selecting for double transformants, e.g. media containing antibiotics for allowing the growth of double transformants, then transfecting double transformants with plasmid 3 and selecting for triple transformants, e.g. media containing antibiotics for allowing the growth of triple transformants. In one embodiment, triple transformants are grown in media containing an inducer(s) for the inducible plasmids (2 and 3) in combination with the three antibiotics for producing products having at least some inhibitory activity for the chosen enzyme of plasmid 1, made by the enzymes provided by the combination of enzymes expressed by plasmids 2 and 3.

Further, as described herein, laboratory stains of *E. coli* were engineered to comprise up to four types of expression plasmids by first transforming host cells with plasmids 1 and 2, simultaneously, into a strain that already harbors plasmid 4, then selecting for triple transformants (growing colonies) on/in antibiotic containing media wherein non-transformants do not grow, then further transforming successful triple transformants with plasmid 3 and selecting for quadruple transformants, e.g. media containing antibiotics that allow for the growth of quadruple transformants. In one embodiment, quadruple transformants are grown in media containing (i) an inducer(s) for the inducible plasmids (2 and 3), (ii) a metabolic precursor for metabolite biosynthesis, e.g., mevalonate, and (iii) five antibiotics (i.e., one for each plasmid and one under control of the genetically encoded system in plasmid 1) for producing products having at least some inhibitory activity on the chosen enzyme of plasmid 1, made by the combination of enzymes expressed by plasmids 2 and 3.

In some embodiments, a terpenoid operon pathway intenedeed for insertion into or already within plasmid 2, may be altered by swapping in a different gene for terpene synthases (i.e., in each row of FIG. 36, the metabolic pathway differs in the identity of the gene for a terpene synthase; when ADS or TXS are present, GGPPS is also present).

In FIGS. 41A, 41B, 41G, and 41D, for examples, we mutate (rather than swap) a single gene of a metabolic pathway: e.g. induce at least one mutation in a gene endocing amorphadiene synthase. After doing so, we show that a metabolic pathway can be mutated to generate a library of pathways, and that these pathways can be screened to identify pathways that generate more potent inhibitors of PTP1B than the unmutated parent pathway.

To summarize, we provided a demonstration that (i) the B2H system (detection operon) and (ii) a metabolic pathway for terpenoid biosynthesis can be combined within a host organisum to identify genes involved with production of small-molecules and evolve genes related to production of small-molecules that may be inhibitors that enable the microbial synthesis of PTP1B inhibitors.

In preferred embodiments, small-molecule products are derived from one general metabolic pathway (the mevalonate-dependent pathway for terpenoid biosynthesis from *Saccharomyces cerevisiae*), and one host organism (*Escherichia coli*). These small-molecule products produced as described herein, are contemplated for use as treatments of type 2 diabetes, obesity, and breast cancer, among other diseases.

Without being bound by theory, when a genetically encoded system for detecting the activity of a specified test enzyme is located within a host bacterium, a constitutive promoter expresses part A of the detection system (e.g. detection operon). So long as the phosphatase (or other test enzyme) expressed by part A is active, an expressed kinase enzyme, e.g. Src kinase, attaches a phosphate (P) group to the expressed second fusion protein comprising a substrate recognition domain (S) attached to a protein capable of recruiting RNA polymerase to DNA (e.g., the $RP_\omega$ subunit of RNA polymerase), and the phosphatase removes that phosphate group so that few molecules of phosphorylated fusion protein 2 stay bound to fusion protein 1 and, thus, few complexes between fusion proteins 2 and 1 form to initiate transcription of a gene of interest (GOI).

Thus, transcription of part B is off and the expression of a GOI is low, e.g. as observed when a GOI is a luminescent protein, so long as the placZ inducible promoter is not being induced. In this embodiment of an operon, the placZ inducible promoter is induced in order to allow the expression of a gene of interest in the absence of an inhibitor when not testing for inhibitor molecules.

However, in the presence of a small molecule that inhibits the phosphatase, a molecule either made endogenously from a metabolic pathway harbored by plasmids 2 and 3, or added to the growth media, then an excess of phosphorylated fusion protein 2 within the substrate binding region attaches to the substrate recognition domain of fusion protein 1 then when both are bound to the operator and the RB binding site then the GOI is expressed indicating the presence of a phosphatase inhibitor.

For practical purposes, it does not matter which fusion protein possesses a DNA-binding protein and which possesses a protein capable of recruiting RNA polymerase to DNA, so long as the DNA-binding protein constitutes part of one fusion protein and the protein that recruits RNA polymerase constitutes part of the other fusion protein, see FIG. 40, FIG. 10, for examples.

*E. coli* DH10B was used for molecular cloning and for preliminary analyses of terpenoid production; *E. coli* s1030[1] was used for luminescence studies and for experiments involving terpenoid-mediated selection (e.g., molecular evolution); and *E. coli* Bl21 was used for experiments involving the heterologous expression and subsequent purification of proteins. However, it is not intended to limit the host bacteria strain to these *E. coli* strains. Indeed, any bacteria strain that supports the expression of the operons, DNA sequences and plasmids as described herein may be used as a host bacteria strain.

In preferred embodiments, small molecule products are derived from one general metabolic pathway (the mevalonate-dependent pathway for terpenoid biosynthesis from *Saccharomyces cerevisiae*), and one host organism (*Escherichia coli*). These small molecule products produced as described herein, are contemplated for use as treatments of type 2 diabetes, obesity, and breast cancer, among other diseases.

A. Bacterial Two-Hybrid (B2H) Systems (Operons) for the Identification of Microbially Synthesizable Inhibitors of PTP1B.

In one embodiment, an application of the B2H system to the evolution of genes that enable the microbial synthesis of molecules that (i) inhibit PTP1B and (ii) may be identified (i.e., structurally characterized) with standard analytical methods. In brief, the B2H system links the inactivation of PTP1B to the expression of a gene for antibiotic resistance. Accordingly, when a strain of *E. coli* (or other host bacterium) harbors both (i) the B2H system and (ii) a metabolic pathway for terpenoid biosynthesis, it will survive in the presence of antibiotics when it produces terpenoids that inhibit PTP1B.

A bacterial two-hybrid (B2H) system as described herein comprises one embodiment of an operon as described herein. Data displayed on left side of the plot in FIG. 33D (i.e., p130cas [also called liras] and MidT substrates) is the same data displayed in FIG. 29A with the addition of providing more details of the B2H system in light of development.

Figure 41A:
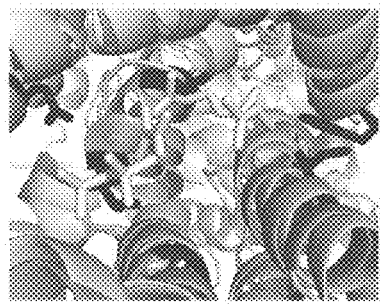
FIG. 41A depicts an exemplary strategy for the evolution of inhibitors of PTP1B.

We propose to use directed evolution to evolve new inhibitors; that is, we will manually introduce mutations into specific genes (or sets of genes) within a metabolic pathway to generate a library of metabolic pathways that can be screened alongside the B2H system. FIG. 41A describes a general approach to introduce mutations; Example C provides a very specific approach represented by FIG. 41A. To screen our library, we transform it into B2H-containing cells, and we grow them on plates containing various concentrations of spectinomycin; colonies that form on plates with high concentrations of spectinomycin contain a pathway capable of generating molecules that activate the B2H system (i.e., inhibit PTP1B). This pathway will not naturally evolve on its own. We can, thus, remove it from the first host cell, and transform it into another strain of E. coli to make high concentrations of inhibitors.

Embodiments of the system described herein enables the rapid identification of drug leads that can be readily synthesized in microbial hosts. It allows for a simultaneous solutions to two problems encountered during pharmaceutical development that are often examined separately 1) the identification of leads and 2) subsequent synthesis of those leads identified in 1).

Systems described herein have at least five uses:
1. Enables the identification of genes for proteins that generate inhibitors of the drug target. In brief, when the pathway for terpenoid biosynthesis generates target-inhibiting molecules, the cell survives at high antibiotic concentrations. By swapping out genes for terpene synthesizing and/or functionalizing enzymes, we can identify genes for enzymes that build such inhibitors.
2. Enables the construction of novel—and, perhaps, unnatural—inhibitors. By mutating the pathway for terpenoid biosynthesis, we can generate pathways that confer survival at high antibiotic concentrations. These pathways contain mutated (i.e., unnatural) genes and, thus, can generate inhibitor molecules not found in Nature.
3. Enables the construction of inhibitors that overcome drug resistance. Briefly, after building a strain that generates a target-inhibiting molecule, we can carry out two steps: (i) We can mutate the drug target until it becomes resistant to that inhibitor. (ii) We can mutate the metabolic pathway until it generates an inhibitor of the mutated drug target. In this way, we can both (i) predict drug-resistance mutations and (ii) address those mutations by generating new inhibitors that overcome them.
4. Enables the construction of inhibitors of protein tyrosine kinases. Using a selection strategy similar to that described in 3.ii, we can mutate a metabolic pathway until it generates an inhibitor of Src kinase.

B. A Genetically Encoded System that Links the Inhibition of a Protein Tyrosine Phosphatase to Cell Survival.

In one preferred embodiment, a genetically encoded system was developed and used, as described herein, for detecting the presence of a small-molecule inhibitor of the catalytic domain of a chosen enzyme, e.g. a drug target enzyme, while allowing the survival of a host cell in the presence of a selective growth media. In other words, when the genetically encoded system is part of an expression plasmid in E. coli.

In one embodiment, an exemplary drug target enzyme was chosen, e.g. protein tyrosine phosphatase enzyme, protein tyrosine phosphatase 1B (PTP1B), In one embodiment, the genetically encoded system is part of an expression plasmid. In one embodiment, the sensing operon is operably linked to a constitutive promoter for expression in E. coli.

FIG. 33A-E illustrates an embodiment of a genetically encoded system that links the activity of an enzyme to the expression of a gene of interest (GOI). Error bars in FIG. 33B-E denote standard deviation with n=3 biological replicates.

Figure 33A:
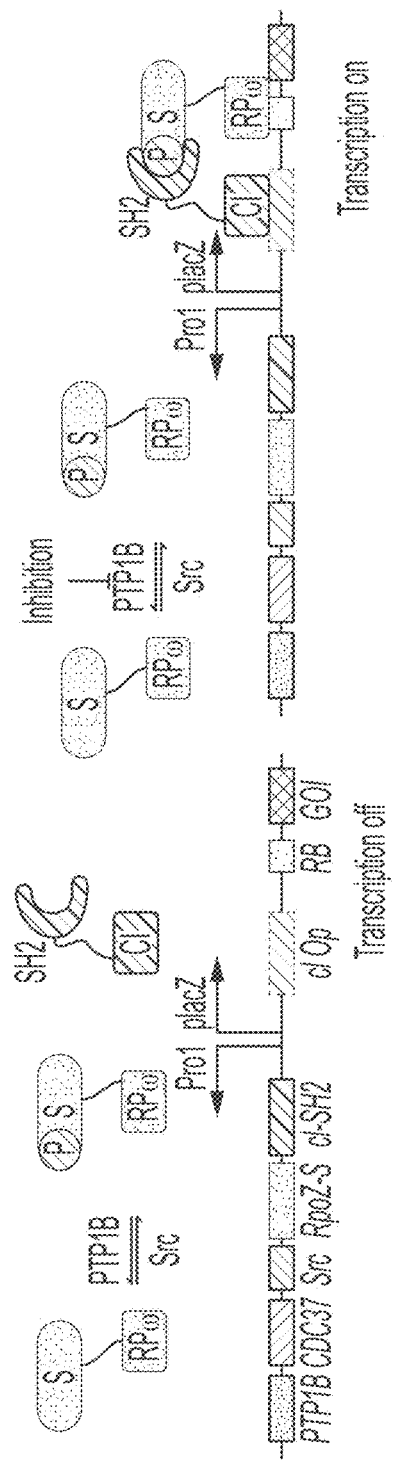
FIG. 33A-E illustrates an embodiment of a genetically encoded system that links the activity of an enzyme to the expression of a gene of interest (GOI). Error bars in FIG. 33B-E denote standard deviation with n=3 biological replicates.
Figure 33B:
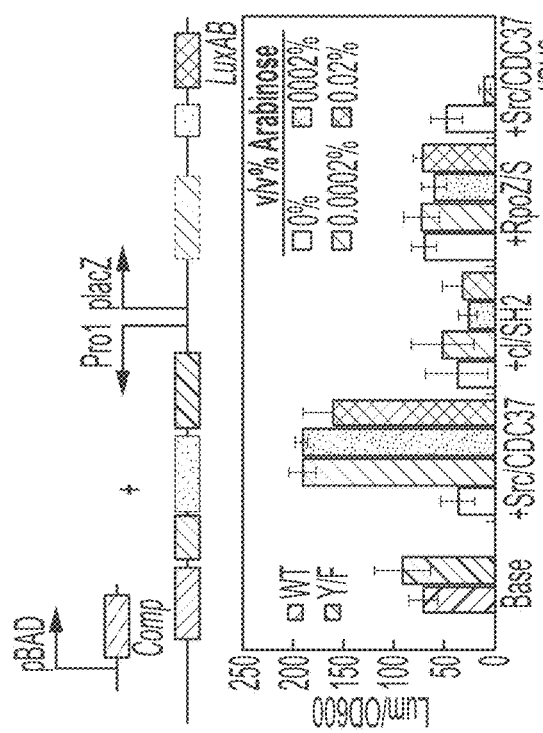
Figures 33C, 33D:
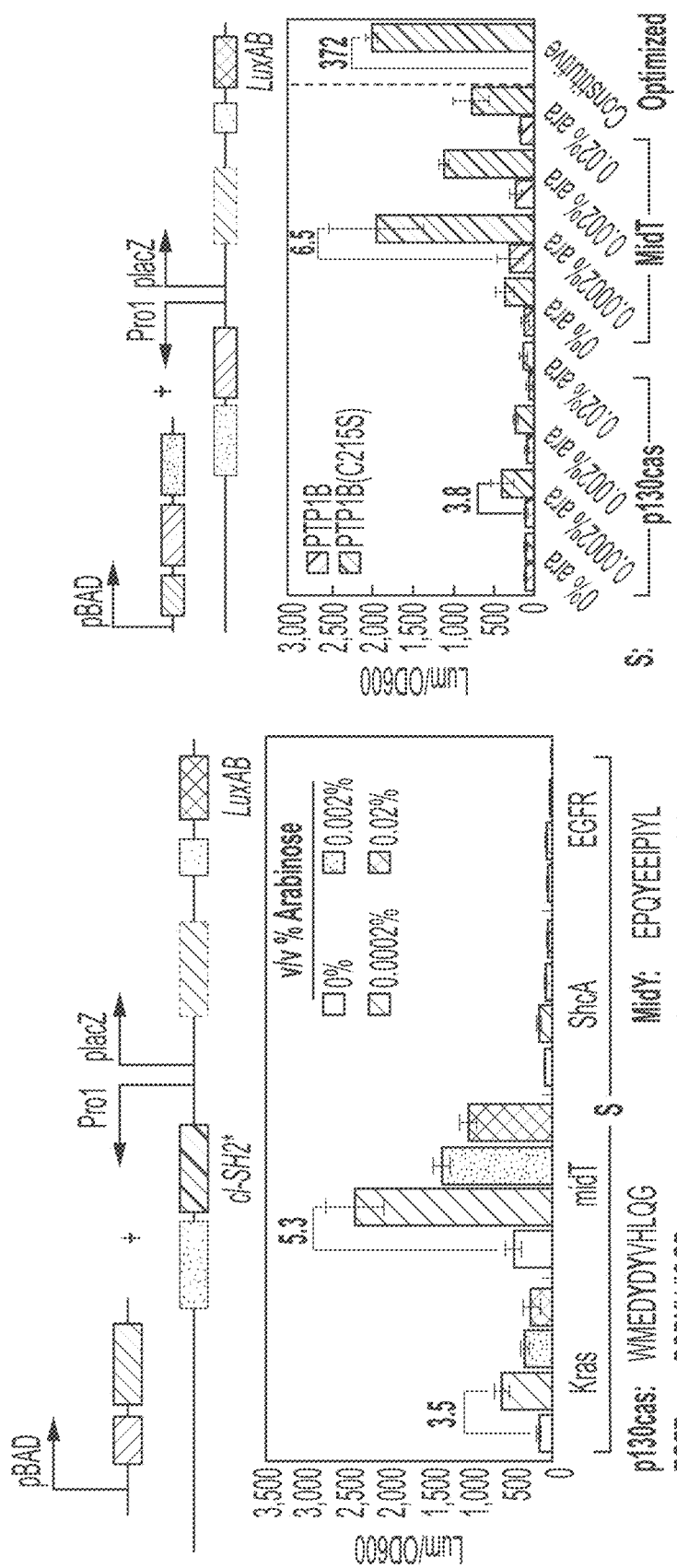
Figure 33E:
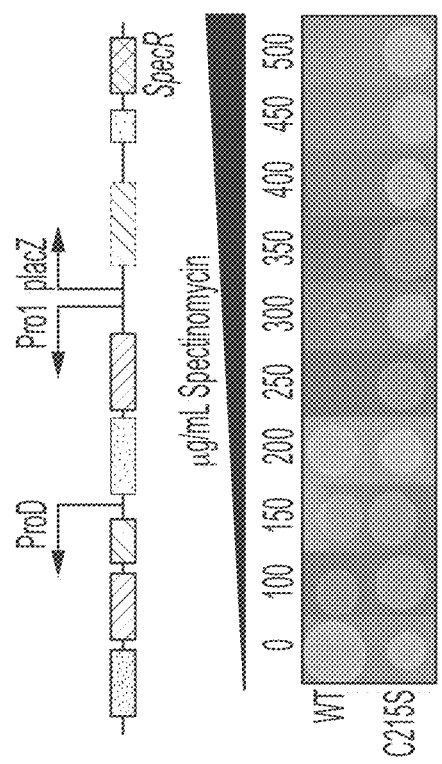

FIG. 33A illustrates an embodiment of a bacterial two-hybrid system that detects phosphorylation-dependent protein-protein interactions. Components include (i) a substrate domain fused to the omega subunit of RNA polymerase (yellow), (ii) an SH2 domain fused to the 434 phage cI repressor (light blue), (iii) an operator for 434cI (dark green), (iv) a binding site for RNA polymerase (purple), (v) Src kinase, and (vi) PTP1B. Src-catalyzed phosphorylation of the substrate domain enables a substrate-SH2 interaction that activates transcription of a gene of interest (GOI, black). PTP1B-catalyzed dephosphorylation of the substrate domain prevents that interaction; inhibition of PTP1B re-enables it. FIG. 33B refers to an embodiment of the two-hybrid system from FIG. 33A that (i) lacks PTP1B and (ii) contains luxAB as the GOI. We used an inducible plasmid to increase expression of specific components; overexpression of Src enhanced luminescence. FIG. 33C refers to an embodiment of the two-hybrid system from FIG. 33A that (i) lacks both PTP1B and Src and (ii) includes a "superbinder" SH2 domain (SH2*, i.e., an SH2 domain with mutations that enhance its affinity for phosphopeptides), a variable substrate domain, and LuxAB as the GOI. We used an inducible plasmid to increase expression of Src; luminescence increased most prominently for p130cas and MidT, suggesting that Src acts on both substrate domains. FIG. 33D refers to an embodiment of a two-hybrid system from FIG. 33C with one of two substrates: p130cas or MidT. We used a second plasmid to overexpress either (i) Src and PTP1B or (ii) Src and an inactive variant of PTP1B (C215S). The difference in luminescence between systems containing PTP1B or PTP1B(C215S) was greatest for MidT, suggesting that PTP1B acts on this substrate. Right: An optimized version of the two-hybrid system (with bb030 as the RBS for PTP1B) appears for reference. FIG. 33E displays the results of an exemplary growth-coupled assay performed using an optimized B2H including SH2*, a midT substrate, optimized promoters and ribosome binding sites (bb034 for PTP1B), and SpecR as the GOI. This system is illustrated at the top of the figure. Exemplary growth results demonstrate that inactivation of PTP1B enables strain of E. coli harboring this system to survive at high concentrations of spectinomycin (>250 µg/ml).

1. Sequential Optimization of a Two-Hybrid System with LuxAB as the GOI.

Phase 1: We examined two different promoters for Src in a system that lacked PTP1B. Phase 2: We examined two different ribosome binding sites (RBSs) for Src in a system that lacked PTP1B. Phase 3: We examined two different RBSs for PTP1B in a complete system. Note: In phases 1 and 2, the operon contains wild-type (WT) or non-phosphorylate-able (mutant, Y/F) versions of the substrate domain. In phase 3, the operon contains wild-type (WT) or catalytically inactive (mutant, C215S) version so PTP1B. See, FIG. 34.

Figure 34:
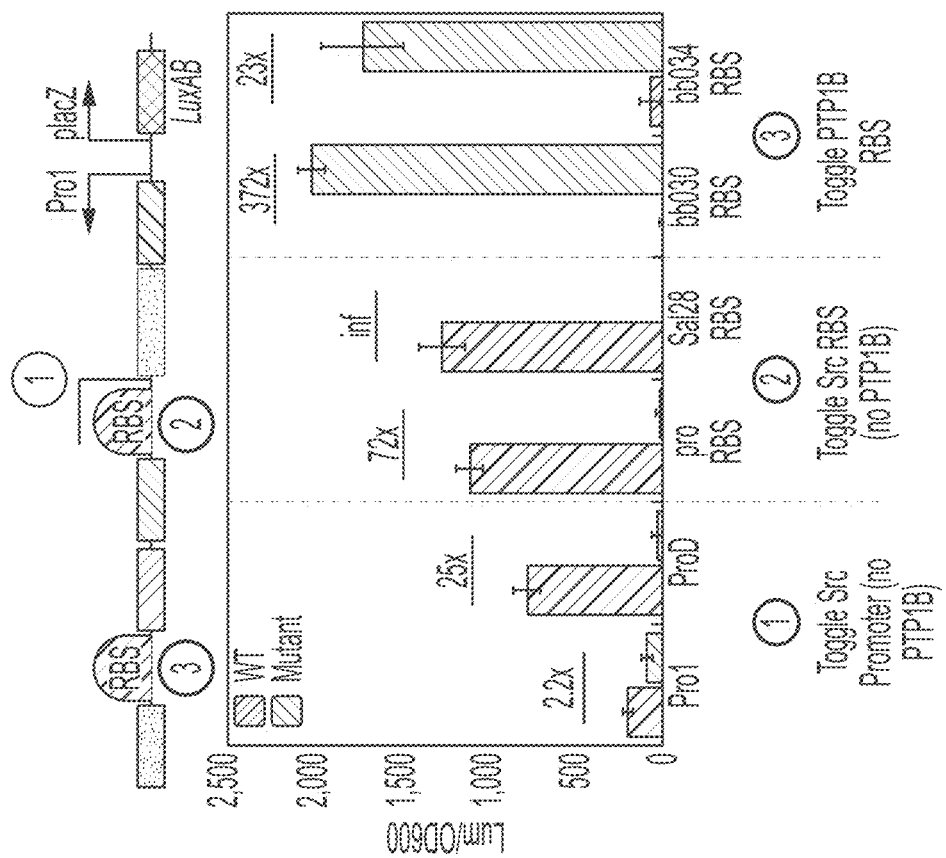
FIG. 34 illustrates exemplary experiments used to optimized the B2H system depicted in FIG. 33.

FIG. 34 illustrates exemplary experiments used to optimize the B2H system depicted in FIG. 33.

2. Comparing RB Sites.

We grew strains of *E. coli* harboring versions of the bacterial two-hybrid that contained different RBSs for PTP1B (bb034 or bb030) on various concentrations of spectinomycin (left to right) and plated them on various concentrations of spectinomycin (top to bottom). We used bb034 for one emboidment of an "optimized" two-hybrid system shown in FIG. 33E. See, FIG. 35.

Figure 35:
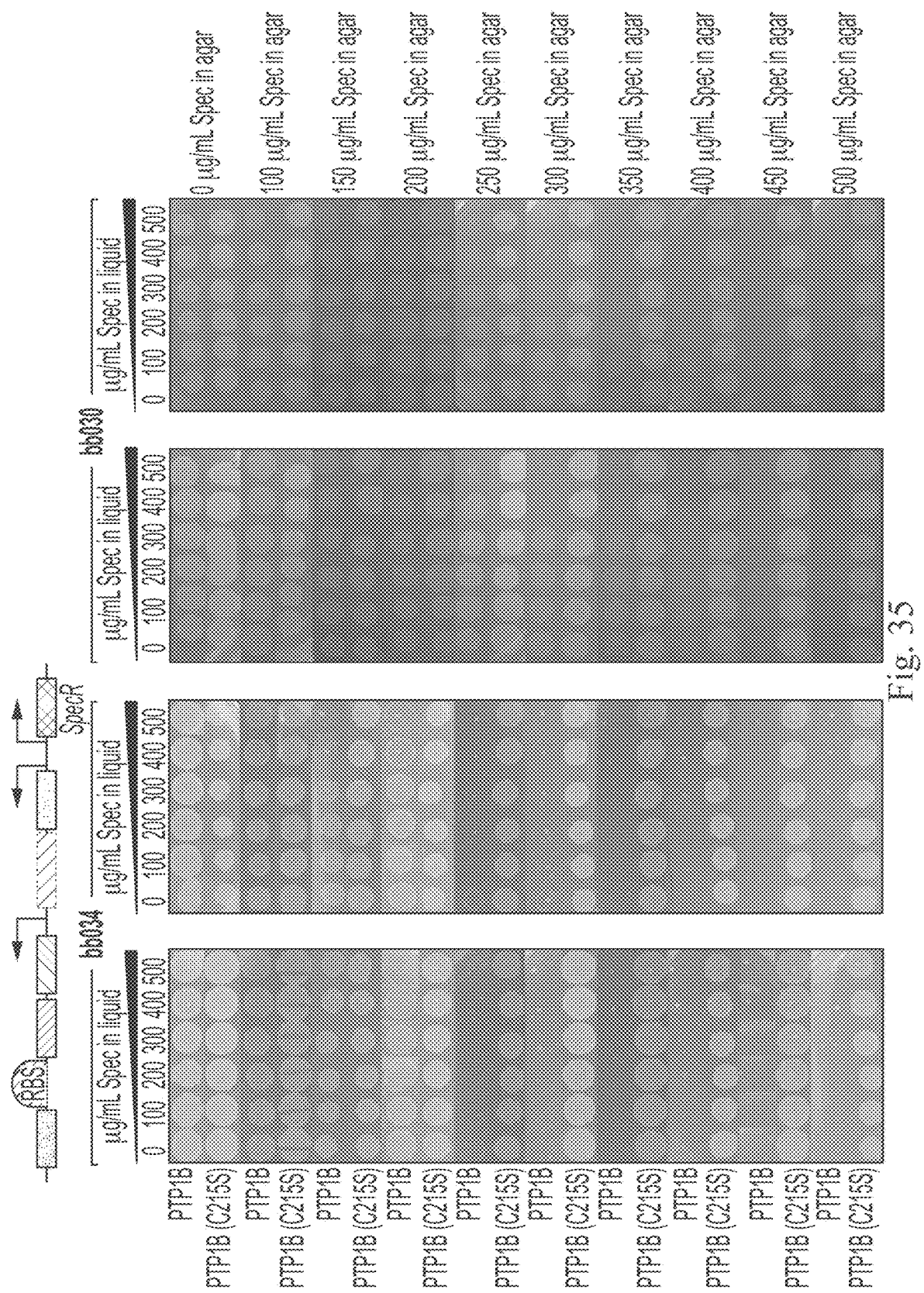
FIG. 35 illustrates exemplary experiments used to optimize the B2H system depicted in FIG. 33 for growth-coupled assays.

FIG. 35 FIG. 3 illustrates exemplary experiments used to optimize the B2H system depicted in FIG. 33 for growth-coupled assays.

Rice, P., Longden, L. & Bleasby, A. EMBOSS: The European Molecular Biology Open Software Suite. *Trends Genet.* 16, 276-277 (2000).

C. Biosynthesis of PTP1B-Inhibiting Terpenoids Enables Cell Survival.

When pTS contains ADS or GHS, it does not contain GGPPS; when pTS contains ABS or TXS, it also contains GGPPS; $ABS_{D404A/D621A}$ refers to a catalytically inactive variant of ABS; and B2H* contains PTP1B(C215S). ADS and, marginally, ABS enabled survival in the presence of spectinomycin, a result suggestive of the ability of these to terpene synthases to generate inhibitors of PTP1B.

Figure 36A:
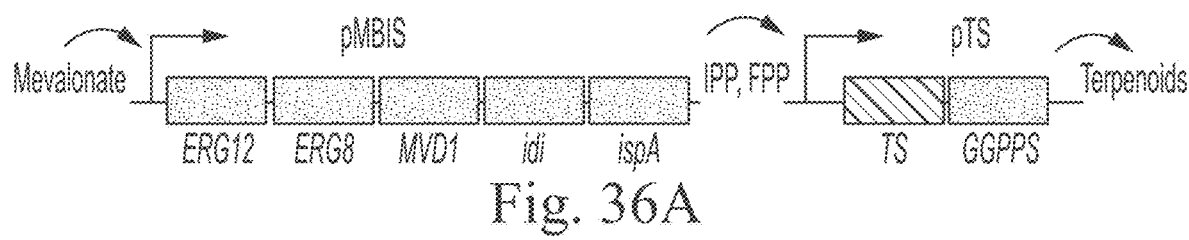
FIG. 36A-C depicts an exemplary metabolic pathway for the biosynthesis of terpenoids.
Figure 36B:
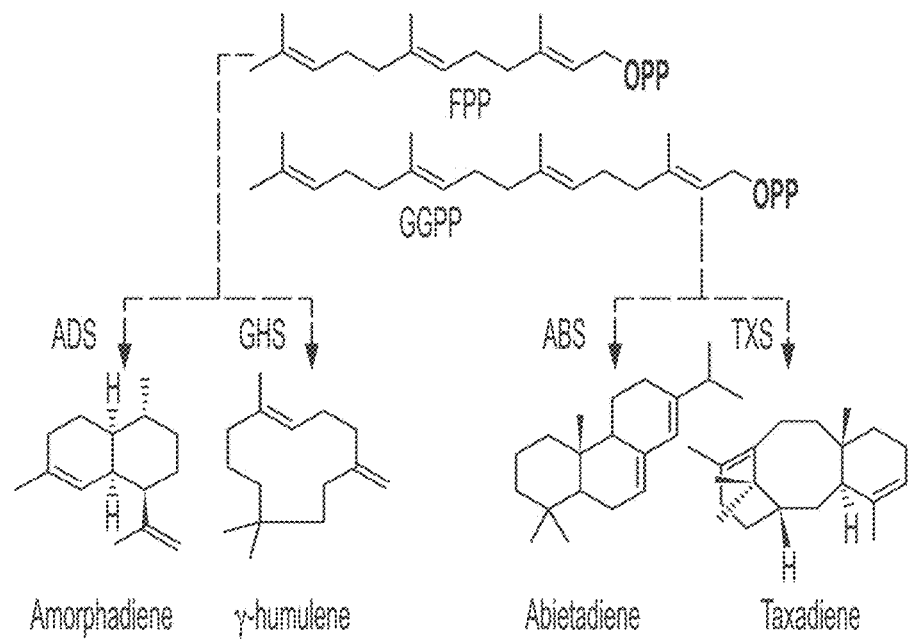
Figure 36C:
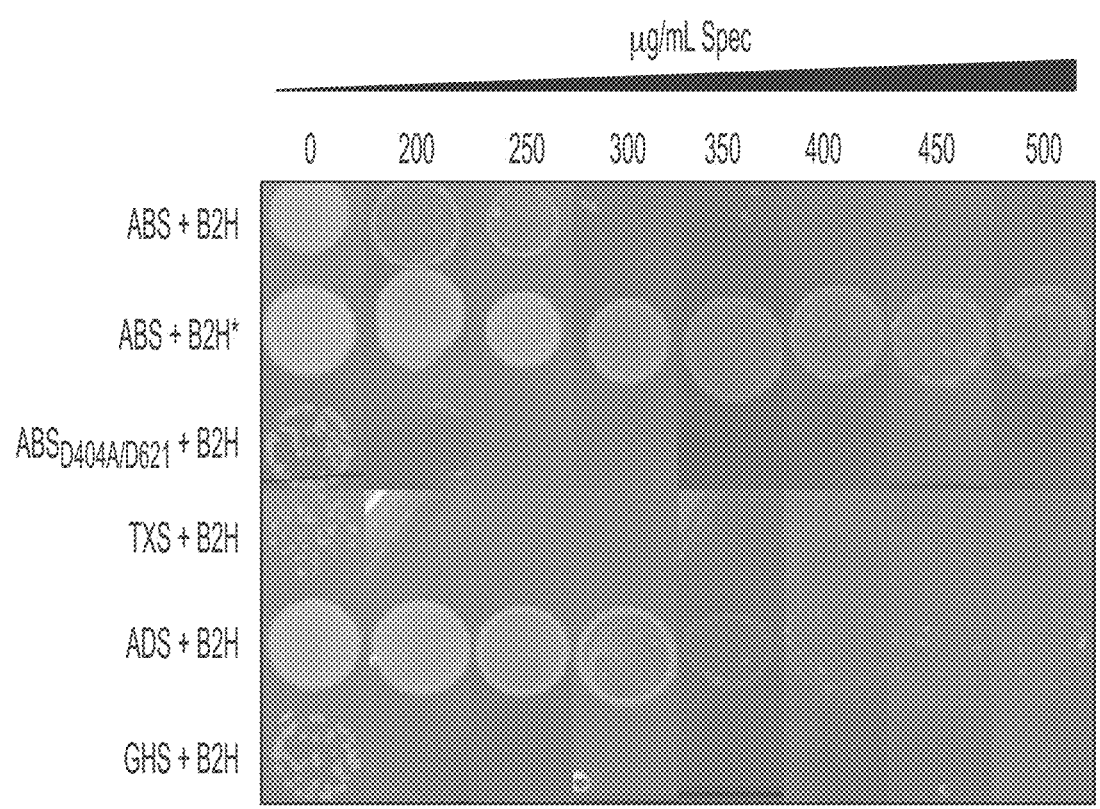

FIG. 36A-C FIG. 4 I shows an illustration of an operon (FIG. 36A) used for providing exemplary results during biosynthesis of PTP1B-inhibiting terpenoids FIG. 36B enabling cell survival FIG. 36C.

FIG. 36A-C FIG. 4 depicts an exemplary metabolic pathway for the biosynthesis of terpenoids.

FIG. 36A depicts a plasmid-borne pathway for terpenoid biosynthesis: (i) pMBIS, which harbors the mevalonate-dependent isoprenoid pathway of *S. cerevisiae*, converts mevalonate to isopentyl pyrophosphate (IPP) and farnesyl pyrophosphate (FPP). (ii) pTS, which encodes a terpene synthase (TS) and, when necessary, a geranylgeranyl diphosphate synthase (GPPS), converts IPP and FPP to sesquiterpenes and/or diterpenes.

FIG. 36B depicts exemplary terpene synthases: amorphadiene synthase (ADS) from *Artemisia annua*, γ-humulene synthase (GHS) from *Abies grandis*, abietadiene synthase (ABS) from *Abies grandis*, and taxadiene synthase (TXS) from *Taxus brevifolia*.

FIG. 36C shows the results of an exemplary growth-coupled assay of strain of *E. coli* that contains both (i) an embodiment of the optimized bacterial two-hybrid (B2H) system (i.e., the B2H system from FIG. 33E) and (ii) an embodiment of a pathway for terpenoid biosynthesis (i.e., the pathway from FIG. 35A).

Briefly, we grew strains of *E. coli* that harbored (i) the same pathway for producing linear isoprenoid precursors and (ii) a different plasmid encoding a terpene synthase (pTS). The pTS plasmid contained on of the following: (i) amorphadiene synthase (ADS) from *Artemisia annua*, (ii) γ-humulene synthase (GHS) from *Abies grandis*, (iii) abietadiene synthase (ABS) from *Abies grandis* in operable combination with a geranylgeranyl diphosphate synthase (GGPPS, (iv) taxadiene synthase (TXS) from *Taxus brevifolia* in operable combination with a GGPPS, (v) a inactive variant of ABS (i.e., $ABS_{xx}$, which corresponds to $ABS_{D404A/D621A}$), or (vi) the L450Y mutant of GHS. After growing these strains, we compared the ability of their products to inhibit PTP1B by carrying out the following steps: (i) We used a hexane overlay to extract hydrophobic products (e.g., terpene-like products) from each culture, we then dried the products in a rotary evaporator, we dissolved the dried extract in dimethyl sulfoxide (DMSO), and we measured PTP1B-catalyzed hydrolysis of p-nitrophenyl phosphate (pNPP) in the presence and absence of extract-containing DMSO. We note: The L450Y mutant of GHS was included in our analysis because the wild-type form of GHS does not permit B2H-mediated growth in the presence of an antibiotic, but our preliminary data indicate that the L450Y mutant of GHS does permit such growth. Accordingly, we hypothesized that this mutant produced a molecule that is a stronger inhibitor of PTP1B than the molecules generated by wild-type GHS. See, FIG. 37A-C Demonstration of differential inhibition by structurally distinct terpenoids.

Figure 37A:
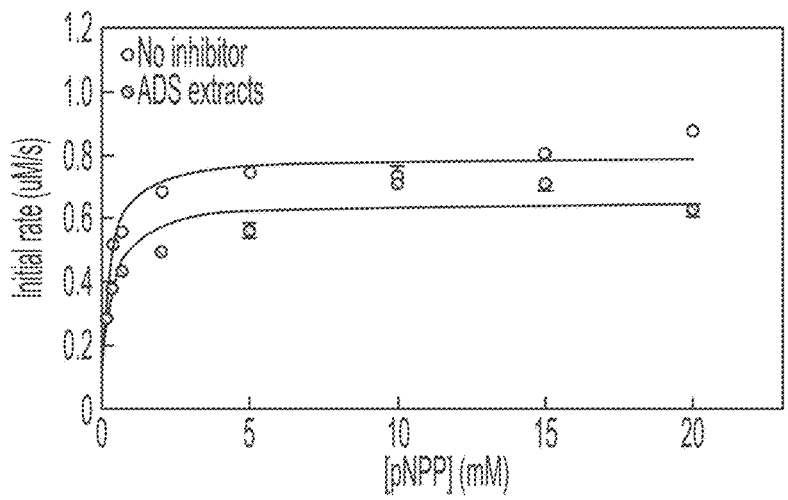
FIG. 37A-C provides an exemplary analysis of the inhibitory effects of terpenoids generated by different strains of E. coli.
Figure 37B:
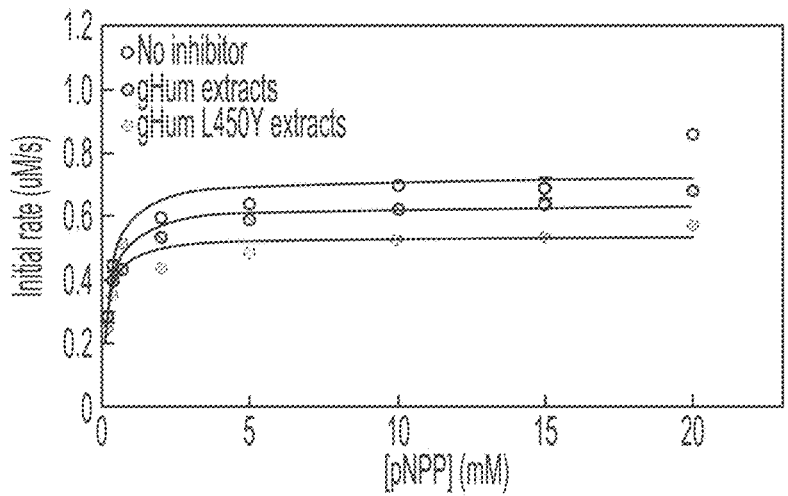
Figure 37C:
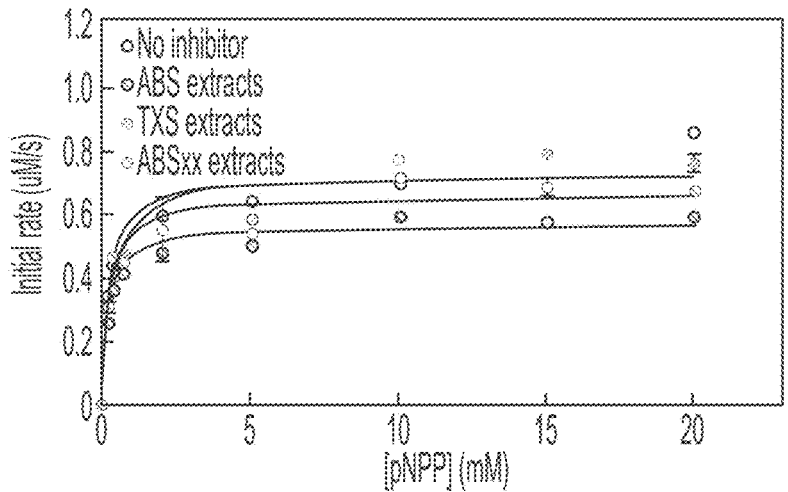

In examining FIG. 37A-C, we observed a trend: Extracts from strains containing terpene synthases that confer resistance to high concentrations of antibiotic (see FIG. 36) where ADS and $GHS_{L450Y}$ were more inhibitory than extracts from strains that did not confer resistance, e.g., TXS and $ABS_{xx}$. We note: strains containing ADS and GHS also included the optimized bacterial two-hybrid (B2H) system, but selection was not performed in the experiments used to product terpenoids for the experiments described by these figures.

FIG. 37A-C provides an exemplary analysis of the inhibitory effects of terpenoids generated by different strains of *E. coli*.

FIG. 37A depicts the results of our analysis of the inhibitory effect of DMSO containing (i) no inhibitor and (ii) extracted compounds from the culture broth of the ADS-containing strain. FIG. 37B depicts the results of our analysis of the inhibitory effect of DMSO containing (i) extracted compounds from the culture broth of the GHS-containing strain (gHUM) or (ii) extracted compounds from the culture broth of the strain including the L450Y mutant of GHS. FIG. 37C depicts the results of our analysis of the inhibitory effect of DMSO containing (i) no inhibitor, (ii) extracted compounds from the culture broth of the ABS-containing strain, (iii) extracted compounds from the culture broth of the TXS-containing strain, and (iv) extracted compounds from the culture broth of the train strain containing a catalytically inactive variant of ABS.

Briefly, we grew strains of *E. coli* containing both (i) the optimized bacterial two-hybrid system and (ii) a terpenoid pathway with mutants γ-humulene synthase (GHS; 1 mutant/cell) on varying concentrations of spectinomycin. Above: product profiles of strains with GHS mutants that conferred survival at high antibiotic concentrations. See, FIG. 38.

Figure 38:
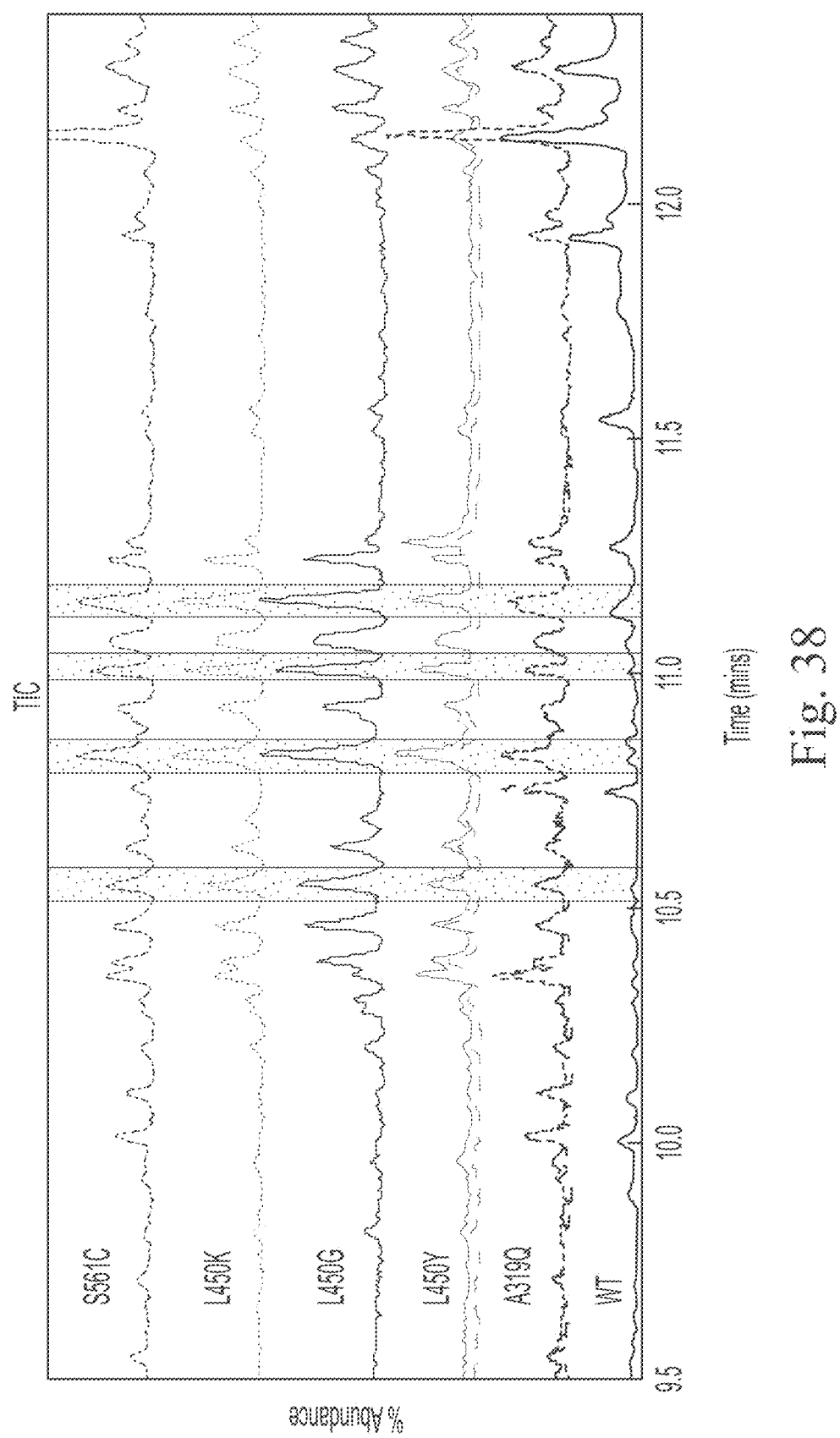
FIG. 38 shows exemplary analysis of the product profiles of mutants of GHS that enabled growth in the presence of spectinomcyin.

FIG. 38 shows exemplary analysis of the product profiles of mutants of GHS that enabled growth in the presence of spectinomcyin.

In brief, we constructed versions of the bacterial two-hybrid system that include SH2*, the midT substrate, optimized promoters and ribosome binding sites, SpecR, and alternative PTPs: the catalytic domain of PTPN6 (e.g., SHP-1) and PTP1B405 (the full-length version of PTP1B). Note: these systems are identical to the B2H system depicted in FIG. 33E, except they possess only one of the following PTP genes: PTP1B (as in FIG. 33E), PTPN6 (different from FIG. 33E), or full-length PTP1B. Inactivation of the catalytic domain of both PTPN6 and the full-length PTP1B enabled strains of *E. coli* harboring corresponding operons to survive at high concentrations of spectinomycin (>400

µg/ml). To extend our operon to other PTPs, we plan on modifying the substrate, SH2, and/or kinase domains. See, FIG. 39.

Figure 39:
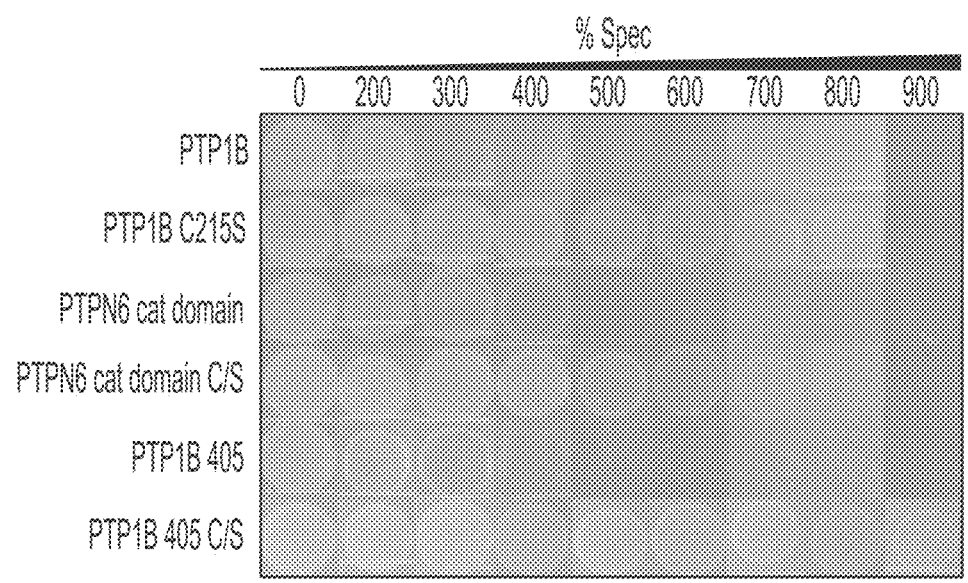
FIG. 39 shows an analysis of an exemplary B2H systems that link the inhibition of other PTPs to cell survival.

FIG. 39 An analysis of exemplary B2H systems that link the inhibition of other PTPs to cell survival.

We also generated versions of the bacterial two-hybrid system that include SH2*, the midT substrate, optimized promoters and ribosome binding sites, SpecR, and alternative PTPs: the catalytic domain of PTPN6 (e.g., SHP-1) and PTP1B405 (the full-length version of PTP1B). Inactivation of the catalytic domain of PTPN6 and the full-length PTP1B enabled strains of E. coli harboring corresponding operons to survive at high concentrations of spectinomycin (>400 µg/ml). To extend our operon to other PTPs, we plan on modifying the substrate, SH2, and/or kinase domains.

FIG. 40A-E depicts exemplary embodiments of genetically encoded systems that link the activity of an enzyme to the expression of a gene of interest, and the application of those embodiments to (i) the prediction of resistance mutations, (ii) the construction of inhibitors that combat resistance mutations, and (ii) the evolution of inhibitors of kinases.

Figure 40E:
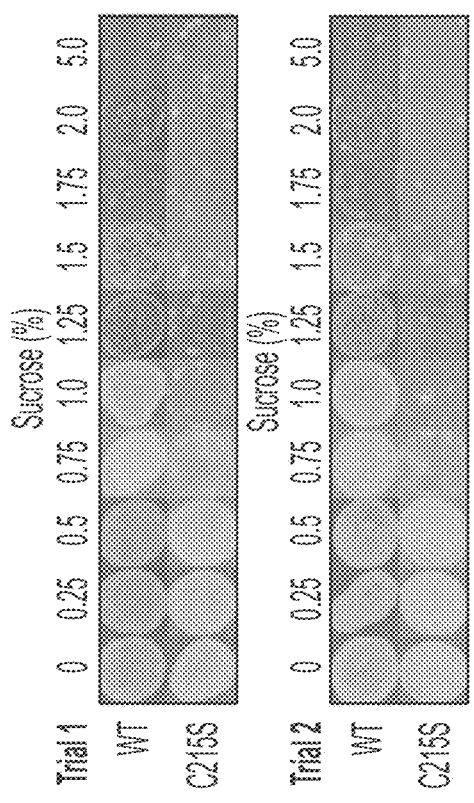
Figure 40D:
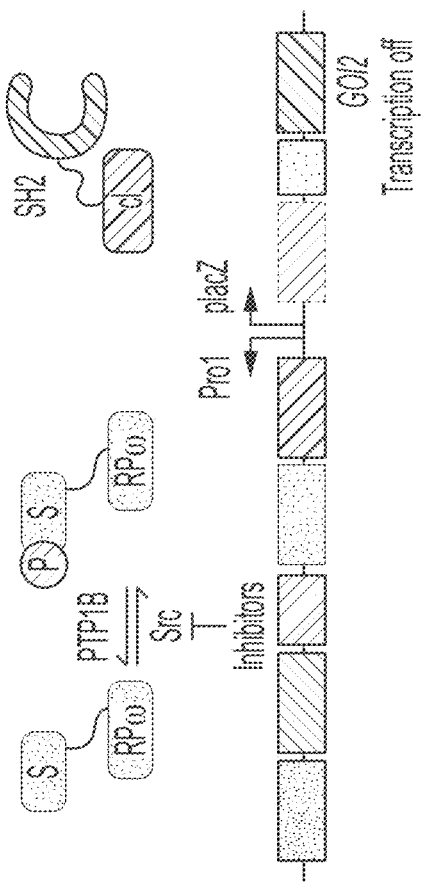

FIG. 40A depicts an exemplary first step in examining potential resistance mutations. By evolving a metabolic pathway to produce molecules that inhibit a known drug target (e.g., PTP1B); these molecules will permit expression of a gene of interest (GOI) that confers survival in the presence of a selection pressure (e.g., the presence of spectinomycin, an antibiotic). FIG. 40B depicts an exemplary second step in examining potential resistance mutations. In a second strain of E. coli, we will replace the original gene of interest with a second (GOI2) that confers conditional toxicity (e.g., SacB, which converts sucrose to levan, a toxic product); we will evolve the drug target to become resistant to the endogenous inhibitors, while still retaining its activity. This mutant will prevent expression of the toxic gene. FIG. 40C depicts an exemplary third step in combating resistance mutations. In a third strain of E. coli, we will evolve a metabolic pathway that produces molecules that inhibit the mutated drug target. In this way, we will both predict—and, through our second evolved pathway, address—mutations that might cause resistance to terpenoid-based drugs. We note: FIG. 40A-40C describe the use of our genetically encoded system to evolve inhibitors, but the steps 2 and 3 could be used to predict mutations that permit resistance to endogenously supplied inhibitors and, subsequently, to identify new endogenously supplied inhibitors that might combat that resistance. FIG. 40D depicts an exemplary genetically encoded system that detects inhibitors of an Src kinase. In brief, Src activity enables expression of a toxic gene (GOI2); inhibition of Src, in turn, would confer survival.

One embodiment of a configuration of the B2H architecture that enables survival PTP1B is active, that is, when the activity of Src kinase is successfully canceled out. In the absence of PTP1B, this configuration could be used to evolve inhibitors of Src kinase such an inhibitor would act similarly to PTP1B by preventing the phosphorylation of the substrate domain (as shown in FIG. 40E). Src kinase is a validated drug target; tyrosine kinases are targets of over 40 FDA-approved drugs.

FIG. 40E demonstrates one embodiment of a roof of principle for the B2H system describe in FIG. 40B. The system shown here includes two GOIs: SpecR and SacB. Expression of the GOIs confers survival in the presence of spectinomycin; expression of the GOIs causes toxicity in the presence of sucrose. The images depict the results of a growth-coupled assay performed on a strain of E. coli in the presence of various concentrations of sucrose. The strain harboring an active form of PTP1B (WT) grows better at high sucrose concentrations that the strain harboring an inactive form of PTP1B (C215S).

FIG. 41A depicts an exemplary strategy for the evolution of inhibitors of PTP1B.

Figure 41B:
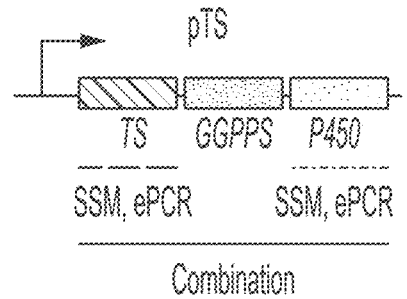
FIG. 41B depicts an exemplary strategy for introducing diversity into libraries of metabolic pathways: An iterative combination of SSM of key sites on a terpene synthase (as in a), error-prone PCR (ePCR) of the entire terpene synthase gene, SSM of sites on a terpene-functionalizing enzyme (e.g., P450), and ePCR of the entire terpene-functionalizing enzyme.
Figure 41C:
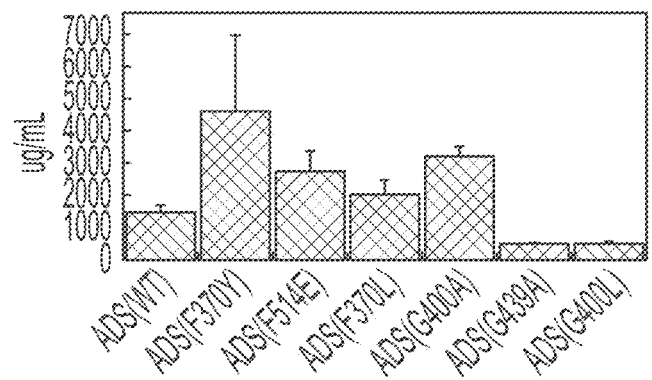
FIG. 41C depicts an exemplary quantification the total terpenoids present in DMSO samples with extracts of various TS-containing strains. In brief, we performed site-saturation mutagenesis of six sites on ADS (analogous to the sites shown in FIG. 41A); we plated the SSM library on agar plates containing different concentrations of spectinomycin; we picked colonies that grew on a plate containing a high concentration (800 µg/ml) of spectinomycin and used each colony to inoculate a separate culture; we used a hexane overlay to extract the terpenoids secreted into each culture broth; we dried the hexane extract in a rotary evaporator and re-suspended the solid in DMSO; and we used a GC-MS to quantify the total amount of terpenoids present in the DMSO.

FIG. 41A depicts an exemplary structural analysis used to identify targets for mutagenesis in the active sites of terpene synthases. It shows an alignment of the class I active site of ABS (gray, PDB entry 3s9v) and TXS (blue, PDB entry 3p5r) with the locations of sites targeted for site-saturation mutagenesis (SSM) highlighted on ABS (red). A substrate analogue (yellow) of TXS appears for reference. FIG. 41B depicts an exemplary strategy for introducing diversity into libraries of metabolic pathways: An iterative combination of SSM of key sites on a terpene synthase (as in a), error-prone PCR (ePCR) of the entire terpene synthase gene, SSM of key sites on a terpene-functionalizing enzyme (e.g., P450), and ePCR of the entire terpene-functionalizing enzyme. FIG. 41C depicts an exemplary quantification the total terpenoids present in DMSO samples with extracts of various TS-containing strains. In brief, we performed site-saturation mutagenesis of six sites on ADS (analogous to the sites shown in a); we plated the SSM library on agar plates containing different concentrations of spectinomycin; we picked colonies that grew on a plate containing a high concentration (800 µg/ml) of spectinomycin and used each colony to inoculate a separate culture; we used a hexane overlay to extract the terpenoids secreted into each culture broth; we dried the hexane extract in a rotary evaporator and re-suspended the solid in DMSO; and we used a GC-MS to quantify the total amount of terpenoids present in the DMSO.

"ADS WT", "ADS F514E", "ADS F370L", "ADS G400A", "ADS G439A", and "ADS G400L" describe mixtures of molecules generated by strains of E. coli harboring mutants of amorphadiene synthase (ADS). The labels describe the mutant: "G439A" corresponds to a mutant of abietadiene synthase in which glycine 439 has been mutated to alanine, and so on. In future work, we plan on (i) purifying different terpenoids from these mixtures, (ii) assessing their inhibitory effect on PTP1 B in vitro, (iii) assaying their inhibitory effect on other PTPs (notably TC-PTP and PTPN11) in vitro, and (iv) assaying their influence on mammalian cells. See, FIG. 41D.

Figure 41D:
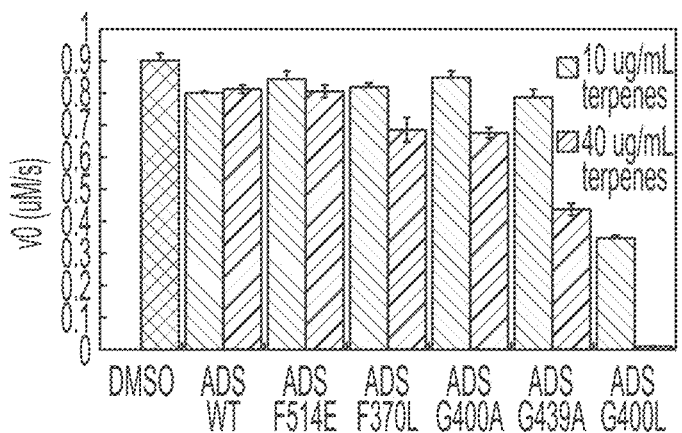
FIG. 41D depicts an exemplary analysis of the inhibitory effect of various extracts on PTP1B. In brief, the figure shows initial rates of PTP1B-catalyzed hydrolysis of p-nitrophenyl phosphate (pNPP) in the presence of terpenoids quantified in FIG. 41C. Two mutants of ADS (G439A and G400L) generate particularly potent inhibitors of PTP1B.

FIG. 41D depicts an exemplary analysis of the inhibitory effect of various extracts on PTP1B. In brief, the figure shows initial rates of PTP1B-catalyzed hydrolysis of p-nitrophenyl phosphate (pNPP) in the presence of terpenoids quantified in FIG. 41C. Two mutants of ADS (G439A and G400L) generate particularly potent inhibitors of PTP1B.

Figure 42:
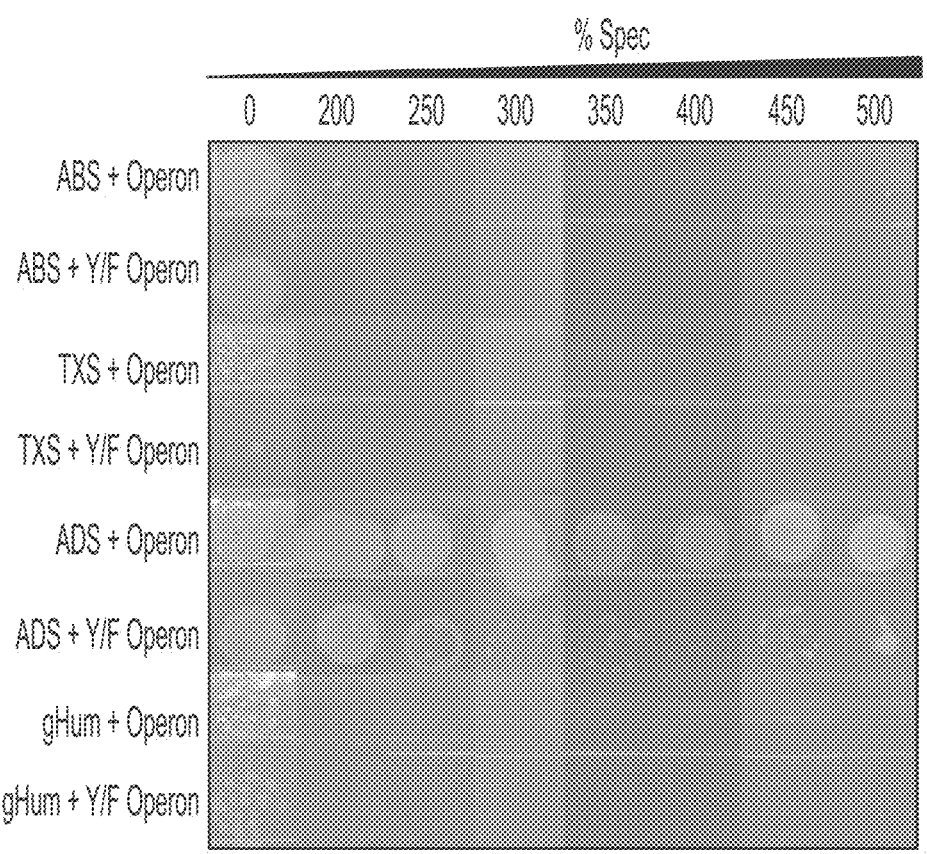
FIG. 42 depicts an exemplary analysis of the link between B2H activation and cell survival. An exemplary strain of *E. coli* that contains both (i) the optimized bacterial two-hybrid (B2H) system (FIG. 33E) and (ii) the terpenoid pathway depicted in FIG. 36A. Note: pTS includes GGPPS only when ABS or TXS are present; the "Y/F" operon corresponds to a B2H system in which the substrate domain cannot be phosphorylated. Survival at high concentrations of spectinomycin requires activation of the B2H system (i.e., phosphorylation of the substrate domain, a process facilitated by inhibition of PTP1B).

FIG. 42 depicts an exemplary analysis of the link between B2H activation and cell survival. An exemplary strain of E. coli that contains both (i) the optimized bacterial two-hybrid (B2H) system (FIG. 33E) and (ii) the terpenoid pathway depicted in FIG. 36A. Note: pTS includes GGPPS only when ABS or TXS are present; the "Y/F" operon corresponds to a B2H system in which the substrate domain cannot be phosphorylated. Survival at high concentrations of spectinomycin requires activation of the B2H system (i.e., phosphorylation of the substrate domain, a process facilitated by inhibition of PTP1B).

Figure 43:
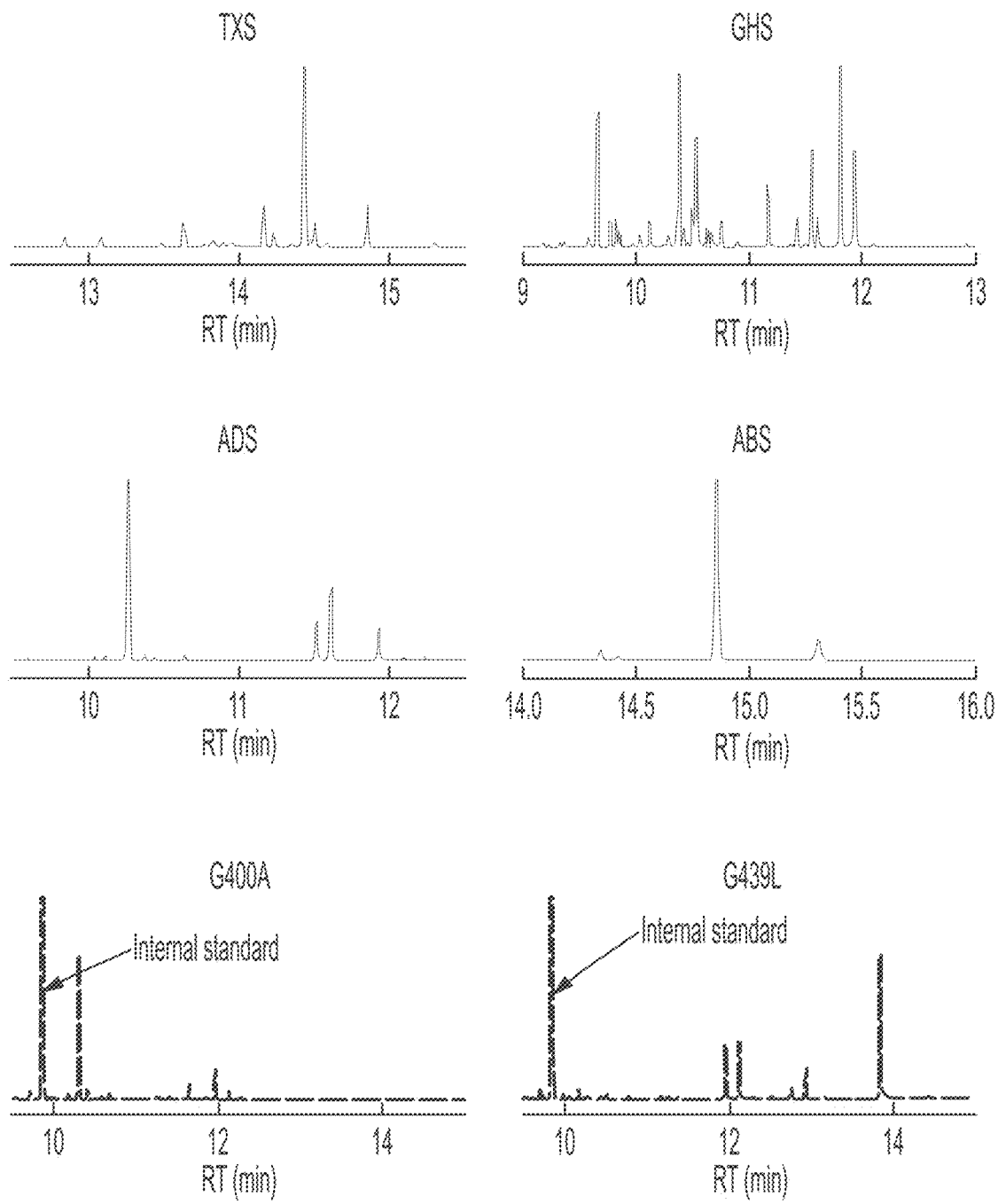
FIG. 43 provides exemplary product profiles of strains of *E. coli* harboring various terpene synthases. For this figure, the strain of *E. coli* harbored (i) the optimized B2H system (FIG. 33E) and (ii) the terpenoid pathway (FIG. 36A). The pathways corresponding to each profile differ only in the composition of the pTS plasmid, which contains TXS (taxadiene synthase from *Taxus brevifolia* and a geranylgeranyl diphosphate synthase from *Taxus Canadensis*); GHS (γ-humulene synthase from *Abies grandis*); ADS (amorphadiene synthase from *Artemisia annua*); ABS (abietadiene synthase from *Abies grandis* and a geranylgeranyl diphosphate synthase from *Taxus Canadensis*); G400A (the G400A mutant of amorphadiene synthase from *Artemisia annua*); and G439L (the G439L mutant of amorphadiene synthase from *Artemisia annua*). Note that the two mutants of ADS yield different product profiles than the wild-type enzyme (ADS); our resuls indicate that products generated by these two mutants are more inhibitory than those generated by the wild-type enzyme (FIG. 41E).

FIG. 43 provides exemplary product profiles of strains of E. coli harboring various terpene synthases. For this figure, the strain of E. coli harbored (i) the optimized B2H system (FIG. 33E) and (ii) the terpenoid pathway (FIG. 36A). The pathways corresponding to each profile differ only in the composition of the pTS plasmid, which contains TXS (taxadiene synthase from *Taxus brevifolia* and a geranylgeranyl diphosphate synthase from *Taxus Canadensis*); GHS (γ-humulene synthase from *Abies grandis*); ADS (amorphadiene synthase from *Artemisia annua*); ABS (abietadiene synthase from *Abies grandis* and a geranylgeranyl diphosphate synthase from *Taxus Canadensis*); G400A (the G400A mutant of amorphadiene synthase from *Artemisia annua*); and G439L (the G439L mutant of amorphadiene synthase from *Artemisia annua*). Note that the two mutants of ADS yield different product profiles than the wild-type enzyme (ADS); our resuls indicate that products generated by these two mutants are more inhibitory than those generated by the wild-type enzyme (FIG. 41E).

D. Identification of Sites for Site Saturation Mutagenesis (SSM).

The active sites of terpene synthases and cytochrome P450s contain constellations of amino acids that guide catalysis in two ways: (i) They control the conformation space available to reacting substrates, and (ii) they alter the organization of water that surrounds substrates[8-10]. We identified "plastic" residues likely to modulate these attributes in the class I active sites of terpene synthase by carrying out the following steps: (i) We aligned the crystal structure of ABS with the crystal structure of TXS. (ii) We selected all residues within 8 angstoms of the substrate analog (2-fluoro-geranylgeranyl diphosphate) of the class I active site of TXS, and we identified a subset of sites that differed between ABS and TXS. (iii) We aligned the sequences of ABS, $$S = \frac{\sigma_V^2}{n_v} + \frac{\sigma_{HW}^2}{n_{HW}}$$

GHS, delta-selenine synthase (DSS), and epi-isozizaene synthase (EIS). (iv) We used Eq. 51 to score each site based on its variability in size and hydrophilicity across the five enzymes analyzed. In this equation, $\sigma_V^2$ is the variance in volume, $\sigma_{HW}^2$ is the variance in Hopp-Woods index, and $n_v$ and $n_{HW}$ are normalization factors (based on the highest variances measured in this study). (v) We ranked each site according to S and selected the six highest-scoring sites. We note: For this analysis, we chose ABS and TXS because they are structurally similar enzymes (i.e., both possess α, β, and γ domains) with crystal structures; we chose GHS, DSS, and EIS because they have been shown to exhibit mutation-responsive product profiles.

FIG. 44A-D provides exemplary structural and sequence-based evidence that supports the extension the B2H system to other protein tyrosine phosphatases (PTPs).

Figures 44A, 44B:
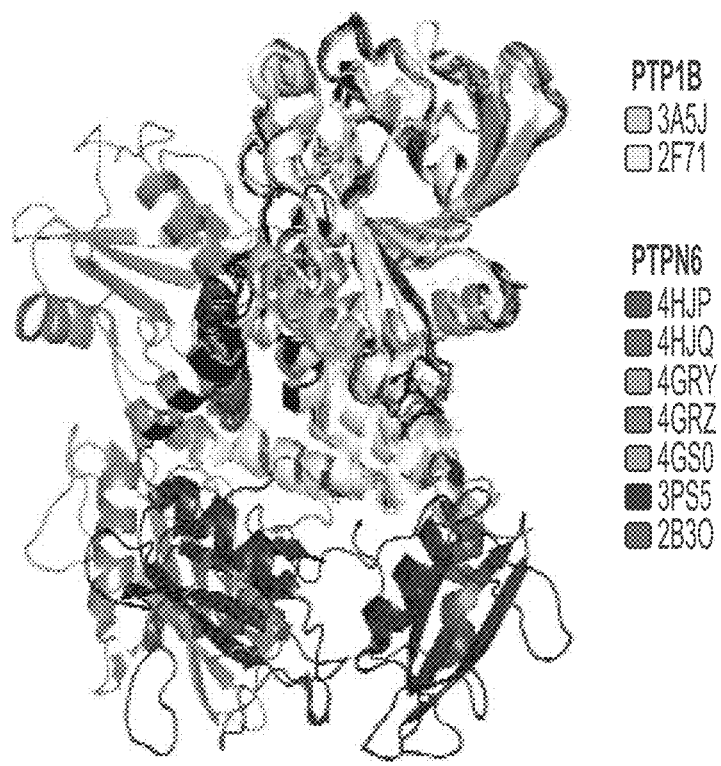

FIG. 44A provides an exemplary structural alignment PTP1B and PTPN6, two PTPs that are compatible with the B2H system (see FIGS. 1e and 7 of Update A for evidence of compatibility). We used the align function of PyMol to align each structure of PTPN6 with either (i) the ligand-free (3A5J) or (ii) ligand-bound (2F71) structure of the catalytic domain of PTP1B. The align function carries out a sequence alignment followed by a structural superposition and, thus, effectively aligns the catalytic domains of both proteins. FIG. 44B provides an exemplary structural comparison of PTP1B and PTPN6; the root-mean-square deviations (RMSD) of aligned structures of PTP1B and PTPN6 range from 0.75 to 0.94 Å. FIG. 44C proves an exemplary sequence alignment of the catalytic domains of PTP1B and PTPN6 (EMBOSS Needle[1]). FIG. 44D provides an exemplary sequence comparison of the catalytic domains of PTP1B and TPPN6. The sequences share 34.1% sequence identity and 53.5% sequence similarity. In summary, the results of this figure indicate that our B2H system can be readily extended to PTPs that possess catalytic domains that are (i) structurally similar to the catalytic domain of PTP1B (here, we define structural similarity as two structures that when aligned, have with an RMSD of ≤0.94 Å RMSD with the framework similar to the one used by the align function of PyMol) and/or (ii) sequence similar to the catalytic domain of PTP1B (here, we define sequence similarity as ≥34% sequence identity or ≥53.5% sequence similarity as defined by the EMBOSS Needle algorithm).

To identify "plastic" residues capable of adjusting the activity of $P450_{BM3}$, we carried out an approach similar to that described above: (i) We used the mutant database[11] (http://www.MuteinDB.org) to identify the 25 most commonly mutated sites in functional variants of $P450_{BM3}$. (ii) We used Eq. 51 to score each site based on its variability in size and hydrophobicity across different mutants. (iii) We ranked each site according to S and selected the 7 highest-scoring sites. Site S1024 scored highly based on S but was omitted due to its location on the P450 reductase domain.

E. Exemplary Purification of Products.

See section relating to flash chromatography and HPLC[1-3].

F. Exemplary Concentration Range for Testing Products.

We plan on incubating mammalian cells with 1-400 μM of inhibitors; we will assess the biochemical influence of those inhibitors by using the assays described below.

G. Exemplary Cell-Based Assays.

We will characterize the biological activity of newly developed inhibitors in at least two ways:

1. We will assay the influence of inhibitors on insulin receptor phosphorylation. In brief, we will expose HepG2, Hela, Hek393t, MCF-7, and/or Cho-hIR cells to insulin shock in the presence and absence of inhibitors, and we will use a western blot and/or an enzyme-linked immunosorbent assay (ELISA) to measure the influence of the inhibitors on insulin receptor phosphorylation. In some embodiments we may use cell-permeable inhibitors of PTP1B to enhance insulin receptor phosphorylation.

2. We will examine the morphological and/or growth effects inhibitors identified in a system described herein on cellular models of HER2(+) and TN breast cancer.

In brief, we will examine the relevance of inhibitors to HER2(+) breast cancer by evaluating their ability to inhibit the migration of BT474 and SKBR3 cells, which are HER2(+), but not MCF-7 and MDA-MB-231 cells, which are HER2(−). We will examine the relevance of inhibitors to triple negative breast cancer, in turn, by carrying out viability and proliferation assays on panels of TN cell lines (e.g., ATCC TCP-1002). All cell lines are available from the ATCC (ATCC.org) and have been used previously to characterize potential therapeutics for HER2(+) and TN subtypes[4,5].

It is not meant to limit a pathway to terpenoid synthesis. Indeed, an alkaloid biosynthesis pathway is contemplated for use to identify, An exemplary pathway for alkaloid biosynthesis consists of three modules (Nakagawa, A. et al. A bacterial platform for fermentative production of plant alkaloids. Nat. Commun. (2011). doi:10.1038/ncomms1327, herein incorporated by reference) (i) the first enables the overexpression of our enzymes for L-tyrosine overproduction: TKT, PEPS, fbr-DAHPS, and fbr-CM/PDH; (ii) the second enables the expression of three enzymes necessary for the construction of dopamine and 3,4-DHPAA: TYR, DODC, and MAO; and (iii) the third enable the expression of four enzymes for the construction of (S) reticuline from 3,4-DHPAA and dopamine: NCS, 6OMT, CNMT, and 4'OMT. Enzymes are as follows: TKT, transketolase (tktA, GenBank accession number X68025); PEPS, phosphoenolpyruvate (PEP) synthetase (ppsA, GenBank accession number X59381); fbr-DAHPS, feedback-inhibition resistant 3-deoxy-D-arabino-heptulosonate-7-phosphate synthase (aroGfbr, GenBank accession number J01591); fbr-CM/PDH, feedback-inhibition resistant chorismate mutase/prephenate dehydrogenase (tyrAfbr, GenBank accession number M10431); TYR, tyrosinase of *Streptomyces castaneoglobisporus* (ScTYR containing tyrosinase and its adaptor protein, ORF378, GenBank accession numbers AY254101 and AY254102); DODC, DOPA decarboxylase of *Pseudomonas putida* (GenBank accession number AE015451); MAO, monoamine oxidase of *Micrococcus luteus* (GenBank accession number AB010716); NCS, norcoclaurine synthetase of *C. japonica* (GenBank accession number AB267399); 6OMT, norcoclaurine 6-O-methyltransferase of *C. japonica* (GenBank accession number D29811); CNMT, coclaurine-N-methyltransferase of *Coptis japonica* (GenBank accession number AB061863); 4'OMT, 3'-hydroxy-N-methylcoclaurine 4'-O-methyltransferase of *C. japonica* (GenBank accession number D29812). We note; these three modules may be encoded by two plasmids.

REFERENCES FOR SECTION V, HEREIN INCORPORATED BY REFERENCE IN THEIR ENTIRETY

1. Jia, M., Potter, K. C. & Peters, R. J. Extreme promiscuity of a bacterial and a plant diterpene synthase enables combinatorial biosynthesis. *Metab. Eng.* 37, 24-34 (2016).
2. Criswell, J., Potter, K., Shephard, F., Beale, M. H. & Peters, R. J. A single residue change leads to a hydroxylated product from the class II diterpene cyclization catalyzed by abietadiene synthase. *Org. Lett.* 14, 5828-5831 (2012).
3. Morrone, D. et al. Increasing diterpene yield with a modular metabolic engineering system in *E. coli*: Comparison of MEV and MEP isoprenoid precursor pathway engineering. *Appl. Microbiol. Biotechnol.* 85, 1893-1906 (2010).
4. Dagliyan, O. et al. Engineering extrinsic disorder to control protein activity in living cells. *Science (80-.).* 354, 1441-1444 (2016).
5. Lehmann, B. D. et al. Identification of human triple-negative breast cancer subtypes and preclinical models for selection of targeted therapies. *J. Clin. Invest.* (2011). doi:10.1172/JC145014
6. Dempke, W. C. M., Uciechowski, P., Fenchel, K. & Chevassut, T. Targeting SHP-1, 2 and SHIP Pathways: A novel strategy for cancer treatment? *Oncology (Switzerland)* (2018). doi:10.1159/000490106
7. Nakagawa, A. et al. A bacterial platform for fermentative production of plant alkaloids. *Nat. Commun.* (2011). doi:10.1038/ncomms1327
8. Christianson, D. W. Structural biology and chemistry of the terpenoid cyclases. *Chem. Rev.* 106, 3412-3442 (2006).
9. Fasan, R. Tuning P450 enzymes as oxidation catalysts. *ACS Catalysis* 2, 647-666 (2012).
10. Jung, S. T., Lauchli, R. & Arnold, F. H. Cytochrome P450: Taming a wild type enzyme. *Current Opinion in Biotechnology* 22, 809-817 (2011).
11. Braun, A. et al. MuteinDB: The mutein database linking substrates, products and enzymatic reactions directly with genetic variants of enzymes. *Database* (2012). doi: 10.1093/database/bas028

VI. Evolving Optogenetic Actuators: Photoswitchable Constructs.

A. Optical Control with Red and Infrared Light.

Contemporary efforts for using light to control enzyme activity have relied on at least two optogenetic actuators: LOV2, which has terminal helices that are destabilized by blue light (~450 nm)[2,18,48], and Dronpa, which switches from a dimer to a monomer in response to green light (~500 nm)[19]. Unfortunately, blue and green light suffer from problems of phototoxicity, penetration depth, and spectral similarity that limit their use in signaling studies[21]. Thus, in one embodiment, photoswitchable enzymes stimulated by red or infrared light are contemplated for development. These wavelengths have lower phototoxicities and greater penetration depths than blue and green light[20,21], and will permit multi-color actuation alongside blue or green light.

B. An Operon to Evolve Photoswitchable Constructs.

Figure 3A:
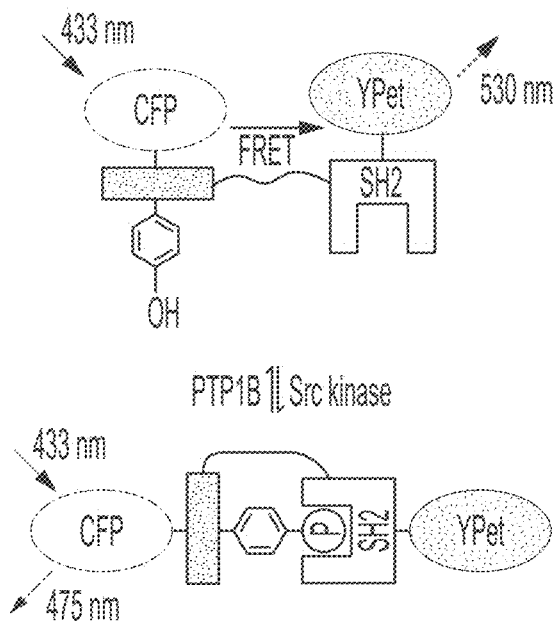
FIG. 3A-D demonstrates exemplary Fluorescence-based Biosensors having PTP1B activity.
Figure 3B:
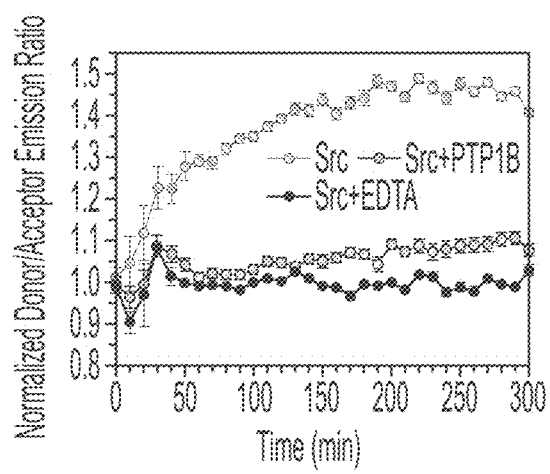
Figure 3C:
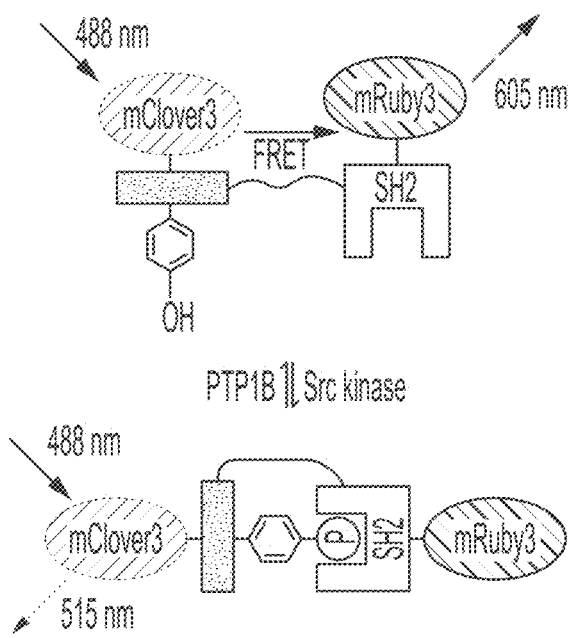
Figure 3D:
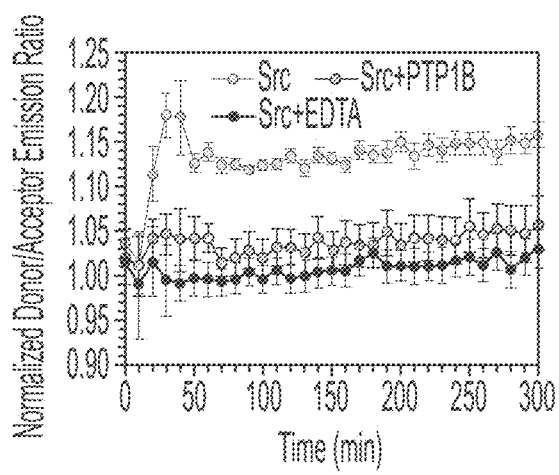
Figure 4A:
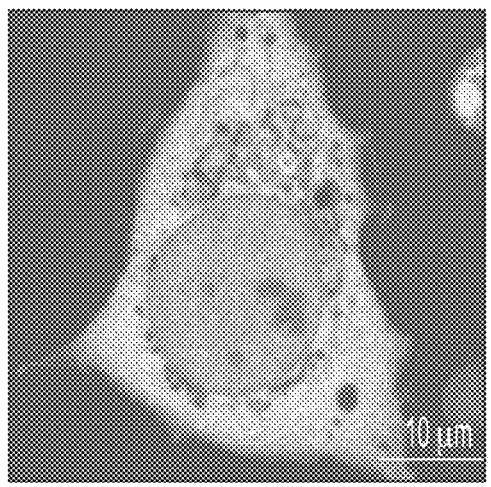
FIG. 4A-H demonstrates exemplary Evidence of phosphatase activity within living cells using photoconstructs and fluorescent tags.
Figure 4B:
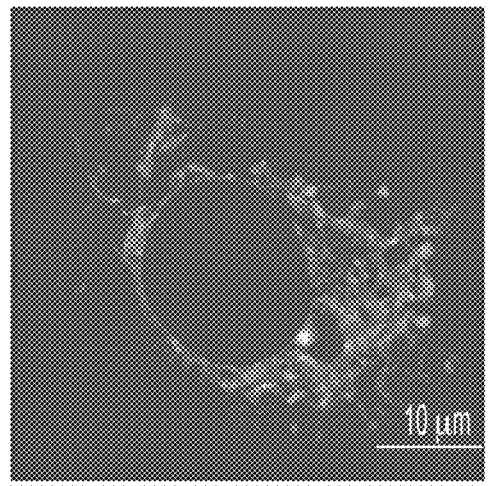
Figure 4C:
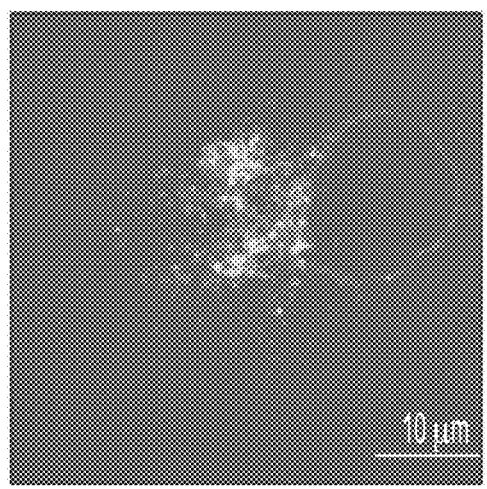
Figure 4D:
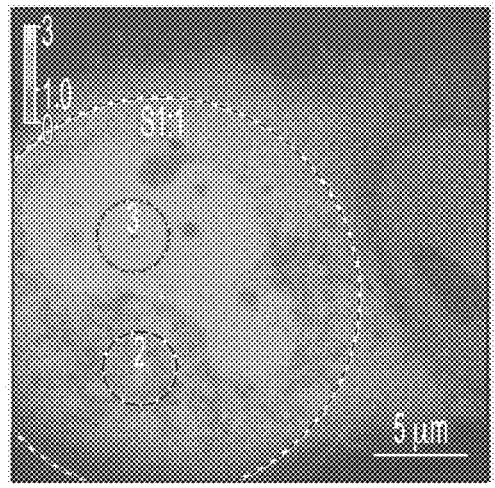
Figure 4E:
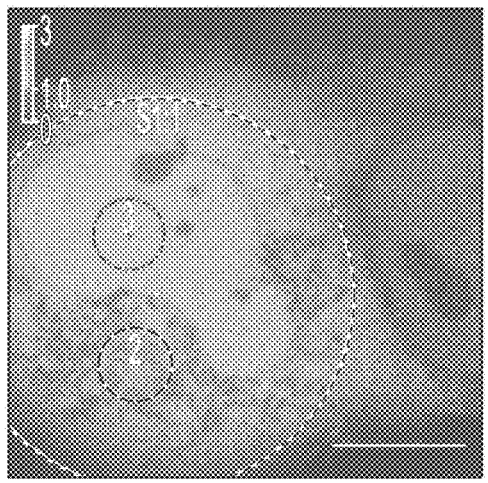
Figure 4F:
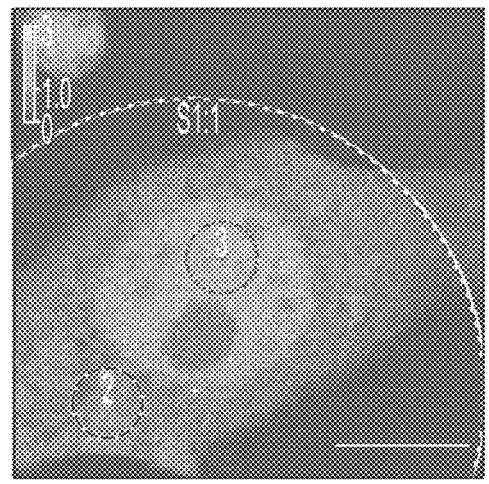
Figure 4G:
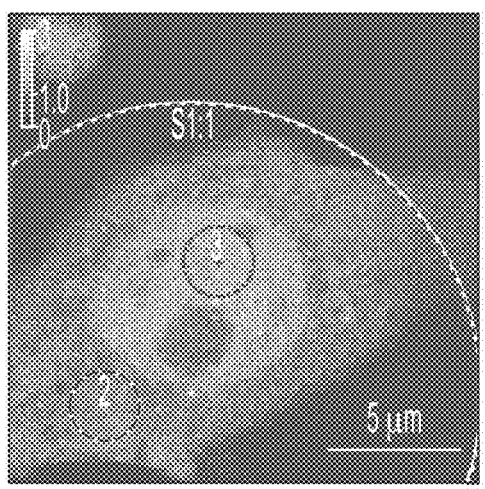
Figure 4H:
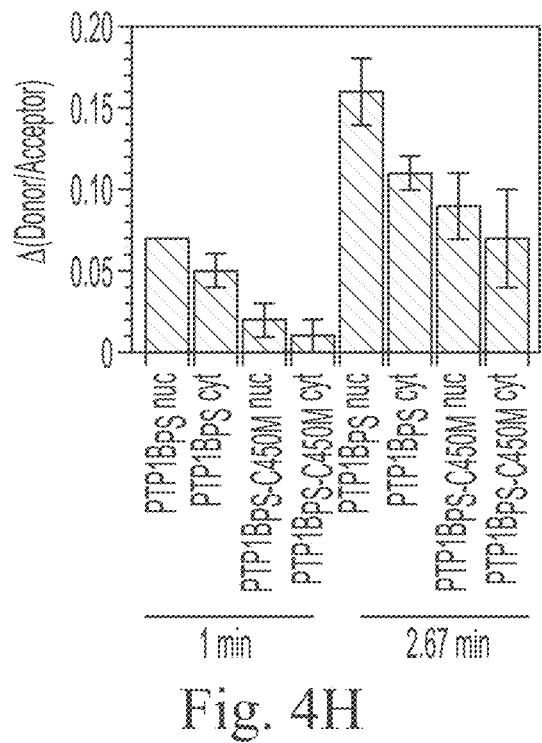

In one embodiment, an operon that links the activity of PTP1B to cell growth is contemplated. In brief, this operon is based on the following control strategy (some additional details in FIG. 10): A kinase stimulates the binding of two proteins, which in turn, promote transcription of an essential gene; PTP1B suppresses the binding of these two proteins and, thus, inhibits transcription. This operon allows cells in possession of photoswitchable variants of PTP1B to grow faster in the presence of one light source than in the present of another (e.g., 750 nm vs. 650 nm). The difference in growth rates enables the identification of functional chimeras. Initial experiments with an operon based on Lux-based luminescence (based on a system developed by Liu and colleagues[53]) show a 20-fold difference in luminescence between a strain expressing two model binding partners and a strain expressing one (FIG. 3E). We will continue to develop this operon by adding a protein-protein interaction that is modulated by a PTP and PTK (see below).

This operon allows cells in possession of photoswitchable variants of PTP1B to grow faster in the presence of one light source than in the present of another (e.g., 750 nm vs. 650 nm). The difference in growth rates enables the identification of functional chimeras. Initial experiments with an operon based on Lux-based luminescence (based on a system developed by Liu and colleagues 53) show a 20-fold difference in luminescence between a strain expressing two model binding partners and a strain expressing one (FIG. 3E). We will continue to develop this operon by adding a protein-protein interaction that is modulated by a PTP and PTK.

FRET sensors. We will use Forster resonance energy transfer (FRET) to monitor the activity of PTP1B in living cells. Our preliminary sensor exhibits a 20% reduction in FRET signal when treated with Src kinase (FIG. 3F). Previous imaging studies indicate that a 20% change in FRET is sufficient to monitor intracellular kinase activity54"56. To enhance spatial resolution in imaging studies, we will attempt to optimize our sensor further (and use it to measure the activity of PTP1B in vitro).

1. To Evolve Phosphatases and Kinases Modulated by Red and Infrared Light.

This section uses directed evolution to build enzymes that can be turned "on" and "off" with red and infrared light. We will know that we are successful when we have (i) built a genetic operon that links the activity of PTP1B to antibiotic resistance, (ii) A used that operon to build a PTP1 B-phytochrome chimera that exhibits a three- to ten-fold change in activity in response to red and infrared light, and (iii) built similar phytochrome chimeras of STEP and PTK6.

Hypothesis. Phytochrome proteins exhibit global conformational changes when exposed to red and infrared light[27, 28], but to date, have eluded rational integration into photoswitchable enzymes. We hypothesize that a genetic operon that links PTP or PTK activity to cell growth will enable the evolution of PTP- or PTK-phytochrome chimeras stimulated by red or infrared light.

Experimental approach: We will build an operon that links PTP1B inhibition to antibiotic resistance, and we will use that operon to evolve photoswitchable PTP1 B-phytochrome chimeras. This effort will involve (i) the construction a library of PTP1 B-phytochrome chimeras that differ in linker composition and/or linker length, (ii) the use of our operon to screen that library for functional mutants, (iii) a kinetic and biostructural characterization of the most photoswitchable mutants, and (iv) the extension of this approach to STEP and PTK6. This effort has two major goals: a variant of PTP1B modulated by red and/or infrared light, and a general approach for using directed evolution to extend optical control to new enzymes and different wavelengths of light.

2. Development of a Synthetic Operon for Evolving PTP1 B-Phytochrome Chimeras.

We will build a variant of PTP1B that can be modulated by red and infrared light by attaching its C-terminal a-helix to the N-terminal a-helix of bacterial phytochrome protein 1 (BphP1) from *Rhodopseudomonas palustris* (FIG. 9); this protein undergoes a reversible conformational change when exposed to 650 nm and 750 nm light. Phytochromes such as BphP1 are valuable for photocontrol because they can be actively toggled between conformations (i.e., turned "on" and "off"). Their structures, however, are not compatible with cage-based actuation (they do not undergo large-scale "unwinding"); they have, thus, been overlooked in previous efforts to develop photoswitchable enzymes.

We will evolve photoswitchable PTP1B-BphP1 chimeras by using a genetic operon that links PTP1B activity to antibiotic resistance. This operon will consist of six components (FIG. 10A-B): (i) a PTP1B substrate domain tethered to a DNA-binding protein, (ii) a substrate recognition domain (i.e., a substrate homology 2 domain, or SH2) tethered to the subunit of an RNA polymerase, (iii) an Src kinase (a kinase capable of phosphorylating a wide range of substrates), (iv) PTP1B (or a potentially photoswitchable variant of PTP1B), (v) a gene for antibiotic resistance, and (vi) an operator for that gene.

With this system, light-induced inactivation of PTP1B will enable transcription of the gene for antibiotic resistance. Previous groups have used similar operons to evolve protein-protein binding partners (our system is based on an operon used by Liu et al. to evolve insecticidal proteins[53]); here, we take the additional (new) steps of (i) using a protein-protein interaction mediated by enzymes (phosphatases and kinases) and (ii) screening that interaction in the presence and absence of light.

We have begun to develop our operon by using a Lux-based luminescence as an output. Preliminary results show that model protein-protein binding partners can elicit a 20-fold change in luminescence (FIG. 3E). We plan to swap out these binding partners with substrate and SH2 domains, and test the new system alongside simultaneously expressed PTP1B and Src kinase (which have some complementary activities, and can be expressed in *E. coli*[68,69]).

Figure 5B:
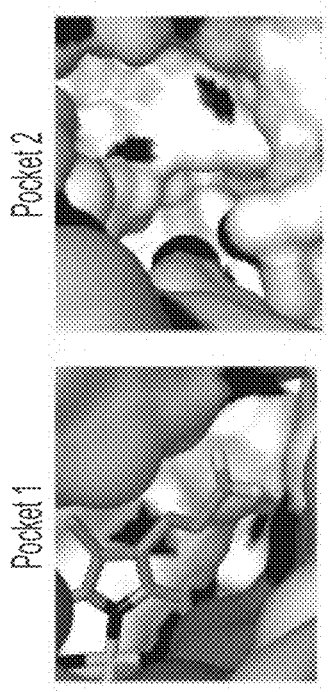
FIG. 5A-C illustrates embodiments of drug discovery.
Figure 5C:
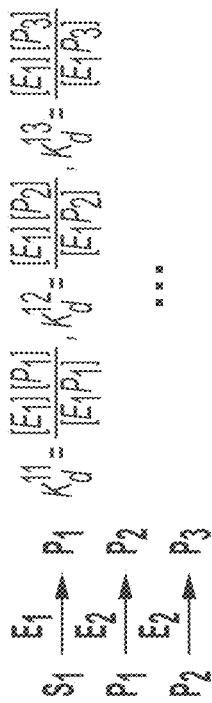
Figure 5A:
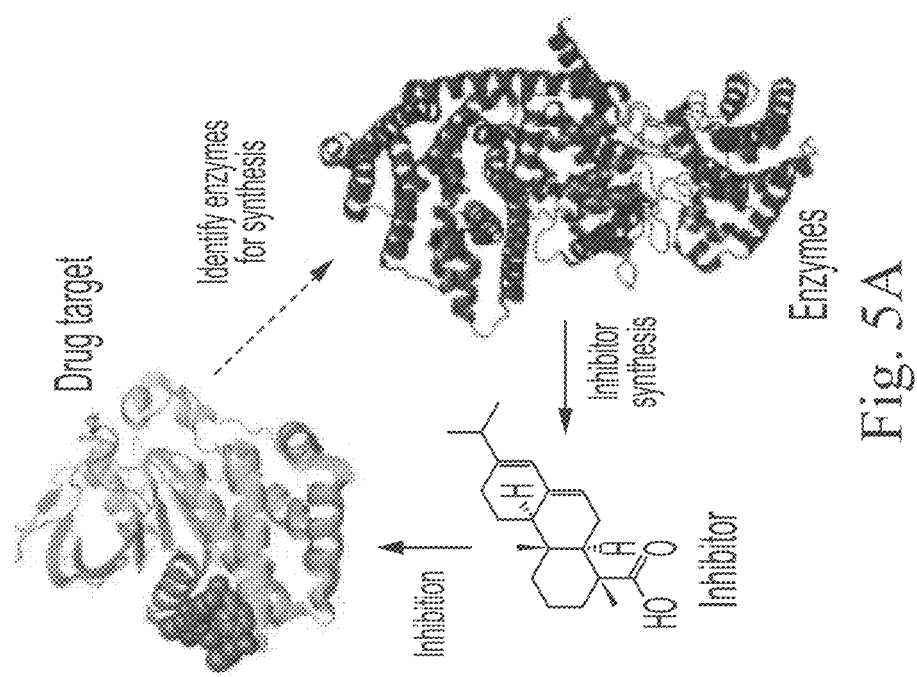

Advantages of using operons expressing photosensitive phosphatases includes but is not limited to enabling high-throughput screens of mutants of photoswitchable enzymes and provides a method for screening the libraries of enzymes that they motivate, see, FIG. 5A for example. In contrast, have shown that mutagenesis a photoswitchable enzyme can adjust (i.e., improve) its dynamic range (i.e., ratio of dark-state activity to light-state activity); while some published studies, such as WO2011002977. Genetically Encoded Photomanipulation Of Protein And Peptide Activity. Published Jan. 6, 2011, have proposed, but not shown, that mutagenesis of protein light switches might enable spectral tuning of photoswitchable enzymes. WO2011002977, provides a list of sites that could be mutated to modify the flavin-binding pocket of LOV2 to accept flavins that absorb light at alternative wavelengths. However, their construct is described as a LOV2 domain of *Avena sativa* (oat) phototropin 1 (404-546), including the C-terminal helical extension J alpha where Ja unwinds instead of the A alpha helix described herein. Nonetheless, there is no available method for carrying out high-throughput screens of mutants with modified binding pockets for which the invention described herein provides a platform for doing so. Further, in contrast to WO2013016693. "Near-infrared light-activated proteins." Publication Date Jan. 31, 2013, inventions described herein provide a platform for screening potentially improved/modified variants of photoswitchable proteins, such as a plant phototropin 1 LOV2.

Additionally, methods for screening the libraries of enzymes enable the detection of (i) molecules or (ii) photoswitchable domains that change the activity of any enzyme that, in turn, can modulate the affinity, or outcome associated with, a protein-protein interaction: protein tyrosine phosphatase (PTPs) and protein tyrosine kinases (PTKs) are demonstrated. Moreover, proteases are contemplated as proteins to add to this system.

C. Directed Evolution.

We will build libraries of PTP1B-BphP1 chimeras by pairing overlap extension PCR (oePCR) with error-prone PCR (epPCR). Specifically, we will use oePCR to build chimeras that differ in linker length (here, we define the linker as the ~20 residue region comprised of the C-terminal a-helix of PTP1B and the N-terminal a-helix of BphP1), and we will use epPCR to vary linker composition. Depending on the results of this initial library, we may extend error-prone PCR into the BphP1 gene, but we will not mutate PTP1B beyond its C-terminal a-helix.

Figure 11B:
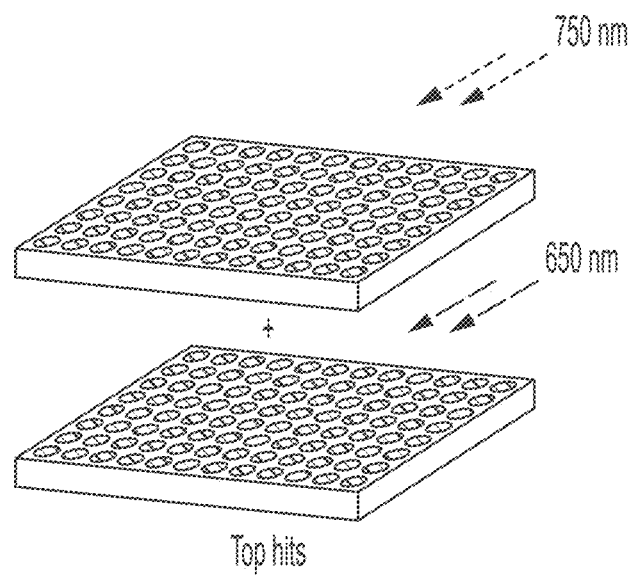

In the presence of a small amount of antibiotic (i.e. an amount that impedes the growth of *E. coli*), our genetic operon will cause cells that contain functional PTP1B-BphP1 chimeras to exhibit different growth rates under red and infrared light. We will exploit these differences to identify cells that harbor photoswitchable constructs. In brief, we will (i) generate two replicate plates of cell colonies, (ii) grow one under red light and one under infrared light (FIG. 11 A), and (iii) select a subset of colonies (top hits) that show differential growth. We will further characterize our top hits by growing them in small-scale liquid cultures (e.g., 96-well plates with ~1 ml/well; FIG. 11B) under red and infrared light, and by sequencing the PTP1 B-BphP1 genes of colonies that show the greatest different in growth rates.

We will attempt to build enzyme-phytochrome chimeras of STEP and PTK6 by pursuing two strategies: (i) We will replace PTP1B in our final PTP1B-BphP1 chimera with STEP or PTK6; this strategy will allow us to assess the modularity of our final design, (ii) We will use our operon-based approach to evolve functional STEP-BphP1 and PTK6-BphP1 chimeras; this strategy will allow us to assess the generalizability of our approach to evolution.

Operons for evolving STEP-BphP1 and PTK6-BphP1 chimeras will closely resemble the PTP TB-specific operon. For STEP, we will use a STEP-specific substrate and SH2 domain (Src kinase, which has a broad substrate specificity, is likely to have complementary activities on a subset of STEP substrates); for PTK6, we will use a recognition process that is inhibited—not activated—by phosphorylation (here, we can use PTP1B$_{WT}$ as the complementary enzyme).

D. Extension of Approach.

We will attempt to build enzyme-phytochrome chimeras of STEP and PTK6 by pursuing two strategies: (i) We will replace PTP1B in our final PTP1B-BphP1 chimera with STEP or PTK6; this strategy will allow us to assess the modularity of our final design, (ii) We will use our operon-based approach to evolve functional STEP-BphP1 and PTK6-BphP1 chimeras; this strategy will allow us to assess the generalizability of our approach to evolution.

Operons for evolving STEP-BphP1 and PTK6-BphP1 chimeras will closely resemble the PTP TB-specific operon. For STEP, we will use a STEP-specific substrate and SH2 domain (Src kinase, which has a broad substrate specificity, is likely to have complementary activities on a subset of STEP substrates); for PTK6, we will use a recognition process that is inhibited—not activated—by phosphorylation (here, we can use PTP1BWT as the complementary enzyme)

F. Exemplary Contemplated Characterization: Biophysical Characterization of Enzyme-Phytochrome Chimeras.

We will examine the structural basis of photocontrol in the most photoswitchable chimeras by using a subset of crystallographic and kinetic analyses. X-ray crystal structures will show how BphP1 affects the structures of PTP1B, STEP, and PTK6. Kinetic studies will show how BphP1 affects substrate specificity and binding affinity (or more specifically, Km, which is affected by binding affinity).

TABLE 1

Exemplary Promoters.

| Name | DNA Sequence | SEQ ID NO. # |
|---|---|---|
| Pro1 | TTCTAGAGCACAGCTAACACCACGTCGTCCCTATCTGCTGCCCTAGGTCTA TGAGTGGTTGCTGGATAACTTTACGGGCATGCATAAGGCTCGGTATCTATA TTCAGGGAGACCACAACGGTTTCCCTCTACAAATAATTTTGTTTAACTTTT ACTAGAG | SEQ ID NO: 25 |
| ProD | GCACAGCTAACACCACGTCGTCCCTATCTGCTGCCCTAGGTCTATGAGTGG TTGCTGGATAACTTTACGGGCATGCATAAGGCTCGTATAATATATTCAGGG AGACCACAACGGTTTCCCTCTACAAATAATTTTGTTTAACTTTTACTAGAG | SEQ ID NO: 26 |
| pBAD | AGAAACCAATTGTCCATATTGCATCAGACATTGCCGTCACTGCGTCTTTTA CTGGCTCTTCTCGCTAACCAAACCGGTAACCCCGCTTATTAAAAGCATTCT GTAACAAAGCGGGACCAAAGCCATGACAAAAACGCGTAACAAAAGTGTC TATAATCACGGCAGAAAAGTCCACATTGATTATTTGCACGGCGTCACACTT TGCTATGCCATAGCATTTTTATCCATAAGATTAGCGGATCCTACCTGACGC TTTTTATCGCAACTCTCTACTGTTTCTCCATACCCGTTTTTTTGGGCTAGC | SEQ ID NO: 27 |
| pLacZOpt (operator bolded) | ACAAGAAAGTTTGTTCATTAGGCACCCCGGGCTTTACTCGTAAAGCTTCC GGCGCGTATGTTGTGTCGACCG | SEQ ID NO: 28 |
| pTrc | CGACTGCACGGTGCACCAATGCTTCTGGCGTCAGGCAGCCATCGGAAGCT GTGGTATGGCTGTGCAGGTCGTAAATCACTGCATAATTCGTGTCGCTCAAG GCGCACTCCCGTTCTGGATAATGTTTTTTGCGCCGACATCATAACGGTTCT GGCAAATATTCTGAAATGAGCTGTTGACAATTAATCATCCGGCTCGTATAA TGTGTGGAATTGTGAGCGGATAACAATTTCACACAGGAAACAG | SEQ ID NO: 29 |
| T7 | CCTATAGTGAGTCGTATTA | SEQ ID NO: 30 |

TABLE 2

Exemplary Ribosome Binding Sites.

| Name | DNA Sequence | SEQ ID NO. # |
|---|---|---|
| proRBS | TTAAAGAGGAGAAAGGTC | SEQ ID NO: 31 |
| Sal28 RBS | CGAAAAAAAGTAAGGCGGTAATCC | SEQ ID NO: 32 |
| bb034 RBS | TGCAGAAAGAGGAGAAATACTAG | SEQ ID NO: 33 |
| bb030 | ATTAAAGAGGAGAAATACTAG | SEQ ID NO: 34 |
| RBSfor GOI in B2H | GTGCAGTAAGGAGGAAAAAAAA | SEQ ID NO: 35 |
| bbAH | GCTAGCTTTAAGAAGGAGATATACC | SEQ ID NO: 36 |

TABLE 3

Exemplary Protein Sequences (includes truncations).

| Name | Amino Acid Sequence | SEQ ID NO. # |
|---|---|---|
| RpoZ (linker bolded) | MARVTVQDAVEKIGNRFDLVLVAARRARQMQVGGKDPLVPEENDKTTV IALREIEEGLINNQILDVRERQEQQEAAELQAVTAIAEGRRAAA | SEQ ID NO: 37 |
| cI (linker bolded) | MSISSRVKSKRIQLGLNQAELAQKVGTTQQSIEQLENGKTKRPRFLPELAS ALGVSVDWLLNGTSDSNVRFVGHVEPKGKYPLISMVRARSWCEACEPYD IKDIDEWYDSDVNLLGNGFWLKVEGDSMTSPVGQSIPEGHMVLVDTGRE PVNGSLVVAKLTDANEATFKKLVIDGGQYLKGLNPSWPMTPINGNCKII GVVVEARVKFVDYKDDDDK | SEQ ID NO: 38 |
| SH2 | WYFGKITRRESERLLLNPENPRGTFLVRESETVKGAYALSVSDFDNAKGL NVKHYLIRKLDSGGFYITSRTQFSSLQQLVAYYSKHADGLCHRLTNVC | SEQ ID NO: 39 |
| Kras Substrate | WMEDYDYVHLQG | SEQ ID NO: 40 |
| MidT Substrate | EPQYEEIPIYL | SEQ ID NO: 41 |
| ShcA Substrate | DHQYYNDFPG | SEQ ID NO: 42 |
| EGFR Substrate | PQRYLVIQGD | SEQ ID NO: 43 |
| Src | MSKPQTQGLAKDAWEIPRESLRLEVKLGQGCFGEVWMGTWNGTTRVAI KTLKPGTMSPEAFLQEAQVMKKLRHEKLVQLYAVVSEEPIYIVTEYMSKG SLLDFLKGETGKYLRLPQLVDMAAQIASGMAYVERMNYVHRDLRAANIL VGENLVCKVADFGLARLIEDNEYTARQGAKFPIKWTAPEAALYGRFTIKS DVWSFGILLTELTTKGRVPYPGMVNREVLDQVERGYRMPCPPECPESLHD LMCQCWRKEPEERPTFEYLQAFLEDYFTSTEPQYQPGENL | SEQ ID NO: 44 |
| CDC37 | MVDYSVWDHIEVSDDEDETHPNIDTASLFRWRHQARVERMEQFQKEKEE LDRGCRECKRKVAECQRKLKELEVAEGGKAELERLQAEAQQLRKEERSW EQKLEEMRKKEKSMPWNVDTLSKDGFSKSMVNTKPEKTEEDSEEVREQK HKTFVEKYEKQIKHFGMLRRWDDSQKYLSDNVHLVCEETANYLVIWCID LEVEEKCALMEQVAHQTIVMQFILELAKSLKVDPRACFRQFFTKIKTADR QYMEGFNDELEAFKERVRGRAKLRIEKAMKEYEEEERKKRLGPGGLDPV EVYESLPEELQKCFDVKDVQMLQDAISKMDPTDAKYHMQRCIDSGLWVP NSKASEAKEGEEAGPGDPLLEAVPKTGDEKDVSV | SEQ ID NO: 45 |
| PTP1B | MEMEKEFEQIDKSGSWAAIYQDIRHEASDFPCRVAKLPKNKNRNRYRDV SPFDHSRIKLHQEDNDYINASLIKMEEAQRSYILTQGPLPNTCGHFWEMV WEQKSRGVVMLNRVMEKGSLKCAQYWPQKEEKEMIFEDTNLKLTLISED IKSYYTVRQLELENLTTQETREILHFHYTTWPDFGVPESPASFLNFLFKVRE SGSLSPEHGPVVVHSSAGIGRSGTFCLADTCLLLMDKRKDPSSVDIKKVLL EMRKFRMGLIQTADQLRFSYLAVIEGAKFIMGDSSVQDQWKELSHEDLEP PPEHIPPPPRPPKRILEPHN | SEQ ID NO: 46 |
| MBP | MKIEEGKLVIWINGDKGYNGLAEVGKKFEKDTGIKVTVEHPDKLEEKFP QVAATGDGPDIIFWAHDRFGGYAQSGLLAEITPDKAFQDKLYPFTWDA VRYNGKLIAYPIAVEALSLIYNKDLLPNPPKTWEEIPALDKELKAKGKS ALMFNLQEPYFTWPLIAADGGYAFKYENGKYDIKDVGVDNAGAKAGL TFLVDLIKNKHMNADTDYSIAEAAFNKGETAMTINGPWAWSNIDTSKV NYGVTVLPTFKGQPSKPFVGVLSAGINAASPNKELAKEFLENYLLTDEG LEAVNKDKPLGAVALKSYEEELAKDPRIAATMENAQKGEIMPNIPQMS AFWYAVRTAVINAASGRQTVDEALKDAQTRITK | SEQ ID NO: 47 |
| LuxAB | MKFGNFLLTYQPPQFSQTEVMKRLVKLGRISEECGFDTVWLLEHHFTEF GLLGNPYVAAAYLLGATKKLNVGTAAIVLPTAHPVRQLEDVNLLDQM SKGRFRFGICRGLYNKDFRVFGTDMNNSRALAECWYGLIKNGMTEGYM EADNEHIKFHKVKVNPAAYSRGGAPVYVVAESASTTEWAAQFGLPMIL SWIINTNEKKAQLELYNEVAQEYGHDIHNIDHCLSYITSVDHDSIKAKEIC RKFLGHWYDSYVNATTIFDDSDQTRGYDFNKGQWRDFVLKGHKDTNRR IDYSYEINPVGTPQECIDIIQKDIDATGISNICCGFEANGTVDEIIASMKLFQ SDVMPFLKEKQRSLLYYGGGSGGGGSGGGGSGGGGSKFGLFFLNFINS TTVQEQSIVRMQEITEYVDKLNFEQILVYENHFSDNGVVGAPLTVSGFLL GLTEKIKIGSLNHIITTHHPVRIAEEEACLLDQLSEGRFILGFSDCEKKDEMH FFNRPVEYQQQLFEECYEIINDALTTGYCNPDNDFYSFPKISVNPHAYTPG GPRKYVTATSHHIVEWAAKKGIPLIFKWDDSNDVRYEYAERYKAVADKY DVDLSEIDHQLMILVNYNEDSNKAKQETRAFISDYVLEMHPNENFENKLE EIIAENAVGNYTECITAAKLAIEKCGAKSVLLSFEPMNDLMSQKNVINIV DDNIKKYHTEYT | SEQ ID NO: 48 |

TABLE 3-continued

Exemplary Protein Sequences (includes truncations).

| Name | Amino Acid Sequence | SEQ ID NO. # |
|---|---|---|
| SpecR | MREAVIAEVSTQLSEVVGVIERHLEPTLLAVHLYGSAVDGGLKPHSDIDL LVTVTVRLDETTRRALINDLLETSASPGESEILRAVEVTIVVHDDIIPWRY PAKRELQFGEWQRNDILAGIFEPATIDIDLAILLTKAREHSVALVGPAAE ELFDPVPEQDLFEALNETLTLWNSPPDWAGDERNVVLTLSRIWYSAVTG KIAPKDVAADWAMERLPAQYQPVILEARQAYLGQEEDRLASRADQLEE FVHYVKGEITKVVGK | SEQ ID NO: 49 |
| AgAs | MVKREFPPGFWKDDLIDSLTSSHKVAASDEKRIETLISEIKNMFRCMGY GETNPSAYDTAWVARIPAVDGSDNPHFPETVEWILQNQLKDGSWGEG FYFLAYDRILATLACIITLTLWRTGETQVQKGIEFFRTQAGKMEDEADSH RPSGFEIVFPAMLKEAKILGLDLPYDLPFLKQIIEKREAKLKRIPTDVLYA LPTTLLYSLEGLQEIVDWQKIMKLQSKDGSFLSSPASTAAVFMRTGNKKC LDFLNFVLKKFGNHVPCHYPLDLFERLWAVDTVERLGIDRHFKEEIKEAL DYVYSHWDERGIGWARENPVPDIDDTAMGLRILRLHGYNVSSDVLKTFR DENGEFFCFLGQTQRGVTDMLNVNRCSHVSFPGETIMEEAKLCTERYLRN ALENVDAFDKWAFKKNIRGEVEYALKYPWHKSMPRLEARSYIENYGPDD VWLGKTVYMMPYISNEKYLELAKLDFNKVQSIHQTELQDLRRWWKSSGF TDLNFTRERVTEIYFSPASFIFEPEFSKCREVYTKTSNFTVILDDLYDAHGSL DDLKLFTESVKRWDLSLVDQMPQQMKICFVGFYNTFNDIAKEGRERQGR DVLGYIQNVWKVQLEAYTKEAEWSEAKYVPSFNEYIENASVSIALGTVVL ISALFTGEVLTDEVLSKIDRESRFLQLMGLTGRLVNDTKTYQAERGQGEV ASAIQCYMKDHPKISEEEALQHVYSVMENALEELNREFVNNKIPDIYKRL VFETARIMQLFYMQGDGLTLSHDMEIKEHVKNCLFQPVA | SEQ ID NO: 50 |
| GGPPS | MFDFNEYMKSKAVAVDAALDKAIPLEYPEKIHESMRYSLLAGGKRVRPA LCIAACELVGGSQDLAMPTACAMEMIHTMSLIHDDLPCMDNDDFRRGKP TNHKVFGEDTAVLAGDALLSFAFEHIAVATSKTVPSDRTLRVISELGKTIG SQGLVGGQVVDITSEGDANVDLKTLEWIHIHKTAVLLECSVVSGGILGGA TEDEIARIRRYARCVGLLFQVVDDILDVTKSSEELGKTAGKDLLTDKATYP KLMGLEKAKEFAAELATRAKEELSSFDQIKAAPLLGLADYIAFRQN | SEQ ID NO: 51 |
| P450 | MTIKEMPQPKTFGELKNLPLLNTDKPVQALMKIADELGEIFKFEAPGRVTR YLSSQRLIKEACDESRFDKNLSQALKFVRDFAGDGLFTSWTHEKNWKKA HNILLPSFSQQAMKGYHAMMVDIAVQLVQKWERLNADEHIEVPEDMTRL TLDTIGLCGFNYRFNSFYRDQPHPFITSMVRALDEAMNKLQRANPDDPAY DENKRQFQEDIKVMNDLVDKIIADRKASGEQSDDLLTHMLNGKDPETGEP LDDENIRYQIITFLIAGHETTSGLLSFALYFLVKNPHVLQKAAEEAARVLV DPVPSYKQVKQLKYVGMVLNEALRLWPTAPAFSLYAKEDTVLGGEYPLE KGDELMVLIPQLHRDKTIWGDDVEEFRPERFENPSAIPQHAFKPFGNGQR ACIGQQFALHEATLVLGMMLKHFDFEDHTNYELDIKETLTLKPEGFVVKA KSKKIPLGGIPSPSTEQSAKKVRKKAENAHNTPLLVLYGSNMGTAEGTAR DLADIAMSKGFAPQVATLDSHAGNLPREGAVLIVTASYNGHPPDNAKQF VDWLDQASADEVKGVRYSVFGCGDKNWATTYQKVPAFIDETLAAKGAE NIADRGEADASDDFEGTYEEWREHMWSDVAAYFNLDIENSEDNKSTLSL QFVDSAADMPLAKMHGAFSTNVVASKELQQPGSARSTRHLEIELPKEASY QEGDHLGVIPRNYEGIVNRVTARFGLDASQQIRLEAEEEKLAHLPLAKTVS VEELLQYVELQDPVTRTQLRAMAAKTVCPPHKVELEALLEKQAYKEQVL AKRLTMLELLEKYPACEMKFSEFIALLPSIRPRYYSISSSPRVDEKQASITVS VVSGEAWSGYGEYKGIASNYLAELQEGDTITCFISTPQSEFTLPKDPETPLI MVGPGTGVAPFRGFVQARKQLKEQGQSLGEAHLYFGCRSPHEDYLYQEE LENAQSEGIITLHTAFSRMPNQPKTYVQHVMEQDGKKLIELLDQGAHFYI CGDGSQMAPAVEATLMKSYADVHQVSEADARLWLQQLEEKGRYAKDV WAG | SEQ ID NO: 52 |
| LOV2 | AATLERIEKNFVITDPRLPDNPIIFASDSFLQLTEYSREEILGRNCRFLQGPET DRATVRKIRDAIDNQTEVTVQLINYTKSGKKFWNLFHLQPMRDQKGDVQ YFIGVQLDGTEHVRDAAEREGVMLIKKTAENIDEAAKEL | SEQ ID NO: 53 |
| BphP1 | MASVAGHASGSPAFGTADLSNCEREEIHLAGSIQPHGALLVVSEPDHRIIQ ASANAAEFLNLGSVLGVPLAEIDGDLLIKILPHLDPTAEGMPVAVRCRIGN PSTEYDGLMHRPPEGGLIIELERAGPPIDLSGTLAPALERIRTAGSLRALCD DTALLFQQCTGYDRVMVYRFDEQGHGEVFSERHVPGLESYFGNRYPSSDI PQMARRLYERQRVRVLVDVSYQPVPLEPRLSPLTGRDLDMSGCFLRSMSP IHLQYLKNMGVRATLVVSLVVGGKLWGLVACHHYLPRFMHFELRAICEL LAEAIATRITALESFAQSQSELFVQRLEQRMIEAITREGDWRAAIFDTSQSIL QPLHAAGCALVYEDQIRTIGDVPSTQDVREIAGWLDRQPRAAVTSTASLG LDVPELAHLTRMASGVVAAPISDHRGEFLMWFRPERVHTVTWGGDPKKP FTMGDTPADLSPRRSFAKWHQVVEGTSDPWTAADLAAARTIGQTVADIV LQFRAVRTLIAREQYEQFSSQVHASMQPVLITDAEGRILLMNDSFRDMLP AGSPSAVHLDDLAGFFVESNDFLRNVAELIDHGRGWRGEVLLRGAGNRP LPLAVRADPVTRTEDQSLGFVLIFSDATDRRTADAARTRFQEGILASARPG VRLDSKSDLLHEKLLSALVENAQLAALEITYGVETGRIAELLEGVRQSML RTAEVLGHLVQHAARTAGSDSSNGSQNKKEFDSAGSAGSAGTS | SEQ ID NO: 54 |

TABLE 3-continued

Exemplary Protein Sequences (includes truncations).

| Name | Amino Acid Sequence | SEQ ID NO. # |
|---|---|---|
| TC-PTP | MGMPTTIEREFEELDTQRRWQPLYLEIRNESHDYPHRVAKFPENRNRNRY RDVSPYDHSRVKLQNAENDYINASLVDIEEAQRSYILTQGPLPNTCCHFW LMVWQQKTKAVVMLNRIVEKESVKCAQYWPTDDQEMLFKETGFSVKLL SEDVKSYYTVHLLQLENINSGETRTISHFHYTTWPDFGVPESPASFLNFLFK VRESGSLNPDHGPAVIHCSAGIGRSGTFSLVDTCLVLMEKGDDINIKQVLL NMRKYRMGLIQTPDQLRFSYMAIIEGAKCIKGDSSIQKRWKELS | SEQ ID NO: 55 |
| PTP1B$_{1-435}$ | MEMEKEFEQIDKSGSWAAIYQDIRHEASDFPCRVAKLPKNKNRNRYRDV SPFDHSRIKLHQEDNDYINASLIKMEEAQRSYILTQGPLPNTCGHFWEMV WEQKSRGVVMLNRVMEKGSLKCAQYWPQKEEKEMIFEDTNLKLTLISED IKSYYTVRQLELENLTTQETREILHFHYTTWPDFGVPESPASFLNFLFKVRE SGSLSPEHGPVVVHCSAGIGRSGTFCLADTCLLLMDKRKDPSSVDIKKVLL EMRKFRMGLIQTADQLRFSYLAVIEGAKFIMGDSSVQDQWKELSHEDLEP PPEHIPPPPRPPKRILEPHNGKCREFFPNHQWVKEETQEDKDCPIKEEKGSP LNAAPYGIESMSQDTEVRSRVVGGSLRGAQAASPAKGEPSLPEKDEDHAL SYWKPFLVNMCVATVLTAGAYLCYRFLFNSNT | SEQ ID NO: 56 |
| SacB | MNIKKFAKQATVLTFTTALLAGGATQAFAKETNQKPYKETYGISHITRHD MLQIPEQQKNEKYQVPEFDSSTIKNISSAKGLDVWDSWPLQNADGTVAN YHGYHIVFALAGDPKNADDTSIYMFYQKVGETSIDSWKNAGRVFKDSDK FDANDSILKDQTQEWSGSATFTSDGKIRLFYTDFSGKHYGKQTLTTAQVN VSASDSSLNINGVEDYKSIFDGDGKTYQNVQQFIDEGNYSSGDNHTLRDP HYVEDKGHKYLVFEANTGTEDGYQGEESLFNKAYYGKSTSFFRQESQKL LQSDKKRTAELANGALGMIELNDDYTLKKVMKPLIASNTVTDEIERANVF KMNGKWYLFTDSRGSKMTIDGITSNDIYMLGYVSNSLTGPYKPLNKTGL VLKMDLDPNDVTFTYSHFAVPQAKGNNVVITSYMTNRGFYADKQSTFAP SFLLNIKGKKTSVVKDSILEQGQLTVNK | SEQ ID NO: 57 |
| GalK | MSLKEKTQSLFANAFGYPATHTIQAPGRVNLIGEHTDYNDGFVLPCAIDY QTVISCAPRDDRKVRVMAADYENQLDEFSLDAPIVAHENYQWANYVRG VVKHLQLRNNSFGGVDMVISGNVPQGAGLSSSASLEVAVGTVLQQLYHL PLDGAQIALNGQEAENQFVGCNCGIMDQLISALGKKDHALLIDCRSLGTK AVSMPKGVAVVIINSNFKRTLVGSEYNTRREQCETGARFFQQPALRDVTIE EFNAVAHELDPIVAKRVRHILTENARTVEAASALEQGDLKRMGELMAES HASMRDDFEITVPQIDTLVEIVKAVIGDKGGVRMTGGGFGGCIVALIPEEL VPAVQQAVAEQYEAKTGIKETFYVCKPSQGAGQC | SEQ ID NO: 58 |
| GHS | MAQISESVSPSTDLKSTESSITSNRHGNMWEDDRIQSLNSPYGAPAYQERS EKLIEEIKLLFLSDMDDSCNDSDRDLIKRLEIVDTVECLGIDRHFQPEIKLAL DYVYRCWNERGIGEGSRDSLKKDLNATALGFRALRLHRYNVSSGVLENF RDDNGQFFCGSTVEEEGAEAYNKHVRCMLSLSRASNILFPGEKVMEEAK AFTTNYLKKVLAGREATHVDESLLGEVKYALEFPWHCSVQRWEARSFIEI FGQIDSELKSNLSKKMLELAKLDFNILQCTHQKELQIISRWFADSSIASLNF YRKCYVEFYFWMAAAISEPEFSGSRVAFTKIAILMTMLDDLYDTHGTLDQ LKIFTEGVRRWDVSLVEGLPDFMKIAFEFWLKTSNELIAEAVKAQGQDMA AYIRKNAWERYLEAYLQDAEWIATGHVPTFDEYLNNGTPNTGMCVLNLI PLLLMGEHLPIDILEQIFLPSRFHHLIELASRLVDDARDFQAEKDHGDLSCIE CYLKDHPESTVEDALNHVNGLLGNCLLEMNWFLKKQDSVPLSCKKYSF HVLARSIQFMYNQGDGFSISNKVIKDQVQKVLIVPVPI* | SEQ ID NO: 59 |
| ADS | MALTEEKPIRPIANFPPSIWGDQFLIYEKQVEQGVEQIVNDLKKEVRQLLK EALDIPMKHANLLKLIDEIQRLGIPYHFEREIDHALQCIYETYGDNWNGDR SSLWFRLMRKQGYYVTCDVFNNYKDKNGAFKQSLANDVEGLLELYEAT SMRVPGEIILEDALGFTRSRLSIMTKDAFSTNPALFTEIQRALKQPLWKRLP RIEAAQYIPFYQQQDSHNKTLLKLAKLEFNLLQSLHKEELSHVCKWWKAF DIKKNAPCLRDRIVECYFWGLGSGYEPQYSRARVFFTKAVAVITLIDDTYD AYGTYEELKIFTEAVERWSITCLDTLPEYMKPIYKLFMDTYTEMEEFLAKE GRTDLFNCGKEFVKEFVRNLMVEAKWANEGHIPTTEEHDPVVIITGANL LTTTCYLGMSDIFTKESVEWAVSAPPLFRYSGILGRRLNDLMTHKAEQER KHSSSSLESYMKEYNVNEEYAQTLIYKEVEDVWKDINREYLTTKNIPRPLL MAVIYLCQFLEVQYAGKDNFTRMGDEYKHLIKSLLVYPMSI* | SEQ ID NO: 60 |
| TXS | MSSSTGTSKVVSETSSTIVDDIPRLSANYHGDLWHHNVIQTLETPFRESSTY QERADELVVKIKDMFNALGDGDISPSAYDTAWVARLATISSDGSEKPRFP QALNWVFNNQLQDGSWGIESHFSLCDRLLNTTNSVIALSVWKTGHSQVQ QGAEFIAENLRLLNEEDELSPDFQIIPPALLQKAKALGINLPYDLPFIKYLST TREARLTDVSAAADNIPANMLNALEGLEEVIDWNKIMRFQSKDGSFLSSP ASTACVLMNTGDEKCFTFLNNLLDKFGGCVPCMYSIDLLERLSLVDNIEH LGIGRHFKQEIKGALDVYRHWSERGIGWGRDSLVPDLNTTALGLRTLR MHGYNVSSDVLNNFKDENGRFFSSAGQTHVELSVVNLFRASDLAFPDE RAMDDARKFAEPYLREALATKISTNTKLFKEIEYVVEYPWHMSIPRLEAR SYIDSYDDNYVWQRKTLYRMPSLSNSKCELAKLDFNIVQSLHQEELKLL TRWWKESGMADINFTRHRVAEVYFSSATFEPEYSATRIAFTKIGCLQVLFD DMADIFATLDELKSFTEGVKRWDTSLLHEIPECMQTCFKVWFKLMEEVN NDVVKVQGRDMLAHIRKPWELYFNCYVQEREWLEAGYIPTFEEYLKTYA | SEQ ID NO: 61 |

TABLE 3-continued

Exemplary Protein Sequences (includes truncations).

| Name | Amino Acid Sequence | SEQ ID NO. # |
|---|---|---|
| | ISVGLGPCTLQPILLMGELVKDDVVEKVHYPSNMFELVSLSWRLTNDTKT YQAEKARGQQASGIACYMKDNPGATEEDAIKHICRVVDRALKEASFEYF KPSNDIPMGCKSFIFNLRLCVQIFYKFIDGYGIANEEIKDYIRKVYIDPIQV* | |
| TC-PTP | MPTTIEREFEELDTQRRWQPLYLEIRNESHDYPHRVAKFPENRNRNRYRD VSPYDHSRVKLQNAENDYINASLVDIEEAQRSYILTQGPLPNTCCHFWLM VWQQKTKAVVMLNRIVEKESVKCAQYWPTDDQEMLFKETGFSVKLLSE DVKSYYTVHLLQLENINSGETRTISHFHYTTWPDFGVPESPASFLNPLFKV RESGSLNPDHGPAVIHCSAGIGRSGTFSLVDTCLVLMEKGDDINIKQVLLN MRKYRMGLIQTPDQLRFSYMAIIEGAKCIKGDSSIQKRWKELSKEDLSPAF DHSPNKIMTEKYNGNR | SEQ ID NO: 62 |
| PTPN5 | MSSGVDLGTENLYFQSMSRVLQAEELHEKALDPFLLQAEFFEIPMNFVDP KEYDIPGLVRKNRYKTILPNPHSRVCLTSPDPDDPLSSYINANYIRGYGGEE KVYIATQGPIVSTVADFWRMVWQEHTPIIVMITNIEEMNEKCTEYWPEEQ VAYDGVEITVQKVIHTEDYRLRLISLKSGTEERGLKHYWFTSWPDQKTPD RAPPLLHLVREVEEAAQQEGPHCAPIIVHCSAGIGRTGCFIATSICCQQLRQ EGVVDILKTTCQLRQDRGGMIQTCEQYQFVHHVMSLYEKQLSHQS* | SEQ ID NO: 63 |
| PTPN6 | MVRWFHRDLSGLDAETLLKGRGVHGSFLARPSRKNQGDFSLSVRVGDQV THIRIQNSGDFYDLYGGEKFATLTELVEYYTQQQGVVQDRDGTIIHLKYPL NCSDPTSERWYHGHMSGGQAETLLQAKGEPWTFLVRESLSQPGDFVLSV LSDQPKAGPGSPLRVTHIKVMCEGGRYTVGGLETFDSLTDLVEHFKKTGI EEASGAFVYLRQPYYATRVNAADIENRVLELNKKQESEDTAKAGFWEEF ESLQKQEVKNLHQRLEGQRPENKGKNRYKNILPFDHSRVILQGRDSNIPGS DYINANYIKNQLLGPDENAKTYIASQGCLEATVNDFWQMAWQENSRVIV MTTREVEKGRNKCVPYWPEVGMQRAYGPYSVTNCGEHDTTEYKLRTLQ VSPLDNGDLIREIWHYQYLSWPDHGVPSEPGGVLSFLDQINQRQESLPHA GPIIVHCSAGIGRTGTIIVIDMLMENISTKGLDCDIDIQKTIQMVRAQRSGM VQTEAQYKFIYVAIAQFIETTKKKLEVLQSQKGQESEYGNITYPPAMKNA HAKASRTSSKHKEDVYENLHTKNKREEKVKKQRSADKEKSKGSLKRK* | SEQ ID NO: 64 |
| PTPN11 | MTSRRWFHPNITGVEAENLLLTRGVDGSFLARPSKSNPGDFTLSVRRNGA VTHIKIQNTGDYYDLYGGEKFATLAELVQYYMEHHGQLKEKNGDVIELK YPLNCADPTSERWFHGHLSGKEAEKLLTEKGKHGSFLVRESQSHPGDFVL SVRTGDDKGESNDGKSKVTHVMIRCQELKYDVGGGERFDSLTDLVEHYK KNPMVETLGTVLQLKQPLNTTRINAAEIESRVRELSKLAETTDKVKQGFW EEFETLQQQECKLLYSRKEGQRQENKNKNRYKNILPFDHTRVVLHDGDP NEPVSDYINANIIMPEFETKCNNSKPKKSYIATQGCLQNTVNDFWRMVFQ ENSRVIVMTTKEVERGKSKCVKYWPDEYALKEYGVMRVRNVKESAAHD YTLRELKLSKVGQGNTERTVWQYHFRTWPDHGVPSDPGGVLDFLEEVHH KQESIMDAGPVVVHCSAGIGRTGTFIVIDILIDIIREKGVDCDIDVPKTIQMV RSQRSGMVQTEAQYRFIYMAVQHYIETLQRRIEEEQKSKRKGHEYTNIKY SLADQTSGDQSPLPPCTPTPPCAEMREDSARVYENVGLMQQQKSFR* | SEQ ID NO: 65 |
| PTN12 | MEQVEILRKFIQRVQAMKSPDHNGEDNFARDFMRLRRLSTKYRTEKIYPT ATGEKEENVKKNRYKDILPFDHSRVKLTLKTPSQDSDYINANFIKGVYGP KAYVATQGPLANTVIDFWRMVWEYNVVIIVMACREFEMGRKKCERYWP LYGEDPITFAPPFKISCEDEQARTDYFIRTLLLEFQNESRRLYQFHYVNWPD HDVPSSFDSILDMISLMRKYQEHEDVPICIHCSAGCGRTGAICAIDYTWNL LKAGKIPEEFNVFNLIQEMRTQRHSAVQTKEQYELVHRAIAQLFEKQLQL YEIHGAQKIADGVNEINTENMVSSIEPEKQDSPPPKPPRTRSCLVEGDAKEE ILQPPEPHPVPPILTPSPPSAFPTVTTVWQDNDRYHPKPVLQWFHQNNIQQT STETIVNQQNFQGKMNQQLNR | SEQ ID NO: 66 |
| PTPN22 | MDQREILQKFLDEAQSKKITKEEFANEFLKLKRQSTKYKADKTYPTTVAE KPKNIKKNRYKDILPYDYSRVELSLITSDEDSSYINANFIKGVYGPKAYIAT QGPLSTTLLDFWRMIWEYSVLIIVMACMEYEMGKKKCERYWAEPGEMQ LEFGPFSVSCEAEKRKSDYIIRTLKVKFNSETRTIYQFHYKNWPDHDVPSSI DPILELIWDVRCYQEDDSVPICIHCSAGCGRTGVICAIDYTWMLLKDGIIPE NFSVFSLIREMRTQRPSLVQTQEQYELVYNAVLELFKRQMDVIRD | SEQ ID NO: 67 |
| sfGFP | MRKGEELFTGVVPILVELDGDVNGHKFSVRGEGEGDATNGKLTLKFICTT GKLPVPWPTLVTTLTYGVQCFARYPDHMKQHDFFKSAMPEGYVQERTIS FKDDGTYKTRAEVKFEGDTLVNRIELKGIDFKEDGNILGHKLEYNFNSHN VYITADKQKNGIKANFKIRHNVEDGSVQLADHYQQNTPIGDGPVLLPDNH YLSTQSVLSKDPNEKRDHMVLLEFVTAAGITHGMDELYK* | SEQ ID NO: 68 |
| mClover | MHHHHHHVSKGEELFTGVVPILVELDGDVNGHKFSVRGEGEGDATNGKL TLKFICTTGKLPVPWPTLVTTFGYGVACFSRYPDHMKQHDFFKSAMPEGY VQERTISFKDDGTYKTRAEVKFEGDTLVNRIELKGIDFKEDGNILGHKLEY NFNSHNVYITADKQKNGIKANFKIRHNVEDGSVQLADHYQQNTPIGDGPV LLPDNHYLSHQSALSKDPNEKRDHMVLLEFVTAAGITHGMDELYK | SEQ ID NO: 69 |

TABLE 4

Exemplary Terminators.

| Name | DNA Sequence | SEQ ID No. # |
|---|---|---|
| T7 | ATCCGGATATAGTTCCTCCTTTCAGCAAAAAACCCCTCAAGACCCGTTTAGAGG CCCCAAGGGGTTATGCTAGTTATTGCTCAGCGGTGGCAGCAGCCAACTCAGCTT CCTTTCGGGCTTTGTTAGCAG | SEQ ID NO: 70 |
| rrnB T1/T2 | GGCTGTTTTGGCGGATGAGAGAAGATTTTCAGCCTGATACAGATTAAATCAGAA CGCAGAAGCGGTCTGATAAAACAGAATTTGCCTGGCGGCAGTAGCGCGGTGGT CCCACCTGACCCCATGCCGAACTCAGAAGTGAAACGCCGTAGCGCCGATGGTA GTGTGGGGTCACCCCATGCGAGAGTAGGGAACTGCCAGGCATCAAATAAAACG AAAGGCTCAGTCGAAAGACTGGGCCTTTCGTTTTATCTGTTGTTTGTCGGTGAA CGCTCTCCTGAGTAGGACAAATCCGCCGGGAGCGGATTTGAACGTTGCGAAGC AACGGCCCGGAGGGTGGCGGGCAGGACGCCCGCCATAAACTGCCAGGCATCAA ATTAAGCAGAAGGCCATCCTGACGGATGGCCTTTTTGCGTTTCTACAAACTCT | SEQ ID NO: 71 |
| TrrnB | TGCCTGGCGGCAGTAGCGCGGTGGTCCCACCTGACCCCATGCCGAACTCAGAA GTGAAACGCCGTAGCGCCGATGGTAGTGTGGGGTCTCCCCATGCGAGAGTAGG GAACTGCCAGGCATCAAATAAAACGAAAGGCTCAGTCGAAAGACTGGGCCTTT | SEQ ID NO: 72 |

TABLE 5

Exemplary DNA Sequences (includes truncations):

| Comp. | Organism | DNA Sequence | SEQ ID No. # |
|---|---|---|---|
| Src | H. sapiens | ATGGGCTCCAAGCCGCAGACTCAGGGCCTGGCCAAGGATGCCTGGGA GATCCCTCGGGAGTCGCTGCGGCTGGAGGTCAAGCTGGGCCAGGGCT GCTTTGGCGAGGTGTGGATGGGGACCTGGAACGGTACCACCAGGGTG GCCATCAAAACCCTGAAGCCTGGCACGATGTCTCCAGAGGCCTTCCTG CAGGAGGCCCAGGTCATGAAGAAGCTGAGGCATGAGAAGCTGGTGCA GTTGTATGCTGTGGTTTCAGAGGAGCCCATTTACATCGTCACGGAGTA CATGAGCAAGGGGAGTTTGCTGGACTTTCTCAAGGGGGAGACAGGCA AGTACCTGCGGCTGCCTCAGCTGGTGGACATGGCTGCTCAGATCGCCT CAGGCATGGCGTACGTGGAGCGGATGAACTACGTCCACCGGGACCTTC GTGCAGCCAACATCCTGGTGGGAGAGAACCTGGTGTGCAAAGTGGCC GACTTTGGGCTGGCTCGGCTCATTGAAGACAATGAGTACACGGCGCGG CAAGGTGCCAAATTCCCCATCAAGTGGACGGCTCCAGAAGCTGCCCTC TATGGCCGCTTCACCATCAAGTCGGACGTGTGGTCCTTCGGGATCCTG CTGACTGAGCTCACCACAAAGGGACGGGTGCCCTACCCTGGGATGGTG AACCGCGAGGTGCTGGACCAGGTGGAGCGGGGCTACCGGATGCCCTG CCCGCCGGAGTGTCCCGAGTCCCTGCACGACCTCATGTGCCAGTGCTG GCGGAAGGAGCCTGAGGAGCGGCCCACCTTCGAGTACCTGCAGGCCT TCCTGGAGGACTACTTCACGTCCACCGAGCCCCAGTACCAGCCCGGGG AGAACCTCTAA | SEQ ID NO: 73 |
| CDC37 | H. sapiens | ATGGTGGACTACAGCGTGTGGGACCACATTGAGGTGTCTGATGATGAA GACGAGACGCACCCCAACATCGACACGGCCAGTCTCTTCCGCTGGCGG CATCAGGCCCGGGTGGAACGCATGGAGCAGTTCCAGAAGGAGAAGGA GGAACTGGACAGGGGCTGCCGCGAGTGCAAGCGCAAGGTGGCCGAGT GCCAGAGGAAACTGAAGGAGCTGGAGGTGGCCGAGGGCGGCAAGGC AGAGCTGGAGCGCCTGCAGGCCGAGGCACAGCAGCTGCGCAAGGAGG AGCGGAGCTGGGAGCAGAAGCTGGAGGAGATGCGCAAGAAGGAGAA GAGCATGCCCTGGAACGTGGACACGCTCAGCAAAGACGGCTTCAGCA AGAGCATGGTAAATACCAAGCCCGAGAAGACGGAGGAGGACTCAGAG GAGGTGAGGGAGCAGAAACACAAGACCTTCGTGGAAAAATACGAGAA ACAGATCAAGCACTTTGGCATGCTTCGCCGCTGGGATGACAGCCAAAA GTACCTGTCAGACAACGTCCACCTGGTGTGCGAGGAGACAGCCAATTA CCTGGTCATTTGGTGCATTGACCTAGAGGTGGAGGAGAAATGTGCACT CATGGAGCAGGTGGCCCACCAGACAATCGTCATGCAATTTATCCTGGA GCTGGCCAAGAGCCTAAAGGTGGACCCCCGGGCCTGCTTCCGGCAGTT CTTCACTAAGATTAAGACAGCCGATCGCCAGTACATGGAGGGCTTCAA CGACGAGCTGGAAGCCTTCAAGGAGCGTGTGCGGGGCCGTGCCAAGC TGCGCATCGAGAAGGCCATGAAGGAGTACGAGGAGGAGGAGCGCAA GAAGCGGCTCGGCCCCGGCGGCCTGGACCCCGTCGAGGTCTACGAGTC CCTCCCTGAGGAACTCCAGAAGTGCTTCGATGTGAAGGACGTGCAGAT GCTGCAGGACGCCATCAGCAGCAAGATGGACCCCACGACGCAAAGTACC ACATGCAGCGCTGCATTGACTCTGGCCTCTGGGTCCCCAACTCTAAGG CCAGCGAGGCCAAGGAGGGAGAGGAGGCAGGTCCTGGGGACCCATTA CTGGAAGCTGTTCCCAAGACGGGCGATGAGAAGGATGTCAGTGTGTA A | SEQ ID NO: 74 |

TABLE 5-continued

Exemplary DNA Sequences (includes truncations):

| Comp. | Organism | DNA Sequence | SEQ ID No. # |
|---|---|---|---|
| PTP1B$_{1-435}$ | H. sapiens | ATGGAGATGGAAAAGGAGTTCGAGCAGATCGACAAGTCCGGGAGCTG<br>GGCGGCCATTTACCAGGATATCCGACATGAAGCCAGTGACTTCCCATG<br>TAGAGTGGCCAAGCTTCCTAAGAACAAAAACCGAAATAGGTACAGAG<br>ACGTCAGTCCCTTTGACCATAGTCGGATTAAACTACATCAAGAAGATA<br>ATGACTATATCAACGCTAGTTTGATAAAAATGGAAGAAGCCCAAAGG<br>AGTTACATTCTTACCCAGGGCCCTTTGCCTAACACATGCGGTCACTTTT<br>GGGAGATGGTGTGGGAGCAGAAAAGCAGGGGTGTCGTCATGCTCAAC<br>AGAGTGATGGAGAAAGGTTCGTTAAAATGCGCACAATACTGGCCACA<br>AAAAGAAGAAAAGAGATGATCTTTGAAGACACAAATTTGAAATTAA<br>CATTGATCTCTGAAGATATCAAGTCATATTATACAGTGCGACAGCTAG<br>AATTGGAAAACCTTACAACCCAAGAAACTCGAGAGATCTTACATTTCC<br>ACTATACCACATGGCCTGACTTTGGAGTCCCTGAATCACCAGCCTCAT<br>TCTTGAACTTTCTTTTCAAAGTCCGAGAGTCAGGGTCACTCAGCCCGG<br>AGCACGGGCCCGTTGTGGTGCACTGCAGTGCAGGCATCGGCAGGTCTG<br>GAACCTTCTGTCTGGCTGATACCTGCCTCTTGCTGATGGACAAGAGGA<br>AAGACCCTTCTTCCGTTGATATCAAGAAAGTGCTGTTAGAAATGAGGA<br>AGTTTCGGATGGGGCTGATCCAGACAGCCGACCAGCTGCGCTTCTCCT<br>ACCTGGCTGTGATCGAAGGTGCCAAATTCATCATGGGGGACTCTTCCG<br>TGCAGGATCAGTGGAAGGAGCTTTCCCACGAGGACCTGGAGCCCCCA<br>CCCGAGCATATCCCCCCACCTCCCCGGCCACCCAAACGAATCCTGGAG<br>CCACACAATGGGAAATGCAGGGAGTTCTTCCCAAATCACCAGTGGGTG<br>AAGGAAGAGACCCAGGAGGATAAAGACTGCCCCATCAAGGAAGAAA<br>AAGGAAGCCCCTTAAATGCCGCACCCTACGGCATCGAAAGCATGAGT<br>CAAGACACTGAAGTTAGAAGTCGGGTCGTGGGGGGAAGTCTTCGAGG<br>TGCCCAGGCTGCCTCCCCAGCCAAAGGGGAGCCGTCACTGCCCGAGA<br>AGGACGAGGACCATGCACTGAGTTACTGGAAGCCCTTCCTGGTCAACA<br>TGTGCGTGGCTACGGTCCTCACGGCCGGCGCTTACCTCTGCTACAGGT<br>TCCTGTTCAACAGCAACACATAG | SEQ ID NO: 75 |
| LuxAB | Bacterial | ATGAAATTTGGAAACTTTTTGCTTACATACCAACCTCCCCAATTTTCCC<br>AAACAGAGGTAATGAAACGTTTGGTTAAATTAGGTCGCATCTCTGAGG<br>AGTGTGGTTTTGATACCGTATGGTTACTGGAGCATCATTTCACGGAGTT<br>TGGTTTGCTTGGTAACCCTTATGTCGCTGCTGCATATTTACTTGGCGCG<br>ACTAAAAAATTGAATGTAGGAACTGCCGCTATTGTTCTTCCCACAGCC<br>CATCCAGTACGCCAACTTGAAGATGTGAATTTATTGGATCAAATGTCA<br>AAAGGACGATTTCGGTTTGGTATTTGCCGAGGGCTTTACAACAAGGAC<br>TTTCGCGTATTCGGCACAGATATGAATAACAGTCGCGCCTTAGCGGAA<br>TGCTGGTACGGGCTGATAAAGAATGGCATGACAGAGGGATATATGGA<br>AGCTGATAATGAACATATCAAGTTCCATAAGGTAAAAGTAAACCCCGC<br>GGCGTATAGCAGAGGTGGCGCACCGGTTTATGTGGTGGCTGAATCAGC<br>TTCGACGACTGAGTGGGCTGCTCAATTTGGCCTACCGATGATATTAAG<br>TTGGATTATAAATACTAACGAAAAGAAAGCACAACTTGAGCTTTATAA<br>TGAAGTGGCTCAAGAATATGGGCACGATATTCATAATATCGACCATTG<br>CTTATCATATATAACATCTGTAGATCATGACTCAATTAAAGCGAAAGA<br>GATTTGCCGGAAATTTCTGGGGCATTGGTATGATTCTTATGTGAATGCT<br>ACGACTATTTTTGATGATTCAGACCAAACAAGAGGTTATGATTTCAAT<br>AAAGGGCAGTGGCGTGACTTTGTATTAAAAGGACATAAAGATACTAA<br>TCGCCGTATTGATTACAGTTACGAAATCAATCCCGTGGGAACGCCGCA<br>GGAATGTATTGACATAATTCAAAAAGACATTGATGCTACAGGAATATC<br>AAATATTTGTTGTGGATTTGAAGCTAATGGAACAGTAGACGAAATTAT<br>TGCTTCCATGAAGCTCTTCCAGTCTGATGTCATGCCATTTCTTAAAGAA<br>AAACAACGTTCGCTATTATATTATTAA | SEQ ID NO: 76 |
| LuxB | V. fischeri | ATGAGCAAATTTGGATTGTTCTTCCTTAACTTCATCAATTCAACAACTG<br>TTCAAGAACAGAGTATAGTTCGCATGCAGGAAATAACGGAGTATGTTG<br>ATAAGTTGAATTTTGAACAGATTTTAGTGTATGAAATCATTTTTCAGA<br>TAATGGTGTTGTCGGCGCTCCTCTGACTGTTTCTGGTTTTCTGCTCGGT<br>TTAACAGAGAAATTAAAATTGGTTCATTAAATCACATCATTACAACT<br>CATCATCCTGTCCGCATAGCGGAGGAAGCTTGCTTATTGGATCAGTTA<br>AGTGAAGGGAGATTATTTTAGGGTTTAGTGATTGCGAAAAAAAGAT<br>GAAATGCATTTTTTTAATCGCCCGGTTGAATATCAACAGCAACTATTTG<br>AAGAGTGTTATGAAATCATTAACGATGCTTTAACAACAGGCTATTGTA<br>ATCCAGATAACGATTTTTATAGCTTCCCTAAAATATCTGTAAATCCCCA<br>TGCTTATACGCCAGGCGGACCTCGGAAATATGTAACAGCAACCAGTCA<br>TCATATTGTTGAGTGGGCGGCCAAAAAAGGTATTCCTCTCATCTTTAA<br>GTGGGATGATTCTAATGATGTTAGATATGAATATGCTGAAAGATATAA<br>AGCCGTTGCGGATAAATATGACGTTGACCTATCAGAGATAGACCATCA<br>GTTAATGATATTAGTTAACTATAACGAAGATAGTAATAAAGCTAAACA<br>AGAAACGCGTGCATTTATTAGTGATTATGTTCTTGAAATGCACCCTAA<br>TGAAATTTCGAAAATAAACTTGAAGAAATAATTGCAGAAAACGCTG<br>TCGGAAATTATACGGAGTGTATAACTGCGGCTAAGTTGGCAATTGAAA<br>AGTGTGGTGCGAAAAGTGTATTGCTGTCCTTTGAACCAATGAATGATT<br>TGATGAGCCAAAAAAATGTAATCAATATTGTTGATGATAATATTAAGA<br>AGTACCACACGGAATATACCTAA | SEQ ID NO: 77 |

TABLE 5-continued

Exemplary DNA Sequences (includes truncations):

| Comp. | Organism | DNA Sequence | SEQ ID No. # |
|---|---|---|---|
| RpoZ | Escherichia coli | ATGGCACGCGTAACTGTTCAGGACGCTGTAGAGAAAATTGGTAACCGT TTTGACCTGGTACTGGTCGCCGCGCGTCGCGCTCGTCAGATGCAGGTA GGCGGAAAGGATCCGCTGGTACCGGAAGAAAACGATAAAACCACTGT AATCGCGCTGCGCGAAATCGAAGAAGGTCTGATCAACAACCAGATCC TCGACGTTCGCGAACGCCAGGAACAGCAAGAGCAGGAAGCCGCTGAA TTACAAGCCGTTACCGCTATTGCTGAAGGTCGTCGTTAA | SEQ ID NO: 78 |
| cI | Lambda bacteriophage | ATGAGTATCAGCAGCAGGGTAAAAAGCAAAAGAATTCAGCTTGGACT TAACCAGGCTGAACTTGCTCAAAAGGTGGGGACTACCCAGCAGTCTAT AGAGCAGCTCGAAAACGGTAAAACTAAGCGACCACGCTTTTTACCAG AACTTGCGTCAGCTCTTGGCGTAAGTGTTGACTGGCTGTCAATGGCA CCTCTGATTCGAATGTTAGATTTGTTGGGCACGTTGAGCCCAAAGGGA AATATCCATTGATTAGCATGGTTAGAGCTCGTTCGTGGTGTGAAGCTT GTGAACCCTACGATATCAAGGACATTGATGAATGGTATGACAGTGACG TTAACTTATTAGGCAATGGATTCTGGCTGAAGGTTGAAGGTGATTCCA TGACCTCACCTGTAGGTCAAAGCATCCCTGAAGGTCATATGGTGTTAG TAGATACTGGACGGGAGCCAGTGAATGGAAGCTTGTTGTAGCCAAA CTGACTGACGCGAACGAAGCAACATTCAAGAAACTGGTCATAGATGG CGGTCAGAAGTACCTGAAAGGCCTGAATCCTTCATGGCCTATGACTCC TATCAACGGAAACTGCAAGATTATCGGTGTTGTCGTGGAAGCGAGGGT AAAATTCGTAGACTAA | SEQ ID NO: 79 |
| SH2 | Rous sarcoma virus | ATGTGGTATTTTGGGAAGATCACTCGTCGGGAGTCCGAGCGGCTGCTG CTCAACCCCGAAAACCCCGGGGAACCTTCTTGGTCCGGGAGAGCGA GACGGTAAAAGGTGCCTATGCCCTCTCCGTTTCTGACTTTGACAACGC CAAGGGGCTCAATGTGAAACACTACCTGATCCGCAAGCTGGACAGCG GCGGCTTCTACATCACCTCACGCACACAGTTCAGCAGCCTGCAGCAGC TGGTGGCCTACTACTCCAAACATGCTGATGGCTTGTGCCACCGCCTGA CCAACGTCTGCTAA | SEQ ID NO: 80 |
| MBP | E. coli | ATGAAAATCGAAGAAGGTAAACTGGTAATCTGGATTAACGGCGATAA AGGCTATAACGGTCTCGCTGAAGTCGGTAAGAAATTCGAGAAAGATA CCGGAATTAAAGTCACCGTTGAGCATCCGGATAAACTGGAAGAGAAA TTCCCACAGGTTGCGGCAACTGGCGATGGCCCTGACATTATCTTCTGG GCACACGACCGCTTTGGTGGCTACGCTCAATCGGCCTGTTGGCTGAA ATCACCCCCGGACAAAGCGTTCCAGGACAAGCTGTATCCGTTTACCTGG GATGCCGTACGTTACAACGGCAAGCTGATTGCTTACCCGATCGCTGTT GAAGCGTTATCGCTGATTTATAACAAAGATCTGCTGCCGAACCCGCCA AAAACCTGGGAAGAGATCCCGGCGCTGGATAAAGAACTGAAAGCGAA AGGTAAGAGCGCGCTGATGTTCAACCTGCAAGAACCGTACTTCACCTG GCCGCTGATTGCTGCTGACGGGGGTTATGCGTTCAAGTATGAAAACGG CAAGTACGACATTAAAGACGTGGGCGTGGATAACGCTGGCGCGAAAG CGGGTCTGACCTTCCTGGTTGACCTGATTAAAAACAAACACATGAATG CAGACACCGATTACTCCATCGCAGAAGCTGCCTTTAATAAAGGCGAAA CAGCGATGACCATCAACGGCCCGTGGGCATGGTCCAACATCGACACC AGCAAAGTGAATTATGGTGTAACGGTACTGCCGACCTTCAAGGGTCAA CCATCCAAACCGTTCGTTGGCGTGCTGAGCGCAGGTATTAACGCCGCC AGTCCGAACAAAGAGCTGGCGAAAGAGTTCCTCGAAAACTATCTGCT GACTGATGAAGGTCTGGAAGCGGTTAATAAAGACAAACCGCTGGGTG CCGTAGCGCTGAAGTCTTACGAGGAAGAGTTGGCGAAAGATCCACGT ATTGCCGCCACCATGGAAAACGCCCAGAAAGGTGAAATCATGCCGAA CATCCCGCAGATGTCCGCTTTCTGGTATGCCGTGCGTACTGCGGTGATC AACGCCGCCAGCGGTCGTCAGACTGTCGATGAAGCCCTGAAAGACGC GCAGACTCGTATCACCAAGTAA | SEQ ID NO: 81 |
| p130cas (or Kras) substrate | H. sapiens | TGGATGGAGGACTATGACTACGTCCACCTACAGGGG | SEQ ID NO: 82 |
| MidT substrate | Hamster polyoma virus | GAACCGCAGTATGAAGAAATTCCGATTTATCTG | SEQ ID NO: 83 |
| EGFR substrate | H. sapiens | CCGCAGCGCTATCTGGTGATTCAGGGCGAT | SEQ ID NO: 84 |
| ShcA substrate | H. sapiens | GATCATCAGTATTATAACGATTTTCCGGGC | SEQ ID NO: 85 |

TABLE 5-continued

Exemplary DNA Sequences (includes truncations):

| Comp. | Organism | DNA Sequence | SEQ ID No. # |
|---|---|---|---|
| MBIS | S. cerevisiae (from pMBIS Addgene#: 17817) | ATGTCATTACCGTTCTTAACTTCTGCACCGGGAAAGGTTATTATTTTTG GTGAACACTCTGCTGTGTACAACAAGCCTGCCGTCGCTGCTAGTGTGT CTGCGTTGAGAACCTACCTGCTAATAAGCGAGTCATCTGCACCAGATA CTATTGAATTGGACTTCCCGGACATTAGCTTTAATCATAAGTGGTCAT CAATGATTTCAATGCCATCACCGAGGATCAAGTAAACTCCCAAAAATT GGCCAAGGCTCAACAAGCCACCGATGGCTTGTCTCAGGAACTCGTTAG TCTTTTGGATCCGTTGTTAGCTCAACTATCCGAATCCTTCCACTACCAT GCAGCGTTTTGTTTCCTGTATATGTTTGTTTGCCTATGCCCCCATGCCA AGAATATTAAGTTTTCTTTAAAGTCTACTTTACCCATCGGTGCTGGGTT GGGCTCAAGCGCCTCTATTTCTGTATCACTGGCCTTAGCTATGGCCTAC TTGGGGGGGTTAATAGGATCTAATGACTTGGAAAAGCTGTCAGAAAA CGATAAGCATATAGTGAATCAATGGGCCTTCATAGGTGAAAAGTGTAT TCACGGTACCCCTTCAGGAATAGATAACGCTGTGGCCACTTATGGTAA TGCCCTGCTATTTGAAAAAGACTCACATAATGGAACAATAAACACAAA CAATTTTAAGTTCTTAGATGATTTCCCAGCCATTCCAATGATCCTAACC TATACTAGAATTCCAAGGTCTACAAAAGATCTTGTTGCTCGCGTTCGT GTGTTGGTCACCGAGAAATTTCCTGAAGTTATGAAGCCAATTCTAGAT GCCATGGGTGAATGTGCCCTACAAGGCTTAGAGATCATGACTAAGTTA AGTAAATGTAAAGGCACCGATGACGAGGCTGTAGAAACTAATAATGA ACTGTATGAACAACTATTGGAATTGATAAGAATAAATCATGGACTGCT TGTCTCAATCGGTGTTTCTCATCCTGGATTAGAACTTATTAAAAATCTG AGCGATGATTTGAGAATTGGCTCCACAAAACTTACCGGTGCTGGTGGC GGCGGTTGCTCTTTGACTTTGTTACGAAGAGACATTACTCAAGAGCAA ATTGACAGCTTCAAAAAGAAATTGCAAGATGATTTTAGTTACGAGACA TTTGAAACAGACTTGGGTGGGACTGGCTGCTGTTTGTTAAGCGCAAAA AATTTGAATAAAGATCTTAAAATCAAATCCCTAGTATTCCAATTATTTG AAAATAAAACTACCACAAAGCAACAAATTGACGATCTATTATTGCCAG GAAACACGAATTTNCCATGGACTTCATAGGAGGCAGATCAAATGTCA GAGTTGAGAGCCTTCAGTGCCCCAGGGAAAGCGTTACTAGCTGGTGGA TATTTAGTTTTAGATACAAAATATGAAGCATTTGTAGTCGGATTATCG GCAAGAATGCATGCTGTAGCCCATCCTTACGGTTCATTGCAAGGGTCT GATAAGTTTGAAGTGCGTGTGAAAAGTAAACAATTTAAAGATGGGGA GTGGCTGTACCATATAAGTCCTAAAAGTGGCTTCATTCCTGTTTCGATA GGCGGATCTAAGAACCCTTTCATTGAAAAAGTTATCGCTAACGTATTT AGCTACTTTAAACCTAACATGGACGACTACTGCAATAGAAACTTGTTC GTTATTGATATTTTCTCTGATGATGCCTACCATTCTCAGGAGGATAGCG TTACCGAACATCGTGGCAACAGAAGATTGAGTTTTCATTCGCACAGAA TTGAAGAAGTTCCCAAAACAGGGCTGGGCCTCTCGGCAGGTTTAGTCA CAGTTTTAACTACAGCTTTGGCCTCCTTTTTTGTATCGGACCTGGAAAA TAATGTAGACAAATATAGAGAAGTTATTCATAATTTAGCACAAGTTGC TCATTGTCAAGCTCAGGGTAAAATTGGAAGCGGGTTTGATGTAGCGGC GGCAGCATATGGATCTATCAGATATAGAAGATTCCCACCCGCATTAAT CTCTAATTTGCCAGATATTGGAAGTGCTACTTTACGGCAGTAAACTGGC GCATTTGGTTGATGAAGAAGACTGGAATATTACGATTAAAAGTAACCA TTTACCTTCGGGATTAACTTTATGGATGGGCGATATTAAGAATGGTTC AGAAACAGTAAAACTGGTCCAGAAGGTAAAAATTGGTATGATTCGC ATATGCCAGAAAGCTTGAAAATATATACAGAACTCGATCATGCAAATT CTAGATTTATGGATGGACTATCTAAACTAGATCGCTTACACGAGACTC ATGACGATTACAGCGATCAGATATTTGAGTCTCTTGAGAGGAATGACT GTACCTGTCAAAAGTATCCTGAAATCACAGAAGTTAGAGATGCAGTTG CCACAATTAGACGTTCCTTTAGAAAAATAACTAAAGAATCTGGTGCCG ATATCGAACCTCCCGTACAAACTAGCTTATTGGATGATTGCCAGACCT TAAAAGGAGTTCTTACTTGCTTAATACCTGGTGCTGGTGGTTATGACG CCATTGCAGTGATTACTAAGCAAGATGTTGATCTTAGGGCTCAAACCG CTAATGACAAAAGATTTTCTAAGGTTCAATGGCTGGATGTAACTCAGG CTGACTGGGGTGTTAGGAAAGAAAAAGATCCGGAAACTTATCTTGATA AATAGGAGGTAATACTCATGACCGTTTACACAGCATCCGTTACCGCAC CGTCAACATCGCAACCCTTAAGTATTGGGGAAAAGGGACACGAAG TTGAATCTGCCCACCAATTCGTCCATATCAGTGACTTATCGCAAGATG ACCTCAGAACGTTGACCTCTGCGGCTACTGCACCTGAGTTTGAACGCG ACACTTTGTGGTTAAATGGAGAACCACACAGCATCGACAATGAAGA ACTCAAAATTGTCTGCGCGACCTACGCCAATTAAGAAAGGAAATGGA ATCGAAGGACGCCTCATTGCCCACATTATCTCAATGGAAACTCCACAT TGTCTCCGAAAATAACTTTCCTACAGCAGCTGGTTTAGCTTCCTCCGCT GCTGGCTTTGCTGCATTGGTCTCTGCAATTGCTAAGTTATACCAATTAC CACAGTCAACTTCAGAAATATCTAGAATAGCAAGAAAGGGGTCTGGTT CAGCTTGTAGATCGTTGTTTGGCGGATACGTGGCCTGGGAAATGGGAA AAGCTGAAGATGGTCATGATTCCATGGCAGTACAAATCGCAGACAGCT CTGACTGGCCTCAGATGAAAGCTTGTGTCCTAGTTGTCAGCGATATTA AAAAGGATGTGAGTTCCACTCAGGGTATGCAATTGACCGTGGCAACCT CCGAACTATTTAAAGAAGAATTGAACATGTCGTACCAAAGAGATTTG AAGTCATGCGTAAAGCCATTGTTGAAAAGATTTCGCCACCTTTGCAA AGGAAACAATGATGGATTCCAACTCTTTCCATGCCACATGTTTGGACT | SEQ ID NO: 86 |

TABLE 5-continued

Exemplary DNA Sequences (includes truncations):

| Comp. | Organism | DNA Sequence | SEQ ID No. # |
|---|---|---|---|
| | | CTTTCCCTCCAATATTCTACATGAATGACACTTCCAAGCGTATCATCAG<br>TTGGTGCCACACCATTAATCAGTTTTACGGAGAAACAATCGTTGCATA<br>CACGTTTGATGCAGGTCCAAATGCTGTGTTGTACTACTTAGCTGAAAA<br>TGAGTCGAAACTCTTTGCATTTATCTATAAATTGTTTGGCTCTGTTCCT<br>GGATGGGACAAGAAATTTACTACTGAGCAGCTTGAGGCTTTCAACCAT<br>CAATTTGAATCATCTAACTTTACTGCACGTGAATTGGATCTTGAGTTGC<br>AAAAGGATGTTGCCAGAGTGATTTTAACTCAAGTCGGTTCAGGCCCAC<br>AAGAAACAAACGAATCTTTGATTGACGCAAAGACTGGTCTACCAAAG<br>GAATAACTGCAGCCCGGGAGGAGGATTACTATATGCAAACGGAACAC<br>GTCATTTTATTGAATGCACAGGGAGTTCCCACGGGTACGCTGGAAAAG<br>TATGCCGCACACACGGCAGACACCCGCTTACATCTCGCGTTCTCCAGT<br>TGGCTGTTTAATGCCAAAGGACAATTATTAGTTACCCGCCGCGCACTG<br>AGCAAAAAAGCATGGCCTGGCGTGTGGACTAACTCGGTTTGTGGGCAC<br>CCACAACTGGGAGAAAGCAACGAAGACGCAGTGATCCGCCGTTGCCG<br>TTATGAGCTTGGCGTGGAAATTACGCCTCCTGAATCTATCTATCCTGAC<br>TTTCGCTACCGCGCCACCGATCCGAGTGGCATTGTGGAAAATGAAGTG<br>TGTCCGGTATTTGCCGCACGCACCACTAGTGCGTTACAGATCAATGAT<br>GATGAAGTGATGGATTATCAATGGTGTGATTTAGCAGATGTATTACAC<br>GGTATTGATGCCACGCCGTGGCGTTCAGTCCGTGGATGGTGATGCAG<br>GCGACAAATCGCGAAGCCAGAAAACGATTATCTGCATTTACCCAGCTT<br>AAATAACCCGGGGGATCCACTAGTTCTAGAGCGGCCGCCACCGCGGA<br>GGAGGAATGAGTAATGGACTTTCCGCAGCAACTCGAAGCCTGCGTTAA<br>GCAGGCCAACCAGGCGCTGAGCCGTTTTATCGCCCCACTGCCCTTTCA<br>GAACACTCCCGTGGTCGAAACCATGCAGTATGGCGCATTATTAGGTGG<br>TAAGCGCCTGCGACCTTTCCTGGTTTATGCCACCGGTCATATGTTCGGC<br>GTTAGCACAAACACGCTGGACGCACCCGCTGCCGCCGTTGAGTGTATC<br>CACGCTTACTCATTAATTCATGATGATTTACCGGCAATGGATGATGAC<br>GATCTGCGTCGCGGTTTGCCAACCTGCCATGTGAAGTTTGGCGAAGCA<br>AACGCGATTCTCGCTGGCGACGCTTTACAAACGCTGGCGTTCTCGATT<br>TTAAGCGATGCCGATATGCCGGAAGTGTCGGACCGCGACAGAATTTCG<br>ATGATTTCTGAACTGGCGAGCGCCAGTGGTATTGCCGGAATGTGCGGT<br>GGTCAGGCATTAGATTTAGACGCGGAAGGCAAACACGTACCTCTGGA<br>CGCGCTTGAGCGTATTCATCGTCATAAAACCGGCGCATTGATTCGCGC<br>CGCCGTTCGCCTTGGTGCATTAAGCGCCGGAGATAAAGGACGTCGTGC<br>TCTGCCGGTACTCGACAAGTATGCAGAGAGCATCGGCCTTGCCTTCCA<br>GGTTCAGGATGACATCCTGGATGTGGTGGGAGATACTGCAACGTTGGG<br>AAAACGCCAGGGTGCCGACCAGCAACTTGGTAAAAGTACCTACCCTG<br>CACTTCTGGGTCTTGAGCAAGCCCGGAAGAAAGCCCGGGATCTGATCG<br>ACGATGCCCGTCAGTCGCTGAAACAACTGGCTGAACAGTCACTCGATA<br>CCTCGGCACTGGAAGCGCTAGCGGACTACATCATCCAGCGTAATAAAT<br>AA | |
| ADS | Artemisia<br>annua | GCCCTGACCGAAGAGAAACCGATCCGCCCGATCGCTAACTTCCCGCCG<br>TCTATCTGGGGTGACCAGTTCCTGATCTACGAAAAGCAGGTTGAGCAG<br>GGTGTTGAACAGATCGTAAACGACCTGAAGAAAGAAGTTCGTCAGCT<br>GCTGAAAGAAGCTCTGGACATCCCGATGAAACACGCTAACCTGTTGAA<br>GCTGATCGACGAGATCCAGCGTCTGGGTATCCCGTACCACTTCGAACG<br>CGAAATCGACCACGCACTGCAGTGCATCTACGAAACCTACGGCGACA<br>ACTGGAACGGCGACCGTTCTTCTCTGTGGTTTCGTCTGATGCGTAAAC<br>AGGGCTACTACGTTACCTGTGACGTTTTTAACAACTACAAGGACAAGA<br>ACGGTGCTTTCAAACAGTCTCTGGCTAACGACGTTGAAGGCCTGCTGG<br>AACTGTACGAAGCGACCTCCATGCGTGTACCGGGTGAAATCATCCTGG<br>AGGACGCGCTGGGTTTCACCCGTTCTCGTCTGTCCATTATGACTAAAG<br>ACGCTTTCTCTACTAACCCGGCTCTGTTCACCGAAATCCAGCGTGCTCT<br>GAAACAGCCGCTGTGGAAACGTCTGCCGCGTATCGAAGCAGCACAGT<br>ACATTCCGTTTTACCAGCAGCAGGACTCTCACAACAAGACCCTGCTGA<br>AACTGGCTAAGCTGGAATTCAACCTGCTGCAGTCTCTGCACAAGAAG<br>AACTGTCTCACGTTTGTAAGTGGTGGAAGGCATTTGACATCAAGAAAA<br>ACGCGCCGTGCCTGCGTGACCGTATCGTTGAATGTTACTTCTGGGGTCT<br>GGGTTCTGGTTATGAACCACAGTACTCCCGTGCACGTGTGTTCTTCACT<br>AAAGCTGTAGCTGTTTATCACCCTGATCGATGACACTTACGATGCTTAC<br>GGCACCTACGAAGAACTGAAGATCTTTACTGAAGCTGTAGAACGCTGG<br>TCTATCACTTGCCTGGACACTCTGCCGGAGTACATGAAACCGATCTAC<br>AAACTGTTCATGGATACCTACACCGAAATGGAGGAATTCCTGGCAAAA<br>GAAGGCCGTACCGACCTGTTCAACTGCGGTAAAGAGTTTGTTAAAGAA<br>TTCGTACGTAACCTGATGGTTGAAGCTAAATGGGCTAACGAAGGCCAT<br>ATCCCGACTACCGAAGAACATGACCCGGTTGTTATCATCACCGGCGGT<br>GCAAACCTGCTGACCACCACTTGCTATCTGGGTATGTCCGACATCTTTA<br>CCAAGGAATCTGTTGAATGGGCTGTTTCTGCACCGCCGCTGTTCCGTTA<br>CTCCGGTATTCTGGGTCGTCGTCTGAACGACCTGATGACCCACAAAGC<br>AGAGCAGGAACGTAAACACTCTTCCTCCTCTCTGGAATCCTACATGAA<br>GGAATATAACGTTAACGAGGAGTACGCACAGACTCTGATCTATAAAG<br>AAGTTGAAGACGTATGAAAGACATCAACCGTGAATACCTGACTACT<br>AAAAACATCCCGCGCCCGCTGCTGATGGCAGTAATCTACCTGTGCCAG | SEQ ID NO: 87 |

TABLE 5-continued

Exemplary DNA Sequences (includes truncations):

| Comp. | Organism | DNA Sequence | SEQ ID No. # |
|---|---|---|---|
| | | TTCCTGGAAGTACAGTACGCTGGTAAAGATAACTTCACTCGCATGGGC GACGAATACAAACACCTGATCAAATCCCTGCTGGTTTACCCGATGTCC ATCTGA | |
| GHS | Abies grandis | ATGGCTCAAATCAGCGAATCAGTGTCTCCAAGCACCGACCTTAAAAGC ACGGAATCTTCTATTACCAGCAACCGCCACGGTAACATGTGGGAAGAT GACCGCATTCAGAGCTTAAACAGCCCATATGGCGCACCCGCTTATCAG GAACGTAGCGAAAAATTGATTGAAGAAATTAAGCTCCTGTTTCTGTCC GATATGGACGATAGTTGCAATGATTCGGATCGCGACTTGATCAAACGC CTGGAGATCGTAGATACGGTTGAGTGTCTGGGCATTGATCGTCATTTC CAACCTGAAATTAAGCTGGCGCTGGATTACGTGTACCGTTGCTGGAAT GAGCGTGGCATCGGAGAAGGTAGCCGTGATAGCTTAAAAAAGGACCT GAATGCGACCGCCTTGGGCTTTCGGGCTTTACGCTTACACCGTTATAAT GTAAGCTCAGGAGTGCTGGAGAACTTCCGTGATGACAATGGTCAATTC TTTTGCGGTTCTACTGTGGAGGAGGAAGGCGCGGAGGCCTACAATAAA CATGTACGTTGCATGCTGTCCCTGTCCCGCGCTTCCAATATTTTATTCC CGGGCGAGAAAGTGATGGAAGAAGCGAAGGCGTTTACGACCAACTAT CTTAAGAAAGTCCTGGCGGGTCGTGAAGCAACTCATGTCGACGAGAGT CTCCTTGGAGAGGTCAAGTATGCACTAGAATTTCCGTGGCATTGTTCC GTGCAGCGCTGGGAGGCACGTTCTTTTATCGAAATTTTCGGTCAGATT GATAGTGAACTGAAAAGCAACCTCTCTAAAAAAATGCTCGAACTCGC AAAACTTGATTTTAACATACTCCAGTGTACGCATCAAAAAGAGCTCCA GATCATTAGTCGATGGTTCGCCGATTCAAGTATCGCAAGTCTGAACTT TTACCGTAAATGCTATGTGGAATTTTACTTCTGGATGGCCGCGGCAATT TCAGAACCAGAATTTAGTGGCTCTCGCGTGGCATTCACTAAAATTGCG ATCTTGATGACAATGTTAGATGACTTATACGACACGCATGGGACGCTG GATCAATTGAAAATATTTACCGAAGGTGTGCGCAGGTGGGACGTGTCG CTGGTGGAGGGCCTGCCGGATTTCATGAAAATTGCCTTTGAGTTCTGG TTAAAGACCTCCAACGAACTGATTGCGGAGGCGGTTAAGGCCCAAGG CCAGGATATGGCGGCCTATATCCGCAAAAACGCTTGGGAACGCTATCT GGAAGCGTATTTGCAGGATGCCGAATGGATCGCCACCGGTCACGTTCC GACATTCGATGAATATCTGAACAATGGCACCCCCAACACCGGTATGTG TGTACTTAATCTGATCCCGTTGCTGCTTATGGGCGAACACTTGCCGATC GATATTCTTGAACAGATCTTTCTGCCGAGCCGGTTCCACCATCTGATTG AACTGGCTAGCCGACTGGTCGATGATGCGAGAGATTTTCAAGCCGAAA AAGATCATGGTGATTATCCTGCATCGAATGCTACCTGAAAGACCATC CGGAATCAACAGTTGAAGACGCCCTGAATCACGTCAACGGCCTGCTGG GGAATTGTTTGCTGGAAATGAATTGGAAATTTCTGAAAAAACAGGACT CGGTACCTCTGTCGTGTAAAAAATACTCATTCCACGTCCTGGCGCGGT CGATTCAGTTTATGTATAACCAGGGGACGGGTTTTCGATTTCGAACA AAGTTATTAAAGACCAGGTCCAGAAAGTTCTAATCGTTCCGGTTCCTA TATAA | SEQ ID NO: 88 |
| ABS | Abies grandis | TGAAACGAGAATTTCCTCCAGGATTTTGGAAGGATGATCTTATCGATT CTCTAACGTCATCTCACAAGGTTGCAGCATCAGACGAGAAGCGTATCG AGACATTAATATCCGAGATTAAGAATATGTTTAGATGTATGGGCTATG GCGAAACGAATCCCTCTGCATATGACACTGCTTGGGTAGCAAGGATTC CAGCAGTTGATGGCTCTGACAACCCTCACTTTCCTGAGACGGTTGAAT GGATTCTTCAAAATCAGTTGAAAGATGGGTCTTGGGGTGAAGGATTCT ACTTCTTGGCATATGACAGAATACTGGCTACACTTGCATGTATTATTAC CCTTACCCTCTGGCGTACTGGGGAGACACAAGTACAGAAAGGTATTGA ATTCTTCAGGACACAAGCTGGAAAGATGGAAGATGAAGCTGATAGTC ATAGGCCAAGTGGATTTGAAATAGTATTTCCTGCAATGCTAAAGGAAG CTAAAATCTTAGGCTTGGATCTGCCTTACGATTTGCCATTCCTGAAACA AATCATCGAAAAGCGGGAGGCTAAGCTTAAAAGGATTCCC ACTGATGTTCTCTATGCCCTTCCAACAACGTTATTGTATTCTTTGGAAG GTTTACAAGAAATAGTAGACTGGCAGAAAATAATGAAACTTCAATCC AAGGATGGATCATTTCTCAGCTCTCCGGCATCTACAGCGGCTGTATTC ATGCGTACAGGGAACAAAAAGTGCTTGGATTTCTTGAACTTTGTCTTG AAGAAATTCGGAAACCATGTGCCTTGTCACTATCCGCTTGATCTATTTG AACGTTTGTGGGCGGTTGATACAGTTGAGCGGCTAGGTATCGATCGTC ATTTCAAAGAGGAGATCAAGGAAGCATTGGATTATGTTTACAGCCATT GGGACGAAAGAGGCATTGGATGGGCGAGAGAGAATCCTGTTCCTGAT ATTGATGATACAGCCATGGGCCTTCGAATCTTGAGATTACATGGATAC AATGTATCCTCAGATGTTTTAAAAACATTTAGAGATGAGAATGGGGAG TTCTTTTGCTTCTTGGGTCAAACACAGAGAGGAGTTACAGACATGTTA AACGTCAATCGTTGTTCACATGTTTCATTTCCGGGAGAAACGATCATG GAAGAAGCAAAACTCTGTACCGAAAGGTATCTGAGGAATGCTCTGGA AAATGTGGATGCCTTTGACAAATGGGCTTTTAAAAAGAATATTCGGGG AGAGGTAGAGTATGCACTCAAATATCCCTGGCATAAGAGTATGCCAA GGTTGGAGGCTAGAAGCTATATTGAAACTATGGGCCAGATGATGTGT GGCTTGGAAAAACTGTATATATGATGCCATACATTTCGAATGAAAAGT ATTTAGAACTAGCGAAACTGGACTTCAATAAGGTGCAGTCTATACACC AAACAGAGCTTCAAGATCTTCGAAGGTGGTGGAAATCATCCGGTTTCA | SEQ ID NO: 89 |

TABLE 5-continued

Exemplary DNA Sequences (includes truncations):

| Comp. | Organism | DNA Sequence | SEQ ID No. # |
|---|---|---|---|
| | | CGGATCTGAATTTCACTCGTGAGCGTGTGACGGAAATATATTTCTCAC<br>CGGCATCCTTTATCTTTGAGCCCGAGTTTTCTAAGTGCAGAGAGGTTTA<br>TACAAAAACTTCCAATTTCACTGTTATTTTAGATGATCTTTATGACGCC<br>CATGGATCTTTAGACGATCTTAAGTTGTTCACAGAATCAGTCAAAAGA<br>TGGGATCTATCACTAGTGGACCAAATGCCACAACAAATGAAAATATGT<br>TTTGTGGGTTTCTACAATACTTTTAATGATATAGCAAAAGAAGGACGT<br>GAGAGGCAAGGGCGCGATGTGCTAGGCTACATTCAAAATGTTTGGAA<br>AGTCCAACTTGAAGCTTACACGAAAGAAGCAGAATGGTCTGAAGCTA<br>AATATGTGCCATCCTTCAATGAATACATAGAGAATGCGAGTGTGTCAA<br>TAGCATTGGGAACAGTCGTTCTCATTAGTGCTCTTTTCACTGGGGAGGT<br>TCTTACAGATGAAGTACTCTCCAAAATTGATCGCGAATCTAGATTTCTT<br>CAACTCATGGGCTTAACAGGGCGTTTGGTGAATGACACCAAAACTTAT<br>CAGGCAGAGAGAGGTCAAGGTGAGGTGGCTTCTGCCATACAATGTTAT<br>ATGAAGGACCATCCTAAAATCTCTGAAGAAGAAGCTCTACAACATGTC<br>TATAGTGTCATGGAAAATGCCCTCGAAGAGTTGAATAGGGAGTTTGTG<br>AATAACAAAATACCGGATATTTACAAAAGACTGGTTTTTGAAACTGCA<br>AGAATAATGCAACTCTTTTATATGCAAGGGGATGGTTTGACACTATCA<br>CATGATATGGAAATTAAAGAGCATGTCAAAAATTGCCTCTTCCAACCA<br>GTTGCC | |
| TXS | Taxus brevifola | ATGAGCAGCAGCACTGGCACTAGCAAGGTGGTTTCCGAGACTTCCAGT<br>ACCATTGTGGATGATATCCCTCGACTCTCCGCCAATTATCATGGCGATC<br>TGTGGCACCACAATGTTATACAAACTCTGGAGACACCGTTTCGTGAGA<br>GTTCTACTTACCAAGAACGGGCAGATGAGCTGGTTGTGAAAATTAAAG<br>ATATGTTCAATGCGCTCGGAGACGGAGATATCAGTCCGTCTGCATACG<br>ACACTGCGTGGGTGGCGAGGCTGGCGACCATTTCCTCTGATGGATCTG<br>AGAAGCCACGGTTTCCTCAGGCCCTCAACTGGGTTTTCAACAACCAGC<br>TCCAGGATGGATCGTGGGGTATCGAATCGCACTTTAGTTTATGCGATC<br>GATTGCTTAACACGACCAATTCTGTTATCGCCCTCTCGGTTTGGAAAAC<br>AGGGCACAGCCAAGTACAACAAGGTGCTGAGTTTATTGCAGAGAATC<br>TAAGATTACTCAATGAGGAAGATGAGTTGTCCCCGGATTTCCAAATAA<br>TCTTTCCTGCTCTGCTGCAAAAGGCAAAAGCGTTGGGGATCAATCTTC<br>CTTACGATCTTCCATTTATCAAATATTTGTCGACAACACGGGAAGCCA<br>GGCTTACAGATGTTTCTGCGGCAGCAGACAATATTCCAGCCAACATGT<br>TGAATGCGTTGGAAGGACTCGAGGAAGTTATTGACTGGAACAAGATT<br>ATGAGGTTTCAAAGTAAAGATGGATCTTTCCTGAGCTCCCCTGCCTCC<br>ACTGCCTGTGTACTGATGAATACAGGGGACGAAAAATGTTTCACTTTT<br>CTCAACAATCTGCTCGACAAATTCGGCGGCTGCGTGCCCTGTATGTAT<br>TCCATCGATCTGCTGGAACGCCTTTCGCTGGTTGATAACATTGAGCATC<br>TCGGAATCGGTCGCCATTTCAAACAAGAAATCAAAGGAGCTCTTGATT<br>ATGTCTACAGACATTGGAGTGAAAGGGGCATCGGTTGGGGCAGAGAC<br>AGCCTTGTTCCAGATCTCAACACCACAGCCCTCGGCCTGCGAACTCTT<br>CGCATGCACGGATACAATGTTTCTTCAGACGTTTTGAATAATTTCAAA<br>GATGAAAACGGGCGGTTCTTCTCCTCTGCGGGCCAAACCCATGTCGAA<br>TTGAGAAGCGTGGTGAATCTTTTCAGAGCTTCCGACCTTGCATTTCCTG<br>ACGAAAGAGCTATGGACGATGCTAGAAAATTTGCAGAACCATATCTTA<br>GAGAGGCACTTGCAACGAAAATCTCAACCAATACAAAACTATTCAAA<br>GAGATTGAGTACGTGGTGGAGTACCCTTGGCACATGAGTATCCCACGC<br>TTAGAAGCCAGAAGTTATATTGATTCATATGACGACAATTATGTATGG<br>CAGAGGAAGACTCTATATAGAATGCCATCTTTGAGTAATTCAAAATGT<br>TTAGAATTGGCAAAATTGGACTTCAATATCGTACAATCTTTGCATCAA<br>GAGGAGTTGAAGCTTCTAACAAGATGGTGGAAGGAATCCGGCATGGC<br>AGATATAAATTTCACTCGACACCGAGTGGCGGAGGTTTATTTTTCATC<br>AGCTACATTTGAACCCGAATATTCTGCCACTAGAATTGCCTTCACAAA<br>AATTGGTTGTTTACAAGTCCTTTTTGATGATATGGCTGACATCTTTGCA<br>ACACTAGATGAATTGAAAAGTTTCACTGAGGGAGTAAAGAGATGGGA<br>TACATCTTTGCTACATGAGATTCCAGAGTGTATGCAAACTTGCTTTAAA<br>GTTTGGTTCAAATTAATGGAAGAAGTAAATAATGATGTGGTTAAGGTA<br>CAAGGACGTGACATGCTCGCTCACATAAGAAAACCCTGGGAGTTGTAC<br>TTCAATTGTTATGTACAAGAAAGGGAGTGGCTTGAAGCCGGGTATATA<br>CCAACTTTTGAAGAGTACTTAAAGACTTATGCTATATCAGTAGGCCTT<br>GGACCGTGTACCCTACAACCAATACTACTAATGGGTGAGCTTGTGAAA<br>GATGATGTTGTTGAGAAAGTGCACTATCCCTCAAATATGTTTGAGCTT<br>GTATCCTTGAGCTGGCGACTAACAAACGACACCAAAACATATCAGGCT<br>GAAAAGGCTCGAGGACAACAAGCCTCAGGCATAGCATGCTATATGAA<br>GGATAATCCAGGAGCAACTGAGGAAGATGCCATTAAGCACATATGTC<br>GTGTTGTTGATCGGGCCTTGAAAGAAGCAAGCTTTGAATATTTCAAAC<br>CATCCAATGATATCCCAATGGGTTGCAAGTCCTTTATTTTTAACCTTAG<br>ATTGTGTGTCCAAATCTTTTACAAGTTTATAGATGGGTACGGAATCGC<br>CAATGAGGAGATTAA<br>GGACTATATAAGAAAAGTTTATATTGATCCAATTCAAGTATGA | SEQ ID NO: 90 |

TABLE 5-continued

Exemplary DNA Sequences (includes truncations):

| Comp. | Organism | DNA Sequence | SEQ ID No. # |
|---|---|---|---|
| GGPPS | Taxus Canadensis | ATGTTTGATTTCAATGAATATATGAAAAGTAAGGCTGTTGCGGTAGAC GCGGCTCTGGATAAAGCGATTCCGCTGGAATATCCCGAGAAGATTCAC GAATCGATGCGCTACTCCCTGTTAGCAGGAGGGAAACGCGTTCGTCCG GCATTATGCATCGCGGCCTGTGAACTCGTCGGCGGTTCACAGGACTTA GCAATGCCAACTGCTTGCGCAATGGAAATGATTCACACAATGAGCCTG ATTCATGATGATTTGCCTTGCATGGACAACGATGACTTTCGGCGCGGT AAACCTACTAATCATAAGGTTTTTGGCGAAGATACTGCAGTGCTGGCG GGCGATGCGCTGCTGTCGTTTGCCTTCGAACATATCGCCGTCGCGACC TCGAAAACCGTCCCGTCGGACCGTACGCTTCGCGTGATTTCCGAGCTG GGAAAGACCATCGGCTCTCAAGGACTCGTGGGTGGTCAGGTAGTTGAT ATCACGTCTGAGGGTGACGCGAACGTGGACCTGAAAACCCTGGAGTG GATCCATATTCACAAAACGGCCGTGCTGCTGGAATGTAGCGTGGTGTC AGGGGGGGATCTTGGGGGGGCGCCACGGAGGATGAAATCGCGCGTATTC GTCGTTATGCCCGCTGTGTTGGACTGTATTTCAGGTGGTGGATGACAT CCTGGATGTCACAAAATCCAGCGAAGAGCTTGGCAAGACCGCGGGCA AAGACCTTCTGACGGATAAGGCTACATACCCCGAAATTGATGGGCTTGG AGAAAGCCAAGGAGTTCGCAGCTGAACTTGCCACGCGGGCGAAGGAA GAACTCTCTTCTTTCGATCAAATCAAAGCCGCGCCACTGCTGGGCCTC GCCGATTACATTGCGTTTCGTCAGAACTGA | SEQ ID NO: 91 |
| P450$_{BM3}$ | Bacillus megaterium | ATGACAATTAAAGAAATGCCTCAGCCAAAAACGTTTGGAGAGCTTAA AAATTTACCGTTATTAAACACAGATAAACCGGTTCAAGCTTTGATGAA AATTGCGGATGAATTAGGAGAAATCTTTAAATTCGAGGCGCCTGGTCG TGTAACGCGCTACTTATCAAGTCAGCGTCTAATTAAAGAAGCATGCGA TGAATCACGCTTTGATAAAAACTTAAGTCAAGCGCTTAAATTTGTACG TGATTTTGCAGGAGACGGGTTATTTACAAGCTGGACGCATGAAAAAA TTGGAAAAAAGCGCATAATATCTTACTTCCAAGCTTCAGTCAGCAGGC AATGAAAGGCTATCATGCGATGATGGTCGATATCGCCGTGCAGCTTGT TCAAAAGTGGGAGCGTCTAAATGCAGATGAGCATATTGAAGTACCGG AAGACATGACACGTTTAACGCTTGATACAATTGGTCTTTGCGGCTTTA ACTATCGCTTTAACAGCTTTTACCGAGATCAGCCTCATCCATTTATTAC AAGTATGGTCCGTGCACTGGATGAAGCAATGAACAAGCTGCAGCGAG CAAATCCAGACGACCCAGCTTATGATGAAAACAAGCGCCAGTTTCAA GAAGATATCAAGGTGATGAACGACCTAGTAGATAAAATTATTGCAGA TCGCAAAGCAAGCGGTGAACAAAGCGATGATTTATTAACGCATATGCT AAACGGAAAAGATCCAGAAACGGGTGAGCCGCTTGATGACGAGAACA TTCGCTATCAAATTATTACATTCTTAATTGCGGGACACGAAACAACAA GTGGTCTTTTATCATTTGCGCTGTATTTCTTAGTGAAAAATCCACATGT ATTACAAAAAGCAGCAGAAGAAGCAGCACGAGTTCTAGTAGATCCTG TTCCAAGCTACAAACAAGTCAAACAGCTTAAATATGTCGGCATGGTCT TAAACGAAGCGCTGCGCTTATGGCCAACTGCTCCTGCGTTTTCCCTATA TGCAAAAGAAGATACGGTGCTTGGAGGAGAATATCCTTTAGAAAAG GCGACGAACTAATGGTTCTGATTCCTCAGCTTCACCGTGATAAAACAA TTTGGGGAGACGATGTGGAAGAGTTCCGTCCAGAGCGTTTTGAAAATC CAAGTGCGATTCCGCAGCATGCGTTTAAACCGTTTGGAAACGGTCAGC GTGCGTGTATCGGTCAGCAGTTCGCTCTTCATGAAGCAACGCTGGTAC TTGGTATGATGCTAAAACACTTTGACTTTGAAGATCATACAAACTACG AGCTGGATATTAAAGAAACTTTAACGTTAAAACCTGAGGCTTTGTGG TAAAAGCAAAATCGAAAAAAATTCCGCTTGGCGGTATTCCTTCACCTA GCACTGAACAGTCTGCTAAAAAAGTACGCAAAAAGGCAGAAAACGCT CATAATACGCCGCTGCTTGTGCTATACGGTTCAAATATGGGAACAGCT GAAGGAACGGCGCGTGATTTAGCAGATATTGCAATGAGCAAAGGATT TGCACCGCAGGTCGCAACGCTTGATTCACACGCCGGAAATCTTCCGCG CGAAGGAGCTGTATTAATTGTAACGGCGTCTTATAACGGTCATCCGCC TGATAACGCAAAGCAATTTGTCGACTGGTTAGACCAAGCGTCTGCTGA TGAAGTAAAAGGCGTTCGCTACTCCGTATTTGGATGCGGCGATAAAAA CTGGGCTACTACGTATCAAAAAGTGCCTGCTTTTATCGATGAAACGCT TGCCGCTAAAGGGGCAGAAAACATCGCTGACCGCGGTGAAGCAGATG CAAGCGACGACTTTGAAGGCACATATGAAGAATGGCGTGAACATATG TGGAGTGACGTAGCAGCCTACTTTAACCTCGACATTGAAAACAGTGAA GATAATAAATCTACTCTTTCACTTCAATTTGTCGACAGCGCCGCGGAT ATGCCGCTTGCGAAAATGCACGGTGCGTTTTCAACGAACGTCGTAGCA AGCAAAGAACTTCAACAGCCAGGCAGTGCACGAAGCACGCGACATCT TGAAATTGAACTTCCAAAAGAAGCTTCTTATCAAGAAGGAGATCATTT AGGTGTTATTCCTCGCAACTATGAAGGAATAGTAAACCGTGTAACAGC AAGGTTCGGCCTAGATGCATCACAGCAAATCCGTCTGGAAGCAGAAG AAGAAAAATTAGCTCATTTGCCACTCGCTAAAACAGTATCCGTAGAAG AGCTTCTGCAATACGTGGAGCTTCAAGATCCTGTTACGCGCACGCAGC TTCGCGCAATGGCTGCTAAAACGGTCTGCCCGCCGCATAAAGTAGAGC TTGAAGCCTTGCTTGAAAAGCAAGCCTACAAAGAACAAGTGCTGGCA AAACGTTTAACAATGCTTGAACTGCTTGAAAAATACCCGGCGTGTGAA ATGAAATTCAGCGAATTTATCGCCCTTCTGCCAAGCATACGCCCGCGC TATTACTCGATTTCTTCATCACCTCGTGTCGATGAAAAACAAGCAAGC ATCACGGTCAGCGTTGTCTCAGGAGAAGCGTGGAGCGGATATGGAGA | SEQ ID NO: 92 |

TABLE 5-continued

Exemplary DNA Sequences (includes truncations):

| Comp. | Organism | DNA Sequence | SEQ ID No. # |
|---|---|---|---|
| | | ATATAAAGGAATTGCGTCGAACTATCTTGCCGAGCTGCAAGAAGGAG<br>ATACGATTACGTGCTTTATTTCCACACCGCAGTCAGAATTTACGCTGCC<br>AAAAGACCCTGAAACGCCGCTTATCATGGTCGGACCGGGAACAGGCG<br>TCGCGCCGTTTAGAGGCTTTGTGCAGGCGCGCAAACAGCTAAAAGAAC<br>AAGGACAGTCACTTGGAGAAGCACATTTATACTTCGGCTGCCGTTCAC<br>CTCATGAAGACTATCTGTATCAAGAAGAGCTTGAAAACGCCCAAAGC<br>GAAGGCATCATTACGCTTCATACCGCTTTTTCTCGCATGCCAAATCAGC<br>CGAAAACATACGTTCAGCACGTAATGGAACAAGACGGCAAGAAATTG<br>ATTGAACTTCTTGATCAAGGAGCGCACTTCTATATTTGCGGAGACGGA<br>AGCCAAATGGCACCTGCCGTTGAAGCAACGCTTATGAAAAGCTATGCT<br>GACGTTCACCAAGTGAGTGAAGCAGACGCTCGCTTATGGCTGCAGCAG<br>CTAGAAGAAAAAGGCCGATACGCAAAAGACGTGTGGGCTGGGTAA | |
| SpecR | Bacterial | ATGAGGGAAGCGGTGATCGCCGAAGTATCGACTCAACTATCAGAGGT<br>AGTTGGCGTCATCGAGCGCCATCTCGAACCGACGTTGCTGGCCGTACA<br>TTTGTACGGCTCCGCAGTGGATGGCGGCCTGAAGCCACACAGTGATAT<br>TGATTTGCTGGTTACGGTGACCGTAAGGCTTGATGAAACAACGCGGCG<br>AGCTTTGATCAACGACCTTTTGGAAACTTCGGCTTCCCCTGGAGAGAG<br>CGAGATTCTCCGCGCTGTAGAAGTCACCATTGTTGTGCACGACGACAT<br>CATTCCGTGGCGTTATCCAGCTAAGCGCGAACTGCAATTTGGAGAATG<br>GCAGCGCAATGACATTCTTGCAGGTATCTTCGAGCCAGCCACGATCGA<br>CATTGATCTGGCTATCTTGCTGACAAAAGCAAGAGAACATAGCGTTGC<br>CTTGGTAGGTCCAGCGGCGGAGGAACTCTTTGATCCGGTTCCTGAACA<br>GGATCTATTTGAGGCGCTAAATGAAACCTTAACGCTATGGAACTCGCC<br>GCCCGACTGGGCTGCGATGAGCGAAATGTAGTGCTTACGTTGTCCCG<br>CATTTGGTACAGCGCAGTAACCGGCAAAATCGCGCCGAAGGATGTCG<br>CTGCCGACTGGGCAATGGAGCGCCTGCCGGCCCAGTATCAGCCCGTCA<br>TACTTGAAGCTAGACAGGCTTATCTTGGACAAGAAGAAGATCGCTTGG<br>CCTCGCGCGCAGATCAGTTGGAAGAATTTGTCCACTACGTGAAAGGCG<br>AGATCACCAAGGTAGTCGGCAAA | SEQ ID NO: 93 |
| LOV2 | Avena sativa | TTGGCTACTACACTTGAACGTATTGAGAAGAACTTTGTCATTACTGAC<br>CCAAGGTTGCCAGATAATCCCATTATATTCGCGTCCGATAGTTTCTTGC<br>AGTTGACAGAATATAGCCGTGAAGAAATTTTGGGAAGAAACTGCAGG<br>TTTCTACAAGGTCCTGAAACTGATCGCGCGACAGTGAGAAAAATTAGA<br>GATGCCATAGATAACCAAACAGAGGTCACTGTTCAGCTGATTAATTAT<br>ACAAAGAGTGGTAAAAAGTTCTGGAACCTCTTTCACTTGCAGCCTATG<br>CGAGATCAGAAGGGAGATGTCCAGTACTTTATTGGGGTTCAGTTGGAT<br>GGAACTGAGCATGTCCGAGATGCTGCCGAGAGAGGGGAGTCATGCT<br>GATTAAGAAAACTGCAGAAAATATTGATGAGGCGGCAAAAGAACTTC<br>CA | SEQ ID NO: 94 |
| BphP1 | Rhodopseudomonas palustris | ATGGCTAGCGTGGCAGGTCATGCCTCTGGCAGCCCCGCATTCGGGACC<br>GCCGATCTTTCGAATTGCGAACGTGAAGAGATCCACCTCGCCGGCTCG<br>ATCCAGCCGCATGGCGCGCTTCTGGTCGTCAGCGAGCCGGATCATCGC<br>ATCATCCAGGCCAGCGCCAACGCCGCGGAATTTCTGAATCTCGGAAGC<br>GTGCTCGGCGTTCCGCTCGCCGAGATCGACGGCGATCTGTTGATCAAG<br>ATCCTGCCGCATCTCGATCCCACCGCCGAAGGCATGCCGGTCGCGGTG<br>CGCTGCCGGATCGGCAATCCCTCCACGGAGTACGACGGTCTGATGCAT<br>CGGCCTCCGGAAGGCGGGCTGATCATCGAGCTCGAACGTGCCGGCCC<br>GCCGATCGATCTGTCCGGCACGCTGGCGCCGGCGCTGGAGCGGATCCG<br>CACGGCGGGCTCGCTGCGCGCGCTGTGCGATGACACCGCGCTGCTGTT<br>TCAGCAGTGCACCGGCTACGACCGGGTGATGGTGTATCGCTTCGACGA<br>GCAGGGCCACGGCGAAGTGTTCTCCGAGCGCCACGTGCCCGGGCTCG<br>AATCCTATTTCGGCAACCGCTATCCGTCGTCGGACATTCCGCAGATGG<br>CGCGGCGGCTGTACGAGCGGCAGCGCGTTCCGCGTGCTGGTCGACGTCA<br>GCTATCAGCCGGTGCCGCTGGAGCCGCGGCTGTCGCCGCTGACCGGGC<br>GCGATCTCGACATGTCGGGCTGCTTCCTGCGCTCGATGTCGCCGATCC<br>ATCTGCAGTACCTGAAGAACATGGGCGTGCGCGCCACCCTGGTGGTGT<br>CGCTGGTGGTCGGCGGCAAGCTGTGGGGCCTGGTTGCCTGTCATCATT<br>ATCTGCCGCGCTTCATGCATTTCGAGCTGCGGGCGATCTGCGAACTGC<br>TCGCCGAAGCGATCGCGACGCGGATCACCGCGCTTGAGAGCTTCGCGC<br>AGAGCCAGTCGGAGCTGTTCGTGCAGCGGCTGAACAGCGCATGATC<br>GAAGCGATTACCCGTGAAGGCGATTGGCGCGCAGCGATTTTCGACACC<br>AGCCAATCGATCCTGCAGCCGCTGCACGCCGCCGGTTGCGCGCTGGTG<br>TACGAAGACCAGATCAGGACCATCGGCGACGTGCCTTCCACGCAGGA<br>TGTGCGCGAGATCGCCGGGTGGCTCGATCGCCAGCCGCGCGGCGGT<br>GACCTCGACCGCGTCGCTCGGTCTCGACGTGCCGGAGCTCGCGCATCT<br>GACGCGGATGGCGAGCGGCGTGTCGCGGCGCGTCGATTTCGGATCATC<br>GCGGCGAGTTTCTGATGTGGTTCCGCCCCGAGCGCGTCCACACCGTTA<br>CCTGGGGCGGCGATCCGAAGAAGCCGTTCACGATGGGCGATACACCG<br>GCGGATCTGTCGCCGCGGCGCTCCTTCGCCAAATGGCATCAGGTTGTC<br>GAAGGCACGTCCGATCCGTGGACGGCCGCCGATCTCGCCGCGGCTCGC<br>ACCATCGGTCAGACCGTCGCCGACATCGTGCTGCAATTCCGCGCGGTG | SEQ ID NO: 95 |

TABLE 5-continued

Exemplary DNA Sequences (includes truncations):

| Comp. | Organism | DNA Sequence | SEQ ID No. # |
|---|---|---|---|
| | | CGGACACTGATCGCCCGCGAACAGTACGAACAGTTTTCGTCCCAGGTG<br>CACGCTTCGATGCAGCCGGTGCTGATCACCGACGCCGAAGGCCGCATC<br>CTGCTGATGAACGACTCGTTCCGCGACATGTTGCCGGCGGGTTCGCCA<br>TCCGCCGTCCATCTCGACGATCTCGCCGGGTTCTTCGTCGAATCGAAC<br>GATTTCCTGCGCAACGTCGCCGAACTGATCGATCACGGCCGCGGGTGG<br>CGCGGCGAAGTTCTGCTGCGCGGCGCAGGCAACCGCCCGTTGCCGCTG<br>GCAGTGCGCGCCGATCCGGTGACGCGCACGGAGGACCAGTCGCTCGG<br>CTTCGTGCTGATCTTCAGCGACGCTACCGATCGTCGCACCGCAGATGC<br>CGCACGCACGCGTTTCCAGGAAGGCATTCTTGCCAGCGCACGTCCCGG<br>CGTGCGGCTCGACTCCAAGTCCGACCTGTTGCACGAGAAGCTGCTGTC<br>CGCGCTGGTCGAGAACGCGCAGCTTGCCGCATTGGAAATCACTTACGG<br>CGTCGAGACCGGACGCATCGCCGAGCTGCTCGAAGGCGTCCGCCAGTC<br>GATGCTGCGCACCGCCGAAGTGCTCGGCCATCTGGTGCAGCACGCGGC<br>GCGCACGGCCGGCAGCGACAGCTCGAGCAATGGCTCGCAGAACAAGA<br>AGGAATTCGATAGTGCTGGTAGTGCTGGTAGTGCTGGTACTAGT | |
| PTP1B$_{1-435}$ | H. Sapiens | ATGGAGATGGAAAAGGAGTTCGAGCAGATCGACAAGTCCGGGAGCTG<br>GGCGGCCATTTACCAGGATATCCGACATGAAGCCAGTGACTTCCCATG<br>TAGAGTGGCCAAGCTTCCTAAGAACAAAAACCGAAATAGGTACAGAG<br>ACGTCAGTCCCTTTGACCATAGTCGGATTAAACTACATCAAGAAGATA<br>ATGACTATATCAACGCTAGTTTGATAAAAATGGAAGAAGCCCAAAGG<br>AGTTACATTCTTACCCAGGGCCCTTTGCCTAACACATGCGGTCACTTTT<br>GGGAGATGGTGTGGGAGCAGAAAAGCAGGGGTGTCGTCATGCTCAAC<br>AGAGTGATGGAGAAAGGTTCGTTAAAATGCGCACAATACTGGCCACA<br>AAAAGAAGAAAAGAGATGATCTTTGAAGACACAAATTTGAAATTAA<br>CATTGATCTCTGAAGATATCAAGTCATATTATACAGTGCGACAGCTAG<br>AATTGGAAAACCTTACAACCCAAGAAACTCGAGAGATCTTACATTTCC<br>ACTATACCACATGGCCTGACTTTGGAGTCCCTGAATCACCAGCCTCAT<br>TCTTGAACTTTCTTTTCAAAGTCCGAGAGTCAGGGTCACTCAGCCCGG<br>AGCACGGGCCCGTTGTGGTGCACTGCAGTGCAGGCATCGGCAGGTCTG<br>GAACCTTCTGTCTGGCTGATACCTGCCTCTTGCTGATGGACAAGAGGA<br>AAGACCCTTCTTCCGTTGATATCAAGAAAGTGCTGTTAGAAATGAGGA<br>AGTTTCGGATGGGGCTGATCCAGACAGCCGACCAGCTGCGCTTCTCCT<br>ACCTGGCTGTGATCGAAGGTGCCAAATTCATCATGGGGGACTCTTCCG<br>TGCAGGATCAGTGGAAGGAGCTTTCCCACGAGGACCTGGAGCCCCCA<br>CCCGAGCATATCCCCCCACCTCCCCGGCCACCCAAACGAATCCTGGAG<br>CCACACAATGGGAAATGCAGGGAGTTCTTCCCAAATCACCAGTGGGTG<br>AAGGAAGAGACCCAGGAGGATAAAGACTGCCCCATCAAGGAAGAAA<br>AAGGAAGCCCCTTAAATGCCGCACCCTACGGCATCGAAAGCATGAGT<br>CAAGACACTGAAGTTAGAAGTCGGGTCGTGGGGGGAAGTCTTCGAGG<br>TGCCCAGGCTGCCTCCCCAGCCAAAGGGGAGCCGTCACTGCCCGAGA<br>AGGACGAGGACCATGCACTGAGTTACTGGAAGCCCTTCCTGGTCAACA<br>TGTGCGTGGCTACGGTCCTCACGGCCGGCGCTTACCTCTGCTACAGGT<br>TCCTGTTCAACAGCAACACATAG | SEQ ID NO: 96 |
| TC-PTP (full) | H. Sapiens | ATGCCCACCACCATCGAGCGGGAGTTCGAAGAGTTGGATACTCAGCGT<br>CGCTGGCAGCCGCTGTACTTGGAAATTCGAAATGAGTCCCATGACTAT<br>CCTCATAGAGTGGCCAAGTTTCCAGAAAACAGAAATCGAAACAGATA<br>CAGAGATGTAAGCCCATATGATCACAGTCGTGTTAAACTGCAAAATGC<br>TGAGAATGATTATATTAATGCCAGTTTAGTTGACATAGAAGAGGCACA<br>AAGGAGTTACATCTTAACACAGGGTCCACTTCCTAACACATGCTGCCA<br>TTTCTGGCTTATGGTTTGGCAGCAGAAGACCAAAGCAGTTGTCATGCT<br>GAACCGCATTGTGGAGAAAGAATCGGTTAAATGTGCACAGTACTGGC<br>CAACAGATGACCAAGAGATGCTGTTTAAAGAAACAGGATTCAGTGTG<br>AAGCTCTTGTCAGAAGATGTGAAGTCGTATTATACAGTACATCTACTA<br>CAATTAGAAAATATCAATAGTGGTGAAACCAGAACAATATCTCACTTT<br>CATTATACTACCTGGCCAGATTTTGGAGTCCCTGAATCACCAGCTTCAT<br>TTCTCAATTTCTTGTTTAAAGTGAGAGAATCTGGCTCCTTGAACCCTGA<br>CCATGGGCCTGCGGTGATCCACTGTAGTGCAGGCATTGGGCGCTCTGG<br>CACCTTCTCTCTGGTAGACACTTGTCTTGTTTTGATGGAAAAAGGAGAT<br>GATATTAACATAAAACAAGTGTTACTGAACATGAGAAAATACCGAAT<br>GGGTCTTATTCAGACCCCAGATCAACTGAGATTCTCATACATGGCTAT<br>AATAGAAGGAGCAAAATGTATAAAGGGAGATTCTAGTATACAGAAAC<br>GATGGAAAGAACTTTCTAAGGAAGACTTATCTCCTGCCTTTGATCATT<br>CACCAAACAAAATAATGACTGAAAAATACAATGGGAACAGA | SEQ ID NO: 97 |
| PTPN5 | H. sapiens | ATGTCTTCTGGTGTAGATCTGGGTACCGAGAACCTGTACTTCCAATCC<br>ATGTCCCGTGTCCTCCAAGCAGAAGAGCTTCATGAAAAGGCCCTGGAC<br>CCTTTCCTGCTGCAGGCGGAATTCTTTGAAATCCCCATGAACTTTGTGG<br>ATCCGAAAGAGTACGACATCCCTGGGCTGGTGCGGAAGAACCGGTAC<br>AAAACCATACTTCCCAACCCTCACAGCAGAGTGTGTCTGACCTCACCA<br>GACCCTGACGACCCTCTGAGTTCCTACATCAATGCCAACTACATCCGG<br>GGCTATGGTGGGAGGAGAAGGTGTACATCGCCACTCAGGGACCCAT<br>CGTCAGCACGGTCGCCGACTTCTGGCGCATGGTGTGGCAGGAGCACAC | SEQ ID NO: 98 |

TABLE 5-continued

Exemplary DNA Sequences (includes truncations):

| Comp. | Organism | DNA Sequence | SEQ ID No. # |
|---|---|---|---|
| | | GCCCATCATTGTCATGATCACCAACATCGAGGAGATGAACGAGAAAT GCACCGAGTATTGGCCGGAGGAGCAGGTGGCGTACGACGGTGTTGAG ATCACTGTGCAGAAAGTCATTCACACGGAGGATTACCGGCTGCGACTC ATCTCCCTCAAGAGTGGGACTGAGGAGCGAGGCCTGAAGCATTACTG GTTCACATCCTGGCCCGACCAGAAGACCCCAGACCGGGCCCCCCCACT CCTGCACCTGGTGCGGGAGGTGGAGGAGGCAGCCCAGCAGGAGGGGC CCCACTGTGCCCCCATCATCGTCCACTGCAGTGCAGGGATTGGGAGGA CCGGCTGCTTCATTGCCACCAGCATCTGCTGCCAGCAGCTGCGGCAGG AGGGTGTAGTGGACATCCTGAAGACCACGTGCCAGCTCCGTCAGGAC AGGGGCGGCATGATCCAGACATGCGAGCAGTACCAGTTTGTGCACCA CGTCATGAGCCTCTACGAAAAGCAGCTGTCCCACCAGTCCTGA | |
| PTPN6 | H. sapiens | ATGGTGAGGTGGTTTCACCGAGACCTCAGTGGGCTGGATGCAGAGACC CTGCTCAAGGGCCGAGGTGTCCACGGTAGCTTCCTGGCTCGGCCCAGT CGCAAGAACCAGGGTGACTTCTCGCTCTCCGTCAGGGTGGGGGATCAG GTGACCCATATTCGGATCCAGAACTCAGGGGATTTCTATGACCTGTAT GGAGGGGAGAAGTTTGCGACTCTGACAGAGCTGGTGGAGTACTACAC TCAGCAGCAGGGTGTGGTGCAGGACCGCGACGGCACCATCATCCACCT CAAGTACCCGCTGAACTGCTCCGATCCCACTAGTGAGAGGTGGTACCA TGGCCACATGTCTGGCGGGCAGGCAGAGACGCTGCTGCAGGCCAAGG GCGAGCCCTGGACGTTTCTTGTGCGTGAGAGCCTCAGCCAGCCTGGAG ACTTCGTGCTTTCTGTGCTCAGTGACCAGCCCAAGGCTGGCCCAGGCT CCCCGCTCAGGGTCACCCACATCAAGGTCATGTGCGAGGGTGGACGCT ACACAGTGGGTGGTTTGGAGACCTTCGACAGCCTCACGGACCTGGTGG AGCATTTCAAGAAGACGGGGATTGAGGAGGCCTCAGGCGCCTTTGTCT ACCTGCGGCAGCCGTACTATGCCACGAGGGTGAATGCGGCTGACATTG AGAACCGAGTGTTGGAACTGAACAAGAAGCAGGAGTCCGAGGATACA GCCAAGGCTGGCTTCTGGGAGGAGTTTGAGAGTTTGCAGAAGCAGGA GGTGAAGAACTTGCACCAGCGTCTGGAAGGGCAACGGCCAGAGAACA AGGGCAAGAACCGCTACAAGAACATTCTCCCCTTTGACCACAGCCGAG TGATCCTGCAGGGACGGGACAGTAACATCCCCGGGTCCGACTACATCA ATGCCAACTACATCAAGAACCAGCTGCTAGGCCCTGATGAGAACGCTA AGACCTACATCGCCAGCCAGGGCTGTCTGGAGGCCACGGTCAATGACT TCTGGCAGATGGCGTGGCAGGAGAACAGCCGTGTCATCGTCATGACCA CCCGAGAGGTGGAGAAAGGCCGGAACAAATGCGTCCCATACTGGCCC GAGGTGGGCATGCAGCGTGCTTATGGGCCCTACTCTGTGACCAACTGC GGGGAGCATGACACAACCGAATACAAACTCCGTACCTTACAGGTCTCC CCGCTGGACAATGGAGACCTGATTCGGGAGATCTGGCATTACCAGTAC CTGAGCTGGCCCGACCATGGGTCCCCAGTGAGCCTGGGGGTGTCCTC AGCTTCCTGGACCAGATCAACCAGCGGCAGGAAAGTCTGCCTCACGCA GGGCCCATCATCGTGCACTGCAGCGCCGGCATCGGCCGCACAGGCACC ATCATTGTCATCGACATGCTCATGGAGAACATCTCCACCAAGGGCCTG GACTGTGACATTGACATCCAGAAGACCATCCAGATGGTGCGGGCGCA GCGCTCGGGCATGGTGCAGACGGAGGCGCAGTACAAGTTCATCTACGT GGCCATCGCCCAGTTCATTGAAACCACTAAGAAGAAGCTGGAGGTCCT GCAGTCGCAGAAGGGCCAGGAGTCGGAGTACGGGAACATCACCTATC CCCCAGCCATGAAGAATGCCCATGCCAAGGCCTCCCGCACCTCGTCCA AACACAAGGAGGATGTGTATGAGAACCTGCACACTAAGAACAAGAGG GAGGAGAAAGTGAAGAAGCAGCGGTCAGCAGACAAGGAGAAGAGCA AGGGTTCCCTCAAGAGGAAGTGA | SEQ ID NO: 99 |
| PTPN11 | H. sapiens | ATGACATCGCGGAGATGGTTTCACCCAAATATCACTGGTGTGGAGGCA GAAAACCTACTGTTGACAAGAGGAGTTGATGGCAGTTTTTTGGCAAGG CCTAGTAAAAGTAACCCTGGAGACTTCACACTTTCCGTTAGAAGAAAT GGAGCTGTCACCCACATCAAGATTCAGAACACTGGTGATTACTATGAC CTGTATGGAGGGGAGAAATTTGCCACTTTGGCTGAGTTGGTCCAGTAT TACATGGAACATCACGGGCAATTAAAAGAGAAGAATGGAGATGTCAT TGAGCTTAAATATCCTCTGAACTGTGCAGATCCTACCTCTGAAAGGTG GTTTCATGGACATCTCTCTGGGAAAGAAGCAGAGAAATTATTAACTGA AAAAGGAAAACATGGTAGTTTTCTTGTACGAGAGAGCCAGAGCCACC CTGGAGATTTTGTTCTTTCTGTGCGCACTGGTGATGACAAAGGGGAGA GCAATGACGGCAAGTCTAAAGTGACCCATGTTATGATTCGCTGTCAGG AACTGAAATACGACGTTGGTGGAGGAGAACGGTTTGATTCTTTGACAG ATCTTGTGGAACATTATAAGAAGAATCCTATGGTGGAAACATTGGGTA CAGTACTACAACTCAAGCAGCCCCTTAACACGACTCGTATAAATGCTG CTGAAATAGAAAGCAGAGTTCGAGAACTAAGCAAATTAGCTGAGACC ACAGATAAAGTCAAACAAGGCTTTTGGGAAGAATTGAGACACTACA ACAACAGGAGTGCAAACTTCTCTACAGCCGAAAAGAGGGTCAAAGGC AAGAAAAACAAAAACAAATGATATAAAAACATCCTGCCCTTTGAT CATACCAGGGTTGTCCTACACGATGGTGATCCCAATGAGCCTGTTTCA GATTACATCAATGCAAATATCATCATGCCTGAATTTGAAACCAAGTGC AACAATTCAAAGCCCAAAAAGAGTTACATTGCCACACAAGGCTGCCT GCAAAACACGGTGAATGACTTTTGGCGGATGGTGTTCCAAGAAAACTC CCGAGTGATTGTCATGACAACGAAAGAAGTGGAGAGAGGAAAGAGTA | SEQ ID NO: 100 |

TABLE 5-continued

Exemplary DNA Sequences (includes truncations):

| Comp. | Organism | DNA Sequence | SEQ ID No. # |
|---|---|---|---|
| | | AATGTGTCAAATACTGGCCTGATGAGTATGCTCTAAAAGAATATGGCG<br>TCATGCGTGTTAGGAACGTCAAAGAAAGCGCCGCTCATGACTATACGC<br>TAAGAGAACTTAAACTTTCAAAGGTTGGACAAGGGAATACGGAGAGA<br>ACGGTCTGGCAATACCACTTTCGGACCTGGCCGGACCACGGCGTGCCC<br>AGCGACCCTGGGGGCGTGCTGGACTTCCTGGAGGAGGTGCACCATAA<br>GCAGGAGAGCATCATGGATGCAGGGCCGGTCGTGGTGCACTGCAGTG<br>CTGGAATTGGCCGGACAGGGACGTTCATTGTGATTGATATTCTTATTG<br>ACATCATCAGAGAGAAAGGTGTTGACTGCATATTGACGTTCCCAAAA<br>CCATCCAGATGGTGCGGTCTCAGAGGTCAGGGATGGTCCAGACAGAA<br>GCACAGTACCGATTTATCTATATGGCGGTCCAGCATTATATTGAAACA<br>CTACAGCGCAGGATTGAAGAAGAGCAGAAAAGCAAGAGGAAAGGGC<br>ACGAATATACAAATATTAAGTATTCTCTAGCGGACCAGACGAGTGGAG<br>ATCAGAGCCCTCTCCCGCCTTGTACTCCAACGCCACCCTGTGCAGAAA<br>TGAGAGAAGACAGTGCTAGAGTCTATGAAAACGTGGGCCTGATGCAA<br>CAGCAGAAAAGTTTCAGATGA | |
| PTPN12 | H. sapiens | ATGGAGCAAGTGGAGATCCTGAGGAAATTCATCCAGAGGGTCCAGGC<br>CATGAAGAGTCCTGACCACAATGGGGAGGACAACTTCGCCCGGGACT<br>TCATGCGGTTAAGAAGATTGTCTACCAAATATAGAACAGAAAAGATAT<br>ATCCCACAGCCACTGGAGAAAAAGAAGAAAATGTTAAAAAGAACAGA<br>TACAAGGACATACTGCCATTTGATCACAGCCGAGTTAAATTGACATTA<br>AAGACTCCTTCACAAGATTCAGACTATATCAATGCAAATTTTATAAAG<br>GGCGTCTATGGGCCAAAAGCATATGTAGCAACTCAAGGACCTTTAGCA<br>AATACAGTAATAGATTTTTGGAGGATGGTATGGGAGTATAATGTTGTG<br>ATCATTGTAATGGCCTGCCGAGAATTTGAGATGGGAAGGAAAAAATG<br>TGAGCGCTATTGGCCTTTGTATGGAGAAGACCCCATAACGTTTGCACC<br>ATTTAAAATTTCTTGTGAGGATGAACAAGCAAGAACAGACTACTTCAT<br>CAGGACACTCTTACTTGAATTTCAAAATGAATCTCGTAGGCTGTATCA<br>GTTTCATTATGTGAACTGGCCAGACCATGATGTTCCTTCATCATTTGAT<br>TCTATTCTGGACATGATAAGCTTAATGAGGAAATATCAAGAACATGAA<br>GATGTTCCTATTTGTATTCATTGCAGTGCAGGCTGTGGAAGAACAGGT<br>GCCATTTGTGCCATAGATTATACGTGGAATTTACTAAAAGCTGGGAAA<br>ATACCAGAGGAATTTAATGTATTTAATTTAATACAAGAAATGAGAACA<br>CAAAGGCATTCTGCAGTACAAACAAAGGAGCAATATGAACTTGTTCAT<br>AGAGCTATTGCCCAACTGTTTGAAAAACAGCTACAACTATATGAAATT<br>CATGGAGCTCAGAAAATTGCTGATGGAGTGAATGAAATTAACACTGA<br>AAACATGGTCAGCTCCATAGAGCCTGAAAAACAAGATTCTCCTCCTCC<br>AAAACCACCAAGGACCCGCAGTTGCCTTGTTGAAGGGGATGCTAAAG<br>AAGAAATACTGCAGCCACCGGAACCTCATCCAGTGCCACCCATCTTGA<br>CACCTTCTCCCCCTTCAGCTTTTCCAACAGTCACTACTGTGTGGCAGGA<br>CAATGATAGATACCATCCAAAGCCAGTGTTGCAATGGTTTCATCAGAA<br>CAACATTCAGCAGACCTCAACAGAAACTATAGTAAATCAACAGAACTT<br>CCAGGGAAAAATGAATCAACAATTGAACAGA | SEQ ID NO: 101 |
| PTPN22 | H. sapiens | ATGGACCAAAGAGAAATTCTGCAGAAGTTCCTGGATGAGGCCCAAAG<br>CAAGAAAATTACTAAAGAGGAGTTTGCCAATGAATTTCTGAAGCTGAA<br>AAGGCAATCTACCAAGTACAAGGCAGACAAAACCTATCCTACAACTG<br>TGGCTGAGAAGCCCAAGAATATCAAGAAAAACAGATATAAGGATATT<br>TTGCCCTATGATTATAGCCGGGTAGAACTATCCCTGATAACCTCTGAT<br>GAGGATTCCAGCTACATCAATGCCAACTTCATTAAGGGAGTTTATGGA<br>CCCAAGGCTTATATTGCCACCCAGGGTCCTTTATCTACAACCCTCCTGG<br>ACTTCTGGAGGATGATTTGGGAATATAGTGTCCTTATCATTGTTATGGC<br>ATGCATGGAGTATGAAATGGGAAAGAAAAAGTGTGAGCGCTACTGGG<br>CTGAGCCAGGAGAGATGCAGCTGGAATTTGGCCCTTTCTCTGTATCCT<br>GTGAAGCTGAAAAAGGAAATCTGATTATATAATCAGGACTCTAAAA<br>GTTAAGTTCAATAGTGAAACTGAACTATCTACCAGTTTCATTACAAG<br>AATTGGCCAGACCATGATGTACCTTCATCTATAGACCCTATTCTTGAGC<br>TCATCTGGGATGTACGTTGTTACCAAGAGGATGACAGTGTTCCCATAT<br>GCATTCACTGCAGTGCTGGCTGTGAAGGACTGGTGTATTTGTGCTA<br>TTGATTACATGGATGTTGCTAAAAGATGGGATAATTCCTGAGAACT<br>TCAGTGTTTTCAGTTTGATCCGGGAAATGCGGACACAGAGGCCTTCAT<br>TAGTTCAAACGCAGGAACAATATGAACTGGTCTACAATGCTGTATTAG<br>AACTATTTAAGAGACAGATGGATGTTATCAGAGATAA | SEQ ID NO: 102 |
| GalK | Escherichia coli | ATGAGTCTGAAAGAAAAAACACAATCTCTGTTTGCCAACGCATTTGGC<br>TACCCTGCCACTCACACCATTCAGGCGCCTGGCCGCGTGAATTTGATT<br>GGTGAACACACCGACTACAACGACGGTTTCGTTCTGCCCTGCGCGATT<br>GATTATCAAACCGTGATCAGTTGTGCACCACGCGATGACCGTAAAGTT<br>CGCGTGATGGCAGCCGATTATGAAAATCAGCTCGACGAGTTTCCCCTC<br>GATGCGCCCATTGTCGCACATGAAAACTATCAATGGGCTAACTACGTT<br>CGTGGCGTGGTGAAACATCTGCAACTGCGTAACAACAGCTTCGGCGGC<br>GTGGACATGGTGATCAGCGGCAATGTGCCGCAGGGTGCCGGGTTAAG<br>TTCTTCCGCTTCACTGGAAGTCGCGGTCGGAACCGTATTGCAGCAGCT<br>TTATCATCTGCCGCTGGACGGCGCACAAATCGCGCTTAACGGTCAGGA | SEQ ID NO: 103 |

TABLE 5-continued

Exemplary DNA Sequences (includes truncations):

| Comp. | Organism | DNA Sequence | SEQ ID No. # |
|---|---|---|---|
| | | AGCAGAAAACCAGTTTGTAGGCTGTAACTGCGGGATCATGGATCAGCT AATTTCCGCGCTCGGCAAGAAAGATCATGCCTTGCTGATCGATTGCCG CTCACTGGGGACCAAAGCAGTTTCCATGCCCAAAGGTGTGGCTGTCGT CATCATCAACAGTAACTTCAAACGTACCCTGGTTGGCAGCGAATACAA CACCCGTCGTGAACAGTGCGAAACCGGTGCGCGTTTCTTCCAGCAGCC AGCCCTGCGTGATGTCACCATTGAAGAGTTCAACGCTGTTGCGCATGA ACTGGACCCGATCGTGGCAAAACGCGTGCGTCATATACTGACTGAAAA CGCCCGCACCGTTGAAGCTGCCAGCGCGCTGGAGCAAGGCGACCTGA AACGTATGGGCGAGTTGATGGCGGAGTCTCATGCCTCTATGCGCGATG ATTTCGAAATCACCGTGCCGCAAATTGACACTCTGGTAGAAATCGTCA AAGCTGTGATTGGCGACAAAGGTGGCGTACGCATGACCGGCGGCGGA TTTGGCGGCTGTATCGTCGCGCTGATCCCGGAAGAGCTGGTGCCTGCC GTACAGCAAGCTGTCGCTGAACAATATGAAGCAAAAACAGGTATTAA AGAGACTTTTTACGTTTGTAAACCATCACAAGGAGCAGGACAGTGCTG A | |
| SacB | *Bacillus subtilis* | ATGAACATCAAAAAGTTTGCAAAACAAGCAACAGTATTAACCTTTACT ACCGCACTGCTGGCAGGAGGCGCAACTCAAGCGTTTGCGAAAGAAAC GAACCAAAAGCCATATAAGGAAACATACGGCATTTCCCATATTACACG CCATGATATGCTGCAAATCCCTGAACAGCAAAAAAATGAAAAATATC AAGTTCCTGAATTCGATTCGTCCACAATTAAAAATATCTCTTCTGCAAA AGGCCTGGACGTTTGGGACAGCTGGCCATTACAAAACGCTGACGGCA CTGTCGCAAACTATCACGGCTACCACATCGTCTTTGCATTAGCCGGAG ATCCTAAAAATGCGGATGACACATCGATTTACATGTTCTATCAAAAAG TCGGCGAAACTTCTATTGACAGCTGGAAAAACGCTGGCCGCGTCTTTA AAGACAGCGACAAATTCGATGCAAATGATTCTATCCTAAAAGACCAA ACACAAGAATGGTCAGGTTCAGCCACATTTACATCTGACGGAAAAATC CGTTTATTCTACACTGATTTCTCCGGTAAACATTACGGCAAACAAACA CTGACAACTGCACAAGTTAACGTATCAGCATCAGACAGCTCTTTGAAC ATCAACGGTGTAGAGGATTATAAATCAATCTTTGACGGTGACGGAAAA ACGTATCAAAATGTACAGCAGTTCATCGATGAAGGCAACTACAGCTCA GGCGACAACCATACGCTGAGAGATCCTCACTACGTAGAAGATAAAGG CCACAAATACTTAGTATTTGAAGCAAACACTGGAACTGAAGATGGCTA CCAAGGCGAAGAATCTTTATTTAACAAAGCATACTATGGCAAAAGCAC ATCATTCTTCCGTCAAGAAAGTCAAAAACTTCTGCAAAGCGATAAAAA ACGCACGGCTGAGTTAGCAAACGGCGCTCTCGGTATGATTGAGCTAAA CGATGATTACACACTGAAAAAAGTGATGAAACCGCTGATTGCATCTAA CACAGTAACAGATGAAATTGAACGCGCGAACGTCTTTAAAATGAACG GCAAATGGTACCTGTTCACTGACTCCCGCGGATCAAAAATGACGATTG ACGGCATTACGTCTAACGATATTTACATGCTTGGTTATGTTTCTAATTC TTTAACTGGCCCATACAAGCCGCTGAACAAAACTGGCCTTGTGTTAAA AATGGATCTTGATCCTAACGATGTAACCTTTACTTACTCACACTTCGCT GTACCTCAAGCGAAAGGAAACAATGTCGTGATTACAAGCTATATGAC AAACAGAGGATTCTACGCAGACAAACAATCAACGTTTGCGCCAAGCTT CCTGCTGAACATCAAAGGCAAGAAAACATCTGTTGTCAAAGACAGCA TCCTTGAACAAGGACAATTAACAGTTAACAAATAA | SEQ ID NO: 104 |

ABBREVIATIONS

PTP IB, protein tyrosine phosphatase IB; TC-PTP, T-cell protein tyrosine phosphatase; SHP2, protein tyrosine phosphatase non-receptor type 11; BBR, 3-(3,5-Dibromo-4-hydroxy-benzoyl)-2-ethyl-benzofuran-6-sulfonicacid-(4-(thiazol-2-ylsulfamyl)-phenyl)-amide; TCS401, 2-[(Carboxycarbonyl)amino]-4,5,6,7-tetrahydro-thieno[2,3-c]pyridine-3-carboxylic acid hydrochloride; AA, abietic acid; SCA, statistical coupling analysis. PTP1B$_{1-435}$, protein tyrosine phosphatase 1B (full-length); SacB, levansucrase; GHS, γ-humulene synthase; ADS, amorphadiene synthase; ABS (or AgAs), abietadiene synthase; TXS, taxadiene synthase; PTPN5, protein tyrosine phosphatase non-receptor type 5; PTPN6, protein tyrosine phosphatase non-receptor type 6; PTPN11, protein tyrosine phosphatase non-receptor type 11; PTPN12, protein tyrosine phosphatase non-receptor type 12; PPTN22, protein tyrosine phosphatase non-receptor type 22; RpoZ, omega subunit of RNA polymerase; cI (or c1434), cI repressor protein from lambda phage; Kras (or p130cas), p130cas phosphotyrosine substrate; MidT, phosphotyrosine substrate from hamster polyoma virus; EGFR substrate, phosphotyrosine substrate from epidermal growth factor receptor; Src, Src kinase; CDC137, Hsp90 co-chaperone Cdc37; MBP, maltose-binding protein; LuxAB, bacterial luciferase modules A and B; SpecR, spectinomycin resistance gene; GGPPS, geranylgeranyl diphosphate synthase; P450 (or P450$_{BM3}$) Cytochrome P450; LOV2, light-oxygen-voltage domain 2 from phototropin 1; BphP1, bacterial phytochrome; Galk, galatokinase.

Examples

The following examples are offered to illustrate various embodiments of the invention, but should not be viewed as limiting the scope of the invention.

Statistical Analysis of Kinetic Models. We evaluated four kinetic models of inhibition as described previously (19). In brief, we used an F-test to compare a two-parameter mixed model to several single-parameter models, and we used Akaike's Information Criterion (AIC, or Ai) to compare the single-parameter models to one another. Mixed models with p<0.05 are superior to all single-parameter models, and single-parameter models with Aj>10 are inferior to the reference (i.e., "best fit") model.

Exemplary Estimation of IC50. We estimated the half maximal inhibitory concentration (IC50) of BBR by using kinetic models to estimate the concentration of inhibitor required to reduce initial rates of PTP-catalyzed hydrolysis of 20 mM of pNPP by 50%, and we used the MATLAB function "nlparci" to determine the confidence intervals on those estimates (19).

All publications and patents mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in medicine, molecular biology, cell biology, genetics, statistics or related fields are intended to be within the scope of the following claims.

SEQUENCE LISTING

```
<160> NUMBER OF SEQ ID NOS: 104

<210> SEQ ID NO 1
<211> LENGTH: 27
<212> TYPE: PRT
<213> ORGANISM: Artificial Sequence
<220> FEATURE:
<223> OTHER INFORMATION: Synthetic Polypeptide

<400> SEQUENCE: 1

Met Gly Asp Ser Ser Val Gln Asp Gln Trp Lys Glu Leu Ser His Glu
1               5                   10                  15

Asp Leu Glu Pro Pro Glu His Ile Pro Pro
            20                  25

<210> SEQ ID NO 2
<211> LENGTH: 27
<212> TYPE: PRT
<213> ORGANISM: Artificial Sequence
<220> FEATURE:
<223> OTHER INFORMATION: Synthetic Polypeptide

<400> SEQUENCE: 2

Glu Ser Phe Asp Asp Glu Leu Arg Arg Lys Glu Met Arg Arg Gly Ile
1               5                   10                  15

Asp Leu Ala Thr Thr Leu Glu Arg Ile Glu Lys
            20                  25

<210> SEQ ID NO 3
<211> LENGTH: 298
<212> TYPE: PRT
<213> ORGANISM: Artificial Sequence
<220> FEATURE:
<223> OTHER INFORMATION: Synthetic Polypeptide

<400> SEQUENCE: 3

Met Glu Met Glu Lys Glu Phe Glu Gln Ile Asp Lys Ser Gly Ser Trp
1               5                   10                  15

Ala Ala Ile Tyr Gln Asp Ile Arg His Glu Ala Ser Asp Phe Pro Cys
            20                  25                  30

Arg Val Ala Lys Leu Pro Lys Asn Lys Asn Arg Asn Arg Tyr Arg Asp
        35                  40                  45

Val Ser Pro Phe Asp His Ser Arg Ile Lys Leu His Gln Glu Asp Asn
    50                  55                  60

Asp Tyr Ile Asn Ala Ser Leu Ile Lys Met Glu Glu Ala Gln Arg Ser
65                  70                  75                  80

Tyr Ile Leu Thr Gln Gly Pro Leu Pro Asn Thr Cys Gly His Phe Trp
                85                  90                  95

Glu Met Val Trp Glu Gln Lys Ser Arg Gly Val Val Met Leu Asn Arg
```

```
                    100                 105                 110
Val Met Glu Lys Gly Ser Leu Lys Cys Ala Gln Tyr Trp Pro Gln Lys
                115                 120                 125

Glu Glu Lys Glu Met Ile Phe Glu Asp Thr Asn Leu Lys Leu Thr Leu
            130                 135                 140

Ile Ser Glu Asp Ile Lys Ser Tyr Tyr Thr Val Arg Gln Leu Glu Leu
145                 150                 155                 160

Glu Asn Leu Thr Thr Gln Glu Thr Arg Glu Ile Leu His Phe His Tyr
                165                 170                 175

Thr Thr Trp Pro Asp Phe Gly Val Pro Glu Ser Pro Ala Ser Phe Leu
            180                 185                 190

Asn Phe Leu Phe Lys Val Arg Glu Ser Gly Ser Leu Ser Pro Glu His
                195                 200                 205

Gly Pro Val Val Val His Cys Ser Ala Gly Ile Gly Arg Ser Gly Thr
            210                 215                 220

Phe Cys Leu Ala Asp Thr Cys Leu Leu Leu Met Asp Lys Arg Lys Asp
225                 230                 235                 240

Pro Ser Ser Val Asp Ile Lys Lys Val Leu Leu Glu Met Arg Lys Phe
                245                 250                 255

Arg Met Gly Leu Ile Gln Thr Ala Asp Gln Leu Arg Phe Ser Tyr Leu
            260                 265                 270

Ala Val Ile Glu Gly Ala Lys Phe Ile Met Gly Asp Ser Ser Val Gln
                275                 280                 285

Asp Gln Trp Lys Glu Leu Ser His Glu Asp
            290                 295

<210> SEQ ID NO 4
<211> LENGTH: 303
<212> TYPE: PRT
<213> ORGANISM: Artificial Sequence
<220> FEATURE:
<223> OTHER INFORMATION: Synthetic Polypeptide

<400> SEQUENCE: 4

Leu Glu Leu Asn Lys Lys Gln Glu Ser Glu Asp Thr Ala Lys Ala Gly
1               5                   10                  15

Phe Trp Glu Glu Phe Glu Ser Leu Gln Lys Gln Glu Val Lys Asn Leu
            20                  25                  30

His Gln Arg Leu Glu Gly Gln Arg Pro Glu Asn Lys Gly Lys Asn Arg
        35                  40                  45

Tyr Lys Asn Ile Leu Pro Phe Asp His Ser Arg Val Ile Leu Gln Gly
50                  55                  60

Arg Asp Ser Asn Ile Pro Gly Ser Asp Tyr Ile Asn Ala Asn Tyr Ile
65                  70                  75                  80

Lys Asn Gln Leu Leu Gly Pro Asp Glu Asn Ala Lys Thr Tyr Ile Ala
                85                  90                  95

Ser Gln Gly Cys Leu Glu Ala Thr Val Asn Asp Phe Trp Gln Met Ala
            100                 105                 110

Trp Gln Glu Asn Ser Arg Val Ile Val Met Thr Thr Arg Glu Val Glu
        115                 120                 125

Lys Gly Arg Asn Lys Cys Val Pro Tyr Trp Pro Glu Val Gly Met Gln
    130                 135                 140

Arg Ala Tyr Gly Pro Tyr Ser Val Thr Asn Cys Gly Glu His Asp Thr
145                 150                 155                 160

Thr Glu Tyr Lys Leu Arg Thr Leu Gln Val Ser Pro Leu Asp Asn Gly
```

```
                165                 170                 175
Asp Leu Ile Arg Glu Ile Trp His Tyr Gln Tyr Leu Ser Trp Pro Asp
            180                 185                 190

His Gly Val Pro Ser Glu Pro Gly Val Leu Ser Phe Leu Asp Gln
        195                 200                 205

Ile Asn Gln Arg Gln Glu Ser Leu Pro His Ala Gly Pro Ile Ile Val
    210                 215                 220

His Cys Ser Ala Gly Ile Gly Arg Thr Gly Thr Ile Ile Val Ile Asp
225                 230                 235                 240

Met Leu Met Glu Asn Ile Ser Thr Lys Gly Leu Asp Cys Asp Ile Asp
                245                 250                 255

Ile Gln Lys Thr Ile Gln Met Val Arg Ala Gln Arg Ser Gly Met Val
            260                 265                 270

Gln Thr Glu Ala Gln Tyr Lys Phe Ile Tyr Val Ala Ile Ala Gln Phe
        275                 280                 285

Ile Glu Thr Thr Lys Lys Lys Leu Glu Val Leu Gln Ser Gln Lys
    290                 295                 300

<210> SEQ ID NO 5
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 5

Leu Ser His Glu Asp Leu Ala Thr Thr Leu
1               5                   10

<210> SEQ ID NO 6
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 6

Leu Ser His Glu Asp
1               5

<210> SEQ ID NO 7
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 7

Leu Ala Thr Thr Leu
1               5

<210> SEQ ID NO 8
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 8

Leu Ser His Glu Asp Ala Thr Thr Leu
1               5
```

<210> SEQ ID NO 9
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 9

Leu Ser His Glu Asp Thr Thr Leu
1               5

<210> SEQ ID NO 10
<211> LENGTH: 13
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (7)..(7)
<223> OTHER INFORMATION: phosphorylated

<400> SEQUENCE: 10

Glu Thr Gly Thr Glu Glu Tyr Met Lys Met Asp Leu Gly
1               5                   10

<210> SEQ ID NO 11
<211> LENGTH: 13
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (9)..(9)
<223> OTHER INFORMATION: phosphorylated

<400> SEQUENCE: 11

Arg Arg Leu Ile Glu Asp Ala Glu Tyr Ala Ala Arg Gly
1               5                   10

<210> SEQ ID NO 12
<211> LENGTH: 1347
<212> TYPE: DNA
<213> ORGANISM: Artificial Sequence
<220> FEATURE:
<223> OTHER INFORMATION: Synthetic Polynucleotide

<400> SEQUENCE: 12

| | | |
|---|---|---|
| atggagatgg aaaaggagtt cgagcagatc gacaagtccg ggagctgggc ggccatttac | 60 |
| caggatatcc gacatgaagc cagtgacttc ccatgtagag tggccaagct tcctaagaac | 120 |
| aaaaaccgaa ataggtacag agacgtcagt cccttttgacc atagtcggat taaactacat | 180 |
| caagaagata atgactatat caacgctagt ttgataaaaa tggaagaagc ccaaaggagt | 240 |
| tacattctta cccagggccc tttgcctaac acatgcggtc acttttggga gatggtgtgg | 300 |
| gagcagaaaa gcagggtgt cgtcatgctc aacagagtga tggagaaagg ttcgttaaaa | 360 |
| tgcgcacaat actggccaca aaagaagaa aagagatga tctttgaaga cacaaatttg | 420 |
| aaattaacat tgatctctga agatatcaag tcatatttata cagtgcgaca gctagaattg | 480 |
| gaaaacctta caacccaaga aactcgagag atcttacatt ccactatac cacatggcct | 540 |
| gactttggag tccctgaatc accagcctca ttcttgaact ttctttttcaa agtccgagag | 600 |
| tcagggtcac tcagcccgga gcacgggccc gttgtggtgc actgcagtgc aggcatcggc | 660 |
| aggtctggaa ccttctgtct ggctgatacc tgcctcttgc tgatggacaa gaggaaagac | 720 |

```
ccttcttccg ttgatatcaa gaaagtgctg ttagaaatga ggaagtttcg gatggggctg    780
atccagacag ccgaccagct gcgcttctcc tacctggctg tgatcgaagg tgccaaattc    840
atcatggggg actcttccgt gcaggatcag tggaaggagc tttcccacga ggacgctgct    900
acacttgaac gtattgagaa gaactttgtc attactgacc caaggttgcc agataatccc    960
attatattcg cgtccgatag tttcttgcag ttgacagaat atagccgtga agaaattttg   1020
ggaagaaact gcaggtttct acaaggtcct gaaactgatc gcgcgacagt gagaaaaatt   1080
agagatgcca tagataacca aacagaggtc actgttcagc tgattaatta tacaaagagt   1140
ggtaaaaagt tctggaacct ctttcacttg cagcctatgc gagatcagaa gggagatgtc   1200
cagtacttta ttggggttca gttggatgga actgagcatg tccgagatgc tgccgagaga   1260
gagggagtca tgctgattaa gaaaactgca gaaaatattg atgaggcggc aaaagaactt   1320
ctcgagcacc accaccacca ccactga                                       1347

<210> SEQ ID NO 13
<211> LENGTH: 448
<212> TYPE: PRT
<213> ORGANISM: Artificial Sequence
<220> FEATURE:
<223> OTHER INFORMATION: Synthetic Polypeptide

<400> SEQUENCE: 13

Met Glu Met Glu Lys Glu Phe Glu Gln Ile Asp Lys Ser Gly Ser Trp
1               5                   10                  15

Ala Ala Ile Tyr Gln Asp Ile Arg His Glu Ala Ser Asp Phe Pro Cys
            20                  25                  30

Arg Val Ala Lys Leu Pro Lys Asn Lys Asn Arg Asn Arg Tyr Arg Asp
        35                  40                  45

Val Ser Pro Phe Asp His Ser Arg Ile Lys Leu His Gln Glu Asp Asn
    50                  55                  60

Asp Tyr Ile Asn Ala Ser Leu Ile Lys Met Glu Glu Ala Gln Arg Ser
65                  70                  75                  80

Tyr Ile Leu Thr Gln Gly Pro Leu Pro Asn Thr Cys Gly His Phe Trp
                85                  90                  95

Glu Met Val Trp Glu Gln Lys Ser Arg Gly Val Val Met Leu Asn Arg
            100                 105                 110

Val Met Glu Lys Gly Ser Leu Lys Cys Ala Gln Tyr Trp Pro Gln Lys
        115                 120                 125

Glu Glu Lys Glu Met Ile Phe Glu Asp Thr Asn Leu Lys Leu Thr Leu
    130                 135                 140

Ile Ser Glu Asp Ile Lys Ser Tyr Tyr Thr Val Arg Gln Leu Glu Leu
145                 150                 155                 160

Glu Asn Leu Thr Thr Gln Glu Thr Arg Glu Ile Leu His Phe His Tyr
                165                 170                 175

Thr Thr Trp Pro Asp Phe Gly Val Pro Glu Ser Pro Ala Ser Phe Leu
            180                 185                 190

Asn Phe Leu Phe Lys Val Arg Glu Ser Gly Ser Leu Ser Pro Glu His
        195                 200                 205

Gly Pro Val Val Val His Cys Ser Ala Gly Ile Gly Arg Ser Gly Thr
    210                 215                 220

Phe Cys Leu Ala Asp Thr Cys Leu Leu Leu Met Asp Lys Arg Lys Asp
225                 230                 235                 240

Pro Ser Ser Val Asp Ile Lys Lys Val Leu Leu Glu Met Arg Lys Phe
```

|  |  |  | 245 |  |  |  |  | 250 |  |  |  |  | 255 |  |
|---|---|---|---|---|---|---|---|---|---|---|---|---|---|---|
| Arg | Met | Gly | Leu | Ile | Gln | Thr | Ala | Asp | Gln | Leu | Arg | Phe | Ser | Tyr | Leu |
|  |  |  | 260 |  |  |  |  | 265 |  |  |  |  | 270 |  |  |
| Ala | Val | Ile | Glu | Gly | Ala | Lys | Phe | Ile | Met | Gly | Asp | Ser | Ser | Val | Gln |
|  |  |  | 275 |  |  |  |  | 280 |  |  |  |  | 285 |  |  |
| Asp | Gln | Trp | Lys | Glu | Leu | Ser | His | Glu | Asp | Ala | Ala | Thr | Leu | Glu | Arg |
|  |  | 290 |  |  |  |  | 295 |  |  |  |  | 300 |  |  |  |
| Ile | Glu | Lys | Asn | Phe | Val | Ile | Thr | Asp | Pro | Arg | Leu | Pro | Asp | Asn | Pro |
| 305 |  |  |  |  | 310 |  |  |  |  | 315 |  |  |  |  | 320 |
| Ile | Ile | Phe | Ala | Ser | Asp | Ser | Phe | Leu | Gln | Leu | Thr | Glu | Tyr | Ser | Arg |
|  |  |  |  | 325 |  |  |  |  | 330 |  |  |  |  | 335 |  |
| Glu | Glu | Ile | Leu | Gly | Arg | Asn | Cys | Arg | Phe | Leu | Gln | Gly | Pro | Glu | Thr |
|  |  |  | 340 |  |  |  |  | 345 |  |  |  |  | 350 |  |  |
| Asp | Arg | Ala | Thr | Val | Arg | Lys | Ile | Arg | Asp | Ala | Ile | Asp | Asn | Gln | Thr |
|  |  |  | 355 |  |  |  |  | 360 |  |  |  |  | 365 |  |  |
| Glu | Val | Thr | Val | Gln | Leu | Ile | Asn | Tyr | Thr | Lys | Ser | Gly | Lys | Lys | Phe |
|  | 370 |  |  |  |  | 375 |  |  |  |  | 380 |  |  |  |  |
| Trp | Asn | Leu | Phe | His | Leu | Gln | Pro | Met | Arg | Asp | Gln | Lys | Gly | Asp | Val |
| 385 |  |  |  |  | 390 |  |  |  |  | 395 |  |  |  |  | 400 |
| Gln | Tyr | Phe | Ile | Gly | Val | Gln | Leu | Asp | Gly | Thr | Glu | His | Val | Arg | Asp |
|  |  |  |  | 405 |  |  |  |  | 410 |  |  |  |  | 415 |  |
| Ala | Ala | Glu | Arg | Glu | Gly | Val | Met | Leu | Ile | Lys | Lys | Thr | Ala | Glu | Asn |
|  |  |  | 420 |  |  |  |  | 425 |  |  |  |  | 430 |  |  |
| Ile | Asp | Glu | Ala | Ala | Lys | Glu | Leu | Leu | Glu | His | His | His | His | His | His |
|  |  |  | 435 |  |  |  |  | 440 |  |  |  |  | 445 |  |  |

<210> SEQ ID NO 14
<211> LENGTH: 1347
<212> TYPE: DNA
<213> ORGANISM: Artificial Sequence
<220> FEATURE:
<223> OTHER INFORMATION: Synthetic Polynucleotide

<400> SEQUENCE: 14

| atggagatgg aaaaggagtt cgagcagatc gacaagtccg ggagctgggc ggccatttac | 60 |
| caggatatcc gacatgaagc cagtgacttc ccatgtagag tggccaagct tcctaagaac | 120 |
| aaaaaccgaa ataggtacag agacgtcagt cccttgacc atagtcggat taaactacat | 180 |
| caagaagata atgactatat caacgctagt ttgataaaaa tggaagaagc ccaaaggagt | 240 |
| tacattctta cccagggccc tttgcctaac acatgcggtc acttttggga gatggtgtgg | 300 |
| gagcagaaaa gcaggggtgt cgtcatgctc aacagagtga tggagaaagg ttcgttaaaa | 360 |
| tgcgcacaat actggccaca aaagaagaa aagagatga tctttgaaga cacaaatttg | 420 |
| aaattaacat tgatctctga agatatcaag tcatattata cagtgcgaca gctagaattg | 480 |
| gaaaacctta caaccaaga aactcgagag atcttacatt ccactatac acatggcct | 540 |
| gactttggag tccctgaatc accagcctca ttcttgaact ttcttttcaa agtccgagag | 600 |
| tcagggtcac tcagcccgga gcacgggccc gttgtggtgc actgcagtgc aggcatcggc | 660 |
| aggtctggaa ccttctgtct ggctgatacc tgcctcttgc tgatggacaa gaggaaagac | 720 |
| ccttcttccg ttgatatcaa gaaagtgctg ttagaaatga ggaagtttcg gatggggctg | 780 |
| atccagacag ccgaccagct gcgcttctcc tacctggctg tgatcgaagg tgccaaattc | 840 |
| atcatggggg actctgccgt gcaggatcag tggaaggagc tttcccacga ggacgctact | 900 |
| acacttgaac gtattgagaa gaactttgtc attactgacc caaggttgcc agataatccc | 960 |

-continued

```
attatattcg cgtccgatag tttcttgcag ttgacagaat atagccgtga agaaattttg   1020
ggaagaaact gcaggtttct acaaggtcct gaaactgatc gcgcgacagt gagaaaaatt   1080
agagatgcca tagataacca aacagaggtc actgttcagc tgattaatta tacaaagagt   1140
ggtaaaaagt tctggaacct ctttcacttg cagcctatgc gagatcagaa gggagatgtc   1200
cagtacttta ttggggttca gttggatgga actgagcatg tccgagatgc tgccgagaga   1260
gagggagtca tgctgattaa gaaaactgca gaaatattg atgaggcggc aaaagaactt    1320
ctcgagcacc accaccacca ccactga                                       1347
```

<210> SEQ ID NO 15
<211> LENGTH: 448
<212> TYPE: PRT
<213> ORGANISM: Artificial Sequence
<220> FEATURE:
<223> OTHER INFORMATION: Synthetic Polypeptide

<400> SEQUENCE: 15

```
Met Glu Met Glu Lys Glu Phe Glu Gln Ile Asp Lys Ser Gly Ser Trp
1               5                   10                  15

Ala Ala Ile Tyr Gln Asp Ile Arg His Glu Ala Ser Asp Phe Pro Cys
            20                  25                  30

Arg Val Ala Lys Leu Pro Lys Asn Lys Asn Arg Asn Arg Tyr Arg Asp
        35                  40                  45

Val Ser Pro Phe Asp His Ser Arg Ile Lys Leu His Gln Glu Asp Asn
    50                  55                  60

Asp Tyr Ile Asn Ala Ser Leu Ile Lys Met Glu Ala Gln Arg Ser
65                  70                  75                  80

Tyr Ile Leu Thr Gln Gly Pro Leu Pro Asn Thr Cys Gly His Phe Trp
                85                  90                  95

Glu Met Val Trp Glu Gln Lys Ser Arg Gly Val Val Met Leu Asn Arg
            100                 105                 110

Val Met Glu Lys Gly Ser Leu Lys Cys Ala Gln Tyr Trp Pro Gln Lys
        115                 120                 125

Glu Glu Lys Glu Met Ile Phe Glu Asp Thr Asn Leu Lys Leu Thr Leu
    130                 135                 140

Ile Ser Glu Asp Ile Lys Ser Tyr Tyr Thr Val Arg Gln Leu Glu Leu
145                 150                 155                 160

Glu Asn Leu Thr Thr Gln Glu Thr Arg Glu Ile Leu His Phe His Tyr
                165                 170                 175

Thr Thr Trp Pro Asp Phe Gly Val Pro Glu Ser Pro Ala Ser Phe Leu
            180                 185                 190

Asn Phe Leu Phe Lys Val Arg Glu Ser Gly Ser Leu Ser Pro Glu His
        195                 200                 205

Gly Pro Val Val Val His Cys Ser Ala Gly Ile Gly Arg Ser Gly Thr
    210                 215                 220

Phe Cys Leu Ala Asp Thr Cys Leu Leu Leu Met Asp Lys Arg Lys Asp
225                 230                 235                 240

Pro Ser Ser Val Asp Ile Lys Lys Val Leu Leu Glu Met Arg Lys Phe
                245                 250                 255

Arg Met Gly Leu Ile Gln Thr Ala Asp Gln Leu Arg Phe Ser Tyr Leu
            260                 265                 270

Ala Val Ile Glu Gly Ala Lys Phe Ile Met Gly Asp Ser Ala Val Gln
        275                 280                 285
```

```
Asp Gln Trp Lys Glu Leu Ser His Glu Asp Ala Thr Thr Leu Glu Arg
    290                 295                 300
Ile Glu Lys Asn Phe Val Ile Thr Asp Pro Arg Leu Pro Asp Asn Pro
305                 310                 315                 320
Ile Ile Phe Ala Ser Asp Ser Phe Leu Gln Leu Thr Glu Tyr Ser Arg
                325                 330                 335
Glu Glu Ile Leu Gly Arg Asn Cys Arg Phe Leu Gln Gly Pro Glu Thr
            340                 345                 350
Asp Arg Ala Thr Val Arg Lys Ile Arg Asp Ala Ile Asp Asn Gln Thr
        355                 360                 365
Glu Val Thr Val Gln Leu Ile Asn Tyr Thr Lys Ser Gly Lys Lys Phe
    370                 375                 380
Trp Asn Leu Phe His Leu Gln Pro Met Arg Asp Gln Lys Gly Asp Val
385                 390                 395                 400
Gln Tyr Phe Ile Gly Val Gln Leu Asp Gly Thr Glu His Val Arg Asp
                405                 410                 415
Ala Ala Glu Arg Glu Gly Val Met Leu Ile Lys Lys Thr Ala Glu Asn
            420                 425                 430
Ile Asp Glu Ala Ala Lys Glu Leu Leu Glu His His His His His His
        435                 440                 445
```

<210> SEQ ID NO 16
<211> LENGTH: 1350
<212> TYPE: DNA
<213> ORGANISM: Artificial Sequence
<220> FEATURE:
<223> OTHER INFORMATION: Synthetic Polynucleotide

<400> SEQUENCE: 16

| | | | | | |
|---|---|---|---|---|---|
| atgcccacca | ccatcgagcg | ggagttcgaa | gagttggata | tcagcgtcg | ctggcagccg | 60 |
| ctgtacttgg | aaattcgaaa | tgagtcccat | gactatcctc | atagagtggc | caagtttcca | 120 |
| gaaaacagaa | atcgaaacag | atacagagat | gtaagcccat | atgatcacag | tcgtgttaaa | 180 |
| ctgcaaaatg | ctgagaatga | ttatattaat | gccagtttag | ttgacataga | gaggcacaa | 240 |
| aggagttaca | tcttaacaca | gggtccactt | cctaacacat | gctgccattt | ctggcttatg | 300 |
| gtttggcagc | agaagaccaa | agcagttgtc | atgctgaacc | gcgtgatgga | gaaaggttcg | 360 |
| ttaaaatgtg | cacagtactg | gccaacagat | gaccaagaga | tgctgtttaa | agaaacagga | 420 |
| ttcagtgtga | agctcttgtc | agaagatgtg | aagtcgtatt | atacagtaca | tctactacaa | 480 |
| ttagaaaata | tcaatagtgg | tgaaaccaga | acaatatctc | actttcatta | tactacctgg | 540 |
| ccagattttg | gagtccctga | atcaccagct | tcatttctca | atttcttgtt | taaagtgaga | 600 |
| gaatctggct | ccttgaaccc | tgaccatggg | cctgcggtga | tccactgtag | tgcaggcatt | 660 |
| gggcgctctg | gcaccttctc | tctggtagac | acttgtcttt | tgctgatgga | caagaggaaa | 720 |
| gacccttctt | ccgttgatat | caagaaagtg | ctgttagaaa | tgaggaagtt | tcggatgggg | 780 |
| ctgatccaga | cagccgacca | gctgcgcttc | tcctacctgg | ctgtgatcga | aggtgccaaa | 840 |
| ttcatcatgg | gggactcttc | cgtgcaggat | cagtggaagg | agctttccca | cgaggacgct | 900 |
| gctacacttg | aacgtattga | gaagaacttt | gtcattactg | acccaaggtt | gccagataat | 960 |
| cccattatat | tcgcgtccga | tagtttcttg | cagttgacag | aatatagccg | tgaagaaatt | 1020 |
| ttgggaagaa | actgcaggtt | tctacaaggt | cctgaaactg | atcgcgcgac | agtgagaaaa | 1080 |
| attagagatg | ccatagataa | ccaaacagag | gtcactgttc | agctgattaa | ttatacaaag | 1140 |
| agtggtaaaa | agttctggaa | cctctttcac | ttgcagccta | tgcgagatca | gaagggagat | 1200 |

-continued

```
gtccagtact ttattggggt tcagttggat ggaactgagc atgtccgaga tgctgccgag    1260
agagagggag tcatgctgat taagaaaact gcagaaaata ttgatgaggc ggcaaaagaa    1320
cttctcgagc accaccacca ccaccactga                                     1350
```

<210> SEQ ID NO 17
<211> LENGTH: 449
<212> TYPE: PRT
<213> ORGANISM: Artificial Sequence
<220> FEATURE:
<223> OTHER INFORMATION: Synthetic Polypeptide

<400> SEQUENCE: 17

```
Met Pro Thr Thr Ile Glu Arg Glu Phe Glu Glu Leu Asp Thr Gln Arg
1               5                   10                  15

Arg Trp Gln Pro Leu Tyr Leu Glu Ile Arg Asn Glu Ser His Asp Tyr
            20                  25                  30

Pro His Arg Val Ala Lys Phe Pro Glu Asn Arg Asn Arg Asn Arg Tyr
        35                  40                  45

Arg Asp Val Ser Pro Tyr Asp His Ser Arg Val Lys Leu Gln Asn Ala
    50                  55                  60

Glu Asn Asp Tyr Ile Asn Ala Ser Leu Val Asp Ile Glu Glu Ala Gln
65                  70                  75                  80

Arg Ser Tyr Ile Leu Thr Gln Gly Pro Leu Pro Asn Thr Cys Cys His
                85                  90                  95

Phe Trp Leu Met Val Trp Gln Gln Lys Thr Lys Ala Val Val Met Leu
            100                 105                 110

Asn Arg Val Met Glu Lys Gly Ser Leu Lys Cys Ala Gln Tyr Trp Pro
        115                 120                 125

Thr Asp Asp Gln Glu Met Leu Phe Lys Glu Thr Gly Phe Ser Val Lys
    130                 135                 140

Leu Leu Ser Glu Asp Val Lys Ser Tyr Tyr Thr Val His Leu Leu Gln
145                 150                 155                 160

Leu Glu Asn Ile Asn Ser Gly Glu Thr Arg Thr Ile Ser His Phe His
                165                 170                 175

Tyr Thr Thr Trp Pro Asp Phe Gly Val Pro Glu Ser Pro Ala Ser Phe
            180                 185                 190

Leu Asn Phe Leu Phe Lys Val Arg Glu Ser Gly Ser Leu Asn Pro Asp
        195                 200                 205

His Gly Pro Ala Val Ile His Cys Ser Ala Gly Ile Gly Arg Ser Gly
    210                 215                 220

Thr Phe Ser Leu Val Asp Thr Cys Leu Leu Leu Met Asp Lys Arg Lys
225                 230                 235                 240

Asp Pro Ser Ser Val Asp Ile Lys Lys Val Leu Leu Glu Met Arg Lys
                245                 250                 255

Phe Arg Met Gly Leu Ile Gln Thr Ala Asp Gln Leu Arg Phe Ser Tyr
            260                 265                 270

Leu Ala Val Ile Glu Gly Ala Lys Phe Ile Met Gly Asp Ser Ser Val
        275                 280                 285

Gln Asp Gln Trp Lys Glu Leu Ser His Glu Asp Ala Ala Thr Leu Glu
    290                 295                 300

Arg Ile Glu Lys Asn Phe Val Ile Thr Asp Pro Arg Leu Pro Asp Asn
305                 310                 315                 320

Pro Ile Ile Phe Ala Ser Asp Ser Phe Leu Gln Leu Thr Glu Tyr Ser
                325                 330                 335
```

```
Arg Glu Glu Ile Leu Gly Arg Asn Cys Arg Phe Leu Gln Gly Pro Glu
            340                 345                 350

Thr Asp Arg Ala Thr Val Arg Lys Ile Arg Asp Ala Ile Asp Asn Gln
            355                 360                 365

Thr Glu Val Thr Val Gln Leu Ile Asn Tyr Thr Lys Ser Gly Lys Lys
        370                 375                 380

Phe Trp Asn Leu Phe His Leu Gln Pro Met Arg Asp Gln Lys Gly Asp
385                 390                 395                 400

Val Gln Tyr Phe Ile Gly Val Gln Leu Asp Gly Thr Glu His Val Arg
                405                 410                 415

Asp Ala Ala Glu Arg Glu Gly Val Met Leu Ile Lys Lys Thr Ala Glu
            420                 425                 430

Asn Ile Asp Glu Ala Ala Lys Glu Leu Leu Glu His His His His His
            435                 440                 445

His

<210> SEQ ID NO 18
<211> LENGTH: 1350
<212> TYPE: DNA
<213> ORGANISM: Artificial Sequence
<220> FEATURE:
<223> OTHER INFORMATION: Synthetic Polynucleotide

<400> SEQUENCE: 18
atgcccacca ccatcgagcg ggagttcgaa gagttggata ctcagcgtcg ctggcagccg      60
ctgtacttgg aaattcgaaa tgagtcccat gactatcctc atagagtggc caagtttcca     120
gaaaacagaa atcgaaacag atacagagat gtaagcccat atgatcacag tcgtgttaaa     180
ctgcaaaatg ctgagaatga ttatattaat gccagtttag ttgacataga agaggcacaa     240
aggagttaca tcttaacaca gggtccactt cctaacacat gctgccattt ctggcttatg     300
gtttggcagc agaagaccaa agcagttgtc atgctgaacc gcattgtgga aaagaatcg      360
gttaaatgtg cacagtactg gccaacagat gaccaagaga tgctgtttaa agaaacagga     420
ttcagtgtga agctcttgtc agaagatgtg aagtcgtatt atacagtaca tctactacaa     480
ttagaaaata tcaatagtgg tgaaaccaga acaatatctc actttcatta tactacctgg     540
ccagattttg gagtccctga atcaccagct tcatttctca atttcttgtt taaagtgaga     600
gaatctggct ccttgaaccc tgaccatggg cctgcggtga tccactgtag tgcaggcatt     660
gggcgctctg gcaccttctc tctggtagac acttgtctt tgctgatgga caagaggaaa     720
gaccttctt ccgttgatat caagaaagtg ctgttagaaa tgaggaagtt tcggatgggg     780
ctgatccaga cagccgacca gctgcgcttc tcctacctgg ctgtgatcga aggtgccaaa     840
ttcatcatgg gggactcttc cgtgcaggat cagtggaagg agctttccca cgaggacgct     900
gctacacttg aacgtattga agaaactttt gtcattactg acccaaggtt gccagataat     960
cccattatat tcgcgtccga tagtttcttg cagttgacag aatatagccg tgaagaaatt    1020
ttgggaagaa actgcaggtt tctacaaggt cctgaaactg atcgcgcgac agtgagaaaa    1080
attagagatg ccatagataa ccaaacagag gtcactgttc agctgattaa ttatacaaag    1140
agtggtaaaa agttctggaa cctctttcac ttgcagccta tgcgagatca aaagggagat    1200
gtccagtact ttattggggt tcagttggat ggaactgagc atgtccgaga tgctgccgag    1260
agagagggag tcatgctgat taagaaaact gcagaaaata ttgatgaggc ggcaaaagaa    1320
cttctcgagc accaccacca ccaccactga                                     1350
```

```
<210> SEQ ID NO 19
<211> LENGTH: 449
<212> TYPE: PRT
<213> ORGANISM: Artificial Sequence
<220> FEATURE:
<223> OTHER INFORMATION: Synthetic Polypeptide

<400> SEQUENCE: 19
```

Met Pro Thr Thr Ile Glu Arg Glu Phe Glu Glu Leu Asp Thr Gln Arg
1               5                   10                  15

Arg Trp Gln Pro Leu Tyr Leu Glu Ile Arg Asn Glu Ser His Asp Tyr
            20                  25                  30

Pro His Arg Val Ala Lys Phe Pro Glu Asn Arg Asn Arg Asn Arg Tyr
        35                  40                  45

Arg Asp Val Ser Pro Tyr Asp His Ser Arg Val Lys Leu Gln Asn Ala
    50                  55                  60

Glu Asn Asp Tyr Ile Asn Ala Ser Leu Val Asp Ile Glu Glu Ala Gln
65                  70                  75                  80

Arg Ser Tyr Ile Leu Thr Gln Gly Pro Leu Pro Asn Thr Cys Cys His
                85                  90                  95

Phe Trp Leu Met Val Trp Gln Lys Thr Lys Ala Val Val Met Leu
            100                 105                 110

Asn Arg Ile Val Glu Lys Glu Ser Val Lys Cys Ala Gln Tyr Trp Pro
        115                 120                 125

Thr Asp Asp Gln Glu Met Leu Phe Lys Glu Thr Gly Phe Ser Val Lys
    130                 135                 140

Leu Leu Ser Glu Asp Val Lys Ser Tyr Tyr Thr Val His Leu Leu Gln
145                 150                 155                 160

Leu Glu Asn Ile Asn Ser Gly Glu Thr Arg Thr Ile Ser His Phe His
                165                 170                 175

Tyr Thr Thr Trp Pro Asp Phe Gly Val Pro Glu Ser Pro Ala Ser Phe
            180                 185                 190

Leu Asn Phe Leu Phe Lys Val Arg Glu Ser Gly Ser Leu Asn Pro Asp
        195                 200                 205

His Gly Pro Ala Val Ile His Cys Ser Ala Gly Ile Gly Arg Ser Gly
    210                 215                 220

Thr Phe Ser Leu Val Asp Thr Cys Leu Leu Met Asp Lys Arg Lys
225                 230                 235                 240

Asp Pro Ser Ser Val Asp Ile Lys Lys Val Leu Leu Glu Met Arg Lys
                245                 250                 255

Phe Arg Met Gly Leu Ile Gln Thr Ala Asp Gln Leu Arg Phe Ser Tyr
            260                 265                 270

Leu Ala Val Ile Glu Gly Ala Lys Phe Ile Met Gly Asp Ser Ser Val
        275                 280                 285

Gln Asp Gln Trp Lys Glu Leu Ser His Glu Asp Ala Ala Thr Leu Glu
    290                 295                 300

Arg Ile Glu Lys Asn Phe Val Ile Thr Asp Pro Arg Leu Pro Asp Asn
305                 310                 315                 320

Pro Ile Ile Phe Ala Ser Asp Ser Phe Leu Gln Leu Thr Glu Tyr Ser
                325                 330                 335

Arg Glu Glu Ile Leu Gly Arg Asn Cys Arg Phe Leu Gln Gly Pro Glu
            340                 345                 350

Thr Asp Arg Ala Thr Val Arg Lys Ile Arg Asp Ala Ile Asp Asn Gln
        355                 360                 365

```
Thr Glu Val Thr Val Gln Leu Ile Asn Tyr Thr Lys Ser Gly Lys Lys
    370                 375                 380

Phe Trp Asn Leu Phe His Leu Gln Pro Met Arg Asp Gln Lys Gly Asp
385                 390                 395                 400

Val Gln Tyr Phe Ile Gly Val Gln Leu Asp Gly Thr Glu His Val Arg
                405                 410                 415

Asp Ala Ala Glu Arg Glu Gly Val Met Leu Ile Lys Lys Thr Ala Glu
                420                 425                 430

Asn Ile Asp Glu Ala Ala Lys Glu Leu Leu Glu His His His His
    435                 440                 445

His

<210> SEQ ID NO 20
<211> LENGTH: 1827
<212> TYPE: DNA
<213> ORGANISM: Artificial Sequence
<220> FEATURE:
<223> OTHER INFORMATION: Synthetic Polynucleotide

<400> SEQUENCE: 20
atgcatcatc atcatcatca tgtgagcaag ggcgaggagc tgttcaccgg ggtggtgccc      60
atcctggtcg agctggacgg cgacgtaaac ggccacaagt tcagcgtccg cggcgagggc     120
gagggcgatg ccaccaacgg caagctgacc ctgaagttca tctgcaccac cggcaagctg     180
cccgtgccct ggcccaccct cgtgaccacc ttcggctacg gcgtggcctg cttcagccgc     240
taccccgacc acatgaagca gcacgacttc ttcaagtccg ccatgcccga aggctacgtc     300
caggagcgca ccatctcttt caaggacgac ggtacctaca agacccgcgc cgaggtgaag     360
ttcgagggca cacccctggt gaaccgcatc gagctgaagg gcatcgactt caaggaggac     420
ggcaacatcc tggggcacaa gctggagtac aacttcaaca gccactacgt ctatatcacg     480
gccgacaagc agaagaactg catcaaggct aacttcaaga tccgccacaa cgttgaggac     540
ggcagcgtgc agctcgccga ccactaccag cagaacaccc ccatcggcga cggccccgtg     600
ctgctgcccg acaaccacta cctgagccat cagtccaagc tgagcaaaga ccccaacgag     660
aagcgcgatc acatggtcct gctggagttc gtgaccgccg ccgggattac acatggcatg     720
gacgagctgt acaagtggta ttttgggaag atcactcgtc gggagtccga gcggctgctg     780
ctcaaccccg aaaaccccg ggaaccttc ttggtccggg agagcgagac gacaaaaggt     840
gcctattgcc tctccgtttc tgactttgac aacgccaagg gctcaatgt gaagcactac     900 aagatccgca agctggacag cggcggcttc tacatcacct cacgcacaca gttcagcagc     960
ctgcagcagc tggtggccta ctactccaaa catgctgatg gcttgtgcca ccgcctgact    1020
aacgtctgtg gtctacatc tggatctggg aagccgggtt ctggtgaggg ttcttggatg    1080
gaggactatg actacgtcca cctacagggg gagctcgtgt ctaagggcga agagctgatc    1140
aaggaaaata tgcgtatgaa ggtggtcatg gaaggttcgg tcaacggcca ccaattcaaa    1200
tgcacaggtg aaggagaagg cagaccgtac gagggaactc aaaccatgag gatcaaagtc    1260
atcgagggag accccctgcc atttgccttt gacattcttg ccacgtcgtt catgtatggc    1320
agccgtactt ttatcaagta cccggccgac atccctgatt tctttaaaca gtcctttcct    1380
gagggtttta cttgggaaag agttacgaga tacgaagatg gtggagtcgt caccgtcacg    1440
caggacacca gccttgagga tggcgagctc gtctacaacg tcaaggtcag aggggtaaac    1500
tttccctcca atggtcccgt gatgcagaag aagaccaagg gttgggagcc taatacagag    1560
```

```
atgatgtatc cagcagatgg tggtctgaga ggatacactg acatcgcact gaaagttgat    1620
ggtggtggcc atctgcactg caacttcgtg acaacttaca ggtcaaaaaa gaccgtcggg    1680
aacatcaaga tgcccggtgt ccatgccgtt gatcaccgcc tggaaaggat cgaggagagt    1740
gacaatgaaa cctacgtagt gcaacgcgaa gtggcagttg ccaaatacag caaccttggt    1800
ggtggcatgg acgagctgta caagtaa                                         1827
```

<210> SEQ ID NO 21
<211> LENGTH: 608
<212> TYPE: PRT
<213> ORGANISM: Artificial Sequence
<220> FEATURE:
<223> OTHER INFORMATION: Synthetic Polypeptide

<400> SEQUENCE: 21

```
Met His His His His His Val Ser Lys Gly Glu Glu Leu Phe Thr
1               5                   10                  15

Gly Val Val Pro Ile Leu Val Glu Leu Asp Gly Asp Val Asn Gly His
            20                  25                  30

Lys Phe Ser Val Arg Gly Glu Gly Glu Gly Asp Ala Thr Asn Gly Lys
        35                  40                  45

Leu Thr Leu Lys Phe Ile Cys Thr Thr Gly Lys Leu Pro Val Pro Trp
    50                  55                  60

Pro Thr Leu Val Thr Thr Phe Gly Tyr Gly Val Ala Cys Phe Ser Arg
65                  70                  75                  80

Tyr Pro Asp His Met Lys Gln His Asp Phe Phe Lys Ser Ala Met Pro
                85                  90                  95

Glu Gly Tyr Val Gln Glu Arg Thr Ile Ser Phe Lys Asp Asp Gly Thr
            100                 105                 110

Tyr Lys Thr Arg Ala Glu Val Lys Phe Glu Gly Asp Thr Leu Val Asn
        115                 120                 125

Arg Ile Glu Leu Lys Gly Ile Asp Phe Lys Glu Asp Gly Asn Ile Leu
    130                 135                 140

Gly His Lys Leu Glu Tyr Asn Phe Asn Ser His Tyr Val Tyr Ile Thr
145                 150                 155                 160

Ala Asp Lys Gln Lys Asn Cys Ile Lys Ala Asn Phe Lys Ile Arg His
                165                 170                 175

Asn Val Glu Asp Gly Ser Val Gln Leu Ala Asp His Tyr Gln Gln Asn
            180                 185                 190

Thr Pro Ile Gly Asp Gly Pro Val Leu Leu Pro Asp Asn His Tyr Leu
        195                 200                 205

Ser His Gln Ser Lys Leu Ser Lys Asp Pro Asn Glu Lys Arg Asp His
    210                 215                 220

Met Val Leu Leu Glu Phe Val Thr Ala Ala Gly Ile Thr His Gly Met
225                 230                 235                 240

Asp Glu Leu Tyr Lys Trp Tyr Phe Gly Lys Ile Thr Arg Arg Glu Ser
                245                 250                 255

Glu Arg Leu Leu Leu Asn Pro Glu Asn Pro Arg Gly Thr Phe Leu Val
            260                 265                 270

Arg Glu Ser Glu Thr Thr Lys Gly Ala Tyr Cys Leu Ser Val Ser Asp
        275                 280                 285

Phe Asp Asn Ala Lys Gly Leu Asn Val Lys His Tyr Lys Ile Arg Lys
    290                 295                 300

Leu Asp Ser Gly Gly Phe Tyr Ile Thr Ser Arg Thr Gln Phe Ser Ser
```

```
                305                 310                 315                 320
Leu Gln Gln Leu Val Ala Tyr Tyr Ser Lys His Ala Asp Gly Leu Cys
                325                 330                 335

His Arg Leu Thr Asn Val Cys Gly Ser Thr Ser Gly Ser Gly Lys Pro
                340                 345                 350

Gly Ser Gly Glu Gly Ser Trp Met Glu Asp Tyr Asp Tyr Val His Leu
                355                 360                 365

Gln Gly Glu Leu Val Ser Lys Gly Glu Glu Leu Ile Lys Glu Asn Met
                370                 375                 380

Arg Met Lys Val Val Met Glu Gly Ser Val Asn Gly His Gln Phe Lys
385                 390                 395                 400

Cys Thr Gly Glu Gly Glu Gly Arg Pro Tyr Glu Gly Thr Gln Thr Met
                405                 410                 415

Arg Ile Lys Val Ile Glu Gly Gly Pro Leu Pro Phe Ala Phe Asp Ile
                420                 425                 430

Leu Ala Thr Ser Phe Met Tyr Gly Ser Arg Thr Phe Ile Lys Tyr Pro
                435                 440                 445

Ala Asp Ile Pro Asp Phe Phe Lys Gln Ser Phe Pro Glu Gly Phe Thr
                450                 455                 460

Trp Glu Arg Val Thr Arg Tyr Glu Asp Gly Gly Val Val Thr Val Thr
465                 470                 475                 480

Gln Asp Thr Ser Leu Glu Asp Gly Glu Leu Val Tyr Asn Val Lys Val
                485                 490                 495

Arg Gly Val Asn Phe Pro Ser Asn Gly Pro Val Met Gln Lys Lys Thr
                500                 505                 510

Lys Gly Trp Glu Pro Asn Thr Glu Met Met Tyr Pro Ala Asp Gly Gly
                515                 520                 525

Leu Arg Gly Tyr Thr Asp Ile Ala Leu Lys Val Asp Gly Gly His
                530                 535                 540

Leu His Cys Asn Phe Val Thr Thr Tyr Arg Ser Lys Lys Thr Val Gly
545                 550                 555                 560

Asn Ile Lys Met Pro Gly Val His Ala Val Asp His Arg Leu Glu Arg
                565                 570                 575

Ile Glu Glu Ser Asp Asn Glu Thr Tyr Val Val Gln Arg Glu Val Ala
                580                 585                 590

Val Ala Lys Tyr Ser Asn Leu Gly Gly Gly Met Asp Glu Leu Tyr Lys
                595                 600                 605

<210> SEQ ID NO 22
<211> LENGTH: 70
<212> TYPE: DNA
<213> ORGANISM: Artificial Sequence
<220> FEATURE:
<223> OTHER INFORMATION: Synthetic Polynucleotide

<400> SEQUENCE: 22
gcaaatgggc ggtaggcgtg tacggtggga ggtctatata agcagagctg gtttagtgaa      60
ccgtcagatc                                                              70

<210> SEQ ID NO 23
<211> LENGTH: 66
<212> TYPE: DNA
<213> ORGANISM: Artificial Sequence
<220> FEATURE:
<223> OTHER INFORMATION: Synthetic Polynucleotide

<400> SEQUENCE: 23
```

```
ggcagcggcg ccaccaactt ctccctgctg aagcaggccg gcgacgtgga ggagaacccc    60
ggcccc                                                               66

<210> SEQ ID NO 24
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 24

Gly Ser Gly Ala Thr Asn Phe Ser Leu Leu Lys Gln Ala Gly Asp Val
1               5                  10                  15

Glu Glu Asn Pro Gly Pro
            20

<210> SEQ ID NO 25
<211> LENGTH: 160
<212> TYPE: DNA
<213> ORGANISM: Artificial Sequence
<220> FEATURE:
<223> OTHER INFORMATION: Synthetic Polynucleotide

<400> SEQUENCE: 25
ttctagagca cagctaacac cacgtcgtcc ctatctgctg ccctaggtct atgagtggtt    60
gctggataac tttacgggca tgcataaggc tcggtatcta tattcaggga gaccacaacg   120
gtttccctct acaaataatt tgtttaact tttactagag                          160

<210> SEQ ID NO 26
<211> LENGTH: 153
<212> TYPE: DNA
<213> ORGANISM: Artificial Sequence
<220> FEATURE:
<223> OTHER INFORMATION: Synthetic Polynucleotide

<400> SEQUENCE: 26
gcacagctaa caccacgtcg tccctatctg ctgccctagg tctatgagtg gttgctggat    60
aactttacgg gcatgcataa ggctcgtata atatattcag ggagaccaca acggtttccc   120
tctacaaata attttgttta acttttacta gag                                153

<210> SEQ ID NO 27
<211> LENGTH: 304
<212> TYPE: DNA
<213> ORGANISM: Artificial Sequence
<220> FEATURE:
<223> OTHER INFORMATION: Synthetic Polynucleotide

<400> SEQUENCE: 27
agaaaccaat tgtccatatt gcatcagaca ttgccgtcac tgcgtctttt actggctctt    60
ctcgctaacc aaaccggtaa ccccgcttat taaaagcatt ctgtaacaaa gcgggaccaa   120
agccatgaca aaaacgcgta acaaaagtgt ctataatcac ggcagaaaag tccacattga   180
ttatttgcac ggcgtcacac tttgctatgc catagcattt ttatccataa gattagcgga   240
tcctacctga cgctttttat cgcaactctc tactgtttct ccatacccgt ttttttgggc   300
tagc                                                               304

<210> SEQ ID NO 28
<211> LENGTH: 72
<212> TYPE: DNA
```

```
<213> ORGANISM: Artificial Sequence
<220> FEATURE:
<223> OTHER INFORMATION: Synthetic Polynucleotide

<400> SEQUENCE: 28
acaagaaagt tgttcatta ggcaccccgg gctttactcg taaagcttcc ggcgcgtatg    60
ttgtgtcgac cg                                                       72

<210> SEQ ID NO 29
<211> LENGTH: 246
<212> TYPE: DNA
<213> ORGANISM: Artificial Sequence
<220> FEATURE:
<223> OTHER INFORMATION: Synthetic Polynucleotide

<400> SEQUENCE: 29
cgactgcacg gtgcaccaat gcttctggcg tcaggcagcc atcggaagct gtggtatggc    60
tgtgcaggtc gtaaatcact gcataattcg tgtcgctcaa ggcgcactcc cgttctggat   120
aatgtttttt gcgccgacat cataacggtt ctggcaaata ttctgaaatg agctgttgac   180
aattaatcat ccggctcgta taatgtgtgg aattgtgagc ggataacaat ttcacacagg   240
aaacag                                                              246

<210> SEQ ID NO 30
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 30
cctatagtga gtcgtatta                                                19

<210> SEQ ID NO 31
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 31
ttaaagagga gaaaggtc                                                 18

<210> SEQ ID NO 32
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 32
cgaaaaaaag taaggcggta atcc                                          24

<210> SEQ ID NO 33
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 33
tgcagaaaga ggagaaatac tag                                           23
```

<210> SEQ ID NO 34
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 34
attaaagagg agaaatacta g                                          21

<210> SEQ ID NO 35
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 35
gtgcagtaag gaggaaaaaa aa                                         22

<210> SEQ ID NO 36
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 36
gctagcttta agaaggagat atacc                                      25

<210> SEQ ID NO 37
<211> LENGTH: 94
<212> TYPE: PRT
<213> ORGANISM: Artificial Sequence
<220> FEATURE:
<223> OTHER INFORMATION: Synthetic Polypeptide

<400> SEQUENCE: 37

Met Ala Arg Val Thr Val Gln Asp Ala Val Glu Lys Ile Gly Asn Arg
1               5                   10                  15

Phe Asp Leu Val Leu Val Ala Ala Arg Arg Ala Arg Gln Met Gln Val
            20                  25                  30

Gly Gly Lys Asp Pro Leu Val Pro Glu Glu Asn Asp Lys Thr Thr Val
        35                  40                  45

Ile Ala Leu Arg Glu Ile Glu Glu Gly Leu Ile Asn Asn Gln Ile Leu
    50                  55                  60

Asp Val Arg Glu Arg Gln Glu Gln Glu Gln Glu Ala Ala Glu Leu
65                  70                  75                  80

Gln Ala Val Thr Ala Ile Ala Glu Gly Arg Arg Ala Ala Ala
            85                  90

<210> SEQ ID NO 38
<211> LENGTH: 218
<212> TYPE: PRT
<213> ORGANISM: Artificial Sequence
<220> FEATURE:
<223> OTHER INFORMATION: Synthetic Polypeptide

<400> SEQUENCE: 38

Met Ser Ile Ser Ser Arg Val Lys Ser Lys Arg Ile Gln Leu Gly Leu
1               5                   10                  15

Asn Gln Ala Glu Leu Ala Gln Lys Val Gly Thr Thr Gln Gln Ser Ile
            20                  25                  30

Glu Gln Leu Glu Asn Gly Lys Thr Lys Arg Pro Arg Phe Leu Pro Glu
            35                  40                  45

Leu Ala Ser Ala Leu Gly Val Ser Val Asp Trp Leu Leu Asn Gly Thr
 50                  55                  60

Ser Asp Ser Asn Val Arg Phe Val Gly His Val Glu Pro Lys Gly Lys
 65                  70                  75                  80

Tyr Pro Leu Ile Ser Met Val Arg Ala Arg Ser Trp Cys Glu Ala Cys
                 85                  90                  95

Glu Pro Tyr Asp Ile Lys Asp Ile Asp Glu Trp Tyr Asp Ser Asp Val
            100                 105                 110

Asn Leu Leu Gly Asn Gly Phe Trp Leu Lys Val Glu Gly Asp Ser Met
            115                 120                 125

Thr Ser Pro Val Gly Gln Ser Ile Pro Glu Gly His Met Val Leu Val
130                 135                 140

Asp Thr Gly Arg Glu Pro Val Asn Gly Ser Leu Val Val Ala Lys Leu
145                 150                 155                 160

Thr Asp Ala Asn Glu Ala Thr Phe Lys Lys Leu Val Ile Asp Gly Gly
                165                 170                 175

Gln Lys Tyr Leu Lys Gly Leu Asn Pro Ser Trp Pro Met Thr Pro Ile
            180                 185                 190

Asn Gly Asn Cys Lys Ile Ile Gly Val Val Val Glu Ala Arg Val Lys
            195                 200                 205

Phe Val Asp Tyr Lys Asp Asp Asp Lys
            210                 215

<210> SEQ ID NO 39
<211> LENGTH: 98
<212> TYPE: PRT
<213> ORGANISM: Artificial Sequence
<220> FEATURE:
<223> OTHER INFORMATION: Synthetic Polypeptide

<400> SEQUENCE: 39

Trp Tyr Phe Gly Lys Ile Thr Arg Arg Glu Ser Glu Arg Leu Leu Leu
1               5                  10                  15

Asn Pro Glu Asn Pro Arg Gly Thr Phe Leu Val Arg Glu Ser Glu Thr
            20                  25                  30

Val Lys Gly Ala Tyr Ala Leu Ser Val Ser Asp Phe Asp Asn Ala Lys
         35                  40                  45

Gly Leu Asn Val Lys His Tyr Leu Ile Arg Lys Leu Asp Ser Gly Gly
     50                  55                  60

Phe Tyr Ile Thr Ser Arg Thr Gln Phe Ser Ser Leu Gln Gln Leu Val
65                  70                  75                  80

Ala Tyr Tyr Ser Lys His Ala Asp Gly Leu Cys His Arg Leu Thr Asn
                85                  90                  95

Val Cys

<210> SEQ ID NO 40
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 40

Trp Met Glu Asp Tyr Asp Tyr Val His Leu Gln Gly
1               5                  10

```
<210> SEQ ID NO 41
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 41

Glu Pro Gln Tyr Glu Glu Ile Pro Ile Tyr Leu
1               5                   10

<210> SEQ ID NO 42
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 42

Asp His Gln Tyr Tyr Asn Asp Phe Pro Gly
1               5                   10

<210> SEQ ID NO 43
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 43

Pro Gln Arg Tyr Leu Val Ile Gln Gly Asp
1               5                   10

<210> SEQ ID NO 44
<211> LENGTH: 287
<212> TYPE: PRT
<213> ORGANISM: Artificial Sequence
<220> FEATURE:
<223> OTHER INFORMATION: Synthetic Polypeptide

<400> SEQUENCE: 44

Met Ser Lys Pro Gln Thr Gln Gly Leu Ala Lys Asp Ala Trp Glu Ile
1               5                   10                  15

Pro Arg Glu Ser Leu Arg Leu Glu Val Lys Leu Gly Gln Gly Cys Phe
                20                  25                  30

Gly Glu Val Trp Met Gly Thr Trp Asn Gly Thr Thr Arg Val Ala Ile
            35                  40                  45

Lys Thr Leu Lys Pro Gly Thr Met Ser Pro Glu Ala Phe Leu Gln Glu
        50                  55                  60

Ala Gln Val Met Lys Lys Leu Arg His Glu Lys Leu Val Gln Leu Tyr
65                  70                  75                  80

Ala Val Val Ser Glu Glu Pro Ile Tyr Ile Val Thr Glu Tyr Met Ser
                85                  90                  95

Lys Gly Ser Leu Leu Asp Phe Leu Lys Gly Glu Thr Gly Lys Tyr Leu
                100                 105                 110

Arg Leu Pro Gln Leu Val Asp Met Ala Ala Gln Ile Ala Ser Gly Met
            115                 120                 125

Ala Tyr Val Glu Arg Met Asn Tyr Val His Arg Asp Leu Arg Ala Ala
        130                 135                 140

Asn Ile Leu Val Gly Glu Asn Leu Val Cys Lys Val Ala Asp Phe Gly
145                 150                 155                 160
```

```
Leu Ala Arg Leu Ile Glu Asp Asn Glu Tyr Thr Ala Arg Gln Gly Ala
                165                 170                 175

Lys Phe Pro Ile Lys Trp Thr Ala Pro Glu Ala Ala Leu Tyr Gly Arg
            180                 185                 190

Phe Thr Ile Lys Ser Asp Val Trp Ser Phe Gly Ile Leu Leu Thr Glu
        195                 200                 205

Leu Thr Thr Lys Gly Arg Val Pro Tyr Pro Gly Met Val Asn Arg Glu
    210                 215                 220

Val Leu Asp Gln Val Glu Arg Gly Tyr Arg Met Pro Cys Pro Pro Glu
225                 230                 235                 240

Cys Pro Glu Ser Leu His Asp Leu Met Cys Gln Cys Trp Arg Lys Glu
                245                 250                 255

Pro Glu Glu Arg Pro Thr Phe Glu Tyr Leu Gln Ala Phe Leu Glu Asp
            260                 265                 270

Tyr Phe Thr Ser Thr Glu Pro Gln Tyr Gln Pro Gly Glu Asn Leu
        275                 280                 285

<210> SEQ ID NO 45
<211> LENGTH: 378
<212> TYPE: PRT
<213> ORGANISM: Artificial Sequence
<220> FEATURE:
<223> OTHER INFORMATION: Synthetic Polypeptide

<400> SEQUENCE: 45

Met Val Asp Tyr Ser Val Trp Asp His Ile Glu Val Ser Asp Asp Glu
1               5                   10                  15

Asp Glu Thr His Pro Asn Ile Asp Thr Ala Ser Leu Phe Arg Trp Arg
                20                  25                  30

His Gln Ala Arg Val Glu Arg Met Glu Gln Phe Gln Lys Glu Lys Glu
            35                  40                  45

Glu Leu Asp Arg Gly Cys Arg Glu Cys Lys Arg Lys Val Ala Glu Cys
        50                  55                  60

Gln Arg Lys Leu Lys Glu Leu Glu Val Ala Glu Gly Gly Lys Ala Glu
65                  70                  75                  80

Leu Glu Arg Leu Gln Ala Glu Ala Gln Gln Leu Arg Lys Glu Glu Arg
                85                  90                  95

Ser Trp Glu Gln Lys Leu Glu Glu Met Arg Lys Lys Glu Lys Ser Met
            100                 105                 110

Pro Trp Asn Val Asp Thr Leu Ser Lys Asp Gly Phe Ser Lys Ser Met
        115                 120                 125

Val Asn Thr Lys Pro Glu Lys Thr Glu Glu Asp Ser Glu Glu Val Arg
    130                 135                 140

Glu Gln Lys His Lys Thr Phe Val Glu Lys Tyr Glu Lys Gln Ile Lys
145                 150                 155                 160

His Phe Gly Met Leu Arg Arg Trp Asp Asp Ser Gln Lys Tyr Leu Ser
                165                 170                 175

Asp Asn Val His Leu Val Cys Glu Glu Thr Ala Asn Tyr Leu Val Ile
            180                 185                 190

Trp Cys Ile Asp Leu Glu Val Glu Glu Lys Cys Ala Leu Met Glu Gln
        195                 200                 205

Val Ala His Gln Thr Ile Val Met Gln Phe Ile Leu Glu Leu Ala Lys
    210                 215                 220

Ser Leu Lys Val Asp Pro Arg Ala Cys Phe Arg Gln Phe Phe Thr Lys
225                 230                 235                 240
```

```
Ile Lys Thr Ala Asp Arg Gln Tyr Met Glu Gly Phe Asn Asp Glu Leu
                245                 250                 255

Glu Ala Phe Lys Glu Arg Val Arg Gly Arg Ala Lys Leu Arg Ile Glu
            260                 265                 270

Lys Ala Met Lys Glu Tyr Glu Glu Glu Arg Lys Lys Arg Leu Gly
        275                 280                 285

Pro Gly Gly Leu Asp Pro Val Glu Val Tyr Glu Ser Leu Pro Glu Glu
    290                 295                 300

Leu Gln Lys Cys Phe Asp Val Lys Asp Val Gln Met Leu Gln Asp Ala
305                 310                 315                 320

Ile Ser Lys Met Asp Pro Thr Asp Ala Lys Tyr His Met Gln Arg Cys
                325                 330                 335

Ile Asp Ser Gly Leu Trp Val Pro Asn Ser Lys Ala Ser Glu Ala Lys
            340                 345                 350

Glu Gly Glu Glu Ala Gly Pro Gly Asp Pro Leu Leu Glu Ala Val Pro
        355                 360                 365

Lys Thr Gly Asp Glu Lys Asp Val Ser Val
    370                 375
```

<210> SEQ ID NO 46
<211> LENGTH: 321
<212> TYPE: PRT
<213> ORGANISM: Artificial Sequence
<220> FEATURE:
<223> OTHER INFORMATION: Synthetic Polypeptide

<400> SEQUENCE: 46

```
Met Glu Met Glu Lys Glu Phe Glu Gln Ile Asp Lys Ser Gly Ser Trp
1               5                   10                  15

Ala Ala Ile Tyr Gln Asp Ile Arg His Glu Ala Ser Asp Phe Pro Cys
                20                  25                  30

Arg Val Ala Lys Leu Pro Lys Asn Lys Asn Arg Asn Arg Tyr Arg Asp
            35                  40                  45

Val Ser Pro Phe Asp His Ser Arg Ile Lys Leu His Gln Glu Asp Asn
        50                  55                  60

Asp Tyr Ile Asn Ala Ser Leu Ile Lys Met Glu Glu Ala Gln Arg Ser
65                  70                  75                  80

Tyr Ile Leu Thr Gln Gly Pro Leu Pro Asn Thr Cys Gly His Phe Trp
                85                  90                  95

Glu Met Val Trp Glu Gln Lys Ser Arg Gly Val Val Met Leu Asn Arg
            100                 105                 110

Val Met Glu Lys Gly Ser Leu Lys Cys Ala Gln Tyr Trp Pro Gln Lys
        115                 120                 125

Glu Glu Lys Glu Met Ile Phe Glu Asp Thr Asn Leu Lys Leu Thr Leu
    130                 135                 140

Ile Ser Glu Asp Ile Lys Ser Tyr Tyr Thr Val Arg Gln Leu Glu Leu
145                 150                 155                 160

Glu Asn Leu Thr Thr Gln Glu Thr Arg Glu Ile Leu His Phe His Tyr
                165                 170                 175

Thr Thr Trp Pro Asp Phe Gly Val Pro Glu Ser Pro Ala Ser Phe Leu
            180                 185                 190

Asn Phe Leu Phe Lys Val Arg Glu Ser Gly Ser Leu Ser Pro Glu His
        195                 200                 205

Gly Pro Val Val Val His Ser Ser Ala Gly Ile Gly Arg Ser Gly Thr
    210                 215                 220
```

```
Phe Cys Leu Ala Asp Thr Cys Leu Leu Met Asp Lys Arg Lys Asp
225                 230                 235                 240

Pro Ser Ser Val Asp Ile Lys Lys Val Leu Leu Glu Met Arg Lys Phe
                245                 250                 255

Arg Met Gly Leu Ile Gln Thr Ala Asp Gln Leu Arg Phe Ser Tyr Leu
            260                 265                 270

Ala Val Ile Glu Gly Ala Lys Phe Ile Met Gly Asp Ser Ser Val Gln
        275                 280                 285

Asp Gln Trp Lys Glu Leu Ser His Glu Asp Leu Glu Pro Pro Pro Glu
    290                 295                 300

His Ile Pro Pro Pro Arg Pro Pro Lys Arg Ile Leu Glu Pro His
305                 310                 315                 320

Asn

<210> SEQ ID NO 47
<211> LENGTH: 371
<212> TYPE: PRT
<213> ORGANISM: Artificial Sequence
<220> FEATURE:
<223> OTHER INFORMATION: Synthetic Polypeptide

<400> SEQUENCE: 47

Met Lys Ile Glu Glu Gly Lys Leu Val Ile Trp Ile Asn Gly Asp Lys
1               5                   10                  15

Gly Tyr Asn Gly Leu Ala Glu Val Gly Lys Lys Phe Glu Lys Asp Thr
            20                  25                  30

Gly Ile Lys Val Thr Val Glu His Pro Asp Lys Leu Glu Glu Lys Phe
        35                  40                  45

Pro Gln Val Ala Ala Thr Gly Asp Gly Pro Asp Ile Ile Phe Trp Ala
    50                  55                  60

His Asp Arg Phe Gly Gly Tyr Ala Gln Ser Gly Leu Leu Ala Glu Ile
65                  70                  75                  80

Thr Pro Asp Lys Ala Phe Gln Asp Lys Leu Tyr Pro Phe Thr Trp Asp
                85                  90                  95

Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
        115                 120                 125

Thr Trp Glu Glu Ile Pro Ala Leu Asp Lys Glu Leu Lys Ala Lys Gly
    130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
            180                 185                 190

Leu Thr Phe Leu Val Asp Leu Ile Lys Asn Lys His Met Asn Ala Asp
        195                 200                 205

Thr Asp Tyr Ser Ile Ala Glu Ala Ala Phe Asn Lys Gly Glu Thr Ala
    210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
```

```
                    260                 265                 270
Asn Lys Glu Leu Ala Lys Glu Phe Leu Glu Asn Tyr Leu Leu Thr Asp
            275                 280                 285
Glu Gly Leu Glu Ala Val Asn Lys Asp Lys Pro Leu Gly Ala Val Ala
            290                 295                 300
Leu Lys Ser Tyr Glu Glu Leu Ala Lys Asp Pro Arg Ile Ala Ala
305                 310                 315                 320
Thr Met Glu Asn Ala Gln Lys Gly Glu Ile Met Pro Asn Ile Pro Gln
                    325                 330                 335
Met Ser Ala Phe Trp Tyr Ala Val Arg Thr Ala Val Ile Asn Ala Ala
            340                 345                 350
Ser Gly Arg Gln Thr Val Asp Glu Ala Leu Lys Asp Ala Gln Thr Arg
            355                 360                 365
Ile Thr Lys
    370

<210> SEQ ID NO 48
<211> LENGTH: 707
<212> TYPE: PRT
<213> ORGANISM: Artificial Sequence
<220> FEATURE:
<223> OTHER INFORMATION: Synthetic Polypeptide

<400> SEQUENCE: 48

Met Lys Phe Gly Asn Phe Leu Leu Thr Tyr Gln Pro Pro Gln Phe Ser
1               5                   10                  15
Gln Thr Glu Val Met Lys Arg Leu Val Lys Leu Gly Arg Ile Ser Glu
            20                  25                  30
Glu Cys Gly Phe Asp Thr Val Trp Leu Leu Glu His His Phe Thr Glu
        35                  40                  45
Phe Gly Leu Leu Gly Asn Pro Tyr Val Ala Ala Tyr Leu Leu Gly
    50                  55                  60
Ala Thr Lys Lys Leu Asn Val Gly Thr Ala Ala Ile Val Leu Pro Thr
65                  70                  75                  80
Ala His Pro Val Arg Gln Leu Glu Asp Val Asn Leu Leu Asp Gln Met
                85                  90                  95
Ser Lys Gly Arg Phe Arg Phe Gly Ile Cys Arg Gly Leu Tyr Asn Lys
            100                 105                 110
Asp Phe Arg Val Phe Gly Thr Asp Met Asn Asn Ser Arg Ala Leu Ala
        115                 120                 125
Glu Cys Trp Tyr Gly Leu Ile Lys Asn Gly Met Thr Glu Gly Tyr Met
    130                 135                 140
Glu Ala Asp Asn Glu His Ile Lys Phe His Lys Val Lys Val Asn Pro
145                 150                 155                 160
Ala Ala Tyr Ser Arg Gly Gly Ala Pro Val Tyr Val Ala Glu Ser
                165                 170                 175
Ala Ser Thr Thr Glu Trp Ala Ala Gln Phe Gly Leu Pro Met Ile Leu
            180                 185                 190
Ser Trp Ile Ile Asn Thr Asn Glu Lys Lys Ala Gln Leu Glu Leu Tyr
        195                 200                 205
Asn Glu Val Ala Gln Glu Tyr Gly His Asp Ile His Asn Ile Asp His
    210                 215                 220
Cys Leu Ser Tyr Ile Thr Ser Val Asp His Asp Ser Ile Lys Ala Lys
225                 230                 235                 240
Glu Ile Cys Arg Lys Phe Leu Gly His Trp Tyr Asp Ser Tyr Val Asn
```

```
                        245                 250                 255
Ala Thr Thr Ile Phe Asp Asp Ser Asp Gln Thr Arg Gly Tyr Asp Phe
                260                 265                 270

Asn Lys Gly Gln Trp Arg Asp Phe Val Leu Lys Gly His Lys Asp Thr
            275                 280                 285

Asn Arg Arg Ile Asp Tyr Ser Tyr Glu Ile Asn Pro Val Gly Thr Pro
290                 295                 300

Gln Glu Cys Ile Asp Ile Ile Gln Lys Asp Ile Asp Ala Thr Gly Ile
305                 310                 315                 320

Ser Asn Ile Cys Cys Gly Phe Glu Ala Asn Gly Thr Val Asp Glu Ile
                325                 330                 335

Ile Ala Ser Met Lys Leu Phe Gln Ser Asp Val Met Pro Phe Leu Lys
                340                 345                 350

Glu Lys Gln Arg Ser Leu Leu Tyr Tyr Gly Gly Gly Ser Gly Gly
            355                 360                 365

Gly Gly Ser Gly Gly Gly Ser Gly Gly Gly Ser Lys Phe Gly
            370                 375                 380

Leu Phe Phe Leu Asn Phe Ile Asn Ser Thr Thr Val Gln Glu Gln Ser
385                 390                 395                 400

Ile Val Arg Met Gln Glu Ile Thr Glu Tyr Val Asp Lys Leu Asn Phe
                405                 410                 415

Glu Gln Ile Leu Val Tyr Glu Asn His Phe Ser Asp Asn Gly Val Val
                420                 425                 430

Gly Ala Pro Leu Thr Val Ser Gly Phe Leu Leu Gly Leu Thr Glu Lys
                435                 440                 445

Ile Lys Ile Gly Ser Leu Asn His Ile Ile Thr Thr His His Pro Val
450                 455                 460

Arg Ile Ala Glu Glu Ala Cys Leu Leu Asp Gln Leu Ser Glu Gly Arg
465                 470                 475                 480

Phe Ile Leu Gly Phe Ser Asp Cys Glu Lys Lys Asp Glu Met His Phe
                485                 490                 495

Phe Asn Arg Pro Val Glu Tyr Gln Gln Gln Leu Phe Glu Glu Cys Tyr
            500                 505                 510

Glu Ile Ile Asn Asp Ala Leu Thr Thr Gly Tyr Cys Asn Pro Asp Asn
            515                 520                 525

Asp Phe Tyr Ser Phe Pro Lys Ile Ser Val Asn Pro His Ala Tyr Thr
            530                 535                 540

Pro Gly Gly Pro Arg Lys Tyr Val Thr Ala Thr Ser His His Ile Val
545                 550                 555                 560

Glu Trp Ala Ala Lys Lys Gly Ile Pro Leu Ile Phe Lys Trp Asp Asp
                565                 570                 575

Ser Asn Asp Val Arg Tyr Glu Tyr Ala Glu Arg Tyr Lys Ala Val Ala
            580                 585                 590

Asp Lys Tyr Asp Val Asp Leu Ser Glu Ile Asp His Gln Leu Met Ile
            595                 600                 605

Leu Val Asn Tyr Asn Glu Asp Ser Asn Lys Ala Lys Gln Glu Thr Arg
            610                 615                 620

Ala Phe Ile Ser Asp Tyr Val Leu Glu Met His Pro Asn Glu Asn Phe
625                 630                 635                 640

Glu Asn Lys Leu Glu Glu Ile Ile Ala Glu Asn Ala Val Gly Asn Tyr
                645                 650                 655

Thr Glu Cys Ile Thr Ala Ala Lys Leu Ala Ile Glu Lys Cys Gly Ala
                660                 665                 670
```

```
Lys Ser Val Leu Leu Ser Phe Glu Pro Met Asn Asp Leu Met Ser Gln
        675                 680                 685

Lys Asn Val Ile Asn Ile Val Asp Asp Asn Ile Lys Lys Tyr His Thr
        690                 695                 700

Glu Tyr Thr
705

<210> SEQ ID NO 49
<211> LENGTH: 263
<212> TYPE: PRT
<213> ORGANISM: Artificial Sequence
<220> FEATURE:
<223> OTHER INFORMATION: Synthetic Polypeptide

<400> SEQUENCE: 49

Met Arg Glu Ala Val Ile Ala Glu Val Ser Thr Gln Leu Ser Glu Val
1               5                   10                  15

Val Gly Val Ile Glu Arg His Leu Glu Pro Thr Leu Leu Ala Val His
            20                  25                  30

Leu Tyr Gly Ser Ala Val Asp Gly Gly Leu Lys Pro His Ser Asp Ile
        35                  40                  45

Asp Leu Leu Val Thr Val Thr Val Arg Leu Asp Glu Thr Thr Arg Arg
    50                  55                  60

Ala Leu Ile Asn Asp Leu Leu Glu Thr Ser Ala Ser Pro Gly Glu Ser
65                  70                  75                  80

Glu Ile Leu Arg Ala Val Glu Val Thr Ile Val Val His Asp Asp Ile
                85                  90                  95

Ile Pro Trp Arg Tyr Pro Ala Lys Arg Glu Leu Gln Phe Gly Glu Trp
            100                 105                 110

Gln Arg Asn Asp Ile Leu Ala Gly Ile Phe Glu Pro Ala Thr Ile Asp
        115                 120                 125

Ile Asp Leu Ala Ile Leu Leu Thr Lys Ala Arg Glu His Ser Val Ala
    130                 135                 140

Leu Val Gly Pro Ala Ala Glu Glu Leu Phe Asp Pro Val Pro Glu Gln
145                 150                 155                 160

Asp Leu Phe Glu Ala Leu Asn Glu Thr Leu Thr Leu Trp Asn Ser Pro
                165                 170                 175

Pro Asp Trp Ala Gly Asp Glu Arg Asn Val Val Leu Thr Leu Ser Arg
            180                 185                 190

Ile Trp Tyr Ser Ala Val Thr Gly Lys Ile Ala Pro Lys Asp Val Ala
        195                 200                 205

Ala Asp Trp Ala Met Glu Arg Leu Pro Ala Gln Tyr Gln Pro Val Ile
    210                 215                 220

Leu Glu Ala Arg Gln Ala Tyr Leu Gly Gln Glu Asp Arg Leu Ala
225                 230                 235                 240

Ser Arg Ala Asp Gln Leu Glu Glu Phe Val His Tyr Val Lys Gly Glu
                245                 250                 255

Ile Thr Lys Val Val Gly Lys
            260

<210> SEQ ID NO 50
<211> LENGTH: 785
<212> TYPE: PRT
<213> ORGANISM: Artificial Sequence
<220> FEATURE:
<223> OTHER INFORMATION: Synthetic Polypeptide
```

```
<400> SEQUENCE: 50

Met Val Lys Arg Glu Phe Pro Pro Gly Phe Trp Lys Asp Asp Leu Ile
1               5                   10                  15

Asp Ser Leu Thr Ser Ser His Lys Val Ala Ser Asp Glu Lys Arg
            20                  25                  30

Ile Glu Thr Leu Ile Ser Glu Ile Lys Asn Met Phe Arg Cys Met Gly
            35                  40                  45

Tyr Gly Glu Thr Asn Pro Ser Ala Tyr Asp Thr Ala Trp Val Ala Arg
    50                  55                  60

Ile Pro Ala Val Asp Gly Ser Asp Asn Pro His Phe Pro Glu Thr Val
65              70                  75                  80

Glu Trp Ile Leu Gln Asn Gln Leu Lys Asp Gly Ser Trp Gly Glu Gly
                85                  90                  95

Phe Tyr Phe Leu Ala Tyr Asp Arg Ile Leu Ala Thr Leu Ala Cys Ile
                100                 105                 110

Ile Thr Leu Thr Leu Trp Arg Thr Gly Glu Thr Gln Val Gln Lys Gly
            115                 120                 125

Ile Glu Phe Phe Arg Thr Gln Ala Gly Lys Met Glu Asp Glu Ala Asp
130                 135                 140

Ser His Arg Pro Ser Gly Phe Glu Ile Val Phe Pro Ala Met Leu Lys
145                 150                 155                 160

Glu Ala Lys Ile Leu Gly Leu Asp Leu Pro Tyr Asp Leu Pro Phe Leu
                165                 170                 175

Lys Gln Ile Ile Glu Lys Arg Glu Ala Lys Leu Lys Arg Ile Pro Thr
                180                 185                 190

Asp Val Leu Tyr Ala Leu Pro Thr Thr Leu Leu Tyr Ser Leu Glu Gly
            195                 200                 205

Leu Gln Glu Ile Val Asp Trp Gln Lys Ile Met Lys Leu Gln Ser Lys
210                 215                 220

Asp Gly Ser Phe Leu Ser Ser Pro Ala Ser Thr Ala Ala Val Phe Met
225                 230                 235                 240

Arg Thr Gly Asn Lys Lys Cys Leu Asp Phe Leu Asn Phe Val Leu Lys
                245                 250                 255

Lys Phe Gly Asn His Val Pro Cys His Tyr Pro Leu Asp Leu Phe Glu
                260                 265                 270

Arg Leu Trp Ala Val Asp Thr Val Glu Arg Leu Gly Ile Asp Arg His
            275                 280                 285

Phe Lys Glu Glu Ile Lys Glu Ala Leu Asp Tyr Val Tyr Ser His Trp
290                 295                 300

Asp Glu Arg Gly Ile Gly Trp Ala Arg Glu Asn Pro Val Pro Asp Ile
305                 310                 315                 320

Asp Asp Thr Ala Met Gly Leu Arg Ile Leu Arg Leu His Gly Tyr Asn
                325                 330                 335

Val Ser Ser Asp Val Leu Lys Thr Phe Arg Asp Glu Asn Gly Glu Phe
                340                 345                 350

Phe Cys Phe Leu Gly Gln Thr Gln Arg Gly Val Thr Asp Met Leu Asn
            355                 360                 365

Val Asn Arg Cys Ser His Val Ser Phe Pro Gly Glu Thr Ile Met Glu
370                 375                 380

Glu Ala Lys Leu Cys Thr Glu Arg Tyr Leu Arg Asn Ala Leu Glu Asn
385                 390                 395                 400

Val Asp Ala Phe Asp Lys Trp Ala Phe Lys Lys Asn Ile Arg Gly Glu
                405                 410                 415
```

Val Glu Tyr Ala Leu Lys Tyr Pro Trp His Lys Ser Met Pro Arg Leu
                420                 425                 430

Glu Ala Arg Ser Tyr Ile Glu Asn Tyr Gly Pro Asp Val Trp Leu
            435                 440                 445

Gly Lys Thr Val Tyr Met Met Pro Tyr Ile Ser Asn Glu Lys Tyr Leu
        450                 455                 460

Glu Leu Ala Lys Leu Asp Phe Asn Lys Val Gln Ser Ile His Gln Thr
465                 470                 475                 480

Glu Leu Gln Asp Leu Arg Arg Trp Trp Lys Ser Ser Gly Phe Thr Asp
                485                 490                 495

Leu Asn Phe Thr Arg Glu Arg Val Thr Glu Ile Tyr Phe Ser Pro Ala
                500                 505                 510

Ser Phe Ile Phe Glu Pro Glu Phe Ser Lys Cys Arg Glu Val Tyr Thr
            515                 520                 525

Lys Thr Ser Asn Phe Thr Val Ile Leu Asp Asp Leu Tyr Asp Ala His
    530                 535                 540

Gly Ser Leu Asp Asp Leu Lys Leu Phe Thr Glu Ser Val Lys Arg Trp
545                 550                 555                 560

Asp Leu Ser Leu Val Asp Gln Met Pro Gln Gln Met Lys Ile Cys Phe
                565                 570                 575

Val Gly Phe Tyr Asn Thr Phe Asn Asp Ile Ala Lys Glu Gly Arg Glu
                580                 585                 590

Arg Gln Gly Arg Asp Val Leu Gly Tyr Ile Gln Asn Val Trp Lys Val
            595                 600                 605

Gln Leu Glu Ala Tyr Thr Lys Glu Ala Glu Trp Ser Glu Ala Lys Tyr
        610                 615                 620

Val Pro Ser Phe Asn Glu Tyr Ile Glu Asn Ala Ser Val Ser Ile Ala
625                 630                 635                 640

Leu Gly Thr Val Val Leu Ile Ser Ala Leu Phe Thr Gly Glu Val Leu
                645                 650                 655

Thr Asp Glu Val Leu Ser Lys Ile Asp Arg Glu Ser Arg Phe Leu Gln
                660                 665                 670

Leu Met Gly Leu Thr Gly Arg Leu Val Asn Asp Thr Lys Thr Tyr Gln
            675                 680                 685

Ala Glu Arg Gly Gln Gly Glu Val Ala Ser Ala Ile Gln Cys Tyr Met
        690                 695                 700

Lys Asp His Pro Lys Ile Ser Glu Glu Glu Ala Leu Gln His Val Tyr
705                 710                 715                 720

Ser Val Met Glu Asn Ala Leu Glu Glu Leu Asn Arg Glu Phe Val Asn
                725                 730                 735

Asn Lys Ile Pro Asp Ile Tyr Lys Arg Leu Val Phe Glu Thr Ala Arg
                740                 745                 750

Ile Met Gln Leu Phe Tyr Met Gln Gly Asp Gly Leu Thr Leu Ser His
            755                 760                 765

Asp Met Glu Ile Lys Glu His Val Lys Asn Cys Leu Phe Gln Pro Val
        770                 775                 780

Ala
785

<210> SEQ ID NO 51
<211> LENGTH: 296
<212> TYPE: PRT
<213> ORGANISM: Artificial Sequence
<220> FEATURE:

<223> OTHER INFORMATION: Synthetic Polypeptide

<400> SEQUENCE: 51

Met Phe Asp Phe Asn Glu Tyr Met Lys Ser Lys Ala Val Ala Val Asp
1               5                   10                  15

Ala Ala Leu Asp Lys Ala Ile Pro Leu Glu Tyr Pro Glu Lys Ile His
            20                  25                  30

Glu Ser Met Arg Tyr Ser Leu Leu Ala Gly Gly Lys Arg Val Arg Pro
        35                  40                  45

Ala Leu Cys Ile Ala Ala Cys Glu Leu Val Gly Gly Ser Gln Asp Leu
    50                  55                  60

Ala Met Pro Thr Ala Cys Ala Met Glu Met Ile His Thr Met Ser Leu
65                  70                  75                  80

Ile His Asp Asp Leu Pro Cys Met Asp Asn Asp Asp Phe Arg Arg Gly
                85                  90                  95

Lys Pro Thr Asn His Lys Val Phe Gly Glu Asp Thr Ala Val Leu Ala
            100                 105                 110

Gly Asp Ala Leu Leu Ser Phe Ala Phe Glu His Ile Ala Val Ala Thr
        115                 120                 125

Ser Lys Thr Val Pro Ser Asp Arg Thr Leu Arg Val Ile Ser Glu Leu
    130                 135                 140

Gly Lys Thr Ile Gly Ser Gln Gly Leu Val Gly Gln Val Val Asp
145                 150                 155                 160

Ile Thr Ser Glu Gly Asp Ala Asn Val Asp Leu Lys Thr Leu Glu Trp
                165                 170                 175

Ile His Ile His Lys Thr Ala Val Leu Leu Glu Cys Ser Val Val Ser
            180                 185                 190

Gly Gly Ile Leu Gly Gly Ala Thr Glu Asp Glu Ile Ala Arg Ile Arg
        195                 200                 205

Arg Tyr Ala Arg Cys Val Gly Leu Leu Phe Gln Val Val Asp Asp Ile
    210                 215                 220

Leu Asp Val Thr Lys Ser Ser Glu Glu Leu Gly Lys Thr Ala Gly Lys
225                 230                 235                 240

Asp Leu Leu Thr Asp Lys Ala Thr Tyr Pro Lys Leu Met Gly Leu Glu
                245                 250                 255

Lys Ala Lys Glu Phe Ala Ala Glu Leu Ala Thr Arg Ala Lys Glu Glu
            260                 265                 270

Leu Ser Ser Phe Asp Gln Ile Lys Ala Ala Pro Leu Leu Gly Leu Ala
        275                 280                 285

Asp Tyr Ile Ala Phe Arg Gln Asn
    290                 295

<210> SEQ ID NO 52
<211> LENGTH: 1049
<212> TYPE: PRT
<213> ORGANISM: Artificial Sequence
<220> FEATURE:
<223> OTHER INFORMATION: Synthetic Polypeptide

<400> SEQUENCE: 52

Met Thr Ile Lys Glu Met Pro Gln Pro Lys Thr Phe Gly Glu Leu Lys
1               5                   10                  15

Asn Leu Pro Leu Leu Asn Thr Asp Lys Pro Val Gln Ala Leu Met Lys
            20                  25                  30

Ile Ala Asp Glu Leu Gly Glu Ile Phe Lys Phe Glu Ala Pro Gly Arg
        35                  40                  45

```
Val Thr Arg Tyr Leu Ser Ser Gln Arg Leu Ile Lys Glu Ala Cys Asp
 50                  55                  60

Glu Ser Arg Phe Asp Lys Asn Leu Ser Gln Ala Leu Lys Phe Val Arg
 65                  70                  75                  80

Asp Phe Ala Gly Asp Gly Leu Phe Thr Ser Trp Thr His Glu Lys Asn
                 85                  90                  95

Trp Lys Lys Ala His Asn Ile Leu Leu Pro Ser Phe Ser Gln Gln Ala
                100                 105                 110

Met Lys Gly Tyr His Ala Met Met Val Asp Ile Ala Val Gln Leu Val
            115                 120                 125

Gln Lys Trp Glu Arg Leu Asn Ala Asp Glu His Ile Glu Val Pro Glu
        130                 135                 140

Asp Met Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Thr
                165                 170                 175

Ser Met Val Arg Ala Leu Asp Glu Ala Met Asn Lys Leu Gln Arg Ala
                180                 185                 190

Asn Pro Asp Asp Pro Ala Tyr Asp Glu Asn Lys Arg Gln Phe Gln Glu
            195                 200                 205

Asp Ile Lys Val Met Asn Asp Leu Val Asp Lys Ile Ile Ala Asp Arg
        210                 215                 220

Lys Ala Ser Gly Glu Gln Ser Asp Asp Leu Leu Thr His Met Leu Asn
225                 230                 235                 240

Gly Lys Asp Pro Glu Thr Gly Glu Pro Leu Asp Asp Glu Asn Ile Arg
                245                 250                 255

Tyr Gln Ile Ile Thr Phe Leu Ile Ala Gly His Glu Thr Thr Ser Gly
                260                 265                 270

Leu Leu Ser Phe Ala Leu Tyr Phe Leu Val Lys Asn Pro His Val Leu
            275                 280                 285

Gln Lys Ala Ala Glu Glu Ala Ala Arg Val Leu Val Asp Pro Val Pro
        290                 295                 300

Ser Tyr Lys Gln Val Lys Gln Leu Lys Tyr Val Gly Met Val Leu Asn
305                 310                 315                 320

Glu Ala Leu Arg Leu Trp Pro Thr Ala Pro Ala Phe Ser Leu Tyr Ala
                325                 330                 335

Lys Glu Asp Thr Val Leu Gly Gly Glu Tyr Pro Leu Glu Lys Gly Asp
                340                 345                 350

Glu Leu Met Val Leu Ile Pro Gln Leu His Arg Asp Lys Thr Ile Trp
            355                 360                 365

Gly Asp Asp Val Glu Glu Phe Arg Pro Glu Arg Phe Glu Asn Pro Ser
        370                 375                 380

Ala Ile Pro Gln His Ala Phe Lys Pro Phe Gly Asn Gly Gln Arg Ala
385                 390                 395                 400

Cys Ile Gly Gln Gln Phe Ala Leu His Glu Ala Thr Leu Val Leu Gly
                405                 410                 415

Met Met Leu Lys His Phe Asp Phe Glu Asp His Thr Asn Tyr Glu Leu
                420                 425                 430

Asp Ile Lys Glu Thr Leu Thr Leu Lys Pro Glu Gly Phe Val Val Lys
            435                 440                 445

Ala Lys Ser Lys Lys Ile Pro Leu Gly Gly Ile Pro Ser Pro Ser Thr
450                 455                 460
```

```
Glu Gln Ser Ala Lys Lys Val Arg Lys Lys Ala Glu Asn Ala His Asn
465                 470                 475                 480

Thr Pro Leu Leu Val Leu Tyr Gly Ser Asn Met Gly Thr Ala Glu Gly
                485                 490                 495

Thr Ala Arg Asp Leu Ala Asp Ile Ala Met Ser Lys Gly Phe Ala Pro
            500                 505                 510

Gln Val Ala Thr Leu Asp Ser His Ala Gly Asn Leu Pro Arg Glu Gly
        515                 520                 525

Ala Val Leu Ile Val Thr Ala Ser Tyr Asn Gly His Pro Pro Asp Asn
    530                 535                 540

Ala Lys Gln Phe Val Asp Trp Leu Asp Gln Ala Ser Ala Asp Glu Val
545                 550                 555                 560

Lys Gly Val Arg Tyr Ser Val Phe Gly Cys Gly Asp Lys Asn Trp Ala
                565                 570                 575

Thr Thr Tyr Gln Lys Val Pro Ala Phe Ile Asp Glu Thr Leu Ala Ala
            580                 585                 590

Lys Gly Ala Glu Asn Ile Ala Asp Arg Gly Glu Ala Asp Ala Ser Asp
        595                 600                 605

Asp Phe Glu Gly Thr Tyr Glu Glu Trp Arg Glu His Met Trp Ser Asp
    610                 615                 620

Val Ala Ala Tyr Phe Asn Leu Asp Ile Glu Asn Ser Glu Asp Asn Lys
625                 630                 635                 640

Ser Thr Leu Ser Leu Gln Phe Val Asp Ser Ala Ala Asp Met Pro Leu
                645                 650                 655

Ala Lys Met His Gly Ala Phe Ser Thr Asn Val Val Ala Ser Lys Glu
            660                 665                 670

Leu Gln Gln Pro Gly Ser Ala Arg Ser Thr Arg His Leu Glu Ile Glu
        675                 680                 685

Leu Pro Lys Glu Ala Ser Tyr Gln Glu Gly Asp His Leu Gly Val Ile
    690                 695                 700

Pro Arg Asn Tyr Glu Gly Ile Val Asn Arg Val Thr Ala Arg Phe Gly
705                 710                 715                 720

Leu Asp Ala Ser Gln Gln Ile Arg Leu Glu Ala Glu Glu Lys Leu
                725                 730                 735

Ala His Leu Pro Leu Ala Lys Thr Val Ser Val Glu Glu Leu Leu Gln
            740                 745                 750

Tyr Val Glu Leu Gln Asp Pro Val Thr Arg Thr Gln Leu Arg Ala Met
        755                 760                 765

Ala Ala Lys Thr Val Cys Pro Pro His Lys Val Glu Leu Glu Ala Leu
    770                 775                 780

Leu Glu Lys Gln Ala Tyr Lys Glu Gln Val Leu Ala Lys Arg Leu Thr
785                 790                 795                 800

Met Leu Glu Leu Leu Glu Lys Tyr Pro Ala Cys Glu Met Lys Phe Ser
                805                 810                 815

Glu Phe Ile Ala Leu Leu Pro Ser Ile Arg Pro Arg Tyr Tyr Ser Ile
            820                 825                 830

Ser Ser Ser Pro Arg Val Asp Glu Lys Gln Ala Ser Ile Thr Val Ser
        835                 840                 845

Val Val Ser Gly Glu Ala Trp Ser Gly Tyr Gly Glu Tyr Lys Gly Ile
    850                 855                 860

Ala Ser Asn Tyr Leu Ala Glu Leu Gln Glu Gly Asp Thr Ile Thr Cys
865                 870                 875                 880

Phe Ile Ser Thr Pro Gln Ser Glu Phe Thr Leu Pro Lys Asp Pro Glu
```

```
                    885                 890                 895

Thr Pro Leu Ile Met Val Gly Pro Gly Thr Gly Val Ala Pro Phe Arg
                900                 905                 910

Gly Phe Val Gln Ala Arg Lys Gln Leu Lys Glu Gln Gly Gln Ser Leu
            915                 920                 925

Gly Glu Ala His Leu Tyr Phe Gly Cys Arg Ser Pro His Glu Asp Tyr
        930                 935                 940

Leu Tyr Gln Glu Glu Leu Glu Asn Ala Gln Ser Glu Gly Ile Ile Thr
945                 950                 955                 960

Leu His Thr Ala Phe Ser Arg Met Pro Asn Gln Pro Lys Thr Tyr Val
                965                 970                 975

Gln His Val Met Glu Gln Asp Gly Lys Lys Leu Ile Glu Leu Leu Asp
            980                 985                 990

Gln Gly Ala His Phe Tyr Ile Cys  Gly Asp Gly Ser Gln  Met Ala Pro
        995                 1000                1005

Ala Val  Glu Ala Thr Leu Met  Lys Ser Tyr Ala Asp  Val His Gln
    1010                1015                1020

Val Ser  Glu Ala Asp Ala Arg  Leu Trp Leu Gln Gln  Leu Glu Glu
    1025                1030                1035

Lys Gly  Arg Tyr Ala Lys Asp  Val Trp Ala Gly
    1040                1045

<210> SEQ ID NO 53
<211> LENGTH: 142
<212> TYPE: PRT
<213> ORGANISM: Artificial Sequence
<220> FEATURE:
<223> OTHER INFORMATION: Synthetic Polypeptide

<400> SEQUENCE: 53

Ala Ala Thr Leu Glu Arg Ile Glu Lys Asn Phe Val Ile Thr Asp Pro
1               5                   10                  15

Arg Leu Pro Asp Asn Pro Ile Ile Phe Ala Ser Asp Ser Phe Leu Gln
            20                  25                  30

Leu Thr Glu Tyr Ser Arg Glu Glu Ile Leu Gly Arg Asn Cys Arg Phe
        35                  40                  45

Leu Gln Gly Pro Glu Thr Asp Arg Ala Thr Val Arg Lys Ile Arg Asp
    50                  55                  60

Ala Ile Asp Asn Gln Thr Glu Val Thr Val Gln Leu Ile Asn Tyr Thr
65                  70                  75                  80

Lys Ser Gly Lys Lys Phe Trp Asn Leu Phe His Leu Gln Pro Met Arg
                85                  90                  95

Asp Gln Lys Gly Asp Val Gln Tyr Phe Ile Gly Val Gln Leu Asp Gly
            100                 105                 110

Thr Glu His Val Arg Asp Ala Ala Glu Arg Glu Gly Val Met Leu Ile
        115                 120                 125

Lys Lys Thr Ala Glu Asn Ile Asp Glu Ala Ala Lys Glu Leu
    130                 135                 140

<210> SEQ ID NO 54
<211> LENGTH: 748
<212> TYPE: PRT
<213> ORGANISM: Artificial Sequence
<220> FEATURE:
<223> OTHER INFORMATION: Synthetic Polypeptide

<400> SEQUENCE: 54
```

```
Met Ala Ser Val Ala Gly His Ala Ser Gly Ser Pro Ala Phe Gly Thr
1               5                   10                  15
Ala Asp Leu Ser Asn Cys Glu Arg Glu Ile His Leu Ala Gly Ser
            20                  25                  30
Ile Gln Pro His Gly Ala Leu Leu Val Val Ser Glu Pro Asp His Arg
        35                  40                  45
Ile Ile Gln Ala Ser Ala Asn Ala Ala Glu Phe Leu Asn Leu Gly Ser
    50                  55                  60
Val Leu Gly Val Pro Leu Ala Glu Ile Asp Gly Asp Leu Leu Ile Lys
65                  70                  75                  80
Ile Leu Pro His Leu Asp Pro Thr Ala Glu Gly Met Pro Val Ala Val
                85                  90                  95
Arg Cys Arg Ile Gly Asn Pro Ser Thr Glu Tyr Asp Gly Leu Met His
            100                 105                 110
Arg Pro Pro Glu Gly Gly Leu Ile Ile Glu Leu Glu Arg Ala Gly Pro
        115                 120                 125
Pro Ile Asp Leu Ser Gly Thr Leu Ala Pro Ala Leu Glu Arg Ile Arg
    130                 135                 140
Thr Ala Gly Ser Leu Arg Ala Leu Cys Asp Asp Thr Ala Leu Leu Phe
145                 150                 155                 160
Gln Gln Cys Thr Gly Tyr Asp Arg Val Met Val Tyr Arg Phe Asp Glu
            165                 170                 175
Gln Gly His Gly Glu Val Phe Ser Glu Arg His Val Pro Gly Leu Glu
        180                 185                 190
Ser Tyr Phe Gly Asn Arg Tyr Pro Ser Ser Asp Ile Pro Gln Met Ala
    195                 200                 205
Arg Arg Leu Tyr Glu Arg Gln Arg Val Arg Val Leu Asp Val Ser
210                 215                 220
Tyr Gln Pro Val Pro Leu Glu Pro Arg Leu Ser Pro Leu Thr Gly Arg
225                 230                 235                 240
Asp Leu Asp Met Ser Gly Cys Phe Leu Arg Ser Met Ser Pro Ile His
            245                 250                 255
Leu Gln Tyr Leu Lys Asn Met Gly Val Arg Ala Thr Leu Val Val Ser
        260                 265                 270
Leu Val Val Gly Gly Lys Leu Trp Gly Leu Val Ala Cys His His Tyr
    275                 280                 285
Leu Pro Arg Phe Met His Phe Glu Leu Arg Ala Ile Cys Glu Leu Leu
290                 295                 300
Ala Glu Ala Ile Ala Thr Arg Ile Thr Ala Leu Glu Ser Phe Ala Gln
305                 310                 315                 320
Ser Gln Ser Glu Leu Phe Val Gln Arg Leu Glu Gln Arg Met Ile Glu
            325                 330                 335
Ala Ile Thr Arg Glu Gly Asp Trp Arg Ala Ala Ile Phe Asp Thr Ser
        340                 345                 350
Gln Ser Ile Leu Gln Pro Leu His Ala Ala Gly Cys Ala Leu Val Tyr
    355                 360                 365
Glu Asp Gln Ile Arg Thr Ile Gly Asp Val Pro Ser Thr Gln Asp Val
370                 375                 380
Arg Glu Ile Ala Gly Trp Leu Asp Arg Gln Pro Arg Ala Ala Val Thr
385                 390                 395                 400
Ser Thr Ala Ser Leu Gly Leu Asp Val Pro Glu Leu Ala His Leu Thr
            405                 410                 415
Arg Met Ala Ser Gly Val Val Ala Ala Pro Ile Ser Asp His Arg Gly
```

-continued

```
                420                 425                 430
Glu Phe Leu Met Trp Phe Arg Pro Glu Arg Val His Thr Val Thr Trp
            435                 440                 445

Gly Gly Asp Pro Lys Lys Pro Phe Thr Met Gly Asp Thr Pro Ala Asp
        450                 455                 460

Leu Ser Pro Arg Arg Ser Phe Ala Lys Trp His Gln Val Val Glu Gly
465                 470                 475                 480

Thr Ser Asp Pro Trp Thr Ala Asp Leu Ala Ala Ala Arg Thr Ile
                485                 490                 495

Gly Gln Thr Val Ala Asp Ile Val Leu Gln Phe Arg Ala Val Arg Thr
            500                 505                 510

Leu Ile Ala Arg Glu Gln Tyr Glu Gln Phe Ser Ser Gln Val His Ala
        515                 520                 525

Ser Met Gln Pro Val Leu Ile Thr Asp Ala Glu Gly Arg Ile Leu Leu
    530                 535                 540

Met Asn Asp Ser Phe Arg Asp Met Leu Pro Ala Gly Ser Pro Ser Ala
545                 550                 555                 560

Val His Leu Asp Asp Leu Ala Gly Phe Phe Val Glu Ser Asn Asp Phe
                565                 570                 575

Leu Arg Asn Val Ala Glu Leu Ile Asp His Gly Arg Gly Trp Arg Gly
            580                 585                 590

Glu Val Leu Leu Arg Gly Ala Gly Asn Arg Pro Leu Pro Leu Ala Val
        595                 600                 605

Arg Ala Asp Pro Val Thr Arg Thr Glu Asp Gln Ser Leu Gly Phe Val
    610                 615                 620

Leu Ile Phe Ser Asp Ala Thr Asp Arg Arg Thr Ala Asp Ala Ala Arg
625                 630                 635                 640

Thr Arg Phe Gln Glu Gly Ile Leu Ala Ser Ala Arg Pro Gly Val Arg
                645                 650                 655

Leu Asp Ser Lys Ser Asp Leu Leu His Glu Lys Leu Leu Ser Ala Leu
            660                 665                 670

Val Glu Asn Ala Gln Leu Ala Ala Leu Glu Ile Thr Tyr Gly Val Glu
        675                 680                 685

Thr Gly Arg Ile Ala Glu Leu Leu Glu Gly Val Arg Gln Ser Met Leu
    690                 695                 700

Arg Thr Ala Glu Val Leu Gly His Leu Val Gln His Ala Ala Arg Thr
705                 710                 715                 720

Ala Gly Ser Asp Ser Ser Ser Asn Gly Ser Gln Asn Lys Lys Glu Phe
                725                 730                 735

Asp Ser Ala Gly Ser Ala Gly Ser Ala Gly Thr Ser
            740                 745

<210> SEQ ID NO 55
<211> LENGTH: 295
<212> TYPE: PRT
<213> ORGANISM: Artificial Sequence
<220> FEATURE:
<223> OTHER INFORMATION: Synthetic Polypeptide

<400> SEQUENCE: 55

Met Gly Met Pro Thr Thr Ile Glu Arg Glu Phe Glu Glu Leu Asp Thr
1               5                   10                  15

Gln Arg Arg Trp Gln Pro Leu Tyr Leu Glu Ile Arg Asn Glu Ser His
            20                  25                  30

Asp Tyr Pro His Arg Val Ala Lys Phe Pro Glu Asn Arg Asn Arg Asn
```

```
            35                  40                  45
Arg Tyr Arg Asp Val Ser Pro Tyr Asp His Ser Arg Val Lys Leu Gln
 50                  55                  60

Asn Ala Glu Asn Asp Tyr Ile Asn Ala Ser Leu Val Asp Ile Glu Glu
 65                  70                  75                  80

Ala Gln Arg Ser Tyr Ile Leu Thr Gln Gly Pro Leu Pro Asn Thr Cys
                 85                  90                  95

Cys His Phe Trp Leu Met Val Trp Gln Gln Lys Thr Lys Ala Val Val
             100                 105                 110

Met Leu Asn Arg Ile Val Glu Lys Glu Ser Val Lys Cys Ala Gln Tyr
         115                 120                 125

Trp Pro Thr Asp Asp Gln Glu Met Leu Phe Lys Glu Thr Gly Phe Ser
     130                 135                 140

Val Lys Leu Leu Ser Glu Asp Val Lys Ser Tyr Tyr Thr Val His Leu
145                 150                 155                 160

Leu Gln Leu Glu Asn Ile Asn Ser Gly Glu Thr Arg Thr Ile Ser His
                165                 170                 175

Phe His Tyr Thr Thr Trp Pro Asp Phe Gly Val Pro Glu Ser Pro Ala
            180                 185                 190

Ser Phe Leu Asn Phe Leu Phe Lys Val Arg Glu Ser Gly Ser Leu Asn
        195                 200                 205

Pro Asp His Gly Pro Ala Val Ile His Cys Ser Ala Gly Ile Gly Arg
    210                 215                 220

Ser Gly Thr Phe Ser Leu Val Asp Thr Cys Leu Val Leu Met Glu Lys
225                 230                 235                 240

Gly Asp Asp Ile Asn Ile Lys Gln Val Leu Leu Asn Met Arg Lys Tyr
                245                 250                 255

Arg Met Gly Leu Ile Gln Thr Pro Asp Gln Leu Arg Phe Ser Tyr Met
            260                 265                 270

Ala Ile Ile Glu Gly Ala Lys Cys Ile Lys Gly Asp Ser Ser Ile Gln
        275                 280                 285

Lys Arg Trp Lys Glu Leu Ser
    290                 295

<210> SEQ ID NO 56
<211> LENGTH: 435
<212> TYPE: PRT
<213> ORGANISM: Artificial Sequence
<220> FEATURE:
<223> OTHER INFORMATION: Synthetic Polypeptide

<400> SEQUENCE: 56

Met Glu Met Glu Lys Glu Phe Glu Gln Ile Asp Lys Ser Gly Ser Trp
 1               5                  10                  15

Ala Ala Ile Tyr Gln Asp Ile Arg His Glu Ala Ser Asp Phe Pro Cys
             20                  25                  30

Arg Val Ala Lys Leu Pro Lys Asn Lys Asn Arg Asn Arg Tyr Arg Asp
         35                  40                  45

Val Ser Pro Phe Asp His Ser Arg Ile Lys Leu His Gln Glu Asp Asn
     50                  55                  60

Asp Tyr Ile Asn Ala Ser Leu Ile Lys Met Glu Ala Gln Arg Ser
65                  70                  75                  80

Tyr Ile Leu Thr Gln Gly Pro Leu Pro Asn Thr Cys Gly His Phe Trp
                 85                  90                  95

Glu Met Val Trp Glu Gln Lys Ser Arg Gly Val Val Met Leu Asn Arg
```

100                 105                 110
Val Met Glu Lys Gly Ser Leu Lys Cys Ala Gln Tyr Trp Pro Gln Lys
            115                 120                 125

Glu Glu Lys Glu Met Ile Phe Glu Asp Thr Asn Leu Lys Leu Thr Leu
            130                 135                 140

Ile Ser Glu Asp Ile Lys Ser Tyr Tyr Thr Val Arg Gln Leu Glu Leu
145                 150                 155                 160

Glu Asn Leu Thr Thr Gln Glu Thr Arg Glu Ile Leu His Phe His Tyr
            165                 170                 175

Thr Thr Trp Pro Asp Phe Gly Val Pro Glu Ser Pro Ala Ser Phe Leu
            180                 185                 190

Asn Phe Leu Phe Lys Val Arg Glu Ser Gly Ser Leu Ser Pro Glu His
            195                 200                 205

Gly Pro Val Val Val His Cys Ser Ala Gly Ile Gly Arg Ser Gly Thr
            210                 215                 220

Phe Cys Leu Ala Asp Thr Cys Leu Leu Leu Met Asp Lys Arg Lys Asp
225                 230                 235                 240

Pro Ser Ser Val Asp Ile Lys Lys Val Leu Leu Glu Met Arg Lys Phe
            245                 250                 255

Arg Met Gly Leu Ile Gln Thr Ala Asp Gln Leu Arg Phe Ser Tyr Leu
            260                 265                 270

Ala Val Ile Glu Gly Ala Lys Phe Ile Met Gly Asp Ser Ser Val Gln
            275                 280                 285

Asp Gln Trp Lys Glu Leu Ser His Glu Asp Leu Glu Pro Pro Pro Glu
            290                 295                 300

His Ile Pro Pro Pro Arg Pro Pro Lys Arg Ile Leu Glu Pro His
305                 310                 315                 320

Asn Gly Lys Cys Arg Glu Phe Phe Pro Asn His Gln Trp Val Lys Glu
            325                 330                 335

Glu Thr Gln Glu Asp Lys Asp Cys Pro Ile Lys Glu Glu Lys Gly Ser
            340                 345                 350

Pro Leu Asn Ala Ala Pro Tyr Gly Ile Glu Ser Met Ser Gln Asp Thr
            355                 360                 365

Glu Val Arg Ser Arg Val Val Gly Ser Leu Arg Gly Ala Gln Ala
            370                 375                 380

Ala Ser Pro Ala Lys Gly Glu Pro Ser Leu Pro Glu Lys Asp Glu Asp
385                 390                 395                 400

His Ala Leu Ser Tyr Trp Lys Pro Phe Leu Val Asn Met Cys Val Ala
            405                 410                 415

Thr Val Leu Thr Ala Gly Ala Tyr Leu Cys Tyr Arg Phe Leu Phe Asn
            420                 425                 430

Ser Asn Thr
        435

<210> SEQ ID NO 57
<211> LENGTH: 473
<212> TYPE: PRT
<213> ORGANISM: Artificial Sequence
<220> FEATURE:
<223> OTHER INFORMATION: Synthetic Polypeptide

<400> SEQUENCE: 57

Met Asn Ile Lys Lys Phe Ala Lys Gln Ala Thr Val Leu Thr Phe Thr
1               5                   10                  15

Thr Ala Leu Leu Ala Gly Gly Ala Thr Gln Ala Phe Ala Lys Glu Thr

-continued

```
                20                  25                  30
Asn Gln Lys Pro Tyr Lys Glu Thr Tyr Gly Ile Ser His Ile Thr Arg
                35                  40                  45
His Asp Met Leu Gln Ile Pro Glu Gln Gln Lys Asn Glu Lys Tyr Gln
                50                  55                  60
Val Pro Glu Phe Asp Ser Ser Thr Ile Lys Asn Ile Ser Ala Lys
 65                  70                  75                  80
Gly Leu Asp Val Trp Asp Ser Trp Pro Leu Gln Asn Ala Asp Gly Thr
                85                  90                  95
Val Ala Asn Tyr His Gly Tyr His Ile Val Phe Ala Leu Ala Gly Asp
                100                 105                 110
Pro Lys Asn Ala Asp Asp Thr Ser Ile Tyr Met Phe Tyr Gln Lys Val
                115                 120                 125
Gly Glu Thr Ser Ile Asp Ser Trp Lys Asn Ala Gly Arg Val Phe Lys
                130                 135                 140
Asp Ser Asp Lys Phe Asp Ala Asn Asp Ser Ile Leu Lys Asp Gln Thr
145                 150                 155                 160
Gln Glu Trp Ser Gly Ser Ala Thr Phe Thr Ser Asp Gly Lys Ile Arg
                165                 170                 175
Leu Phe Tyr Thr Asp Phe Ser Gly Lys His Tyr Gly Lys Gln Thr Leu
                180                 185                 190
Thr Thr Ala Gln Val Asn Val Ser Ala Ser Asp Ser Ser Leu Asn Ile
                195                 200                 205
Asn Gly Val Glu Asp Tyr Lys Ser Ile Phe Asp Gly Asp Gly Lys Thr
                210                 215                 220
Tyr Gln Asn Val Gln Gln Phe Ile Asp Glu Gly Asn Tyr Ser Ser Gly
225                 230                 235                 240
Asp Asn His Thr Leu Arg Asp Pro His Tyr Val Glu Asp Lys Gly His
                245                 250                 255
Lys Tyr Leu Val Phe Glu Ala Asn Thr Gly Thr Glu Asp Gly Tyr Gln
                260                 265                 270
Gly Glu Glu Ser Leu Phe Asn Lys Ala Tyr Tyr Gly Lys Ser Thr Ser
                275                 280                 285
Phe Phe Arg Gln Glu Ser Gln Lys Leu Leu Gln Ser Asp Lys Lys Arg
                290                 295                 300
Thr Ala Glu Leu Ala Asn Gly Ala Leu Gly Met Ile Glu Leu Asn Asp
305                 310                 315                 320
Asp Tyr Thr Leu Lys Lys Val Met Lys Pro Leu Ile Ala Ser Asn Thr
                325                 330                 335
Val Thr Asp Glu Ile Glu Arg Ala Asn Val Phe Lys Met Asn Gly Lys
                340                 345                 350
Trp Tyr Leu Phe Thr Asp Ser Arg Gly Ser Lys Met Thr Ile Asp Gly
                355                 360                 365
Ile Thr Ser Asn Asp Ile Tyr Met Leu Gly Tyr Val Ser Asn Ser Leu
                370                 375                 380
Thr Gly Pro Tyr Lys Pro Leu Asn Lys Thr Gly Leu Val Leu Lys Met
385                 390                 395                 400
Asp Leu Asp Pro Asn Asp Val Thr Phe Thr Tyr Ser His Phe Ala Val
                405                 410                 415
Pro Gln Ala Lys Gly Asn Asn Val Val Ile Thr Ser Tyr Met Thr Asn
                420                 425                 430
Arg Gly Phe Tyr Ala Asp Lys Gln Ser Thr Phe Ala Pro Ser Phe Leu
                435                 440                 445
```

Leu Asn Ile Lys Gly Lys Lys Thr Ser Val Val Lys Asp Ser Ile Leu
    450                 455                 460

Glu Gln Gly Gln Leu Thr Val Asn Lys
465                 470

<210> SEQ ID NO 58
<211> LENGTH: 382
<212> TYPE: PRT
<213> ORGANISM: Artificial Sequence
<220> FEATURE:
<223> OTHER INFORMATION: Synthetic Polypeptide

<400> SEQUENCE: 58

Met Ser Leu Lys Glu Lys Thr Gln Ser Leu Phe Ala Asn Ala Phe Gly
1               5                   10                  15

Tyr Pro Ala Thr His Thr Ile Gln Ala Pro Gly Arg Val Asn Leu Ile
            20                  25                  30

Gly Glu His Thr Asp Tyr Asn Asp Gly Phe Val Leu Pro Cys Ala Ile
        35                  40                  45

Asp Tyr Gln Thr Val Ile Ser Cys Ala Pro Arg Asp Asp Arg Lys Val
    50                  55                  60

Arg Val Met Ala Ala Asp Tyr Glu Asn Gln Leu Asp Glu Phe Ser Leu
65                  70                  75                  80

Asp Ala Pro Ile Val Ala His Glu Asn Tyr Gln Trp Ala Asn Tyr Val
                85                  90                  95

Arg Gly Val Val Lys His Leu Gln Leu Arg Asn Asn Ser Phe Gly Gly
            100                 105                 110

Val Asp Met Val Ile Ser Gly Asn Val Pro Gln Gly Ala Gly Leu Ser
        115                 120                 125

Ser Ser Ala Ser Leu Glu Val Ala Val Gly Thr Val Leu Gln Gln Leu
    130                 135                 140

Tyr His Leu Pro Leu Asp Gly Ala Gln Ile Ala Leu Asn Gly Gln Glu
145                 150                 155                 160

Ala Glu Asn Gln Phe Val Gly Cys Asn Cys Gly Ile Met Asp Gln Leu
                165                 170                 175

Ile Ser Ala Leu Gly Lys Lys Asp His Ala Leu Leu Ile Asp Cys Arg
            180                 185                 190

Ser Leu Gly Thr Lys Ala Val Ser Met Pro Lys Gly Val Ala Val Val
        195                 200                 205

Ile Ile Asn Ser Asn Phe Lys Arg Thr Leu Val Gly Ser Glu Tyr Asn
    210                 215                 220

Thr Arg Arg Glu Gln Cys Glu Thr Gly Ala Arg Phe Phe Gln Gln Pro
225                 230                 235                 240

Ala Leu Arg Asp Val Thr Ile Glu Glu Phe Asn Ala Val Ala His Glu
                245                 250                 255

Leu Asp Pro Ile Val Ala Lys Arg Val Arg His Ile Leu Thr Glu Asn
            260                 265                 270

Ala Arg Thr Val Glu Ala Ala Ser Ala Leu Glu Gln Gly Asp Leu Lys
        275                 280                 285

Arg Met Gly Glu Leu Met Ala Glu Ser His Ala Ser Met Arg Asp Asp
    290                 295                 300

Phe Glu Ile Thr Val Pro Gln Ile Asp Thr Leu Val Glu Ile Val Lys
305                 310                 315                 320

Ala Val Ile Gly Asp Lys Gly Gly Val Arg Met Thr Gly Gly Gly Phe
                325                 330                 335

```
Gly Gly Cys Ile Val Ala Leu Ile Pro Glu Glu Leu Val Pro Ala Val
            340                 345                 350

Gln Gln Ala Val Ala Glu Gln Tyr Glu Ala Lys Thr Gly Ile Lys Glu
            355                 360                 365

Thr Phe Tyr Val Cys Lys Pro Ser Gln Gly Ala Gly Gln Cys
            370                 375                 380

<210> SEQ ID NO 59
<211> LENGTH: 593
<212> TYPE: PRT
<213> ORGANISM: Artificial Sequence
<220> FEATURE:
<223> OTHER INFORMATION: Synthetic Polypeptide

<400> SEQUENCE: 59

Met Ala Gln Ile Ser Glu Ser Val Ser Pro Ser Thr Asp Leu Lys Ser
1               5                   10                  15

Thr Glu Ser Ser Ile Thr Ser Asn Arg His Gly Asn Met Trp Glu Asp
            20                  25                  30

Asp Arg Ile Gln Ser Leu Asn Ser Pro Tyr Gly Ala Pro Ala Tyr Gln
        35                  40                  45

Glu Arg Ser Glu Lys Leu Ile Glu Glu Ile Lys Leu Leu Phe Leu Ser
    50                  55                  60

Asp Met Asp Asp Ser Cys Asn Asp Ser Asp Arg Asp Leu Ile Lys Arg
65                  70                  75                  80

Leu Glu Ile Val Asp Thr Val Glu Cys Leu Gly Ile Asp Arg His Phe
                85                  90                  95

Gln Pro Glu Ile Lys Leu Ala Leu Asp Tyr Val Tyr Arg Cys Trp Asn
            100                 105                 110

Glu Arg Gly Ile Gly Glu Gly Ser Arg Asp Ser Leu Lys Lys Asp Leu
        115                 120                 125

Asn Ala Thr Ala Leu Gly Phe Arg Ala Leu Arg Leu His Arg Tyr Asn
    130                 135                 140

Val Ser Ser Gly Val Leu Glu Asn Phe Arg Asp Asp Asn Gly Gln Phe
145                 150                 155                 160

Phe Cys Gly Ser Thr Val Glu Glu Glu Gly Ala Glu Ala Tyr Asn Lys
                165                 170                 175

His Val Arg Cys Met Leu Ser Leu Ser Arg Ala Ser Asn Ile Leu Phe
            180                 185                 190

Pro Gly Glu Lys Val Met Glu Glu Ala Lys Ala Phe Thr Thr Asn Tyr
        195                 200                 205

Leu Lys Lys Val Leu Ala Gly Arg Glu Ala Thr His Val Asp Glu Ser
    210                 215                 220

Leu Leu Gly Glu Val Lys Tyr Ala Leu Glu Phe Pro Trp His Cys Ser
225                 230                 235                 240

Val Gln Arg Trp Glu Ala Arg Ser Phe Ile Glu Ile Phe Gly Gln Ile
                245                 250                 255

Asp Ser Glu Leu Lys Ser Asn Leu Ser Lys Lys Met Leu Glu Leu Ala
            260                 265                 270

Lys Leu Asp Phe Asn Ile Leu Gln Cys Thr His Gln Lys Glu Leu Gln
        275                 280                 285

Ile Ile Ser Arg Trp Phe Ala Asp Ser Ser Ile Ala Ser Leu Asn Phe
    290                 295                 300

Tyr Arg Lys Cys Tyr Val Glu Phe Tyr Phe Trp Met Ala Ala Ala Ile
305                 310                 315                 320
```

```
Ser Glu Pro Glu Phe Ser Gly Ser Arg Val Ala Phe Thr Lys Ile Ala
                325                 330                 335

Ile Leu Met Thr Met Leu Asp Asp Leu Tyr Asp Thr His Gly Thr Leu
            340                 345                 350

Asp Gln Leu Lys Ile Phe Thr Glu Gly Val Arg Arg Trp Asp Val Ser
        355                 360                 365

Leu Val Glu Gly Leu Pro Asp Phe Met Lys Ile Ala Phe Glu Phe Trp
370                 375                 380

Leu Lys Thr Ser Asn Glu Leu Ile Ala Glu Ala Val Lys Ala Gln Gly
385                 390                 395                 400

Gln Asp Met Ala Ala Tyr Ile Arg Lys Asn Ala Trp Glu Arg Tyr Leu
                405                 410                 415

Glu Ala Tyr Leu Gln Asp Ala Glu Trp Ile Ala Thr Gly His Val Pro
            420                 425                 430

Thr Phe Asp Glu Tyr Leu Asn Asn Gly Thr Pro Asn Thr Gly Met Cys
        435                 440                 445

Val Leu Asn Leu Ile Pro Leu Leu Met Gly Glu His Leu Pro Ile
450                 455                 460

Asp Ile Leu Glu Gln Ile Phe Leu Pro Ser Arg Phe His Leu Ile
465                 470                 475                 480

Glu Leu Ala Ser Arg Leu Val Asp Asp Ala Arg Asp Phe Gln Ala Glu
                485                 490                 495

Lys Asp His Gly Asp Leu Ser Cys Ile Glu Cys Tyr Leu Lys Asp His
            500                 505                 510

Pro Glu Ser Thr Val Glu Asp Ala Leu Asn His Val Asn Gly Leu Leu
        515                 520                 525

Gly Asn Cys Leu Leu Glu Met Asn Trp Lys Phe Leu Lys Lys Gln Asp
530                 535                 540

Ser Val Pro Leu Ser Cys Lys Lys Tyr Ser Phe His Val Leu Ala Arg
545                 550                 555                 560

Ser Ile Gln Phe Met Tyr Asn Gln Gly Asp Gly Phe Ser Ile Ser Asn
                565                 570                 575

Lys Val Ile Lys Asp Gln Val Gln Lys Val Leu Ile Val Pro Val Pro
            580                 585                 590

Ile

<210> SEQ ID NO 60
<211> LENGTH: 546
<212> TYPE: PRT
<213> ORGANISM: Artificial Sequence
<220> FEATURE:
<223> OTHER INFORMATION: Synthetic Polypeptide

<400> SEQUENCE: 60

Met Ala Leu Thr Glu Glu Lys Pro Ile Arg Pro Ile Ala Asn Phe Pro
1               5                   10                  15

Pro Ser Ile Trp Gly Asp Gln Phe Leu Ile Tyr Glu Lys Gln Val Glu
                20                  25                  30

Gln Gly Val Glu Gln Ile Val Asn Asp Leu Lys Lys Glu Val Arg Gln
            35                  40                  45

Leu Leu Lys Glu Ala Leu Asp Ile Pro Met Lys His Ala Asn Leu Leu
50                  55                  60

Lys Leu Ile Asp Glu Ile Gln Arg Leu Gly Ile Pro Tyr His Phe Glu
65                  70                  75                  80
```

-continued

```
Arg Glu Ile Asp His Ala Leu Gln Cys Ile Tyr Glu Thr Tyr Gly Asp
                 85                  90                  95
Asn Trp Asn Gly Asp Arg Ser Ser Leu Trp Phe Arg Leu Met Arg Lys
            100                 105                 110
Gln Gly Tyr Tyr Val Thr Cys Asp Val Phe Asn Asn Tyr Lys Asp Lys
            115                 120                 125
Asn Gly Ala Phe Lys Gln Ser Leu Ala Asn Asp Val Glu Gly Leu Leu
            130                 135                 140
Glu Leu Tyr Glu Ala Thr Ser Met Arg Val Pro Gly Glu Ile Ile Leu
145                 150                 155                 160
Glu Asp Ala Leu Gly Phe Thr Arg Ser Arg Leu Ser Ile Met Thr Lys
                165                 170                 175
Asp Ala Phe Ser Thr Asn Pro Ala Leu Phe Thr Glu Ile Gln Arg Ala
                180                 185                 190
Leu Lys Gln Pro Leu Trp Lys Arg Leu Pro Arg Ile Glu Ala Ala Gln
                195                 200                 205
Tyr Ile Pro Phe Tyr Gln Gln Asp Ser His Asn Lys Thr Leu Leu
            210                 215                 220
Lys Leu Ala Lys Leu Glu Phe Asn Leu Leu Gln Ser Leu His Lys Glu
225                 230                 235                 240
Glu Leu Ser His Val Cys Lys Trp Trp Lys Ala Phe Asp Ile Lys Lys
                245                 250                 255
Asn Ala Pro Cys Leu Arg Asp Arg Ile Val Glu Cys Tyr Phe Trp Gly
                260                 265                 270
Leu Gly Ser Gly Tyr Glu Pro Gln Tyr Ser Arg Ala Arg Val Phe Phe
            275                 280                 285
Thr Lys Ala Val Ala Val Ile Thr Leu Ile Asp Asp Thr Tyr Asp Ala
290                 295                 300
Tyr Gly Thr Tyr Glu Glu Leu Lys Ile Phe Thr Glu Ala Val Glu Arg
305                 310                 315                 320
Trp Ser Ile Thr Cys Leu Asp Thr Leu Pro Glu Tyr Met Lys Pro Ile
                325                 330                 335
Tyr Lys Leu Phe Met Asp Thr Tyr Thr Glu Met Glu Glu Phe Leu Ala
            340                 345                 350
Lys Glu Gly Arg Thr Asp Leu Phe Asn Cys Gly Lys Glu Phe Val Lys
            355                 360                 365
Glu Phe Val Arg Asn Leu Met Val Glu Ala Lys Trp Ala Asn Glu Gly
            370                 375                 380
His Ile Pro Thr Thr Glu Glu His Asp Pro Val Val Ile Ile Thr Gly
385                 390                 395                 400
Gly Ala Asn Leu Leu Thr Thr Thr Cys Tyr Leu Gly Met Ser Asp Ile
                405                 410                 415
Phe Thr Lys Glu Ser Val Glu Trp Ala Val Ser Ala Pro Leu Phe
            420                 425                 430
Arg Tyr Ser Gly Ile Leu Gly Arg Arg Leu Asn Asp Leu Met Thr His
            435                 440                 445
Lys Ala Glu Gln Glu Arg Lys His Ser Ser Ser Leu Glu Ser Tyr
450                 455                 460
Met Lys Glu Tyr Asn Val Asn Glu Glu Tyr Ala Gln Thr Leu Ile Tyr
465                 470                 475                 480
Lys Glu Val Glu Asp Val Trp Lys Asp Ile Asn Arg Glu Tyr Leu Thr
                485                 490                 495
Thr Lys Asn Ile Pro Arg Pro Leu Leu Met Ala Val Ile Tyr Leu Cys
```

```
                    500                 505                 510
Gln Phe Leu Glu Val Gln Tyr Ala Gly Lys Asp Asn Phe Thr Arg Met
            515                 520                 525

Gly Asp Glu Tyr Lys His Leu Ile Lys Ser Leu Leu Val Tyr Pro Met
        530                 535                 540

Ser Ile
545

<210> SEQ ID NO 61
<211> LENGTH: 802
<212> TYPE: PRT
<213> ORGANISM: Artificial Sequence
<220> FEATURE:
<223> OTHER INFORMATION: Synthetic Polypeptide

<400> SEQUENCE: 61

Met Ser Ser Ser Thr Gly Thr Ser Lys Val Val Ser Glu Thr Ser Ser
1               5                   10                  15

Thr Ile Val Asp Asp Ile Pro Arg Leu Ser Ala Asn Tyr His Gly Asp
            20                  25                  30

Leu Trp His His Asn Val Ile Gln Thr Leu Glu Thr Pro Phe Arg Glu
        35                  40                  45

Ser Ser Thr Tyr Gln Glu Arg Ala Asp Glu Leu Val Val Lys Ile Lys
    50                  55                  60

Asp Met Phe Asn Ala Leu Gly Asp Gly Asp Ile Ser Pro Ser Ala Tyr
65                  70                  75                  80

Asp Thr Ala Trp Val Ala Arg Leu Ala Thr Ile Ser Ser Asp Gly Ser
                85                  90                  95

Glu Lys Pro Arg Phe Pro Gln Ala Leu Asn Trp Val Phe Asn Asn Gln
            100                 105                 110

Leu Gln Asp Gly Ser Trp Gly Ile Glu Ser His Phe Ser Leu Cys Asp
        115                 120                 125

Arg Leu Leu Asn Thr Thr Asn Ser Val Ile Ala Leu Ser Val Trp Lys
    130                 135                 140

Thr Gly His Ser Gln Val Gln Gln Gly Ala Glu Phe Ile Ala Glu Asn
145                 150                 155                 160

Leu Arg Leu Leu Asn Glu Glu Asp Glu Leu Ser Pro Asp Phe Gln Ile
                165                 170                 175

Ile Phe Pro Ala Leu Leu Gln Lys Ala Lys Ala Leu Gly Ile Asn Leu
            180                 185                 190

Pro Tyr Asp Leu Pro Phe Ile Lys Tyr Leu Ser Thr Thr Arg Glu Ala
        195                 200                 205

Arg Leu Thr Asp Val Ser Ala Ala Ala Asp Asn Ile Pro Ala Asn Met
    210                 215                 220

Leu Asn Ala Leu Glu Gly Leu Glu Glu Val Ile Asp Trp Asn Lys Ile
225                 230                 235                 240

Met Arg Phe Gln Ser Lys Asp Gly Ser Phe Leu Ser Ser Pro Ala Ser
                245                 250                 255

Thr Ala Cys Val Leu Met Asn Thr Gly Asp Glu Lys Cys Phe Thr Phe
            260                 265                 270

Leu Asn Asn Leu Leu Asp Lys Phe Gly Gly Cys Val Pro Cys Met Tyr
        275                 280                 285

Ser Ile Asp Leu Leu Glu Arg Leu Ser Leu Val Asp Asn Ile Glu His
    290                 295                 300

Leu Gly Ile Gly Arg His Phe Lys Gln Glu Ile Lys Gly Ala Leu Asp
```

```
            305                 310                 315                 320
        Tyr Val Tyr Arg His Trp Ser Glu Arg Gly Ile Gly Trp Gly Arg Asp
                        325                 330                 335

Ser Leu Val Pro Asp Leu Asn Thr Thr Ala Leu Gly Leu Arg Thr Leu
                        340                 345                 350

Arg Met His Gly Tyr Asn Val Ser Ser Asp Val Leu Asn Asn Phe Lys
                        355                 360                 365

Asp Glu Asn Gly Arg Phe Phe Ser Ser Ala Gly Gln Thr His Val Glu
                        370                 375                 380

Leu Arg Ser Val Val Asn Leu Phe Arg Ala Ser Asp Leu Ala Phe Pro
        385                 390                 395                 400

Asp Glu Arg Ala Met Asp Asp Ala Arg Lys Phe Ala Glu Pro Tyr Leu
                        405                 410                 415

Arg Glu Ala Leu Ala Thr Lys Ile Ser Thr Asn Thr Lys Leu Phe Lys
                        420                 425                 430

Glu Ile Glu Tyr Val Val Glu Tyr Pro Trp His Met Ser Ile Pro Arg
                        435                 440                 445

Leu Glu Ala Arg Ser Tyr Ile Asp Ser Tyr Asp Asp Asn Tyr Val Trp
                        450                 455                 460

Gln Arg Lys Thr Leu Tyr Arg Met Pro Ser Leu Ser Asn Ser Lys Cys
        465                 470                 475                 480

Leu Glu Leu Ala Lys Leu Asp Phe Asn Ile Val Gln Ser Leu His Gln
                        485                 490                 495

Glu Glu Leu Lys Leu Leu Thr Arg Trp Trp Lys Glu Ser Gly Met Ala
                        500                 505                 510

Asp Ile Asn Phe Thr Arg His Arg Val Ala Glu Val Tyr Phe Ser Ser
                        515                 520                 525

Ala Thr Phe Glu Pro Glu Tyr Ser Ala Thr Arg Ile Ala Phe Thr Lys
                        530                 535                 540

Ile Gly Cys Leu Gln Val Leu Phe Asp Asp Met Ala Asp Ile Phe Ala
        545                 550                 555                 560

Thr Leu Asp Glu Leu Lys Ser Phe Thr Glu Gly Val Lys Arg Trp Asp
                        565                 570                 575

Thr Ser Leu Leu His Glu Ile Pro Glu Cys Met Gln Thr Cys Phe Lys
                        580                 585                 590

Val Trp Phe Lys Leu Met Glu Glu Val Asn Asn Asp Val Val Lys Val
                        595                 600                 605

Gln Gly Arg Asp Met Leu Ala His Ile Arg Lys Pro Trp Glu Leu Tyr
                        610                 615                 620

Phe Asn Cys Tyr Val Gln Glu Arg Glu Trp Leu Glu Ala Gly Tyr Ile
        625                 630                 635                 640

Pro Thr Phe Glu Glu Tyr Leu Lys Thr Tyr Ala Ile Ser Val Gly Leu
                        645                 650                 655

Gly Pro Cys Thr Leu Gln Pro Ile Leu Leu Met Gly Glu Leu Val Lys
                        660                 665                 670

Asp Asp Val Val Glu Lys Val His Tyr Pro Ser Asn Met Phe Glu Leu
                        675                 680                 685

Val Ser Leu Ser Trp Arg Leu Thr Asn Asp Thr Lys Thr Tyr Gln Ala
                        690                 695                 700

Glu Lys Ala Arg Gly Gln Gln Ala Ser Gly Ile Ala Cys Tyr Met Lys
        705                 710                 715                 720

Asp Asn Pro Gly Ala Thr Glu Glu Asp Ala Ile Lys His Ile Cys Arg
                        725                 730                 735
```

```
Val Val Asp Arg Ala Leu Lys Glu Ala Ser Phe Glu Tyr Phe Lys Pro
            740                 745                 750

Ser Asn Asp Ile Pro Met Gly Cys Lys Ser Phe Ile Phe Asn Leu Arg
            755                 760                 765

Leu Cys Val Gln Ile Phe Tyr Lys Phe Ile Asp Gly Tyr Gly Ile Ala
            770                 775                 780

Asn Glu Glu Ile Lys Asp Tyr Ile Arg Lys Val Tyr Ile Asp Pro Ile
785                 790                 795                 800

Gln Val

<210> SEQ ID NO 62
<211> LENGTH: 317
<212> TYPE: PRT
<213> ORGANISM: Artificial Sequence
<220> FEATURE:
<223> OTHER INFORMATION: Synthetic Polypeptide

<400> SEQUENCE: 62

Met Pro Thr Thr Ile Glu Arg Glu Phe Glu Glu Leu Asp Thr Gln Arg
1               5                   10                  15

Arg Trp Gln Pro Leu Tyr Leu Gly Ile Arg Asn Glu Ser His Asp Tyr
            20                  25                  30

Pro His Arg Val Ala Lys Phe Pro Glu Asn Arg Asn Arg Asn Arg Tyr
            35                  40                  45

Arg Asp Val Ser Pro Tyr Asp His Ser Arg Val Lys Leu Gln Asn Ala
        50                  55                  60

Glu Asn Asp Tyr Ile Asn Ala Ser Leu Val Asp Ile Glu Glu Ala Gln
65                  70                  75                  80

Arg Ser Tyr Ile Leu Thr Gln Gly Pro Leu Pro Asn Thr Cys Cys His
                85                  90                  95

Phe Trp Leu Met Val Trp Gln Gln Lys Thr Lys Ala Val Val Met Leu
            100                 105                 110

Asn Arg Ile Val Glu Lys Glu Ser Val Lys Cys Ala Gln Tyr Trp Pro
            115                 120                 125

Thr Asp Asp Gln Glu Met Leu Phe Lys Glu Thr Gly Phe Ser Val Lys
        130                 135                 140

Leu Leu Ser Glu Asp Val Lys Ser Tyr Tyr Thr Val His Leu Leu Gln
145                 150                 155                 160

Leu Glu Asn Ile Asn Ser Gly Glu Thr Arg Thr Ile Ser His Phe His
                165                 170                 175

Tyr Thr Thr Trp Pro Asp Phe Gly Val Pro Glu Ser Pro Ala Ser Phe
            180                 185                 190

Leu Asn Phe Leu Phe Lys Val Arg Glu Ser Gly Ser Leu Asn Pro Asp
            195                 200                 205

His Gly Pro Ala Val Ile His Cys Ser Ala Gly Ile Gly Arg Ser Gly
        210                 215                 220

Thr Phe Ser Leu Val Asp Thr Cys Leu Val Leu Met Glu Lys Gly Asp
225                 230                 235                 240

Asp Ile Asn Ile Lys Gln Val Leu Leu Asn Met Arg Lys Tyr Arg Met
                245                 250                 255

Gly Leu Ile Gln Thr Pro Asp Gln Leu Arg Phe Ser Tyr Met Ala Ile
            260                 265                 270

Ile Glu Gly Ala Lys Cys Ile Lys Gly Asp Ser Ser Ile Gln Lys Arg
        275                 280                 285
```

```
Trp Lys Glu Leu Ser Lys Glu Asp Leu Ser Pro Ala Phe Asp His Ser
        290                 295                 300

Pro Asn Lys Ile Met Thr Glu Lys Tyr Asn Gly Asn Arg
305                 310                 315
```

<210> SEQ ID NO 63
<211> LENGTH: 299
<212> TYPE: PRT
<213> ORGANISM: Artificial Sequence
<220> FEATURE:
<223> OTHER INFORMATION: Synthetic Polypeptide

<400> SEQUENCE: 63

```
Met Ser Ser Gly Val Asp Leu Gly Thr Glu Asn Leu Tyr Phe Gln Ser
1               5                   10                  15

Met Ser Arg Val Leu Gln Ala Glu Glu Leu His Glu Lys Ala Leu Asp
            20                  25                  30

Pro Phe Leu Leu Gln Ala Glu Phe Phe Glu Ile Pro Met Asn Phe Val
        35                  40                  45

Asp Pro Lys Glu Tyr Asp Ile Pro Gly Leu Val Arg Lys Asn Arg Tyr
    50                  55                  60

Lys Thr Ile Leu Pro Asn Pro His Ser Arg Val Cys Leu Thr Ser Pro
65                  70                  75                  80

Asp Pro Asp Asp Pro Leu Ser Ser Tyr Ile Asn Ala Asn Tyr Ile Arg
                85                  90                  95

Gly Tyr Gly Gly Glu Glu Lys Val Tyr Ile Ala Thr Gln Gly Pro Ile
            100                 105                 110

Val Ser Thr Val Ala Asp Phe Trp Arg Met Val Trp Gln Glu His Thr
        115                 120                 125

Pro Ile Ile Val Met Ile Thr Asn Ile Glu Glu Met Asn Glu Lys Cys
    130                 135                 140

Thr Glu Tyr Trp Pro Glu Glu Gln Val Ala Tyr Asp Gly Val Glu Ile
145                 150                 155                 160

Thr Val Gln Lys Val Ile His Thr Glu Asp Tyr Arg Leu Arg Leu Ile
                165                 170                 175

Ser Leu Lys Ser Gly Thr Glu Glu Arg Gly Leu Lys His Tyr Trp Phe
            180                 185                 190

Thr Ser Trp Pro Asp Gln Lys Thr Pro Asp Arg Ala Pro Pro Leu Leu
        195                 200                 205

His Leu Val Arg Glu Val Glu Glu Ala Ala Gln Gln Glu Gly Pro His
    210                 215                 220

Cys Ala Pro Ile Ile Val His Cys Ser Ala Gly Ile Gly Arg Thr Gly
225                 230                 235                 240

Cys Phe Ile Ala Thr Ser Ile Cys Cys Gln Gln Leu Arg Gln Glu Gly
                245                 250                 255

Val Val Asp Ile Leu Lys Thr Thr Cys Gln Leu Arg Gln Asp Arg Gly
            260                 265                 270

Gly Met Ile Gln Thr Cys Glu Gln Tyr Gln Phe Val His His Val Met
        275                 280                 285

Ser Leu Tyr Glu Lys Gln Leu Ser His Gln Ser
    290                 295
```

<210> SEQ ID NO 64
<211> LENGTH: 595
<212> TYPE: PRT
<213> ORGANISM: Artificial Sequence
<220> FEATURE:

<223> OTHER INFORMATION: Synthetic Polypeptide

<400> SEQUENCE: 64

```
Met Val Arg Trp Phe His Arg Asp Leu Ser Gly Leu Asp Ala Glu Thr
1               5                   10                  15

Leu Leu Lys Gly Arg Gly Val His Gly Ser Phe Leu Ala Arg Pro Ser
            20                  25                  30

Arg Lys Asn Gln Gly Asp Phe Ser Leu Ser Val Arg Val Gly Asp Gln
        35                  40                  45

Val Thr His Ile Arg Ile Gln Asn Ser Gly Asp Phe Tyr Asp Leu Tyr
    50                  55                  60

Gly Gly Glu Lys Phe Ala Thr Leu Thr Glu Leu Val Glu Tyr Tyr Thr
65                  70                  75                  80

Gln Gln Gln Gly Val Val Gln Asp Arg Asp Gly Thr Ile Ile His Leu
                85                  90                  95

Lys Tyr Pro Leu Asn Cys Ser Asp Pro Thr Ser Glu Arg Trp Tyr His
            100                 105                 110

Gly His Met Ser Gly Gly Gln Ala Glu Thr Leu Leu Gln Ala Lys Gly
        115                 120                 125

Glu Pro Trp Thr Phe Leu Val Arg Glu Ser Leu Ser Gln Pro Gly Asp
    130                 135                 140

Phe Val Leu Ser Val Leu Ser Asp Gln Pro Lys Ala Gly Pro Gly Ser
145                 150                 155                 160

Pro Leu Arg Val Thr His Ile Lys Val Met Cys Glu Gly Gly Arg Tyr
                165                 170                 175

Thr Val Gly Gly Leu Glu Thr Phe Asp Ser Leu Thr Asp Leu Val Glu
            180                 185                 190

His Phe Lys Lys Thr Gly Ile Glu Glu Ala Ser Gly Ala Phe Val Tyr
        195                 200                 205

Leu Arg Gln Pro Tyr Tyr Ala Thr Arg Val Asn Ala Ala Asp Ile Glu
    210                 215                 220

Asn Arg Val Leu Glu Leu Asn Lys Lys Gln Glu Ser Glu Asp Thr Ala
225                 230                 235                 240

Lys Ala Gly Phe Trp Glu Glu Phe Glu Ser Leu Gln Lys Gln Glu Val
                245                 250                 255

Lys Asn Leu His Gln Arg Leu Glu Gly Gln Arg Pro Glu Asn Lys Gly
            260                 265                 270

Lys Asn Arg Tyr Lys Asn Ile Leu Pro Phe Asp His Ser Arg Val Ile
        275                 280                 285

Leu Gln Gly Arg Asp Ser Asn Ile Pro Gly Ser Asp Tyr Ile Asn Ala
    290                 295                 300

Asn Tyr Ile Lys Asn Gln Leu Leu Gly Pro Asp Glu Asn Ala Lys Thr
305                 310                 315                 320

Tyr Ile Ala Ser Gln Gly Cys Leu Glu Ala Thr Val Asn Asp Phe Trp
                325                 330                 335

Gln Met Ala Trp Gln Glu Asn Ser Arg Val Ile Val Met Thr Thr Arg
            340                 345                 350

Glu Val Glu Lys Gly Arg Asn Lys Cys Val Pro Tyr Trp Pro Glu Val
        355                 360                 365

Gly Met Gln Arg Ala Tyr Gly Pro Tyr Ser Val Thr Asn Cys Gly Glu
    370                 375                 380

His Asp Thr Thr Glu Tyr Lys Leu Arg Thr Leu Gln Val Ser Pro Leu
385                 390                 395                 400
```

```
Asp Asn Gly Asp Leu Ile Arg Glu Ile Trp His Tyr Gln Tyr Leu Ser
            405                 410                 415

Trp Pro Asp His Gly Val Pro Ser Glu Pro Gly Gly Val Leu Ser Phe
            420                 425                 430

Leu Asp Gln Ile Asn Gln Arg Gln Glu Ser Leu Pro His Ala Gly Pro
            435                 440                 445

Ile Ile Val His Cys Ser Ala Gly Ile Gly Arg Thr Gly Thr Ile Ile
            450                 455                 460

Val Ile Asp Met Leu Met Glu Asn Ile Ser Thr Lys Gly Leu Asp Cys
465                 470                 475                 480

Asp Ile Asp Ile Gln Lys Thr Ile Gln Met Val Arg Ala Gln Arg Ser
            485                 490                 495

Gly Met Val Gln Thr Glu Ala Gln Tyr Lys Phe Ile Tyr Val Ala Ile
            500                 505                 510

Ala Gln Phe Ile Glu Thr Thr Lys Lys Lys Leu Glu Val Leu Gln Ser
            515                 520                 525

Gln Lys Gly Gln Glu Ser Glu Tyr Gly Asn Ile Thr Tyr Pro Pro Ala
            530                 535                 540

Met Lys Asn Ala His Ala Lys Ala Ser Arg Thr Ser Ser Lys His Lys
545                 550                 555                 560

Glu Asp Val Tyr Glu Asn Leu His Thr Lys Asn Lys Arg Glu Glu Lys
            565                 570                 575

Val Lys Lys Gln Arg Ser Ala Asp Lys Glu Lys Ser Lys Gly Ser Leu
            580                 585                 590

Lys Arg Lys
        595
```

<210> SEQ ID NO 65
<211> LENGTH: 593
<212> TYPE: PRT
<213> ORGANISM: Artificial Sequence
<220> FEATURE:
<223> OTHER INFORMATION: Synthetic Polypeptide

<400> SEQUENCE: 65

```
Met Thr Ser Arg Arg Trp Phe His Pro Asn Ile Thr Gly Val Glu Ala
1               5                   10                  15

Glu Asn Leu Leu Leu Thr Arg Gly Val Asp Gly Ser Phe Leu Ala Arg
            20                  25                  30

Pro Ser Lys Ser Asn Pro Gly Asp Phe Thr Leu Ser Val Arg Arg Asn
            35                  40                  45

Gly Ala Val Thr His Ile Lys Ile Gln Asn Thr Gly Asp Tyr Tyr Asp
        50                  55                  60

Leu Tyr Gly Gly Glu Lys Phe Ala Thr Leu Ala Glu Leu Val Gln Tyr
65                  70                  75                  80

Tyr Met Glu His His Gly Gln Leu Lys Glu Lys Asn Gly Asp Val Ile
            85                  90                  95

Glu Leu Lys Tyr Pro Leu Asn Cys Ala Asp Pro Thr Ser Glu Arg Trp
            100                 105                 110

Phe His Gly His Leu Ser Gly Lys Glu Ala Glu Lys Leu Leu Thr Glu
            115                 120                 125

Lys Gly Lys His Gly Ser Phe Leu Val Arg Glu Ser Gln Ser His Pro
            130                 135                 140

Gly Asp Phe Val Leu Ser Val Arg Thr Gly Asp Asp Lys Gly Glu Ser
145                 150                 155                 160
```

```
Asn Asp Gly Lys Ser Lys Val Thr His Val Met Ile Arg Cys Gln Glu
            165                 170                 175

Leu Lys Tyr Asp Val Gly Gly Glu Arg Phe Asp Ser Leu Thr Asp
        180                 185                 190

Leu Val Glu His Tyr Lys Lys Asn Pro Met Val Glu Thr Leu Gly Thr
        195                 200                 205

Val Leu Gln Leu Lys Gln Pro Leu Asn Thr Thr Arg Ile Asn Ala Ala
    210                 215                 220

Glu Ile Glu Ser Arg Val Arg Glu Leu Ser Lys Leu Ala Glu Thr Thr
225                 230                 235                 240

Asp Lys Val Lys Gln Gly Phe Trp Glu Glu Phe Glu Thr Leu Gln Gln
                245                 250                 255

Gln Glu Cys Lys Leu Leu Tyr Ser Arg Lys Glu Gly Gln Arg Gln Glu
            260                 265                 270

Asn Lys Asn Lys Asn Arg Tyr Lys Asn Ile Leu Pro Phe Asp His Thr
        275                 280                 285

Arg Val Val Leu His Asp Gly Asp Pro Asn Glu Pro Val Ser Asp Tyr
        290                 295                 300

Ile Asn Ala Asn Ile Ile Met Pro Glu Phe Glu Thr Lys Cys Asn Asn
305                 310                 315                 320

Ser Lys Pro Lys Lys Ser Tyr Ile Ala Thr Gln Gly Cys Leu Gln Asn
                325                 330                 335

Thr Val Asn Asp Phe Trp Arg Met Val Phe Gln Glu Asn Ser Arg Val
            340                 345                 350

Ile Val Met Thr Thr Lys Glu Val Glu Arg Gly Lys Ser Lys Cys Val
        355                 360                 365

Lys Tyr Trp Pro Asp Glu Tyr Ala Leu Lys Glu Tyr Gly Val Met Arg
        370                 375                 380

Val Arg Asn Val Lys Glu Ser Ala Ala His Asp Tyr Thr Leu Arg Glu
385                 390                 395                 400

Leu Lys Leu Ser Lys Val Gly Gln Gly Asn Thr Glu Arg Thr Val Trp
                405                 410                 415

Gln Tyr His Phe Arg Thr Trp Pro Asp His Gly Val Pro Ser Asp Pro
            420                 425                 430

Gly Gly Val Leu Asp Phe Leu Glu Glu Val His His Lys Gln Glu Ser
        435                 440                 445

Ile Met Asp Ala Gly Pro Val Val His Cys Ser Ala Gly Ile Gly
        450                 455                 460

Arg Thr Gly Thr Phe Ile Val Ile Asp Ile Leu Ile Asp Ile Ile Arg
465                 470                 475                 480

Glu Lys Gly Val Asp Cys Asp Ile Asp Val Pro Lys Thr Ile Gln Met
                485                 490                 495

Val Arg Ser Gln Arg Ser Gly Met Val Gln Thr Glu Ala Gln Tyr Arg
            500                 505                 510

Phe Ile Tyr Met Ala Val Gln His Tyr Ile Glu Thr Leu Gln Arg Arg
        515                 520                 525

Ile Glu Glu Glu Gln Lys Ser Lys Arg Lys Gly His Glu Tyr Thr Asn
        530                 535                 540

Ile Lys Tyr Ser Leu Ala Asp Gln Thr Ser Gly Asp Gln Ser Pro Leu
545                 550                 555                 560

Pro Pro Cys Thr Pro Thr Pro Cys Ala Glu Met Arg Glu Asp Ser
                565                 570                 575

Ala Arg Val Tyr Glu Asn Val Gly Leu Met Gln Gln Gln Lys Ser Phe
```

Arg

<210> SEQ ID NO 66
<211> LENGTH: 425
<212> TYPE: PRT
<213> ORGANISM: Artificial Sequence
<220> FEATURE:
<223> OTHER INFORMATION: Synthetic Polypeptide

<400> SEQUENCE: 66

```
Met Glu Gln Val Glu Ile Leu Arg Lys Phe Ile Gln Arg Val Gln Ala
1               5                   10                  15

Met Lys Ser Pro Asp His Asn Gly Glu Asp Asn Phe Ala Arg Asp Phe
            20                  25                  30

Met Arg Leu Arg Arg Leu Ser Thr Lys Tyr Arg Thr Glu Lys Ile Tyr
        35                  40                  45

Pro Thr Ala Thr Gly Glu Lys Glu Glu Asn Val Lys Lys Asn Arg Tyr
    50                  55                  60

Lys Asp Ile Leu Pro Phe Asp His Ser Arg Val Lys Leu Thr Leu Lys
65                  70                  75                  80

Thr Pro Ser Gln Asp Ser Asp Tyr Ile Asn Ala Asn Phe Ile Lys Gly
                85                  90                  95

Val Tyr Gly Pro Lys Ala Tyr Val Ala Thr Gln Gly Pro Leu Ala Asn
            100                 105                 110

Thr Val Ile Asp Phe Trp Arg Met Val Trp Glu Tyr Asn Val Val Ile
        115                 120                 125

Ile Val Met Ala Cys Arg Glu Phe Glu Met Gly Arg Lys Lys Cys Glu
    130                 135                 140

Arg Tyr Trp Pro Leu Tyr Gly Glu Asp Pro Ile Thr Phe Ala Pro Phe
145                 150                 155                 160

Lys Ile Ser Cys Glu Asp Glu Gln Ala Arg Thr Asp Tyr Phe Ile Arg
                165                 170                 175

Thr Leu Leu Leu Glu Phe Gln Asn Glu Ser Arg Arg Leu Tyr Gln Phe
            180                 185                 190

His Tyr Val Asn Trp Pro Asp His Asp Val Pro Ser Ser Phe Asp Ser
        195                 200                 205

Ile Leu Asp Met Ile Ser Leu Met Arg Lys Tyr Gln Glu His Glu Asp
    210                 215                 220

Val Pro Ile Cys Ile His Cys Ser Ala Gly Cys Gly Arg Thr Gly Ala
225                 230                 235                 240

Ile Cys Ala Ile Asp Tyr Thr Trp Asn Leu Leu Lys Ala Gly Lys Ile
                245                 250                 255

Pro Glu Glu Phe Asn Val Phe Asn Leu Ile Gln Glu Met Arg Thr Gln
            260                 265                 270

Arg His Ser Ala Val Gln Thr Lys Glu Gln Tyr Glu Leu Val His Arg
        275                 280                 285

Ala Ile Ala Gln Leu Phe Glu Lys Gln Leu Gln Leu Tyr Glu Ile His
    290                 295                 300

Gly Ala Gln Lys Ile Ala Asp Gly Val Asn Glu Ile Asn Thr Glu Asn
305                 310                 315                 320

Met Val Ser Ser Ile Glu Pro Glu Lys Gln Asp Ser Pro Pro Pro Lys
                325                 330                 335

Pro Pro Arg Thr Arg Ser Cys Leu Val Glu Gly Asp Ala Lys Glu Glu
            340                 345                 350
```

```
Ile Leu Gln Pro Pro Glu Pro His Pro Val Pro Pro Ile Leu Thr Pro
            355                 360                 365

Ser Pro Pro Ser Ala Phe Pro Thr Val Thr Thr Val Trp Gln Asp Asn
    370                 375                 380

Asp Arg Tyr His Pro Lys Pro Val Leu Gln Trp Phe His Gln Asn Asn
385                 390                 395                 400

Ile Gln Gln Thr Ser Thr Glu Thr Ile Val Asn Gln Gln Asn Phe Gln
                405                 410                 415

Gly Lys Met Asn Gln Gln Leu Asn Arg
            420                 425

<210> SEQ ID NO 67
<211> LENGTH: 299
<212> TYPE: PRT
<213> ORGANISM: Artificial Sequence
<220> FEATURE:
<223> OTHER INFORMATION: Synthetic Polypeptide

<400> SEQUENCE: 67

Met Asp Gln Arg Glu Ile Leu Gln Lys Phe Leu Asp Glu Ala Gln Ser
1               5                   10                  15

Lys Lys Ile Thr Lys Glu Glu Phe Ala Asn Glu Phe Leu Lys Leu Lys
                20                  25                  30

Arg Gln Ser Thr Lys Tyr Lys Ala Asp Lys Thr Tyr Pro Thr Thr Val
            35                  40                  45

Ala Glu Lys Pro Lys Asn Ile Lys Lys Asn Arg Tyr Lys Asp Ile Leu
    50                  55                  60

Pro Tyr Asp Tyr Ser Arg Val Glu Leu Ser Leu Ile Thr Ser Asp Glu
65                  70                  75                  80

Asp Ser Ser Tyr Ile Asn Ala Asn Phe Ile Lys Gly Val Tyr Gly Pro
                85                  90                  95

Lys Ala Tyr Ile Ala Thr Gln Gly Pro Leu Ser Thr Thr Leu Leu Asp
            100                 105                 110

Phe Trp Arg Met Ile Trp Glu Tyr Ser Val Leu Ile Ile Val Met Ala
    115                 120                 125

Cys Met Glu Tyr Glu Met Gly Lys Lys Lys Cys Glu Arg Tyr Trp Ala
130                 135                 140

Glu Pro Gly Glu Met Gln Leu Glu Phe Gly Pro Phe Ser Val Ser Cys
145                 150                 155                 160

Glu Ala Glu Lys Arg Lys Ser Asp Tyr Ile Ile Arg Thr Leu Lys Val
                165                 170                 175

Lys Phe Asn Ser Glu Thr Arg Thr Ile Tyr Gln Phe His Tyr Lys Asn
            180                 185                 190

Trp Pro Asp His Asp Val Pro Ser Ser Ile Asp Pro Ile Leu Glu Leu
    195                 200                 205

Ile Trp Asp Val Arg Cys Tyr Gln Glu Asp Asp Ser Val Pro Ile Cys
210                 215                 220

Ile His Cys Ser Ala Gly Cys Gly Arg Thr Gly Val Ile Cys Ala Ile
225                 230                 235                 240

Asp Tyr Thr Trp Met Leu Leu Lys Asp Gly Ile Ile Pro Glu Asn Phe
                245                 250                 255

Ser Val Phe Ser Leu Ile Arg Glu Met Arg Thr Gln Arg Pro Ser Leu
            260                 265                 270

Val Gln Thr Gln Glu Gln Tyr Glu Leu Val Tyr Asn Ala Val Leu Glu
    275                 280                 285
```

```
Leu Phe Lys Arg Gln Met Asp Val Ile Arg Asp
        290                 295
```

```
<210> SEQ ID NO 68
<211> LENGTH: 238
<212> TYPE: PRT
<213> ORGANISM: Artificial Sequence
<220> FEATURE:
<223> OTHER INFORMATION: Synthetic Polypeptide

<400> SEQUENCE: 68

Met Arg Lys Gly Glu Glu Leu Phe Thr Gly Val Val Pro Ile Leu Val
1               5                   10                  15

Glu Leu Asp Gly Asp Val Asn Gly His Lys Phe Ser Val Arg Gly Glu
            20                  25                  30

Gly Glu Gly Asp Ala Thr Asn Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Thr Tyr Gly Val Gln Cys Phe Ala Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Ser Phe Lys Asp Asp Gly Thr Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Phe Asn Ser His Asn Val Tyr Ile Thr Ala Asp Lys Gln Lys Asn Gly
145                 150                 155                 160

Ile Lys Ala Asn Phe Lys Ile Arg His Asn Val Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Val Leu Ser
        195                 200                 205

Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Lys
225                 230                 235
```

```
<210> SEQ ID NO 69
<211> LENGTH: 245
<212> TYPE: PRT
<213> ORGANISM: Artificial Sequence
<220> FEATURE:
<223> OTHER INFORMATION: Synthetic Polypeptide

<400> SEQUENCE: 69

Met His His His His His Val Ser Lys Gly Glu Glu Leu Phe Thr
1               5                   10                  15

Gly Val Val Pro Ile Leu Val Glu Leu Asp Gly Asp Val Asn Gly His
            20                  25                  30

Lys Phe Ser Val Arg Gly Glu Gly Glu Gly Asp Ala Thr Asn Gly Lys
        35                  40                  45

Leu Thr Leu Lys Phe Ile Cys Thr Thr Gly Lys Leu Pro Val Pro Trp
```

```
                    50                  55                  60
Pro Thr Leu Val Thr Thr Phe Gly Tyr Gly Val Ala Cys Phe Ser Arg
 65                      70                  75                  80

Tyr Pro Asp His Met Lys Gln His Asp Phe Phe Lys Ser Ala Met Pro
                     85                  90                  95

Glu Gly Tyr Val Gln Glu Arg Thr Ile Ser Phe Lys Asp Asp Gly Thr
                100                 105                 110

Tyr Lys Thr Arg Ala Glu Val Lys Phe Glu Gly Asp Thr Leu Val Asn
            115                 120                 125

Arg Ile Glu Leu Lys Gly Ile Asp Phe Lys Glu Asp Gly Asn Ile Leu
        130                 135                 140

Gly His Lys Leu Glu Tyr Asn Phe Asn Ser His Asn Val Tyr Ile Thr
145                 150                 155                 160

Ala Asp Lys Gln Lys Asn Gly Ile Lys Ala Asn Phe Lys Ile Arg His
                165                 170                 175

Asn Val Glu Asp Gly Ser Val Gln Leu Ala Asp His Tyr Gln Gln Asn
            180                 185                 190

Thr Pro Ile Gly Asp Gly Pro Val Leu Leu Pro Asp Asn His Tyr Leu
        195                 200                 205

Ser His Gln Ser Ala Leu Ser Lys Asp Pro Asn Glu Lys Arg Asp His
    210                 215                 220

Met Val Leu Leu Glu Phe Val Thr Ala Ala Gly Ile Thr His Gly Met
225                 230                 235                 240

Asp Glu Leu Tyr Lys
                245

<210> SEQ ID NO 70
<211> LENGTH: 129
<212> TYPE: DNA
<213> ORGANISM: Artificial Sequence
<220> FEATURE:
<223> OTHER INFORMATION: Synthetic Polynucleotide

<400> SEQUENCE: 70
atccggatat agttcctcct ttcagcaaaa aaccccctcaa gacccgttta gaggccccaa     60
ggggttatgc tagttattgc tcagcggtgg cagcagccaa ctcagcttcc tttcgggctt    120
tgttagcag                                                            129

<210> SEQ ID NO 71
<211> LENGTH: 426
<212> TYPE: DNA
<213> ORGANISM: Artificial Sequence
<220> FEATURE:
<223> OTHER INFORMATION: Synthetic Polynucleotide

<400> SEQUENCE: 71
ggctgttttg gcggatgaga aagattttc agcctgatac agattaaatc agaacgcaga      60
agcggtctga taaaacagaa tttgcctggc ggcagtagcg cggtggtccc acctgacccc    120
atgccgaact cagaagtgaa acgccgtagc gccgatggta gtgtggggtc accccatgcg    180
agagtaggga actgccaggc atcaaataaa acgaaaggct cagtcgaaag actgggcctt    240
tcgttttatc tgttgtttgt cggtgaacgc tctcctgagt aggacaaatc cgccgggagc    300
ggatttgaac gttgcgaagc aacgccccgg agggtggcgg gcaggacgcc cgccataaac    360
tgccaggcat caaattaagc agaaggccat cctgacggat ggcctttttg cgtttctaca    420
aactct                                                              426
```

<210> SEQ ID NO 72
<211> LENGTH: 158
<212> TYPE: DNA
<213> ORGANISM: Artificial Sequence
<220> FEATURE:
<223> OTHER INFORMATION: Synthetic Polynucleotide

<400> SEQUENCE: 72

```
tgcctggcgg cagtagcgcg gtggtcccac ctgaccccat gccgaactca gaagtgaaac    60
gccgtagcgc cgatggtagt gtggggtctc cccatgcgag agtagggaac tgccaggcat   120
caaataaaac gaaaggctca gtcgaaagac tgggcctt                           158
```

<210> SEQ ID NO 73
<211> LENGTH: 867
<212> TYPE: DNA
<213> ORGANISM: Artificial Sequence
<220> FEATURE:
<223> OTHER INFORMATION: Synthetic Polynucleotide

<400> SEQUENCE: 73

```
atgggctcca agccgcagac tcagggcctg gccaaggatg cctgggagat ccctcgggag    60
tcgctgcggc tggaggtcaa gctgggccag ggctgctttg gcgaggtgtg gatggggacc   120
tggaacggta ccaccagggt ggccatcaaa accctgaagc ctgcacgat gtctccagag    180 gccttcctgc aggaggccca ggtcatgaag aagctgaggc atgagaagct ggtgcagttg   240
tatgctgtgg tttcagagga gcccatttac atcgtcacgg agtacatgag caaggggagt   300
ttgctggact ttctcaaggg ggagacaggc aagtacctgc ggctgcctca gctggtggac   360
atggctgctc agatcgcctc aggcatggcg tacgtggagc ggatgaacta cgtccaccgg   420
gaccttcgtg cagccaacat cctggtggga gagaacctgg tgtgcaaagt ggccgacttt   480
gggctggctc ggctcattga agacaatgag tacacggcgc ggcaaggtgc caaattcccc   540
atcaagtgga cggctccaga agctgccctc tatggccgct tcaccatcaa gtcggacgtg   600
tggtccttcg ggatcctgct gactgagctc accacaaagg acgggtgcc ctaccctggg    660 atggtgaacc gcgaggtgct ggaccaggtg gagcggggct accggatgcc ctgcccgccg   720
gagtgtcccg agtccctgca cgacctcatg tgccagtgct ggcggaagga gcctgaggag   780
cggcccacct tcgagtacct gcaggccttc ctggaggact acttcacgtc caccgagccc   840
cagtaccagc ccggggagaa cctctaa                                       867
```

<210> SEQ ID NO 74
<211> LENGTH: 1137
<212> TYPE: DNA
<213> ORGANISM: Artificial Sequence
<220> FEATURE:
<223> OTHER INFORMATION: Synthetic Polynucleotide

<400> SEQUENCE: 74

```
atggtggact acagcgtgtg ggaccacatt gaggtgtctg atgatgaaga cgagacgcac    60
cccaacatcg acacggccag tctcttccgc tggcggcatc aggcccgggt ggaacgcatg   120
gagcagttcc agaaggagaa ggaggaactg gacaggggct gccgcgagtg caagcgcaag   180
gtggccgagt gccagaggaa actgaaggag ctggaggtgg ccgagggcgg caaggcagag   240
ctggagcgcc tgcaggccga ggcacagcag ctgcgcaagg aggagcggag ctgggagcag   300
aagctggagg agatgcgcaa gaaggagaag agcatgcct ggaacgtgga cacgctcagc    360
```

| | |
|---|---|
| aaagacggct tcagcaagag catggtaaat accaagcccg agaagacgga ggaggactca | 420 |
| gaggaggtga gggagcagaa acacaagacc ttcgtggaaa atacagaaa acagatcaag | 480 |
| cactttggca tgcttcgccg ctgggatgac agccaaaagt acctgtcaga caacgtccac | 540 |
| ctggtgtgcg aggagacagc caattacctg gtcatttggt gcattgacct agaggtggag | 600 |
| gagaaatgtg cactcatgga gcaggtggcc caccagacaa tcgtcatgca atttatcctg | 660 |
| gagctggcca agagcctaaa ggtggacccc cgggcctgct ccggcagtt cttcactaag | 720 |
| attaagacag ccgatcgcca gtacatggag ggcttcaacg acgagctgga agccttcaag | 780 |
| gagcgtgtgc ggggccgtgc caagctcgcg atcgagaagg ccatgaagga gtacgaggag | 840 |
| gaggagcgca agaagcggct cggccccggc ggcctggacc ccgtcgaggt ctacgagtcc | 900 |
| ctccctgagg aactccagaa gtgcttcgat gtgaaggacg tgcagatgct gcaggacgcc | 960 |
| atcagcaaga tggaccccac cgacgcaaag taccacatgc agcgctgcat tgactctggc | 1020 |
| ctctgggtcc ccaactctaa ggccagcgag gccaaggagg agaggaggc aggtcctggg | 1080 |
| gacccattac tggaagctgt tcccaagacg ggcgatgaga aggatgtcag tgtgtaa | 1137 |

<210> SEQ ID NO 75
<211> LENGTH: 1308
<212> TYPE: DNA
<213> ORGANISM: Artificial Sequence
<220> FEATURE:
<223> OTHER INFORMATION: Synthetic Polynucleotide

<400> SEQUENCE: 75

| | |
|---|---|
| atggagatgg aaaaggagtt cgagcagatc gacaagtccg ggagctgggc ggccatttac | 60 |
| caggatatcc gacatgaagc cagtgacttc ccatgtagag tggccaagct tcctaagaac | 120 |
| aaaaaccgaa ataggtacag agacgtcagt ccctttgacc atagtcggat taaactacat | 180 |
| caagaagata atgactatat caacgctagt ttgataaaaa tggaagaagc ccaaaggagt | 240 |
| tacattctta cccagggccc tttgcctaac acatgcggtc acttttggga gatggtgtgg | 300 |
| gagcagaaaa gcaggggtgt cgtcatgctc aacagagtga tggagaaagg ttcgttaaaa | 360 |
| tgcgcacaat actggccaca aaagaagaa aaagagatga tctttgaaga cacaaatttg | 420 |
| aaattaacat tgatctctga agatatcaag tcatattata cagtgcgaca gctagaattg | 480 |
| gaaaaccta caaccaaga aactcgagag atcttacatt tccactatac cacatggcct | 540 |
| gactttggag tccctgaatc accagcctca ttcttgaact ttcttttcaa agtccgagag | 600 |
| tcagggtcac tcagcccgga gcacgggccc gttgtggtgc actgcagtgc aggcatcggc | 660 |
| aggtctggaa ccttctgtct ggctgatacc tgcctcttgc tgatggacaa gaggaaagac | 720 |
| ccttcttccg ttgatatcaa gaaagtgctg ttagaaatga ggaagtttcg gatggggctg | 780 |
| atccagacag ccgaccagct gcgcttctcc tacctggctg tgatcgaagg tgccaaattc | 840 |
| atcatggggg actcttccgt gcaggatcag tggaaggagc tttcccacga ggacctggag | 900 |
| cccccacccg agcatatccc cccacctccc cggccaccca acgaatcct ggagccacac | 960 |
| aatgggaaat gcagggagtt cttcccaaat caccagtggg tgaaggaaga acccaggag | 1020 |
| gataaagact gccccatcaa ggaagaaaaa ggaagcccct aaatgccgc acctacggc | 1080 |
| atcgaaagca tgagtcaaga cactgaagtt agaagtcggg tcgtgggggg aagtcttcga | 1140 |
| ggtgcccagg ctgcctcccc agccaaaggg gagccgtcac tgcccgagaa ggacgaggac | 1200 |
| catgcactga gttactggaa gcccttcctg gtcaacatgt gcgtggctac ggtcctcacg | 1260 |
| gccggcgctt acctctgcta caggttcctg ttcaacagca acacatag | 1308 |

<210> SEQ ID NO 76
<211> LENGTH: 1086
<212> TYPE: DNA
<213> ORGANISM: Artificial Sequence
<220> FEATURE:
<223> OTHER INFORMATION: Synthetic Polynucleotide

<400> SEQUENCE: 76

| | |
|---|---|
| atgaaatttg gaaacttttt gcttacatac caacctcccc aatttttccca aacagaggta | 60 |
| atgaaacgtt tggttaaatt aggtcgcatc tctgaggagt gtggttttga taccgtatgg | 120 |
| ttactggagc atcatttcac ggagtttggt ttgcttggta acccttatgt cgctgctgca | 180 |
| tatttacttg gcgcgactaa aaaattgaat gtaggaactg ccgctattgt tcttcccaca | 240 |
| gcccatccag tacgccaact tgaagatgtg aatttattgg atcaaatgtc aaaaggacga | 300 |
| tttcggtttg gtatttgccg agggctttac aacaaggact ttcgcgtatt cggcacagat | 360 |
| atgaataaca gtcgcgcctt agcggaatgc tggtacgggc tgataaagaa tggcatgaca | 420 |
| gagggatata tggaagctga taatgaacat atcaagttcc ataaggtaaa agtaaacccc | 480 |
| gcggcgtata gcagaggtgg cgcaccggtt tatgtggtgg ctgaatcagc ttcgacgact | 540 |
| gagtgggctg ctcaatttgg cctaccgatg atattaagtt ggattataaa tactaacgaa | 600 |
| aagaaagcac aacttgagct ttataatgaa gtggctcaag aatatgggca cgatattcat | 660 |
| aatatcgacc attgcttatc atatataaca tctgtagatc atgactcaat taaagcgaaa | 720 |
| gagatttgcc ggaaatttct ggggcattgg tatgattctt atgtgaatgc tacgactatt | 780 |
| tttgatgatt cagaccaaac aagaggttat gatttcaata aagggcagtg gcgtgacttt | 840 |
| gtattaaaag gacataaaga tactaatcgc cgtattgatt acagttacga aatcaatccc | 900 |
| gtgggaacgc cgcaggaatg tattgacata attcaaaaag acattgatgc tacaggaata | 960 |
| tcaaatattt gttgtggatt tgaagctaat ggaacagtag acgaaattat tgcttccatg | 1020 |
| aagctcttcc agtctgatgt catgccattt cttaaagaaa acaacgttc gctattatat | 1080 |
| tattaa | 1086 |

<210> SEQ ID NO 77
<211> LENGTH: 987
<212> TYPE: DNA
<213> ORGANISM: Artificial Sequence
<220> FEATURE:
<223> OTHER INFORMATION: Synthetic Polynucleotide

<400> SEQUENCE: 77

| | |
|---|---|
| atgagcaaat ttggattgtt cttccttaac ttcatcaatt caacaactgt tcaagaacag | 60 |
| agtatagttc gcatgcagga aataacggag tatgttgata gttgaattt tgaacagatt | 120 |
| ttagtgtatg aaaatcattt ttcagataat ggtgttgtcg gcgctcctct gactgtttct | 180 |
| ggttttctgc tcggtttaac agagaaaatt aaaattggtt cattaaatca catcattaca | 240 |
| actcatcatc ctgtccgcat agcggaggaa gcttgcttat tggatcagtt aagtgaaggg | 300 |
| agatttattt tagggtttag tgattgcgaa aaaaagatg aaatgcattt ttttaatcgc | 360 |
| ccggttgaat atcaacagca actatttgaa gagtgttatg aaatcattaa cgatgcttta | 420 |
| acaacaggct attgtaatcc agataacgat ttttatagct tccctaaaat atctgtaaat | 480 |
| ccccatgctt atacgccagg cggacctcgg aaatatgtaa cagcaaccag tcatcatatt | 540 |
| gttgagtggg cggccaaaaa aggtattcct ctcatctta agtgggatga ttctaatgat | 600 |

```
gttagatatg aatatgctga agatataaa gccgttgcgg ataaatatga cgttgaccta      660
tcagagatag accatcagtt aatgatatta gttaactata acgaagatag taataaagct      720
aaacaagaaa cgcgtgcatt tattagtgat tatgttcttg aaatgcaccc taatgaaaat      780
ttcgaaaata aacttgaaga aataattgca gaaaacgctg tcggaaatta tacggagtgt      840
ataactgcgg ctaagttggc aattgaaaag tgtggtgcga aaagtgtatt gctgtccttt      900
gaaccaatga atgatttgat gagccaaaaa aatgtaatca atattgttga tgataatatt      960
aagaagtacc acacggaata tacctaa                                          987

<210> SEQ ID NO 78
<211> LENGTH: 276
<212> TYPE: DNA
<213> ORGANISM: Artificial Sequence
<220> FEATURE:
<223> OTHER INFORMATION: Synthetic Polynucleotide

<400> SEQUENCE: 78
atggcacgcg taactgttca ggacgctgta gagaaaattg gtaaccgttt tgacctggta       60
ctggtcgccg cgcgtcgcgc tcgtcagatg caggtaggcg gaaaggatcc gctggtaccg      120
gaagaaaacg ataaaaccac tgtaatcgcg ctgcgcgaaa tcgaagaagg tctgatcaac      180
aaccagatcc tcgacgttcg cgaacgccag gaacagcaag agcaggaagc cgctgaatta      240
caagccgtta ccgctattgc tgaaggtcgt cgttaa                                276

<210> SEQ ID NO 79
<211> LENGTH: 636
<212> TYPE: DNA
<213> ORGANISM: Artificial Sequence
<220> FEATURE:
<223> OTHER INFORMATION: Synthetic Polynucleotide

<400> SEQUENCE: 79
atgagtatca gcagcagggt aaaaagcaaa agaattcagc ttggacttaa ccaggctgaa       60
cttgctcaaa aggtggggac tacccagcag tctatagagc agctcgaaaa cggtaaaact      120
aagcgaccac gcttttttacc agaacttgcg tcagctcttg gcgtaagtgt tgactggctg      180
ctcaatggca cctctgattc gaatgttaga tttgttgggc acgttgagcc caagggaaa       240 tatccattga ttagcatggt tagagctcgt tcgtggtgtg aagcttgtga acccctacgat     300 atcaaggaca ttgatgaatg gtatgacagt gacgttaact tattaggcaa tggattctgg      360
ctgaaggttg aaggtgattc catgacctca cctgtaggtc aaagcatccc tgaaggtcat      420
atggtgttag tagatactgg acgggagcca gtgaatggaa gccttgttgt agccaaactg      480
actgacgcga acgaagcaac attcaagaaa ctggtcatag atggcggtca gaagtacctg      540
aaaggcctga atccttcatg gcctatgact cctatcaacg gaaactgcaa gattatcggt      600
gttgtcgtgg aagcgagggt aaaattcgta gactaa                                636

<210> SEQ ID NO 80
<211> LENGTH: 300
<212> TYPE: DNA
<213> ORGANISM: Artificial Sequence
<220> FEATURE:
<223> OTHER INFORMATION: Synthetic Polynucleotide

<400> SEQUENCE: 80
atgtggtatt tgggaagat cactcgtcgg gagtccgagc ggctgctgct caaccccgaa        60
aaccccgggg gaaccttctt ggtccgggag agcgagacgg taaaaggtgc ctatgccctc      120
```

```
tccgtttctg actttgacaa cgccaagggg ctcaatgtga aacactacct gatccgcaag    180
ctggacagcg gcggcttcta catcacctca cgcacacagt tcagcagcct gcagcagctg    240
gtggcctact actccaaaca tgctgatggc ttgtgccacc gcctgaccaa cgtctgctaa    300
```

<210> SEQ ID NO 81
<211> LENGTH: 1116
<212> TYPE: DNA
<213> ORGANISM: Artificial Sequence
<220> FEATURE:
<223> OTHER INFORMATION: Synthetic Polynucleotide

<400> SEQUENCE: 81

```
atgaaaatcg aagaaggtaa actggtaatc tggattaacg gcgataaagg ctataacggt     60
ctcgctgaag tcggtaagaa attcgagaaa gataccggaa ttaaagtcac cgttgagcat    120
ccggataaac tggaagagaa attcccacag gttgcggcaa ctggcgatgg ccctgacatt    180
atcttctggg cacacgaccg ctttggtggc tacgctcaat ctggcctgtt ggctgaaatc    240
accccggaca aagcgttcca ggacaagctg tatccgttta cctgggatgc cgtacgttac    300
aacggcaagc tgattgctta cccgatcgct gttgaagcgt tatcgctgat ttataacaaa    360
gatctgctgc cgaacccgcc aaaaacctgg gaagagatcc cggcgctgga taagaactg    420 aaagcgaaag gtaagagcgc gctgatgttc aacctgcaag aaccgtactt cacctggccg    480
ctgattgctg ctgacggggg ttatgcgttc aagtatgaaa acggcaagta cgacattaaa    540
gacgtgggcg tggataacgc tggcgcgaaa gcgggtctga ccttcctggt tgacctgatt    600
aaaaacaaac acatgaatgc agacaccgat tactccatcg cagaagctgc ctttaataaa    660
ggcgaaacag cgatgaccat caacggcccg tgggcatggt ccaacatcga caccagcaaa    720
gtgaattatg gtgtaacggt actgccgacc ttcaagggtc aaccatccaa accgttcgtt    780
ggcgtgctga gcgcaggtat taacgccgcc agtccgaaca agagctggc gaaagagttc    840 ctcgaaaact atctgctgac tgatgaaggt ctggaagcgg ttaataaaga caaaccgctg    900
ggtgccgtag cgctgaagtc ttacgaggaa gagttggcga agatccacg tattgccgcc    960 accatggaaa acgcccagaa aggtgaaatc atgccgaaca tcccgcagat gtccgctttc   1020
tggtatgccg tgcgtactgc ggtgatcaac gccgccagcg tcgtcagac tgtcgatgaa   1080 gccctgaaag acgcgcagac tcgtatcacc aagtaa                             1116
```

<210> SEQ ID NO 82
<211> LENGTH: 36
<212> TYPE: DNA
<213> ORGANISM: Artificial Sequence
<220> FEATURE:
<223> OTHER INFORMATION: Synthetic Polynucleotide

<400> SEQUENCE: 82

```
tggatggagg actatgacta cgtccaccta caggg                                36
```

<210> SEQ ID NO 83
<211> LENGTH: 33
<212> TYPE: DNA
<213> ORGANISM: Artificial Sequence
<220> FEATURE:
<223> OTHER INFORMATION: Synthetic Polynucleotide

<400> SEQUENCE: 83

```
gaaccgcagt atgaagaaat tccgatttat ctg                                  33
```

<210> SEQ ID NO 84
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 84
ccgcagcgct atctggtgat tcagggcgat                               30

<210> SEQ ID NO 85
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 85
gatcatcagt attataacga ttttccgggc                               30

<210> SEQ ID NO 86
<211> LENGTH: 5432
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1317)..(1317)
<223> OTHER INFORMATION: n is a, c, g, or t

<400> SEQUENCE: 86
atgtcattac cgttcttaac ttctgcaccg ggaaaggtta ttattttgg tgaacactct      60
gctgtgtaca acaagcctgc cgtcgctgct agtgtgtctg cgttgagaac ctacctgcta    120
ataagcgagt catctgcacc agatactatt gaattggact tcccggacat tagctttaat    180
cataagtggt ccatcaatga tttcaatgcc atcaccgagg atcaagtaaa ctcccaaaaa    240
ttggccaagg ctcaacaagc caccgatggc ttgtctcagg aactcgttag tcttttggat    300
ccgttgttag ctcaactatc cgaatccttc cactaccatg cagcgttttg tttcctgtat    360
atgtttgttt gcctatgccc ccatgccaag aatattaagt tttctttaaa gtctacttta    420
cccatcggtg ctgggttggg ctcaagcgcc tctatttctg tatcactggc cttagctatg    480
gcctacttgg gggggttaat aggatctaat gacttggaaa agctgtcaga aaacgataag    540
catatagtga atcaatgggc cttcataggt gaaaagtgta ttcacggtac cccttcagga    600
atagataacg ctgtggccac ttatggtaat gccctgctat ttgaaaaaga ctcacataat    660
ggaacaataa acacaaacaa tttttaagttc ttagatgatt tcccagccat tccaatgatc    720
ctaacctata ctagaattcc aaggtctaca aaagatcttg ttgctcgcgt tcgtgtgttg    780
gtcaccgaga aatttcctga agttatgaag ccaattctag atgccatggg tgaatgtgcc    840
ctacaaggct tagagatcat gactaagtta agtaaatgta aaggcaccga tgacgaggct    900
gtagaaacta ataatgaact gtatgaacaa ctattggaat tgataagaat aaatcatgga    960
ctgcttgtct caatcggtgt ttctcatcct ggattagaac ttattaaaaa tctgagcgat   1020
gatttgagaa ttggctccac aaaacttacc ggtgctggtg gcggcggttg ctctttgact   1080
ttgttacgaa gagacattac tcaagagcaa attgacagct tcaaaaagaa attgcaagat   1140
gattttagtt acgagacatt tgaaacagac ttggtgggga ctggctgctg tttgttaagc   1200
gcaaaaaatt tgaataaaga tcttaaaatc aaatccctag tattccaatt atttgaaaat   1260

```
aaaactacca caaagcaaca aattgacgat ctattattgc caggaaacac gaatttncca   1320
tggacttcat aggaggcaga tcaaatgtca gagttgagag ccttcagtgc cccagggaaa   1380
gcgttactag ctggtggata tttagtttta gatacaaaat atgaagcatt tgtagtcgga   1440
ttatcggcaa gaatgcatgc tgtagcccat ccttacggtt cattgcaagg gtctgataag   1500
tttgaagtgc gtgtgaaaag taaacaattt aaagatgggg agtggctgta ccatataagt   1560
cctaaaagtg gcttcattcc tgtttcgata ggcggatcta agaacccttt cattgaaaaa   1620
gttatcgcta acgtatttag ctactttaaa cctaacatgg acgactactg caatagaaac   1680
ttgttcgtta ttgatatttt ctctgatgat gcctaccatt ctcaggagga tagcgttacc   1740
gaacatcgtg gcaacagaag attgagtttt cattcgcaca gaattgaaga agttcccaaa   1800
acagggctgg gctcctcggc aggtttagtc acagttttaa ctacagcttt ggcctccttt   1860
tttgtatcgg acctggaaaa taatgtagac aaatatagag aagttattca taatttagca   1920
caagttgctc attgtcaagc tcagggtaaa attggaagcg ggtttgatgt agcggcggca   1980
gcatatggat ctatcagata tagaagattc ccacccgcat taatctctaa tttgccagat   2040
attggaagtg ctacttacgg cagtaaactg gcgcatttgg ttgatgaaga agactggaat   2100
attacgatta aaagtaacca tttaccttcg ggattaactt tatggatggg cgatattaag   2160
aatggttcag aaacagtaaa actggtccag aaggtaaaaa attggtatga ttcgcatatg   2220
ccagaaagct tgaaaatata tacagaactc gatcatgcaa attctagatt tatggatgga   2280
ctatctaaac tagatcgctt acacgagact catgacgatt acagcgatca gatatttgag   2340
tctcttgaga ggaatgactg tacctgtcaa aagtatcctg aaatcacaga agttagagat   2400
gcagttgcca caattagacg ttcctttaga aaaataacta aagaatctgg tgccgatatc   2460
gaacctcccg tacaaactag cttattggat gattgccaga ccttaaaagg agttcttact   2520
tgcttaatac ctggtgctgg tggttatgac gccattgcag tgattactaa gcaagatgtt   2580
gatcttaggg ctcaaaccgc taatgacaaa agattttcta aggttcaatg ctggatgta   2640 actcaggctg actggggtgt taggaaagaa aaagatccgg aaacttatct tgataaatag   2700
gaggtaatac tcatgaccgt ttacacagca tccgttaccg cacccgtcaa catcgcaacc   2760
cttaagtatt gggggaaaag ggacacgaag ttgaatctgc ccaccaattc gtccatatca   2820
gtgactttat cgcaagatga cctcagaacg ttgacctctg cggctactgc acctgagttt   2880
gaacgcgaca ctttgtggtt aaatggagaa ccacacagca tcgacaatga aagaactcaa   2940
aattgtctgc gcgacctacg ccaattaaga aggaaatgg aatcgaagga cgcctcattg   3000
cccacattat ctcaatggaa actccacatt gtctccgaaa ataactttcc tacagcagct   3060
ggtttagctt cctccgctgc tggctttgct gcattggtct ctgcaattgc taagttatac   3120
caattaccac agtcaacttc agaaatatct agaatagcaa gaaggggtc tggttcagct   3180 tgtagatcgt tgtttggcgg atacgtggcc tgggaaatgg gaaagctga agatggtcat   3240 gattccatgg cagtacaaat cgcagacagc tctgactggc ctcagatgaa gcttgtgtc   3300 ctagttgtca gcgatattaa aaaggatgtg agttccactc agggtatgca attgaccgtg   3360
gcaacctccg aactatttaa agaagaatt gaacatgtcg taccaaagag atttgaagtc   3420
atgcgtaaag ccattgttga aaagatttc gccacctttg caaggaaac aatgatggat   3480 tccaactctt tccatgccac atgtttggac tctttccctc caatattcta catgaatgac   3540
acttccaagc gtatcatcag ttggtgccac accattaatc agttttacgg agaaacaatc   3600
```

```
gttgcataca cgtttgatgc aggtccaaat gctgtgttgt actacttagc tgaaaatgag    3660
tcgaaactct ttgcatttat ctataaattg tttggctctg ttcctggatg ggacaagaaa    3720
tttactactg agcagcttga ggctttcaac catcaatttg aatcatctaa ctttactgca    3780
cgtgaattgg atcttgagtt gcaaaaggat gttgccagag tgattttaac tcaagtcggt    3840
tcaggcccac aagaaacaaa cgaatctttg attgacgcaa agactggtct accaaaggaa    3900
taactgcagc ccgggaggag gattactata tgcaaacgga acacgtcatt ttattgaatg    3960
cacagggagt tcccacgggt acgctggaaa agtatgccgc acacacggca gacacccgct    4020
tacatctcgc gttctccagt tggctgttta atgccaaagg acaattatta gttacccgcc    4080
gcgcactgag caaaaaagca tggcctggcg tgtggactaa ctcggtttgt gggcacccac    4140
aactgggaga agcaacgaa gacgcagtga tccgccgttg ccgttatgag cttggcgtgg    4200
aaattacgcc tcctgaatct atctatcctg actttcgcta ccgcgccacc gatccgagtg    4260
gcattgtgga aaatgaagtg tgtccggtat ttgccgcacg caccactagt gcgttacaga    4320
tcaatgatga tgaagtgatg gattatcaat ggtgtgattt agcagatgta ttacacggta    4380
ttgatgccac gccgtgggcg ttcagtccgt ggatggtgat gcaggcgaca aatcgcgaag    4440
ccagaaaacg attatctgca tttacccagc ttaaataacc cggggatcc actagttcta    4500 gagcggccgc caccgcggag gaggaatgag taatggactt tccgcagcaa ctcgaagcct    4560
gcgttaagca ggccaaccag cgcgctgagcc gtttttatcgc cccactgccc tttcagaaca    4620
ctcccgtggt cgaaaccatg cagtatggcg cattattagg tggtaagcgc ctgcgaccct    4680
tcctggttta tgccaccggt catatgttcg gcgttagcac aaaacacgctg gacgcacccg    4740 ctgccgccgt tgagtgtatc cacgcttact cattaattca tgatgattta ccggcaatgg    4800
atgatgacga tctgcgtcgc ggtttgccaa cctgccatgt gaagtttggc gaagcaaacg    4860
cgattctcgc tggcgacgct ttacaaacgc tggcgttctc gattttaagc gatgccgata    4920
tgccggaagt gtcggaccgc gacagaattt cgatgatttc tgaactggcg agcgccagtg    4980
gtattgccgg aatgtgcggt ggtcaggcat tagatttaga cgcggaaggc aaacacgtac    5040
ctctggacgc gcttgagcgt attcatcgtc ataaaaccgg cgcattgatt cgcgccgccg    5100
ttcgccttgg tgcattaagc gccggagata aggacgtcg tgctctgccg gtactcgaca    5160
agtatgcaga gagcatcggc cttgccttcc aggttcagga tgacatcctg gatgtggtgg    5220 agatactgc aacgttggga aaacgccagg gtgccgacca gcaacttggt aaaagtacct    5280
accctgcact tctgggtctt gagcaagccc ggaagaaagc ccgggatctg atcgacgatg    5340
cccgtcagtc gctgaaacaa ctggctgaac agtcactcga tacctcggca ctggaagcgc    5400
tagcggacta catcatccag cgtaataaat aa                                  5432
```

<210> SEQ ID NO 87
<211> LENGTH: 1638
<212> TYPE: DNA
<213> ORGANISM: Artificial Sequence
<220> FEATURE:
<223> OTHER INFORMATION: Synthetic Polynucleotide

<400> SEQUENCE: 87

```
gccctgaccg aagagaaacc gatccgcccg atcgctaact tcccgccgtc tatctggggt     60
gaccagttcc tgatctacga aaagcaggtt gagcagggtg ttgaacagat cgtaaacgac    120
ctgaagaaag aagttcgtca gctgctgaaa gaagctctgg acatcccgat gaacacgct    180 aacctgttga agctgatcga cgagatccag cgtctgggta tcccgtacca cttcgaacgc    240
```

```
gaaatcgacc acgcactgca gtgcatctac gaaacctacg gcgacaactg aacggcgac      300 cgttcttctc tgtggtttcg tctgatgcgt aaacagggct actacgttac ctgtgacgtt     360
tttaacaact acaaggacaa gaacggtgct ttcaaacagt ctctggctaa cgacgttgaa     420
ggcctgctgg aactgtacga agcgacctcc atgcgtgtac cgggtgaaat catcctggag     480
gacgcgctgg gtttcacccg ttctcgtctg tccattatga ctaaagacgc tttctctact     540
aacccggctc tgttcaccga atccagcgt gctctgaaac agccgctgtg gaaacgtctg      600
ccgcgtatcg aagcagcaca gtacattccg ttttaccagc agcaggactc tcacaacaag     660
accctgctga aactggctaa gctggaattc aacctgctgc agtctctgca aaagaagaa      720 ctgtctcacg tttgtaagtg gtggaaggca tttgacatca gaaaaacgc gccgtgcctg      780 cgtgaccgta tcgttgaatg ttacttctgg ggtctgggtt ctggttatga accacagtac     840
tcccgtgcac gtgtgttctt cactaaagct gtagctgtta tcaccctgat cgatgacact     900
tacgatgctt acggcaccta cgaagaactg aagatcttta ctgaagctgt agaacgctgg     960
tctatcactt gcctggacac tctgccggag tacatgaaac cgatctacaa actgttcatg    1020
gatacctaca ccgaaatgga ggaattcctg caaaagaag gccgtaccga cctgttcaac    1080
tgcggtaaag agtttgttaa agaattcgta cgtaacctga tggttgaagc taaatgggct    1140
aacgaaggcc atatcccgac taccgaagaa catgacccgg ttgttatcat caccggcggt    1200
gcaaacctgc tgaccaccac ttgctatctg ggtatgtccg acatctttac caaggaatct    1260
gttgaatggg ctgttctgc accgccgctg ttccgttact ccggtattct gggtcgtcgt    1320
ctgaacgacc tgatgaccca aaagcagag caggaacgta acactcttc ctcctctctg     1380 gaatcctaca tgaaggaata taacgttaac gaggagtacg cacagactct gatctataaa    1440
gaagttgaag acgtatggaa agacatcaac cgtgaatacc tgactactaa aaacatcccg    1500
cgcccgctgc tgatggcagt aatctacctg tgccagttcc tggaagtaca gtacgctggt    1560
aaagataact tcactcgcat gggcgacgaa tacaaacacc tgatcaaatc cctgctggtt    1620
tacccgatgt ccatctga                                                  1638
```

<210> SEQ ID NO 88
<211> LENGTH: 1782
<212> TYPE: DNA
<213> ORGANISM: Artificial Sequence
<220> FEATURE:
<223> OTHER INFORMATION: Synthetic Polynucleotide

<400> SEQUENCE: 88

```
atggctcaaa tcagcgaatc agtgtctcca agcaccgacc ttaaaagcac ggaatcttct      60
attaccagca accgccacgg taacatgtgg aagatgacc gcattcagag cttaaacagc     120
ccatatggcg cacccgctta tcaggaacgt agcgaaaaat tgattgaaga aattaagctc     180
ctgtttctgt ccgatatgga cgatagttgc aatgattcgg atcgcgactt gatcaaacgc     240
ctggagatcg tagatacggt tgagtgtctg ggcattgatc gtcatttcca acctgaaatt     300
aagctggcgc tggattacgt gtaccgttgc tggaatgagc gtggcatcgg agaaggtagc    360
cgtgatagct aaaaaagga cctgaatgcg accgccttgg gctttcgggc tttacgctta     420
caccgttata atgtaagctc aggagtgctg gagaacttcc gtgatgacaa tggtcaattc     480
ttttgcggtt ctactgtgga ggaggaaggc gcggaggcct acaataaaca tgtacgttgc    540
atgctgtccc tgtcccgcgc ttccaatatt ttattcccgg gcgagaaagt gatggaagaa    600
```

```
gcgaaggcgt ttacgaccaa ctatcttaag aaagtcctgg cgggtcgtga agcaactcat    660
gtcgacgaga gtctccttgg agaggtcaag tatgcactag aatttccgtg cattgttcc    720 gtgcagcgct gggaggcacg ttcttttatc gaaattttcg gtcagattga tagtgaactg    780
aaaagcaacc tctctaaaaa aatgctcgaa ctcgcaaaac ttgattttaa catactccag    840
tgtacgcatc aaaaagagct ccagatcatt agtcgatggt tcgccgattc aagtatcgca    900
agtctgaact tttaccgtaa atgctatgtg gaattttact tctggatggc cgcggcaatt    960
tcagaaccag aatttagtgg ctctcgcgtg gcattcacta aaattgcgat cttgatgaca   1020
atgttagatg acttatacga cacgcatggg acgctggatc aattgaaaat atttaccgaa   1080
ggtgtgcgca ggtgggacgt gtcgctggtg gagggcctgc cggatttcat gaaaattgcc   1140
tttgagttct ggttaaagac ctccaacgaa ctgattgcgg aggcggttaa ggcccaaggc   1200
caggatatgg cggcctatat ccgcaaaaac gcttgggaac gctatctgga agcgtatttg   1260
caggatgccg aatggatcgc caccggtcac gttccgacat cgatgaata tctgaacaat   1320 ggcaccccca acaccggtat gtgtgtactt aatctgatcc cgttgctgct tatgggcgaa   1380
cacttgccga tcgatattct tgaacagatc tttctgccga ccggttcca ccatctgatt   1440 gaactggcta gccgactggt cgatgatgcg agagattttc aagccgaaaa agatcatggt   1500
gatttatcct gcatcgaatg ctacctgaaa gaccatccgg aatcaacagt tgaagacgcc   1560
ctgaatcacg tcaacggcct gctggggaat tgtttgctgg aaatgaattg gaaatttctg   1620
aaaaaacagg actcggtacc tctgtcgtgt aaaaaatact cattccacgt cctggcgcgg   1680
tcgattcagt ttatgtataa ccaggggggac gggttttcga tttcgaacaa agttattaaa   1740
gaccaggtcc agaaagttct aatcgttccg gttcctatat aa                     1782
```

<210> SEQ ID NO 89
<211> LENGTH: 2351
<212> TYPE: DNA
<213> ORGANISM: Artificial Sequence
<220> FEATURE:
<223> OTHER INFORMATION: Synthetic Polynucleotide

<400> SEQUENCE: 89

```
tgaaacgaga atttcctcca ggattttgga aggatgatct tatcgattct ctaacgtcat     60
ctcacaaggt tgcagcatca gacgagaagc gtatcgagac attaatatcc gagattaaga    120
atatgtttag atgtatgggc tatggcgaaa cgaatccctc tgcatatgac actgcttggg    180
tagcaaggat tccagcagtt gatggctctg acaaccctca ctttcctgag acggttgaat    240
ggattcttca aaatcagttg aaagatgggt cttggggtga aggattctac ttcttggcat    300
atgacagaat actggctaca cttgcatgta ttattaccct taccctctgg cgtactgggg    360
agacacaagt acagaaaggt attgaattct tcaggacaca agctggaaag atggaagatg    420
aagctgatag tcataggcca agtggatttg aaatagtatt tcctgcaatg ctaaaggaag    480
ctaaaatctt aggcttggat ctgccttacg atttgccatt cctgaaacaa atcatcgaaa    540
agcgggaggc taagcttaaa aggattccca ctgatgttct ctatgcccct ccaacaacgt    600
tattgtattc tttggaaggt ttacaagaaa tagtagactg gcagaaaata atgaaacttc    660
aatccaagga tggatcattt ctcagctctc cggcatctac agcggctgta ttcatgcgta    720
cagggaacaa aaagtgcttg gatttcttga actttgtctt gaagaaattc ggaaaccatg    780
tgccttgtca ctatccgctt gatctatttg aacgttgtg ggcggttgat acagttgagc    840
ggctaggtat cgatcgtcat ttcaaagagg agatcaagga agcattggat tatgtttaca    900
```

```
gccattggga cgaaagaggc attggatggg cgagagagaa tcctgttcct gatattgatg    960
atacagccat gggccttcga atcttgagat tacatggata caatgtatcc tcagatgttt   1020
taaaaacatt tagagatgag aatggggagt tcttttgctt cttgggtcaa acacagagag   1080
gagttacaga catgttaaac gtcaatcgtt gttcacatgt ttcatttccg ggagaaacga   1140
tcatggaaga agcaaaactc tgtaccgaaa ggtatctgag gaatgctctg gaaaatgtgg   1200
atgcctttga caaatgggct tttaaaaaga atattcgggg agaggtagag tatgcactca   1260
aatatccctg gcataagagt atgccaaggt tggaggctag aagctatatt gaaaactatg   1320
ggccagatga tgtgtggctt ggaaaaactg tatatatgat gccatacatt tcgaatgaaa   1380
agtatttaga actagcgaaa ctggacttca ataaggtgca gtctatacac caaacagagc   1440
ttcaagatct tcgaaggtgg tggaaatcat ccggtttcac ggatctgaat ttcactcgtg   1500
agcgtgtgac ggaaatatat ttctcaccgg catcctttat cttgagccc gagttttcta   1560
agtgcagaga ggtttataca aaaacttcca atttcactgt tattttagat gatctttatg   1620
acgcccatgg atctttagac gatcttaagt tgttcacaga atcagtcaaa agatgggatc   1680
tatcactagt ggaccaaatg ccacaacaaa tgaaaatatg ttttgtgggt ttctacaata   1740
cttttaatga tatagcaaaa gaaggacgtg agaggcaagg gcgcgatgtg ctaggctaca   1800
ttcaaaatgt ttggaaagtc caacttgaag cttacacgaa agaagcagaa tggtctgaag   1860
ctaaatatgt gccatccttc aatgaataca tagagaatgc gagtgtgtca atagcattgg   1920
gaacagtcgt tctcattagt gctcttttca ctggggaggt tcttacagat gaagtactct   1980
ccaaaattga tcgcgaatct agatttcttc aactcatggg cttaacaggg cgtttggtga   2040
atgcaccaa aacttatcag gcagagagag gtcaaggtga ggtggcttct gccatacaat   2100
gttatatgaa ggaccatcct aaaatctctg aagaagaagc tctacaacat gtctatagtg   2160
tcatggaaaa tgccctcgaa gagttgaata gggagtttgt gaataacaaa ataccggata   2220
tttacaaaag actggttttt gaaactgcaa gaataatgca actctttat atgcaagggg   2280
atggtttgac actatcacat gatatggaaa ttaaagagca tgtcaaaaat tgcctcttcc   2340
aaccagttgc c                                                      2351

<210> SEQ ID NO 90
<211> LENGTH: 2409
<212> TYPE: DNA
<213> ORGANISM: Artificial Sequence
<220> FEATURE:
<223> OTHER INFORMATION: Synthetic Polynucleotide

<400> SEQUENCE: 90
atgagcagca gcactggcac tagcaaggtg gtttccgaga cttccagtac cattgtggat     60
gatatccctc gactctccgc caattatcat ggcgatctgt ggcaccacaa tgttatacaa    120
actctggaga caccgtttcg tgagagttct acttaccaag aacgggcaga tgagctggtt    180
gtgaaaatta agatatgtt caatgcgctc ggagacggag atatcagtcc gtctgcatac    240
gacactgcgt gggtggcgag gctggcgacc atttcctctg atggatctga aagccacgg    300
tttcctcagg ccctcaactg gttttcaac aaccagctcc aggatggatc gtggggtatc    360
gaatcgcact ttagtttatg cgatcgattg cttaacacga ccaattctgt tatcgccctc    420
tcggtttgga aaacagggca cagccaagta caacaaggtg ctgagtttat tgcagagaat    480
ctaagattac tcaatgagga agatgagttg tccccggatt tccaaataat ctttcctgct    540
```

```
ctgctgcaaa aggcaaaagc gttggggatc aatcttcctt acgatcttcc atttatcaaa      600
tatttgtcga caacacggga agccaggctt acagatgttt ctgcggcagc agacaatatt      660
ccagccaaca tgttgaatgc gttggaagga ctcgaggaag ttattgactg aacaagatt       720 atgaggtttc aaagtaaaga tggatctttc ctgagctccc ctgcctccac tgcctgtgta      780
ctgatgaata caggggacga aaaatgtttc acttttctca acaatctgct cgacaaattc      840
ggcggctgcg tgccctgtat gtattccatc gatctgctgg aacgcctttc gctggttgat      900
aacattgagc atctcggaat cggtcgccat ttcaaacaag aaatcaaagg agctcttgat      960
tatgtctaca gacattggag tgaaagggc atcggttggg gcagagacag ccttgttcca     1020
gatctcaaca ccacagccct cggcctgcga actcttcgca tgcacggata caatgtttct     1080
tcagacgttt tgaataattt caaagatgaa acgggcggt tcttctcctc tgcgggccaa      1140
acccatgtcg aattgagaag cgtggtgaat cttttcagag cttccgacct tgcatttcct     1200
gacgaaagag ctatgacga tgctagaaaa tttgcagaac catatcttag agaggcactt      1260
gcaacgaaaa tctcaaccaa tacaaaacta ttcaaagaga ttgagtacgt ggtggagtac     1320
ccttggcaca tgagtatccc acgcttagaa gccagaagtt atattgattc atatgacgac     1380
aattatgtat ggcagaggaa gactctatat agaatgccat ctttgagtaa ttcaaaatgt     1440
ttagaattgg caaaattgga cttcaatatc gtacaatctt gcatcaaga ggagttgaag      1500 cttctaacaa gatggtggaa ggaatccggc atggcagata taaatttcac tcgacaccga     1560
gtggcggagg tttatttttc atcagctaca tttgaacccg aatattctgc cactagaatt     1620
gccttcacaa aaattggttg tttacaagtc cttttgatg atatggctga catctttgca      1680
acactagatg aattgaaaag tttcactgag ggagtaaaga gatgggatac atctttgcta     1740
catgagattc cagagtgtat gcaaacttgc tttaaagttt ggttcaaatt aatgaagaa      1800 gtaaataatg atgtggttaa ggtacaagga cgtgacatgc tcgctcacat aagaaaaccc     1860
tgggagttgt acttcaattg ttatgtacaa gaaagggagt ggcttgaagc cgggtatata     1920 ccaactttg aagagtactt aaagactta gctatatcag taggccttgg accgtgtacc       1980
ctacaaccaa tactactaat gggtgagctt gtgaaagatg atgttgttga aaaagtgcac     2040
tatccctcaa atatgtttga gcttgtatcc ttgagctggc gactaacaaa cgacaccaaa     2100
acatatcagg ctgaaaaggc tcgaggacaa caagcctcag gcatagcatg ctatatgaag     2160
gataatccag gagcaactga ggaagatgcc attaagcaca tatgtcgtgt tgttgatcgg     2220
gccttgaaag aagcaagctt tgaatatttc aaaccatcca atgatatccc aatgggttgc     2280
aagtccttta tttttaacct tagattgtgt gtccaaatct tttacaagtt tatagatggg     2340
tacggaatcg ccaatgagga gattaaggac tatataagaa aagtttatat tgatccaatt     2400
caagtatga                                                             2409
```

<210> SEQ ID NO 91
<211> LENGTH: 891
<212> TYPE: DNA
<213> ORGANISM: Artificial Sequence
<220> FEATURE:
<223> OTHER INFORMATION: Synthetic Polynucleotide

<400> SEQUENCE: 91

```
atgtttgatt tcaatgaata tatgaaaagt aaggctgttg cggtagacgc ggctctggat       60
aaagcgattc cgctggaata tcccgagaag attcacgaat cgatgcgcta ctccctgtta      120
gcaggaggga aacgcgttcg tccggcatta tgcatcgcgg cctgtgaact cgtcggcggt      180
```

| | |
|---|---|
| tcacaggact tagcaatgcc aactgcttgc gcaatggaaa tgattcacac aatgagcctg | 240 |
| attcatgatg atttgccttg catggacaac gatgactttc ggcgcggtaa acctactaat | 300 |
| cataaggttt ttggcgaaga tactgcagtg ctggcgggcg atgcgctgct gtcgtttgcc | 360 |
| ttcgaacata tcgccgtcgc gacctcgaaa accgtcccgt cggaccgtac gcttcgcgtg | 420 |
| atttccgagc tgggaaagac catcggctct caaggactcg tgggtggtca ggtagttgat | 480 |
| atcacgtctg agggtgacgc gaacgtggac ctgaaaaccc tggagtggat ccatattcac | 540 |
| aaaacggccg tgctgctgga atgtagcgtg gtgtcagggg ggatcttggg gggcgccacg | 600 |
| gaggatgaaa tcgcgcgtat tcgtcgttat gcccgctgtg ttggactgtt atttcaggtg | 660 |
| gtggatgaca tcctggatgt cacaaaatcc agcgaagagc ttggcaagac cgcgggcaaa | 720 |
| gaccttctga cggataaggc tacatacccg aaattgatgg gcttggagaa agccaaggag | 780 |
| ttcgcagctg aacttgccac gcgggcgaag gaagaactct cttctttcga tcaaatcaaa | 840 |
| gccgcgccac tgctgggcct cgccgattac attgcgtttc gtcagaactg a | 891 |

<210> SEQ ID NO 92
<211> LENGTH: 3150
<212> TYPE: DNA
<213> ORGANISM: Artificial Sequence
<220> FEATURE:
<223> OTHER INFORMATION: Synthetic Polynucleotide

<400> SEQUENCE: 92

| | |
|---|---|
| atgacaatta aagaaatgcc tcagccaaaa acgtttggag agcttaaaaa tttaccgtta | 60 |
| ttaaacacag ataaaccggt tcaagctttg atgaaaattg cggatgaatt aggagaaatc | 120 |
| tttaaattcg aggcgcctgg tcgtgtaacg cgctacttat caagtcagcg tctaattaaa | 180 |
| gaagcatgcg atgaatcacg cttttgataaa aacttaagtc aagcgcttaa atttgtacgt | 240 |
| gattttgcag agacggggtt atttacaagc tggacgcatg aaaaaaattg gaaaaaagcg | 300 |
| cataatatct tacttccaag cttcagtcag caggcaatga aaggctatca tgcgatgatg | 360 |
| gtcgatatcg ccgtgcagct tgttcaaaag tgggagcgtc taaatgcaga tgagcatatt | 420 |
| gaagtaccgg aagacatgac acgtttaacg cttgatacaa ttggtctttg cggctttaac | 480 |
| tatcgcttta acagctttta ccgagatcag cctcatccat ttattacaag tatggtccgt | 540 |
| gcactggatg aagcaatgaa caagctgcag cgagcaaatc cagacgaccc agcttatgat | 600 |
| gaaaacaagc gccagtttca agaagatatc aaggtgatga cgacctagt agataaaatt | 660 |
| attgcagatc gcaaagcaag cggtgaacaa agcgatgatt tattaacgca tatgctaaac | 720 |
| ggaaaagatc cagaaacggg tgagccgctt gatgacgaga cattcgcta tcaaattatt | 780 |
| acattcttaa ttgcgggaca cgaaacaaca agtggtcttt tatcatttgc gctgtatttc | 840 |
| ttagtgaaaa atccacatgt attacaaaaa gcagcagaag aagcagcacg agttctagta | 900 |
| gatcctgttc caagctacaa acaagtcaaa cagcttaaat atgtcggcat ggtcttaaac | 960 |
| gaagcgctgc gcttatggcc aactgctcct gcgttttccc tatatgcaaa agaagatacg | 1020 |
| gtgcttggag gagaatatcc tttagaaaaa ggcgacgaac taatggttct gattcctcag | 1080 |
| cttcaccgtg ataaaacaat tgggggagac gatgtgaag agttccgtcc agagcgtttt | 1140 |
| gaaaatccaa gtgcgattcc gcagcatgcg tttaaaccgt tggaaacgg tcagcgtgcg | 1200 |
| tgtatcggtc agcagttcgc tcttcatgaa gcaacgctgg tacttggtat gatgctaaaa | 1260 |
| cactttgact ttgaagatca tacaaactac gagctggata ttaagaaac tttaacgtta | 1320 |

```
aaacctgaag gctttgtggt aaaagcaaaa tcgaaaaaaa ttccgcttgg cggtattcct    1380
tcacctagca ctgaacagtc tgctaaaaaa gtacgcaaaa aggcagaaaa cgctcataat    1440
acgccgctgc ttgtgctata cggttcaaat atgggaacag ctgaaggaac ggcgcgtgat    1500
ttagcagata ttgcaatgag caaaggattt gcaccgcagg tcgcaacgct tgattcacac    1560
gccggaaatc ttccgcgcga aggagctgta ttaattgtaa cggcgtctta taacggtcat    1620
ccgcctgata acgcaaagca atttgtcgac tggttagacc aagcgtctgc tgatgaagta    1680
aaaggcgttc gctactccgt atttggatgc ggcgataaaa actgggctac tacgtatcaa    1740
aaagtgcctg cttttatcga tgaaacgctt gccgctaaag gggcagaaaa catcgctgac    1800
cgcggtgaag cagatgcaag cgacgacttt gaaggcacat atgaagaatg gcgtgaacat    1860
atgtggagtg acgtagcagc ctactttaac ctcgacattg aaaacagtga agataataaa    1920
tctactcttt cacttcaatt tgtcgacagc gccgcggata tgccgcttgc gaaaatgcac    1980
ggtgcgtttt caacgaacgt cgtagcaagc aaagaacttc aacagccagg cagtgcacga    2040
agcacgcgac atcttgaaat tgaacttcca aaagaagctt cttatcaaga aggagatcat    2100
ttaggtgtta ttcctcgcaa ctatgaagga atagtaaacc gtgtaacagc aaggttcggc    2160
ctagatgcat cacagcaaat ccgtctggaa gcagaagaag aaaaattagc tcatttgcca    2220
ctcgctaaaa cagtatccgt agaagagctt ctgcaatacg tggagcttca agatcctgtt    2280
acgcgcacgc agcttcgcgc aatggctgct aaaacggtct gcccgccgca taagtagag    2340 cttgaagcct tgcttgaaaa gcaagcctac aaagaacaag tgctggcaaa acgtttaaca    2400
atgcttgaac tgcttgaaaa atacccggcg tgtgaaatga aattcagcga atttatcgcc    2460
cttctgccaa gcatacgccc gcgctattac tcgatttctt catcacctcg tgtcgatgaa    2520
aaacaagcaa gcatcacggt cagcgttgtc tcaggagaag cgtggagcgg atatggagaa    2580
tataaaggaa ttgcgtcgaa ctatcttgcc gagctgcaag aaggagatac gattacgtgc    2640
tttatttcca caccgcagtc agaatttacg ctgccaaaag accctgaaac gccgcttatc    2700
atggtcggac cgggaacagg cgtcgcgccg tttagaggct ttgtgcaggc gcgcaaacag    2760
ctaaaagaac aaggacagtc acttggagaa gcacatttat acttcggctg ccgttcacct    2820
catgaagact atctgtatca agaagagctt gaaaacgccc aaagcgaagg catcattacg    2880
cttcataccg cttttctcg catgccaaat cagccgaaaa catacgttca gcacgtaatg    2940
gaacaagacg gcaagaaatt gattgaactt cttgatcaag gagcgcactt ctatatttgc    3000
ggagacggaa gccaaatggc acctgccgtt gaagcaacgc ttatgaaaag ctatgctgac    3060
gttcaccaag tgagtgaagc agacgctcgc ttatggctgc agcagctaga agaaaaaggc    3120
cgatacgcaa aagacgtgtg ggctgggtaa                                    3150
```

<210> SEQ ID NO 93
<211> LENGTH: 789
<212> TYPE: DNA
<213> ORGANISM: Artificial Sequence
<220> FEATURE:
<223> OTHER INFORMATION: Synthetic Polynucleotide

<400> SEQUENCE: 93

```
atgagggaag cggtgatcgc cgaagtatcg actcaactat cagaggtagt tggcgtcatc      60
gagcgccatc tcgaaccgac gttgctggcc gtacatttgt acggctccgc agtggatggc     120
ggcctgaagc cacacagtga tattgatttg ctggttacgg tgaccgtaag gcttgatgaa     180
acaacgcggc gagctttgat caacgacctt ttggaaactt cggcttcccc tggagagagc     240
```

```
gagattctcc gcgctgtaga agtcaccatt gttgtgcacg acgacatcat tccgtggcgt    300
tatccagcta agcgcgaact gcaatttgga gaatggcagc gcaatgacat tcttgcaggt    360
atcttcgagc cagccacgat cgacattgat ctggctatct tgctgacaaa agcaagagaa    420
catagcgttg ccttggtagg tccagcggcg gaggaactct tgatccggt tcctgaacag     480 gatctatttg aggcgctaaa tgaaaccttaa cgctatgga actcgccgcc cgactgggct    540
ggcgatgagc gaaatgtagt gcttacgttg tcccgcattt ggtacagcgc agtaaccggc    600
aaaatcgcgc cgaaggatgt cgctgccgac tgggcaatgg agcgcctgcc ggcccagtat    660
cagcccgtca tacttgaagc tagacaggct tatcttggac aagaagaaga tcgcttggcc    720
tcgcgcgcag atcagttgga agaatttgtc cactacgtga aaggcgagat caccaaggta    780
gtcggcaaa                                                            789

<210> SEQ ID NO 94
<211> LENGTH: 432
<212> TYPE: DNA
<213> ORGANISM: Artificial Sequence
<220> FEATURE:
<223> OTHER INFORMATION: Synthetic Polynucleotide

<400> SEQUENCE: 94
ttggctacta cacttgaacg tattgagaag aactttgtca ttactgaccc aaggttgcca     60
gataatccca ttatattcgc gtccgatagt ttcttgcagt tgacagaata tagccgtgaa    120
gaaattttgg gaagaaactg caggtttcta caaggtcctg aaactgatcg cgcgacagtg    180
agaaaaatta gagatgccat agataaccaa acagaggtca ctgttcagct gattaattat    240
acaaagagtg gtaaaaagtt ctggaacctc tttcacttgc agcctatgcg agatcagaag    300
ggagatgtcc agtactttat tggggttcag ttggatggaa ctgagcatgt ccgagatgct    360
gccgagagag agggagtcat gctgattaag aaaactgcag aaaatattga tgaggcggca    420
aaagaacttc ca                                                        432

<210> SEQ ID NO 95
<211> LENGTH: 2244
<212> TYPE: DNA
<213> ORGANISM: Artificial Sequence
<220> FEATURE:
<223> OTHER INFORMATION: Synthetic Polynucleotide

<400> SEQUENCE: 95
atggctagcg tggcaggtca tgcctctggc agccccgcat cgggaccgc cgatctttcg      60 aattgcgaac gtgaagagat ccacctcgcc ggctcgatcc agccgcatgg cgcgcttctg    120
gtcgtcagcg agccggatca tcgcatcatc caggccagcg ccaacgccgc ggaatttctg    180
aatctcggaa gcgtgctcgg cgttccgctc gccgagatcg acggcgatct gttgatcaag    240
atcctgccgc atctcgatcc caccgccgaa ggcatgccgg tcgcggtgcg ctgccggatc    300
ggcaatccct ccacggagta cgacggtctg atgcatcggc ctccggaagg cgggctgatc    360
atcgagctcg aacgtgccgg cccgccgatc gatctgtccg gcacgctggc gccggcgctg    420
gagcggatcc gcacggcggg ctcgctgcgc gcgctgtgc atgacaccgc gctgctgttt    480
cagcagtgca ccggctacga ccgggtgatg gtgtatcgct tcgacgagca gggccacggc    540
gaagtgttct ccgagcgcca cgtgcccggg ctcgaatcct atttcggcaa ccgctatccg    600
tcgtcggaca ttccgcagat ggcgcggcgg ctgtacgagc ggcagcgcgt ccgcgtgctg    660
```

```
gtcgacgtca gctatcagcc ggtgccgctg gagccgcggc tgtcgccgct gaccgggcgc      720
gatctcgaca tgtcgggctg cttcctgcgc tcgatgtcgc cgatccatct gcagtacctg      780
aagaacatgg gcgtgcgcgc caccctggtg gtgtcgctgg tggtcggcgg caagctgtgg      840
ggcctggttg cctgtcatca ttatctgccg cgcttcatgc atttcgagct gcgggcgatc      900
tgcgaactgc tcgccgaagc gatcgcgacg cggatcaccg cgcttgagag cttcgcgcag      960
agccagtcgg agctgttcgt gcagcggctc aacagcgca tgatcgaagc gattacccgt      1020
gaaggcgatt ggcgcgcagc gattttcgac accagccaat cgatcctgca gccgctgcac      1080
gccgccggtt gcgcgctggt gtacgaagac cagatcagga ccatcggcga cgtgccttcc      1140
acgcaggatg tgcgcgagat cgccgggtgg ctcgatcgcc agccgcgcgc ggcggtgacc      1200
tcgaccgcgt cgctcggtct cgacgtgccg gagctcgcgc atctgacgcg gatggcgagc      1260
ggcgtggtcg cggcgccgat ttcggatcat cgcggcgagt ttctgatgtg gttccgcccc      1320
gagcgcgtcc acaccgttac ctggggcggc gatccgaaga agccgttcac gatgggcgat      1380
acaccggcgg atctgtcgcc gcggcgctcc ttcgccaaat ggcatcaggt tgtcgaaggc      1440
acgtccgatc cgtggacggc cgccgatctc gccgcggctc gcaccatcgg tcagaccgtc      1500
gccgacatcg tgctgcaatt ccgcgcgtg cggacactga tcgcccgcga acagtacgaa      1560
cagttttcgt cccaggtgca cgcttcgatg cagccggtgc tgatcaccga cgccgaaggc      1620
cgcatcctgc tgatgaacga ctcgttccgc gacatgttgc cggcgggttc gccatccgcc      1680
gtccatctcg acgatctcgc cgggttcttc gtcgaatcga acgatttcct gcgcaacgtc      1740
gccgaactga tcgatcacgg ccgcgggtgg cgcggcgaag ttctgctgcg cggcgcaggc      1800
aaccgcccgt tgccgctggc agtgcgcgcc gatccggtga cgcgcacgga ggaccagtcg      1860
ctcggcttcg tgctgatctt cagcgacgct accgatcgtc gcaccgcaga tgccgcacgc      1920 acgcgttttcc aggaaggcat tcttgccagc gcacgtcccg gcgtgcggct cgactccaag      1980
tccgacctgt tgcacgagaa gctgctgtcc gcgctggtcg agaacgcgca gcttgccgca      2040
ttggaaatca cttacggcgt cgagaccgga cgcatcgccg agctgctcga aggcgtccgc      2100
cagtcgatgc tgcgcaccgc cgaagtgctc ggcatctgg tgcagcacgc ggcgcgcacg      2160
gccggcagcg acagctcgag caatggctcg cagaacaaga aggaattcga tagtgctggt      2220
agtgctggta gtgctggtac tagt                                            2244

<210> SEQ ID NO 96
<211> LENGTH: 1308
<212> TYPE: DNA
<213> ORGANISM: Artificial Sequence
<220> FEATURE:
<223> OTHER INFORMATION: Synthetic Polynucleotide

<400> SEQUENCE: 96
atggagatgg aaaaggagtt cgagcagatc gacaagtccg ggagctgggc ggccatttac       60
caggatatcc gacatgaagc cagtgacttc ccatgtagag tggccaagct tcctaagaac      120
aaaaaccgaa ataggtacag agacgtcagt cccttttgacc atagtcggat taaactacat      180
caagaagata tgactatatc aacgctagtt tgataaaaaa tggaagaagc ccaaaggagt      240
tacattctta cccagggccc tttgcctaac acatgcggtc acttttggga gatggtgtgg      300
gagcagaaaa gcaggggtgt cgtcatgctc aacagagtga tggagaaagg ttcgttaaaa      360
tgcgcacaat actggccaca aaaagaagaa aagagatga tctttgaaga cacaaatttg      420
aaattaacat tgatctctga agatatcaag tcatattata cagtgcgaca gctagaattg      480
```

```
gaaaaccttta caacccaaga aactcgagag atcttacatt tccactatac cacatggcct    540
gactttggag tccctgaatc accagcctca ttcttgaact ttcttttcaa agtccgagag    600
tcagggtcac tcagcccgga gcacgggccc gttgtggtgc actgcagtgc aggcatcggc    660
aggtctggaa ccttctgtct ggctgatacc tgcctcttgc tgatggacaa gaggaaagac    720
ccttcttccg ttgatatcaa gaaagtgctg ttagaaatga ggaagtttcg gatggggctg    780
atccagacag ccgaccagct cgcgcttctcc tacctggctg tgatcgaagg tgccaaattc    840
atcatggggg actcttccgt gcaggatcag tggaaggagc tttcccacga ggacctggag    900
cccccacccg agcatatccc cccacctccc cggccaccca acgaatcct ggagccacac    960 aatgggaaat gcagggagtt cttcccaaat caccagtggg tgaaggaaga gacccaggag   1020
gataaagact gccccatcaa ggaagaaaaa ggaagcccct aaatgccgc acctacggc    1080 atcgaaagca tgagtcaaga cactgaagtt agaagtcggg tcgtgggggg aagtcttcga   1140
ggtgcccagg ctgcctcccc agccaaaggg gagccgtcac tgcccgagaa ggacgaggac   1200
catgcactga gttactggaa gcccttcctg gtcaacatgt gcgtggctac ggtcctcacg   1260
gccggcgctt acctctgcta caggttcctg ttcaacagca acacatag               1308

<210> SEQ ID NO 97
<211> LENGTH: 951
<212> TYPE: DNA
<213> ORGANISM: Artificial Sequence
<220> FEATURE:
<223> OTHER INFORMATION: Synthetic Polynucleotide

<400> SEQUENCE: 97
atgcccacca ccatcgagcg ggagttcgaa gagttggata tcagcgtcg ctggcagccg      60 ctgtacttgg aaattcgaaa tgagtcccat gactatcctc atagagtggc caagtttcca    120
gaaaacagaa atcgaaacag atacagagat gtaagcccat atgatcacag tcgtgttaaa    180
ctgcaaaatg ctgagaatga ttatattaat gccagtttag ttgacataga agaggcacaa    240
aggagttaca tcttaacaca gggtccactt cctaacacat gctgccattt ctggcttatg    300
gtttggcagc agaagaccaa agcagttgtc atgctgaacc gcattgtgga gaaagaatcg    360
gttaaatgtg cacagtactg gccaacagat gaccaagaga tgctgttta agaaacagga    420 ttcagtgtga agctcttgtc agaagatgtg aagtcgtatt atacagtaca tctactacaa    480
ttagaaaata tcaatagtgg tgaaaccaga acaatatctc actttcatta tactacctgg    540
ccagattttg gagtccctga atcaccagct tcatttctca atttcttgtt taagtgaga    600 gaatctggct ccttgaaccc tgaccatggg cctgcggtga tccactgtag tgcaggcatt    660
gggcgctctg gcaccttctc tctggtagac acttgtcttg ttttgatgga aaaggagat    720 gatattaaca taaaacaagt gttactgaac atgagaaaat accgaatggg tcttattcag    780
accccagatc aactgagatt ctcatacatg gctataatag aaggagcaaa atgtataaag    840
ggagattcta gtatacagaa acgatggaaa gaactttcta aggaagactt atctcctgcc    900
tttgatcatt caccaaacaa aataatgact gaaaaataca atgggaacag a            951

<210> SEQ ID NO 98
<211> LENGTH: 900
<212> TYPE: DNA
<213> ORGANISM: Artificial Sequence
<220> FEATURE:
<223> OTHER INFORMATION: Synthetic Polynucleotide
```

<400> SEQUENCE: 98

```
atgtcttctg gtgtagatct gggtaccgag aacctgtact tccaatccat gtcccgtgtc    60
ctccaagcag aagagcttca tgaaaaggcc ctggacccct tcctgctgca ggcggaattc   120
tttgaaatcc ccatgaactt tgtggatccg aaagagtacg acatccctgg gctggtgcgg   180
aagaaccggt acaaaaccat acttcccaac cctcacagca gagtgtgtct gacctcacca   240
gaccctgacg accctctgag ttcctacatc aatgccaact acatccgggg ctatggtggg   300
gaggagaagg tgtacatcgc cactcaggga cccatcgtca gcacggtcgc cgacttctgg   360
cgcatggtgt ggcaggagca cacgcccatc attgtcatga tcaccaacat cgaggagatg   420
aacgagaaat gcaccgagta ttggccggag gagcaggtgg cgtacgacgg tgttgagatc   480
actgtgcaga aagtcattca cacggaggat taccggctgc gactcatctc cctcaagagt   540
gggactgagg agcgaggcct gaagcattac tggttcacat cctggcccga ccagaagacc   600
ccagaccggg ccccccccact cctgcacctg gtgcgggagg tggaggaggc agcccagcag   660
gagggggccccc actgtgcccc catcatcgtc cactgcagtg cagggattgg gaggaccggc   720
tgcttcattg ccaccagcat ctgctgccag cagctgcggc aggagggtgt agtggacatc   780
ctgaagacca cgtgccagct ccgtcaggac aggggcggac tgatccagac atgcgagcag   840
taccagtttg tgcaccacgt catgagcctc tacgaaaagc agctgtccca ccagtcctga   900
```

<210> SEQ ID NO 99
<211> LENGTH: 1788
<212> TYPE: DNA
<213> ORGANISM: Artificial Sequence
<220> FEATURE:
<223> OTHER INFORMATION: Synthetic Polynucleotide

<400> SEQUENCE: 99

```
atggtgaggt ggtttcaccg agacctcagt gggctggatg cagagaccct gctcaagggc    60
cgaggtgtcc acgtagcttc cctggctcgg cccagtcgca agaaccaggg tgacttctcg   120
ctctccgtca gggtgggga tcaggtgacc catattcgga tccagaactc aggggatttc   180
tatgacctgt atggagggga gaagtttgcg actctgacag agctggtgga gtactacact   240
cagcagcagg gtgtggtgca ggaccgcgac ggcaccatca tccacctcaa gtaccgctg   300
aactgctccg atcccactag tgagaggtgg taccatggcc acatgtctgg cgggcaggca   360
gagacgctgc tgcaggccaa gggcgagccc tggacgtttc ttgtgcgtga gagcctcagc   420
cagcctggag acttcgtgct ttctgtgctc agtgaccagc ccaaggctgg cccaggctcc   480
ccgctcaggg tcacccacat caaggtcatg tgcgagggtg acgctacac agtgggtggt   540
ttggagacct tcgacagcct cacggacctg gtggagcatt tcaagaagac ggggattgag   600
gaggcctcag gcgcctttgt ctacctgcgg cagccgtact atgccacgag ggtgaatgcg   660
gctgacattg agaaccgagt gttggaactg aacaagaagc aggagtccga ggatacagcc   720
aaggctggct ctggggagga gtttgagagt ttgcagaagc aggaggtgaa gaacttgcac   780
cagcgtctgg aagggcaacg gccagagaac aagggcaaga accgctacaa gaacattctc   840
cccttttgacc acagccgagt gatcctgcag ggacgggaca gtaacatccc cgggtccgac   900
tacatcaatg ccaactacat caagaaccag ctgctaggcc ctgatgagaa cgctaagacc   960
tacatcgcca gccagggctg tctggaggcc acggtcaatg acttctggca gatggcgtgg  1020
caggagaaca gccgtgtcat cgtcatgacc acccgagagg tggagaaagg ccggaacaaa  1080
tgcgtcccat actggcccga ggtgggcatg cagcgtgctt atgggcccta ctctgtgacc  1140
```

```
aactgcgggg agcatgacac aaccgaatac aaactccgta ccttacaggt ctccccgctg   1200
gacaatggag acctgattcg ggagatctgg cattaccagt acctgagctg gcccgaccat   1260
ggggtcccca gtgagcctgg gggtgtcctc agcttcctgg accagatcaa ccagcggcag   1320
gaaagtctgc ctcacgcagg gcccatcatc gtgcactgca cgccggcat cggccgcaca    1380 ggcaccatca ttgtcatcga catgctcatg gagaacatct ccaccaaggg cctggactgt   1440
gacattgaca tccagaagac catccagatg gtgcgggcgc agcgctcggg catggtgcag   1500
acggaggcgc agtacaagtt catctacgtg gccatcgccc agttcattga aaccactaag   1560
aagaagctgg aggtcctgca gtcgcagaag ggccaggagt cggagtacgg gaacatcacc   1620 tatccccag ccatgaagaa tgcccatgcc aaggcctccc gcacctcgtc caaacacaag    1680
gaggatgtgt atgagaacct gcacactaag aacaagaggg aggagaaagt gaagaagcag   1740
cggtcagcag acaaggagaa gagcaagggt ccctcaagga ggaagtga                1788

<210> SEQ ID NO 100
<211> LENGTH: 1782
<212> TYPE: DNA
<213> ORGANISM: Artificial Sequence
<220> FEATURE:
<223> OTHER INFORMATION: Synthetic Polynucleotide

<400> SEQUENCE: 100
atgacatcgc ggagatggtt tcacccaaat atcactggtg tggaggcaga aaacctactg     60
ttgacaagag gagttgatgg cagttttttg gcaaggccta gtaaaagtaa ccctggagac    120
ttcacacttt ccgttagaag aaatggagct gtcacccaca tcaagattca gaacactggt    180
gattactatg acctgtatgg aggggagaaa tttgccactt tggctgagtt ggtccagtat    240
tacatggaac atcacgggca attaaaagag aagaatggag atgtcattga gcttaaatat    300
cctctgaact gtgcagatcc tacctctgaa aggtggtttc atggacatct ctctgggaaa    360
gaagcagaga attattaac tgaaaaagga aaacatggta gttttcttgt acgagagagc     420
cagagccacc ctggagattt tgttctttct gtgcgcactg gtgatgacaa aggggagagc    480
aatgacggca agtctaaagt gacccatgtt atgattcgct gtcaggaact gaaatacgac    540
gttggtggag gagaacggtt tgattctttg acagatcttg tggaacatta taagaagaat    600
cctatggtgg aaacattggg tacagtacta caactcaagc agccccttaa cacgactcgt    660
ataaatgctg ctgaaataga aagcagagtt cgagaactaa gcaaattagc tgagaccaca    720
gataaagtca acaaggcttt tgggaagaat tttgagacac tacaacaaca ggagtgcaaa    780
cttctctaca gccgaaaaga gggtcaaagg caagaaaaca aaacaaaaa tagatataaa    840 aacatcctgc cctttgatca taccaggggt gtcctacacg atggtgatcc caatgagcct    900
gtttcagatt acatcaatgc aaatatcatc atgcctgaat ttgaaaccaa gtgcaacaat    960
tcaaagccca aaagagtta cattgccaca caaggctgcc tgcaaaacac ggtgaatgac   1020
ttttggcgga tggtgttcca agaaaactcc cgagtgattg tcatgacaac gaaagaagtg   1080
gagagaggaa agagtaaatg tgtcaaatac tggcctgatg agtatgctct aaaagaatat   1140
ggcgtcatgc gtgttaggaa cgtcaaagaa agcgccgctc atgactatac gctaagagaa   1200 cttaaactt caaggttgg acaagggaat acggagagaa cggtctggca ataccacttt   1260
cggacctggc cggaccacgg cgtgcccagc gaccctgggg gcgtgctgga cttcctggag   1320
gaggtgcacc ataagcagga gagcatcatg gatgcagggc cggtcgtggt gcactgcagt   1380
```

| | |
|---|---|
| gctggaattg gccggacagg gacgttcatt gtgattgata ttcttattga catcatcaga | 1440 |
| gagaaaggtg ttgactgcga tattgacgtt cccaaaacca tccagatggt gcggtctcag | 1500 |
| aggtcaggga tggtccagac agaagcacag taccgattta tctatatggc ggtccagcat | 1560 |
| tatattgaaa cactacagcg caggattgaa gaagagcaga aaagcaagag gaaagggcac | 1620 |
| gaatatacaa atattaagta ttctctagcg gaccagacga gtggagatca gagccctctc | 1680 |
| ccgccttgta ctccaacgcc accctgtgca gaaatgagag aagacagtgc tagagtctat | 1740 |
| gaaaacgtgg gcctgatgca acagcagaaa agtttcagat ga | 1782 |

<210> SEQ ID NO 101
<211> LENGTH: 1275
<212> TYPE: DNA
<213> ORGANISM: Artificial Sequence
<220> FEATURE:
<223> OTHER INFORMATION: Synthetic Polynucleotide

<400> SEQUENCE: 101

| | |
|---|---|
| atggagcaag tggagatcct gaggaaattc atccagaggg tccaggccat gaagagtcct | 60 |
| gaccacaatg gggaggacaa cttcgcccgg gacttcatgc ggttaagaag attgtctacc | 120 |
| aaatatagaa cagaaaagat atatcccaca gccactggag aaaagaagaa aaatgttaaa | 180 |
| aagaacagat acaaggacat actgccattt gatcacagcc gagttaaatt gacattaaag | 240 |
| actccttcac aagattcaga ctatatcaat gcaaatttta taagggcgt ctatgggcca | 300 |
| aaagcatatg tagcaactca aggaccttta gcaaatacag taatagattt ttggaggatg | 360 |
| gtatgggagt ataatgttgt gatcattgta atggcctgcc gagaatttga gatgggaagg | 420 |
| aaaaaatgtg agcgctattg gcctttgtat ggagaagacc ccataacgtt tgcaccattt | 480 |
| aaaatttctt gtgaggatga acaagcaaga acagactact tcatcaggac actcttactt | 540 |
| gaatttcaaa atgaatctcg taggctgtat cagtttcatt atgtgaactg ccagaccat | 600 |
| gatgttcctt catcatttga ttctattctg gacatgataa gcttaatgag gaaatatcaa | 660 |
| gaacatgaag atgttcctat ttgtattcat tgcagtgcag gctgtggaag aacaggtgcc | 720 |
| atttgtgcca tagattatac gtggaattta ctaaaagctg ggaaaatacc agaggaattt | 780 |
| aatgtatta atttaataca agaaatgaga acacaaaggc attctgcagt acaaacaaag | 840 |
| gagcaatatg aacttgttca tagagctatt gcccaactgt ttgaaaaaca gctacaacta | 900 |
| tatgaaattc atggagctca gaaaattgct gatggagtga atgaaattaa cactgaaaac | 960 |
| atggtcagct ccatagagcc tgaaaaacaa gattctcctc ctccaaaacc accaaggacc | 1020 |
| cgcagttgcc ttgttgaagg ggatgctaaa gaagaaatac tgcagccacc ggaacctcat | 1080 |
| ccagtgccac ccatcttgac accttctccc ccttcagctt ttccaacagt cactactgtg | 1140 |
| tggcaggaca atgatagata ccatccaaag ccagtgttgc aatggtttca tcagaacaac | 1200 |
| attcagcaga cctcaacaga aactatagta aatcaacaga cttccagggg aaaaatgaat | 1260 |
| caacaattga acaga | 1275 |

<210> SEQ ID NO 102
<211> LENGTH: 899
<212> TYPE: DNA
<213> ORGANISM: Artificial Sequence
<220> FEATURE:
<223> OTHER INFORMATION: Synthetic Polynucleotide

<400> SEQUENCE: 102

| | |
|---|---|
| atggaccaaa gagaaattct gcagaagttc ctggatgagg cccaaagcaa gaaaattact | 60 |

```
aaagaggagt tgccaatga atttctgaag ctgaaaaggc aatctaccaa gtacaaggca      120
gacaaaacct atcctacaac tgtggctgag aagcccaaga atatcaagaa aaacagatat     180
aaggatattt tgccctatga ttatagccgg gtagaactat ccctgataac ctctgatgag     240
gattccagct acatcaatgc caacttcatt aagggagttt atggacccaa ggcttatatt     300
gccacccagg gtcctttatc tacaaccctc ctggacttct ggaggatgat ttgggaatat     360
agtgtcctta tcattgttat ggcatgcatg agtatgaaa tgggaaagaa aaagtgtgag      420
cgctactggg ctgagccagg agagatgcag ctggaatttg ccccttctct tgtatcctgt    480
gaagctgaaa aaaggaaatc tgattatata atcaggactc taaaagttaa gttcaatagt    540
gaaactcgaa ctatctacca gtttcattac aagaattggc cagaccatga tgtaccttca    600
tctatagacc ctattcttga gctcatctgg gatgtacgtt gttaccaaga ggatgacagt    660
gttcccatat gcattcactg cagtgctggc tgtggaagga ctggtgttat ttgtgctatt    720
gattatacat ggatgttgct aaaagatggg ataattcctg agaacttcag tgttttcagt    780
ttgatccggg aaatgcggac acagaggcct tcattagttc aaacgcagga acaatatgaa    840
ctggtctaca atgctgtatt agaactattt aagagacaga tggatgttat cagagataa     899

<210> SEQ ID NO 103
<211> LENGTH: 1149
<212> TYPE: DNA
<213> ORGANISM: Artificial Sequence
<220> FEATURE:
<223> OTHER INFORMATION: Synthetic Polynucleotide

<400> SEQUENCE: 103
atgagtctga aagaaaaaac acaatctctg tttgccaacg catttggcta ccctgccact     60
cacaccattc aggcgcctgg ccgcgtgaat ttgattggtg aacacaccga ctacaacgac    120
ggtttcgttc tgccctgcgc gattgattat caaaccgtga tcagttgtgc accacgcgat    180
gaccgtaaag ttcgcgtgat ggcagccgat tatgaaaatc agctcgacga gttttccctc    240
gatgcgccca ttgtcgcaca tgaaaactat caatgggcta actacgttcg tggcgtggtg    300
aaacatctgc aactgcgtaa caacagcttc ggcggcgtgg acatggtgat cagcggcaat    360
gtgccgcagg gtgccgggtt aagttcttcc gcttcactgg aagtcgcggt cggaaccgta    420
ttgcagcagc tttatcatct gccgctggac ggcgcacaaa tcgcgcttaa cggtcaggaa    480
gcagaaaacc agtttgtagg ctgtaactgc gggatcatgg atcagctaat ttccgcgctc    540
ggcaagaaag atcatgcctt gctgatcgat tgccgctcac tggggaccaa agcagtttcc    600
atgcccaaag gtgtggctgt cgtcatcatc aacagtaact tcaaacgtac cctggttggc    660
agcgaataca cacccgtcg tgaacagtgc gaaaccggtg cgcgtttctt ccagcagcca    720
gccctgcgtg atgtcaccat tgaagagttc aacgctgttg cgcatgaact ggacccgatc    780
gtggcaaaac gcgtgcgtca tatactgact gaaaacgccc gcaccgttga agctgccagc    840
gcgctggagc aaggcgacct gaaacgtatg ggcgagttga tggcggagtc tcatgcctct    900
atgcgcgatg atttcgaaat caccgtgccg caaattgaca ctctggtaga atcgtcaaa    960 gctgtgattg gcgacaaagg tggcgtacgc atgaccggcg gcggatttgg cggctgtatc   1020
gtcgcgctga tcccggaaga gctggtgcct gccgtacagc aagctgtcgc tgaacaatat   1080
gaagcaaaaa caggtattaa agagactttt tacgtttgta aaccatcaca aggagcagga   1140
cagtgctga                                                          1149
```

```
<210> SEQ ID NO 104
<211> LENGTH: 1422
<212> TYPE: DNA
<213> ORGANISM: Artificial Sequence
<220> FEATURE:
<223> OTHER INFORMATION: Synthetic Polynucleotide

<400> SEQUENCE: 104
atgaacatca aaaagtttgc aaaacaagca acagtattaa cctttactac cgcactgctg      60
gcaggaggcg caactcaagc gtttgcgaaa gaaacgaacc aaaagccata taggaaaaca     120
tacggcattt cccatattac acgccatgat atgctgcaaa tccctgaaca gcaaaaaaat     180
gaaaaatatc aagttcctga attcgattcg tccacaatta aaaatatctc ttctgcaaaa     240
ggcctggacg tttgggacag ctggccatta caaaacgctg acggcactgt cgcaaactat     300
cacggctacc acatcgtctt tgcattagcc ggagatccta aaaatgcgga tgacacatcg     360
atttacatgt tctatcaaaa agtcggcgaa acttctattg acagctggaa aaacgctggc     420
cgcgtcttta aagacagcga caattcgat gcaaatgatt ctatcctaaa agaccaaaca     480
caagaatggt caggttcagc cacatttaca tctgacggaa aaatccgttt attctacact     540
gatttctccg gtaaacatta cggcaaacaa acactgacaa ctgcacaagt taacgtatca     600
gcatcagaca gctctttgaa catcaacggt gtagaggatt ataaatcaat ctttgacggt     660
gacggaaaaa cgtatcaaaa tgtacagcag ttcatcgatg aaggcaacta cagctcaggc     720
gacaaccata cgctgagaga tcctcactac gtagaagata aaggccacaa atacttagta     780
tttgaagcaa acactggaac tgaagatggc taccaaggcg aagaatcttt atttaacaaa     840
gcatactatg gcaaaagcac atcattcttc cgtcaagaaa gtcaaaaact tctgcaaagc     900
gataaaaaac gcacggctga gttagcaaac ggcgctctcg gtatgattga gctaaacgat     960
gattacacac tgaaaaaagt gatgaaaccg ctgattgcat ctaacacagt aacagatgaa    1020
attgaacgcg cgaacgtctt taaaatgaac ggcaaatggt acctgttcac tgactcccgc    1080
ggatcaaaaa tgacgattga cggcattacg tctaacgata tttacatgct tggttatgtt    1140
tctaattctt taactggccc atacaagccg ctgaacaaaa ctggccttgt gttaaaaatg    1200
gatcttgatc ctaacgatgt aacctttact tactcacact tcgctgtacc tcaagcgaaa    1260
ggaaacaatg tcgtgattac aagctatatg acaaacagag gattctacgc agacaaacaa    1320
tcaacgtttg cgccaagctt cctgctgaac atcaaaggca agaaaacatc tgttgtcaaa    1380
gacagcatcc ttgaacaagg acaattaaca gttaacaaat aa                       1422
```

The invention claimed is:

1. A method of using a genetically encoded detection system, said method comprising:
a. providing:
i. an inhibitor detection system comprising a first region of DNA and a second region of DNA, wherein:
(A) the first region of DNA encodes:
1. a first promoter;
2. a first fusion protein comprising a substrate recognition domain linked to a DNA-binding protein;
3. a second fusion protein comprising a substrate domain linked to a protein capable of recruiting RNA polymerase to DNA;
4. a second promoter;
5. a protein kinase;
6. a molecular chaperone; and
7. a protein phosphatase; and
(B) the second region of DNA encodes:
8. a third promoter;
9. an operator for said DNA-binding protein;
10. a binding site for said RNA polymerase; and
11. a reporter protein; and
ii. an isoprenoid pathway DNA sequence encoding one or more components of an isoprenoid pathway under control of a fourth promoter;
iii. a synthase DNA sequence encoding a synthase enzyme; and
iv. a plurality of cells;
b. introducing into each cell of said plurality of cells said inhibitor detection system under conditions sufficient to express said reporter protein;

c. introducing into each cell of said plurality of cells said isoprenoid pathway DNA sequence under conditions sufficient to express said one or more components of said isoprenoid pathway;

d. introducing into each cell of said plurality of cells said synthase DNA sequence under conditions sufficient to express said synthase enzyme; and e. identifying a cell of said plurality of cells expressing said reporter protein, wherein expression of said reporter protein in said cell is indicative that said cell comprises an inhibitor of said protein phosphatase that is synthesized by said synthase enzyme.

2. The method of claim 1, further comprising:

f. isolating said inhibitor of said protein phosphatase; and g. treating a mammalian cell culture with said inhibitor for reducing activity of said protein phosphatase.

3. The method of claim 2, wherein said reducing said activity of said protein phosphatase reduces growth of mammalian cells of said mammalian cell culture.

4. The method of claim 1, wherein said protein phosphatase is human protein tyrosine phosphatase 1B (PTP1B).

5. The method of claim 1, wherein said protein phosphatase is a wild-type form of said protein phosphatase.

6. The method of claim 1, wherein said protein phosphatase has at least one mutation.

7. The method of claim 1, wherein said one or more components of said isoprenoid pathway comprises mevalonate kinase (ERG12), phosphomevalonate kinase (ERGS), mevalonate pyrophosphate decarboxylatse (MVD 1), Isopentenyl pyrophosphate isomerase (IDI gene), or Farnesyl pyrophosphate (FPP) synthase (ispA), or any combination thereof.

8. The method of claim 1, wherein said synthase enzyme comprises a terpene synthase.

9. The method of claim 8, wherein said terpene synthase comprises amorphadiene synthase (ADS) or y-humulene synthase (GHS).

10. The method of claim 8, wherein said synthase DNA sequence further encodes geranylgeranyl diphosphate synthase (GPPS) and said terpene synthase comprises abietadiene synthase (ABS) or taxadiene synthase (TXS), or any combination thereof.

11. The method of claim 8, wherein said terpene synthase is a wild-type form of said terpene synthase.

12. The method of claim 8, wherein said terpene synthase has at least one mutation.

13. The method of claim 12, wherein said inhibitor comprises a terpenoid or a structural variant of said terpenoid.

14. The method of claim 1, wherein said reporter protein confers antibiotic resistance to said cell.

15. The method of claim 14, wherein said reporter protein confers antibiotic resistance to said cell to two different antibiotics.

16. The method of claim 1, wherein the fourth promoter is an inducible promoter, and wherein said method further comprises introducing into each cell of said plurality of cells an induction molecule for said inducible promoter under conditions sufficient to contact said inducible promoter with said induction molecule.

17. The method of claim 1, wherein said plurality of cells comprises microbial cells.

18. The method of claim 17, wherein said microbial cells comprise *Escherichia coli* (*E. coli*) cells.

19. The method of claim 1, further comprising isolating said inhibitor of said protein phosphatase from said cell.

20. The method of claim 1, wherein said isoprenoid pathway is a mevalonate pathway.

* * * * *